(12) United States Patent
Watson-Hurthig et al.

(10) Patent No.: US 12,139,764 B2
(45) Date of Patent: Nov. 12, 2024

(54) SYSTEMS AND METHODS FOR CHARACTERIZING AND TREATING BREAST CANCER

(71) Applicant: Arizona Board of Regents on Behalf of the University of Arizona, Tucson, AZ (US)

(72) Inventors: Adam Watson-Hurthig, Tucson, AZ (US); Ghassan Mouneimne, Tucson, AZ (US); Casey Romanoski, Tucson, AZ (US); Adam Grant, Tucson, AZ (US); Megha Padi, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 770 days.

(21) Appl. No.: 17/293,578

(22) PCT Filed: Nov. 14, 2019

(86) PCT No.: PCT/US2019/061449
§ 371 (c)(1),
(2) Date: May 13, 2021

(87) PCT Pub. No.: WO2020/102513
PCT Pub. Date: May 22, 2020

(65) Prior Publication Data
US 2022/0025465 A1 Jan. 27, 2022

Related U.S. Application Data

(60) Provisional application No. 62/767,032, filed on Nov. 14, 2018.

(51) Int. Cl.
*C12Q 1/68* (2018.01)
*C12Q 1/6886* (2018.01)
(52) U.S. Cl.
CPC ..... *C12Q 1/6886* (2013.01); *C12Q 2600/158* (2013.01)
(58) Field of Classification Search
CPC .................................................. C12Q 1/6886
See application file for complete search history.

(56) References Cited

U.S. PATENT DOCUMENTS

| | | | |
|---|---|---|---|
| 4,968,103 A | 11/1990 | Mc Nab | |
| 5,283,174 A | 2/1994 | Arnold | |
| 5,538,848 A | 7/1996 | Livak | |
| 5,631,169 A | 5/1997 | Lakowicz | |
| 5,639,606 A | 6/1997 | Willey | |
| 5,643,765 A | 7/1997 | Willey | |
| 5,695,934 A | 12/1997 | Brenner | |
| 5,714,330 A | 2/1998 | Brenner | |
| 5,750,341 A | 5/1998 | Macevicz | |
| 5,814,447 A | 9/1998 | Ishiguro | |
| 5,876,978 A | 3/1999 | Willey | |
| 5,912,148 A | 6/1999 | Eggerding | |
| 5,925,517 A | 7/1999 | Tyagi | |
| 5,928,862 A | 7/1999 | Morrison | |
| 6,130,073 A | 10/2000 | Eggerding | |
| 6,150,097 A | 11/2000 | Tyagi | |
| 6,210,891 B1 | 4/2001 | Nyren | |
| 6,258,568 B1 | 7/2001 | Nyren | |
| 6,306,597 B1 | 10/2001 | Macevicz | |
| 6,432,360 B1 | 8/2002 | Church | |
| 6,485,944 B1 | 11/2002 | Church | |
| 6,511,803 B1 | 1/2003 | Church | |
| 6,787,308 B2 | 9/2004 | Balasubramanian | |
| 6,818,395 B1 | 11/2004 | Quake | |
| 6,833,246 B2 | 12/2004 | Balasubramanian | |
| 6,911,345 B2 | 6/2005 | Quake | |
| 6,969,488 B2 | 11/2005 | Bridgham | |
| 7,115,400 B1 | 10/2006 | Adessi | |
| 7,169,560 B2 | 1/2007 | Lapidus | |
| 7,282,337 B1 | 10/2007 | Harris | |
| 7,329,492 B2 | 2/2008 | Hardin | |
| 7,482,120 B2 | 1/2009 | Buzby | |
| 7,501,245 B2 | 3/2009 | Quake | |
| 7,668,697 B2 | 2/2010 | Volkov | |
| 11,047,847 B2 * | 6/2021 | Skardal | G01N 33/5011 |
| 11,686,720 B2 * | 6/2023 | Plodinec | G01N 33/4833 424/133.1 |
| 2005/0042638 A1 | 2/2005 | Arnold | |
| 2005/0130173 A1 | 6/2005 | Leamon | |
| 2008/0193938 A1 | 8/2008 | Kun | |
| 2008/0241951 A1 | 10/2008 | Battulga | |

(Continued)

FOREIGN PATENT DOCUMENTS

EP 1409727 4/2004
WO WO2000018957 4/2000
(Continued)

OTHER PUBLICATIONS

US 5,962,233 A, 10/1999, Livak (withdrawn)
Adessi et al. (2000). Nucleic Acid Res. 28, E87.
Altenbuchinger, M. et al. Bioinformatics 33, 2790 (2017).
Astier et al., J. Am. Chem. Soc. Feb. 8, 2006; 128(5):1705-10.
Bar-Kochba, E. et al., Exp. Mech. 55, 261-274 (2015).
Bastarrachea et al., Annals of Internal Medicine, 120: 18 [1994].
Bennett et al., 2005, Pharmacogenomics, 6, 373-382.
Birren et al., Genome Analysis : A Laboratory Manual : Analyzing DNA (vol. 1), Chapter 7 (Book) ISBN: 0879694963, (1997).

(Continued)

*Primary Examiner* — Kenneth R Horlick
(74) *Attorney, Agent, or Firm* — Casimir Jones, S.C.; Tanya A. Arenson

(57) ABSTRACT

Provided herein are compositions and methods for characterizing and treating cancer. In particular, provided herein are compositions and methods for identifying subjects with breast cancer with increased likelihood of bone metastasis and providing treatment to prevent such metastases.

3 Claims, 43 Drawing Sheets
Specification includes a Sequence Listing.

(56) References Cited

U.S. PATENT DOCUMENTS

| | | |
|---|---|---|
| 2009/0026082 A1 | 1/2009 | Rothberg |
| 2009/0035777 A1 | 2/2009 | Kokoris |
| 2009/0127589 A1 | 5/2009 | Rothberg |
| 2010/0137143 A1 | 6/2010 | Rothberg |
| 2010/0188073 A1 | 7/2010 | Rothberg |
| 2010/0197507 A1 | 8/2010 | Rothberg |
| 2010/0301398 A1 | 12/2010 | Rothberg |
| 2015/0293100 A1 | 10/2015 | Gomis et al. |
| 2016/0153053 A1 | 6/2016 | Skog et al. |
| 2018/0293100 A1 | 10/2018 | Mukherjee |

FOREIGN PATENT DOCUMENTS

| | | |
|---|---|---|
| WO | WO2006084132 | 8/2006 |
| WO | WO2010042228 | 4/2010 |
| WO | WO2017180587 | 10/2017 |

OTHER PUBLICATIONS

Blake, J. A. et al. Nucleic Acids Res. 37, D712-D719 (2009).
Bobko, A. A. et al. Sci. Rep. 7, 41233 (2017).
Bos, P. D. et al. Nature 459, 1005-1009 (2009).
Brenner et al. (2000). Nat. Biotechnol. 18:630-634.
Buenrostro, J. D. et al., Transposition of native chromatin for fast and sensitive epigenomic profiling of open chromatin, DNA-binding proteins and nucleosome position. Nat. Methods. 2013; 10: 1213-1218.
Coleman, R. E. Clin. Cancer Res. 12, 6243s-6249s (2006).
Corces, M. R. et al. An improved ATAC-seq protocol reduces background and enables interrogation of frozen tissues. Nat. Methods. 2017; 14: 959-962.
Cox, T. R. et al. Nature 522, 106-110 (2015).
Dingal, P. C. D. P. et al. Fractal heterogeneity in minimal matrix models of scars modulates stiff-niche stem-cell responses via nuclear exit of a mechanorepressor. Nat. Mater. 2015; 14: 951-960.
Edwards et al., Journal of Clinical Oncology 16: 2693 [1998].
Elledge et al., Journal of the National Cancer Institute 86: 705 [1994].
Evans, A. et al. Radiology 263, 673-677 (2012).
Feng, X. & Teitelbaum, S. L. Nat. Publ. Gr. Osteoclasts: New Insights. Bone Res. 2013; 1: 11-26.
Ge, C. et al. Identification and Functional Characterization of ERK/MAPK Phosphorylation Sites in the Runx2 Transcription Factor. J. Biol. Chem. 284, 32533-32543 (2009).
Gohongi, T. et al. Nat. Med. 5, 1203-1208 (1999).
Guise, T. A. et al. Clin. Cancer Res. 12, 6213s-6216s (2006).
Heinz, S. et al. Mol. Cell 38, 576-589 (2010).
Hogan, N. T. et al. Elife 6, (2017).
Holliday, D. L. & Speirs, V. Breast Cancer Res. 13, 215 (2011).
Huang, C., Jacobson, K. & Schaller, M. D. J. Cell Sci. 117, 4619-28 (2004).
Inman, C. K. & Shore, P. J. Biol. Chem. 278, 48684-48689 (2003).
International Search Report and Written Opnion; Int'l App No. PCT/US2019/061449; mailed Mar. 24, 2020; 15 pages.
Jansen et al. "Decreased expression of ABAT and STC2 hallmarks ER-positive inflammatory breast cancer and endocrine therapty resistance in advanced disease." Mol Oncol, Mar. 4, 2015, vol. 9, pp. 1218-1233.
Kadauke et al., supra; Moroishi, T. et al., Nat. Rev. Cancer 15, 73-79 (2015).
Kadauke, S. & Blobel, G. A. Epigenetics Chromatin Mitotic bookmarking by transcription factors. Epigenetics Chromatin. 2013; 6: 6.
Köhler, S. et al. Nucleic Acids Res. 42, D966-D974 (2014).
Kuleshov, M. V. et al. Nucleic Acids Res. 44, W90-W97 (2016).
Langemann, H. et al., Int. J. Cancer 43, 1169-1173 (1989).
Leung, C. T. & Brugge, J. S. Nature Outgrowth of single oncogene-expressing cells from suppressive epithelial environments. Nature Feb. 8, 2012;482(7385):410-3.
Li, X.-Q. et al. Molecular and Cellular Pathobiology ITGBL1 Is a Runx2 Transcriptional Target and Promotes Breast Cancer Bone Metastasis by Activating the TGFb Signaling Pathway. Cancer Res. 2015; 75: 3302-3313.
Li, Y. et al., J. Cell. Physiol. Transcriptional network analysis identifies BACH1 as a master regulator of breast cancer bone metastasis. J. Biol. Chem. 2012; 287: 33533-33544.
Liang, Y. et al. Transcriptional network analysis identifies BACH1 as a master regulator of breast cancer bone metastasis. J. Biol. Chem. 2012; 287: 33533-33544.
Little, G. H. et al., Nucleic Acids Res. 40, 3538-47 (2012).
MacLean et al., Nature Rev. Microbiol., 7: 287-296, (2009).
Margulies et al., 2005 Nature 437, 376-380.
McLean, C. Y. et al. GREAT improves functional interpretation of cis-regulatory regions. Nat. Biotechnol. 2010; 28: 495-501.
Mitra et al., 2003, Analytical Biochemistry 320, 55-65.
Model-based analysis of ChIP-Seq (MACS). Genome Biol. 2008; 9: R137.
Nelson et al., Nonisotopic Probing, Blotting, and Sequencing, ch. 17. Academic Press, ISBN-10 : 0124262929, (1995).
Padua, D. et al. Cell 133, 66-77 (2008).
Parfitt, A. M. et al. J. Bone Miner. Res. 2, 595-610 (2009).
Paszek, M. J. et al. Cancer Cell 8, 241-254 (2005).
Plodinec, M. et al. Nat Nano 7, 757-765 (2012).
Pockwinse, S. M. et al. J. Cell. Physiol. 206, 354-362 (2006).
Pratap et al., supra; Bernards, M. T. et al., Colloids Surfaces B Biointerfaces 64, 236-247 (2008).
Pratap, J. et al. Regulatory roles of Runx2 in metastatic tumor and cancer cell interactions with bone. Cancer Metastasis Rev. 2006; 25: 589-600.
Preston Campbell, J. et al. Sci. Rep. 5, 12635 (2015).
Puleo, J. I. et al. Mechanosensing during directed cell migration requires dynamic actin polymerization at focal adhesions. J. Cell Biol. 2019; 218: 4215-4235.
Quinlan, A. R. & Hall, I. M. BEDTools: a flexible suite of utilities for comparing genomic features. Bioinformatics. 2010; 26: 841-842.
Rueda, O. M. et al. Dynamics of breast-cancer relapse reveal late-recurring ER-positive genomic subgroups. Nature 567, pp. 399-404 (2019).
Science 327(5970): 1190 (2010).
Selfors, L. M. et al., Proc. Natl. Acad. Sci. 114, E11276-E11284 (2017).
Shen, C.-J. et al. Biomed Res. Int. 2014, 327538 (2014).
Shendure et al., 2005 Science 309, 1728-1732.
Tandon, M. et al., Runx2 activates PI3K/Akt signaling via mTORC2 regulation in invasive breast cancer cells. Breast Cancer Res. 2014; 16: R16.
The mechanical microenvironment in cancer: how physics affects tumours. Semin. Cancer Biol. 2015; 35: 62-70.
Toyjanova, J. et al. PLoS One 9, e90976 (2014).
Tripathi, S. et al. Cell Host Microbe 18, 723-735 (2015).
Van de Vijver et al. 2002 (N. Engl. J. Med. (2002)).
Venet, D., Dumont, J. E. & Detours, V. PLoS Comput. Biol. (2011).
Voelkerding et al., Clinical Chem., 55: 641-658, 2009.
Wang, D. et al., Tumor Evolution of Glioma-Intrinsic Gene Expression Subtypes Associates with Immunological Changes in the Microenvironment. Cancer Cell Jul. 10, 2017;32(1):42-56.e6.
Yang, C. et al., Mechanical memory and dosing influence stem cell fate. Nat. Mater. 2014; 13: 645-652.
Young, D. W. et al. Mitotic retention of gene expression patterns by the cell fate- determining transcription factor Runx2. Proc. Natl. Acad. Sci. USA. 2007; 104: 3189-3194.
Zhang, X. H. F. et al. Selection of bone metastasis seeds by mesenchymal signals in the primary tumor stroma. Cell. 2013;154:1060-1073.
Zhang, Y. et al. Model-based analysis of ChIP-Seq (MACS). Genome Biol. 2008; 9: R137.
Zheng, G. et al. Nucleic Acids Res. 46, D950-D955 (2018).

* cited by examiner

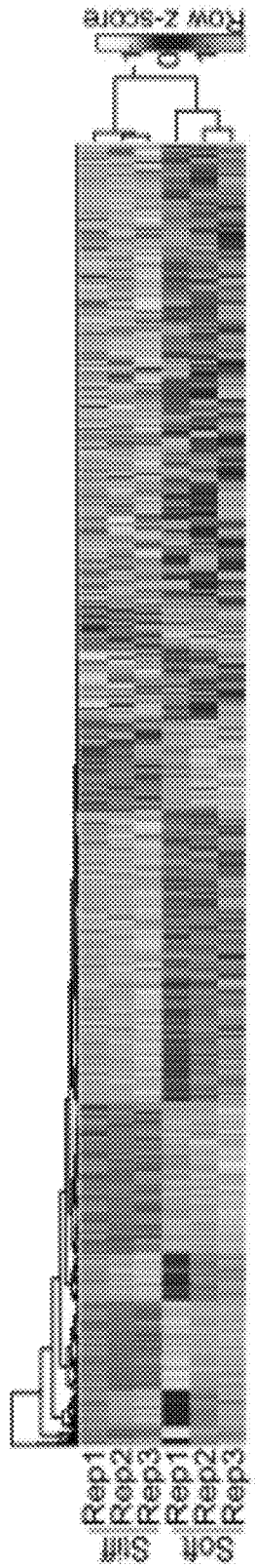
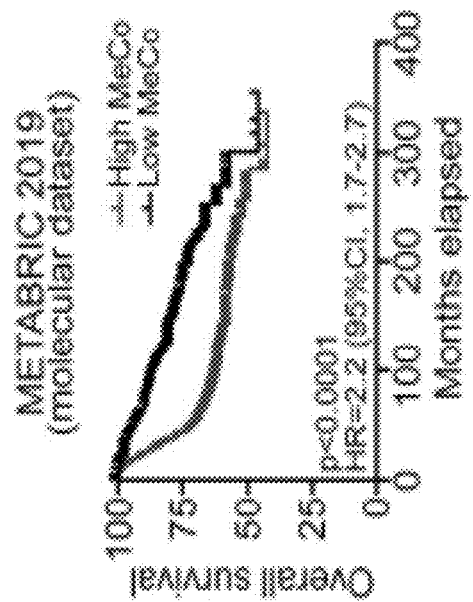
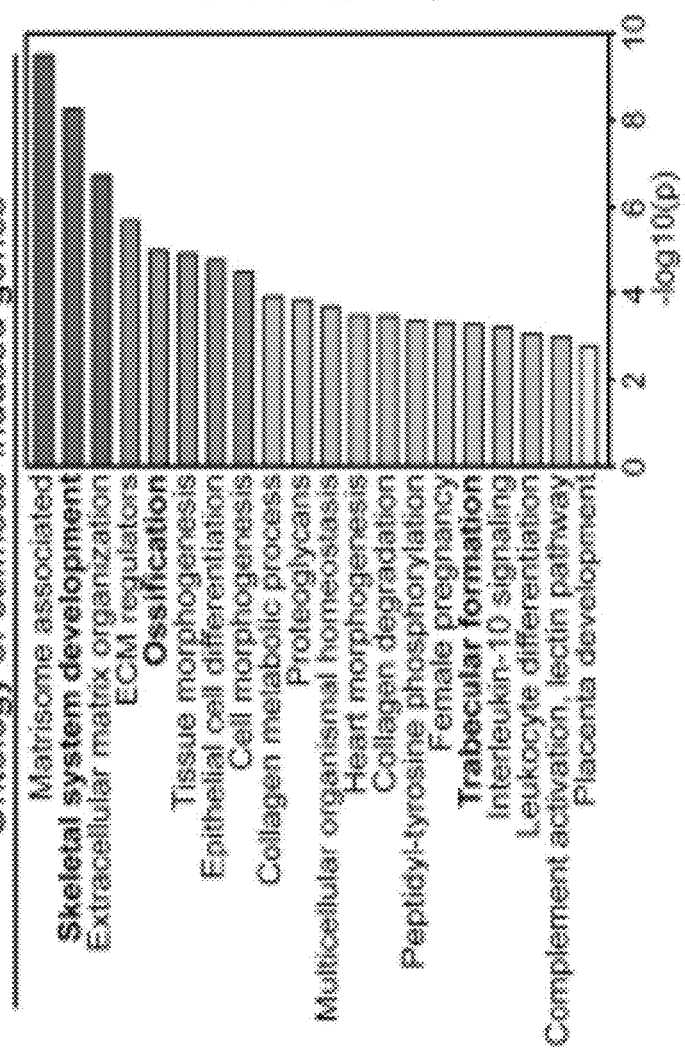
FIG. 2A
FIG. 2B
FIG. 2C

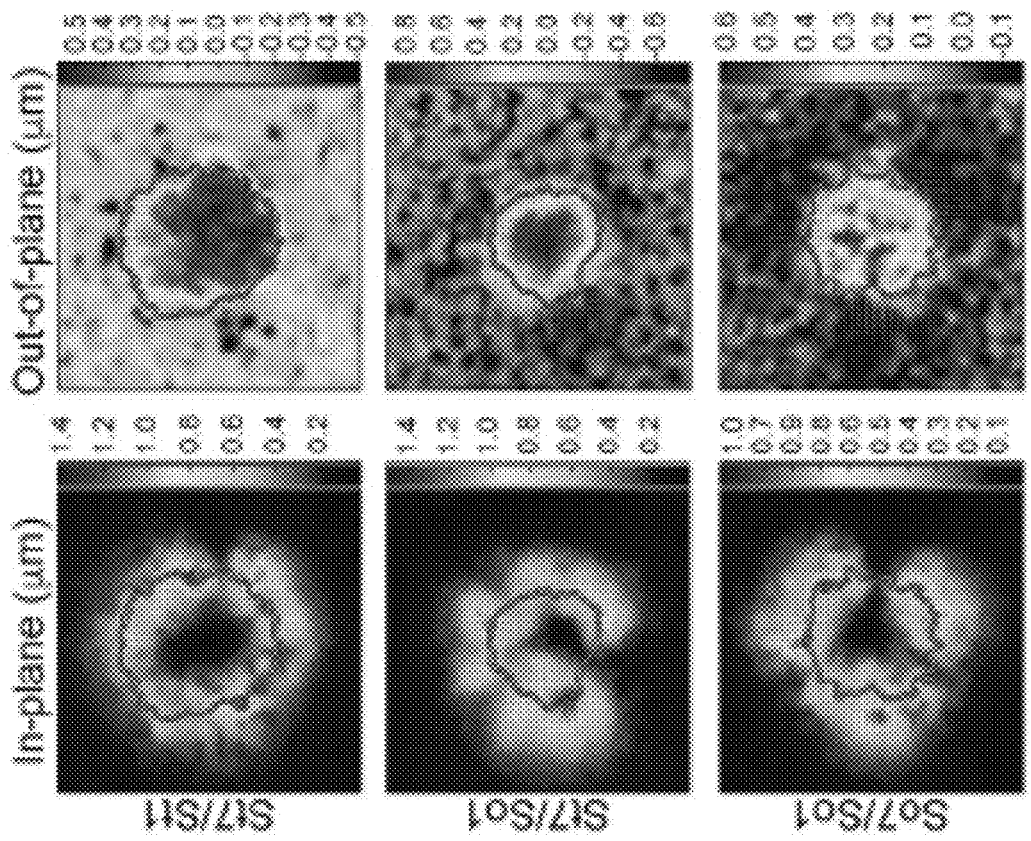
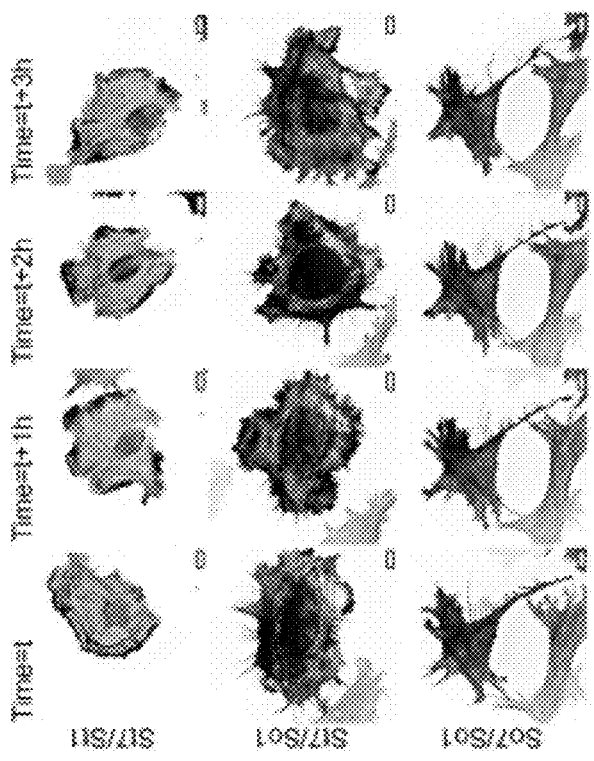
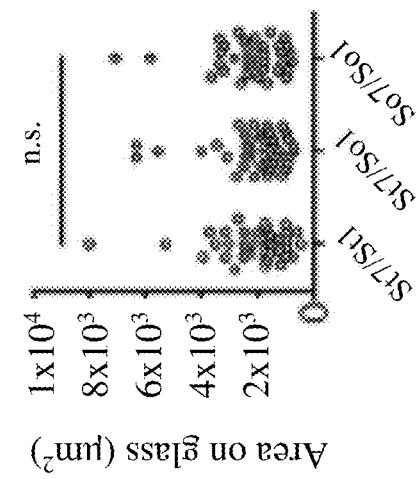
FIG. 5A
FIG. 5B
FIG. 5C

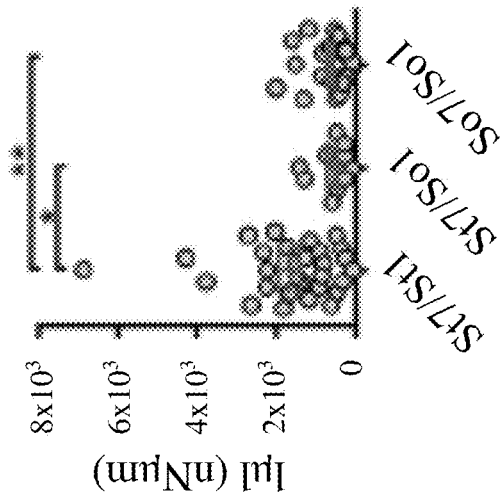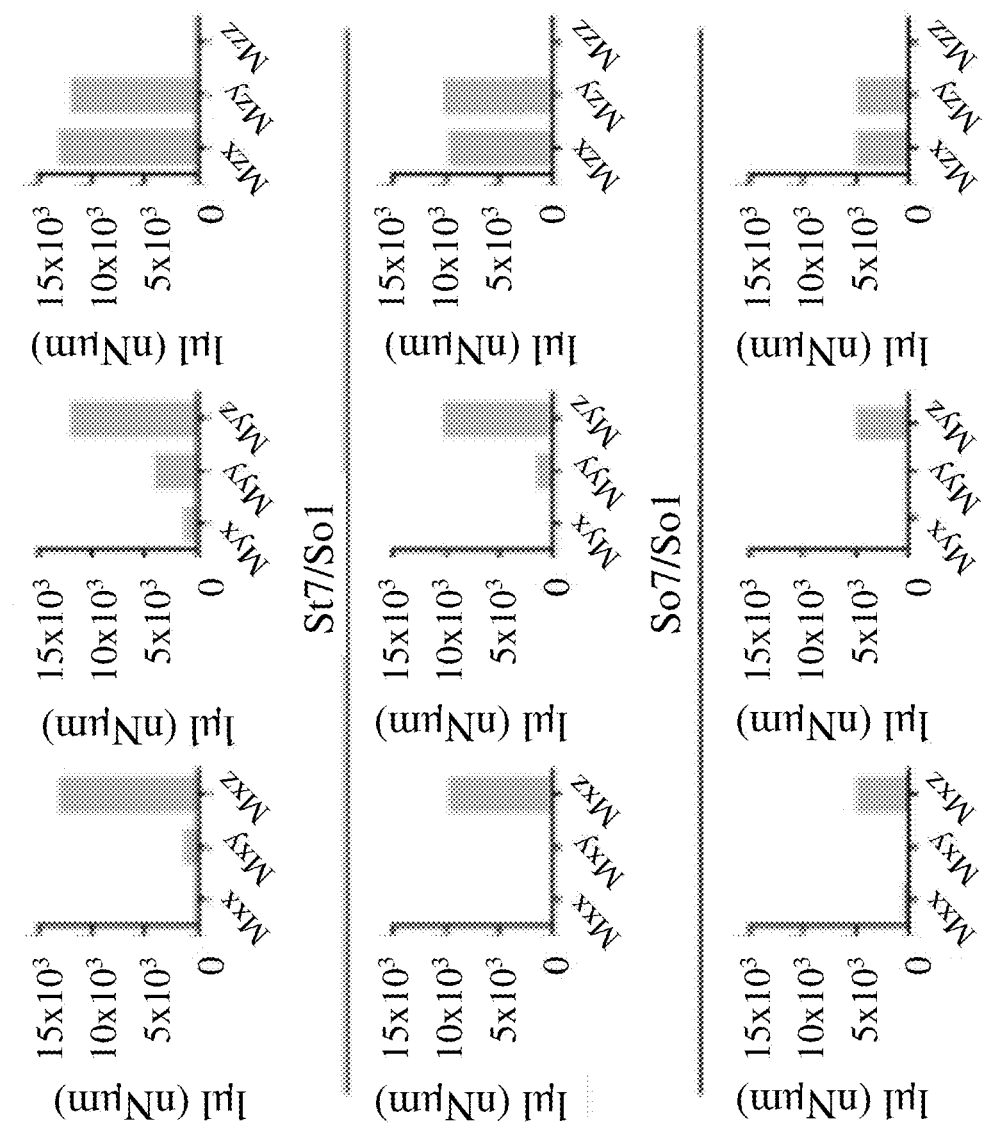
FIG. 5D
FIG. 5E

FIG. 7D

Training dataset (GSE2034+GSE2603+GSE12276): 560 patients
280 Low-MeCo patients: 87 patients with bone mets (31%) vs
280 High MeCo patients: 92 patients with bone mets (33%)
and
279 Low-MeCo$^{REFINED}$ patients: 45 patients with bone mets (16%) vs
281 High-MeCo$^{REFINED}$ patients: 134 patients with bone mets (48%)

NKI dataset: 295 patients
148 Low-MeCo$^{REFINED}$ patients: 19 patients with bone mets (13%) vs
147 High-MeCo$^{REFINED}$ patients: 34 patients with bone mets (23%)

Metabric-2019 dataset: 1686 patients
421 Low-MeCo$^{REFINED}$ patients (<1$^{st}$quart): 46 patients with bone mets (11%) vs
422 High-MeCo$^{REFINED}$ patients (>3$^{rd}$quart): 84 patients with bone mets (20%)

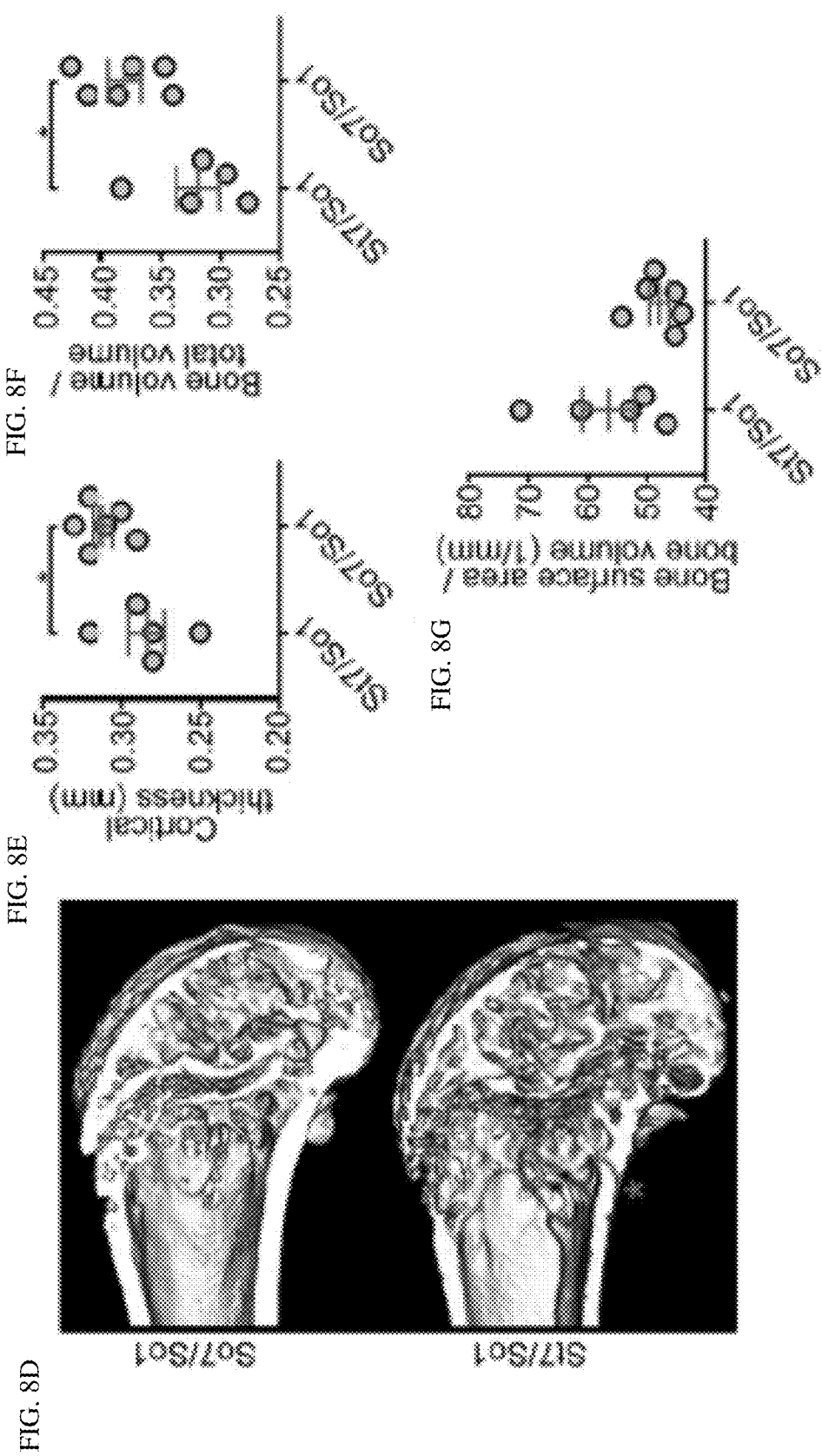

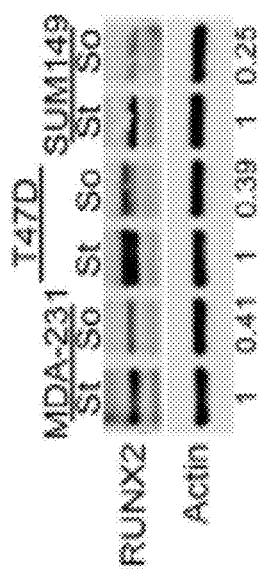
FIG. 9F
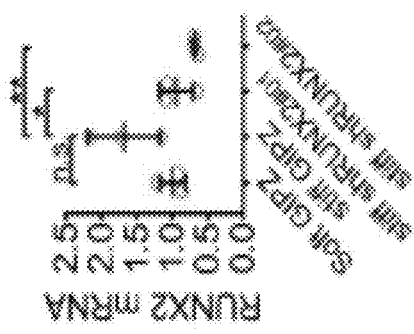
FIG. 9E
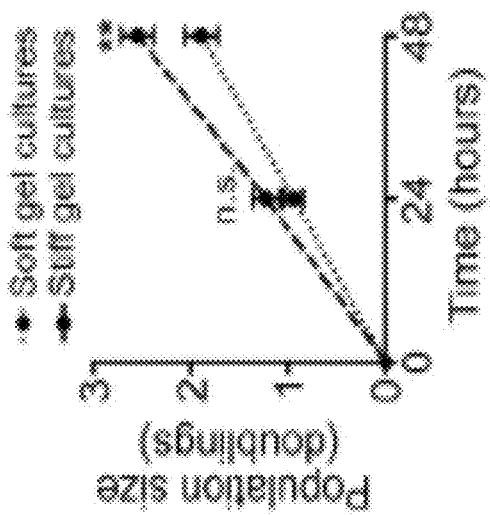
FIG. 9D
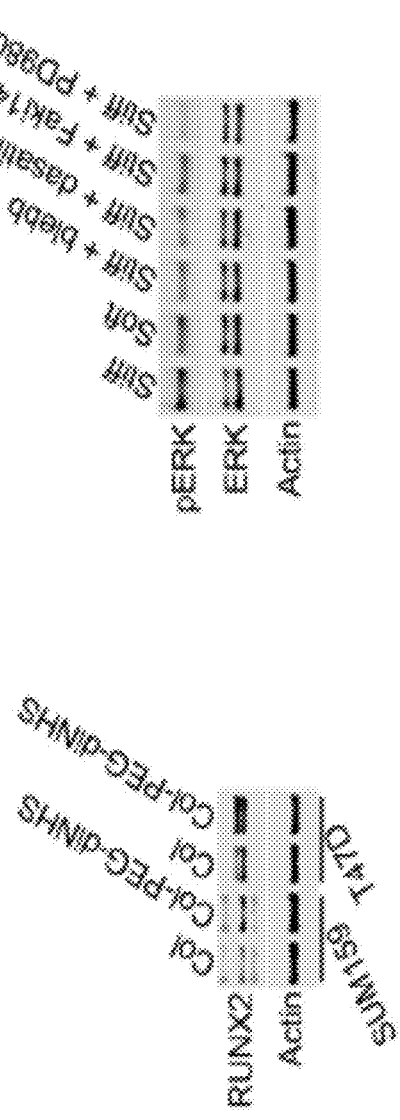
FIG. 9H
FIG. 9G

SYSTEMS AND METHODS FOR CHARACTERIZING AND TREATING BREAST CANCER

CROSS REFERENCE TO RELATED APPLICATIONS

This application is a U.S. 371 national phase entry of International Patent Application No. PCT/US2019/061449, filed Nov. 14, 2019, which claims priority to and the benefit of U.S. Provisional Application No. 62/767,032, filed Nov. 14, 2018, which are hereby incorporated by reference in their entireties.

STATEMENT REGARDING FEDERALLY SPONSORED RESEARCH OR DEVELOPMENT

This invention was made with government support under Grant No. R01 CA196885, awarded by NIH. The government has certain rights in the invention.

FIELD OF THE INVENTION

Provided herein are compositions and methods for characterizing and treating cancer. In particular, provided herein are compositions and methods for identifying subjects with breast cancer with increased likelihood of bone metastasis and providing treatment to prevent such metastases.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of ER and PR levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptor positive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

Overall 30% of cancer patient's cancer metastasizes, and over 70% of these cases involve bone metastasis. Currently, bone metastasis is detected only once symptoms begin to present themselves. The lack of early diagnosis decreases effectiveness of treatments. Therefore, the ability to predict the likelihood of a patient developing bone metastasis and subsequently pre-treating these patients allows for more effective treatment

SUMMARY OF THE INVENTION

The mechanical microenvironment of primary breast tumors plays a significant role in promoting tumor progression. Experiments described herein show that primary tumor stiffness promotes stable yet non-genetically heritable phenotypes in breast cancer cells. This "mechanical memory" instructs cancer cells to adopt and maintain increased cytoskeletal dynamics, traction force, and 3D invasion in vitro, in addition to promoting osteolytic bone metastasis in vivo. A "mechanical conditioning score" (MeCo score) comprised of mechanically-regulated genes was developed in order to proxy tumor stiffness response clinically, and it was shown that it is associated with bone-specific metastasis. Using a discovery approach, mechanical memory was traced in part to ERK-mediated mechanotransductive activation of RUNX2, an osteogenic gene bookmarker and bone metastasis driver. These biophysical data support a generalized model of breast cancer progression in which the primary tumor microenvironment instructs the metastatic microenvironment. The results described herein allow for prediction, prevention, and treatment of bone metastasis before they occur, which is a significant improvement in patient care.

For example, in some embodiments, provided herein is a method of characterizing breast cancer, comprising: determining a mechanical conditioning (MeCo) score in a breast cancer sample from a subject, wherein the MeCo score comprises the average expression of at least five (e.g., at least 10, 20, 50, 100 or more) stiff genes from any one of Tables 2-3 and 7-12 minus the average expression of at least five (e.g., at least 10, 20, 50, 100 or more) soft genes from any one of Tables 2-3 and 7-12. In some embodiments, a high MeCo score is indicative of a shorter period of bone metastasis-free survival, time to bone metastasis, and/or decreased likelihood of survival. Subject may have an ER+ tumor. In some embodiments, the method comprises measuring the expression levels of said genes using an amplification, sequencing, or hybridization method.

MeCo scores are determined to be high or low using any number of suitable method. In some embodiments, the MeCo score comprises the average expression of at least five stiff genes from any one of Tables 2-3 and 7-12 minus the average expression of at least five soft genes from any one of Tables 2-3 and 7-12. For example, in some embodiments, the MeCo score comprises the average expression of at least five genes selected from the group consisting of NAT1, CENPN, COL10A1, PLAT, BMP8A, and PPIC minus the average expression of at least five genes selected from the group consisting of BEX1, RYR1, HDAC11, RARRES3, CD27, PRRG4, XAF1, IL2RG, LPAR2, TP73, HBE1, PSD, SOX5, ARHGEF6, OASL, DCHS2, KCNN1, CD226, NIPSNAP1, STAT4, S1PR5, and FRS3 (e.g., the average expression of NAT1, CENPN, COL10A1, PLAT, BMP8A, and PPIC minus the average expression of BEX1, RYR1, HDAC11, RARRES3, CD27, PRRG4, XAF1, IL2RG, LPAR2, TP73, HBE1, PSD, SOX5, ARHGEF6, OASL, DCHS2, KCNN1, CD226, NIPSNAP1, STAT4, S1PR5, and FRS3).

In some embodiments, a high MeCo score is the top quartile of a group of subjects and a low MeCo score is the bottom quartile of the group of subjects. In some embodiments, the group of subjects is a group of subjects diagnosed with breast cancer.

In some embodiments, the method further comprises the step of treating the subject with an agent that prevents bone metastasis when the MeCo score is high and not treating said subject with an agent that prevents bone metastasis when the MeCo score is low. The present disclosure is not limited to particular agents. In one example, the agent is an anti-firbrotic agent (e.g., pirfenidone or nintedanib). In some embodiments, chemotherapy and/or hormone blocking therapy is administered alone or in the combination with the anti-fibrotic agent.

Further embodiments provide a method of treating breast cancer, comprising: a) determining a mechanical conditioning (MeCo) score in a breast cancer sample from a subject, wherein the MeCo score comprises the average expression of at least five (e.g., at least 10, 20, 50, 100 or more) stiff genes from any one of Tables 2-3 and 7-12 minus the average expression of at least five (e.g., at least 10, 20, 50, 100 or more) soft genes from any one of Tables 2-3 and 7-12; and treating the subject with an agent that prevents bone metastatis when the MeCo score is high and not treating the subject with an agent that prevents bone metastasis when the MeCo score is low.

Additional embodiments provide a method of calculating a MeCo score, comprising: determining a mechanical conditioning (MeCo) score in a breast cancer sample from a subject, wherein the MeCo score comprises the average expression of at least five (e.g., at least 10, 20, 50, 100 or more) stiff genes from any one of Tables 2-3 and 7-12 minus the average expression of at least five (e.g., at least 10, 20, 50, 100 or more) soft genes from any one of Tables 2-3 and 7-12.

Further embodiments provide a composition, kit, or system, comprising: a) a plurality of nucleic acid reagents for specifically detecting the level of expression of at least 5 (e.g., at least 10, 25, 50, 100, 500 or more) stiff genes from any one of Tables 2-3 and 7-12; and b) a plurality of nucleic acid reagents for specifically detecting the level of expression of at least 5 (e.g., at least 10, 25, 50, 100, 500 or more) soft genes from any one of Tables 2-3 and 7-12. The present disclosure is not limited to particular reagents. Examples include but are not limited to, a plurality of nucleic acid probes, a plurality of nucleic acid primers, or a plurality of pairs of nucleic acid primers. In some embodiments, the nucleic acid reagents comprise a label (e.g. an exogenous label).

Certain embodiments provide the use of composition, kit, or system described herein to characterize or treat breast cancer.

Additional embodiments are described herein.

k, RT-qPCR of the RUNX2 gene target OPN, and three YAP targets, CTGF, CYR61 and ANKRD1, in SUM159 cells preconditioned as indicated, and without media-change for 48 hours before sample collection (n=3 biological replicates).

Figure 4:
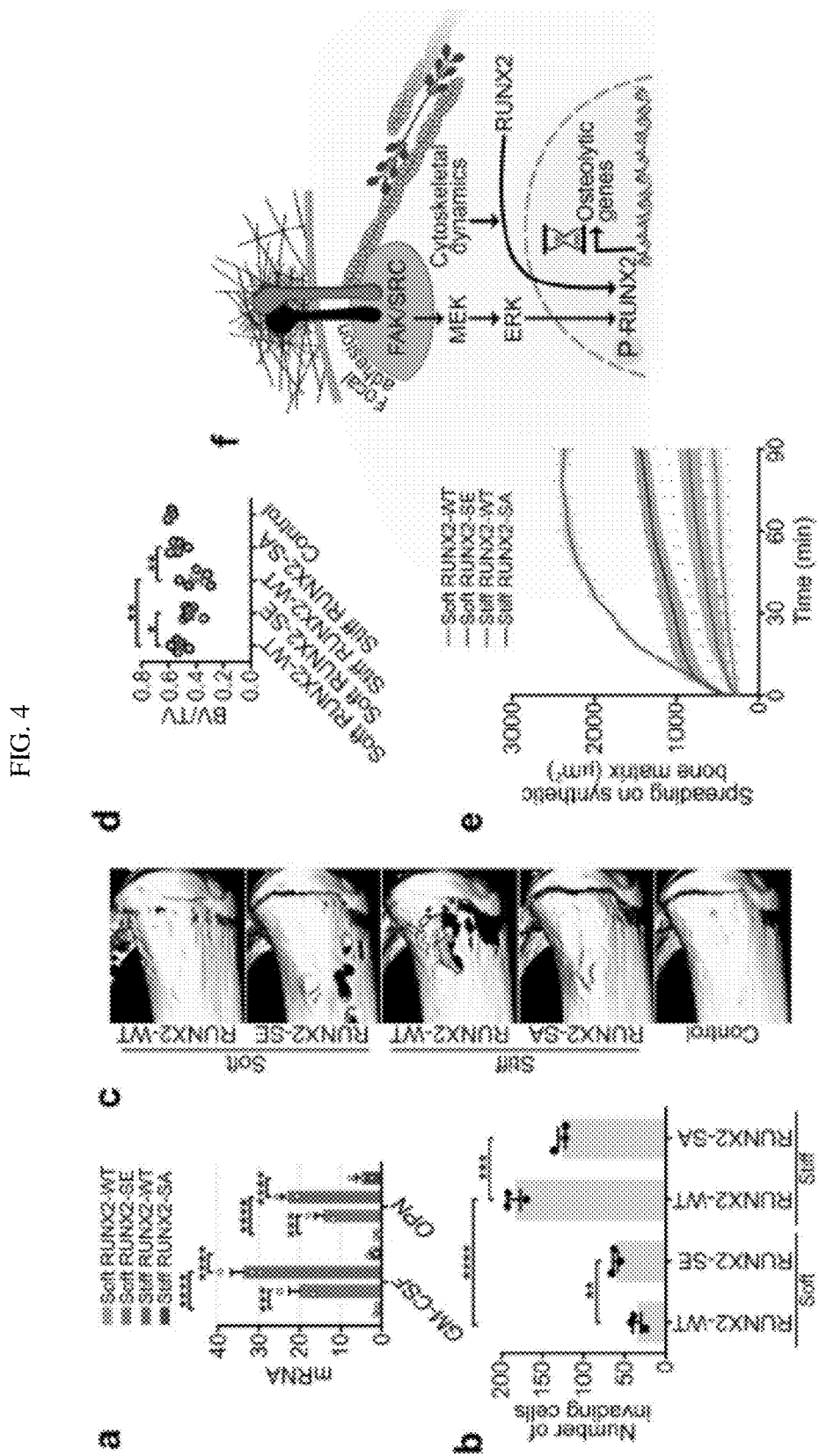
FIG. 4. RUNX2-mediated mechanical memory instructs bone metastasis. a, RT-qPCR of RUNX2 target genes in SUM159 cells overexpressing RUNX2-WT, RUNX2-SE, or RUNX2-SA, preconditioned for 7 days on soft or stiff hydrogels (n=3 biological replicates). b, Quantification of invasion of SUM159 cells preconditioned as indicated in (a). (n=3 biological replicates with n=3 technical replicates). c, Micro-CT 3D reconstructions of proximal tibia from mice 4 weeks after intracardiac injection of SUM159 cells preconditioned as in (a) or no cancer cells (control). d, Micro-CT analysis of bone volume from mice in (c) (n: mice; soft RUNX2-WT 5; soft RUNX2-SE 6; stiff RUNX2-WT 5; stiff RUNX2-SA 5; control 3). e, Time course of SUM159 cells spreading on synthetic bone matrix, preconditioned as in (a) (n=36 cells in each condition from n=3 biological replicates).
Figure 14:
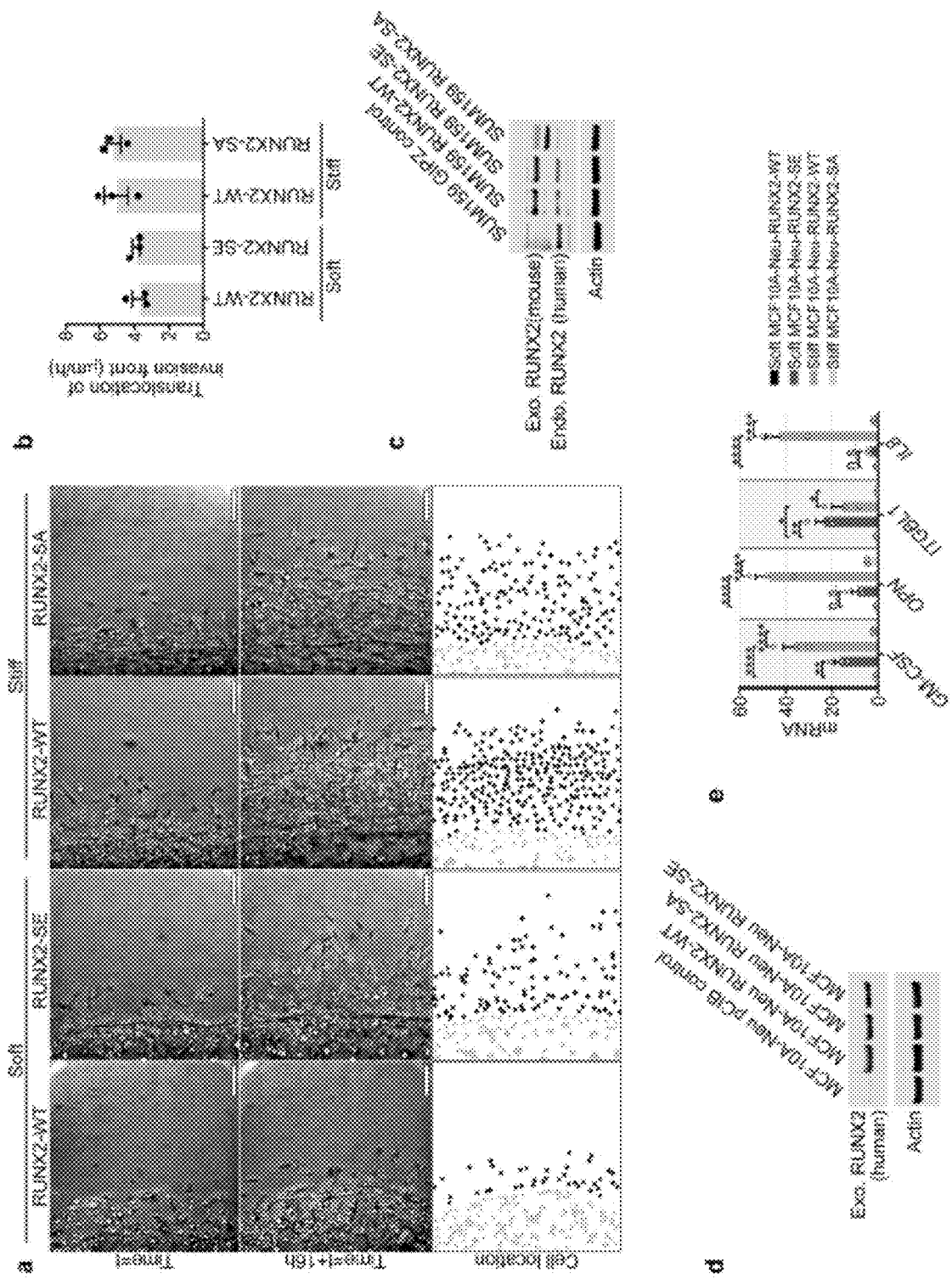
Figure 15A:
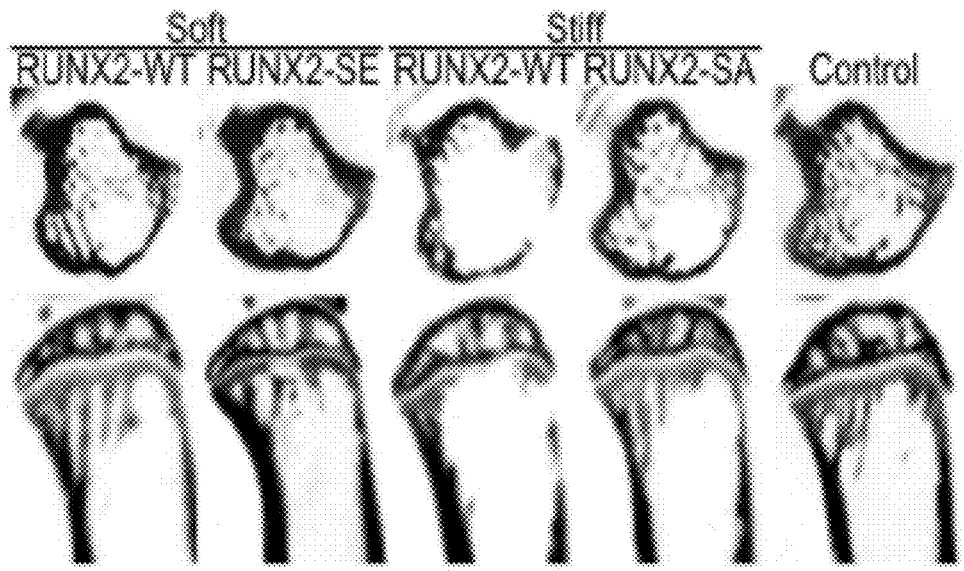
Figure 15B:
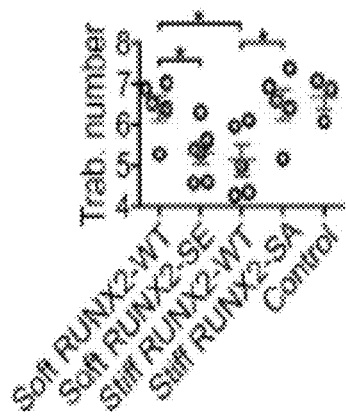
Figure 15C:
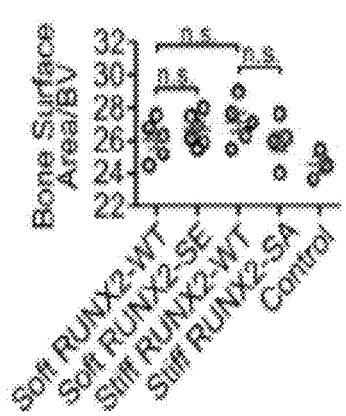
Figure 15D:
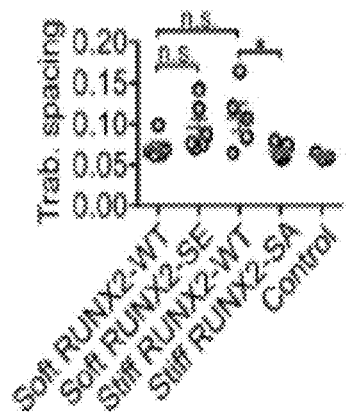
Figure 15E:
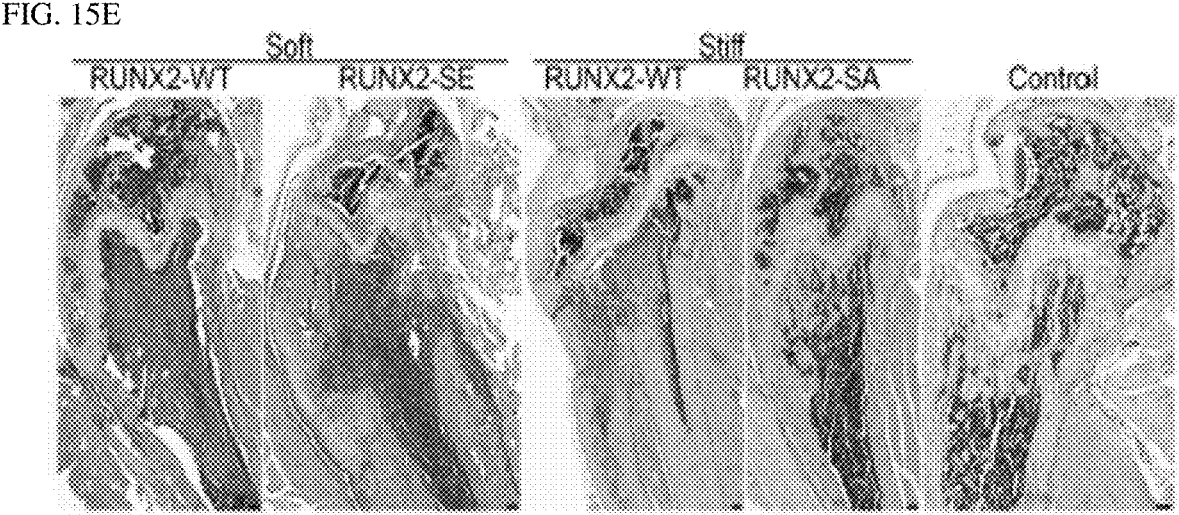
Figure 15F:
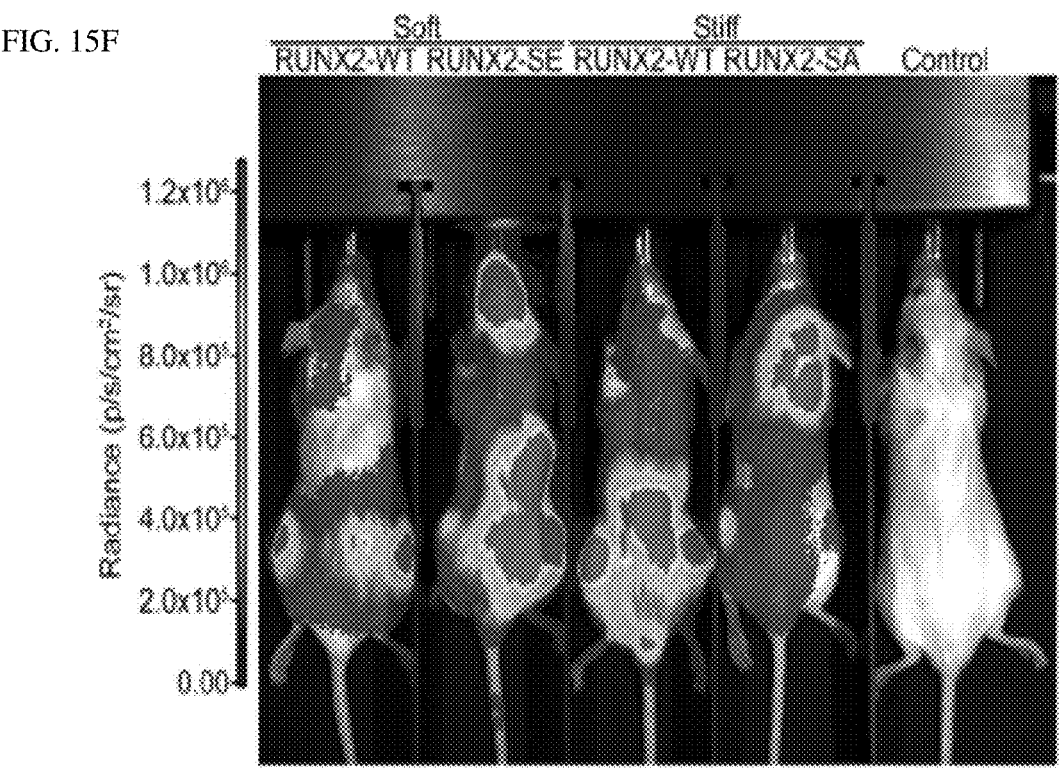
Figure 15G:
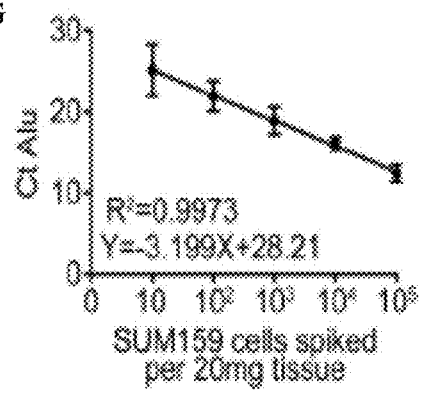
Figure 15H:
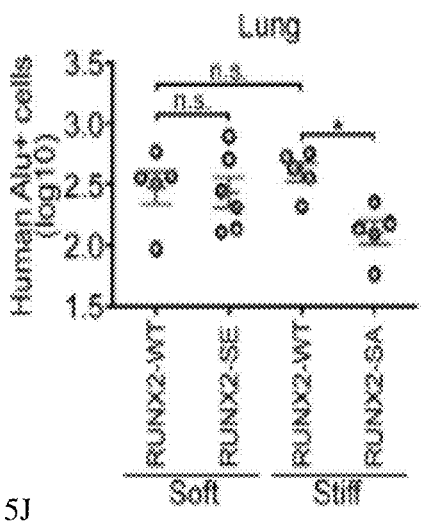
Figure 15I:
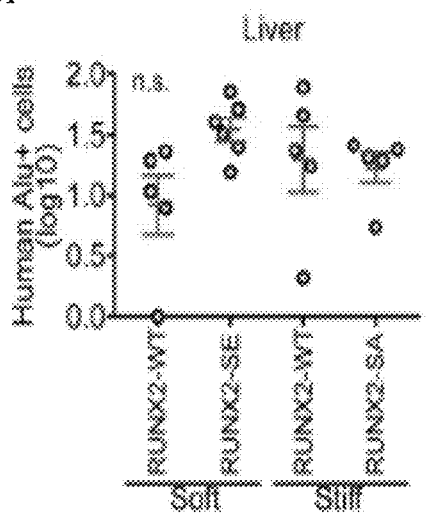
Figure 15J:
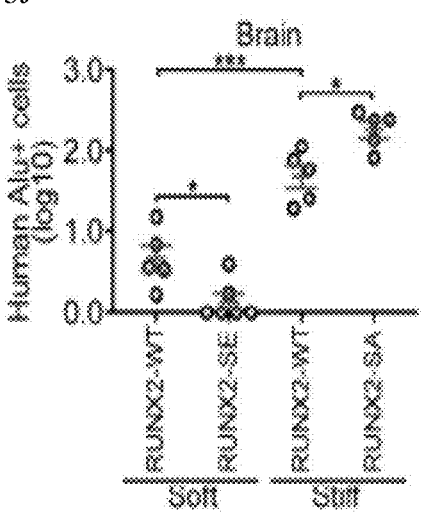
Figure 15K:
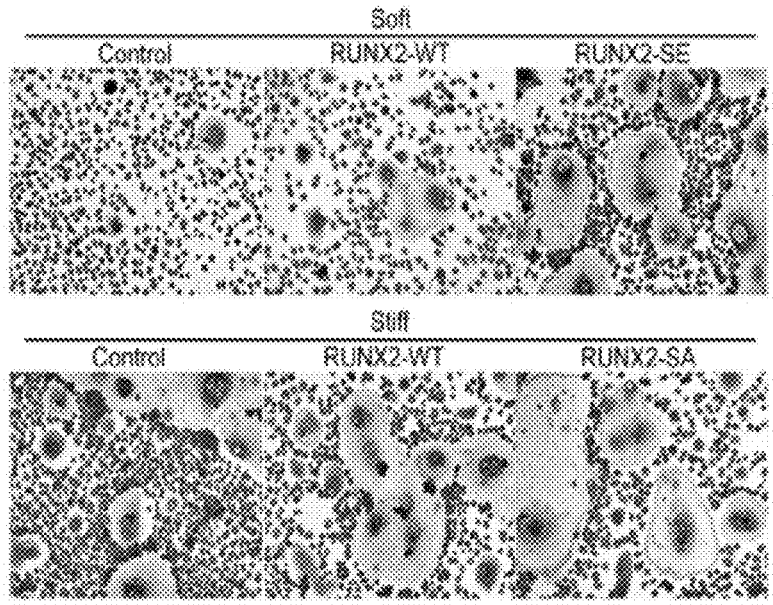
Figure 15L:
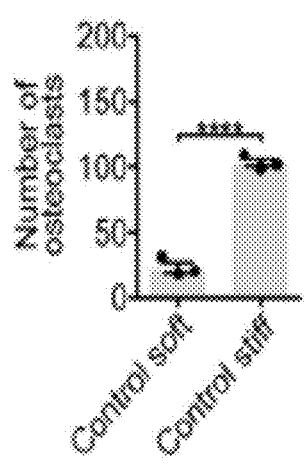
Figure 15M:
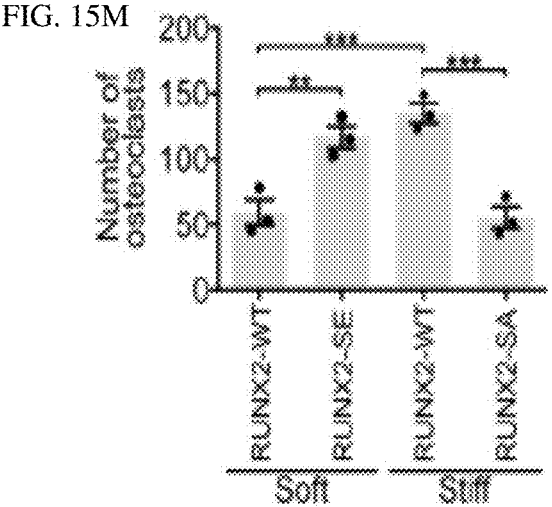
Figure 15N:
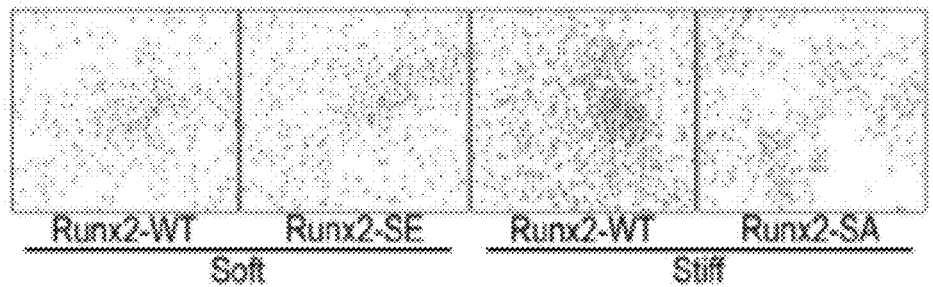
Figure 15O:
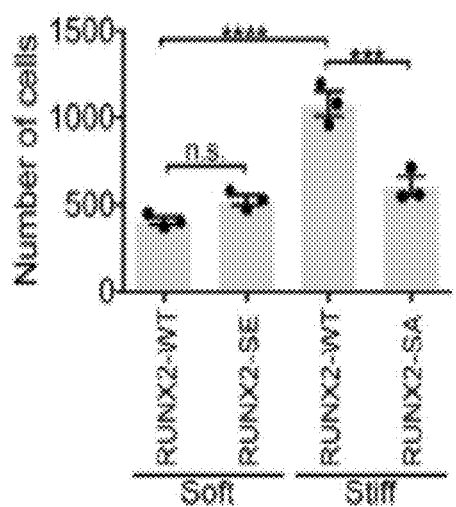
Figure 15P:
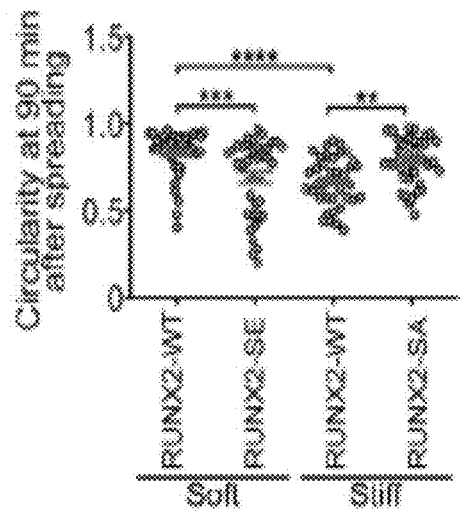

FIG. 14. RUNX2-mediated mechanical memory promotes invasion. a, Invasion fronts of SUM159 cells after 16 hours of live-cell tracking in 3D collagen, Cells overexpressing mouse RUNX2-WT, RUNX2-SA or RUNX2-SE were preconditioned for 7 days on stiff or soft hydrogels, as indicated. See FIG. 4a. Gray dots=non-invasive cells; black dots=invasive cells. b, Rate of translocation of the invasion front from (a) (n=3 biological replicates with n=3 technical replicates). c, Immunoblot of RUNX2 in SUM159 cells overexpressing GIPZ (control), RUNX2-WT, RUNX2-SE, and RUNX2-SA. (n=3 biological replicates). d, Immunoblot of human RUNX2 in MCF10A-Neu cells overexpressing pCIB (control), RUNX2-WT, RUNX2-SE, and RUNX2-SA. (n=3 biological replicates). e, RT-qPCR of 4 RUNX2 target genes in MCF10A-Neu cells expressing human RUNX2 WT or mutants preconditioned for 7 days on soft and stiff hydrogels (n=3 biological replicates).

FIG. 15. RUNX2-mediated mechanical memory instructs osteolytic bone metastasis. a, Two-dimensional cross-sections of tibia from mice bearing no cancer cells (control) or SUM159 cells overexpressing RUNX2-WT, RUNX2-SE, or RUNX2-SA, preconditioned for 7 days on soft or stiff hydrogels as indicated, 4 weeks after intracardiac injection. b-d, Quantification of trabecular number (b), bone surface area/bone volume (c), and trabecular spacing (d) from mice in (a) (n: mice; soft RUNX2-WT 5; soft RUNX2-SE 6; stiff RUNX2-WT 5; stiff RUNX2-SA 5; control 3). e,f, H & E staining (e) and bioluminescence (f) in mice from (a) noting the strong signal in the skull (second from left) and brain/soft tissue (second from right). g, Standard curve from qPCR of human Alu using SUM159 cells spiked into 20 mg of mouse tissue, normalized to mouse actin (n=3). h-j, Quantification of metastases in lung (h), liver (i), and brain (j) from mice in (a). k, TRAP staining of RAW264.7 cells after 7 days incubation: 4 days with 50 ng/mL RANKL in growth media, and then 3 days with 50% SUM159 conditioned media (CM)+50% growth media. 1, m, Quantification of (k) (n=3 biological replicates with n=3 technical replicates). n, Large-stitched images of DAPI-stained (pseudocolored in orange) SUM159 on synthetic bone matrix after 30 minutes of adhesion challenge. o,p, Quantification of cell adhesion (o) and circularity (p) from (n). (n=3 biological replicates with n=3 technical replicates).

Figure 16:
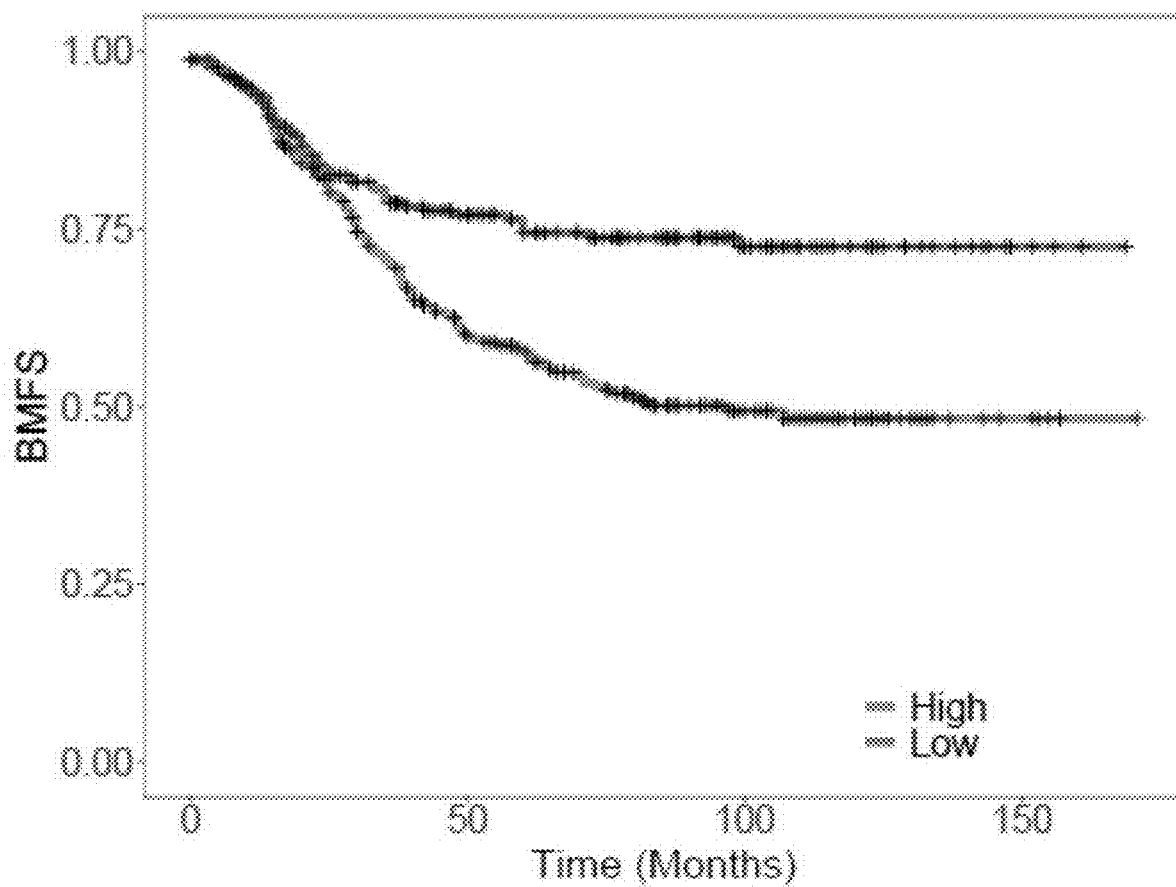
Figure 17:
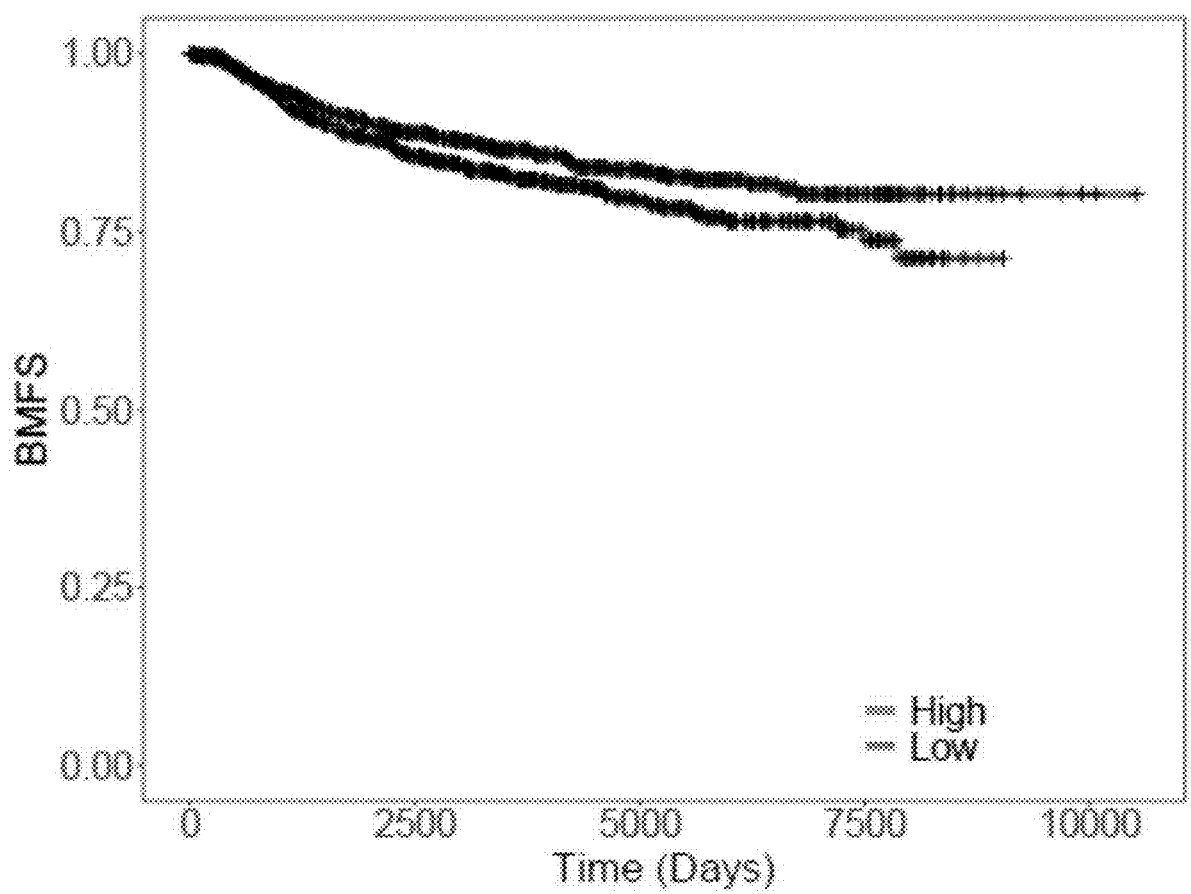
Figure 18:
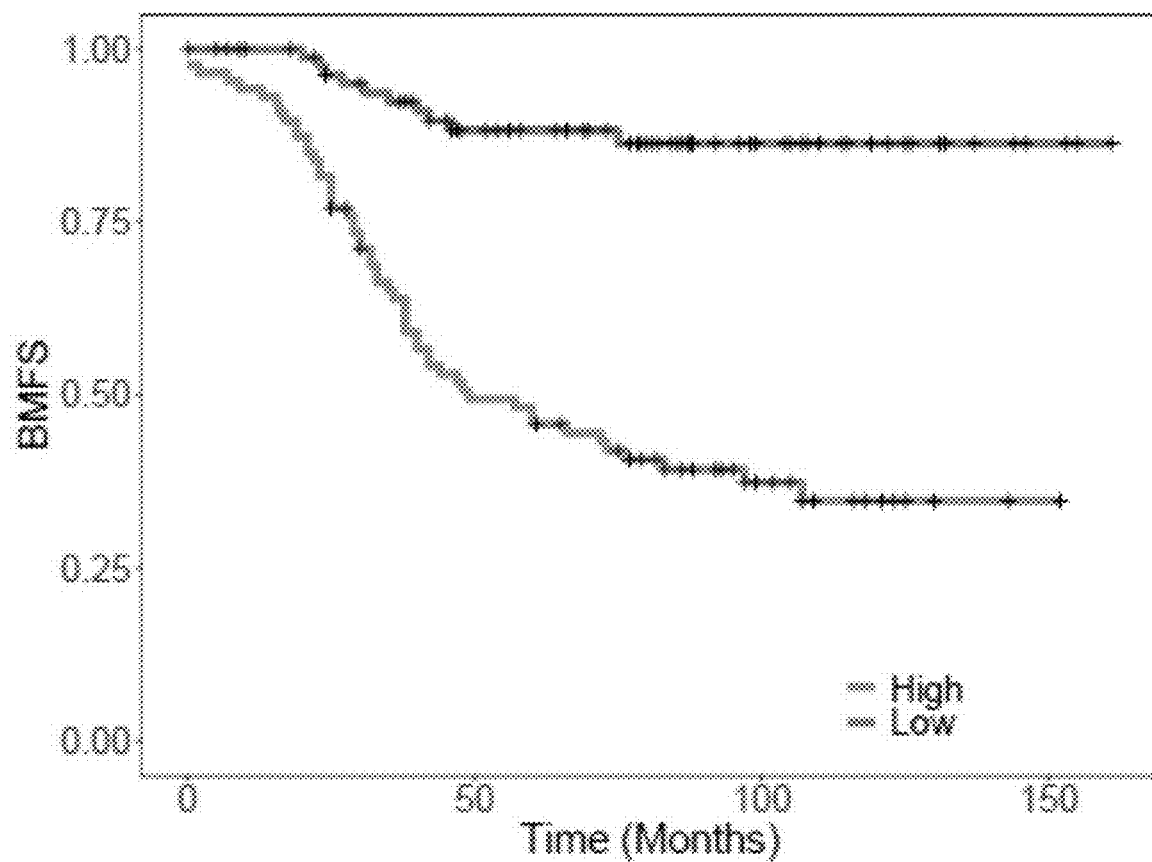
Figure 19:
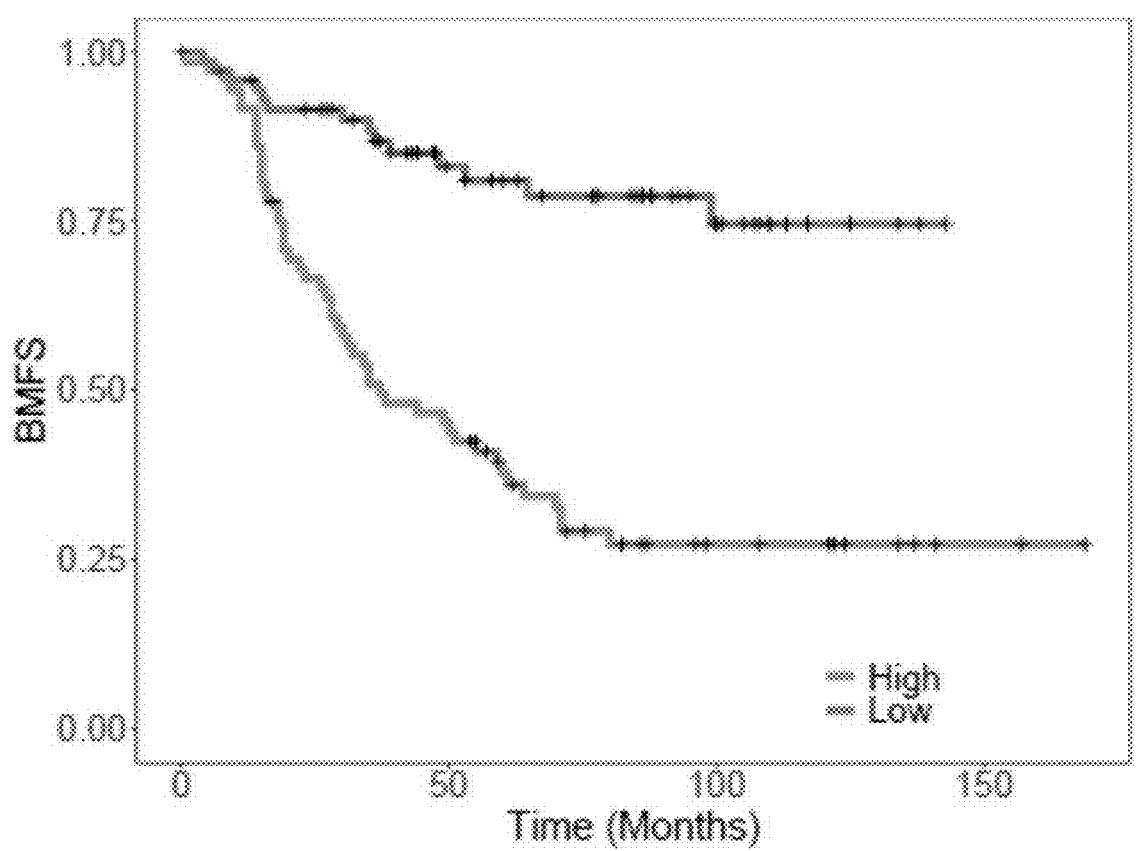
Figure 20:
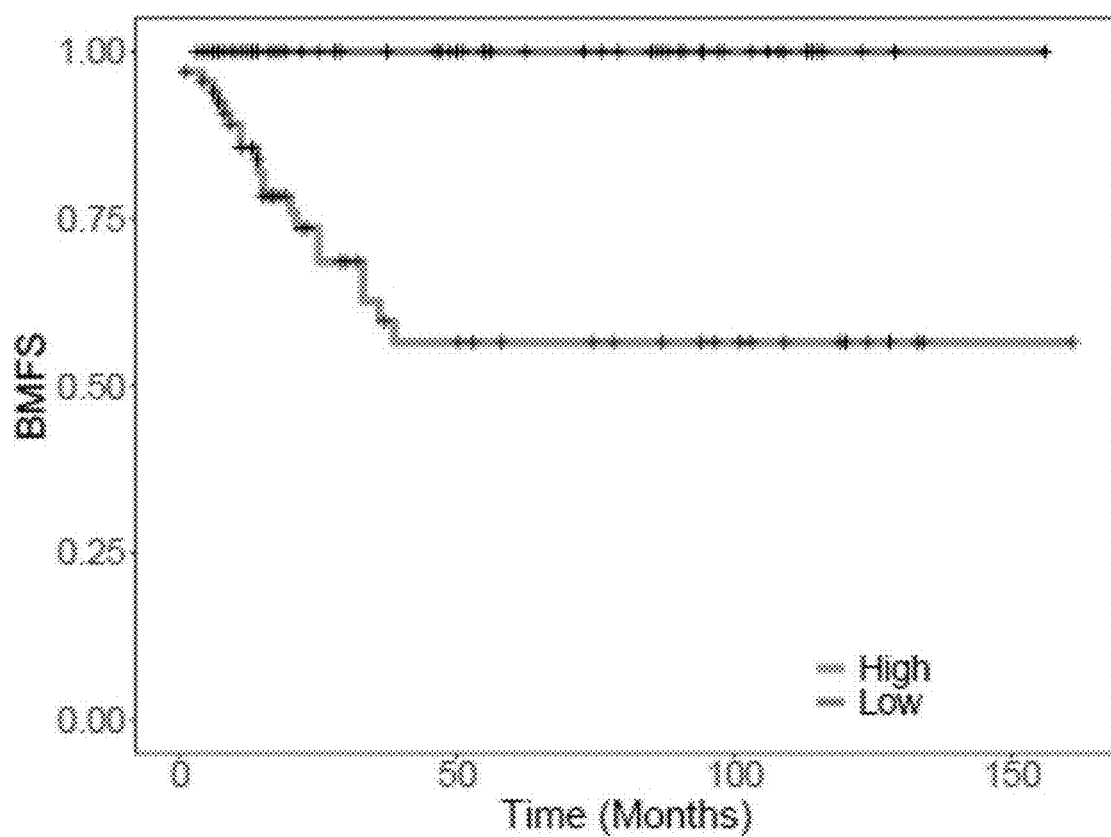
Figure 21:
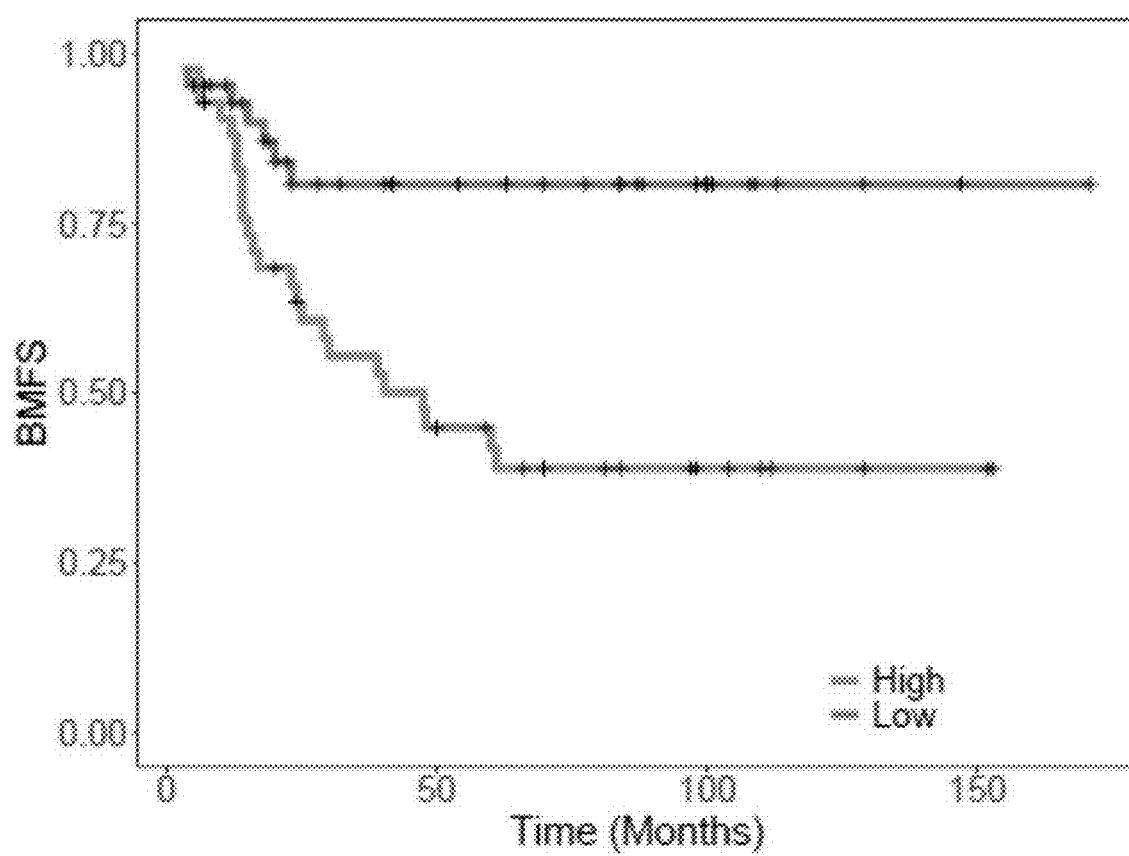
Figure 22:
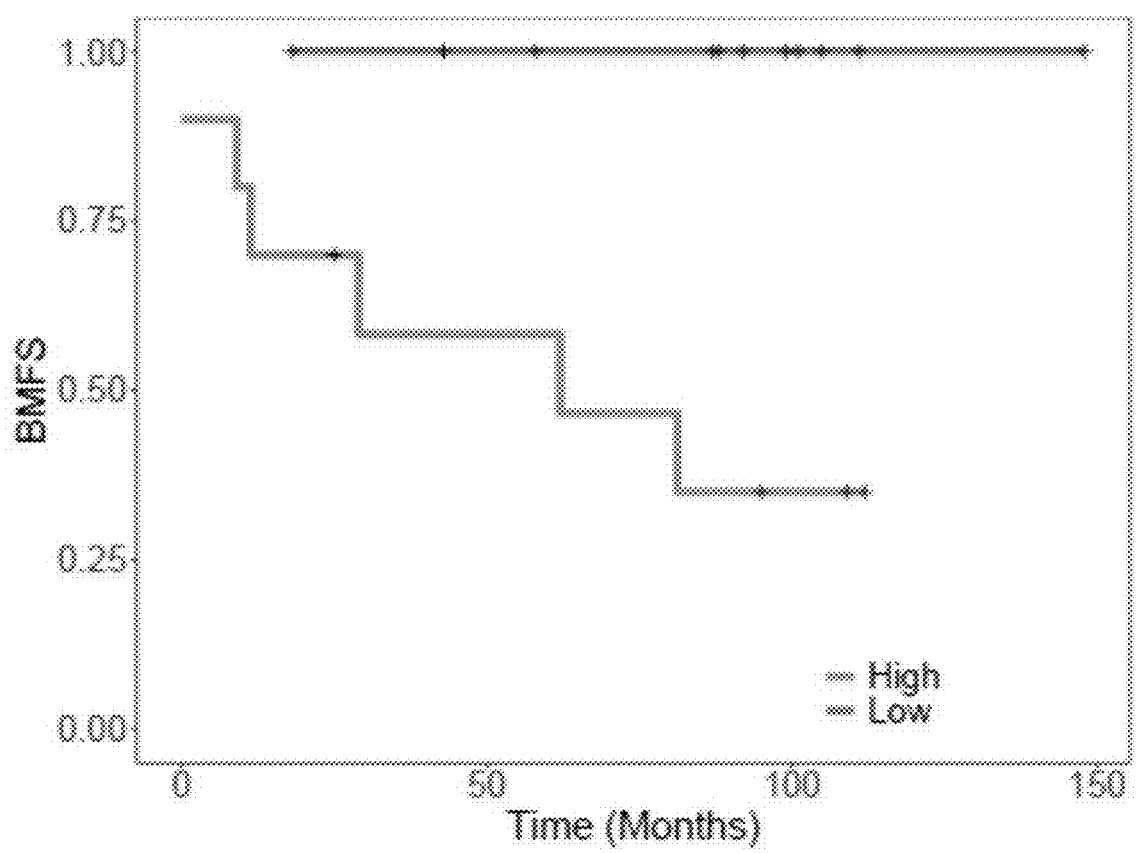

FIG. 16. Kaplan-Meier plot of bone metastasis-free survival (BMFS) of all-subtype patients with high (upper half) vs low (lower half) MeCo-refined-minimal scores (28 constituent genes) in the combined GSE2034+GSE2603+GSE12276 dataset (training cohort). n=559, P=1.7E-05 Log-rank test FIG. 17. Kaplan-Meier plot of bone metastasis-free survival (BMFS) of all-subtype patients with high (upper half) vs low (lower half) MeCo-refined-minimal scores (28 constituent genes) in the METABRIC 2019 distant relapse dataset (validation cohort). n=1686, P=0.034 Log-rank test FIG. 18. Kaplan-Meier plot of bone metastasis-free survival (BMFS) of Luminal A patients with high (upper half) vs low (lower half) 'luminal A' MeCo-minimal scores in the combined GSE2034+GSE2603+GSE12276 dataset. n=175, P=3.91E-10 Log-rank test FIG. 19. Kaplan-Meier plot of bone metastasis-free survival (BMFS) of Luminal B patients with high (upper half) vs low (lower half) luminal B' MeCo-minimal scores in the combined GSE2034+GSE2603+GSE12276 dataset. n=144, P=2.78E-08 Log-rank test FIG. 20. Kaplan-Meier plot of bone metastasis-free survival (BMFS) of Basal patients with high (upper half) vs low (lower half) 'Basal' MeCo-minimal scores in the combined GSE2034+GSE2603+GSE12276 dataset. n=134, P=2.47E-07 Log-rank test FIG. 21. Kaplan-Meier plot of bone metastasis-free survival (BMFS) of HER2 patients with high (upper half) vs low (lower half) 'HER2' MeCo-minimal scores in the combined GSE2034+GSE2603+GSE12276 dataset. n=85, P=0.002 Log-rank test FIG. 22. Kaplan-Meier plot of bone metastasis-free survival (BMFS) of Normal-like patients with high (upper half) vs low (lower half) 'Normal-like' MeCo-minimal scores in the combined GSE2034+GSE2603+GSE12276 dataset. n=21, P=0.003 Log-rank test

DEFINITIONS

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

As used herein, the term "characterizing cancer in a subject" refers to the identification of one or more properties of a cancer sample in a subject, including but not limited to, the likelihood of bone metastasis and chance of long-term survival. Cancers may be characterized by the identification of the expression of one or more cancer marker genes, including but not limited to, those disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form.

When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

Provided herein are compositions and methods for characterizing and treating breast cancer. The present disclosure provides a MeCo score of a subject's breast cancer tissue, indicative of the likelihood of bone metastasis and long-term survival. The compositions and methods described herein find use in therapeutic, screening, research, diagnostic, and prognostic methods. Examplary method of calculating and using MeCo scores are described below.

I. MeCo Score

As described, the present disclosure provides MeCo scores for a variety of uses. Such MeCo scores are calculated based on the level of expression of a plurality of genes. For example, the MeCo score represents expression level of stiff-associated genes (e.g., labeled as "stiff" in Tables 2-3 or 7-12) minus expression level of soft-associated genes (e.g., labeled as "soft" in Tables 2-3 or 7-12). In some embodiments, the MeCo score comprises the average expression of at least five stiff genes from any one of Tables 2-3 and 7-12 minus the average expression of at least five soft genes from any one of Tables 2-3 and 7-12. For example, in some embodiments, the MeCo score comprises the average expression of at least five genes selected from the group consisting of NAT1, CENPN, COL10A1, PLAT, BMP8A, and PPIC minus the average expression of at least five genes selected from the group consisting of BEX1, RYR1, HDAC11, RARRES3, CD27, PRRG4, XAF1, IL2RG, LPAR2, TP73, HBE1, PSD, SOX5, ARHGEF6, OASL, DCHS2, KCNN1, CD226, NIPSNAP1, STAT4, S1PR5, and FRS3 (e.g., the average expression of NAT1, CENPN, COL10A1, PLAT, BMP8A, and PPIC minus the average expression of BEX1, RYR1, HDAC11, RARRES3, CD27, PRRG4, XAF1, IL2RG, LPAR2, TP73, HBE1, PSD, SOX5, ARHGEF6, OASL, DCHS2, KCNN1, CD226, NIPSNAP1, STAT4, S1PR5, and FRS3).

The level of expression of such genes can be determined using any suitable method. Exemplary, non-limiting methods are described below.

Any patient sample comprising the genes of interest may be tested according to methods of embodiments of the present invention. By way of non-limiting examples, the sample may be tissue (e.g., a breast biopsy sample), blood, or a fraction thereof (e.g., plasma, serum, cells).

In some embodiments, the patient sample is subjected to preliminary processing designed to isolate or enrich the sample for the genes. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

In some embodiments, the genes are detected in a multiplex or panel format.

In some preferred embodiments, detection of markers (e.g., including but not limited to, those disclosed herein) is detected by measuring the expression of corresponding mRNA in a tissue sample (e.g., lung tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, CA; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays are utilized for measuring cancer marker mRNA levels. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, the cancer markers are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety).

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through fluorometric detection means.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g., U.S. Pat. No. 5,814,447 (herein incorporated by reference in its entirety).

In some embodiments, nucleic acid sequencing methods are utilized for detection. In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, sequencing is nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, sequencing is HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

In some embodiments, sequencing is the technique developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., MeCo score), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., MeCo score) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

Compositions for use in the diagnostic methods described herein include, but are not limited to, probes, amplification oligonucleotides, and the like. In some embodiments, kits include all components necessary, sufficient or useful for detecting the markers described herein (e.g., reagents, controls, instructions, etc.). The kits described herein find use in research, therapeutic, screening, and clinical applications.

In some embodiments, the present invention provides one or more nucleic acid probes or primers having 8 or more (e.g., 10 or more, 12 or more, 15 or more, 18 or more, etc.) nucleotides, and that specifically bind to nucleic acids encoding a marker described herein.

Embodiments of the present invention provide complexes of marker nucleic acids with nucleic acid primers or probes. In some embodiments, a reaction mixture comprising a marker nucleic acid is provided. In some embodiments, the present invention provides a multiplex (e.g., microarray) comprising reagents that binds to two or more (e.g., 5, 10, 25, 50, 100, or more) marker nucleic acids.

II. Uses

The MeCo scores described herein find use in a variety of applications. In some embodiments, the MeCo score is used to identify subjects at increased risk of bone metastasis or death. In some embodiments, subjects with a high MeCo score are identified as at increased risk of bone metastasis and/or death and subjects with a low MeCo score are identified as at a decreased risk of bone metastasis and/or death.

In some embodiments, a "high MeCo score" is defined as a MeCo score in the top quartile of a population and a "low MeCo score" is defined as a MeCo score in the lower quartile of a population average. In some embodiments, the population is a group of subjects diagnosed with primary breast cancer that has not metastasized. In some embodiments, numerical values for high and low MeCo scores are pre-determined in the art based on a population study. Thus, in some embodiments, a clinician can determine based on the MeCo score whether a subject has a high or low MeCo score. In some embodiments, cut-offs for MeCo scores depend on a subject's age, gender, race, or stage of cancer.

In some embodiments, MeCo scores are used to determine a treatment course of action and/or treat breast cancer in a subject. For example, in some embodiments, subjects with high MeCo scores are administered anti-fibrotic agents and/or chemotherapy, including hormone blocking chemotherapy and subjects with low MeCo score are not administered anti-fibrotic agents and/or chemotherapy. In some embodiments, MeCo scores for a subject are monitored over time to asses continuing risk of bone metastasis (e.g., MeCo score are calculated at different time points). In some embodiments, subjects are monitored once monthly, yearly, or less often. In some embodiments, subjects are monitored during treatment (e.g., anti-fibrotic treatment and/or chemotherapy) to assess the effectiveness of the therapy.

As described below, genes in the MeCo score are associated with fibrosis. Thus, in some embodiments, anti-fibrotic treatment is used to target such genes. The present disclosure is not limited to particular anti-fibrotic therapies. Examples include, but are not limited to, pirfenidone and nintedanib.

EXPERIMENTAL

The following examples are provided in order to demonstrate and further illustrate certain preferred embodiments and aspects of the present invention and are not to be construed as limiting the scope thereof.

Example 1

Methods

Cell Culture

SUM149 and SUM159 cells were cultured in Ham's F12 media (Corning) supplemented with 5% HI-FBS (Gibco), 5 µg/ml insulin (Roche), 1 µg/ml hydrocortisone (Sigma) and antibiotics (100 units/mL penicillin+100 µg/ml streptomycin from Life Technologies, Inc.). MDA-MB-231, HEK293T, BT20, T47D, ZR-75-30, MCF7, BT474 and PC3 cells were cultured in DMEM high glucose media (Corning) supplemented with 10% FBS and antibiotics. HCI-005, HCI-011, HCI-003 and were cultured in Mammocult base media (Stemcell Technologies) supplemented with Mammocult additives. MCF10A cells were cultured in DMEM/F12 media (Corning) with 5% horse serum, 20 ng/ml EGF, 0.5 mg/ml hydrocortisone, 100 ng/ml cholera toxin, 10 µg/ml insulin plus antibiotics. SKBR3 cells were cultured in McCoy's 5A modified media (Corning) supplemented with 10% FBS and antibiotics. MCF10A-Neu cells were a gift from Cheuk Leung (University of Minnesota). MS-SKBR3.1 cells were derived from SKBR3 cells cultured for 6 weeks at 80-100% confluency in DMEM high glucose media supplemented with 10% FBS, 50 µM ascorbic acid 2-phosphate, and 5 mM disodium glycerol-2-phosphate plus antibiotics (mechanical sensitization media; M.S. media). For live-cell imaging experiments, cells were maintained in a climate-controlled chamber (OKOlab). Cell lines were validated by STR testing (Arizona Cancer Center EMSR core facility) and screened for mycoplasma (Biotool).

2D Hydrogels and 3D Conditioning

For mechanical preconditioning, cells were cultured on 2D polyacrylamide, collagen I-conjugated hydrogels, lab-made or purchased (Petrisoft, Matrigen). Soft hydrogels were either 0.5 kPa (Petrisoft) or <1.0 kPa (lab-made), while stiff hydrogels were either 8.0 kPa (Petrisoft) or lab-made (7.0-8.0 kPa). Prior to making hydrogels, glass coverslips were first pre-treated with a 2% solution of 3-aminopropyltrimethoxy silane (Sigma) in isopropanol, for 10 minutes. After washing, coverslips were treated with 1% Glutaraldehyde for 30 minutes, washed, and dried. To generate the hydrogels, a final ratio of 3/0.055% and 5/0.5% acrylamide/bis-acrylamide were used for <1.0 kPa and 7-8 kPa hydrogels, respectively. Acrylamide and bis-acrylamide were diluted in 50 mM Hepes (pH 8.5), with 0.1% APS and 0.2% TEMED added to the gel solution. Following polymerization on pre-treated glass coverslips, hydrogels were stored at 4° C. in PBS until prepared for matrix coating. For matrix coating, hydrogels were treated with 2 mg/ml Sulfo-SANPAH (Life Technologies) and were placed under long wavelength UV light for 5 minutes. Hydrogels were then washed with PBS and coated with 30 µg/ml rat-tail collagen I (Corning) for 1 hour at 37° C., and then washed with PBS again prior to plating. Cells were fed every 2 days and split/assayed at ~80% confluence. Long-term viability was confirmed with LIVE/DEAD Viability/Cytotoxicity (Thermo Fisher) in situ and DAPI exclusion during flow cytometry. For 3D conditioning, cells were grown for 7 days in 1.0 mg/mL rat-tail collagen-I (soft), or 1.0 mg/mL rattail collagen-I crosslinked with 0.0175% PEG-di(NHS) (MP Biomedicals) (stiff). Cells were spun down and collected after 20 min incubation in Collagenase type I (0.25%) (Stemcell Technologies). Hydrogel stiffness was verified by AFM (W. M. Keck Center for Surface and Interface Imaging).

Vectors and Virus Production

The plasmid pCMV-msRUNX2 (a gift from Gerard Karsenty, Columbia) was used as the source for RUNX2 cDNA, and ERK-target site mutants were made using Quikchange (Agilent): RUNX2-2 S301A-S319A (RUNX2-SA) which is unresponsive to ERK stimulation, and RUNX2-S301ES319E (RUNX2-SE) which exhibits high basal transcriptional activity in the absence of ERK Stimulation (Ge, C. et al. Identification and Functional Characterization of ERK/MAPK Phosphorylation Sites in the Runx2 Transcription Factor. J. Biol. Chem. 284, 32533-32543 (2009)). RUNX2-WT, RUNX2-SA and RUNX2-SE were then subcloned into lentiviral transfer plasmid pCIG3 (Addgene #78264, a gift from Felicia Goodrum, which was first modified to express a puromycin resistance gene in place of GFP). These mutants were used for in vitro and in vivo analyses. For human RUNX2 overexpression, RUNX2-I (MRIPV isoform, GeneCopoeia #EX-I2457-Lv105) was subcloned into pCIB (Addgene #119863), and the human-equivalent ERKtarget sites were made using Quikchange and subcloning: wild-type pCIB-hsRUNX2, pCIBhsRUNX2-S280A-S298A and hsRUNX2-S280E-S298E. These were used for additional in vitro validations. For live-cell actin dynamics, pLenti Lifeact-iRFP670-BlastR (Addgene #84385) was used. For constitutive activation of MAPK pathway, pBabe-Puro-MEK-DD (a gift from William Hahn, Addgene #15268) was used. shRNA for RUNX2 were purchased from Dharmacon: shRUNX2 #01 V2LHS_15065 (TCTGGAAGGAGACCGGTCT (SEQ ID NO:1)); shRUNX2 #02 V2LHS_223856 (TACAAATAAATGGACAGTG SEQ ID NO:2). For virus production, HEK293T cells were transfected at 60% confluence using Fugene HD (Promega) in OptiMEM (Corning) with transfer plasmid and second generation lentiviral packaging system (psPAX2 and pMD2.G, Addgene #12260 and #12259, gifts from Didier Trono) or pCL-Ampho (Novus) for lentiviral or retroviral production, respectively. Virus was collected 48-72 hours post-transfection, clarified by 0.45 µm filters. Recipient cells were infected at 50% confluence with virus at a 1:1 dilution with culturing media and polybrene (10 µg/mL). Puromycin selection was started 48 hours post-infection.

Cytoskeletal Dynamics

After mechanical preconditioning, SUM159, SKBR3 and MS-SKBR3.1 cells expressing iRFPLifeAct were trypsinized from their hydrogels and plated onto No. 1.5 glass MatTek dishes which had been pre-treated overnight with DMEM+10% FBS, and then incubated for 10 hours to ensure maximal spreading before analysis (verified by size equilibrium). Cytoskeletal dynamics score was obtained by automatic tracing of iRFP signal and averaging single-cell displacement over three sequential 1 hour intervals. Imaging was acquired with a 20× Plan Apo 0.75 N objective (Nikon) and an ORCA-Flash 4.0 V2 cMOS camera (Hamamatsu).

Multidimensional Traction Force

Cells were mechanically-preconditioned as indicated, and then plated onto 1.7 kPa or 8.5 kPa bead-embedded collagen I-coated hydrogels (30 µg/ml), prepared as detailed above. Imaging commenced 4 hours after plating onto bead-embedded hydrogels that were either 1.7 kPa or 8.5 kPa. Fluorescent microsphere beads (0.5 µm; Life Technologies) were dispersed throughout the hydrogels and excited with a red HeNe diode (561 nm) laser. PKH67-stained cells were visualized with an Argon (488 nm) laser. Three-dimensional image stacks were acquired using a Nikon A-1 confocal system mounted on a Ti-Eclipse inverted optical microscope controlled by NIS-Elements Nikon Software. A Plan Fluor 40× air 0.6 N objective (Nikon) mounted on a piezo objective positioner was used, which allowed imaging speeds of 30 frames per second using a resonant scanner. Confocal image stacks of 512×512×128 voxels (108×108×38 µm3) were recorded every 30 min with a z-step of 0.30 µm. Cell-induced full-field displacements were measured as previously described (Toyjanova, J. et al. PLoS One 9, e90976 (2014)) using the FIDVC algorithm (Bar-Kochba, E. et al., Exp. Mech. 55, 261-274 (2015)).

Invasion Assay

The invasion assays were modified from Padilla-Rodriguez et al (Nat. Commun. (2018)). Briefly, for SUM159 experiments, 75,000 preconditioned single cells were suspended in a dome of 15 µL Matrigel (Corning), spotted onto silanized 8-well coverslip chamber slides (LabTek), incubated for 30 min, and then embedded in 1 mg/mL neutralized rat tail collagen-I (Fisher) crosslinked with 0.0125% PEG-di(NHS) (MP Biomedicals) (see FIG. 1a). Imaging was performed in a 16 hours period, starting 18 hours after embedding. For SKBR3 and MS-SKBR3.1 experiments 180,000 cells were suspended and embedded as above, and then imaging was performed immediately for 24 hours. Invaded cells which divided during the imaging periods were counted as one cell in order to mitigate any differences in proliferation amongst experimental groups. Invasion front translocation was calculated by tracking the midpoint of the cluster of cells at the Matrigel:collagen interface which align perpendicular to the direction of movement using DIC cell tracking in Elements software (Nikon). Imaging was acquired with a 20× Plan Apo 0.75 N objective (Nikon) and an ORCA-Flash 4.0 V2 cMOS camera (Hamamatsu).

RNA-SEQ Library Preparation, Sequencing, and Normalization

SUM159 cells were cultured for 2 weeks on collagen I-conjugated hydrogels that reflect native human breast tumor stiffness corresponding to regions of high cellularity/low matrix deposition (0.5 kPa; Petrisoft, Matrigen), versus low cellularity/high matrix deposition (8.0 kPa; Petrisoft, Matrigen) (Plodinec, M. et al. Nat Nano 7, 757-765 (2012)). Cells were fed every 2 days and were split or analyzed when ~80% confluent (Bar-Kochba et al., supra). biological replicates of each stiffness were processed for RNA extraction using Isolate II RNA kit (Bioline), and 1 µg from each sample was used for polyA selection with [Oligo d(T) Magnetic Beads, New England BioLabs #S1419S]. mRNA was converted into sequencing libraries as previously detailed (Hogan, N. T. et al. Elife 6, (2017)). In brief, RNAs were fragmented and ligated to barcoded adapters (Bioo Scientific, NEXTflex DNA Barcodes). Quantitative RT-PCR was used to determine the optimal number of cycles to amplify each library as to achieve sufficient DNA quantity while maintaining the diversity of the library (10-20 cycles). Libraries were then amplified, and fragments with insert sizes between 225 and 375 bp were isolated by gel purification, pooled at equimolar concentrations, and submitted for massively parallel high-throughput sequencing (single end, 50 base pairs) on a Hi-Seq4000 (Illumina) at the University of Chicago's Genomics Core using manufacturer protocols.

RNA-SEQ Differential Expression, Pathway Enrichment, and Upstream Regulator Analyses De-multiplexed fastq files were mapped to the human transcriptome (hg38) in STAR7 using default settings and organized into tag directories using makeTagDirectory in the HOMER software suite (Heinz, S. et al. Mol. Cell 38, 576-589 (2010)). The number of mapped, uniquely aligned reads suggested good coverage of the transcriptome and diversity in the sample set. Hierarchical clustering recapitulated that samples clustered by group membership, as expected, confirming that differences in transcriptomes were driven by cellular matrix environments.

Differential gene expression was calculated in DESeq (Anders, S. & Huber, W. Genome Biol. 11, R106 (2010)) using a 5% False Discovery Rate (FDR) as defining the differential gene set. Pathway enrichment analysis was performed in Metascape (Tripathi, S. et al. Cell Host Microbe 18, 723-735 (2015)) using additional 4-fold cutoffs to define up- and down-regulated genes between soft and stiff samples. Upstream Regulatory analysis was performed on differentially expressed genes using a more inclusive 2-fold cutoff with Ingenuity Pathway Analysis (IPA) software (Qiagen), which returns a list of genes having enriched curated connections to the input gene set as a method to predict upstream regulators. Candidate regulators were restricted to genes having receptor or transcription factor function because these provide a straightforward mechanism for how the mechanical stiffness signal may become integrated in cells to cause differential gene expression. Candidate upstream regulators with prediction P<0.05 were exported and intersected with the gene set annotated as "Metastasis Associated Genes" from the Human Cancer Metastasis Database (Zheng, G. et al. Nucleic Acids Res. 46, D950-D955 (2018)). From this list of intersecting genes, the literature was searched for those with gene bookmarking function or "transcriptional memory" association. For gene ontologies associated with the stiffness-induced gene set, Enrichr (Kuleshov, M. V. et al. Nucleic Acids Res. 44, W90-W97 (2016)), was used through query of the Human Phenotype Ontology (Kohler, S. et al. Nucleic Acids Res. 42, D966-D974 (2014)) and MGI Mammalian Phenotype (Blake, J. A. et al. Nucleic Acids Res. 37, D712-D719 (2009)) libraries.

Mechanical Conditioning (MeCo) Scoring and Patient Data Analysis

The initial gene set for MeCo scoring was derived from RNA-seq differential expression between SUM159 cells grown on stiff vs soft hydrogels for 2 weeks. Genes that had Padj<0.05 and |log 2FC|>1 were considered differentially expressed (FC=fold change). After removing genes associated with proliferation (Selfors, L. M. et al., Proc. Natl. Acad. Sci. 114, E11276-E11284 (2017)), there were a total of 3,822 remaining differentially expressed genes. Out of these genes, 1,143 had a positive log 2FC while 2,679 had a negative log 2FC. Genes with a positive log 2FC were considered to be associated with stiffness, while genes with a negative log 2FC were associated with softness.

Figure 7A:
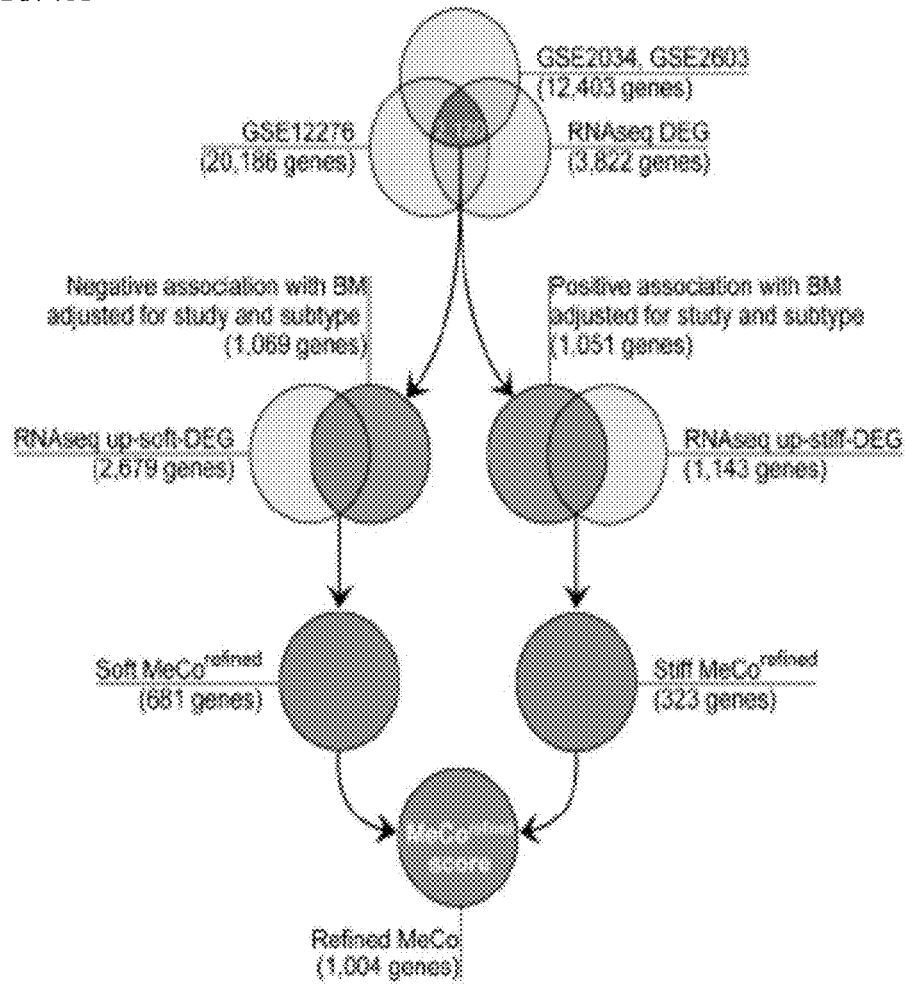
FIG. 7. Stiffness-induced genes and mechanical conditioning are associated with skeletal pathologies and bone metastasis. a, Flowchart of MeCo score refinement, adjusting for study and subtype. b, Flowchart of MeCo score refinement for METABRIC analysis. c, MeCorefined scores of patients from patients in FIG. 2d (n=268 no metastasis, 185 bone metastasis). d, Table showing number and percentages of patients with bone metastasis in the analyzed studies. e, Kaplan-Meier curve of bone metastasis-free survival in the combined cohort, split at median MeCorefined score (n=281 high MeCorefined, 279 low MeCorefined). f, Time to bone metastasis for patients in (e), split at median MeCorefined score (n=93 high MeCorefined, 92 low MeCorefined). g, Distribution of log-rank statistic of BMFS generated from 1000 random gene sets in comparison with MeCorefined score. h, Distribution of log-rank statistic of time-to-BM generated from 1000 random gene sets in comparison with MeCorefined score. i, Kaplan-Meier curve of bone metastasis-free survival in the NKI cohort, split at median MeCorefined score (n=147 high MeCorefined, 148 low MeCorefined). j, Time to bone metastasis for patients in (i), split at median MeCorefined score (n=27 high MeCorefined, 26 low MeCorefined). k, Kaplan-Meier curve of brain metastasis-free survival in the combined cohort, split at median MeCorefined score (n=280 high MeCorefined, 280 low MeCorefined). 1, Kaplan-Meier curve of lung metastasis-free survival in the combined cohort, split at median MeCorefined score (n=280 high MeCorefined, 280 low MeCorefined). m, Kaplan-Meier curve of brain metastasis-free survival in the NKI cohort, split at median MeCorefined score (n=147 high MeCorefined, 148 low MeCorefined). n, Kaplan-Meier curve of lung metastasis-free survival in the NKI cohort, split at median MeCorefined score (n=147 high MeCorefined, 148 low MeCorefined).
Figure 7B:
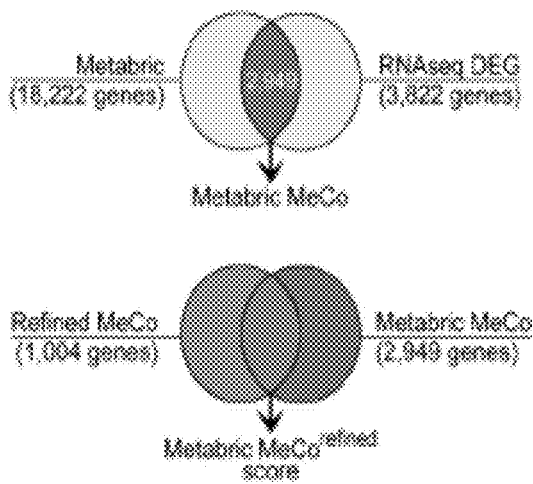
Figure 7C:
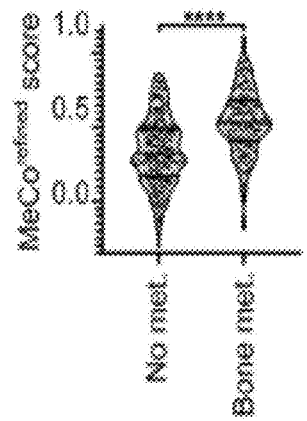
Figure 7E:
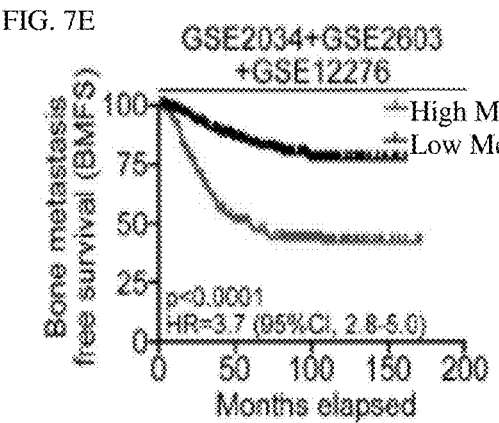
Figure 7F:
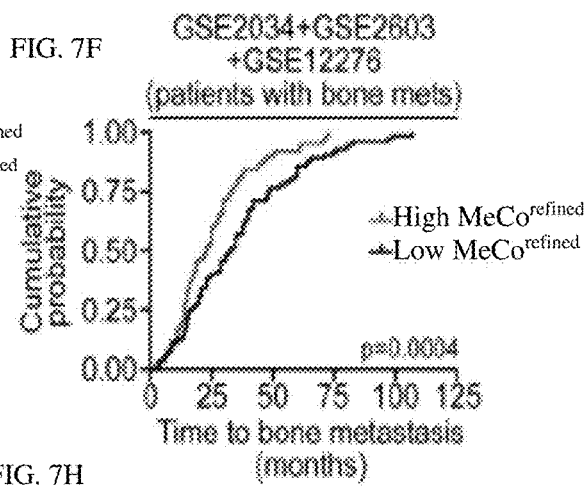

Three microarray studies from the Gene Expression Omnibus (GEO) were queried to test the clinical association between mechanical conditioning and bone metastasis: GSE2034, GSE2603, GSE12276. Studies GSE2034 and GSE2603 were sequenced using the Affymetrix Human Genome U133A array, and study GSE12276 was sequenced using the Affymetrix Human Genome U133 Plus 2.0 array. The normalized expression matrix was downloaded from GEO using the R GEOquery package and all values were log 2 transformed. In addition, breast tumor samples that underwent sequencing in multiple GEO studies were treated as a single sample (Bos, P. D. et al. Nature 459, 1005-1009 (2009)). After merging the studies GSE2034, GSE2603, GSE12276 together, there were 12,403 overlapping genes. Out of these 12,403 genes, 2,210 genes were in common with the 3,822 RNAseq differentially expressed genes. 711 out of the 2,210 genes were associated with stiffness and 1,409 out of the 2,210 were associated with softness (FIG. 7a). In conjunction, the METABRIC 2019 (molecular dataset) was used in the analysis to act as an independent study. There were 2,949 genes that overlapped with the RNA-seq gene signature and the METABRIC dataset (942 stiff-associated and 2,007 soft-associated) (FIG. 7b).

MeCo score calculation for each patient was performed by taking the average gene expression differences between stiff- and soft-associated genes: [mean expression (stiff genes)−mean expression (soft genes)]. Unlike gene signatures normally used to define cancer subtypes, the MeCo score is patient-specific, so the expression profiles of other samples within the same study do not affect the MeCo score. Moreover, because the MeCo signature subtracts normalized contributions from two sets of genes, any chip- or batch-specific effect that is gene-independent will automatically cancel, making it more robust and transferable across studies (Altenbuchinger, M. et al. Bioinformatics 33, 2790 (2017)). Thus, MeCo scores from the GSE2034, GSE2603, GSE12276 studies were combined in order to increase the power of the analysis. It was assumed that the Affymetrix Human Genome U133A array and the Affymetrix Human Genome U133 Plus 2.0 array share similar probe affinities for genes that are in common between arrays.

To optimize the utility of the MeCo score, the RNA-seq gene signature was refined by identifying the overlapping genes that are associated with stiffness or softness, and that are positively and negatively associated with bone metastasis in the three GEO studies described above. The R package limma was used to calculate log 2FC between bone metastasis positive patients and bone metastasis negative patients, while controlling for study and subtype in a linear regression framework. Tumor subtypes were identified using the PAM50 signature from the R package genefu. This analysis produced 1,051 genes upregulated with bone metastases and 1,069 genes downregulated with bone metastases. Of the 1,051 upregulated genes, 323 were associated with stiffness. Of the 1,069 down regulated genes, 681 were associated with softness. In total, there are 1,004 genes in the refined MeCo score. Furthermore, 919 genes from this refined MeCo score overlapped with the genes represented in the METABRIC expression study and were used to reassess overall survival in that cohort.

The genes used for MeCo score calculations are listed in Tables 2-4). For proliferation scoring, the normalized, average gene expression of the proliferation-associated genes (Selfors et al., supra) listed in Table 5 was used.

Two independent datasets were used to validate the MeCorefined score: the NKI dataset from van de Vijver et al. 2002 (N. Engl. J. Med. (2002)) and the METABRIC 2019 (Rueda, O. M. et al. Nature (2019)). Note that for the bone metastasis-free survival (BMFS) analysis using the METABRIC 2019, out of the patient subset with gene expression data (METABRIC molecular dataset), all patients with complete recurrence history were used (Complete.Rec.History=YES). In this analysis, patients with no bone metastasis were censored using their TDR data, which is time until last follow-up or distant relapse; patients with no distant relapse (DR=0) were assumed to not having bone metastasis. Time-to-bone-metastasis (TTBM) analysis was performed using all patients with bone metastasis.

Furthermore, it was tested whether mechanical conditioning contributes significantly to the power of the MeCorefined score, or whether results are driven by the gene expression patterns observed in bone metastasis positive and negative tumors. Motivated by the methodology in Venet et al. 2011 (Venet, D., Dumont, J. E. & Detours, V. PLoS Comput. Biol. (2011)), 1,000 matched random gene sets were generated and their performance compared against MeCorefined. Each gene set initially consisted of 2,120 randomly selected genes to mimic the original MeCo gene set. To simulate the calculation of the MeCorefined score for each of the 1,000 random gene sets, the same linear regression analysis between bone metastasis positive and bone metastasis negative samples as before was used. For each gene set, the top 1,004 genes were ranked and separated based on positive log 2FC and negative log 2FC from the regression analysis. Positive genes were considered to be associated with stiffness and negative genes were associated with softness. The randomized versions of the refined MeCo scores were calculated by taking the difference between the mean gene expression of stiff genes and the mean gene expression of soft genes. Distributions of the log rank statistic of BMFS and TTBM for the randomized gene sets were created using the combined cohort of 560 patients. The log rank statistics for both BMFS and time-to-BM computed from the true MeCorefined gene signature were significantly higher than expected from matched random gene sets ($P<0.05$ and $P<0.001$).

Assay for Transposase Accessible Chromatin ('ATAC-SEQ')

Chromatin accessibility data was compared genome-wide across a 7-day time course of transitioning cells from stiff to soft substrates using the assay for transposase accessible chromatin ('ATAC-seq'). ATAC-seq was performed on 50,000 SUM159 cells using the previously described protocol (Corces, M. R. et al. Nat. Methods (2017)). Libraries were run on a 10% TBE gel and DNA from 175-225 bp was extracted for sequencing. For each time point, triplicate experiments were conducted to allow for quantitative comparisons of accessibility across the time course. After generating libraries, samples were equimolar pooled and sequenced on an Illumina NextSeq High output run (single end 75 bp). After filtering out poor samples based on basic quality control, triplicates were retained for 12 hours after transition (St7/So0.5), 1 day (St7/So1), 2 days (St7/So2), and 5 days (St7/So5), and 2 replicates for the 7-day time point (St7/So7); the third replicate from this time point was excluded because of low sequencing depth (<300,000 unique, autosomal mapped reads vs >6,000,000 for all other samples) and low fraction of reads in peaks called on the sample (0.24 vs 0.39-0.63 for all others). In addition, triplicates were retained for two sets of control samples that were maintained on stiff substrate for 1 day and 7 days after the initial 7-day preconditioning on stiff substrate (St7/St1 and St7/St7, respectively). Peaks of accessibility (also called "hypersensitive sites") were identified on each sample to generate a genome-wide map of accessible regulatory elements using MACS2 (Zhang, Y. et al. Genome Biol. (2008)). To compare the similarity of peaks identified in each time point, BEDTools (Quinlan, A. R. & Hall, I. M. Bioinformatics (2010)) was used to calculate all pairwise Jaccard indices and generated a heatmap with the 'heatmap.2' function in the 'gplots' package in R. To allow for quantitative comparisons in accessibility between time points a master list of peaks, taking the union of all peaks identified in each of the time points was used to count how many reads mapped to each peak for each sample. These values were normalized for read depth by dividing by how many million reads were contained in the union peak set for each sample. Finally, the read depthnormalized values were log 10-transformed (after adding a small constant) and median normalized. Principal component analysis of this matrix confirmed that time was a major predictor of quantitative differences in accessibility for sites common to all samples. A likelihood-ratio test framework was used to identify sites that were differentially accessible in one of the soft matrix time points relative to all of the stiff matrix controls:

$$Y_{ij} = \mu_i + b_i X_j + e_{ij}$$

Yij represents the accessibility of site i for sample j, µI is the mean accessibility for site i, Xj is the status of sample j ("soft" vs. "control"), bi is the effect of time spent on soft substrate on accessibility of site i, and eij is an error term. For each site, a model with a "soft vs control" term was compared to a nested model with just an intercept using a likelihood-ratio test. P-values were adjusted for multiple comparisons using the q-value calculation in the 'qvalues' package in R24. For this analysis the focus was on quick changing versus delayed changing sites. Sites that were characterized as 'quick' are those that exhibited differential accessibility at 12 hours after transitioning to soft substrate; 7,607 sites were identified that became more accessible and 2,430 sites that became less accessible at 12 hours (at a false discovery rate or 'FDR' of 1%). Sites that were characterized as 'delayed' are those that did not change for the first 2 days but then changed accessibility by days 5 and 7. To determine the delayed sites, sites that were significantly differentially accessible by day 5 and 7 (at an FDR of 1%) were identified and then any sites that were also identified at any of the earlier time points (at a relaxed FDR of 10%) were excluded; this analysis yielded 9,816 sites that became more accessible and 7,277 sites that became less accessible. Importantly, the delayed sites would include regulatory elements for genes exhibiting transcriptional memory.

Pathway Enrichment Analysis of ATAC-SEQ Data

In order to ascertain whether differentially accessible sites for each of the dynamic patterns (quick and delayed closing) were enriched near genes in specific pathways the Genomic Regions Enrichment of Annotations Tool was used ('GREAT' McLean, C. Y. et al. Nat. Biotechnol. (2010)). For both the quick closing and delayed closing sites (defined above), a bed file of all sites passing the respective thresholds was uploaded to great.stanford.edu. The whole genome was used as the background to look for ontology enrichments using the default settings.

Motif Enrichment Analysis

De novo motif analysis of ATAC-seq-defined regions was performed using the HOMER software suite (Heinz, S. et al. Mol. Cell (2010)), for subsets of open chromatin regions. Regions unchanged after transitioning to a soft matrix after seven days were open chromatin regions that were not in the 'quick' or 'delayed' closing set. Specifically, enrichments were determined using the findMotifsGenome.pl command with region sizes of 100 basepairs (bp). For quick and delayed changed sites, unchanged sites were used as the background. For unchanged sites, GC-matched 100-bp random genome sequences were used as background.

Immunofluorescence

For RUNX2 localization, cells were preconditioned for 7 days on soft or stiff hydrogels, passaged at ~80% confluence, with media changes every other day. Where drug treatments are indicated, cells were treated with either 1 µg/mL lyso-phosphatidic acid (LPA; indirect Rho kinase activator; Sigma), 10 ug/mL Rho Activator II (Cytoskeleton Inc.), 20 µM Y27632 (ROCK inhibitor; Sigma), 50 nM jasplakinolide (actin filament stabilizer; Sigma), 1 µM taxol (microtubule stabilizer; Sigma), 30 µM blebbistatin (Myosin II inhibitor; Sigma), 10 µM nocodazole (microtubule destabilizer; Sigma), or 0.1% DMSO for 3 hours in fresh growth media, and then fixed in 4% paraformaldehyde for 20 min at 37° C. Cells were permeabilized in 0.5% TX-100 for 20 min, and blocked for 1H at RT in 5% goat serum+0.5% BSA in PBS with DAPI (Sigma) and 2% phalloidin-647 (Invitrogen). Cells were then incubated with primary antibodies for 2 hours at RT, and secondary antibodies for 1 hour at RT. The antibodies used were RUNX2 (Sigma Prestige HPA022040 1:250), Tubulin (Sigma T9026 1:250), Human Cytokeratin (Dako clones AE1/AE3 1:250), Paxillin (BD 612405 1:200), phosphoFAK (Thermo 44-625G 1:200), Alexa Fluor goat anti-rabbit 568 1:250 (Invitrogen) and Alexa Fluor goat anti-mouse 488 1:250 (Invitrogen). Samples were mounted in ProLong Diamond Antifade (Thermo-Fisher) and allowed to cure for at least 24 hours before imaging. Image segmentation was performed on the nuclear (DAPI-stained) image for each field. The cytosolic region was defined as a 2.2 μm wide annulus surrounding the nuclear region using Elements software (Nikon).

Immunoblotting

For mechanotransduction experiments, 250,000 cells were plate on 8.5 cm circular hydrogels, media changed every other day, and passaged at ~80% confluence. Protein lysates were resolved with SDS-PAGE and transferred to nitrocellulose. For ERK immunoblots, the following drugs were added along with fresh media 1 hour before lysis: 20 μM PD98059 (MEK inhibitor; Tocris), 30 μM blebbistatin (Myosin II inhibitor; Sigma), 100 nM dasatinib (Src inhibitor; Tocris) and 1 μM Faki14 (Fak inhibitor; Tocris) or 0.1% DMSO. For mechanical memory extension, cells were pre-conditioned as above with the following drugs: 2 μM palbociclib (CDK4/6 inhibitor; Sigma), 7 μM decitabine (DNMT inhibitor; Sigma), or 0.1% DMSO. Cells were lysed 36 hours after the last media change in RIPA buffer (1% NP-40, 150 mM NaCl, 0.1% SDS, 50 mM Tris-HCl pH 7.4, 0.5% sodium deoxycholate) supplemented with Halt protease inhibitor cocktail (Pierce) and Halt phosphatase inhibitor cocktail (Pierce). For AKT inhibition cells were conditioned on stiff hydrogels for 7 days with drug changes every other day (1 μM MK-2206; Cayman Chemical). Membranes were blocked in 100% Odyssey Blocking Buffer PBS (LI-COR), incubated with primary antibodies overnight at 4° C. in 50% blocking buffer+50% PBST, and secondary antibodies for 1 hour at RT in 50% blocking buffer+50% PBST. The antibodies used were RUNX2 (Sigma Prestige HPA022040 1:1000 and Cell Signaling Technology 8486S 1:1000), OPN (Abcam ab8448 1:1000 and Abcam ab91655 1:1000), ERK (Santa Cruz sc-93-G 1:1000), phospho-ERK (Cell Signaling Technology 4377S 1:1000), AKT (Cell Signaling Technology 2920S 1:1000), phospho-AKT (Cell Signaling Technology 4058S 1:1000), Actin (ProteinTech Group 66009-1 1:5,000), Alexa Fluor goat anti-rabbit 680 1:10,000 (Invitrogen) and Alexa Fluor goat anti-mouse 790 1:10,000 (Invitrogen).

Flow Cytometry and Sorting

Figure 11:
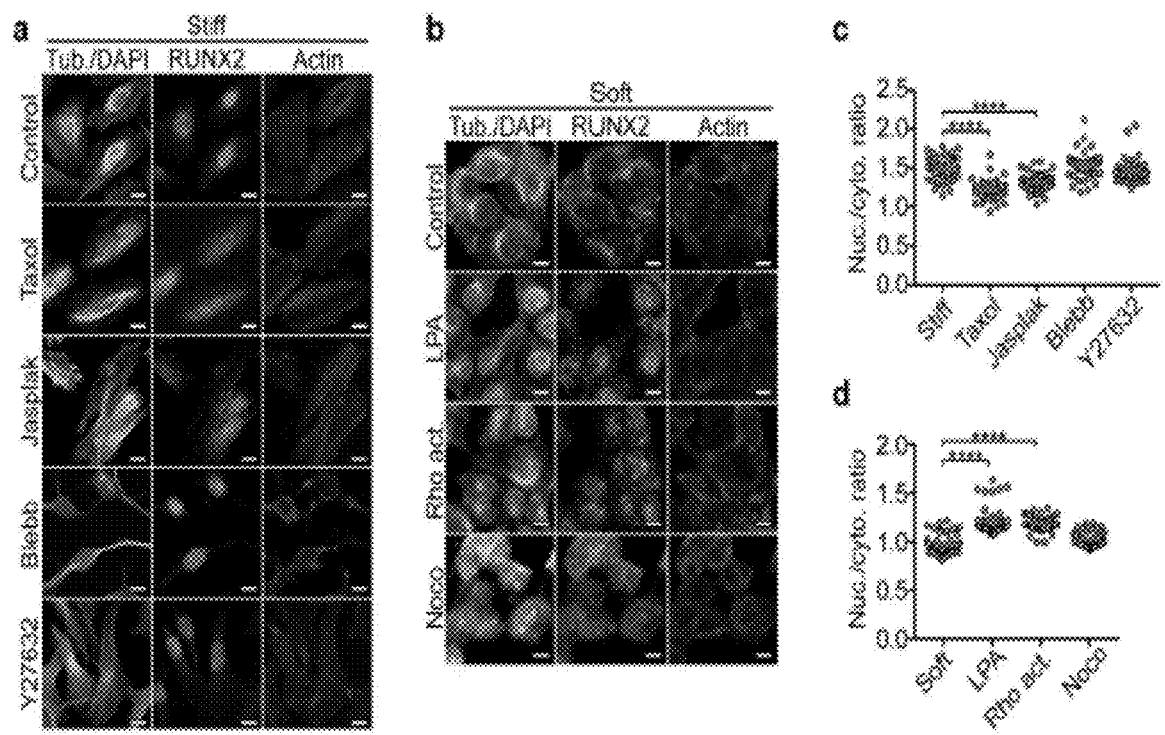
FIG. 11. RUNX2 localization is influenced by cytoskeletal dynamics. a, Immunofluorescence staining of RUNX2 in SUM159 cells preconditioned for 7 days on stiff hydrogels, treated with DMSO (control), 1 µM taxol, 50 nM jasplakinolide, 30 µM blebbistatin or 20 µM Y27632, added 3 hours before fixation. Scale bars=10 b, Immunofluorescence staining of RUNX2 in SUM159 cells preconditioned for 7 days on soft hydrogels, with DMSO (control), 1 µg/mL lysophosphatidic acid (LPA), 10 µg/mL Rho Activator II, or 10 µM nocodazole, added 3 hours before fixation. Scale bars=10 µm. c, Quantification of (a) (n≥40 cells each condition from n=3 biological replicates). d, Quantification of (b) (n≥40 cells each condition from n=3 biological replicates).

Cells were preconditioned on stiff hydrogels for 7 days to encode mechanical memory, and then labelled with CellVue Claret far-red membrane label (Sigma), using 4 μL label in 200 μL Dil C per $1.0 \times 10^6$ cells, before transfer to soft hydrogel conditioning for another 7 days. Cells were fed every 2 days and were split/analyzed when ~80% confluent. Cell sorting was performed on a BD FACSAria III using FACSDiva software. The sequential gating strategy is outlined in FIG. 11. Compensation was done for each experiment using unstained cells and cells stained with individual fluorophores. After sorting, 100,000 cells from CellVueHIGH or CellVueLOW gates were returned to 22 mm×22 mm soft hydrogels in order to generate conditioned media for 24 hours, before assaying OPN and GM-CSF protein expression, or 3D invasion. Flow cytometry was performed on a BD FACSCanto II. To quantify OPN expression, 1 hour room temperature incubation with OPN-PE (Abcam ab210835, 1:2500) or IgG control (Abcam ab72465, 1:2500) was used following −20° C. 90% methanol fixation/permeabilization and blocking in 10% goat serum for 30 min at RT. Flow cytometry data was analyzed using FlowJo using unstained samples to set gates.

Quantitative Real-Time PCR

For RUNX2 knockdown experiments, cells were infected with either GIPZ (non-targeting control), shRUNX2 #01 or shRUNX2 #02 expressing lentivirus (n=3 independent virus preparations each) and selected for 1 week with puromycin. 40,000 cells were plated on soft of stiff hydrogels (22 mm×22 mm) with media changes every other day, and passaged at 80% confluency. For mechanical memory experiments, cells were plated/passaged as above, and cells were lysed 36 hours after last media change. For mechanotransduction drug treatments, cells were treated with either 30 μM blebbistatin (Sigma), 100 nM dasatinib (Tocris), 1 μM Faki14 (Tocris) on collagen I coated (or 0.1% DMSO on poly-D lysine-coated) hydrogels for 7 days with media/drug change every other day, including the day before analysis. Total RNA was isolated using Isolate II RNA kit (Bioline) and cDNA was then synthesized from 1 μg of RNA using XLA script cDNA kit (Quanta BioSciences). Sybr green PCR mix (Bioline) was used for RT-qPCR on the ABI Fast 7500 system Samples were run in triplicates in each experiment and relative mRNA levels were normalized to housekeeping gene EEF1A. Melt curve analysis was performed to verify that each SYBR reaction produced a single PCR product. All SYBR assays were performed using the following PCR cycling conditions: denaturation at 95° C. for 15 min followed by 40 cycles of denaturing at 95° C. for 10 sec, and annealing at 60° C. for 1 min. See Table 1 for a list of all primers used.

Combined Mechanoresponse Assay

All cell lines and patient-derived xenografts were mechanically-conditioned for 36 hours on 0.5 kPa (Petrisoft) or 8.0 kPa (Petrisoft) hydrogels before analysis. Cells were imaged in situ using a 10× Plan Apo 0.75 N objective (Nikon) and an ORCA-Flash 4.0 V2 cMOS camera (Hamamatsu). Manual tracing was done to quantify cell spreading on each stiffness. After image acquisition, RTqPCR analysis of CTGF was performed as detailed above.

Enzyme-Linked Immunosorbent Assay (Elisa)

SUM159 cells were preconditioned for 7 days on stiff hydrogels to encode mechanical memory, and then 500,000 cells were transferred to 8.5 cm soft hydrogels. Media was changed the next day, and then 24 hours after that conditioned media (CM) was collected (2-day-soft CM), spun down to remove cells/debris and snap frozen. Cells were counted and then 500,000 cells were re-plated. This cycle was repeated to generate 4-, 6-, and 8-day soft CM. A GM-CSF Human SimpleStep ELISA kit was used per manufacturer's instructions (Abcam). The colorimetric signal was normalized to total protein lysates from 25% of the cells on the hydrogels after each 2-day conditioning cycle (Coomassie Plus; Pierce). For mechanical memory selection, 100,000 CellVueHIGH or CellVueLOW cells were returned to 22 mm×22 mm soft hydrogels for 24 hours in order to generate conditioned media (see Flow Cytometry and Sorting), and GM-CSF levels were interpolated from a standard curve per manufacturer's instructions.

Quantification of Human Cancer Cells in Mouse Tissues

Fresh brain, liver and lung tissue was snap frozen and stored at −20° C. Whole organs were pulverized after liquid nitrogen treatment, and 20 mg from each was processed for gDNA using GeneJet genomic DNA purification kit (Thermo). The following previously validated primers were purchased from IDT: Human Alu, Fw: YB8-ALU-S68 5'-GTCAGGAGATCGAGACCATCCT-3; SEQ ID NO:3, Rev: YB8-ALU-AS244 5'-AGTGGCGCAATCTCGGC-3; SEQ ID NO:4, Probe: YB8-ALU-167 5'-6-FAM-AGC-TACTCGGGAGGCTGAGGCAGGA-ZEN-IBFQ-3; SEQ ID NO:5 (Preston Campbell, J. et al. Sci. Rep. 5, 12635 (2015)). Mouse Actb PrimeTime Std (Mm.PT.39a.22214843.g) was used as an endogenous control to normalize each sample. All TaqMan assays were performed using the same PCR cycling conditions as listed above.

Synthetic Bone Matrix Adhesion and Spreading

Osteo Assay surface (synthetic bone matrix) 24-well microplates (Corning) were used. For adhesion, 24 hour-old preconditioned media from corresponding experimental groups were collected, and then 200 μL was pre-absorbed to the Osteo plates for 1 hour prior to adding $1.0 \times 10^6$ cells in 100 μL fresh media, and incubated for 30 min. Plates were gently tapped to remove loosely bound cells, and the remaining cells were stained with DAPI and enumerated by microscopy with large-stitch imaging using a 10× Plan Apo 0.75 N objective (Nikon) and an ORCA-Flash 4.0 V2 cMOS camera (Hamamatsu). For spreading measurements on synthetic bone matrix, the above protocol was used except imaging commenced immediately upon addition of cells to the plate. Cell area was quantified at 6 min intervals by manual tracing in Elements software (Nikon), using a 20× Plan Apo 0.75 NA objective (Nikon) and a CoolSNAP MYO CCD camera (Photometrics).

Osteoclastogenesis In Vitro

Osteoclast precursor RAW 264.7 cells were induced for 4 days in 24-well plates with DMEM+10% FBS+50 ng/mL RANKL (Sigma) (growth media), and then cultured with 50% cancer cell preconditioned media (CM)+50% growth media for another 3 days. CM was collected 24 hours after addition to plates with equal cell counts from each experimental group. Tartrate-resistant acid phosphatase staining was done using the Acid Phosphatase, Leukocyte (TRAP) kit (Sigma) according to manufacturer's instructions. Multinuclear cells that stained positive were enumerated in large-stitched images taken with a 10× Plan Apo 0.75 N objective (Nikon) and a DS-Fi2 color CCD camera (Nikon).

In Vivo Models

Adult female 6-8 weeks old NOD.Cg-PrkdcscidIl2rgtm1Wjl/SzJ mice (Jax) were randomly allocated into experimental groups. Mice were maintained in pathogen-free conditions and provided with sterilized food and water ad libitum. In the intracardiac injection model, $2 \times 10^5$ SUM159, SUM159-RUNX2-WT, SUM159-RUNX2-SA or SUM159-RUNX2-SE cells (preconditioned for 7 days on soft hydrogels, stiff hydrogels, or TC plastic, as indicated) were injected (resuspended in 100 μL PBS) into the left cardiac ventricle. Upon harvest, non-osseous tissues were flash frozen for subsequent DNA extraction and human Alu quantification. In the intraosseous injection model, SUM159 cells were first preconditioned for 7 days on either soft or stiff hydrogels, then re-plated onto new soft hydrogels for 24 hours prior to $5 \times 10^4$ cells (in 5 μL PBS) being injected into the intramedullary space of the right distal femur of each animal.

Patient-Derived Xenografts

PDX models were established and gifted by Alana Welm (Huntsman Cancer Institute). For propagation of HCI-005, HCI-011 and HCI-003 tumors, 2 mm×2 mm frozen chunks were implanted subcutaneously and allowed to grow until their diameter exceeded 1.75 cm and necessitated excision, or the animals showed signs of undue pain or distress. Ex vivo analysis of PDX cells was done between p4 and p6. To isolate transformed cells, freshly excised tumor chunks were digested with collagenase/hyaluronidase in DMEM (Stemcell Technologies) for 3 hours at 37° C., using differential adhesion to reduce the proportion of mouse fibroblasts transferred to hydrogels for preconditioning.

Bioluminescence In Vivo

Once a week, mice were injected with 120 mg/kg luciferin and metastatic dissemination was monitored using AMI X (Spectral Instruments). Mice were killed by CO2 asphyxiation 3-4 weeks after tumor cell injection. Metastatic burden was quantified using AMIView (Spectral Instruments). Exclusion criteria for data analysis were pre-established such that those mice terminated before defined experimental endpoints, for ethical reasons or premature death, were not included in analysis. Investigators were blinded to experimental groups during acquisition of bioluminescence data.

X-Ray Imaging

Mice were anesthetized with 80 mg/kg ketamine to 12 mg/kg xylazine (in a 10 mL/kg volume) and radiographs were obtained (Faxitron). Data were analyzed with ImageJ using pixels as the unit of measurement. Investigators were blinded to experimental groups during acquisition and analysis of X-ray data.

Micro-CT Imaging

Legs were removed from euthanized mice and fixed in neutral-buffered formalin for 24 hours, then dissected free of tissue and scanned on a Siemens Inveon micro-CT at 80 kV with a 0.5 mm filter, using an effective pixel size of 28 microns. The scanned images were reconstructed with Inveon Research Workplace (Siemens) using the Feldkamp algorithm and Shepp-Logan filter. In the intracardiac injection model, bone parameters were determined in the distal femur, starting 3 mm from the growth plate to the top of the epiphysis. In the intraosseous model, cortical bone thickness, volume, and surface area were determined in a 4 mm length of midshaft femur; trabecular bone analysis was excluded in the intraosseous model due to potential destruction caused by the syringe. In order to delineate bone marrow, trabecular bone and cortical bone, signal threshold intervals were set identically for all specimens. All histomorphometric parameters were based on the report of the American Society for Bone and Mineral Research nomenclature (Parfitt, A. M. et al. J. Bone Miner. Res. 2, 595-610 (2009)). Investigators were blinded to experimental groups during acquisition and analysis of micro-CT data.

Statistics

Sample sizes were determined based on previous experience with similar experiments (a minimum of 3 to 5 mice for animal studies, or 2 to 4 biological replicates for in vitro/ex vivo assays). Statistical significance was assessed with GraphPad Prism 8, using the appropriate tests. For analysis patient survival data, Kaplan-Meier plots and the Wilcoxon test were used.

Data Availability

RNA-seq and ATAC-seq data are available at the NCBI Gene Expression Omnibus under accession number GSE127887.

Results

The mechanical microenvironment of primary breast tumors plays a substantial role in promoting tumor progression (Nagelkerke, A. et al., Semin. Cancer Biol. 35, 62-70 (2015)). While the transitory response of cancer cells to pathological stiffness in their native microenvironment has been well described (Paszek, M. J. et al. Cancer Cell 8, 241-254 (2005)), it is still unclear how mechanical stimuli in the primary tumor influence distant, late-stage metastatic phenotypes across time and space in absentia. This example demonstrates that primary tumor stiffness promotes stable, nongenetically heritable phenotypes in breast cancer cells. This "mechanical memory" instructs cancer cells to adopt and maintain increased cytoskeletal dynamics, traction force, and 3D invasion in vitro, in addition to promoting osteolytic bone metastasis in vivo. Furthermore, a mechanical conditioning (MeCo) score comprised of mechanically-regulated genes as a global gene expression measurement of tumor stiffness response is described. Clinically, it is demonstrated that a high MeCo score is strongly associated with bone metastasis in patients. Using a discovery approach, mechanical memory is traced in part to ERK-mediated mechanotransductive activation of RUNX2, an osteogenic gene bookmarker and bone metastasis driver (Young, D. W. et al. Proc. Natl. Acad. Sci. U.S.A. (2007); Pratap, J. et al. Cancer and Metastasis Reviews (2006)). The combination of these RUNX2 traits permits the stable transactivation of osteolytic target genes that remain upregulated after cancer cells disseminate from their activating microenvironment in order to modify a distant microenvironment. Using genetic, epigenetic, and functional approaches, it was possible to simulate, repress, select and extend RUNX2-mediated mechanical memory and alter cancer cell behavior accordingly. In concert with previous studies detailing the influence of biochemical properties of the primary tumor stroma on distinct metastatic phenotypes (Zhang, X. H. F. et al. Cell (2013); Cox, T. R. et al. Nature 522, 106-110 (2015); Gohongi, T. et al. Nat. Med. 5, 1203-1208 (1999); Wang, D. et al., (2017); Padua, D. et al. Cell 133, 66-77 (2008)), the findings detailing the influence of biomechanical properties support a generalized model of cancer progression in which the integrated properties of the primary tumor microenvironment govern the secondary tumor microenvironment, i.e., soil instructs soil.

Tumor stiffening is a ubiquitous feature of breast cancer progression which gives rise to a varied mechanical landscape ranging from normal elasticity to fibrotic-like tissue stiffness (Plodinec, M. et al. Nat Nano 7, 757-765 (2012)). When cells engage a stiff matrix through their focal adhesions, the physical resistance triggers mechanotransduction, a rapid conversion of mechanical stimuli into biochemical signals. Mechanotransduction promotes the first steps of metastasis by increasing cytoskeletal dynamics, cell migration, and invasion in situ (Huang, C., Jacobson, K. & Schaller, M. D. J. Cell Sci. 117, 4619-28 (2004)). However, the mechanical stimuli that instruct cell behavior in the primary tumor are not persistent throughout the metastatic cascade, especially when metastatic colonization and outgrowth occur in soft microenvironments (e.g., lung, liver, brain, and bone marrow). Thus, it was determined whether cancer cells maintain their mechanically-induced behavior after transition to dissimilar mechanical microenvironments. A similar concept has been established in normal mesenchymal stem cells, which are able to maintain their mechanically-mediated differentiation state after their mechanical microenvironment is altered (Dingal, P. C. D. P. et al. Nat. Mater. (2015); Yang, C. et al., Nat. Mater. (2014)).

Figure 1:
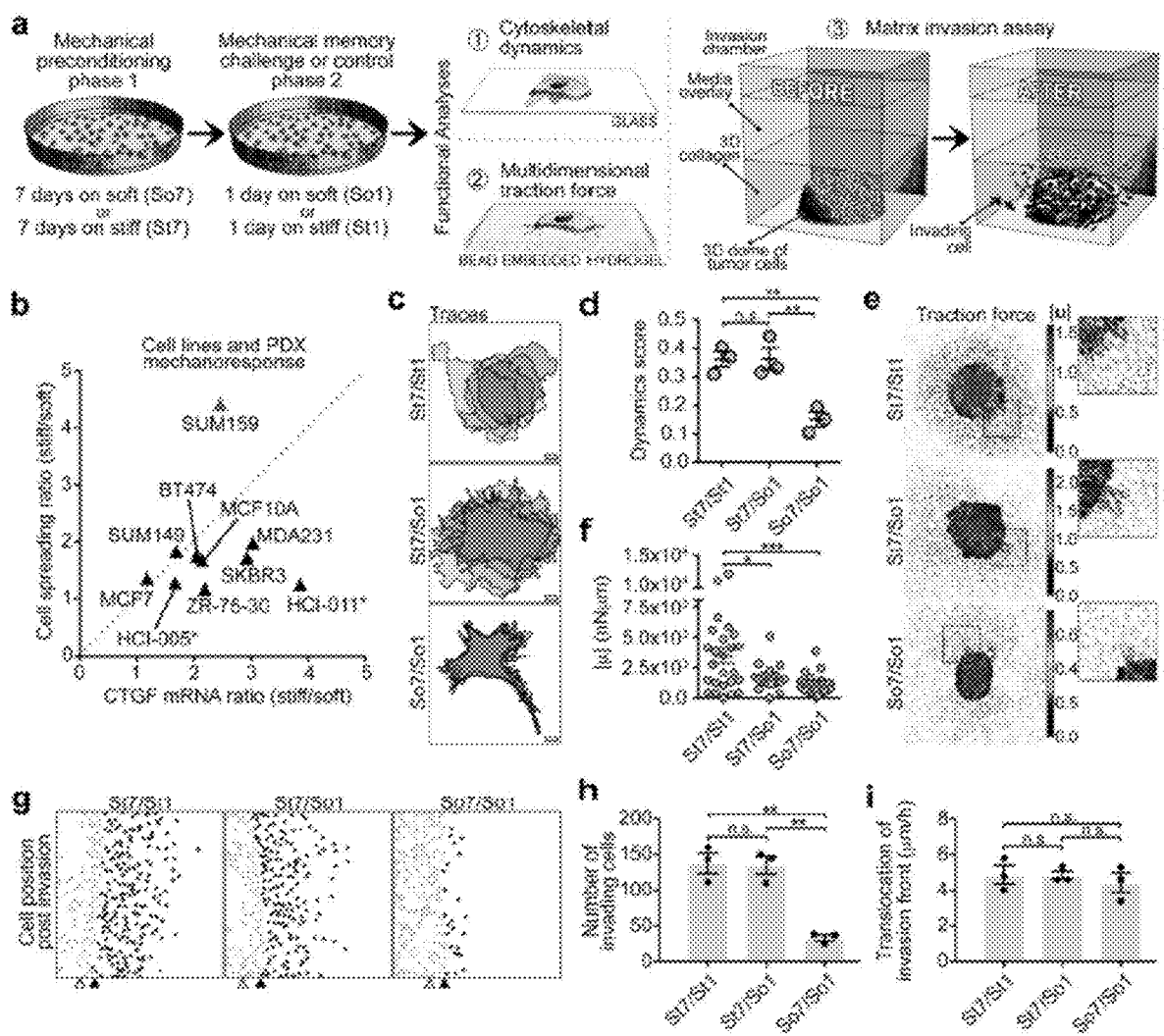
FIG. 1. Mechanical memory manifests distinctively in cellular dynamics and invasion. a, Schematics showing multifunctional analysis workflow for testing mechanical memory. b, Mechanoresponse readouts for a panel of breast cancer cell lines and patient-derived xenografts (denoted by asterisks). c, Cytoskeletal dynamics (overlaid cell traces) of iRFP-Lifeact-expressing SUM159 cells preconditioned on stiff and/or soft hydrogels as indicated, showing 1 hour intervals starting 10 hours after plating on glass. Scale bars=10 µm. d, Quantification of (c) (n=36 cells in each condition from n=3 biological replicates). e, Multidimensional traction force microscopy of SUM159 cells on bead-embedded 8.5 kPa gels, preconditioned on regular stiff and/or soft hydrogels as indicated. Panels show vector maps of displacement magnitude. Heat scales (µm) show bead displacement. f, Quantification of (e) (n=17-28 cells in each condition from n=3 biological replicates). g, SUM159 cell position along invasion fronts after 16 hours of live-cell tracking in 3D collagen. Gray dots=non-invasive cells; black dots=invasive cells; white triangles=invasion front at start of imaging; black triangles=invasion front at end of imaging. h,i, Quantification of (g) (n=3 biological replicates with n=3 technical replicates).
Figure 5F:
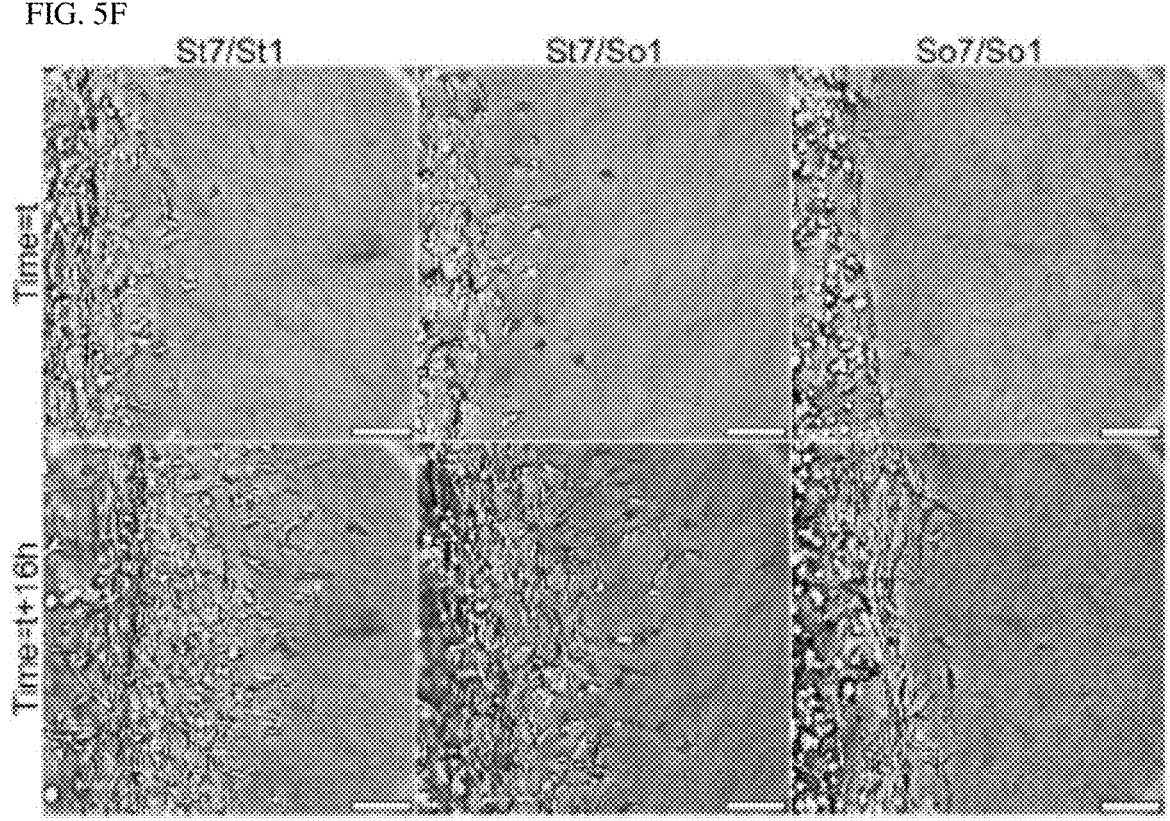
FIG. 5. Retention of mechanical memory is not uniform across different cellular dynamics. a, Cytoskeletal dynamics of iRFP-Lifeact-expressing SUM159 cells related to FIG. 1c, scale bars=10 µm. b, Quantification of cell area for cells represented in (a) (n=36 cells in each condition from n=3 biological replicates). c, Representative heatmaps of 2D traction stress on bead-embedded 8.5 kPa hydrogels of SUM159 cells, preconditioned on stiff and/or soft hydrogels as indicated. d, Dipole moment components from representative cells in (c). e, Quantification of contractile strength on bead-embedded 1.7 kPa hydrogels of SUM159 cells, preconditioned on stiff and/or soft hydrogels as indicated (n=10-29 cells in each condition from n=3 biological replicates). f, Enhanced depth-of-focus DIC images corresponding to FIG. 1g, scale bars=100 µm. g, SUM159 cell invasion tracks from a representative experiment corresponding to FIG. 1g, with 25 min intervals between points. h,i, Quantification of cell speed (h) and directionality (i) from the experiment outlined in FIG. 1g.
Figure 5G:
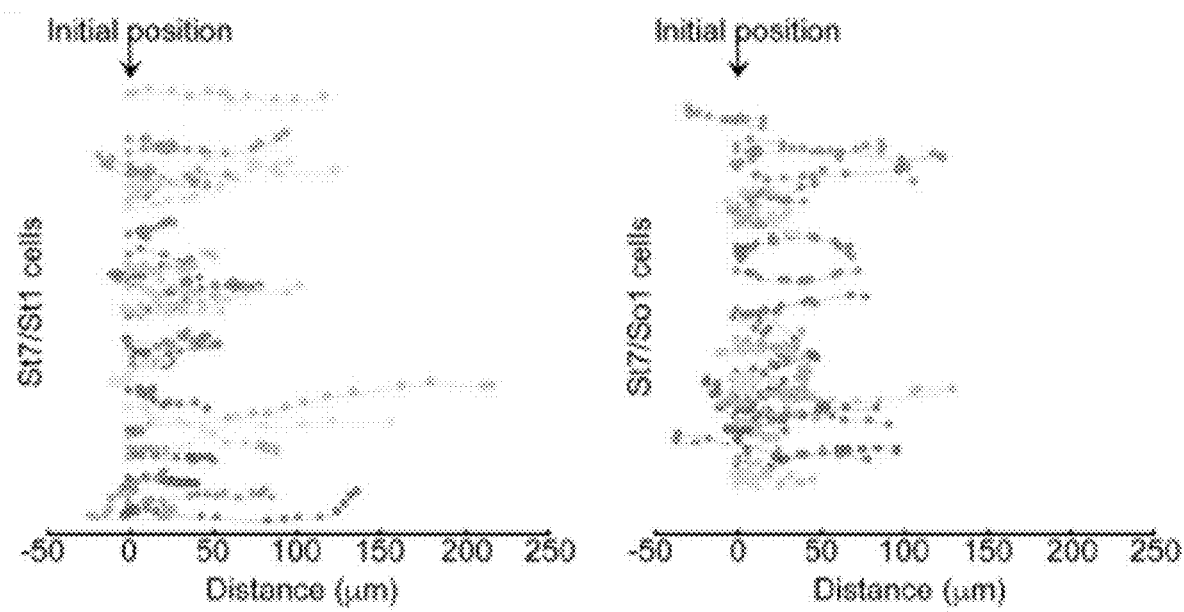
Figures 5H, 5I:
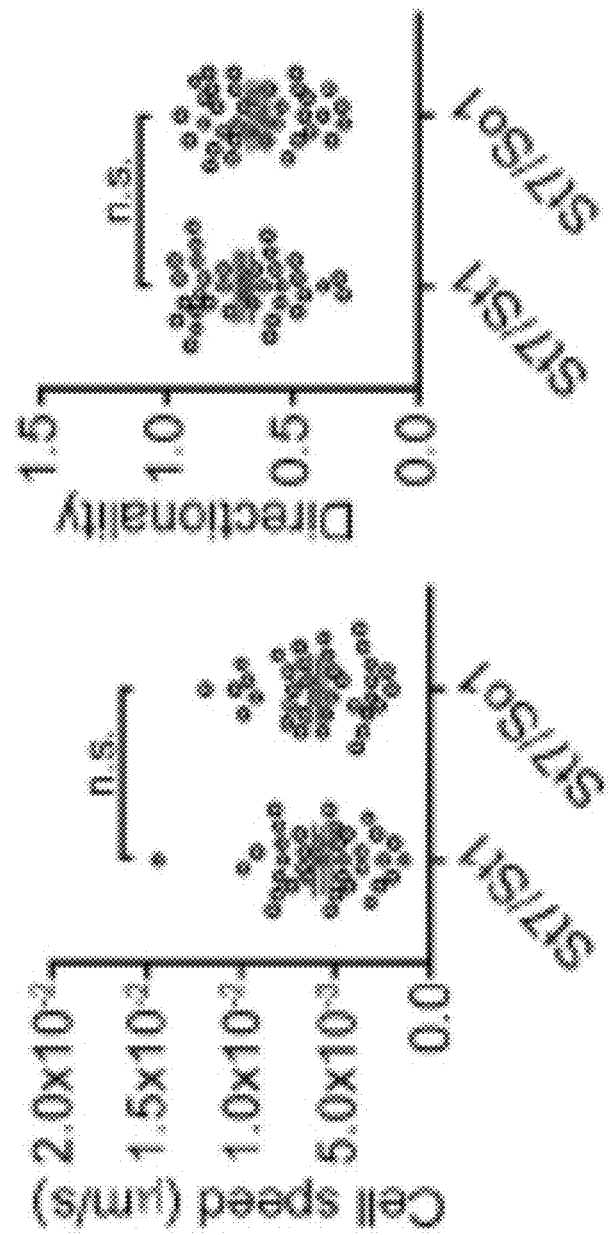

First, a panel of breast cancer cell lines and patient-derived xenograft (PDX) primary cells were screened for mechanoresponse in the relevant range for breast tumors (Plodinec, M. et al. Nat Nano 7, 757-765 (2012)), using stiffness tuned, collagen-coated hydrogels that were either 0.5 kPa (soft) or 8.0 kPa (stiff), and employing well-established mechanosensing and mechanotransduction readouts (differential cell spreading and CTGF gene expression, respectively) (Nagelkerke et al., supra; Puleo, J. I. et al. J. Cell Biol. jcb.201902101 (2019)). While all of the cells tested showed elevated mechanoresponse on stiff hydrogels compared to soft, SUM159 cells showed the greatest combined response (FIG. 1b). To interrogate mechanical memory, a multi-functional analysis workflow comprising a mechanical preconditioning phase and a mechanical memory challenge (or control) phase, followed by multiple functional assays was developed (FIG. 1a). First, SUM159 actin cytoskeletal dynamics were examined in three experimental groups: stiff-preconditioned control cells (St7/St1), which are cultured on stiff hydrogels for 7 days in phase 1 (St7) and then transferred to new stiff hydrogels for 1 day in phase 2 (St1); soft-preconditioned control cells (So7/So1); and stiffness-memory cells (St7/So1), which are stiff-preconditioned cells challenged with 1 day on soft hydrogels before analysis. St7/St1 cells exhibited increased cytoskeletal dynamics compared to So7/So1 cells, which maintained reduced dynamics throughout imaging on glass (FIG. 1c). Stiffness-memory St7/So1 cells fully retained their increased dynamics and behaved similarly to St7/St1 cells (FIG. 1c,d and FIG. 5a,b). This was recapitulated in the traction-induced displacement signatures obtained via multidimensional traction force microscopy; however, while the magnitude of traction induced cell displacements was similar among the St7/St1 and St7/So1 cells (FIG. 1e and FIG. 5c,d), the polarization of contractility, or average spatial arrangement of tractions was slightly diminished in both St7/So1 and So7/So1 cells (FIG. 1f and FIG. 5e). In a live-imaging based invasion assay, stiffness-memory cells retained their stiffness induced invasive capacity, reflected in the number of invading cells and migration dynamics including speed and directionality (FIG. 1g,h and FIG. 5f-i). Although soft-preconditioned control cells invaded less, the translocation of their invasion front was not diminished, suggesting that mechanical memory particularly sustained single-cell dissemination (FIG. 1i). Together, these results demonstrate that mechanical memory manifests distinctively in particular cytoskeletal dynamics and is associated with 3D invasion.

Figure 6A:
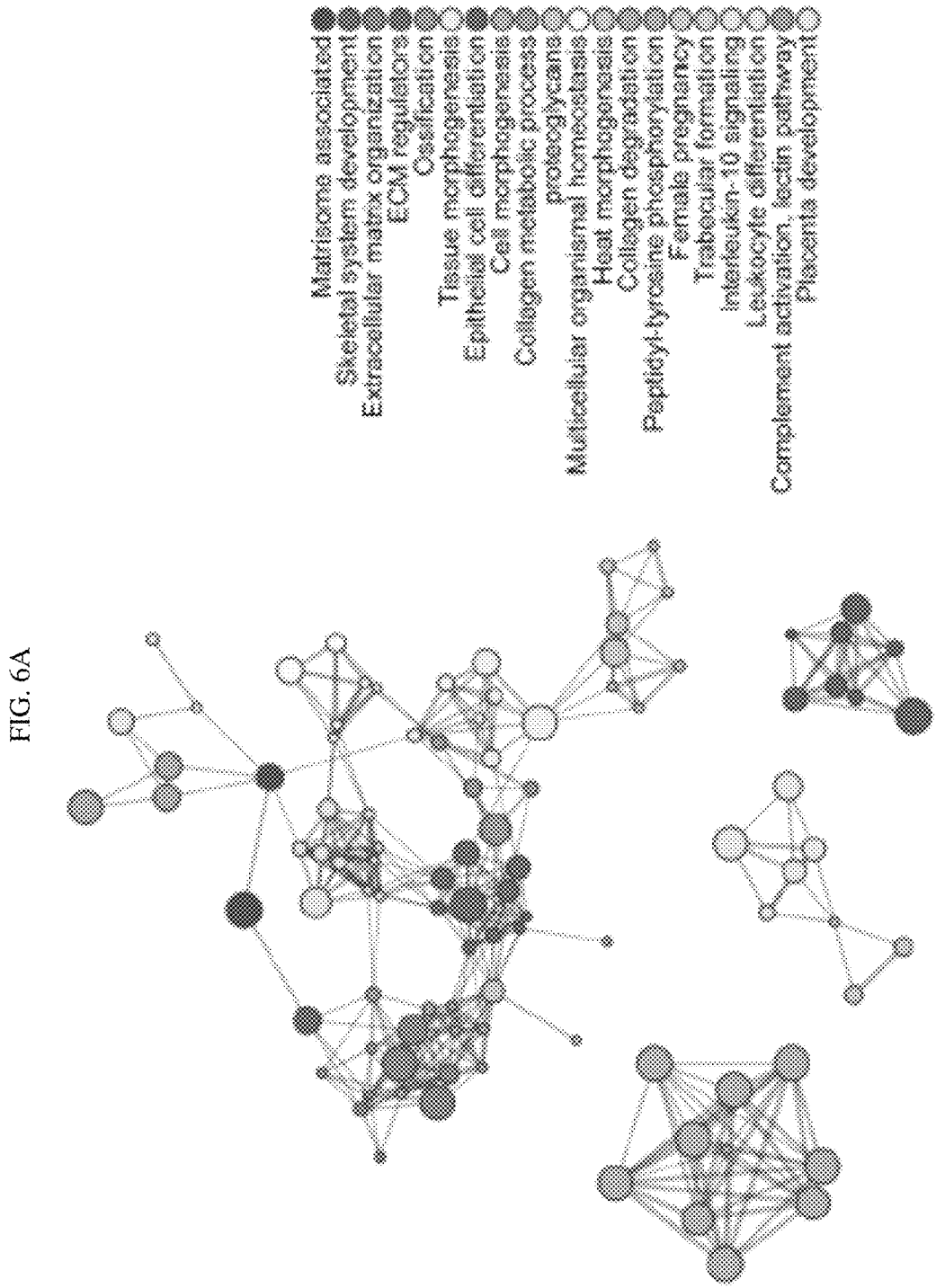
FIG. 6. Stiffness-induced genes and mechanical conditioning are associated with skeletal pathologies and bone metastasis. a, Metascape enrichment network of the stiffness-induced gene set (>4-fold) from SUM159 cells after 2 weeks of mechanical preconditioning. b,c Top ten candidate factors from Enrichr analysis of the gene set in (a) using the Human Phenotype Ontology library (Köhler, S. et al. Nucleic Acids Res. 42, D966-D974 (2014)) (b) and the MGI Mammalian Phenotype library (Blake, J. A. et al. Nucleic Acids Res. 37, D712-D719 (2009)) (c). Red bars=skeletal pathologies. All hits are significant at $P<0.05$. d, Proliferation score of 2-week soft- and stiff-preconditioned SUM159 cells. e, MeCo scores of patients in the combined cohort in FIG. 2d (n=268 no metastasis, 185 bone metastasis). f, MeCo scores for patients in the METABRIC study, stratified by subtype (n=244 Basal, 243 HER2, 596 Luminal A, 764 Luminal B, 54 Normal-like). g, Unsupervised clustering analysis of 2-week soft- and stiff-preconditioned SUM159 cells using the PAM50 gene set.
Figure 6B:
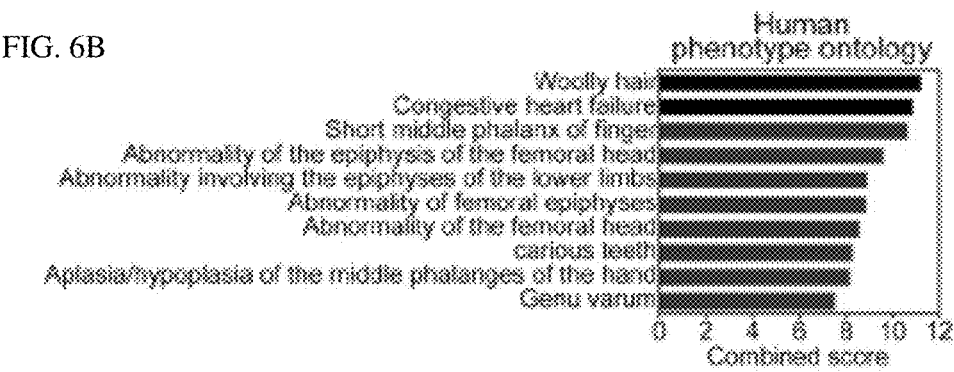
Figure 6C:
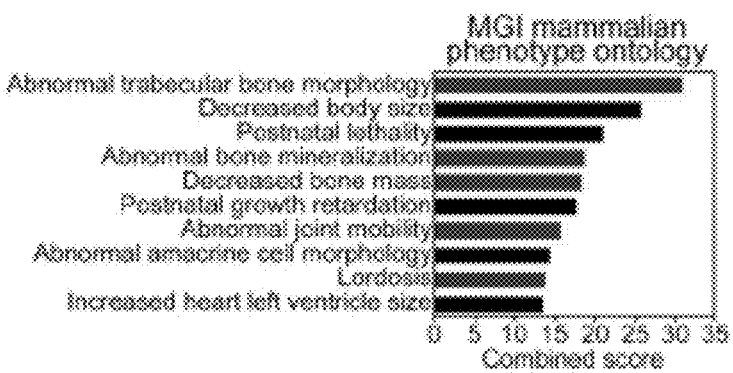

To ascertain the global changes in gene expression in response to fibrotic-like stiffness, differential gene expression analysis was performed on soft- and stiff-preconditioned SUM159 cells using RNA-seq (FIG. 2a). Examining the pathways upregulated revealed enrichments for a number of skeletal gene ontologies (from Metascape (Tripathi, S. et al. Cell Host Microbe 18, 723-735 (2015))) in the stiffness-induced gene set (FIG. 2b and FIG. 6a). Furthermore, a second pathway enrichment analysis (using Enrichr (Kuleshov, M. V. et al. Nucleic Acids Res. 44, W90-W97 (2016))) revealed an association with numerous skeletal pathologies, through query of the Human Phenotype Ontology and MGI Mammalian Phenotype libraries (FIG. 6b,c), which led a consideration of bone metastasis as a possible phenotypic correlate of stiffness-induced gene expression in metastasis-competent cancer cells.

Figure 2D:
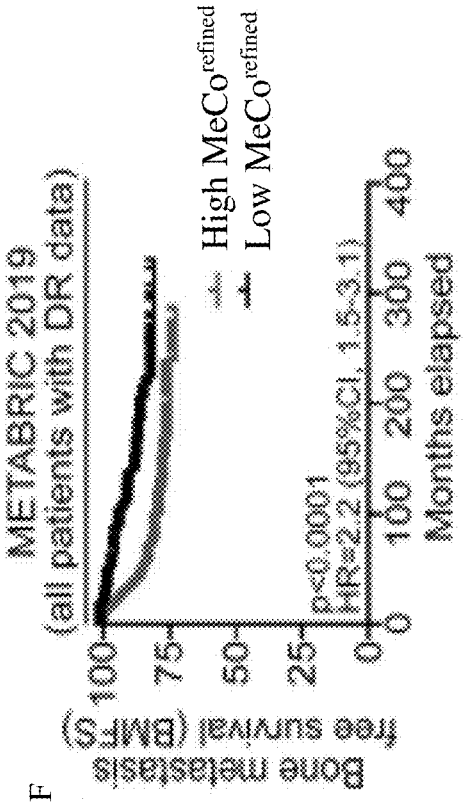
FIG. 2. Primary tumor mechanical conditioning is associated with bone metastasis. a, Heatmap of differentially-regulated genes (≥2-fold) from RNA-seq of 2-week soft- and stiffpreconditioned SUM159 cells, which constitute the raw MeCo genes (n=3 biological replicates). b, Metascape ontology of stiffness-induced genes (>4-fold). Bold text indicates skeletal ontologies. c, Kaplan-Meier curve of patients in the METABRIC 2019 study (molecular dataset cohort), assigning each patient a raw "mechanical conditioning" (MeCo) score derived from the differential gene expression in (a) comparing upper and lower quartiles of MeCo score (n=476 high MeCo, 476 low MeCo). d, Kaplan-Meier curve of bone metastasis-free survival in the combined cohort, split at median MeCo score (n=280 high MeCo, 280 low MeCo). e, Time to bone metastasis for patients in (d) split at median MeCo score (n=93 high MeCo, 92 low MeCo). f, g Large validation cohort for the MeCorefined score showing Kaplan-Meier curve of bone metastasis-free survival (f) and time to bone metastasis (g) in META-BRIC 2019 (using all patients with distant relapse annotation), comparing upper and lower quartiles of MeCorefined score (n=422 high MeCorefined, 421 low MeCorefined in (f), and n=65 high MeCorefined, 64 low MeCorefined in (g). h, Radiograms of tibia from mice injected with 7-day soft-, stiff-, and plastic-preconditioned SUM159 cells, imaged 4 weeks after intracardiac injection. i, Quantification of (h) (n=4 mice per group; TC=tissue culture).
Figure 2E:
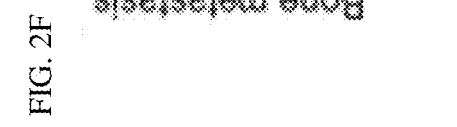
Figure 2E:
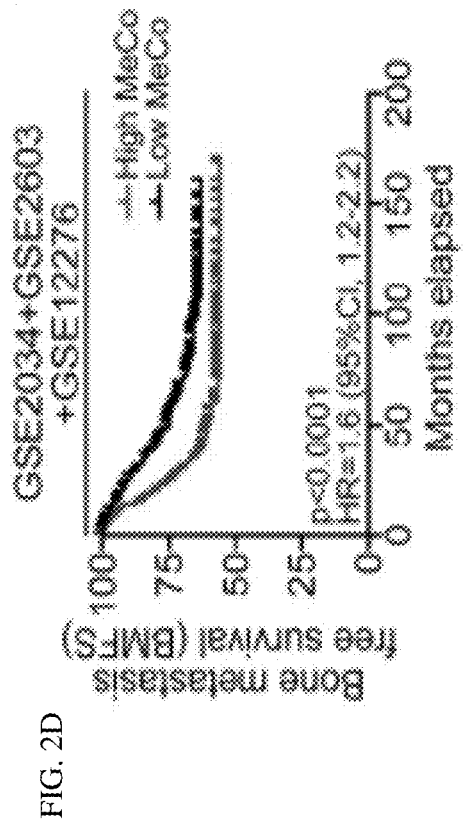
Figure 2F:
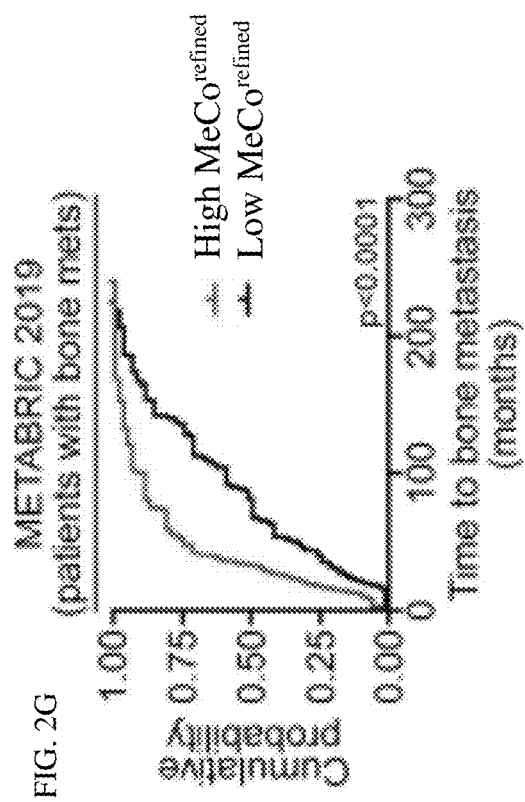
Figure 2G:
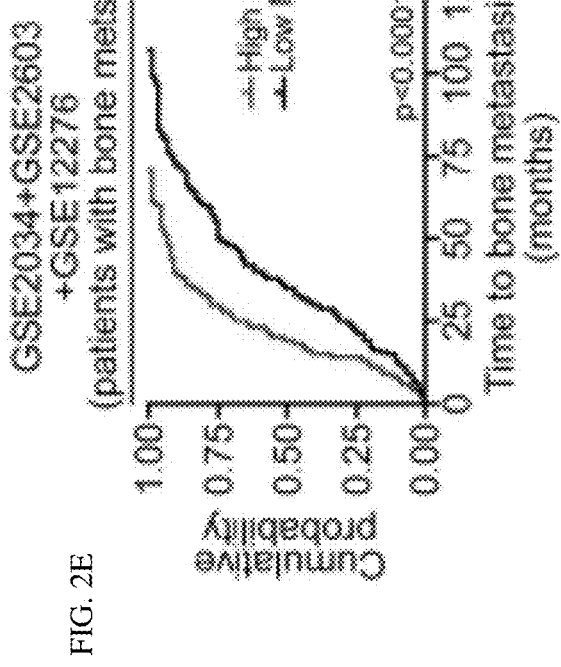
Figure 6D:
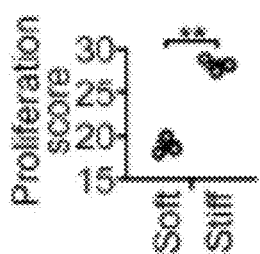
Figure 6E:
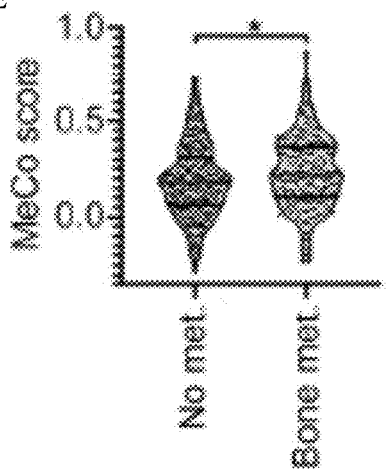
Figure 6F:
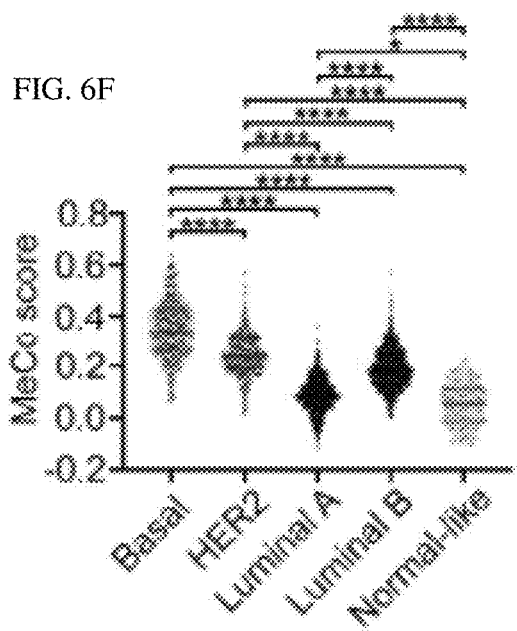
Figure 6G:
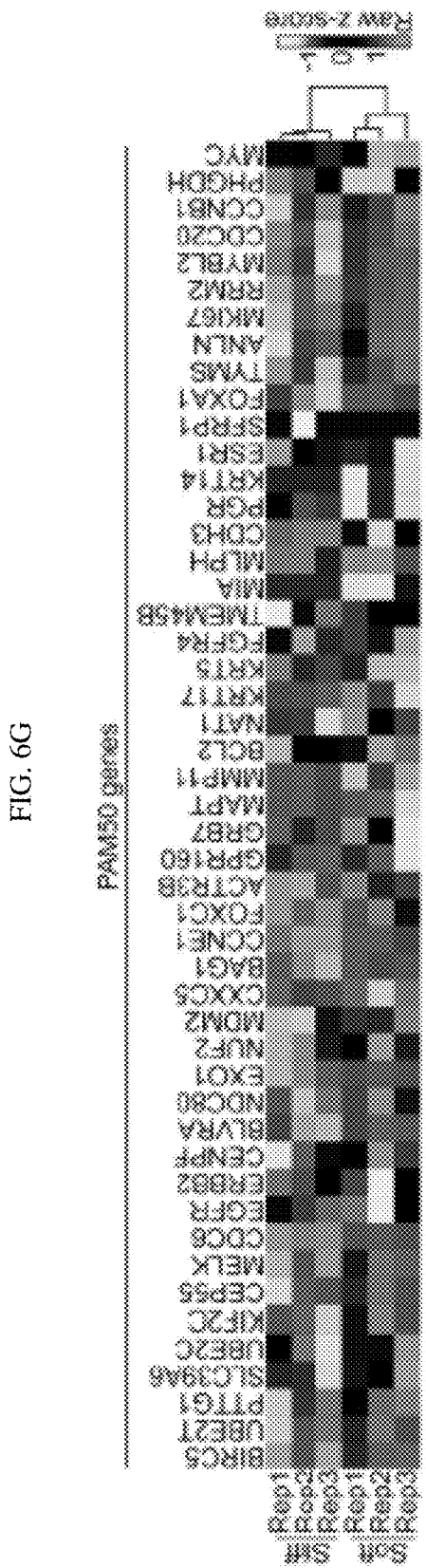
Figure 7G:
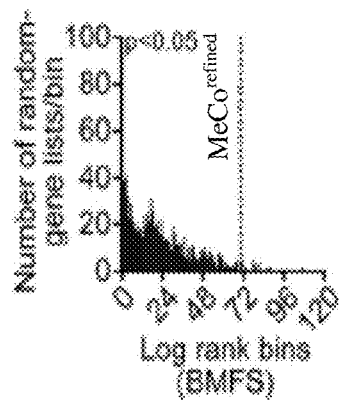
Figure 7H:
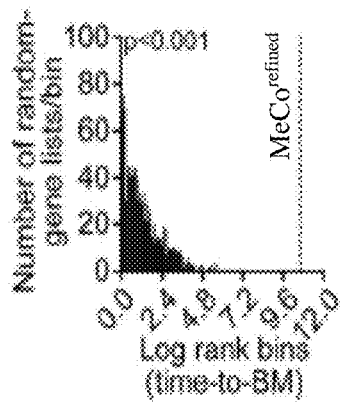
Figure 7I:
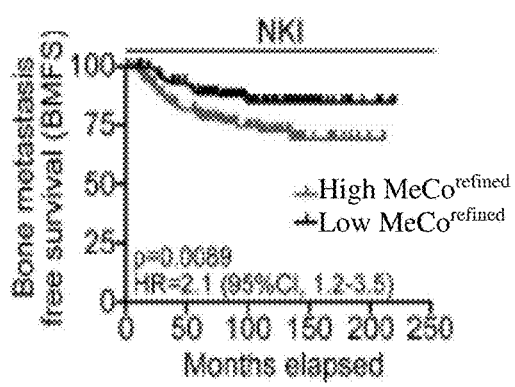
Figure 7J:
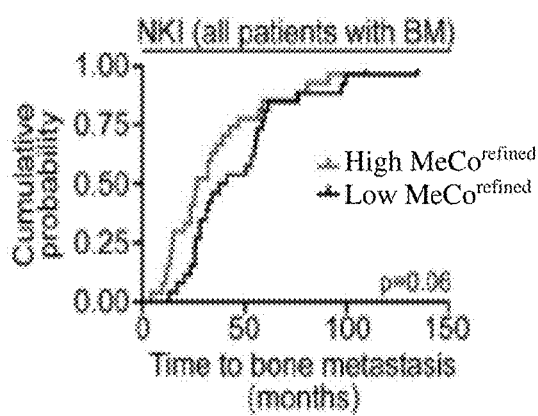
Figure 7K:
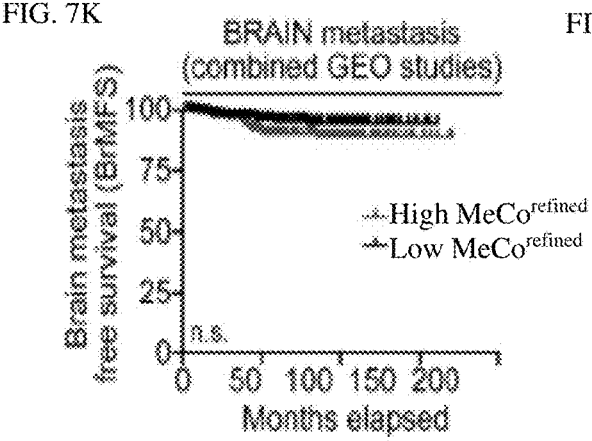
Figure 7L:
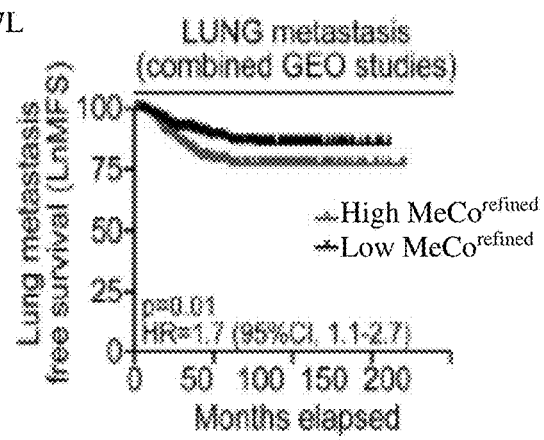
Figure 7M:
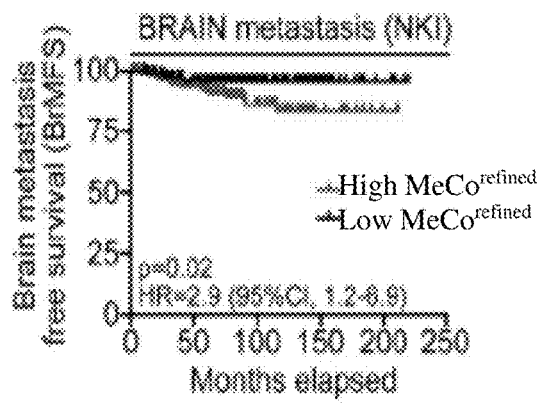
Figure 7N:
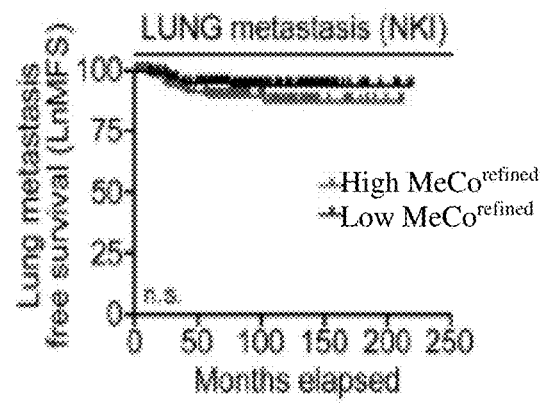

To test for a clinical association between breast tumor stiffness and bone metastasis, a mechanical conditioning (MeCo) multi-gene score was developed and used as a global gene expression measurement of tumor stiffness response. The MeCo score was generated using the entire set of genes that were differentially regulated in response to stiffness in SUM159 cells; however, to mitigate any influence of stiffness-induced proliferation (FIG. 6d), genes that are known to be strongly associated with proliferation were excluded (Selfors, L. M. et al., Proc. Natl. Acad. Sci. 114, E11276-E11284 (2017)). Individual MeCo scores were calculated for primary breast tumors from multiple patient cohorts. In the large METABRIC 2019 (molecular dataset) cohort, high MeCo scores are strongly associated with poor overall survival (FIG. 2c, Hazard Ratio (HR)=2.2, $p<0.0001$). In a separate, combined cohort of 560 patients for whom metastasis status and site were recorded, high MeCo scores were strongly associated with lower bone metastasis-free survival (BMFS) (FIG. 2d, HR=1.6, $p<0.0001$, FIG. 6e). Furthermore, amongst the 185 patients in the combined cohort who developed bone metastasis, the median time to bone metastasis (TTBM) was 19 months for those with high MeCo scores, compared to 35 months for those with low MeCo scores (FIG. 2e). Aggressive PAM50 tumor subtypes, such as basal, HER2 and luminal B, have strikingly higher average MeCo scores compared to the less aggressive luminal A and normal like subtypes (FIG. 6f); this is in line with a contrasting expression pattern of PAM50 genes between soft- and stiff-preconditioned cells (FIG. 6g). These observations are also consistent with data showing that stiffness-preconditioning enhances invasion. To identify the genes that contribute to the association between MeCo score and bone metastasis independently of subtype and patient cohort, linear regression was used to correct for subtype specific effects and differences in platform and subtype composition between studies in the combined cohort of 560 patients (FIG. 7a0c), and the subset of MeCo genes (MeCo$^{refined}$) that were consistently up- or down-regulated between bone-metastatic and non-metastatic primary tumors were identified (FIG. 7d-h). The MeCo$^{refined}$ score was significantly better at predicting BMFS and TTBM than matched gene sets randomly chosen from up- and down-regulated genes between bone-metastatic and non-metastatic primary tumors (FIG. 7g,h). In addition, the MeCo$^{refined}$ score was validated in two independent datasets, NKI (HR=2.1, p<0.009) and METABRIC 2019 (HR=2.2, p<0.0001) (FIG. 2f,g and FIG. 7g,h). In the latter, the median TTBM for patients with high MeCo$^{refined}$ scores was 33 months, compared to 85 months for those with low MeCorefined scores (FIG. 2g). Together, these analyses reveal how mechanical conditioning is associated with bone metastasis at the genome-wide level.

Figures 2H, 2I:
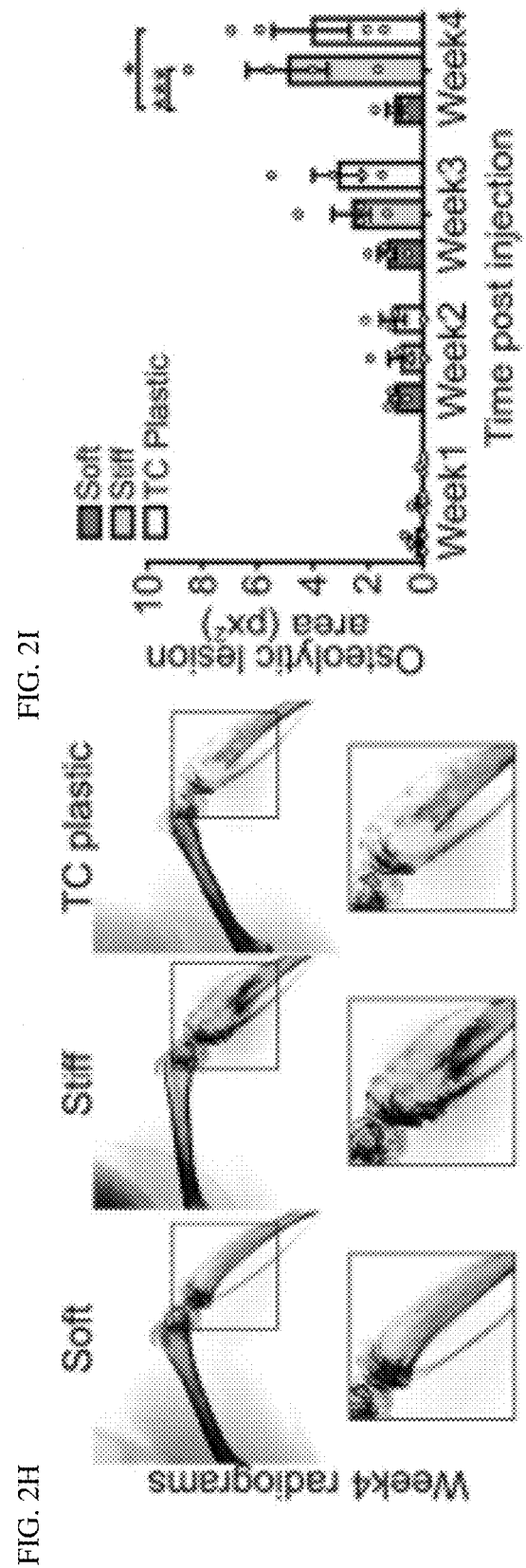
Figure 8A:
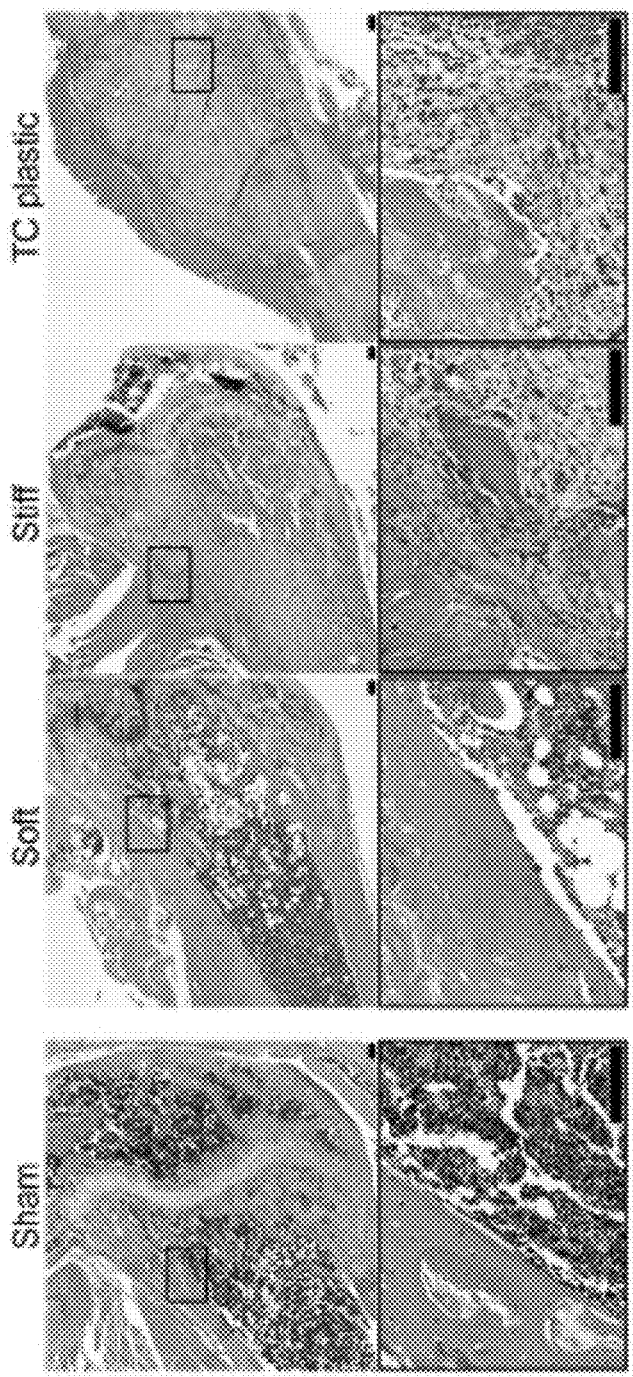
FIG. 8. Primary tumor mechanical conditioning and mechanical memory are associated with bone metastasis. a, H & E staining of femurs from mice bearing 7-day soft-, stiff-, and plastic-preconditioned SUM159 cells, 4 weeks after intracardiac injection. b, Bioluminescence images of stiffness-memory (St7/So1) and soft-preconditioned (So7/So1) SUM159 cells after intrafemoral injection, imaged at 1 week and 3 weeks postinjection. c, Quantification of bioluminescence in (b) (n=3 mice per group). d, Micro-CT 3D reconstructions of femurs from mice bearing stiffness-memory (St7/So1) and soft-preconditioned (So7/So1) SUM159 cells, 4 weeks after intrafemoral injection. e-g, Quantification of cortical thickness (e) bone volume/total volume (f) and bone surface area/bone volume (g) from mice in (d) (n: mice; St7/So1 5; So7/So1 6).
Figure 8C:
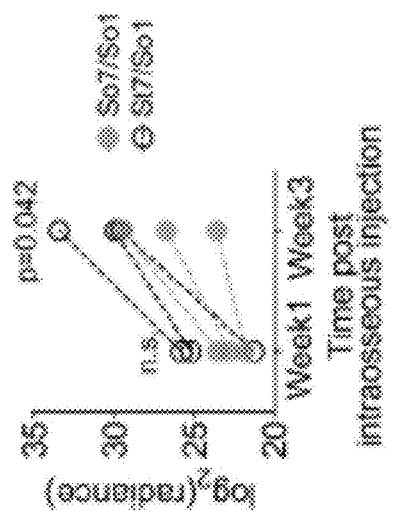
Figure 8B:
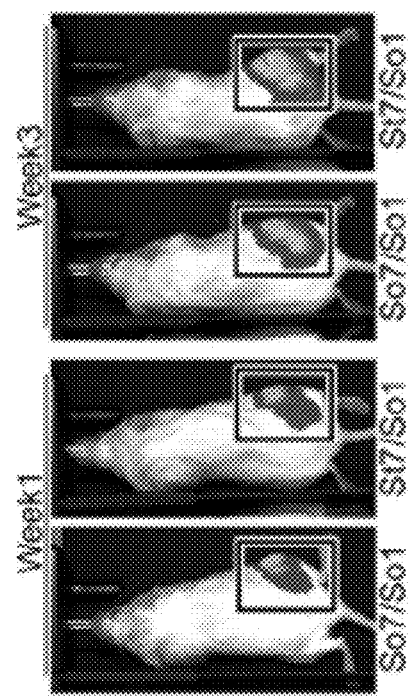

To determine if fibrotic-like stiffness promotes bone metastasis in vivo, NODscid IL2rynull mice were injected with soft-, stiff- or plastic-preconditioned SUM159 cells in the left cardiac ventricle and bone changes were tracked with X-ray imaging. Progressive osteolysis was evident in both the stiff- and plastic-preconditioned groups compared to the soft-preconditioned group (FIG. 2h,i, FIG. 8a)). To test the osteolytic capacity of stiffness-memory cells, and to simultaneously determine whether the colonization deficit in the soft-preconditioned group was extravasation-dependent, intrafemoral injection of St7/So1 or So1/So1 cells was performed in order to bypass systemic circulation. Stiffness-memory St7/So1 cells grew faster in situ, and their growth led to reduced cortical bone volume (FIG. 8b0g). These data strongly support that mechanical memory promotes osteolytic disease in vivo.

Figure 3:
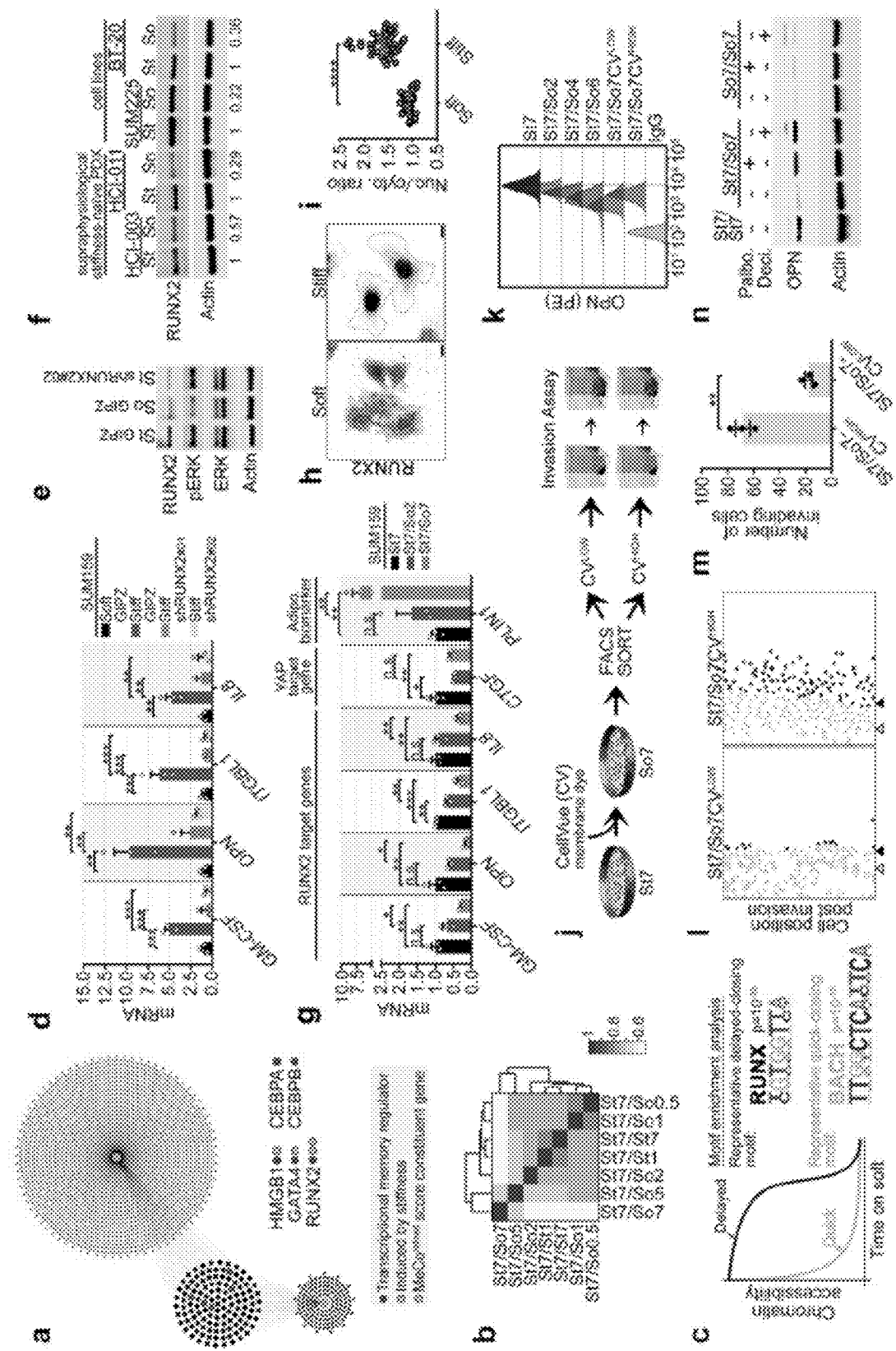
FIG. 3. RUNX2 is activated by stiffness and is associated with proliferation-sensitive mechanical memory. a, Schematics of discovery approach identifying candidate drivers of mechanical memory-mediated metastasis. Gray dots=mechanically-sensitive upstream regulators from RNA-seq analysis (141 genes); blue dots=Human Cancer Metastasis Database metastasis-associated genes (1811 genes); black/red dots=intersecting genes (123 genes). Red dots=intersecting genes that are known gene bookmarkers (5 genes) and inset shows further characterization. See Methods for detailed description. b, Heat map showing clustering of ATACseq samples; scale shows Jaccard index. c, Graphic representation of change in chromatin accessibility over time after changing the mechanical environment; inset shows RUNX and BACH family motifs as representative of the significantly enriched motifs in the delayed-closing and quick-closing sites, respectively (motifs analysis performed by HOMER). d, RT-qPCR of 4 RUNX2 target genes in SUM159 cells preconditioned for 7 days on soft and stiff hydrogels with non-targeting shRNA (GIPZ), or on stiff hydrogels with two shRNAs targeting RUNX2 (n=3 biological replicates). e, Immunoblot of RUNX2, ERK and pERK in SUM159 cells stably expressing lentiviral shRUNX2 or GIPZ (non-targeting control), preconditioned for 7 days on soft or stiff hydrogels (representative of n=3 biological replicates). f, Immunoblot of RUNX2 in patient-derived xenograft (PDX) primary cells and breast cancer cell lines, preconditioned on soft and stiff hydrogels for 7 days (representative of n=2 biological replicates). g, RT-qPCR of RUNX2 and 4 target genes, plus CTGF (YAP target) and PLIN1 (adipogenic biomarker) in SUM159 cells preconditioned as indicated (n=3 biological replicates). h, Immunofluorescence staining of RUNX2 in SUM159 cells on soft and stiff hydrogels. i, Quantification of (e) (n=40 cells in each condition from n=3 biological replicates). j, Schematics showing strategy to enrich highproliferative cells (CV-LOW) vs low-proliferative cells (CVHIGH). k, Time course of mechanical memory loss, showing flow cytometry of SUM159 cells preconditioned as indicated, sorted as in (g) and stained for OPN (n=3 biological replicates). 1, m, SUM159 cell position (i) and quantification (j) after 16 hours of live-cell tracking in 3D collagen. Gray dots=non-invasive cells; black dots=invasive cells; white triangles=invasion front at start of imaging; black triangles=invasion front at end of imaging. n, Immunoblot of OPN showing memory extension in SUM159 cells treated with DMSO, palbociclib (2.5 µM; CDK4/6 inhibitor) or decitabine (7 µM; DNMT1 inhibitor) on soft hydrogels for 7 days in phase 2, after stiff- or soft-preconditioning for 7 days in phase 1.
Figure 9A:
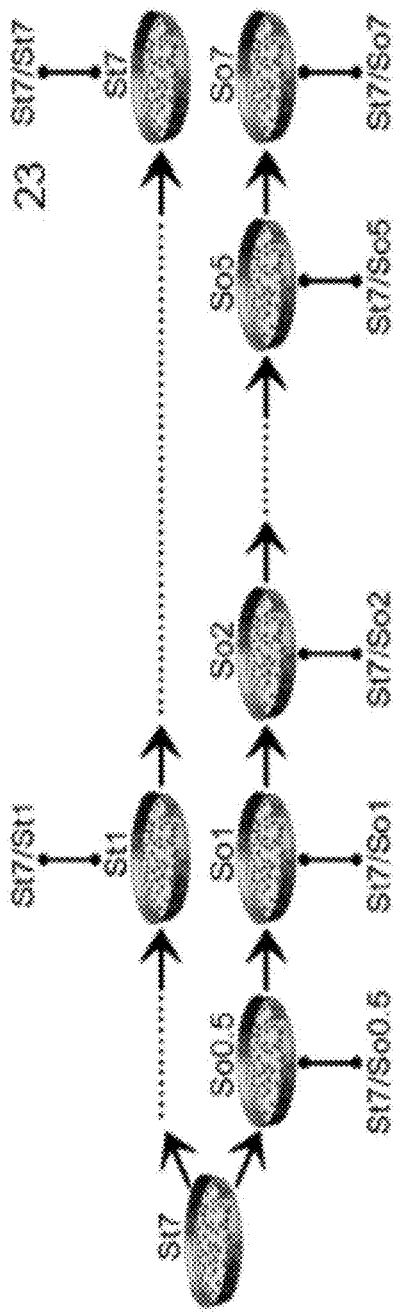
FIG. 9. RUNX2 is activated by mechanotransduction. a, Schematics showing experimental strategy for ATAC-seq experiments; samples were collected at indicated time points after transitioning to either stiff (top row) or soft (bottom row) environments; samples were generated in triplicates. b, Principal component analysis (PCA) of ATAC-seq. c, Upset plot of the intersection of the different time points. d, Population doubling of SUM159 cells at 24 and 48 hours. e, RT-qPCR of RUNX2 in SUM159 cells preconditioned for 7 days on soft and stiff hydrogels with non-targeting shRNA (GIPZ), or on stiff hydrogels with two shRNAs targeting RUNX2 (n=3 biological replicates). f, Immunoblot of RUNX2 in MDA-231, T47D and SUM149 cells preconditioned on soft and stiff hydrogels for 7 days (representative of n=2 biological replicates). g, Immunoblot of RUNX2 in SUM159 and T47D cells cultured for 7 days in 3D matrix consisting of soft 1.0 mg/mL rat-tail collagen-I, or stiff 1.0 mg/mL rat-tail collagen-I crosslinked with PEG-di(NHS) to stiffen the collagen lattice without changing ligand density. (representative of n=3 biological replicates). h, Immunoblot of pERK and ERK in SUM159 cells cultured on stiff hydrogels with 20 µM PD98059, 30 µM blebbistatin, 100 nM dasatinib, 1 µM Faki14 or DMSO for 1 hour prior to lysis. (representative of n=3 biological replicates). i, Immunofluorescence of pFAK, paxillin, and F-actin in SUM159 cells cultured on stiff or soft hydrogels for 7 days. j, Immunoblot of OPN in SUM159 cells preconditioned for 7 days on soft and stiff hydrogels with non-targeting shRNA (GIPZ), on stiff hydrogels with two shRNAs targeting RUNX2, on soft hydrogels with constitutively-active MEK-DD expression, or on stiff hydrogels with MEK inhibitor PD98059 (20 µM). (representative of n=3 biological replicates). k,l, RT-qPCR of OPN (k) and GM-CSF (l) in SUM159 cells preconditioned for 7 days on stiff hydrogels conjugated with either poly D-lysine (PDL) to reduce integrin binding, or collagen-conjugated with DMSO (control), 30 µM blebbistatin, 100 nM dasatinib or 1 µM Faki14 in media changed every other day. (n=3 biological replicates). m, Immunoblot showing phospho-AKT levels in SUM159 cells treated with DMSO (control) or AKT inhibitor (1 µM MK-2206). (representative of n=2 biological replicates). n, RT-qPCR of RUNX2 target genes in SUM159 cells preconditioned for 7 days on stiff hydrogels and treated with DMSO or 1 µM AKT inhibitor MK-2206 (n=3 biological replicates). o, RT-qPCR of RUNX2 target genes and CTGF (YAP target) in MCF10A-Neu and MCF10A-Neu-RUNX2 cells preconditioned as indicated (n=3 biological replicates). p, Immunofluorescence corresponding to FIG. 3e.
Figure 9B:
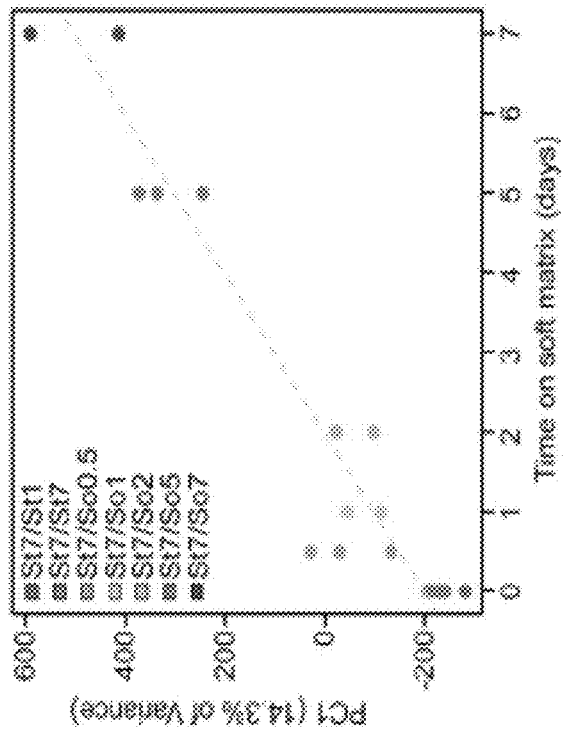
Figure 9C:
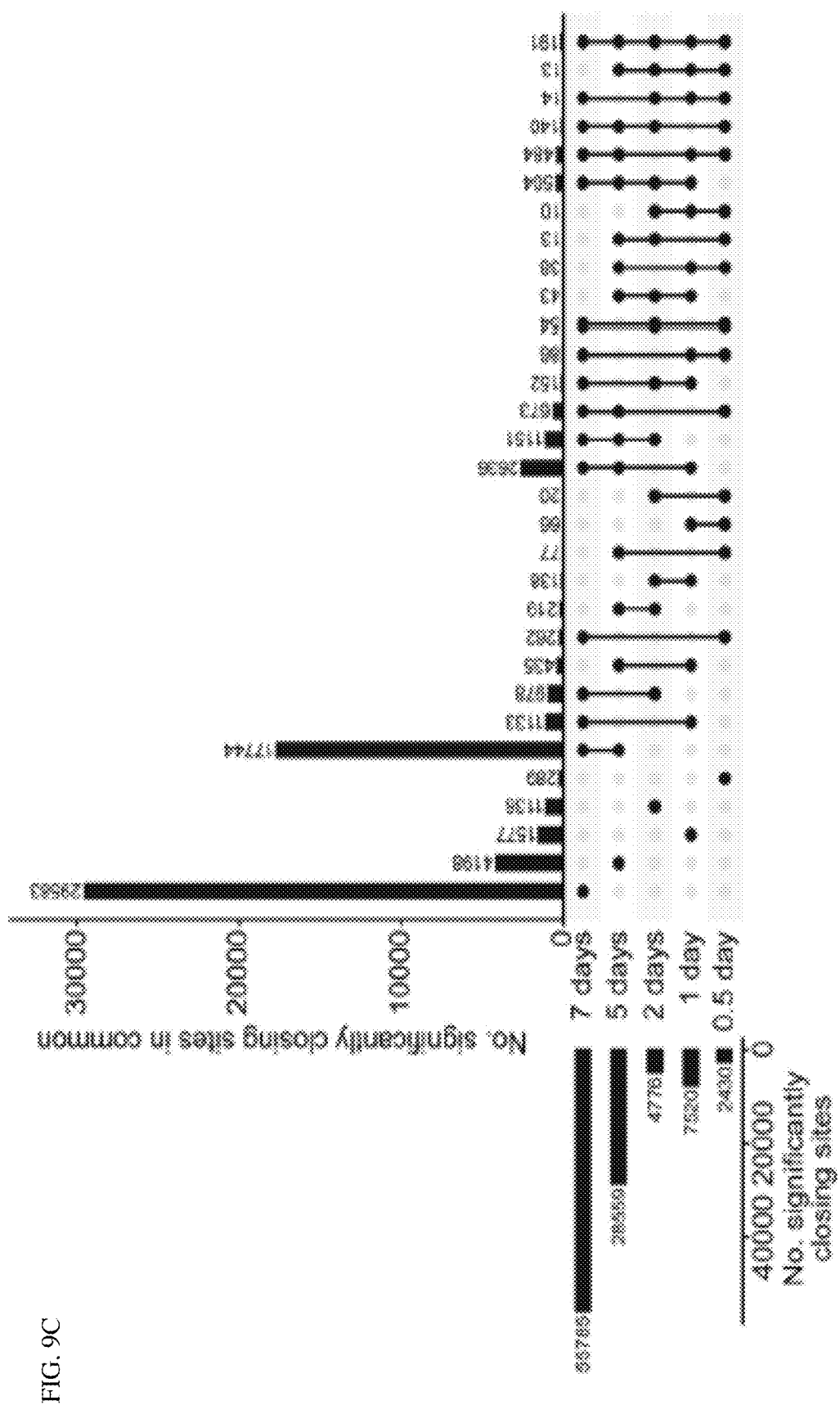
Figure 9I:
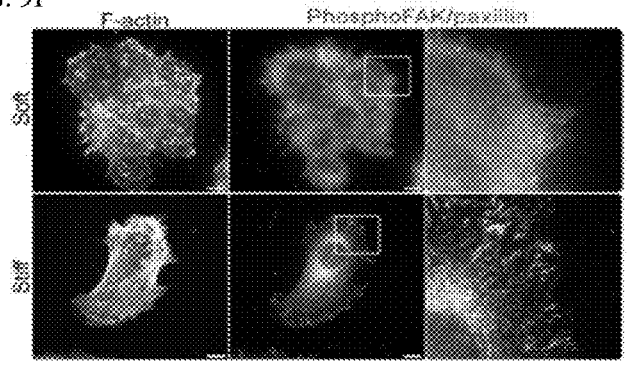
Figure 9J:
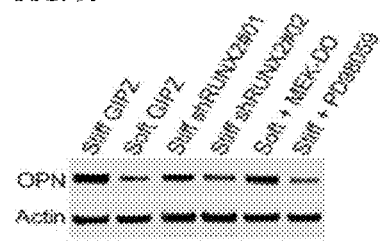
Figure 9K:
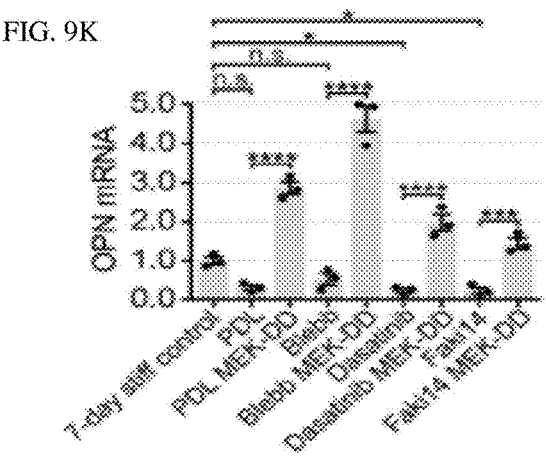

A function-based discovery approach was used to identify candidate drivers of mechanical memory-regulated bone metastasis. Focusing on the induction of transcriptional memory by mechanotransduction, upstream transcriptional regulators were identified using Ingenuity Pathway Analysis and the mechanically-induced gene set. Next, these regulators were cross-listed with a large database of metastasis-associated genes (Zheng, G. et al. Nucleic Acids Res. 46, D950-D955 (2018)); within the list of common genes, those with evidence of transcriptional memory function were selected, with the rationale that such candidates would offer the type of phenotype durability observed after mechanical conditioning. This yielded 5 candidates (FIG. 3a). Among these, the osteogenic transcription factor RUNX2 was especially of interest because of its well-described roles in invasion, bone metastasis and genomic bookmarking, which selectively maintains open chromatin signatures during cell division, thus promoting transcriptional memory in daughter cells (Young et al., supra; Pratap et al., supra; Kadauke, S. & Blobel, G. A. Epigenetics Chromatin 6, 6 (2013)). Using the assay for transposase-accessible chromatin, ATAC-seq (Buenrostro, J. D. et al., Nat. Methods (2013)), the dynamics of chromatin accessibility following the transition from stiff to soft matrices over a 7-day time course, i.e., loss of mechanotransduction was examined (FIG. 9a). The similarity in epigenomes across samples was largely driven by the amount of time cells were conditioned in a soft environment (FIG. 3b and FIG. 9b,c). To better understand the epigenetic code underlying dynamic differences during environmental conditioning, two sets of accessible sites that close upon transition to soft substrate, yet with different patterns of change were examined: a 'delayed-closing' set, and a 'quick-closing' set. Using a likelihood ratio test framework, delayed closing sites were considered as those with no significant change in accessibility by day 2 on soft matrix, but with significantly less accessibility by day 5. In contrast, quick-closing sites were those exhibiting a significant loss of accessibility after only 12 hours in the soft environment, which is a period of time shorter than the mean population doubling (FIG. 9d). 7,277 delayed-closing genomic regions were identified, which should be enriched for regulatory sites responsible for mechanical memory. Using a genomic region-based pathway enrichment analysis (McLean, C. Y. et al. Nat. Biotechnol. (2010)), it was found that these sites are implicated in 'abnormal bone remodeling' (q=0.015), among other pathways (Table 5). Furthermore, using unbiased motif enrichment analysis for the sequences at these loci, it was identified that the RUNX consensus binding motif is enriched in delayed-closing (p=1e-33), but not quick-closing sites (FIG. 3c); importantly, RUNX binding motifs were also significantly enriched in sites that maintained their accessibility throughout the time course after transitioning to soft (p=1e-1458) (Table 6). Together, these data are consistent with the bookmarking function of RUNX2 and its role in promoting mechanical memory. By comparison, the consensus binding motif of BACH (known regulator of bone metastasis (Liang, Y. et al. J. Biol. Chem. (2012))) is enriched in the quick-closing sites, indicating that it does not play a role in mechanical memory. These analyses prioritized RUNX2 for further investigation.

Figure 13A:
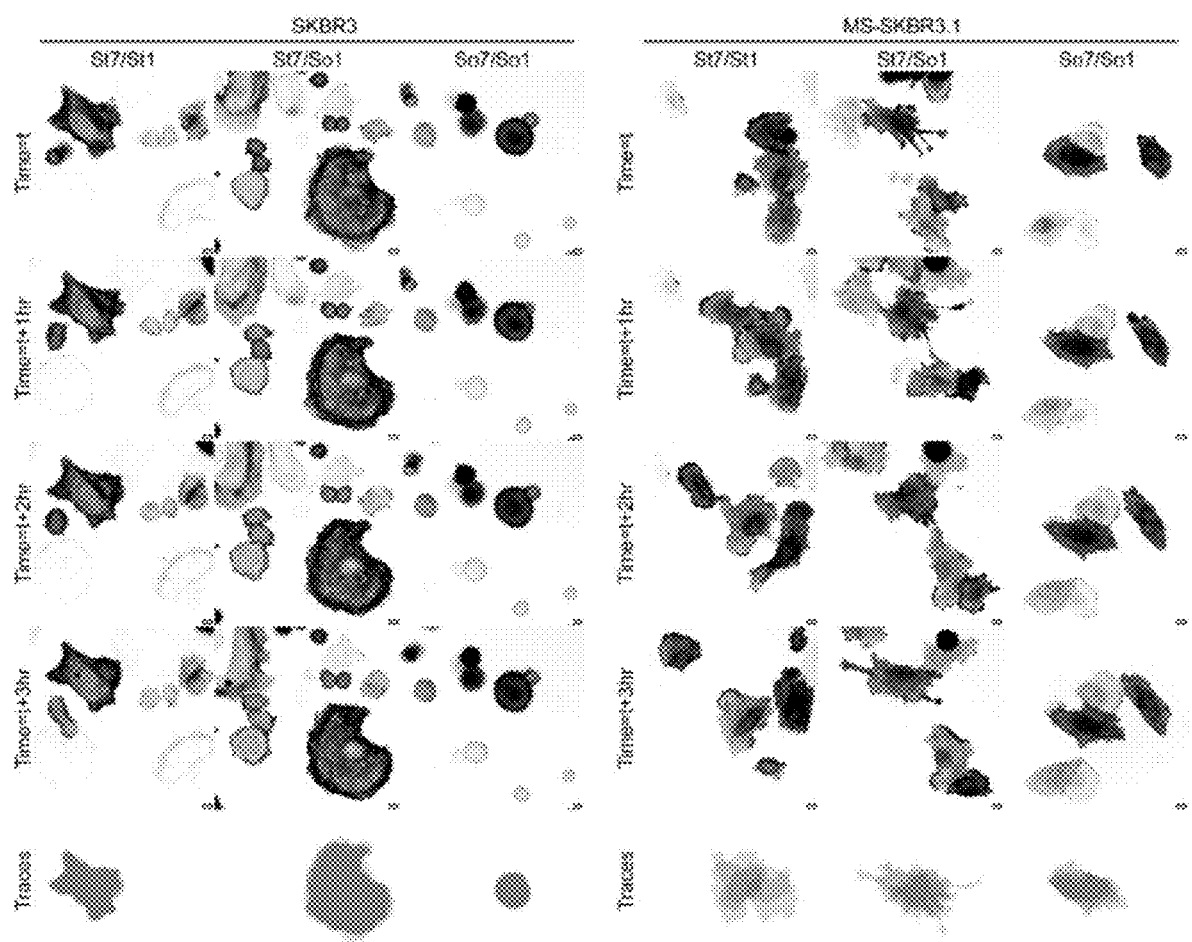
FIG. 13. Mechanically-sensitized MS-SKBR3.1 cells have functional mechanical memory and increased nuclear localization of RUNX2. a, Cytoskeletal dynamics of iRFP-Lifeact-expressing SKBR3 and MS-SKBR3.1 cells, 10 hours after plating on collagencoated glass, preconditioned on stiff and/or soft hydrogels as indicated. b, RT-qPCR of RUNX2 and ERBB2 in cells preconditioned for 7 days on stiff hydrogels (n=3 biological replicates). c, Quantification of cell size from (a), showing differences amongst the SKBR3 cell groups but not MS-SKBR3.1 cell groups (n=36 cells total in each condition from n=3 biological replicates). d, Quantification of dynamics score from (a) showing differences amongst the MS-SKBR3.1 cell groups but not SKBR3 cell groups (n=36 cells total in each condition from n=3 biological replicates). e, Invasion fronts of SKBR3 and MS-SKBR3.1 cells, preconditioned on stiff and/or soft hydrogels as indicated, after 20 hours of live-cell tracking in 3D collagen. Gray dots=non-invasive cells; black dots=invasive cells. f,g, Rate of translocation of the invasion front (f) and number of invading cells per field (g) from (e) (n=3 biological replicates with n=3 technical replicates). h,i, Immunofluorescence staining (h) and quantification of nuclear localization (i) of RUNX2 in SKBR3 and MS-SKBR3.1 cells (n=36 cells each from n=3 biological replicates). j, RT-qPCR of RUNX2 and YAP gene targets and the adipogenic biomarker PLIN1 in SKBR3 and MS-SKBR3.1 cells preconditioned as indicated (n=3 biological replicates).
Figure 13B:
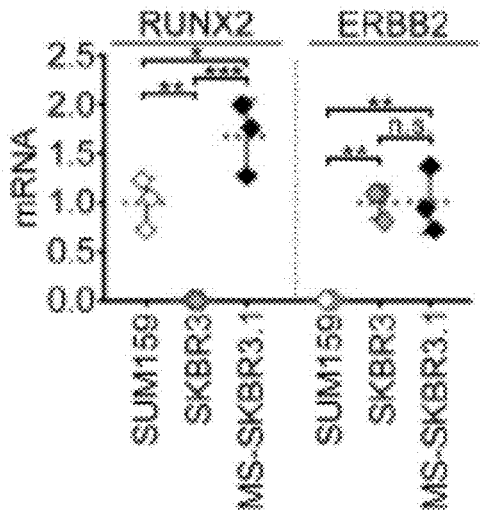
Figure 13C:
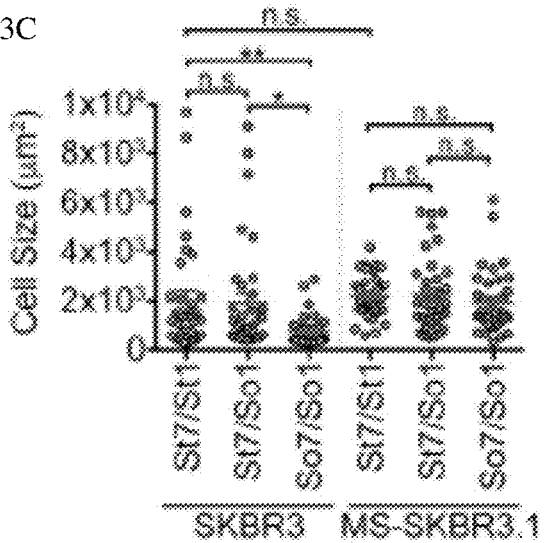
Figure 13D:
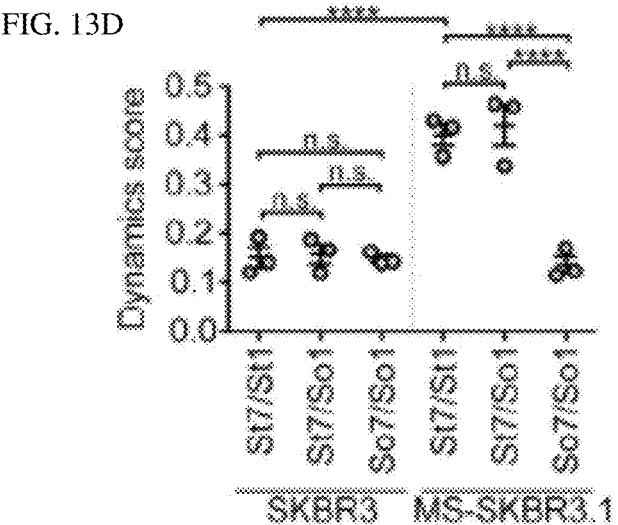
Figure 13E:
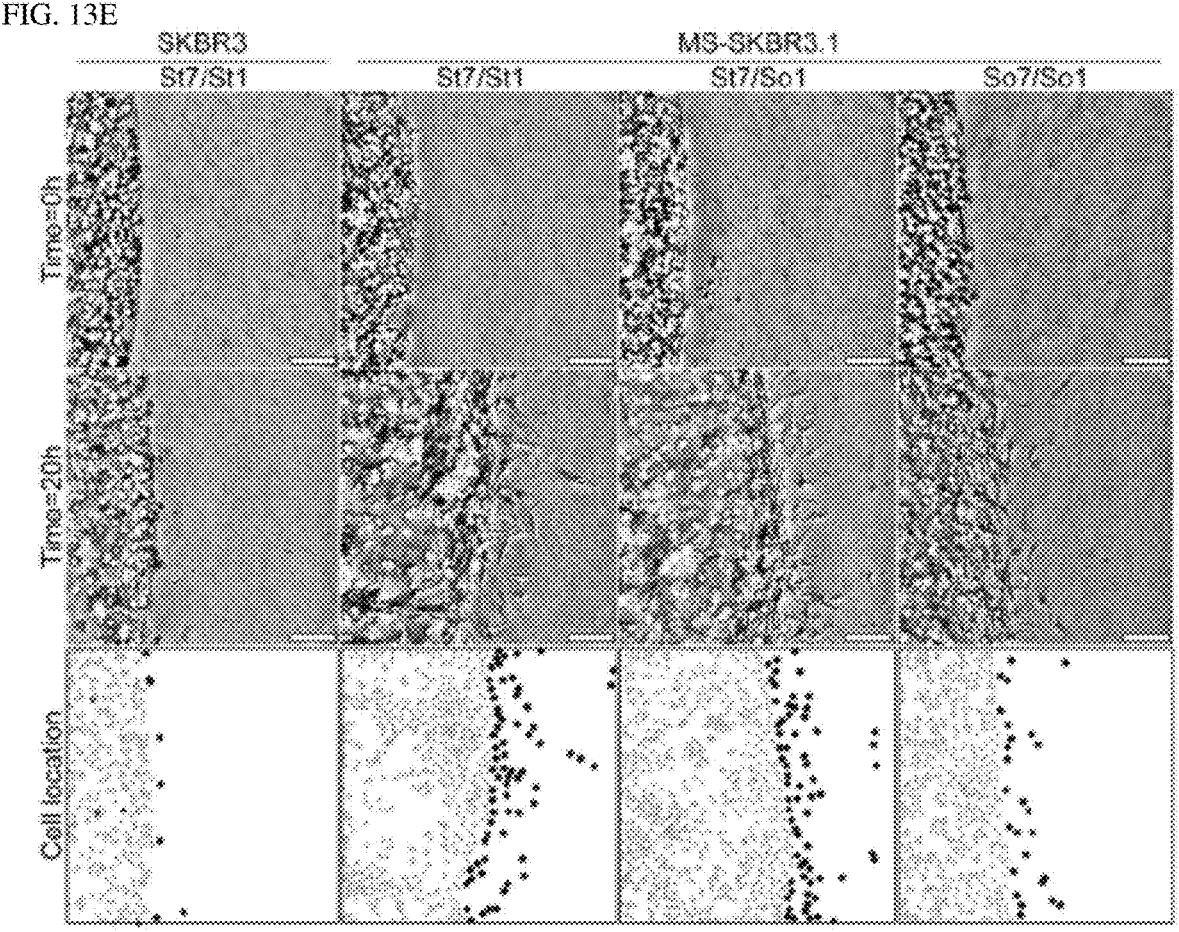
Figure 13F:
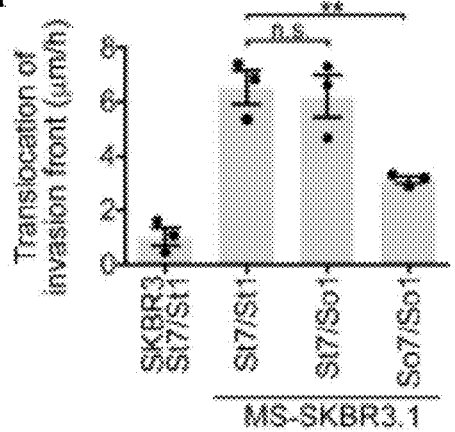
Figure 13G:
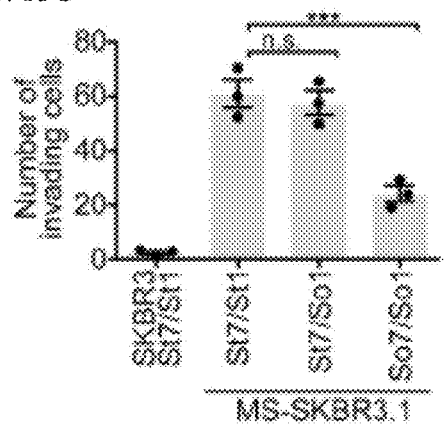
Figure 13H:
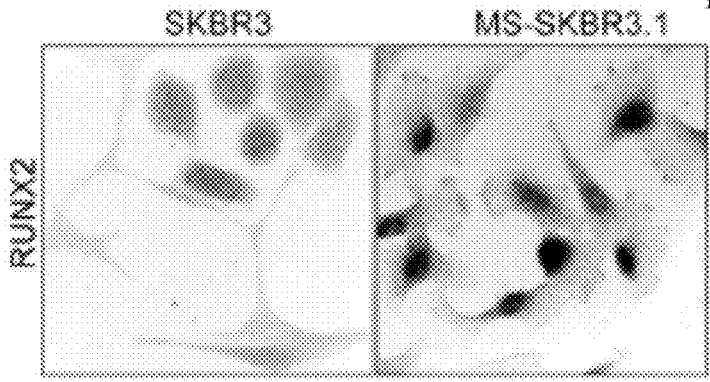
Figure 13I:
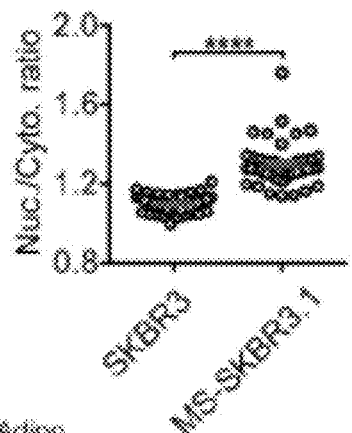
Figure 13J:
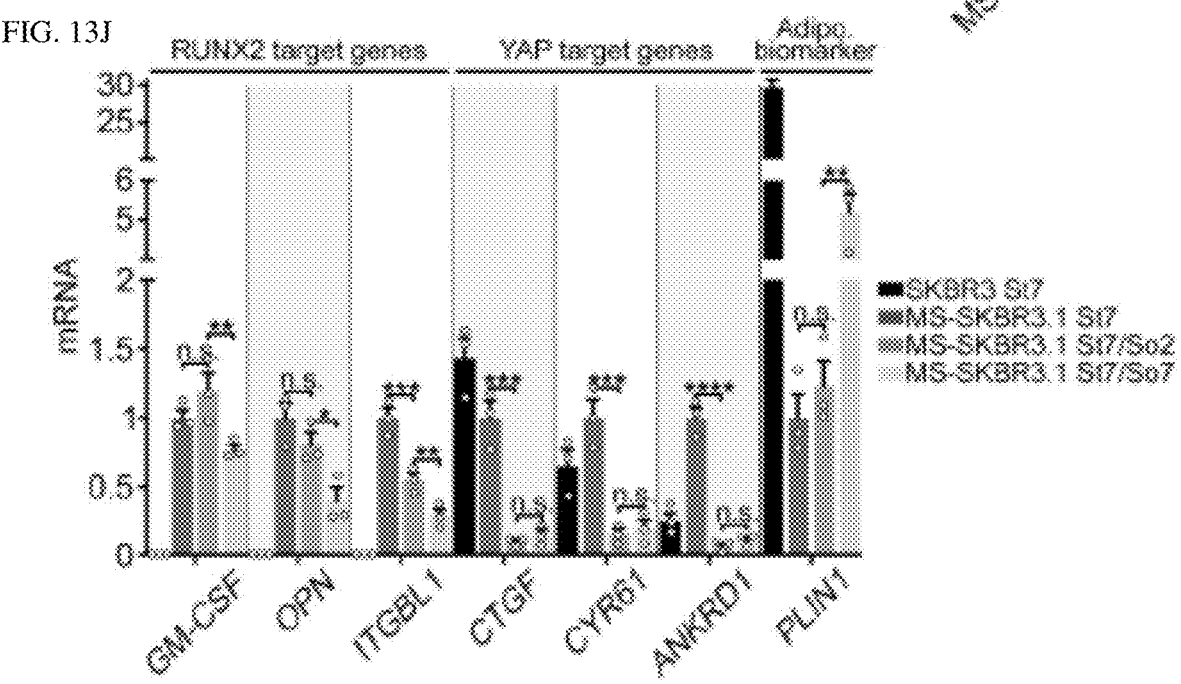
Figure 13K:
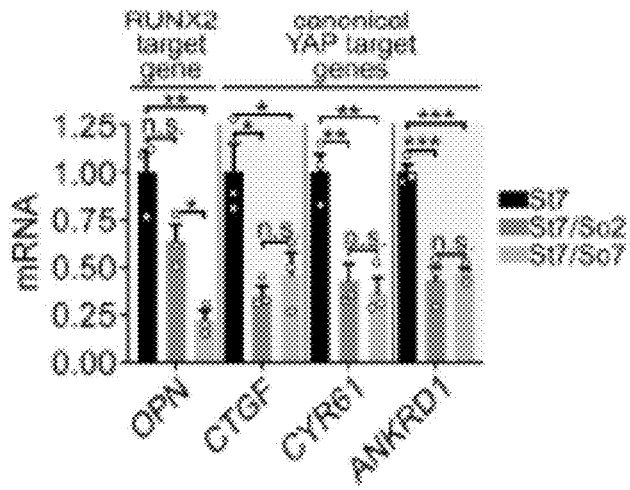

In a panel of cell lines and PDX primary cells, increased RUNX2 was observed in stiff-vs soft-preconditioned cells, in both 2D and 3D culture systems (FIG. 3e,f). Expression of known RUNX2 target genes (Inman, C. K. & Shore, P. J. Biol. Chem. 278, 48684-48689 (2003); Li, X.-Q. et al. (2015); Little, G. H. et al., Nucleic Acids Res. 40, 3538-47 (2012)) was examined, and it was found that the osteolytic genes GM-CSF, OPN, ITGBL1 and IL8 were induced by stiffness in a RUNX2-dependent manner (FIG. 3d and FIG. 9e)). Consistent with mechanical memory, upon removal from stiffness, RUNX2 target transactivation was only gradually lost, concomitant with a gradual increase in PLIN1, an adipogenic biomarker (FIG. 3g). YAP target expression did not persist similarly to RUNX2 targets (FIG. 13k). However, despite being a well-established transducer of mechanical cues, YAP has no known gene bookmarking function (Kadauke et al., supra; Moroishi, T. et al, Nat. Rev. Cancer 15, 73-79 (2015)).

Figure 9M:
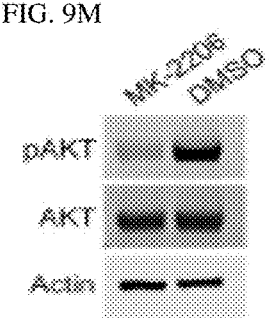
Figure 9L:
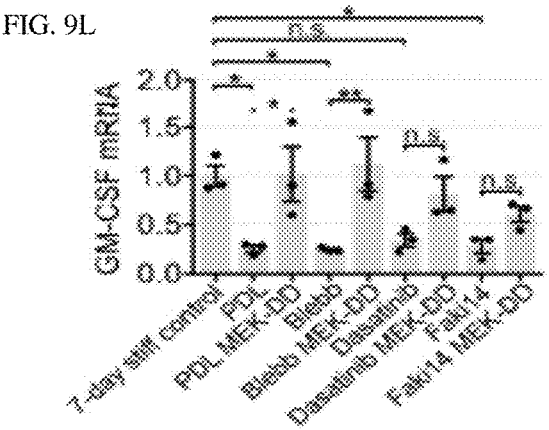
Figure 9N:
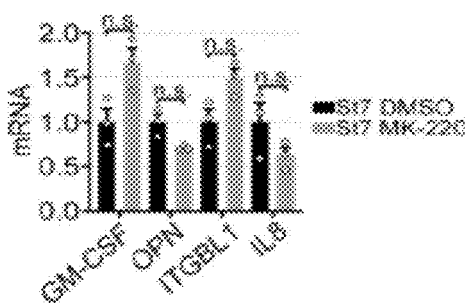

Mechanistically, increased ERK activation was observed on stiff hydrogels, and it was confirmed that expression of RUNX2 targets is downstream of stiffness-induced ERK activation of RUNX2; moreover, this was dependent on the activity of the classic mechano transduction mediators, Src and FAK, in addition to the contractile activity of the actomyosin cytoskeleton (FIG. 9h-l). On the other hand, inhibition of AKT, another regulator of RUNX2 (Tandon, M. et al., Breast Cancer Res. (2014)), did not similarly suppress RUNX2 targets at 8 kPa stiffness (FIG. 9m,n).

Figure 9O:
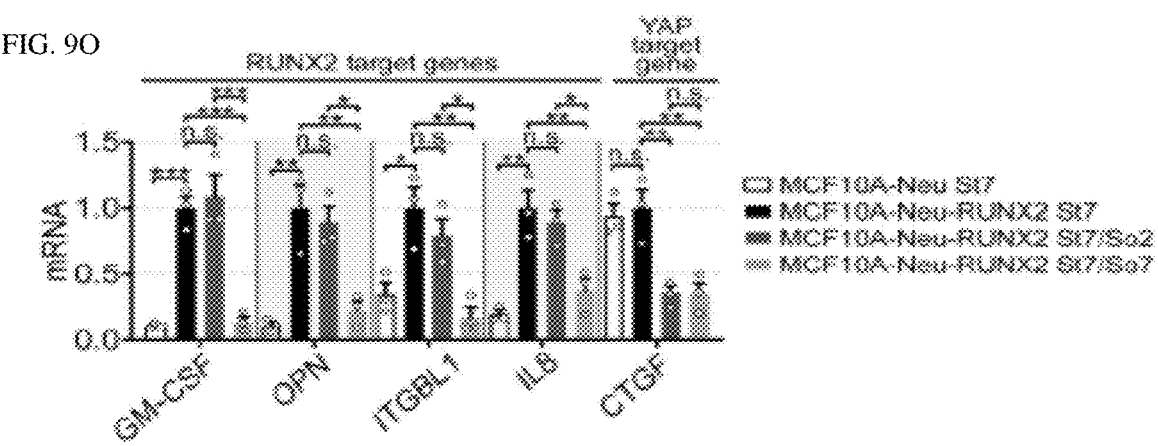

To further validate the involvement of RUNX2 in mechanical memory, MCF10A-Neu-RUNX2 cells were generated by expressing human RUNX2 in Neu-transformed MCF10A cells (Leung, C. T. & Brugge, J. S. Nature (2012)), which express low levels of endogenous RUNX2 (FIG. 14). The expression of the osteolytic RUNX2 target genes was induced by exogenous RUNX2 on a stiff substrate and remained significantly elevated after two days on soft, compared to seven days on soft (FIG. 9o). These data are consistent with the role of RUNX2 in promoting mechanical-memory.

Figure 9P:
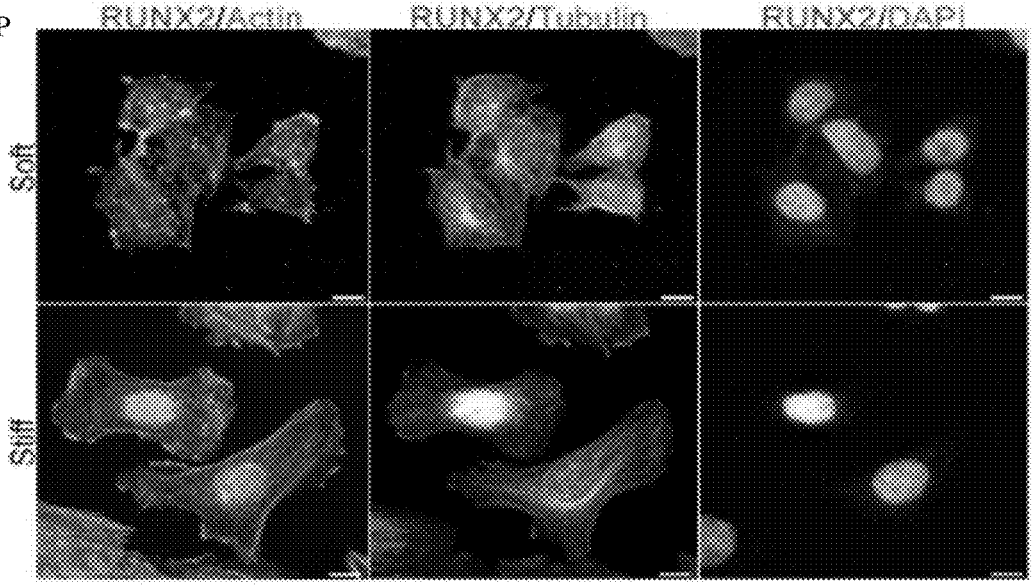
Figure 10:
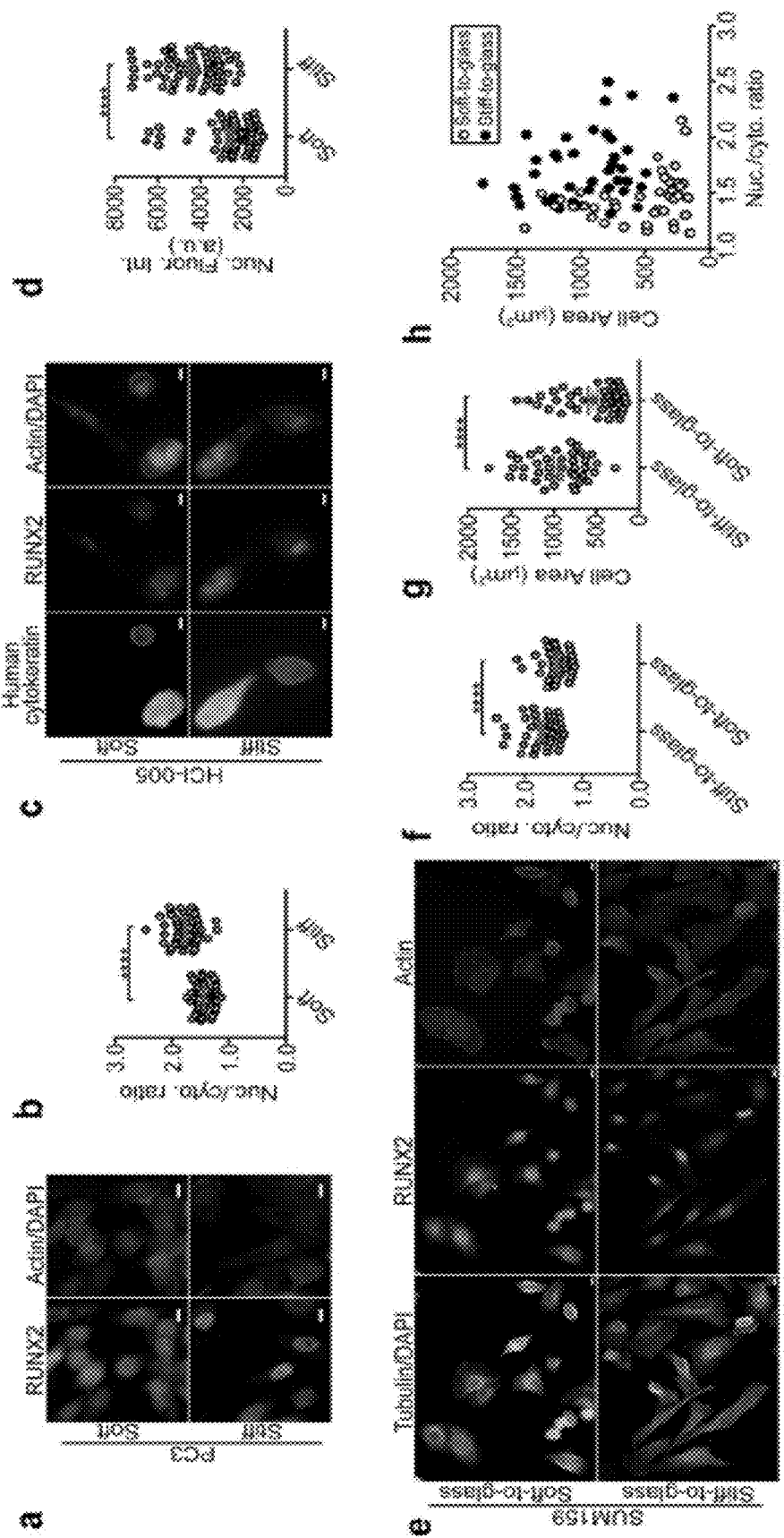
FIG. 10. Substrate stiffness in situ and stiffness-memory both promote nuclear localization of RUNX2, independent of suprastatistical stiffness tolerance or cell spreading. a,b, Immunofluorescence staining (a) and quantification of nuclear localization (b) of RUNX2 in PC3 prostate cancer cells (n=50 cells each from n=3 biological replicates). c,d, Immunofluorescence staining of RUNX2 (c) and quantification of nuclear intensity of RUNX2 in CK+ cells (d) in suprastatistical stiffness-naive patient-derived xenograft HCI-005 tumor cells (n=60 cells each from n=3 biological replicates). e, Immunofluorescence staining in SUM159 cells, preconditioned on soft and stiff hydrogels for 7 days before transferring to collagen-coated glass for 3 hours. f,g, Quantification of nuclear RUNX2 (f) and cell area (g) from cells in (e). h, Correlation analysis of (f,g) showing no positive intracellular correlation between cell spreading and nuclear RUNX2 in either soft- or stiff-preconditioned cells spreading on glass (n=40 cells each from n=3 biological replicates).

With respect to localization, RUNX2 was retained in the cytoplasm in both soft preconditioned cells on glass and soft-cultured cells in situ, compared to stiff-preconditioned cells on glass and stiff-cultured cells in situ. This localization pattern was independent of cell spreading, suggesting that it is not due to volume effect (FIG. 3h, I and FIG. 9p, 10-a-h). Importantly, in supraphysiological stiffness-naive HCI-005 PDX primary cells, nuclear RUNX2 was increased on stiff hydrogels compared to soft, demonstrating that this phenotype is not restricted to plastic tolerant cell lines (FIG. 10c,d). Lastly, previous studies have demonstrated that RUNX2 is retained in the cytoplasm by stabilized microtubules (Pockwinse, S. M. et al. J. Cell. Physiol. 206, 354-362 (2006)); by pharmacologically stabilizing actin or tubulin in stiff-cultured cells, or destabilizing the cytoskeleton in soft-cultured cells, it was possible to confirm this finding through the expected directional changes in cytoplasmic retention of RUNX2 (FIG. 11a-d).

Figure 12:
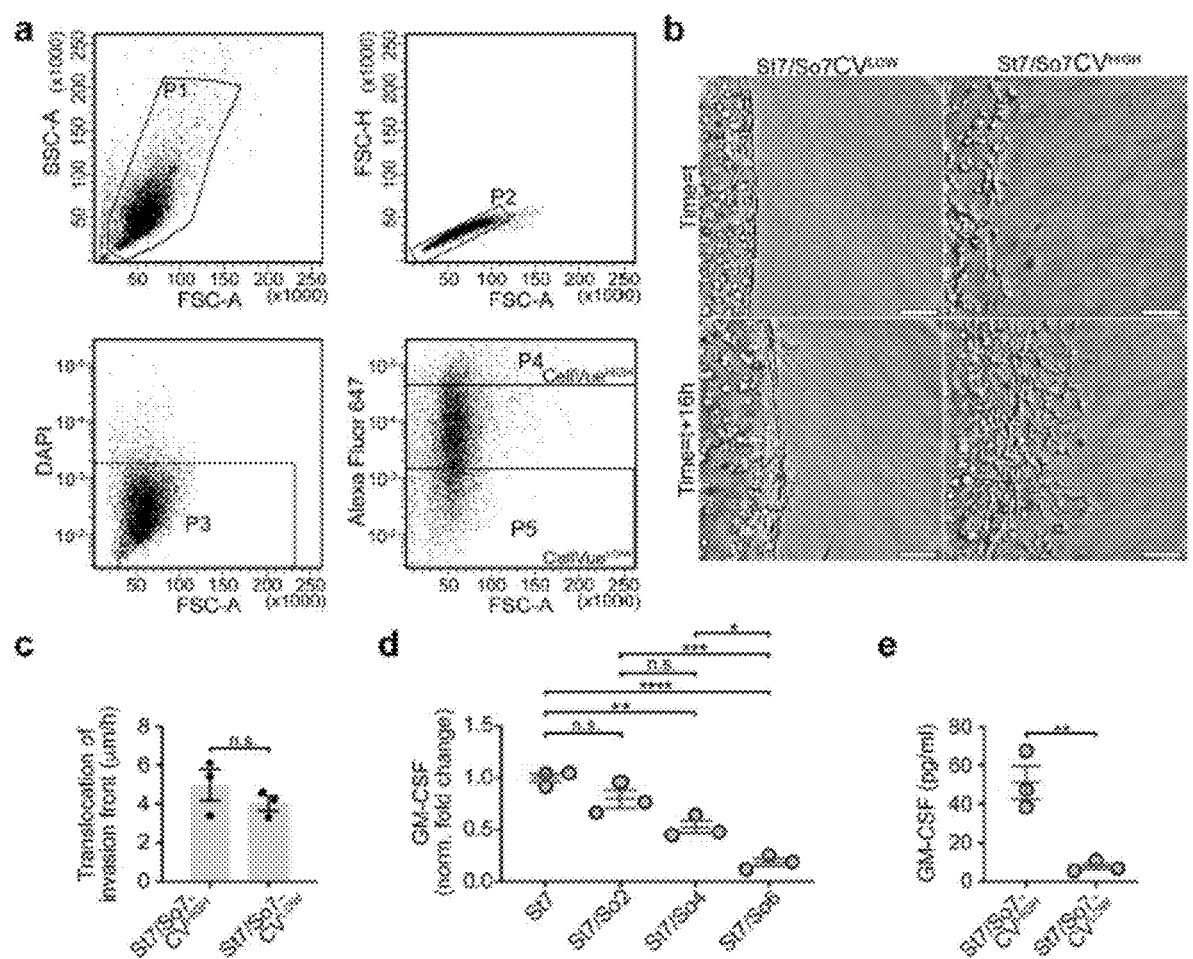
FIG. 12. Mechanical memory is more durable in low-proliferative cells. a, FACS plots depicting the sequential gating strategy for enriching single, live (by exclusion of DAPI), CellVue Claret Far-Red (Alexa Fluor 647) HIGH (P4) and LOW (P5) SUM159 cells. b, Enhanced depth-of-focus DIC images corresponding to FIG. 3i. c, Rate of translocation of the invasion front corresponding to FIG. 3i (n=3 biological replicates with n=3 technical replicates). d,e, GM-CSF ELISA for SUM159 cells preconditioned on stiff and/or soft hydrogels as indicated (n=3 biological replicates with n=3 technical replicates).

As a bookmarking transcription factor, RUNX2 remains bound to chromatin through mitosis to maintain cellular phenotype across cell generations (Young et al., supra). However, without continual activation by matrix stiffness, it was contemplated that RUNX2 activity may decrease after multiple cell divisions. Therefore, it was hypothesized that mechanical memory might be erased via proliferation. To test this, cells were preconditioned on stiff hydrogels for 7 days to encode mechanical memory, and then labelled with CellVue (a membrane dye retention approach to track proliferation) just before switching them to soft hydrogels for 7 days (FIG. 3j and FIG. 12a)). RUNX2 target expression was higher in the low-proliferative St7/So7CellvueHIGH cells compared to St7/So7CellvueLOW cells (FIG. 3k and FIG. 12d,e). In addition, St7/So7CellvueHIGH cells retained greater invasive ability than St7/So7CellvueLOW cells (FIG. 3l,m and FIG. 12b,c). To determine if long-term memory is causally related to reduced proliferation, cell-cycle progression was reducted directly and indirectly. Inhibition of CDK4/6 extended OPN expression upon removal from stiffness, yet it did not induce expression de novo in soft-preconditioned cells that had already lost their memory (FIG. 3n). Similar results were obtained when DNMT1 was inhibited (FIG. 3n), which is also consistent with reports showing OPN expression is regulated by promoter methylation (Shen, C.-J. et al. Biomed Res. Int. 2014, 327538 (2014)). Together, these results indicate that in mechanically-sensitive cells, RUNX2 activity is associated with the maintenance of mechanical memory, and low-proliferative cells possess more durable mechanical memory.

In contrast to SUM159 cells, SKBR3 breast cancer cells did not exhibit substantial changes in cytoskeletal dynamics or invasion in response to mechanical conditioning (FIG. 13-a-g). This correlates with their limited tumorigenicity and low metastatic potential in vivo (Holliday, D. L. & Speirs, V. Breast Cancer Res. 13, 215 (2011)). A new subline, MS-SKBR3.1 cells, were generated by extended culture in a mechanical sensitization media containing ascorbic acid and phosphate, which are osteogenic factors known to be elevated in breast tumors (Langemann, H. et al., Int. J. Cancer 43, 1169-1173 (1989); Bobko, A. A. et al. Sci. Rep. 7, 41233 (2017)). In MS-SKBR3.1 cells, stiffness induced RUNX2 localization to the nucleus, and it triggered mechanical memory that was reflected in cytoskeletal dynamics, RUNX2 target expression, and 3D invasion (FIG. 13a-j). Together, these data further illustrate the link between pathological stiffness response, RUNX2 activity, and bone metastatic competency.

To determine the role of RUNX2-mediated mechanical memory in metastasis, RUNX2 point mutants were generated at two crucial ERK phosphorylation sites: RUNX2-S301A-S319A (RUNX2-SA), which is a non-phosphorylatable mutant that is unresponsive to ERK stimulation, and RUNX2-S301E-S319E (RUNX2-SE), which is a phosphomimetic mutant that exhibits high transcriptional activity irrespective of ERK stimulation (Ge, C. et al. J. Biol. Chem. 284, 32533-32543 (2009)). Crucially, phosphorylation of these sites by ERK is necessary for the epigenetic modification of chromatin by RUNX236, central to its role in transcriptional memory (Li, Y. et al., J. Cell. Physiol. 232, 2427-2435 (2017)). RUNX2-WT cells had higher RUNX2 target expression on stiff hydrogels compared to soft, indicating that stiffness can activate overexpressed wild-type RUNX2; in addition, RUNX2-SE cells on soft hydrogels had partially rescued stiffness-induced target expression, while RUNX2-SA cells on stiff hydrogels had dramatically reduced target expression (FIG. 4a and FIG. 14c-e). These changes in RUNX2 activity were reflected in changes in invasiveness in vitro and in osteolytic bone metastasis after intracardiac injections in vivo (FIG. 4b-d and FIG. 14a-c, 15a-e). Notably, nonosseous metastases, i.e., lung, liver and brain, showed dissimilar patterns of disease burden (FIG. 15f-j). In addition, since RUNX2 targets (particularly OPN) are known to mediate adhesion to bone matrix, and to activate osteoclasts (Pratap et al., supra; Bernards, M. T. et al., Colloids Surfaces B Biointerfaces 64, 236-247 (2008); Feng, X. & Teitelbaum, S. L. Nat. Publ. Gr. 1, 11-26 (2013)), it was determined how stiffness-activated RUNX2 affected these parameters. Compared to soft-preconditioned, stiff preconditioned RUNX2-WT cells adhered/spread faster and protruded more on synthetic bone matrix, and induced more paracrine osteoclastogenesis (FIG. 4e and FIG. 15k-p). This phenotype was mimicked in soft-preconditioned RUNX2-SE cells, and repressed in stiff-preconditioned RUNX2-SA cells, confirming the importance of stiffness induced phosphorylation in promoting mechanical memory.

In an exemplary model (FIG. 4f), mechanical memory is mediated by RUNX2, a mechanically-sensitive gene bookmarker. RUNX2 is activated by fibrotic-like stiffness, first by nuclear localization following increased cytoskeletal dynamics, and then by mechanotransduction via ERK phosphorylation. Mechanical memory can be mimicked in soft-preconditioned cells with overexpression of a phosphomimetic RUNX2 mutant, and repressed in stiff-preconditioned cells with overexpression of a nonphosphorylatable RUNX2 mutant. RUNX2-mediated mechanical memory is necessary and sufficient to enhance adhesion to synthetic bone matrix, to activate osteoclasts, and to promote osteolytic bone metastasis. Mechanical memory is lost gradually upon removal from the encoding microenvironment, concomitant with proliferation. A corollary to this relationship between proliferation and mechanical memory is that osteolytic capacity upon exit from dormancy may be a latent function of this phenomenon. Furthermore, since cancer induced osteolysis is perpetuated by a positive-feedback loop between osteoclasts and cancer cells known as the "vicious cycle," a crucial role for mechanical memory may be to kick-start this process (Guise, T. A. et al. Clin. Cancer Res. 12, 6213s-6216s (2006)).

This study demonstrates that mechanical conditioning is associated with bone metastasis in animal models and clinical data. Since bone metastases inflict the greatest morbidity associated with breast cancer and become incurable in a majority of women with advanced disease (Coleman, R. E. Clin. Cancer Res. 12, 6243s-6249s (2006)), it is important and useful to predict their genesis. The MeCo score is a proxy for assessing tumor stiffness response, rather than stiffness itself. This distinction is advantageous since most invasive breast tumors are stiffer than surrounding tissue (Evans, A. et al. Radiology 263, 673-677 (2012)), yet only a fraction produce osteolytic metastases.

TABLE 1

RT-qPCR primers

| Gene | Forward (5'-3') | SEQ ID NO: | Reverse (3'-5') | SEQ ID NO: |
| --- | --- | --- | --- | --- |
| RUNX2 | ACTGGCGCTGCAACAAGAC | 6 | CACCAATGACAGTACCGCCC | 18 |
| GM-CSF | CACTGCTGCTGAGATCAATGAAA | 7 | CTCGGCTGGACGGATGTCTG | 19 |
| OPN | TTGCAGCCTTCTCAGCCA | 8 | TCTTAACGTCACTAAACGAAAAC | 20 |
| ITGBL1 | AATTCAGATGGAAGTGGACTTGTGT | 9 | CGATGACGTTCCGACCAAGC | 21 |
| IL8 | ACACTGCGCCAACACAGAAA | 10 | AGACAGACCTGGGGTTCCTT | 22 |
| MMP13 | TTCCCAGTGGTGGTGATGAA | 11 | TGGATGTTTAGAGCGCCCTT | 23 |
| CTGF | GCGAGGAGTGGGTGTGTGA | 12 | TGTCTCACCTCGCGGACAAG | 24 |
| PLIN1 | CTATGAGAAGGGCGTGCAGAG | 13 | CTGGTGGACCTCCTTTTCTAGG | 25 |
| EEF1A1 | TCGGGCAAGTCCACCACTAC | 14 | AGTTCATACGGACCCAGAACC | 26 |
| CYR61 | AAGGGGCTGGAATGCAACTT | 15 | GTCAGTCTCCCGTCTGGGAC | 27 |
| ANKRD1 | CGGTGAGACTGAACCGCTAT | 16 | GCTACCTAGACCACGATGTG | 28 |
| ERBB2 | GACTGCCTGTCCCTACAACTACC | 17 | GCTCACACGATACCAGACCC | 29 |

TABLE 2

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| ABCC9 | 10060 | Stiff | MBLIP | 8512 | Stiff | ELF3 | 1999 | Stiff | RTEL1 | 51750 | Stiff |
| ABCF2 | 10061 | Stiff | MBLAC1 | 255374 | Stiff | ELFN1 | 392617 | Stiff | RTEL1-TNFRSF6B | 100533107 | Stiff |
| ABCG2 | 9429 | Stiff | MCAT | 27349 | Stiff | ELMO3 | 79767 | Stiff | RTN4IP1 | 84816 | Stiff |
| ABHD11 | 83451 | Stiff | MCF2 | 4168 | Stiff | EMCB | 10328 | Stiff | RTN4R | 65078 | Stiff |
| ABHD13 | 84945 | Stiff | MCF2L | 23263 | Stiff | EMG1 | 10436 | Stiff | RUNX3 | 864 | Stiff |
| ABHD5 | 51099 | Stiff | MCIDAS | 345643 | Stiff | EN2 | 2020 | Stiff | RUVBL1 | 8607 | Stiff |
| ACAN | 176 | Stiff | MCM10 | 55388 | Stiff | ENDOD1 | 23052 | Stiff | RYR3 | 6263 | Stiff |
| ACOX2 | 8309 | Stiff | MCM8 | 84515 | Stiff | ENOX2 | 10495 | Stiff | S1PR1 | 1901 | Stiff |
| ACSL3 | 2181 | Stiff | MCM8-AS1 | 101929225 | Stiff | ENPP1 | 5167 | Stiff | SAC3D1 | 29901 | Stiff |
| ACTL10 | 170487 | Stiff | MCM9 | 254394 | Stiff | ENTPD1 | 953 | Stiff | SACS | 26278 | Stiff |
| ACTL8 | 81569 | Stiff | MCOLN1 | 57192 | Stiff | ENTPD1-AS1 | 728558 | Stiff | SAMD5 | 389432 | Stiff |
| ACTR5 | 79913 | Stiff | MDFI | 4188 | Stiff | ENTPD7 | 57089 | Stiff | SAP30L-AS1 | 386627 | Stiff |
| ADAM19 | 8728 | Stiff | MED27 | 9442 | Stiff | EPB41L3 | 23136 | Stiff | SAPCD2 | 89958 | Stiff |
| ADAM23 | 8745 | Stiff | MEGF10 | 84466 | Stiff | EPB41L4B | 54566 | Stiff | SBDSP1 | 155370 | Stiff |
| ADAMTS12 | 81792 | Stiff | MESDC1 | 59274 | Stiff | EPHB2 | 2048 | Stiff | SCAMP5 | 192683 | Stiff |
| ADAMTS14 | 140766 | Stiff | METTL1 | 4234 | Stiff | EPHB6 | 2051 | Stiff | SCARA3 | 51435 | Stiff |
| ADAT1 | 23536 | Stiff | MFSD2A | 84879 | Stiff | EPHX3 | 79852 | Stiff | SCLY | 51540 | Stiff |
| ADCY1 | 107 | Stiff | MGAT5B | 146664 | Stiff | EPT1 | 85465 | Stiff | SCO1 | 6341 | Stiff |
| ADCY7 | 113 | Stiff | MGC12916 | 84815 | Stiff | EPYC | 1833 | Stiff | SCUBE1 | 80274 | Stiff |
| ADD2 | 119 | Stiff | MGLL | 11343 | Stiff | ERCC6L | 54821 | Stiff | SDC1 | 6382 | Stiff |
| ADGRG2 | 10149 | Stiff | MICALL1 | 85377 | Stiff | EREG | 2069 | Stiff | SDF2L1 | 23753 | Stiff |
| ADGRG6 | 57211 | Stiff | MIIP | 60672 | Stiff | ESCO2 | 157570 | Stiff | SDSL | 113675 | Stiff |
| ADRM1 | 11047 | Stiff | MIR1237 | 100302280 | Stiff | EXO1 | 9156 | Stiff | SEC11C | 90701 | Stiff |
| AEN | 64782 | Stiff | MIR1306 | 100302197 | Stiff | EXO5 | 64789 | Stiff | SEMA3D | 223117 | Stiff |
| AFAP1L2 | 84632 | Stiff | MIR17HG | 407975 | Stiff | EXOG | 9941 | Stiff | SEMA4D | 10507 | Stiff |
| AFP | 174 | Stiff | MIR22HG | 84981 | Stiff | EXOSC3 | 51010 | Stiff | SEMA7A | 8482 | Stiff |
| AIF1L | 83543 | Stiff | MIR3658 | 100423037 | Stiff | EXOSC4 | 54512 | Stiff | SENP3 | 26168 | Stiff |
| AJAP1 | 55966 | Stiff | MIR3658 | 100500832 | Stiff | EXOSC6 | 118460 | Stiff | SERHL | 94009 | Stiff |
| ALCAM | 214 | Stiff | MIR589 | 693174 | Stiff | EXTL3 | 2137 | Stiff | SERINC2 | 347735 | Stiff |
| ALDH1B1 | 219 | Stiff | MIR600HG | 81571 | Stiff | FAM101B | 359845 | Stiff | SERPINB3 | 6317 | Stiff |
| ALDH4A1 | 8659 | Stiff | MIR664B | 100847052 | Stiff | FAM118B | 79607 | Stiff | SERPINB4 | 6318 | Stiff |
| ALG1 | 56052 | Stiff | MIR6758 | 102465454 | Stiff | FAM169A | 26049 | Stiff | SERPINB7 | 8710 | Stiff |
| ALG1L9P | 285407 | Stiff | MIR6776 | 102465465 | Stiff | FAM171A1 | 221061 | Stiff | SFMBT1 | 51460 | Stiff |
| ALYREF | 10189 | Stiff | MIR6804 | 102465482 | Stiff | FAM189A1 | 23359 | Stiff | SFN | 2810 | Stiff |
| AMD1 | 262 | Stiff | MIS12 | 79003 | Stiff | FAM208B | 54906 | Stiff | SFXN2 | 118980 | Stiff |
| AMICA1 | 120425 | Stiff | MITF | 4286 | Stiff | FAM222A | 84915 | Stiff | SGK223 | 157285 | Stiff |
| AMIGO2 | 347902 | Stiff | MKL1 | 57591 | Stiff | FAM225A | 286333 | Stiff | SGK3 | 23678 | Stiff |
| AMPH | 273 | Stiff | MLP | 90523 | Stiff | FAM43A | 131583 | Stiff | SH2D2A | 9047 | Stiff |
| AMZ1 | 155185 | Stiff | MMP1 | 4312 | Stiff | FAM58A | 92002 | Stiff | SH2D5 | 400745 | Stiff |
| ANAPC7 | 51434 | Stiff | MMP3 | 4314 | Stiff | FAM72C | 554282 | Stiff | SH3RF2 | 153769 | Stiff |
| ANKRD39 | 51239 | Stiff | MON1A | 84315 | Stiff | FAM81A | 145773 | Stiff | SKA3 | 221150 | Stiff |
| ANKRD52 | 283373 | Stiff | MPV17L2 | 51678 | Stiff | FAM84A | 51354 | Stiff | SLC19A1 | 6573 | Stiff |
| ANP32D | 23519 | Stiff | MPZL3 | 196264 | Stiff | FAM86C1 | 55199 | Stiff | SLC20A1 | 6574 | Stiff |
| ANXA3 | 306 | Stiff | MRM1 | 79922 | Stiff | FAM9A | 84769 | Stiff | SLC20A2 | 6575 | Stiff |
| AOC1 | 26 | Stiff | MROH6 | 642475 | Stiff | FAM98A | 25940 | Stiff | SLC25A10 | 1468 | Stiff |
| AP1M2 | 10053 | Stiff | MROH7-TTC4 | 100527960 | Stiff | FANCA | 2175 | Stiff | SLC25A13 | 10165 | Stiff |
| AP4E1 | 23431 | Stiff | | | | FASN | 2194 | Stiff | SLC25A18 | 83733 | Stiff |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| AP5B1 | 91056 | Stiff | MRPL20 | 55052 | Stiff | FAXC | 84553 | Stiff | SLC25A19 | 60386 | Stiff |
| APBA1 | 320 | Stiff | MRPS12 | 6183 | Stiff | FBF1 | 85302 | Stiff | SLC25A25 | 114789 | Stiff |
| APITD1 | 378708 | Stiff | MRTO4 | 51154 | Stiff | FBXL6 | 26233 | Stiff | SLC25A32 | 81034 | Stiff |
| APITD1-CORT | 100526739 | Stiff | MSLN | 10232 | Stiff | FDX1 | 2230 | Stiff | SLC25A33 | 84275 | Stiff |
| APOO | 79135 | Stiff | MSR1 | 4481 | Stiff | FDXACB1 | 91893 | Stiff | SLC25A44 | 9673 | Stiff |
| APOOP5 | 644649 | Stiff | MSRB1 | 51734 | Stiff | FEM1A | 55527 | Stiff | SLC26A2 | 1836 | Stiff |
| ARAP2 | 116984 | Stiff | MSTO1 | 55154 | Stiff | FGD6 | 55785 | Stiff | SLC27A4 | 10999 | Stiff |
| ARC | 23237 | Stiff | MSTO2P | 100129405 | Stiff | FGF1 | 2246 | Stiff | SLC29A3 | 55315 | Stiff |
| AREG | 374 | Stiff | MSX1 | 4487 | Stiff | FGF5 | 2250 | Stiff | SLC2A6 | 11182 | Stiff |
| ARHGEF4 | 50649 | Stiff | MSX2 | 4488 | Stiff | FHOD3 | 80206 | Stiff | SLC35B1 | 10237 | Stiff |
| ARL14 | 80117 | Stiff | MTFR2 | 113115 | Stiff | FICD | 11153 | Stiff | SLC35G1 | 159371 | Stiff |
| ARMC6 | 93436 | Stiff | MTOR | 2475 | Stiff | FJX1 | 24147 | Stiff | SLC36A1 | 206358 | Stiff |
| ARMC7 | 79637 | Stiff | MTOR-AS1 | 100873935 | Stiff | FLAD1 | 80308 | Stiff | SLC37A1 | 54020 | Stiff |
| ARMCX4 | 100131755 | Stiff | MUC13 | 56667 | Stiff | FLG | 2312 | Stiff | SLC38A3 | 10991 | Stiff |
| ARNTL2 | 56938 | Stiff | MUC5AC | 4586 | Stiff | FLI1 | 2313 | Stiff | SLC39A3 | 29985 | Stiff |
| ARNTL2-AS1 | 101928646 | Stiff | MUC6 | 4588 | Stiff | FOXA1 | 3169 | Stiff | SLC43A2 | 124935 | Stiff |
| ARPC5L | 81873 | Stiff | MVB12B | 89853 | Stiff | FOXC1 | 2296 | Stiff | SLC45A3 | 85414 | Stiff |
| ARRDC1-AS1 | 85026 | Stiff | MYBBP1A | 10514 | Stiff | FPR1 | 2357 | Stiff | SLC45A4 | 57210 | Stiff |
| ARSB | 411 | Stiff | MYEOV2 | 150678 | Stiff | FSIP2 | 401024 | Stiff | SLC4A11 | 83959 | Stiff |
| ASRGL1 | 80150 | Stiff | MYH10 | 4628 | Stiff | FTSJ3 | 117246 | Stiff | SLC4A8 | 9498 | Stiff |
| ATAD3A | 55210 | Stiff | MYH15 | 22989 | Stiff | FXN | 2395 | Stiff | SLC52A2 | 79581 | Stiff |
| ATAD3B | 83858 | Stiff | MYLK2 | 85366 | Stiff | FZD9 | 8326 | Stiff | SLC5A6 | 8884 | Stiff |
| ATF5 | 22809 | Stiff | MYOSB | 4645 | Stiff | GAB3 | 139716 | Stiff | SLC7A11 | 23657 | Stiff |
| ATF7IP2 | 80063 | Stiff | MYT1 | 4661 | Stiff | GALNT10 | 55568 | Stiff | SLC7A2 | 6542 | Stiff |
| ATG101 | 60673 | Stiff | MYZAP | 100820829 | Stiff | GALNT14 | 79623 | Stiff | SLC9A2 | 6549 | Stiff |
| ATP2A1-AS1 | 100289092 | Stiff | NAA15 | 80155 | Stiff | GALNT7 | 51809 | Stiff | SLCO1B3 | 28234 | Stiff |
| ATP6V0A2 | 23545 | Stiff | NAPRT | 93100 | Stiff | GALR2 | 8811 | Stiff | SLCO3A1 | 28232 | Stiff |
| ATP6V0D2 | 245972 | Stiff | NAT1 | 9 | Stiff | GAR1 | 54433 | Stiff | SLFN12L | 100506736 | Stiff |
| ATP6V0E2 | 155066 | Stiff | NBPF20 | 100288142 | Stiff | GATAD2A | 54815 | Stiff | SMAGP | 57228 | Stiff |
| ATP6V0E2-AS1 | 401431 | Stiff | NCEH1 | 57552 | Stiff | GCH1 | 2643 | Stiff | SMCO4 | 56935 | Stiff |
| ATP6V1B1-AS1 | 101927750 | Stiff | NDOR1 | 27158 | Stiff | GCLM | 2730 | Stiff | SNAP25 | 6616 | Stiff |
| ATR | 545 | Stiff | NDUFAF4 | 29078 | Stiff | GDA | 9615 | Stiff | SNHG9 | 735301 | Stiff |
| AU N IP | 79000 | Stiff | NDUFAF6 | 137682 | Stiff | GDAP1 | 54332 | Stiff | SNORA10 | 574042 | Stiff |
| B3GALNT1 | 8706 | Stiff | NET02 | 81831 | Stiff | GDPD5 | 81544 | Stiff | SNORA17A | 677804 | Stiff |
| B3GALT1 | 8708 | Stiff | NFKBIB | 4793 | Stiff | GEMIN4 | 50628 | Stiff | SNORA22 | 677807 | Stiff |
| B3GLCT | 145173 | Stiff | NIP7 | 51388 | Stiff | GEMIN6 | 79833 | Stiff | SNORA3B | 677826 | Stiff |
| B3GNT2 | 10678 | Stiff | NIPA2 | 81614 | Stiff | GFM1 | 85476 | Stiff | SNORA48 | 652965 | Stiff |
| B4GALT6 | 9331 | Stiff | NKX3-1 | 4824 | Stiff | GFOD1 | 54438 | Stiff | SNORA51 | 677831 | Stiff |
| BAIAP2L2 | 80115 | Stiff | NLK | 51701 | Stiff | GFRA1 | 2674 | Stiff | SNORA52 | 619565 | Stiff |
| BAMBI | 25805 | Stiff | NLRP2 | 55655 | Stiff | GINS3 | 64785 | Stiff | SNORA55 | 677834 | Stiff |
| BATF3 | 55509 | Stiff | NLRP3 | 114548 | Stiff | GINS4 | 84296 | Stiff | SNORA6 | 574040 | Stiff |
| BCAR3 | 8412 | Stiff | NOC4L | 79050 | Stiff | GIPC1 | 10755 | Stiff | SNORA65 | 26783 | Stiff |
| BCCIP | 56647 | Stiff | NOL12 | 79159 | Stiff | GJA3 | 2700 | Stiff | SNORA71C | 677839 | Stiff |
| BCR | 613 | Stiff | NOL6 | 65083 | Stiff | GLB1L3 | 112937 | Stiff | SNORD101 | 594837 | Stiff |
| BDKRB1 | 623 | Stiff | NOLC1 | 9221 | Stiff | GLDC | 2731 | Stiff | SNORD110 | 692213 | Stiff |
| BEND3 | 57673 | Stiff | NOP16 | 51491 | Stiff | GLMN | 11146 | Stiff | SNORD119 | 100113378 | Stiff |
| BEND? | 222389 | Stiff | NOP2 | 4839 | Stiff | GLRX2 | 51022 | Stiff | SNORD12C | 26765 | Stiff |
| BEST3 | 144453 | Stiff | NOP56 | 10528 | Stiff | GLYCTK | 132158 | Stiff | SNORD14C | 85389 | Stiff |
| BLM | 641 | Stiff | NOS1AP | 9722 | Stiff | GMPPB | 29925 | Stiff | SNORD14D | 85390 | Stiff |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| BMP8A | 353500 | Stiff | NOVA1 | 4857 | Stiff | GNAS-AS1 | 149775 | Stiff | SNORD17 | 692086 | Stiff |
| BMS1P21 | 100288974 | Stiff | NOXO1 | 124056 | Stiff | GNG4 | 2786 | Stiff | SNORD2 | 619567 | Stiff |
| BNC1 | 646 | Stiff | NPB | 256933 | Stiff | GNLY | 10578 | Stiff | SNORD26 | 9302 | Stiff |
| BNC2 | 54796 | Stiff | NPLOC4 | 55666 | Stiff | GPAT3 | 84803 | Stiff | SNORD27 | 9301 | Stiff |
| BORCS8 | 79866 | Stiff | NPR3 | 4883 | Stiff | GPATCH4 | 54865 | Stiff | SNORD28 | 9300 | Stiff |
| BRIX1 | 91 | Stiff | NR1I3 | 9970 | Stiff | GPR1 | 2825 | Stiff | SNORD29 | 9297 | Stiff |
| BRMS1 | 55299 | Stiff | NR2F2 | 7026 | Stiff | GPR3 | 2827 | Stiff | SNORD30 | 9299 | Stiff |
| BYSL | 25855 | Stiff | NRADDP | 100129354 | Stiff | GPR75 | 10936 | Stiff | SNORD45A | 26805 | Stiff |
| C10orf128 | 705 | Stiff | NRG1 | 3084 | Stiff | GPR87 | 53836 | Stiff | SNORD48 | 26801 | Stiff |
| C10orf2 | 170371 | Stiff | NRGN | 4900 | Stiff | GPRIN1 | 114787 | Stiff | SNORD57 | 26792 | Stiff |
| C11orf91 | 56652 | Stiff | NRP2 | 8828 | Stiff | GRHL1 | 29841 | Stiff | SNORD83A | 116937 | Stiff |
| C11orf96 | 100131378 | Stiff | NRROS | 375387 | Stiff | GRWD1 | 83743 | Stiff | SNORD83B | 116938 | Stiff |
| C1orf98 | 387763 | Stiff | NSUN2 | 54888 | Stiff | GSDMC | 56169 | Stiff | SNORD86 | 692201 | Stiff |
| C1orf128 | 102288414 | Stiff | NTMT1 | 28989 | Stiff | GSG2 | 83903 | Stiff | SNPH | 9751 | Stiff |
| C12orf4 | 57102 | Stiff | NTN4 | 59277 | Stiff | GTF2H2 | 2966 | Stiff | SNRNP25 | 79622 | Stiff |
| C12orf43 | 64897 | Stiff | NUDT15 | 55270 | Stiff | GTF2H2B | 653238 | Stiff | SNRNP40 | 9410 | Stiff |
| C12orf49 | 79794 | Stiff | NUDT16 | 131870 | Stiff | GTF2H2C | 728340 | Stiff | SOGA3 | 387104 | Stiff |
| C14orf169 | 79697 | Stiff | NUFIP1 | 26747 | Stiff | GTF2H2C_2 | 730394 | Stiff | SOX7 | 83595 | Stiff |
| C14orf80 | 283643 | Stiff | NUP93 | 9688 | Stiff | GTF3C6 | 112495 | Stiff | SOX9 | 6662 | Stiff |
| C16orf59 | 80178 | Stiff | NXT1 | 29107 | Stiff | GTPBP4 | 23560 | Stiff | SP6 | 80320 | Stiff |
| C17orf51 | 339263 | Stiff | ODC1 | 4953 | Stiff | GXYLT1 | 283464 | Stiff | SP7 | 121340 | Stiff |
| C17orf89 | 284184 | Stiff | OGFOD1 | 55239 | Stiff | GYG2 | 8908 | Stiff | SPAG1 | 6674 | Stiff |
| C19orf47 | 126526 | Stiff | OGFRP1 | 388906 | Stiff | HABP4 | 22927 | Stiff | SPATAS | 166378 | Stiff |
| C1orf73 | 55150 | Stiff | OLAH | 55301 | Stiff | HAPLN1 | 1404 | Stiff | SPECC1 | 92521 | Stiff |
| C1orf106 | 55765 | Stiff | ONECUT2 | 9480 | Stiff | HARBI1 | 283254 | Stiff | SPNS2 | 124976 | Stiff |
| C1orf109 | 54955 | Stiff | OPA3 | 80207 | Stiff | HAS3 | 3038 | Stiff | SPP1 | 6696 | Stiff |
| C1orf226 | 400793 | Stiff | OR2W3 | 343171 | Stiff | HAUS7 | 55559 | Stiff | SPRR2D | 6703 | Stiff |
| C20orf24 | 55969 | Stiff | ORAI1 | 84876 | Stiff | HBEGF | 1839 | Stiff | SPRTN | 83932 | Stiff |
| C2CD2L | 9854 | Stiff | ORC6 | 23594 | Stiff | HEATR3 | 55027 | Stiff | SPTB | 6710 | Stiff |
| C3AR1 | 719 | Stiff | OSBP2 | 23762 | Stiff | HGF | 3082 | Stiff | SPX | 80763 | Stiff |
| C3orf52 | 79669 | Stiff | OSBPL6 | 114880 | Stiff | HGH1 | 51236 | Stiff | SRP19 | 6728 | Stiff |
| C6orf58 | 352999 | Stiff | OSTM1 | 28962 | Stiff | HHAT | 55733 | Stiff | SRPK3 | 26576 | Stiff |
| C7orf26 | 79034 | Stiff | OTUD6B | 51633 | Stiff | HHIP | 64399 | Stiff | SSSCA1 | 10534 | Stiff |
| C7orf43 | 55262 | Stiff | P2RY2 | 5029 | Stiff | HHIP-AS1 | 646576 | Stiff | SSTR1 | 6751 | Stiff |
| C9orf78 | 51759 | Stiff | PAEP | 5047 | Stiff | HHIPL2 | 79802 | Stiff | ST6GALNAC5 | 81849 | Stiff |
| CA2 | 760 | Stiff | PAK1IP1 | 55003 | Stiff | HIRA | 7290 | Stiff | STEAP1 | 26872 | Stiff |
| CABLES1 | 91768 | Stiff | PALM2 | 114299 | Stiff | HIST1H2AE | 3012 | Stiff | STK10 | 6793 | Stiff |
| CAMK2N2 | 94032 | Stiff | PAQR9 | 344838 | Stiff | HIST1H2AG | 8969 | Stiff | STON2 | 85439 | Stiff |
| CAND2 | 23066 | Stiff | PCAT7 | 101928099 | Stiff | HIST1H2AH | 85235 | Stiff | STOX2 | 56977 | Stiff |
| CARD11 | 84433 | Stiff | PCDH9 | 5101 | Stiff | HIST1H2AM | 8336 | Stiff | STRBP | 55342 | Stiff |
| CARD8-AS1 | 100505812 | Stiff | PCDHGA1 | 56114 | Stiff | HIST1H2BC | 8347 | Stiff | STRIP2 | 57464 | Stiff |
| CARD9 | 64170 | Stiff | PCDHGA10 | 56106 | Stiff | HIST1H2BF | 8343 | Stiff | STS | 412 | Stiff |
| CASZ1 | 54897 | Stiff | PCDHGA11 | 56105 | Stiff | HIST1H2BG | 8339 | Stiff | STX11 | 8676 | Stiff |
| CCBE1 | 147372 | Stiff | PCDHGA12 | 26025 | Stiff | HIST1H2BI | 8346 | Stiff | STXBPSL | 9515 | Stiff |
| CCDC137 | 339230 | Stiff | PCDHGA2 | 56113 | Stiff | HIST1H2BJ | 8970 | Stiff | STYK1 | 55359 | Stiff |
| CCDC168 | 643677 | Stiff | PCDHGA3 | 56112 | Stiff | HIST1H2BM | 8342 | Stiff | SURF2 | 6835 | Stiff |
| CCDC86 | 79080 | Stiff | PCDHGA4 | 56111 | Stiff | HIST1H2BO | 8348 | Stiff | SUSD4 | 55061 | Stiff |
| CCDC96 | 257236 | Stiff | PCDHGA5 | 56110 | Stiff | HIST1H3B | 8358 | Stiff | SUV39H1 | 6839 | Stiff |
| CCL20 | 6364 | Stiff | PCDHGA7 | 56108 | Stiff | HIST1H3D | 8351 | Stiff | SVIP | 258010 | Stiff |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| CCNE1 | 898 | Stiff | PCDHGA8 | 9708 | Stiff | HIST1H3F | 8968 | Stiff | SWSAP1 | 126074 | Stiff |
| CCNE2 | 9134 | Stiff | PCDHGA9 | 56107 | Stiff | HIST1H3G | 8355 | Stiff | SYNPO2L | 79933 | Stiff |
| CCNF | 899 | Stiff | PCDHGB1 | 56104 | Stiff | HIST1H4A | 8359 | Stiff | SYT1 | 6857 | Stiff |
| CCNJ | 54619 | Stiff | PCDHGB2 | 56103 | Stiff | HIST1H4B | 8366 | Stiff | TACC2 | 10579 | Stiff |
| CCNO | 10309 | Stiff | PCDHGB3 | 56102 | Stiff | HIST1H4C | 8364 | Stiff | TACO1 | 51204 | Stiff |
| CCNYL1 | 151195 | Stiff | PCDHGB4 | 8641 | Stiff | HIST2H2AC | 8338 | Stiff | TAF13 | 6884 | Stiff |
| CD101 | 9398 | Stiff | PCDHGB5 | 56101 | Stiff | HIST2H2BF | 440689 | Stiff | TAF5 | 6877 | Stiff |
| CD274 | 29126 | Stiff | PCDHGB6 | 56100 | Stiff | HIVEP3 | 59269 | Stiff | TAF5L | 27097 | Stiff |
| CD300C | 10871 | Stiff | PCDHGB7 | 56099 | Stiff | HMGB3 | 3149 | Stiff | TBC1D4 | 9882 | Stiff |
| CD70 | 970 | Stiff | PCDHGC3 | 5098 | Stiff | HNRNPAB | 3182 | Stiff | TBX2 | 6909 | Stiff |
| CDC25A | 993 | Stiff | PCDHGC4 | 56098 | Stiff | HOXB3 | 3213 | Stiff | TCHP | 84260 | Stiff |
| CDC42EP2 | 10435 | Stiff | PCDHGC5 | 56097 | Stiff | HOXD8 | 3234 | Stiff | TC0F1 | 6949 | Stiff |
| CDC6 | 990 | Stiff | PCNXL3 | 399909 | Stiff | HRK | 8739 | Stiff | TDG | 6996 | Stiff |
| CDC7 | 8317 | Stiff | PCSK7 | 9159 | Stiff | HS3ST1 | 9957 | Stiff | TEAD4 | 7004 | Stiff |
| CDCA7 | 83879 | Stiff | PCYT2 | 5833 | Stiff | HS3ST3A1 | 9955 | Stiff | TELO2 | 9894 | Stiff |
| CDH11 | 1009 | Stiff | PDCD2L | 84306 | Stiff | HSH2D | 84941 | Stiff | TENM3 | 55714 | Stiff |
| CDH15 | 1013 | Stiff | PDCD6IPP2 | 646278 | Stiff | HSPA14 | 51182 | Stiff | TEX2 | 55852 | Stiff |
| CELF5 | 60680 | Stiff | PDCL3 | 79031 | Stiff | HSPA1B | 3304 | Stiff | TEX30 | 93081 | Stiff |
| CENPM | 79019 | Stiff | PDE12 | 201626 | Stiff | HSPA6 | 3310 | Stiff | TFB2M | 64216 | Stiff |
| CENPN | 55839 | Stiff | PDE1C | 5137 | Stiff | HSPBAP1 | 79663 | Stiff | TFRC | 7037 | Stiff |
| CENPP | 401541 | Stiff | PDSS1 | 23590 | Stiff | HSPH1 | 10808 | Stiff | TGM2 | 7052 | Stiff |
| CENPV | 201161 | Stiff | PFAS | 5198 | Stiff | HTR7 | 1163 | Stiff | THAP7 | 80764 | Stiff |
| CEP78 | 84131 | Stiff | PFDN2 | 5202 | Stiff | HYAL2 | 8692 | Stiff | THBD | 7056 | Stiff |
| CESIP2 | 390732 | Stiff | PGAM5 | 192111 | Stiff | HYOU1 | 10525 | Stiff | TIAM1 | 7074 | Stiff |
| CFAP157 | 286207 | Stiff | PGP | 283871 | Stiff | IDH3A | 3419 | Stiff | TIGAR | 57103 | Stiff |
| CGNL1 | 84952 | Stiff | PHF19 | 26147 | Stiff | IFRD2 | 7866 | Stiff | TIMM10 | 26519 | Stiff |
| CHAC2 | 494143 | Stiff | PHF5A | 84844 | Stiff | IGF2BP3 | 10643 | Stiff | TIMM17A | 10440 | Stiff |
| CHAD | 1101 | Stiff | PHLDA2 | 7262 | Stiff | IGFN1 | 91156 | Stiff | TIMM22 | 29928 | Stiff |
| CHFR | 55743 | Stiff | PHLPP2 | 23035 | Stiff | IHH | 3549 | Stiff | TIMM23 | 100287932 | Stiff |
| CHL1 | 10752 | Stiff | PHOSPHO1 | 162466 | Stiff | IL12A | 3592 | Stiff | TIMM23B | 100652748 | Stiff |
| CHORDC1 | 26973 | Stiff | PI3 | 5266 | Stiff | IL1A | 3552 | Stiff | TIMM8A | 1678 | Stiff |
| CHRNA3 | 1136 | Stiff | PIGW | 284098 | Stiff | IL1B | 3553 | Stiff | TIPIN | 54962 | Stiff |
| CHRNA5 | 1138 | Stiff | PIK3R4 | 30849 | Stiff | IL6 | 3569 | Stiff | TJP1 | 7082 | Stiff |
| CHUK | 1147 | Stiff | PITX1 | 54984 | Stiff | ILDR2 | 387597 | Stiff | TMC7 | 79905 | Stiff |
| LCN5 | 1184 | Stiff | PITX1 | 5307 | Stiff | INHBA | 3624 | Stiff | TMEFF2 | 23671 | Stiff |
| CLDN1 | 9076 | Stiff | PKI55 | 150967 | Stiff | INSC | 387755 | Stiff | TMEM104 | 54868 | Stiff |
| CLDN10 | 9071 | Stiff | PKMYT1 | 9088 | Stiff | IP013 | 9670 | Stiff | TMEM110-MUSTN1 | 100526772 | Stiff |
| CLDN11 | 5010 | Stiff | PLAT | 5327 | Stiff | IPO5P1 | 100132815 | Stiff | TMEM138 | 51524 | Stiff |
| CLN6 | 54982 | Stiff | PLCD4 | 84812 | Stiff | IPPK | 64768 | Stiff | TMEM154 | 201799 | Stiff |
| CLSPN | 63967 | Stiff | PLCE1 | 51196 | Stiff | ISG20L2 | 81875 | Stiff | TMEM177 | 80775 | Stiff |
| CLTB | 1212 | Stiff | PLCE1-AS1 | 100128054 | Stiff | ISM1 | 140862 | Stiff | TMEM199 | 147007 | Stiff |
| CLUH | 23277 | Stiff | PLD5 | 200150 | Stiff | ISOC1 | 51015 | Stiff | TMEM201 | 199953 | Stiff |
| CMTM7 | 112616 | Stiff | PLK2 | 26499 | Stiff | ISOC2 | 79763 | Stiff | TMEM206 | 55248 | Stiff |
| CNIH3 | 149111 | Stiff | PLK3 | 1263 | Stiff | ITGA6 | 3655 | Stiff | TMEM236 | 653567 | Stiff |
| CNN3 | 1266 | Stiff | PLXNA2 | 5362 | Stiff | ITGAE | 3682 | Stiff | TMEM249 | 340393 | Stiff |
| CNTF | 1270 | Stiff | PLXNA4 | 91584 | Stiff | ITGB1BP2 | 26548 | Stiff | TMEM251 | 26175 | Stiff |
| CNTNAP2 | 26047 | Stiff | PNO1 | 56902 | Stiff | ITGBL1 | 9358 | Stiff | TMEM33 | 55161 | Stiff |
| COA7 | 65260 | Stiff | PNP | 4860 | Stiff | JADE2 | 23338 | Stiff | TMEM5 | 10329 | Stiff |
| COBLL1 | 22837 | Stiff | PNPT1 | 87178 | Stiff | JAM3 | 83700 | Stiff | TMPO | 7112 | Stiff |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| COL10A1 | 1300 | Stiff | PODXL | 5420 | Stiff | JMJD4 | 65094 | Stiff | TNF | 7124 | Stiff |
| COL13A1 | 1305 | Stiff | PODXL2 | 50512 | Stiff | KANK1 | 23189 | Stiff | TNFRSF12A | 51330 | Stiff |
| COL17A1 | 1308 | Stiff | POLA2 | 23649 | Stiff | KBTBD8 | 84541 | Stiff | TNFRSF21 | 27242 | Stiff |
| COL20A1 | 57642 | Stiff | POLE3 | 54107 | Stiff | KCNH2 | 3757 | Stiff | TNFRSF8 | 943 | Stiff |
| CREB5 | 9586 | Stiff | POLR1A | 25885 | Stiff | KCNQ3 | 3786 | Stiff | TNS4 | 84951 | Stiff |
| CREG2 | 200407 | Stiff | POLR3B | 55703 | Stiff | KDM8 | 79831 | Stiff | TOE1 | 114034 | Stiff |
| CREM | 1390 | Stiff | POLR3E | 55718 | Stiff | KIAA0513 | 9764 | Stiff | TOMM40 | 10452 | Stiff |
| CRSP8P | 441089 | Stiff | POLR3G | 10622 | Stiff | KIAA0754 | 643314 | Stiff | TOMM40L | 84134 | Stiff |
| CRY1 | 1407 | Stiff | POLR3K | 51728 | Stiff | KIAA1524 | 57650 | Stiff | TONSL | 4796 | Stiff |
| CRYBA2 | 1412 | Stiff | POMGNT2 | 84892 | Stiff | KIAA1549L | 25758 | Stiff | TONSL-AS1 | 100287098 | Stiff |
| CSF2 | 1437 | Stiff | POP1 | 10940 | Stiff | KIF21B | 23046 | Stiff | TOR1A | 1861 | Stiff |
| CSF2RB | 1439 | Stiff | POP5 | 51367 | Stiff | KLC2 | 64837 | Stiff | TOR3A | 64222 | Stiff |
| CSF3 | 1440 | Stiff | POP7 | 10248 | Stiff | KLF5 | 688 | Stiff | TP53RK | 112858 | Stiff |
| CSGALNACT1 | 55790 | Stiff | POU3F2 | 5454 | Stiff | KLHL18 | 23276 | Stiff | TRAPPC10 | 7109 | Stiff |
| CST7 | 8530 | Stiff | PPARGC1B | 133522 | Stiff | KLHL25 | 64410 | Stiff | TRAPPC13 | 80006 | Stiff |
| CTNND2 | 1478 | Stiff | PPIC | 5480 | Stiff | KLHL9 | 55958 | Stiff | TREX2 | 11219 | Stiff |
| GSTF2 | 1501 | Stiff | PPIF | 10105 | Stiff | KLK4 | 9622 | Stiff | TRHDE-AS1 | 283392 | Stiff |
| CTPS1 | 1503 | Stiff | PPIL1 | 51645 | Stiff | KNOP1 | 400506 | Stiff | TRMO | 55039 | Stiff |
| CTSL | 1514 | Stiff | PPRC1 | 23082 | Stiff | KPNA2 | 3838 | Stiff | TRMT12 | 55039 | Stiff |
| CTSV | 1515 | Stiff | PRADC1 | 84279 | Stiff | KPNA3 | 3839 | Stiff | TRMT6 | 51605 | Stiff |
| CTSW | 1521 | Stiff | PRDM16 | 63976 | Stiff | KRT1 | 3848 | Stiff | TRMT61A | 115708 | Stiff |
| CTU2 | 348180 | Stiff | PREB | 10113 | Stiff | KRT15 | 3866 | Stiff | TRPM2 | 7226 | Stiff |
| CXCL1 | 2919 | Stiff | PRF1 | 5551 | Stiff | KRT3 | 3850 | Stiff | TRPV4 | 59341 | Stiff |
| CXCL2 | 2920 | Stiff | PRKCQ-AS1 | 439949 | Stiff | KRT34 | 3887 | Stiff | TSC22D2 | 9819 | Stiff |
| CXCL3 | 2921 | Stiff | PRLR | 5618 | Stiff | KRT81 | 8844 | Stiff | TSEN54 | 283989 | Stiff |
| CXCL8 | 3576 | Stiff | PRMT6 | 55170 | Stiff | KSR1 | 8844 | Stiff | TSHZ3 | 57616 | Stiff |
| CYB5R2 | 51700 | Stiff | PROSER2 | 254427 | Stiff | L3MBTL2 | 83746 | Stiff | TSPAN17 | 26262 | Stiff |
| CYCS | 54205 | Stiff | PRR22 | 163154 | Stiff | LANCL2 | 55915 | Stiff | TSSC4 | 10078 | Stiff |
| DAB2 | 1601 | Stiff | PRR5 | 55615 | Stiff | LARP4 | 113251 | Stiff | TTC4 | 7268 | Stiff |
| DAW1 | 164781 | Stiff | PRRX1 | 5396 | Stiff | LCMT2 | 9836 | Stiff | TTF2 | 8458 | Stiff |
| DBF4 | 10926 | Stiff | PSEN2 | 5664 | Stiff | LCTL | 197021 | Stiff | TTLL11 | 158135 | Stiff |
| DBF4B | 80174 | Stiff | PSMC4 | 5704 | Stiff | LDLRAP1 | 26119 | Stiff | TTN | 7273 | Stiff |
| DCBLD2 | 131566 | Stiff | PSMD1 | 5707 | Stiff | LETM1 | 3954 | Stiff | TUBB1 | 81027 | Stiff |
| DCTPP1 | 79077 | Stiff | PSMD11 | 5717 | Stiff | LETM2 | 137994 | Stiff | TUBGCP5 | 114791 | Stiff |
| DDIAS | 220042 | Stiff | PSME3 | 10197 | Stiff | LIF | 3976 | Stiff | TXNDC9 | 10190 | Stiff |
| DDX10 | 1662 | Stiff | PSME4 | 23198 | Stiff | LIG3 | 3980 | Stiff | UBASH3B | 84959 | Stiff |
| DDX19A | 55308 | Stiff | PSPC1 | 55269 | Stiff | LINC00311 | 197196 | Stiff | UBE2F-SCLY | 100533179 | Stiff |
| DDX21 | 9188 | Stiff | PTGDR | 11251 | Stiff | LINC00346 | 283487 | Stiff | UB1AD1 | 29914 | Stiff |
| DDX28 | 55794 | Stiff | PTRH1 | 138428 | Stiff | LINC00707 | 100507127 | Stiff | UCA1 | 652995 | Stiff |
| DDX46 | 9879 | Stiff | PTS | 5805 | Stiff | LINC00857 | 439990 | Stiff | UCHL3 | 7347 | Stiff |
| DDX51 | 317781 | Stiff | PTX3 | 5806 | Stiff | LINC00880 | 339894 | Stiff | UFSP1 | 402682 | Stiff |
| DDX52 | 11056 | Stiff | PUM3 | 9933 | Stiff | LINC00941 | 100287314 | Stiff | UHRF1 | 29128 | Stiff |
| DENND5B | 160518 | Stiff | PUS1 | 80324 | Stiff | LINC01117 | 102724224 | Stiff | URB2 | 9816 | Stiff |
| DEPDC1-AS1 | 101927220 | Stiff | PUSL1 | 126789 | Stiff | LINC01224 | 104472717 | Stiff | UTP15 | 84135 | Stiff |
| DGCR11 | 25786 | Stiff | PVR | 5817 | Stiff | LINC01287 | 103724390 | Stiff | UTP20 | 27340 | Stiff |
| DGCR5 | 26220 | Stiff | PVRL1 | 5818 | Stiff | LINC01322 | 103695433 | Stiff | UTP3 | 57050 | Stiff |
| DHCR24 | 1718 | Stiff | PWP2 | 5822 | Stiff | LINC01468 | 101928687 | Stiff | VEPH1 | 79674 | Stiff |
| DGKG | 1608 | Stiff | PYCRL | 65263 | Stiff | LINC01605 | 100507420 | Stiff | VGF | 7425 | Stiff |
| DHRS11 | 79154 | Stiff | PZP | 5858 | Stiff | LIPG | 9388 | Stiff | VPS53 | 55275 | Stiff |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| DHRS2 | 10202 | Stiff | RAB27B | 5874 | Stiff | LIPH | 200879 | Stiff | VPS9D1-AS1 | 100128881 | Stiff |
| DHRS9 | 10170 | Stiff | RAB3B | 5865 | Stiff | LMO7-AS1 | 101927155 | Stiff | VVVA2 | 340706 | Stiff |
| DHX34 | 9704 | Stiff | RABEP1 | 9135 | Stiff | LOC100128361 | 100128361 | Stiff | WDR4 | 10785 | Stiff |
| DHX37 | 57647 | Stiff | RABIF | 5877 | Stiff | LOC100129046 | 100129046 | Stiff | WDR46 | 9277 | Stiff |
| DIO2 | 1734 | Stiff | RANGAP1 | 5905 | Stiff | LOC100130238 | 100130238 | Stiff | WDR62 | 284403 | Stiff |
| DIO2-AS1 | 100628307 | Stiff | RAPGEFL1 | 51195 | Stiff | LOC100287042 | 100287042 | Stiff | WDR77 | 79084 | Stiff |
| DKC1 | 1736 | Stiff | RASGEF1B | 153020 | Stiff | LOC100499489 | 100499489 | Stiff | NFS1 | 7466 | Stiff |
| DLEU2 | 8847 | Stiff | RASGRP1 | 10125 | Stiff | LOC100506302 | 100506302 | Stiff | WNT5B | 81029 | Stiff |
| DLEU2L | 79469 | Stiff | RBM24 | 221662 | Stiff | LOC100507634 | 100507634 | Stiff | WNT9A | 7483 | Stiff |
| DLX3 | 1747 | Stiff | RBM28 | 55131 | Stiff | LOC101926940 | 101926940 | Stiff | WRAP53 | 55135 | Stiff |
| DLX5 | 1749 | Stiff | RBP4 | 5950 | Stiff | LOC101927267 | 101927267 | Stiff | WTAPP1 | 100288077 | Stiff |
| DMRTA2 | 63950 | Stiff | RBPMS2 | 348093 | Stiff | LOC101927746 | 101927746 | Stiff | XIRP2 | 129446 | Stiff |
| DNAJB11 | 51726 | Stiff | RCL1 | 10171 | Stiff | LOC101928163 | 101928163 | Stiff | XPO4 | 64328 | Stiff |
| DNLZ | 728489 | Stiff | RDH10 | 157506 | Stiff | LOC102723729 | 102723729 | Stiff | XRCC2 | 7516 | Stiff |
| DOCK4 | 9732 | Stiff | RECQL4 | 9401 | Stiff | LOC102724434 | 102724434 | Stiff | YRDC | 79693 | Stiff |
| DOCK9 | 23348 | Stiff | RELN | 5649 | Stiff | LOC105370333 | 105370333 | Stiff | ZBTB2 | 57621 | Stiff |
| DOHH | 83475 | Stiff | RFK | 55312 | Stiff | LOC339166 | 339166 | Stiff | ZBTB7C | 201501 | Stiff |
| DOLK | 22845 | Stiff | RFX8 | 731220 | Stiff | LOC341056 | 341056 | Stiff | ZBTB9 | 221504 | Stiff |
| DOLPP1 | 57171 | Stiff | RIMS2 | 9699 | Stiff | LOC541472 | 541472 | Stiff | ZDHHC14 | 79683 | Stiff |
| DPF3 | 8110 | Stiff | RIOK1 | 83732 | Stiff | LOC646762 | 646762 | Stiff | ZFAND4 | 93550 | Stiff |
| DPH2 | 1802 | Stiff | RNASEH1 | 246243 | Stiff | LRP8 | 7804 | Stiff | ZFP69B | 65243 | Stiff |
| DPH3 | 285381 | Stiff | RNASEH1-AS1 | 100506054 | Stiff | LRR1 | 122769 | Stiff | ZICS | 85416 | Stiff |
| DSP | 1832 | Stiff | RNF219 | 79596 | Stiff | LRRC59 | 55379 | Stiff | ZIK1 | 284307 | Stiff |
| DUS1L | 64118 | Stiff | RNF219-AS1 | 100874272 | Stiff | LRWD1 | 222229 | Stiff | ZMPSTE24 | 10269 | Stiff |
| DUS3L | 56931 | Stiff | RNMTL1 | 55178 | Stiff | LSG1 | 55341 | Stiff | ZMYND19 | 116225 | Stiff |
| DUSP5 | 1847 | Stiff | ROR1 | 4919 | Stiff | LSM10 | 84967 | Stiff | ZNF30 | 90075 | Stiff |
| USP8 | 1850 | Stiff | RPGR | 6103 | Stiff | LSMEM2 | 132228 | Stiff | ZNF300 | 91975 | Stiff |
| DUSP9 | 1852 | Stiff | RPP40 | 10799 | Stiff | LTV1 | 84946 | Stiff | ZNF35 | 7584 | Stiff |
| DYSF | 8291 | Stiff | RPS16P5 | 647190 | Stiff | LUM | 4060 | Stiff | ZNF365 | 22891 | Stiff |
| E2F6 | 1876 | Stiff | RPS26 | 6231 | Stiff | LYAR | 55646 | Stiff | ZNF43 | 7594 | Stiff |
| E2F7 | 144455 | Stiff | RPS6KA4 | 8986 | Stiff | LZTS1 | 11178 | Stiff | ZNF469 | 84627 | Stiff |
| EBNA1BP2 | 10969 | Stiff | RPUSD1 | 1130_0 | Stiff | MAGEA3 | 4102 | Stiff | ZNF488 | 118738 | Stiff |
| ECE2 | 110599564 | Stiff | RPUSD2 | 27079 | Stiff | MAGEA6 | 4105 | Stiff | ZNF583 | 147949 | Stiff |
| ECE2 | 110599583 | Stiff | RRP1 | 8568 | Stiff | MAGI2-AS3 | 100505881 | Stiff | ZNF593 | 51042 | Stiff |
| EDEM3 | 80267 | Stiff | RRP12 | 23223 | Stiff | MAGOHB | 55110 | Stiff | ZNF681 | 148213 | Stiff |
| EEF1E1 | 9521 | Stiff | RRP15 | 51018 | Stiff | MAK16 | 84549 | Stiff | ZNF689 | 115509 | Stiff |
| EEF2KMT | 196483 | Stiff | RRP1B | 23076 | Stiff | MAP2K4 | 6416 | Stiff | ZNF736 | 728927 | Stiff |
| EFR3B | 22979 | Stiff | RRP36 | 88745 | Stiff | MAP3K9 | 4293 | Stiff | ZNF778 | 197320 | Stiff |
| EID2 | 163126 | Stiff | RRP7A | 27341 | Stiff | MAP6D1 | 79929 | Stiff | ZNF786 | 136051 | Stiff |
| EIF4E | 1977 | Stiff | RRP7BP | 91695 | Stiff | MARCH3 | 115123 | Stiff | ZNF85 | 7639 | Stiff |
| EIF5A2 | 56648 | Stiff | RRP9 | 9136 | Stiff | MARCH4 | 57574 | Stiff | ZNHIT2 | 741 | Stiff |
| ELAC2 | 60528 | Stiff | RRS1 | 23212 | Stiff | MARS2 | 92935 | Stiff | ZWILCH | 55055 | Stiff |
| ELAVL2 | 1993 | Stiff | RSPH4A | 345895 | Stiff | MB | 4151 | Stiff | LOC101928414 | 101928414 | Soft |
| A1BG | 1 | Soft | LOC101928453 | 101928453 | Soft | EPHA5 | 2044 | Soft | RHPN1 | 114822 | Soft |
| AATBC | 284137 | Soft | LOC101928489 | 101928489 | Soft | EPHA5-AS1 | 100144602 | Soft | RIBC1 | 158787 | Soft |
| AATK | 9625 | Soft | LOC101928673 | 101928673 | Soft | EPHA7 | 2045 | Soft | RIMS3 | 9783 | Soft |
| ABAT | 18 | Soft | LOC101928710 | 101928710 | Soft | EPHX2 | 2053 | Soft | RIMS4 | 140730 | Soft |
| ABCA2 | 20 | Soft | LOC101928718 | 101928718 | Soft | EPOR | 2057 | Soft | RIOK3 | 8780 | Soft |
| ABCA3 | 21 | Soft | LOC101928767 | 101928767 | Soft | EPPK1 | 83481 | Soft | RIPK4 | 54101 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| ABCA4 | 24 | Soft | LOC101928978 | 101928978 | Soft | EPSRI1 | 54869 | Soft | RLN3 | 117579 | Soft |
| ABCA6 | 23460 | Soft | LOCI01929140 | 101929140 | Soft | EPSRI7 | 64787 | Soft | RMIDN2 | 151393 | Soft |
| ABCA8 | 10351 | Soft | LOC101929371 | 101929371 | Soft | EPSTI1 | 94240 | Soft | RNASE4 | 6038 | Soft |
| ABCA9 | 10350 | Soft | LOC101929378 | 101929378 | Soft | ERICH2 | 285141 | Soft | RNASET2 | 8635 | Soft |
| ABCB1 | 5243 | Soft | LOC101929532 | 101929532 | Soft | ERMN | 57471 | Soft | RNF122 | 79845 | Soft |
| ABCC3 | 8714 | Soft | LOC101929709 | 101929709 | Soft | ERV3-1 | 2086 | Soft | RNF128 | 79589 | Soft |
| ABHD1 | 84696 | Soft | LOC101929710 | 101929710 | Soft | ESPNL | 339768 | Soft | RNF150 | 57484 | Soft |
| ABHD4 | 63874 | Soft | LOC101929767 | 101929767 | Soft | ETV7 | 51513 | Soft | RNF165 | 494470 | Soft |
| ABHD8 | 79575 | Soft | LOC102477328 | 102477328 | Soft | EVA1B | 55194 | Soft | RNF180 | 285671 | Soft |
| ABLIM2 | 84448 | Soft | LOC102503427 | 102503427 | Soft | EVA1C | 59271 | Soft | RNF212B | 100507650 | Soft |
| ABTB1 | 80325 | Soft | LOC102723809 | 102723809 | Soft | EXD3 | 54932 | Soft | RNF215 | 200312 | Soft |
| ACAD11 | 84129 | Soft | LOC102724050 | 102724050 | Soft | EXOC3L1 | 283849 | Soft | RNF217 | 154214 | Soft |
| ACADL | 33 | Soft | Loci02724190 | 102724190 | Soft | EYA1 | 2138 | Soft | RNF24 | 11237 | Soft |
| ACADS | 35 | Soft | LOC102724467 | 102724467 | Soft | EYA2 | 2139 | Soft | RNF32 | 140545 | Soft |
| ACAP1 | 9744 | Soft | Locio2724814 | 102724814 | Soft | EYS | 346007 | Soft | RNF39 | 80352 | Soft |
| ACBD4 | 79777 | Soft | LOC102724927 | 102724927 | Soft | F10 | 2159 | Soft | RNF44 | 22838 | Soft |
| ACCS | 84680 | Soft | Loci n021296 | 103021296 | Soft | F11R | 50848 | Soft | RNPC3 | 55599 | Soft |
| ACKR1 | 2532 | Soft | LOC103091866 | 103091866 | Soft | F2RL2 | 2151 | Soft | ROPN1L | 83853 | Soft |
| ACKR3 | 57007 | Soft | LOC105372795 | 105372795 | Soft | F8 | 2157 | Soft | RORA | 6095 | Soft |
| ACOT4 | 122970 | Soft | LOC105447645 | 105447645 | Soft | FAAH | 2166 | Soft- | RORC | 6097 | Soft |
| ACP5 | 54 | Soft | LOC105747689 | 105747689 | Soft | FAM102B | 284611 | Soft | ROS1 | 6098 | Soft |
| ACP6 | 51205 | Soft | LOC113230 | 113230 | Soft | FAM114A1 | 92689 | Soft | RPH3AL | 9501 | Soft |
| ACPP | 55 | Soft | LOC115110 | 115110 | Soft | FAM122C | 159091 | Soft | RPL32P3 | 132241 | Soft |
| ACRC | 93953 | Soft | LOC143666 | 143666 | Soft | FAM131B | 9715 | Soft | RPL34-AS1 | 285456 | Soft |
| ACSF2 | 80221 | Soft | LOC145783 | 145783 | Soft | FAM131C | 348487 | Soft | RPLP0P2 | 113157 | Soft |
| ACSM3 | 6296 | Soft | LOC148696 | 148696 | Soft | FAM134B | 54463 | Soft | RPS10P7 | 376693 | Soft |
| ACSM4 | 341392 | Soft | LOC154761 | 154761 | Soft | FAM13A | 10144 | Soft | RPS15AP10 | 728963 | Soft |
| ACSM5 | 54988 | Soft | LOC155060 | 155060 | Soft | FAM13A-AS1 | 285512 | Soft | RPS29 | 6235 | Soft |
| ACTA2 | 59 | Soft | LOC171391 | 171391 | Soft | FAM149B1 | 317662 | Soft | RRAD | 6236 | Soft |
| ACTA2-AS1 | 100132116 | Soft | LOC202181 | 202181 | Soft | FAM160A1 | 729830 | Soft | RRAGB | 10325 | Soft |
| ACTBL2 | 345651 | Soft | LOC254896 | 254896 | Soft | FAM161B | 145483 | Soft | RRAGD | 58528 | Soft |
| ACVR2B-AS1 | 100128640 | Soft | LOC283038 | 283038 | Soft | FAM162A | 26355 | Soft | RRNAD1 | 51093 | Soft |
| ACYP2 | 98 | Soft | LOC283335 | 283335 | Soft | FAM167B | 83648 | Soft | RSBN1 | 54665 | Soft |
| ADAMS | 101 | Soft | LOC283575 | 283575 | Soft | FAM167B | 84734 | Soft | RSPH3 | 83861 | Soft |
| ADAMTS1 | 9510 | Soft | LOC284080 | 284080 | Soft | FAM168A | 23201 | Soft | RSRP1 | 57035 | Soft |
| ADAMTS10 | 81794 | Soft | LOC284454 | 284454 | Soft | FAM171A2 | 284069 | Soft | RTN4RL2 | 349667 | Soft |
| ADAMTS2 | 9509 | Soft | LOC284930 | 284930 | Soft | FAM179A | 165186 | Soft | RTP4 | 64108 | Soft |
| ADAMTS5 | 11096 | Soft | LOC285819 | 285819 | Soft | FAM183A | 440585 | Soft | RUNDC3B | 154661 | Soft |
| ADAMTS7 | 11173 | Soft | LOC285847 | 285847 | Soft | FAM184B | 27146 | Soft | RUNX1T1 | 862 | Soft |
| ADAMTS7P1 | 390660 | Soft | LOC374443 | 374443 | Soft | FAM 198A | 729085 | Soft | RWDD2A | 112611 | Soft |
| ADAMTS9-AS2 | 100507098 | Soft | LOC388813 | 388813 | Soft | FAM20C | 56975 | Soft | RXFP1 | 59350 | Soft |
| ADAMTSL2 | 9719 | Soft | LOC400706 | 400706 | Soft | FAM212B | 55924 | Soft | RYR1 | 6261 | Soft |
| ADAMTSL4 | 54507 | Soft | LOC401320 | 401320 | Soft | FAM212B-AS1 | 100506343 | Soft | RYR2 | 6262 | Soft |
| ADAP1 | 11033 | Soft | LOC 440028 | 440028 | Soft | FAM213A | 84293 | Soft | S100A3 | 6274 | Soft |
| ADCYAP1R1 | 117 | Soft | LOC440173 | 440173 | Soft | FAM214A | 56204 | Soft | S1PR2 | 9294 | Soft |
| ADD3 | 120 | Soft | LOC441081 | 441081 | Soft | FAM214B | 80256 | Soft | S1PR4 | 8698 | Soft |
| ADGRA2 | 25960 | Soft | LOC554206 | 554206 | Soft | FAM227A | 646851 | Soft | S1PR5 | 53637 | Soft |
| ADGRB3 | 577 | Soft | LOC 554223 | 352962 | Soft | FAM227B | 195951 | Soft | SAA2-SAM | 100528017 | Soft |
| ADGRG1 | 9289 | Soft | LOC 642852 | 642852 | Soft | FAM228B | 375190 | Soft | SAM | 6291 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| ADGRL1 | 22859 | Soft | LOC 644285 | 644285 | Soft | FAM229A | 100128071 | Soft | SALL2 | 6297 | Soft |
| ADGRL2 | 23266 | Soft | LOC644919 | 644919 | Soft | FAM26E | 254228 | Soft | SALL4 | 57167 | Soft |
| ADGRL3 | 23284 | Soft | LOC646471 | 646471 | Soft | FAM46A | 55603 | Soft | SAMD14 | 201191 | Soft |
| ADH6 | 130 | Soft | LOC648987 | 648987 | Soft | FAM46B | 115572 | Soft | SAMD9L | 219285 | Soft |
| ADM | 133 | Soft | LOC653160 | 653160 | Soft | FAM46C | 54855 | Soft | SARDH | 1757 | Soft |
| ADM2 | 79924 | Soft | LOC654841 | 654841 | Soft | FAM47E | 100129583 | Soft | SASH1 | 23328 | Soft |
| ADORAZA-AS1 | 646023 | Soft | LOC728392 | 728392 | Soft | FAM47E-STBD1 | 100631383 | Soft | SATB1 | 6304 | Soft |
| ADPRHL1 | 113622 | Soft | LOC728613 | 728613 | Soft | FAM50B | 26240 | Soft | SBF2-AS1 | 283104 | Soft |
| ADRA1B | 147 | Soft | LOC728730 | 728730 | Soft | FAM63A | 55793 | Soft | SCARA5 | 286133 | Soft |
| ADRB2 | 154 | Soft | LOC728743 | 728743 | Soft | FAM65B | 9750 | Soft | SCARF1 | 8578 | Soft |
| ADSSL1 | 122622 | Soft | LOC729603 | 729603 | Soft | FAM71C | 196472 | Soft | SCARF2 | 91179 | Soft |
| AFF1 | 4299 | Soft | LOG730668 | 730668 | Soft | FAM83H-AS1 | 100128338 | Soft | SCARNAB | 6/1/16 | Soft |
| AFF2 | 2334 | Soft | LOC90246 | 90246 | Soft | FAM86B3P | 286042 | Soft | SCARNA9 | 619383 | Soft |
| AGBL2 | 79841 | Soft | LOH12CR2 | 503693 | Soft | FAM8A1 | 51439 | Soft | SCART1 | 619207 | Soft |
| AGER | 177 | Soft | LOX | 4015 | Soft | FANK1 | 92565 | Soft | SCD5 | 79966 | Soft |
| AGPAT4-IT1 | — | Soft | LOXL1 | 4016 | Soft | FAP | 2191 | Soft | SCN2A | 6326 | Soft |
| AGT | 183 | Soft | LOXL1-AS1 | 100287616 | Soft | FAS-AS1 | 100302740 | Soft | SCNN1B | 6338 | Soft |
| AH_NAK2 | 113146 | Soft | LOXL2 | 4017 | Soft | FAT2 | 2196 | Soft | SCNN1D | 6339 | Soft |
| AHRR | 57491 | Soft | LPAR1 | 1902 | Soft | FAXDC2 | 10826 | Soft | SCNN1G | 6340 | Soft |
| AJ-ISA2 | 130872 | Soft | LPAR2 | 9170 | Soft | FBLIM1 | 54751 | Soft | SCX | 642658 | Soft |
| AIFM3 | 150209 | Soft | LPAR6 | 10161 | Soft | FBLN1 | 2192 | Soft | SDCBP2 | 27111 | Soft |
| AIM2 | 9447 | Soft | LPIN3 | 64900 | Soft | FBLN2 | 2199 | Soft | SDHAP3 | 728609 | Soft |
| AK4 | 205 | Soft | LPP | 4026 | Soft | FBXL16 | 146330 | Soft | SEC14L5 | 9717 | Soft |
| AK7 | 122481 | Soft | LRCH2 | 57631 | Soft | FBXLB | 55336 | Soft | SEC16B | 89866 | Soft |
| AK8 | 158067 | Soft | LRG1 | 116844 | Soft | FBXO15 | 201456 | Soft | SEC1P | 653677 | Soft |
| AKAP3 | 221264 | Soft | LRGUK | 136332 | Soft | FBXO24 | 26261 | Soft | SEC31B | 25956 | Soft |
| AKR1B15 | 441282 | Soft | LRP1 | 4035 | Soft | FBXO32 | 114907 | Soft | SELENBP1 | 8991 | Soft |
| AKR7A3 | 22977 | Soft | LRP1-AS | 105751187 | Soft | FBXO41 | 150726 | Soft | SEMA3B | 7869 | Soft |
| AKR7L | 246181 | Soft | LRP1B | 93.1a3 | Soft | FBXO42 | 54455 | Soft | SEMA4A | 64218 | Soft |
| AKT3 | 10000 | Soft | LRP4 | 4038 | Soft | FBXO44 | 93611 | Soft | SEMA4B | 10509 | Soft |
| ALDH1L1 | 10840 | Soft | LRP4-AS1 | 100507401 | Soft | FBXO6 | 26270 | Soft | SEMA4G | 57715 | Soft |
| ALDH1L2 | 160428 | Soft | LRRC27 | 80313 | Soft | FCGBP | 8857 | Soft | SEMA6B | 10501 | Soft |
| ALDH2 | 217 | Soft | LRRC29 | 26231 | Soft | FCGR2A | 2212 | Soft | SEN P7 | 57337 | Soft |
| ALDH3A1 | 218 | Soft | LRRC37A3 | 374819 | Soft | FCGRT | 2217 | Soft | SEPP1 | 6414 | Soft |
| ALDH3B1 | 221 | Soft | LRRC37A6P | 387646 | Soft | FCHO1 | 23149 | Soft | SEPT1 | 1731 | Soft |
| ALDH6A1 | 4329 | Soft | LRRC37A8P | 100533789 | Soft | FER1L4 | 80307 | Soft | SEPT5 | 5413 | Soft |
| ALDH8A1 | 64577 | Soft | LRRC37B | 114659 | Soft | FEZ1 | 9638 | Soft | SEPT5-GP1BB | 100526833 | Soft |
| ALDOC | 230 | Soft | LRRC56 | 115399 | Soft | FGF11 | 2256 | Soft | SEPT17-AS1 | 101928545 | Soft |
| ALOX12 | 239 | Soft | LRRC6 | 23639 | Soft | FGGY | 55277 | Soft | SERINC4 | 619189 | Soft |
| ALPK1 | 80216 | Soft | LRRC61 | 65999 | Soft | FHAD1 | 114827 | Soft | SERPINA5 | 5104 | Soft |
| ALPK2 | 115701 | Soft | LRRC66 | 339977 | Soft | FHIT | 2272 | Soft | SERPINB1 | 1992 | Soft |
| ALPK3 | 57538 | Soft | LRRC7 | 57554 | Soft | FIBCD1 | 84929 | Soft | SERPINB9 | 5272 | Soft |
| ALS2CL | 259173 | Soft | LRRC73 | 221424 | Soft | FIBIN | 387758 | Soft | SERPINE2 | 5270 | Soft |
| AMT | 275 | Soft | LRRC75B | 388886 | Soft | FLJ31356 | 403150 | Soft | SER PINF1 | 5176 | Soft |
| AMY2B | 280 | Soft | LRRK2 | 120892 | Soft | FLJ37035 | 399821 | Soft | SERPINF2 | 5345 | Soft |
| ANG | 283 | Soft | LRSAM1 | 90678 | Soft | FLJ37453 | 729614 | Soft | SERPING1 | 710 | Soft |
| ANGPT1 | 284 | Soft | LSP1 | 4046 | Soft | FLJ43879 | 401039 | Soft | SESN1 | 27244 | Soft |
| | | Soft | LTBP2 | 4053 | Soft | FLJ45079 | 400624 | Soft | SESN3 | 143686 | Soft |
| ANGPTL4 | 51129 | Soft | LTBP3 | 4054 | Soft | FLJ46906 | 441172 | Soft | SETBP1 | 26040 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| ANK1 | 286 | Soft | LTBP4 | 8425 | Soft | FLRT1 | 23769 | Soft | SEZ6L2 | 26470 | Soft |
| ANKAR | 150709 | Soft | LTF | 4057 | Soft | FMO3 | 2328 | Soft | SGPP2 | 130367 | Soft |
| ANKDD1A | 348094 | Soft | LUADT1 | 106182249 | Soft | FMO4 | 2329 | Soft | SGSM2 | 9905 | Soft |
| ANKFN1 | 162282 | Soft | LUCAT1 | 100505994 | Soft | FMO5 | 2330 | Soft | SH2B2 | 10603 | Soft |
| ANKLE1 | 126549 | Soft | LURAP1 | 541468 | Soft | FN1 | 2335 | Soft | SH2D3A | 10045 | Soft |
| ANKMY2 | 57037 | Soft | LUZP4 | 51213 | Soft | FN3K | 64122 | Soft | SH3BGR | 6450 | Soft |
| ANKRA2 | 57763 | Soft | LVCAT1 | 100506827 | Soft | FNBP1L | 54874 | Soft | SH3BP2 | 6452 | Soft |
| ANKRD2 | 26287 | Soft | LVCAT5 | 105375475 | Soft | FOS | 2353 | Soft | SH3D21 | 79729 | Soft |
| ANKRD24 | 170961 | Soft | LY75 | 4065 | Soft | FOSS | 2354 | Soft | SH3PXD2A | 9644 | Soft |
| ANKRD30B | 374860 | Soft | LY75-CD302 | 100526664 | Soft | FOXD1 | 2297 | Soft | SH3YL1 | 26751 | Soft |
| ANKRD34C | 390616 | Soft | LY96 | 23643 | Soft | FOXL1 | 2300 | Soft | SHC2 | 25759 | Soft |
| ANKRD36C | 400986 | Soft | LYPD1 | 116372 | Soft | FOXO1 | 2308 | Soft | SHC3 | 53358 | Soft |
| ANKRD37 | 353322 | Soft | LYPD3 | 27076 | Soft | FOXO4 | 4303 | Soft | SHF | 90525 | Soft |
| ANKZF1 | 55139 | Soft | LYRM9 | 201229 | Soft | FOXP1 | 27086 | Soft | SKIDA1 | 387640 | Soft |
| ANO9 | 338440 | Soft | MAATS1 | 89876 | Soft | FOXP2 | 93986 | Soft | SKINTL | 391037 | Soft |
| ANXA2R | 389289 | Soft | MAB21L3 | 126868 | Soft | FOXP4-AS1 | 101060264 | Soft | SKOR1 | 390598 | Soft |
| ANXA8L1 | 728113 | Soft | MACROD1 | 28992 | Soft | FRG1DP | 102723316 | Soft | SLAMF8 | 56833 | Soft |
| AOC3 | 8416 | Soft | MAF | 4094 | Soft | FRK | 2444 | Soft | SLAMF9 | 89886 | Soft |
| AP1G2 | 8639 | Soft | MAFB | 9935 | Soft | FRMD4B | 23150 | Soft | SLC12A5 | 57468 | Soft |
| APBB3 | 8906 | Soft | MAGEA11 | 4110 | Soft | FRMD4D | 9758 | Soft | SLC12A7 | 10723 | Soft |
| APC2 | 10297 | Soft | MAMDC2 | 256691 | Soft | FRRS1 | 391059 | Soft | SLC12A8 | 84561 | Soft |
| APCDD1 | 147495 | Soft | MAML2 | 84441 | Soft | FRS3 | 10817 | Soft | SLC13A4 | 26266 | Soft |
| APH1B | 83464 | Soft | MAN1B1-AS1 | 100289341 | Soft | FRZB | 2487 | Soft | SLC14A1 | 6563 | Soft |
| APLN | 8862 | Soft | MANEA-AS1 | 101927288 | Soft | FUCA1 | 2517 | Soft | SLC15A3 | 51296 | Soft |
| APOA4 | 337 | Soft | MAOA | 4128 | Soft | FUT11 | 170384 | Soft | SLC16A2 | 6567 | Soft |
| APOBEC3D | 140564 | Soft | MAOB | 4129 | Soft | FUT2 | 2524 | Soft | SLC17A5 | 26503 | Soft |
| APOBEC3F | 200316 | Soft | MAP1A | 4130 | Soft | GAA | 2548 | Soft | SLC17A7 | 57030 | Soft |
| APOBEC3G | 60489 | Soft | MAP1LC3A | 84557 | Soft | GAB1 | 2549 | Soft | SLC1A4 | 6509 | Soft |
| APOC1 | 341 | Soft | MAP3K12 | 7786 | Soft | GABRB2 | 2561 | Soft | SLC22A13 | 9390 | Soft |
| APOC3 | 345 | Soft | MAP3K13 | 9175 | Soft | GADD45G | 10912 | Soft | SLC22A14 | 9389 | Soft |
| APOD | 347 | Soft | MAP3K8 | 1326 | Soft | GAL | 51083 | Soft | SLC22A18 | 5002 | Soft |
| APOE | 348 | Soft | MAP7D2 | 256714 | Soft | GAL3ST3 | 89792 | Soft | SLC22A18AS | 5003 | Soft |
| APOL3 | 80833 | Soft | MAPK10 | 5602 | Soft | GAL3ST4 | 79690 | Soft | SLC22A23 | 63027 | Soft |
| APOLD1 | 81575 | Soft | MAPK3 | 5595 | Soft | GALNS | 2588 | Soft | SLC23A3 | 151295 | Soft |
| APPL1 | 26060 | Soft | MAPRE3 | 22924 | Soft | GALNT15 | 117248 | Soft | SLC25A27 | 9481 | Soft |
| AQP1 | 358 | Soft | MAPT | 4137 | Soft | GALNT16 | 57452 | Soft | SLC25A42 | 284439 | Soft |
| AQP3 | 360 | Soft | MARCH9 | 92979 | Soft | GALNTL6 | 442117 | Soft | SLC25A4,5 | 283130 | Soft |
| AR | 367 | Soft | MARK4 | 57787 | Soft | GAMT | 2593 | Soft | SLC26A6 | 65010 | Soft |
| ARFGEF3 | 57221 | Soft | MASP1 | 5648 | Soft | GAS1 | 2619 | Soft | SLC26A9 | 115019 | Soft |
| ARHGAP20 | 57569 | Soft | MAST1 | 22983 | Soft | GAS1RR | 100506834 | Soft | SLC27A1 | 376497 | Soft |
| ARHGAP24 | 83478 | Soft | MATN1-AS1 | 100129196 | Soft | GAS6-AS2 | 100506394 | Soft | SLC29A2 | 3177 | Soft |
| ARHGAP4 | 393 | Soft | MATN2 | 4147 | Soft | GAS8-AS1 | 750 | Soft | SLC29A4 | 222962 | Soft |
| ARHGAP44 | 9912 | Soft | MBD5 | 55777 | Soft | GATA6-AS1 | 100128893 | Soft | SLC2A1-AS1 | 440584 | Soft |
| ARHGAP6 | 395 | Soft | MCC | 4163 | Soft | GATSL3 | 652968 | Soft | SLC2A10 | 81031 | Soft |
| ARHGAP8 | 23779 | Soft | MCOLN2 | 255231 | Soft | GBGT1 | 26301 | Soft | SLC2A11 | 66035 | Soft |
| ARHGEF10L | 55160 | Soft | MDGA1 | 266727 | Soft | GBP2 | 2634 | Soft | SLC2A14 | 144195 | Soft |
| ARHGEF16 | 27237 | Soft | MDH1B | 130752 | Soft | GBP4 | 115361 | Soft | SLC2A3 | 6515 | Soft |
| ARHGEF17 | 9828 | Soft | MDK | 4192 | Soft | GBP5 | 115362 | Soft | SLC2A4 | 6517 | Soft |
|  |  |  | MEF2A | 4205 | Soft | GCA | 25801 | Soft | SLC2A5 | 6518 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| ARHGEF19 | 128272 | Soft | MEF2C | 4208 | Soft | GDF1 | 2657 | Soft | SLC2A9 | 56606 | Soft |
| ARHGEF25 | 115557 | Soft | MEFV | 4210 | Soft | GDF5 | 8200 | Soft | SLC35E2 | 9906 | Soft |
| ARHGEF37 | 389337 | Soft | MEGF6 | 1953 | Soft | GDPD1 | 284161 | Soft | SLC38A5 | 92745 | Soft |
| ARHGEF40 | 55701 | Soft | MEGF8 | 1954 | Soft | GDPD3 | 79153 | Soft | SLC40A1 | 30061 | Soft |
| ARHGEF6 | 9459 | Soft | MEIS1 | 4211 | Soft | GEM | 2669 | Soft | SLC41A2 | 84102 | Soft |
| ARID4A | 5926 | Soft | MEIS1-AS2 | 100873998 | Soft | GEI1 | 2672 | Soft | SLC43A1 | 8501 | Soft |
| ARL4C | 10123 | Soft | MEIS3 | 56917 | Soft | GGA2 | 23062 | Soft | SLC44A5 | 204962 | Soft |
| ARMC12 | 221481 | Soft | MEOX1 | 4222 | Soft | GGN | 199720 | Soft | SLC45A1 | 50651 | Soft |
| ARNT2 | 9915 | Soft | METTL20 | 254013 | Soft | GGT7 | 2686 | Soft | SLC47A2 | 146802 | Soft |
| ARRB1 | 408 | Soft | METTL21B | 25895 | Soft | GHDC | 84514 | Soft | SLC4A5 | 57835 | Soft |
| ARRDC2 | 27106 | Soft | METTL7A | 25840 | Soft | GIMAP2 | 26157 | Soft | SLC5A9 | 200010 | Soft |
| ARRDC3 | 57561 | Soft | MEX3A | 92312 | Soft | GIPR | 2696 | Soft | SLC6A1 | 6529 | Soft |
| ARRDC3-AS1 | 100129716 | Soft | MEX3B | 84206 | Soft | GJA9 | 81025 | Soft | SLC6A16 | 28968 | Soft |
| ARRDC4 | 91947 | Soft | MFAP4 | 4239 | Soft | GJC2 | 57165 | Soft | SLO6A3 | 6531 | Soft |
| ARSG | 22901 | Soft | MFI2 | 4241 | Soft | GLDN | 342035 | Soft | SLC9A3 | 6550 | Soft |
| ARTN | 9048 | Soft | MFI2-AS1 | 100507057 | Soft | GLI1 | 2735 | Soft | SLCO1A2 | 6579 | Soft |
| AS3MT | 57412 | Soft | MFSD7 | 84179 | Soft | GLIPR1L1 | 256710 | Soft | SLCO2A1 | 6578 | Soft |
| ASAP3 | 55616 | Soft | MGC16275 | 85001 | Soft | GLIS2 | 84662 | Soft | SLITRK2 | 84631 | Soft |
| ASCL1 | 429 | Soft | MGP | 4256 | Soft | GLIS3 | 169792 | Soft | SLITRK4 | 139065 | Soft |
| ASIC1 | 41 | Soft | MIAT | 440823 | Soft | GLRX | 2745 | Soft | SLITRK6 | 84189 | Soft |
| ASIC3 | 9311 | Soft | MIATNB | 102724827 | Soft | GLT8D2 | 83468 | Soft | SMAD6 | 4091 | Soft |
| ASIP | 434 | Soft | MIB2 | 142678 | Soft | GLTSCR2-AS1 | 106144593 | Soft | SMAD7 | 4092 | Soft |
| ASPG | 374569 | Soft | MIEF2 | 125170 | Soft | GLUL | 2752 | Soft | SMAD9 | 4093 | Soft |
| ASPRV1 | 151516 | Soft | MILR1 | 284021 | Soft | GLYATL2 | 219970 | Soft | SMARCA1 | 6594 | Soft |
| ASS1 | 445 | Soft | MIR1228 | 100302201 | Soft | GMDS-AS1 | 100508120 | Soft | SMARCD3 | 6604 | Soft |
| ASTN2 | 23245 | Soft | MIR1260B | 100422991 | Soft | GMFG | 9535 | Soft | SMC2-AS1 | 101938550 | Soft |
| ATG14 | 22863 | Soft | MIR1287 | 100302133 | Soft | GNAI1 | 2770 | Soft | SMCO3 | 440087 | Soft |
| ATG16L2 | 89849 | Soft | MIR155HG | 114614 | Soft | GNAO1 | 2775 | Soft | SMIM1 | 388588 | Soft |
| ATHL1 | 80162 | Soft | MIR181A2HG | 100379345 | Soft | GNAZ | 2781 | Soft | SMIM3 | 85027 | Soft |
| ATOH8 | 84913 | Soft | MIR193BHG | 100129781 | Soft | GNG2 | 54331 | Soft | SMTNL1 | 219537 | Soft |
| ATP1A1-AS1 | 84852 | Soft | MIR199A2 | 406977 | Soft | GNG7 | 2788 | Soft | SNCA | 6622 | Soft |
| ATP1A2 | 477 | Soft | MIR210 | 406992 | Soft | GNRH1 | 2796 | Soft | SNED1 | 25992 | Soft |
| ATP2A3 | 489 | Soft | MIR210HG | 100506211 | Soft | GOLGA2P5 | 55592 | Soft | SNHG18 | 100505806 | Soft |
| ATP2B2 | 491 | Soft | MIR214 | 406996 | Soft | GOLGA7B | 401647 | Soft | SNTA1 | 6640 | Soft |
| ATP2C2 | 9914 | Soft | MIR23A | 407010 | Soft | GOLGABB | 440270 | Soft | SNTB1 | 6641 | Soft |
| ATP6AP1L | 92270 | Soft | MIR24-2 | 407013 | Soft | GP1BB | 2812 | Soft | SNX21 | 90203 | Soft |
| ATP6V1B1 | 525 | Soft | MIR27A | 407018 | Soft | GPM6B | 2824 | Soft | SNX32 | 254122 | Soft |
| ATP6V1G2 | 534 | Soft | MIR29C | 407026 | Soft | GPNMB | 10457 | Soft | SNX33 | 257364 | Soft |
| ATP7A | 538 | Soft | MIR3120 | 100422882 | Soft | GPR146 | 115330 | Soft | SOD3 | 6649 | Soft |
| ATP8B3 | 148229 | Soft | MIR324 | 442898 | Soft | GPR 155 | 151556 | Soft | SOHLH2 | 54937 | Soft |
| ATXN3 | 4287 | Soft | MIR34AHG | 106614088 | Soft | GPR162 | 27239 | Soft | SORBS1 | 10580 | Soft |
| AURKC | 6795 | Soft | MIR3681HG | 100506457 | Soft | GPR173 | 54328 | Soft | SORCS2 | 57537 | Soft |
| AZGP1 | 563 | Soft | MIR4635 | 100616479 | Soft | GPR19 | 2842 | Soft | SOX4 | 6659 | Soft |
| AZIN2 | 113451 | Soft | MIR4680 | 100616113 | Soft | GPR35 | 2859 | Soft | SOX5 | 6660 | Soft |
| B3GALT4 | 8705 | Soft | MIR4712 | 100616396 | Soft | GPR37 | 2861 | Soft | SP5 | 389058 | Soft |
| B3GNT4 | 79369 | Soft | MIR4800 | 100616358 | Soft | GPR39 | 2863 | Soft | SPACA6P-AS | 102238594 | Soft |
| B3GNT7 | 93010 | Soft | MIR5193 | 100847010 | Soft | GPR62 | 118442 | Soft | SPAG4 | 6676 | Soft |
| B4GALNT2 | 124872 | Soft | MIR548AR | 100847035 | Soft | GPRASP1 | 9737 | Soft | SPAG8 | 26206 | Soft |
| B4GALNT4 | 338707 | Soft | MIR612 | 693197 | Soft | GPRIN3 | 285513 | Soft | SPATA12 | 353324 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| BACE1-AS | 100379571 | Soft | MIR641 | 693226 | Soft | GPT | 2875 | Soft | SPATA17 | 128153 | Soft |
| BACH1 | 571 | Soft | MIR675 | 100033819 | Soft | GRAMD1C | 54762 | Soft | SPATA17-AS1 | 103752555 | Soft |
| BACH2 | 60468 | Soft | MIR6757 | 102466193 | Soft | GRAMD3 | 65983 | Soft | SPATA18 | 132671 | Soft |
| BAHCC1 | 57597 | Soft | MIR6891 | 102465537 | Soft | GRB7 | 2886 | Soft | SPATA25 | 128497 | Soft |
| BALAP2-AS1 | 440465 | Soft | MIR711 | 100313843 | Soft | GREB1 | 9687 | Soft | SPATA6 | 54558 | Soft |
| BALAP3 | 8938 | Soft | MIR7847 | 102465993 | Soft | GREM1 | 26585 | Soft | SPATA6L | 55064 | Soft |
| BASP1P1 | 646201 | Soft | MIR99AHG | 388815 | Soft | GRIA1 | 2890 | Soft | SPATA7 | 55812 | Soft |
| BBC3 | 27113 | Soft | MKLN1-AS | 100506881 | Soft | GRIK1-AS2 | 100379661 | Soft | SPATC1 | 375686 | Soft |
| BBOF1 | 80127 | Soft | MLXIPL | 51085 | Soft | GRIK2 | 2898 | Soft | SPEF1 | 25876 | Soft |
| BBS1 | 582 | Soft | MME | 4311 | Soft | GRIK4 | 2900 | Soft | SPEG | 10290 | Soft |
| BBS12 | 166379 | Soft | MMP11 | 4320 | Soft | GRIK5 | 2901 | Soft | SPIN2B | 474343 | Soft |
| BBS2 | 583 | Soft | MMP17 | 4326 | Soft | GRIN2A | 2903 | Soft | SPIN3 | 169981 | Soft |
| BBS9 | 27241 | Soft | MMP19 | 4327 | Soft | GRIN2D | 2906 | Soft | SPINK5 | 11005 | Soft |
| BCAN | 63827 | Soft | MMP24 | 10893 | Soft | GS1-259H13.2 | 100289187 | Soft | SPINT1 | 6692 | Soft |
| BCAS3 | 54828 | Soft | MMP25-AS1 | 100507419 | Soft | GSAP | 54103 | Soft | SPRY1 | 10252 | Soft |
| BCHE | 590 | Soft | MMP7 | 4316 | Soft | GSDMB | 55876 | Soft | SRCIN1 | 80725 | Soft |
| BCKDHA | 593 | Soft | MMRN2 | 79812 | Soft | GSN | 2934 | Soft | SRD5A3 | 79644 | Soft |
| BCL11A | 53335 | Soft | MORN1 | 79906 | Soft | GSN-AS1 | 57000 | Soft | SRGAP3 | 9901 | Soft |
| BCL11B | 64919 | Soft | MOSPD3 | 64598 | Soft | GSTA4 | 2941 | Soft | SRP14-AS1 | 100131089 | Soft |
| BCL6 | 604 | Soft | MPI | 4351 | Soft | GSTM2 | 2946 | Soft | SRRM3 | 222183 | Soft |
| BCORL1 | 63035 | Soft | MR1 | 3140 | Soft | GSTM4 | 2948 | Soft | SSBP2 | 23635 | Soft |
| BDKRB2 | 624 | Soft | MRAP2 | 112609 | Soft | GTF2IRD2 | 84163 | Soft | SSBP3-AS1 | 619518 | Soft |
| BDNF-AS | 497258 | Soft | MRC2 | 9902 | Soft | GTF2IRD2B | 389524 | Soft | SSC4D | 136853 | Soft |
| BEAN1 | 146227 | Soft | MROH2A | 339766 | Soft | GUCY1B3 | 2983 | Soft | SSC5D | 284297 | Soft |
| BEND5 | 79656 | Soft | MRPL23-AS1 | 100133545 | Soft | GULP1 | 51454 | Soft | SSH3 | 54961 | Soft |
| BEST1 | 7439 | Soft | MRV11 | 10335 | Soft | GUSBP4 | 375513 | Soft | SSPN | 8082 | Soft |
| BEX1 | 5F4159 | Soft | MSC-AS1 | 100128891 | Soft | GXYLT2 | 727936 | Soft | SSR4P1 | 728039 | Soft |
| BFSP1 | 631 | Soft | MSRB2 | 22921 | Soft | GYPC | 2995 | Soft | ST3GAL3 | 6487 | Soft |
| BGN | 633 | Soft | MST1 | 4485 | Soft | H19 | 283120 | Soft | ST3GAL4-AS1 | 399972 | Soft |
| BHLHB9 | 80823 | Soft | MST1L | 11223 | Soft | H6PD | 9563 | Soft | ST3GAL5 | 8869 | Soft |
| BHLHE40 | 8553 | Soft | MST1P2 | 11209 | Soft | HAL | 3034 | Soft | ST6GALNAC2 | 10610 | Soft |
| BHLHE41 | 79365 | Soft | MT1F | 4494 | Soft | HAR1A | 768096 | Soft | ST8SIA1 | 6489 | Soft |
| BISPR | 105221694 | Soft | MTA3 | 57504 | Soft | HAS2 | 3037 | Soft | ST8SIA5 | 29906 | Soft |
| BLK | 640 | Soft | MTHFD2P1 | 100287639 | Soft | HAS2-AS1 | 594842 | Soft | STAC2 | 342667 | Soft |
| BMF | 90427 | Soft | MTL5 | 9633 | Soft | HBE1 | 3046 | Soft | STAG3 | 10734 | Soft |
| BMP3 | 651 | Soft | MTMR11 | 10903 | Soft | HBG2 | 3048 | Soft | STAP2 | 55620 | Soft |
| BMP4 | 652 | Soft | MTMR9LP | 339483 | Soft | HBP1 | 26959 | Soft | STARD13-AS | 100874241 | Soft |
| BMP8B | 656 | Soft | MTTP | 4547 | Soft | HCAR2 | 338442 | Soft | STARD5 | 80765 | Soft |
| BMPR1B | 658 | Soft | MTUS1 | 57509 | Soft | HCAR3 | 8843 | Soft | STARD9 | 57519 | Soft |
| BNIP3 | 664 | Soft | MTUS2 | 23281 | Soft | HCFC1R1 | 54985 | Soft | STAT2 | 6773 | Soft |
| BNIP3L | 665 | Soft | MUC1 | 4582 | Soft | HCG26 | 352961 | Soft | STAT4 | 6775 | Soft |
| BOC | 91653 | Soft | MUC12 | 10071 | Soft | HCG27 | 253018 | Soft | STBD1 | 8987 | Soft |
| BOLA1 | 51027 | Soft | MUC15 | 143662 | Soft | HCG4 | 54435 | Soft | STK32A | 202374 | Soft |
| BOLA3-AS1 | 100507171 | Soft | MUC20 | 200958 | Soft | HCG8 | 80862 | Soft | STOM | 2040 | Soft |
| BORCS7-ASMT | 100528007 | Soft | MUM1L1 | 139221 | Soft | HCP5 | 10866 | Soft | STON1 | 11037 | Soft |
| BPIFB4 | 149954 | Soft | MUSK | 4593 | Soft | HDAC11 | 79885 | Soft | STON1-GTF2A1L | 286749 | Soft |
| BRSK1 | 84446 | Soft | MX1 | 4599 | Soft | HDAC5 | 10014 | Soft | STOX1 | 219736 | Soft |
| BTBD16 | 118663 | Soft | MX2 | 4600 | Soft | HDGFL1 | 154150 | Soft | STRA6 | 64220 | Soft |
| BTBD19 | 149478 | Soft | MXD4 | 10608 | Soft | HECW2 | 57520 | Soft | STX1B | 112755 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| BTBD8 | 284697 | Soft | MXI1 | 4601 | Soft | HEPH | 9843 | Soft | STXBP2 | 6813 | Soft |
| BTG1 | 694 | Soft | MYBPC1 | 4604 | Soft | HEXDC | 284004 | Soft | SUGCT | 79783 | Soft |
| BTN2A2 | 10385 | Soft | MYCBPAP | 84073 | Soft | HEXIM2 | 124790 | Soft | SUGT1P1 | 441394 | Soft |
| BTN2A3P | 54718 | Soft | MYL5 | 4636 | Soft | HHLA3 | 11147 | Soft | SULF1 | 23213 | Soft |
| BTN3A1 | 11119 | Soft | MYL9 | 10398 | Soft | HILPDA | 29923 | Soft | SULF2 | 55959 | Soft |
| BTN3A3 | 10384 | Soft | MYLK3 | 91807 | Soft | HIST1H3E | 8353 | Soft | SU LT 1E1 | 6783 | Soft |
| BTNL9 | 153579 | Soft | MYLK4 | 340156 | Soft | HIST2H2BC | 337873 | Soft | SVEP1 | 79987 | Soft |
| C10orf10 | 11067 | Soft | MYO15A | 51168 | Soft | HIST3H2A | 92815 | Soft | SYN2 | 6854 | Soft |
| C10orf11 | 83938 | Soft | MYO15B | 80022 | Soft | HKR1 | 284459 | Soft | SYNE2 | 21224 | Soft |
| C10orf25 | 220979 | Soft | MYO16 | 23026 | Soft | HLA-DMA | 3108 | Soft | SYNE4 | 163183 | Soft |
| C10orf54 | 64115 | Soft | MYO1F | 4542 | Soft | HLA-F | 3134 | Soft | SYNGAP1 | 8831 | Soft |
| C11orf21 | 29125 | Soft | MYO38 | 140469 | Soft | HLA-F-AS1 | 285830 | Soft | SYNGR1 | 9145 | Soft |
| C11orf54 | 28970 | Soft | MYOM1 | 8736 | Soft | HLA-J | 3137 | Soft | SYNGR3 | 9143 | Soft |
| C11orf70 | 85016 | Soft | MYOZ2 | 51778 | Soft | HLF | 3131 | Soft | SYNPO | 11346 | Soft |
| C12orf60 | 144608 | Soft | MYRF | 745 | Soft | HLTF | 6596 | Soft | SYNPO2 | 171024 | Soft |
| C12orf76 | 400073 | Soft | MZF1 | 7593 | Soft | HLTF-AS1 | 100873945 | Soft | SYS1-OBNDD2 | 767557 | Soft |
| C14orf132 | 56967 | Soft | MZF1-AS1 | 100131691 | Soft | HMBOX1 | 79618 | Soft | SYT11 | 23208 | Soft |
| C14orf93 | 60686 | Soft | N4BP2L1 | 90634 | Soft | HMCN1 | 83872 | Soft | SYT12 | 91683 | Soft |
| C15orf62 | 643338 | Soft | N4BP2L2-IT2 | 116828 | Soft | HMGCL | 3155 | Soft | SYT13 | 57586 | Soft |
| C16orf45 | 89927 | Soft | N4BP3 | 23138 | Soft | HNF1A | 6927 | Soft | SYT17 | 51760 | Soft |
| C16orf74 | 404550 | Soft | NAALADL2 | 254827 | Soft | HNRNPA3P1 | 10151 | Soft | SYT7 | 9066 | Soft |
| C16orf89 | 146556 | Soft | NACAD | 23148 | Soft | HOGA1 | 112817 | Soft | SYT8 | 90019 | Soft |
| C17orf100 | 188327 | Soft | NALT1 | 101928483 | Soft | HOMEZ | 57594 | Soft | SYTL1 | 84958 | Soft |
| C18orf65 | 400658 | Soft | NANOS1 | 340719 | Soft | HOOK2 | 29911 | Soft | SYTL2 | 54843 | Soft |
| G19orf54 | 284325 | Soft | NAP1L6 | 645996 | Soft | HOTAIR | 100124700 | Soft | TAF1A-AS1 | 100506161 | Soft |
| C19orf57 | 79173 | Soft | NAPSA | 9476 | Soft | HOTS | 103344718 | Soft | TAGLN | 6876 | Soft |
| C19orf62 | 128346 | Soft | NATD1 | 256302 | Soft | HOXA-AS2 | 285943 | Soft | TAS2R4 | 50832 | Soft |
| C19orf67 | 284498 | Soft | NBEA | 26960 | Soft | HOXA11-AS | 221883 | Soft | TAS2R5 | 54429 | Soft |
| C19orf204 | 284677 | Soft | NCK1-AS1 | 101927597 | Soft | HOXA13 | 3209 | Soft | TBC 1D 10A | 83874 | Soft |
| C1orf21 | 81563 | Soft | NCKAP1L | 3071 | Soft | HOXA4 | 3201 | Soft | TBC 1D 17 | 79735 | Soft |
| C1orf220 | 400798 | Soft | NCKIPSD | 51517 | Soft | HOXA5 | 3202 | Soft | T BC 1D 32 | 221322 | Soft |
| C1orf228 | 339541 | Soft | NDNF | 79625 | Soft | HOXA6 | 3203 | Soft | T BC 1D 3H | 729877 | Soft |
| C1orf54 | 79630 | Soft | NDRG1 | 10397 | Soft | HOXC-AS1 | 100874363 | Soft | T BC 1D 31 | 102724862 | Soft |
| C1QL1 | 10882 | Soft | NDRG4 | 65009 | Soft | HOXC-AS2 | 100874364 | Soft | TBC1D3L | 101060376 | Soft |
| C1QTNF1 | 114897 | Soft | NDUFA4L2 | 56901 | Soft | HPCA | 3208 | Soft | T BC 1D 8B | 54885 | Soft |
| C1QTNF1-AS1 | 100507410 | Soft | NEAT1 | 283131 | Soft | HPD | 3242 | Soft | TBKBP1 | 9755 | Soft |
| C1QTNF3 | 114899 | Soft | NEBL | 10529 | Soft | HPGD | 3248 | Soft | TBX19 | 9095 | Soft |
| C1QTNF6 | 114904 | Soft | NEBL-AS1 | 100128511 | Soft | HR | 55806 | Soft | TBX6 | 6911 | Soft |
| C1R | 715 | Soft | NEDD9 | 4739 | Soft | HRAT17 | 101928036 | Soft | TBXA2R | 6915 | Soft |
| C1RL | 51279 | Soft | NEIL1 | 79661 | Soft | HRAT5 | 102467073 | Soft | TBXAS1 | 6916 | Soft |
| C1RL-AS1 | 283314 | Soft | NEIL3 | 79858 | Soft | HRAT92 | 441307 | Soft | TC2N | 123036 | Soft |
| C1S | 716 | Soft | NEK11 | 129807 | Soft | HRCT1 | 646962 | Soft | TCAF2 | 285966 | Soft |
| C2 | 717 | Soft | NEU4 | 54492 | Soft | HRNR | 388697 | Soft | TCEA3 | 6920 | Soft |
| C20orf194 | 25943 | Soft | NEURL1B | 54492 | Soft | HS6ST3 | 266722 | Soft | TCF4 | 6925 | Soft |
| C20orf195 | 79025 | Soft | NEURL2 | 140825 | Soft | HSBP1L1 | 440498 | Soft | TCE7 | 6932 | Soft |
| C20orf33 | 8209 | Soft | NEUROG2 | 63973 | Soft | HSD11B1 | 3290 | Soft | TCF7L1 | 83439 | Soft |
| C20orf34 | 348645 | Soft | NFATC4 | 4776 | Soft | HSD11B1L | 374875 | Soft | TCL6 | 27004 | Soft |
| C22orf15 | 150590 | Soft | NFE2L3 | 9603 | Soft | HSD17B14 | 51171 | Soft | TCP11L2 | 255394 | Soft |
| C2orf81 | 388963 | Soft | NFIL3 | 4783 | Soft | HSD17B6 | 8630 | Soft | TCTE1 | 202500 | Soft |

TABLE 2-continued

MeCo genes

| Gene. Symb | gene_id | Status | Gene. Sym | Gene. Symbol | gene_id | Status | Gene. Symbol | gene_id | Status |
|---|---|---|---|---|---|---|---|---|---|
| C3 | 718 | Soft | NFKBIL1 | HSD17B7P2 | 4795 | Soft | TCTN1 | 79600 | Soft |
| C3orf18 | 51161 | Soft | NGFRAP1 | HSD3B7 | 27018 | Soft | TDO2 | 6999 | Soft |
| C3orf36 | 80111 | Soft | NHLRC3 | HSF4 | 387921 | Soft | TDRD9 | 122402 | Soft |
| C3orf67 | 200844 | Soft | NHLRC4 | HSPA1L | 283948 | Soft | TENM1 | 10178 | Soft |
| C4A | 720 | Soft | NHS | HSPB7 | 4810 | Soft | TENM2 | 57451 | Soft |
| C4B | 721 | Soft | NHSL2 | HSPG2 | 340527 | Soft | TES | 26136 | Soft |
| C4B_2 | 100293534 | Soft | NICN1 | HTR2C | 84276 | Soft | TESK2 | 10420 | Soft |
| C4orf3 | 401152 | Soft | NID2 | HTRA1 | 22795 | Soft | TET1 | 80312 | Soft |
| C4orf47 | 441054 | Soft | NFK-AS1 | ICAM1 | 254128 | Soft | TEX9 | 374618 | Soft |
| C5 | 727 | Soft | NIM1K | ICAM2 | 167359 | Soft | TFCP2L1 | 29842 | Soft |
| C5AR1 | 728 | Soft | NIPAL2 | ICAM4 | 79815 | Soft | TFDP2 | 7029 | Soft |
| C5AR2 | 27202 | Soft | NIPAL4 | ICAM5 | 348938 | Soft | TFPI | 7035 | Soft |
| C5orf46 | 389336 | Soft | NIPSNAP1 | ID2-AS1 | 8508 | Soft | TFR2 | 7036 | Soft |
| C6orf223 | 221416 | Soft | NIPSNAP3B | IDUA | 55335 | Soft | TG | 7038 | Soft |
| C7orf13 | 100506380 | Soft | NKD1 | IFI44 | 10561 | Soft | TGFA | 7039 | Soft |
| C7orf61 | 402573 | Soft | NKD2 | IFI44L | 85407 | Soft | TGFB1I1 | 7041 | Soft |
| C8orf31 | 286122 | Soft | NLGN2 | IFI6 | 10964 | Soft | TGFBR3 | 7049 | Soft |
| C8orf34 | 116328 | Soft | NLGN3 | IFIH1 | 64135 | Soft | TGFBR3L | 100507588 | Soft |
| C8orf4 | 56892 | Soft | NLRC5 | IFIT1 | 3434 | Soft | THAP2 | 83591 | Soft |
| C8orf44 | 56260 | Soft | NLRP1 | IFIT2 | 3433 | Soft | THAP7-AS1 | 439931 | Soft |
| C8orf48 | 157773 | Soft | NMNAT2 | IFIT3 | 3437 | Soft | THAP8 | 199745 | Soft |
| C8orf58 | 541565 | Soft | NMNAT3 | IFITM1 | 8519 | Soft | THBS2 | 7058 | Soft |
| C9orf173 | 441476 | Soft | NMRK1 | IFITM10 | 402778 | Soft | THBS3 | 7059 | Soft |
| C9orf173-AS1 | 100129722 | Soft | NMU | IFITM4P | 10874 | Soft | THBS4 | 7060 | Soft |
| C9orf3 | 84909 | Soft | NOD2 | IFT140 | 64127 | Soft | THEMIS2 | 9473 | Soft |
| C9orf9 | 11092 | Soft | NOL3 | IFT80 | 8996 | Soft | THRA | 7067 | Soft |
| CA11 | 770 | Soft | NOLAL | IFT81 | 140688 | Soft | THRB | 7068 | Soft |
| CA3 | 761 | Soft | NOTCH3 | IGBP1P1 | 4854 | Soft | TIMP3 | 7078 | Soft |
| CA5B | 11238 | Soft | NOTUM | IGF2BP1 | 147111 | Soft | TLCD2 | 727910 | Soft |
| CA9 | 768 | Soft | NOXA1 | IGFBP2 | 10811 | Soft | TLE2 | 7089 | Soft |
| CACFD1 | 11094 | Soft | NOXRED1 | IGFBP3 | 122945 | Soft | TLE6 | 79816 | Soft |
| CACNA1B | 774 | Soft | NPAS1 | IGFBP5 | 4861 | Soft | TLR1 | 7096 | Soft |
| CACNA1C | 775 | Soft | NPAS2 | IGFBP7-AS1 | 4862 | Soft | TLR9 | 54106 | Soft |
| CACNA1G | 8913 | Soft | N PC 1L1 | IGIP | 29881 | Soft | TM4SF1-AS1 | 100874091 | Soft |
| CACNA1H | 8912 | Soft | NPHP1 | IGSF10 | 4867 | Soft | TM7SF2 | 7108 | Soft |
| CACNA1I | 8911 | Soft | NPHP3 | IGSF22 | 27031 | Soft | TMCC1-AS1 | 100507032 | Soft |
| CACNA2D2 | 9254 | Soft | NPHP3ACAD11 | IGSF8 | 93185 | Soft | TMEM100 | 55273 | Soft |
| CACNA2D3 | 55799 | Soft | NPM2 | IGSF9 | 57549 | Soft | TMEM102 | 284114 | Soft |
| CACNB1 | 782 | Soft | NPTN-IT1 | IL11RA | 3590 | Soft | TMEM107 | 84314 | Soft |
| CACNB3 | 784 | Soft | NPTX1 | IL13RA2 | 4884 | Soft | TMEM116 | 89894 | Soft |
| CADM1 | 23705 | Soft | NPW | IL15 | 283869 | Soft | TMEM130 | 222865 | Soft |
| CADM3 | 57863 | Soft | NPY2R | IL16 | 4887 | Soft | TMEM132B | 114795 | Soft |
| CADM3-AS1 | 100131825 | Soft | NR1D1 | IL17B | 9572 | Soft | TMEM136 | 219902 | Soft |
| CADM4 | 199731 | Soft | NR1H3 | IL17RC | 10062 | Soft | TMEM143 | 55260 | Soft |
| CAHM | 100526820 | Soft | NR2F1-AS1 | IL17RE | 441094 | Soft | TMEM145 | 284339 | Soft |
| CALCOCO1 | 57658 | Soft | NRBP2 | IL18BP | 10068 | Soft | TMEM159 | 57146 | Soft |
| CALHM3 | 119395 | Soft | NRN1 | IL1R2 | 7850 | Soft | TMEM173 | 340061 | Soft |
| CAMK2B | 816 | Soft | NRN1L | IL23R | 123904 | Soft | TMEM178B | 100507421 | Soft |
| CAMKV | 79012 | Soft | NRSN2-AS1 | IL2RG | 100507459 | Soft | TMEM187 | 8269 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| CAND1.11 | 100130460 | Soft | NRTN | 4902 | Soft | IL34 | 146433 | Soft | TMEM1988 | 440104 | Soft |
| CAPN3 | 825 | Soft | NRXN2 | 9379 | Soft | IMPG2 | 50939 | Soft | TMEM25 | 84866 | Soft |
| CAPS | 828 | Soft | NRXN3 | 9369 | Soft | INADL | 10207 | Soft | TMEM255A | 55026 | Soft |
| CARD14 | 79092 | Soft | NSG1 | 27065 | Soft | INAFM1 | 255783 | Soft | TMEM27 | 57393 | Soft |
| CARF | 79800 | Soft | NT5M | 56953 | Soft | INE2 | 8551 | Soft | TMEM37 | 140738 | Soft |
| CARMN | 728264 | Soft | NTN3 | 4917 | Soft | ING4 | 51147 | Soft | TMEM38A | 79041 | Soft |
| CARNS1 | 57571 | Soft | NTNS | 126147 | Soft | INHA | 3623 | Soft | TMEM42 | 131616 | Soft |
| CASC10 | 399726 | Soft | NUDT13 | 25961 | Soft | INHBE | 83729 | Soft | TMEM45A | 55076 | Soft |
| CASC2 | 255082 | Soft | NUDT14 | 256281 | Soft | INMT | 11185 | Soft | TMEM47 | 83604 | Soft |
| CASC9 | 101805492 | Soft | NUDT7 | 283927 | Soft | INSIG2 | 51141 | Soft | TMEM51-AS1 | 200197 | Soft |
| CATSPER2P1 | 440278 | Soft | NUGGC | 389643 | Soft | INTS6-AS1 | 100507298 | Soft | TMEM59L | 25789 | Soft |
| CBLN3 | 643866 | Soft | NUPR1 | 26471 | Soft | IP6K2 | 51447 | Soft | TMEM63C | 57156 | Soft |
| CBS | 875 | Soft | NXNL2 | 158046 | Soft | IP6K3 | 117283 | Soft | TMEM67 | 91147 | Soft |
| CBX7 | 23492 | Soft | NXPH4 | 11247 | Soft | IPMK | 253430 | Soft | TMEM74B | 55321 | Soft |
| CCBL1 | 883 | Soft | NYAP1 | 222950 | Soft | IQCD | 115811 | Soft | TMEM80 | 283232 | Soft |
| CCDC102A | 92922 | Soft | NYNRIN | 57523 | Soft | IQCH-AS1 | 100506686 | Soft | TMEM8B | 51754 | Soft |
| CC DC 1028 | 79839 | Soft | OAS1 | 4938 | Soft | IQGAP2 | 10788 | Soft | TMEM91 | 641649 | Soft |
| CCDC103 | 388389 | Soft | OAS2 | 4939 | Soft | IQUB | 154865 | Soft | TMEM92 | 162461 | Soft |
| CCDC110 | 256309 | Soft | OASL | 8638 | Soft | IRAK3 | 11213 | Soft | TMEM92-AS1 | 103752589 | Soft |
| CCDC146 | 57639 | Soft | OBSCN | 84033 | Soft | IRF6 | 3664 | Soft | TMEM9B-AS1 | 493900 | Soft |
| CCDC148 | 130940 | Soft | OBSL1 | 23363 | Soft | IRF9 | 10379 | Soft | TNFAIP8 | 25816 | Soft |
| CCDC151 | 115948 | Soft | OCEL1 | 79629 | Soft | IRX3 | 79191 | Soft | TNFRSF10C | 8794 | Soft |
| CCDC152 | 100129792 | Soft | ODF3B | 440836 | Soft | ISG20 | 3669 | Soft | TNFRSF14 | 8764 | Soft |
| CCDC158 | 339965 | Soft | ODF3L1 | 161753 | Soft | ISLR | 3671 | Soft | TNFRSF25 | 8718 | Soft |
| CCDC17 | 149483 | Soft | OGFR-AS1 | 101409261 | Soft | ISLR2 | 57611 | Soft | TNFSF13B | 10673 | Soft |
| CCDC18-AS1 | 100131564 | Soft | OLFML2A | 93145 | Soft | ITGA1 | 3672 | Soft | TNFSF14 | 8740 | Soft |
| CCDC180 | 100499483 | Soft | OLFML2B | 169611 | Soft | ITGA10 | 8515 | Soft | TNFSF4 | 7292 | Soft |
| CCDC183 | 84960 | Soft | OLFML3 | 25903 | Soft | ITGA11 | 22801 | Soft | TNK1 | 8711 | Soft |
| CCDC184 | 387856 | Soft | OLMALINC | 56944 | Soft | ITGA2B | 3674 | Soft | TNNI2 | 7136 | Soft |
| CCDC191 | 57577 | Soft | OOEP | 90271 | Soft | ITGAX | 3687 | Soft | TNNI3K | 51086 | Soft |
| CCDC40 | 55036 | Soft | OPLAH | 441161 | Soft | ITGB2 | 3689 | Soft | TNNT1 | 7138 | Soft |
| CCDC64B | 146439 | Soft | OPN3 | 26873 | Soft | ITGB2-AS1 | 100505746 | Soft | TNNT3 | 7140 | Soft |
| CCDC65 | 85478 | Soft | OPRL1 | 23596 | Soft | ITGB4 | 3691 | Soft | TNS1 | 7145 | Soft |
| CCDC74A | 90557 | Soft | OR10V2P | 4987 | Soft | ITGB8 | 3696 | Soft | TNXB | 7148 | Soft |
| CCDC80 | 151887 | Soft | OR51B4 | 81343 | Soft | ITIH4 | 3700 | Soft | TOB1-AS1 | 400604 | Soft |
| CCDC92 | 80212 | Soft | OR51B5 | 4992 | Soft | ITIH4-AS1 | 100873993 | Soft | TOB2P1 | 222699 | Soft |
| CCL26 | 10344 | Soft | ORAI3 | 79339 | Soft | ITPR1 | 3708 | Soft | TOLLIP-AS1 | 255512 | Soft |
| CCL5 | 6352 | Soft | ORM1 | 282763 | Soft | ITPR1-AS1 | 100996539 | Soft | TP53I11 | 9537 | Soft |
| CCND2 | 894 | Soft | OSBPL5 | 93129 | Soft | IZUMO4 | 113177 | Soft | TP53INP1 | 94241 | Soft |
| CCND2-AS1 | 103752584 | Soft | OSCAR | 5004 | Soft | JAG2 | 3714 | Soft | TP53INP2 | 58476 | Soft |
| CCNG2 | 901 | Soft | OSCP1 | 114879 | Soft | JAK3 | 3718 | Soft | TP53TG1 | 11257 | Soft |
| CCNYL2 | 414194 | Soft | OSER1-AS1 | 126014 | Soft | JAM2 | 58494 | Soft | TP63 | 8626 | Soft |
| CCR10 | 2826 | Soft | OSR2 | 127700 | Soft | JPH2 | 57158 | Soft | TP73 | 7161 | Soft |
| CCT6B | 10693 | Soft | OVCH1 | 100505783 | Soft | JUP | 3728 | Soft | TP73-AS1 | 57212 | Soft |
| CD180 | 4064 | Soft | OXR1 | 116039 | Soft | KALRN | 8997 | Soft | TPO | 7173 | Soft |
| CD226 | 10666 | Soft | P2RX6 | 341350 | Soft | KATNAL2 | 83473 | Soft | TPP1 | 1200 | Soft |
| CD24 | 100133941 | Soft | P2RX6 | 9127 | Soft | KAZALD1 | 81621 | Soft | TPPP | 11076 | Soft |
| CD27 | 939 | Soft | P2RX7 | 5027 | Soft | KAZN | 23254 | Soft | TPPP3 | 51673 | Soft |
| CD27-AS1 | 678655 | Soft | P2RX7 | 5027 | Soft | KBTBD3 | 143879 | Soft | TPRG1 | 285386 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| CD36 | 948 | Soft | P4HA1 | 5033 | Soft | KBTBD7 | 84078 | Soft | TPRG1-AS1 | 100874043 | Soft |
| CD40 | 958 | Soft | P4HA2-AS1 | 100861518 | Soft | KC6 | 641516 | Soft | TPSG1 | 25823 | Soft |
| CD68 | 968 | Soft | P4HTM | 54681 | Soft | KCCAT211 | 102724550 | Soft | TPT1-AS1 | 100190939 | Soft |
| CD7 | 924 | Soft | PACS2 | 23241 | Soft | KCNAB2 | 8514 | Soft | TRABD2B | 388630 | Soft |
| CD72 | 971 | Soft | PAD13 | 51702 | Soft | KCND1 | 3750 | Soft | TRAPPC6A | 79090 | Soft |
| CD74 | 972 | Soft | PAGE2 | 203569 | Soft | KCNE3 | 10008 | Soft | TREM1 | 54210 | Soft |
| CD82 | 3732 | Soft | PAGE2B | 389860 | Soft | KCNE4 | 23704 | Soft | TRIB2 | 28951 | Soft |
| CDC42EP5 | 148170 | Soft | PAGE3 | 139793 | Soft | KCNH1 | 3756 | Soft | TRIM17 | 51127 | Soft |
| CDH13 | 1012 | Soft | PAIP2B | 400961 | Soft | KCNH3 | 23416 | Soft | TRIM22 | 10346 | Soft |
| CDH19 | 28513 | Soft | PALD1 | 27143 | Soft | KCNH5 | 27133 | Soft | TRIM29 | 23650 | Soft |
| CDH22 | 64405 | Soft | PAMR1 | 25891 | Soft | KCNH8 | 131096 | Soft | TRIM34 | 53840 | Soft |
| CDHR5 | 53841 | Soft | PAN2 | 9924 | Soft | KCNIP2 | 30819 | Soft | TRIM4 | 89122 | Soft |
| CDK18 | 5129 | Soft | PAPLN | 89932 | Soft | KCNJ9 | 3765 | Soft | TRIM46 | 80128 | Soft |
| CDK19 | 23097 | Soft | PAPPA | 5069 | Soft | KCNK15-AS1 | 106144538 | Soft | TRIM52 | 84a51 | Soft |
| CDKL2 | 8999 | Soft | PAPPA-AS1 | 493913 | Soft | KCNK2 | 3776 | Soft | TRIM54 | 57159 | Soft |
| CDKN1B | 1027 | Soft | PAPPA2 | 60676 | Soft | KCNK3 | 3777 | Soft | TRIM6-TRIM34 | 445372 | Soft |
| CDNF | 441549 | Soft | PAQR6 | 79957 | Soft | KCNMB2-AS1 | 104797538 | Soft | TRIM63 | 84676 | Soft |
| CDON | 50937 | Soft | PAQR8 | 85315 | Soft | KCNN1 | 3780 | Soft | TRIM66 | 9866 | Soft |
| CDR1 | 1038 | Soft | PARD6G-AS1 | 100130522 | Soft | KCNN4 | 3783 | Soft | TRIM69 | 140691 | Soft |
| CECR1 | 51816 | Soft | PARK2 | 5071 | Soft | KCNT2 | 343450 | Soft | TRIML1 | 339976 | Soft |
| CECR2 | 27443 | Soft | PARM1 | 25849 | Soft | KCTD11 | 147040 | Soft | TRIOBP | 11078 | Soft |
| CECR5-AS1 | 100130717 | Soft | PARP10 | 84875 | Soft | KCTD16 | 57528 | Soft | TRIQK | 286144 | Soft |
| CELF6 | 60677 | Soft | PARP16 | 54956 | Soft | KCTD19 | 146212 | Soft | TRO | 7216 | Soft |
| CELSR3 | 1951 | Soft | PARP3 | 10039 | Soft | KDF1 | 126695 | Soft | TRPC1 | 7220 | Soft |
| CEMIP | 57214 | Soft | PAX9 | 5083 | Soft | KDM3A | 55818 | Soft | TRPM4 | 54795 | Soft |
| CEP112 | 201134 | Soft | PBXIP1 | 57326 | Soft | KDM4B | 23030 | Soft | TRPS1 | 7227 | Soft |
| CEP126 | 57562 | Soft | PCAT2 | 84875 | Soft | KDM4C | 23081 | Soft | TRPT1 | 83707 | Soft |
| CEP68 | 23177 | Soft | PCAT5 | 103164619 | Soft | KDM58 | 10765 | Soft | TRPV1 | 7442 | Soft |
| CERS1 | 10715 | Soft | PCAT6 | 102578074 | Soft | KDR | 3791 | Soft | TS02203 | 1831 | Soft |
| CERS4 | 79603 | Soft | PCBP1-AS1 | 100506696 | Soft | KIAA0825 | 285600 | Soft | TSHZ2 | 128553 | Soft |
| CES3 | 23491 | Soft | PCBP3 | 400960 | Soft | KIAA0895L | 653319 | Soft | TSLP | 85480 | Soft |
| CFAP126 | 257177 | Soft | PCDH18 | 54039 | Soft | KIAA1107 | 23285 | Soft | TSNARE1 | 203062 | Soft |
| CFAP206 | 154313 | Soft | PCDH20 | 54510 | Soft | KIAA1109 | 84162 | Soft | TSNAXIP1 | 55815 | Soft |
| CFAP221 | 200373 | Soft | PCDH7 | 5099 | Soft | KIAA1462 | 57608 | Soft | TSPAN1 | 10103 | Soft |
| CFAP43 | 80217 | Soft | PCDHB5 | 26167 | Soft | KIAA1683 | 80726 | Soft | TSPAN15 | 23555 | Soft |
| CFAP44 | 55779 | Soft | PCDHB9 | 56127 | Soft | KIAA1958 | 158405 | Soft | TSPAN18 | 90139 | Soft |
| CFAP47 | 286464 | Soft | PCED1A | 64773 | Soft | KIF26A | 26153 | Soft | TSPAN19 | 144448 | Soft |
| CFAP53 | 220136 | Soft | PCMTD1 | 115294 | Soft | KIF3C | 3797 | Soft | TSPAN31 | 6302 | Soft |
| CFAP54 | 144535 | Soft | PCOLCE | 5118 | Soft | KIFSA | 3798 | Soft | TSPAN7 | 7102 | Soft |
| CFAP57 | 149465 | Soft | PCOLCE-AS1 | 100129845 | Soft | KIF5C | 3800 | Soft | TSPANB | 7103 | Soft |
| CFAP58-AS1 | 100505869 | Soft | PCP2 | 126006 | Soft | KIFC2 | 90990 | Soft | TSSK3 | 81629 | Soft |
| CEAP70 | 118491 | Soft | PCSK1 | 5122 | Soft | KISS1R | 84634 | Soft | TSSK6 | 83983 | Soft |
| CFB | 629 | Soft | PCSK4 | 54760 | Soft | KIZ | 55857 | Soft | TTBK2 | 146057 | Soft |
| CFD | 1675 | Soft | PDCD4 | 27250 | Soft | KIZ-AS1 | 101929591 | Soft | TTC21A | 199223 | Soft |
| CFH | 3075 | Soft | PDCD4-AS1 | 282997 | Soft | KLC4 | 89953 | Soft | TTC25 | 83538 | Soft |
| CFHR3 | 10878 | Soft | PDE2A | 5138 | Soft | KLF2 | 10365 | Soft | TTC30A | 92104 | Soft |
| CFI | 3426 | Soft | PDE4C | 5143 | Soft | KLF7 | 8609 | Soft | TTC39A | 22996 | Soft |
| CHD5 | 26038 | Soft | PDE4DIP | 9659 | Soft | KLF8 | 11279 | Soft | TTC39B | 158219 | Soft |
| CHD6 | 84181 | Soft | PDE5A | 8654 | Soft | KLHDC1 | 122773 | Soft | TTLL1 | 25809 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| CHRM3 | 1131 | Soft | PDE7B | 27115 | Soft | KLHDC8B | 200942 | Soft | TTLL3 | 26140 | Soft |
| CHRNB1 | 1140 | Soft | PDE8B | 8622 | Soft | KLHL24 | 54800 | Soft | TTYH2 | 94015 | Soft |
| CHST1 | 8534 | Soft | PDGFB | 5155 | Soft | KLHL28 | 54813 | Soft | TUB | 7275 | Soft |
| CHST15 | 51363 | Soft | PDGFD | 80310 | Soft | KLHL3 | 26249 | Soft | TUBA3FP | 113691 | Soft |
| CIART | 148523 | Soft | PDGFRA | 5156 | Soft | KLHL30 | 377007 | Soft | TUBAS | 51807 | Soft |
| CIITA | 4261 | Soft | PDGFRB | 5159 | Soft | KLHL31 | 401265 | Soft | TUBAL3 | 79861 | Soft |
| CISH | 1154 | Soft | PDK1 | 5163 | Soft | KLHL36 | 79786 | Soft | TUBB2B | 347733 | Soft |
| CITED2 | 10370 | Soft | PDK3 | 5165 | Soft | KLHL38 | 340359 | Soft | TWIST1 | 7291 | Soft |
| CKB | 1152 | Soft | PDK4 | 5166 | Soft | KLHL7-AS1 | 100775104 | Soft | TXK | 7294 | Soft |
| CLCNKA | 1187 | Soft | PDLIM2 | 64236 | Soft | KLRC2 | 3822 | Soft | TXLNB | 167838 | Soft |
| CLCN16 | 10686 | Soft | PDZD2 | 23037 | Soft | KLRC3 | 3823 | Soft | TXNIP | 10628 | Soft |
| CLDN18 | 51208 | Soft | PDZD7 | 79955 | Soft | KLRC4-KLRK1 | 100528032 | Soft | TYMP | 1890 | Soft |
| CLDN9 | 9080 | Soft | PDZK1IP1 | 10158 | Soft | KLRK1 | 22914 | Soft | TYRP1 | 7306 | Soft |
| CLDND2 | 125875 | Soft | PEAR1 | 375033 | Soft | KMO | 8564 | Soft | UBA6-AS1 | 550112 | Soft |
| CLEC11A | 6320 | Soft | PELI2 | 57161 | Soft | KMT2E-AS1 | 100216545 | Soft | UBA7 | 7318 | Soft |
| CLEC2B | 9976 | Soft | PEX11A | 8800 | Soft | KRBA2 | 124751 | Soft | UBAP1L | 390595 | Soft |
| CLEC2D | 29121 | Soft | PEX11G | 92960 | Soft | KRCC1 | 51315 | Soft | UBE2O2P1 | 388165 | Soft |
| CLEC3B | 7123 | Soft | PEX5L | 51555 | Soft | KREMEN1 | 83999 | Soft | UCN | 7349 | Soft |
| CLHC1 | 130162 | Soft | PEX6 | 5190 | Soft | KREMEN2 | 79412 | Soft | UCN2 | 90226 | Soft |
| CLIC2 | 1193 | Soft | PFKFB4 | 5210 | Soft | KRT17 | 3872 | Soft | UGDH-AS1 | 100885776 | Soft |
| CLIC5 | 53405 | Soft | PFN1P2 | 767846 | Soft | KRT5 | 3852 | Soft | UGT1A1 | 54658 | Soft |
| CLIP1-AS1 | 100507066 | Soft | PGAM2 | 5224 | Soft | KRT79 | 338785 | Soft | UGT1A10 | 54575 | Soft |
| CLIP3 | 25999 | Soft | PGAP1 | 80055 | Soft | KRT84 | 3890 | Soft | UGT1A3 | 54659 | Soft |
| CLK1 | 1195 | Soft | PGF | 5228 | Soft | KRTAP1-5 | 83895 | Soft | UGT1A4 | 54657 | Soft |
| CLK4 | 57396 | Soft | PGPEP1 | 54858 | Soft | KY | 339855 | Soft | UGT1A5 | 54579 | Soft |
| CLMN | 79789 | Soft | PGR | 5241 | Soft | L1CAM | 3897 | Soft | UGT1A6 | 54578 | Soft |
| CLSTN3 | 9746 | Soft | PHEX | 5251 | Soft | L3MBTL1 | 26013 | Soft | UGT1A7 | 54577 | Soft |
| CLUL1 | 27098 | Soft | PHF21A | 51317 | Soft | L3MBL4 | 91133 | Soft | UGT1A8 | 54576 | Soft |
| CLYBL | 171425 | Soft | PHLDB3 | 653583 | Soft | LAMB2 | 3913 | Soft | UGT1A9 | 54600 | Soft |
| CMKLR1 | 1240 | Soft | PHYHD1 | 254295 | Soft | LAMB2P1 | 22973 | Soft | UGT2A1 | 10941 | Soft |
| CNBD1 | 168975 | Soft | PHYKPL | 85007 | Soft | LAPTM5 | 7805 | Soft | UGT2A2 | 574537 | Soft |
| CNNM2 | 54805 | Soft | PIEZO2 | 63895 | Soft | LBH | 81606 | Soft | ULBP1 | 80329 | Soft |
| CNOT8 | 9337 | Soft | PIGV | 55650 | Soft | LBX2 | 85474 | Soft | ULK1 | 8408 | Soft |
| CNR1 | 1268 | Soft | PIGZ | 80235 | Soft | LBX2-AS1 | 151534 | Soft | UNG13C | 440279 | Soft |
| CNRIP1 | 25927 | Soft | PIH1D2 | 120379 | Soft | LCA5 | 167691 | Soft | UNC58 | 219699 | Soft |
| CNTN3 | 5067 | Soft | PIK3C2B | 5287 | Soft | LDB3 | 11155 | Soft | UNCSB-AS1 | 728978 | Soft |
| CNTN5 | 53942 | Soft | PIK3CD-AS2 | 101929074 | Soft | LDHD | 197257 | Soft | URAHP | 100130015 | Soft |
| CNTNAP4 | 85445 | Soft | PIK3IP1 | 113791 | Soft | LDLRAD2 | 401944 | Soft | USP27X-AS1 | 158572 | Soft |
| COL11A2 | 1302 | Soft | PIM1 | 5292 | Soft | LENG8-AS1 | 104355426 | Soft | USP30 | 84749 | Soft |
| COL14A1 | 7373 | Soft | PIP5KL1 | 138429 | Soft | LEPR | 3953 | Soft | VAMP1 | 6843 | Soft |
| COL18A1 | 80781 | Soft | PIPDX | 51268 | Soft | LEPROT | 54741 | Soft | VAMP2 | 6844 | Soft |
| COL21A1 | 81578 | Soft | PITPNM3 | 83394 | Soft | LETMD1 | 25875 | Soft | VASN | 114990 | Soft |
| COL28A1 | 340267 | Soft | PIWIL4 | 143689 | Soft | LGALS9 | 3965 | Soft | VCAM1 | 7412 | Soft |
| COL3A1 | 1281 | Soft | PK01 | 5310 | Soft | LGI4 | 163175 | Soft | VCAN | 1462 | Soft |
| COL4A2 | 1284 | Soft | PKD1L2 | 114780 | Soft | LHPP | 64077 | Soft | VEGFA | 7422 | Soft |
| COL4A2-AS1 | 100874203 | Soft | PKDCC | 91461 | Soft | LHX9 | 56956 | Soft | VIM-AS1 | 100507347 | Soft |
| COL4A3 | 1285 | Soft | PKDREJ | 10343 | Soft | LIN7A | 8825 | Soft | VLDLR | 7436 | Soft |
| COL4A4 | 1286 | Soft | PKHD1 | 5314 | Soft | LINC-PINT | 378805 | Soft | VLDLR-AS1 | 401491 | Soft |
| COL5A1 | 1289 | Soft | PKH DIL1 | 93035 | Soft | LINC00163 | 727699 | Soft | VMAC | 400673 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| COL5A3 | 50509 | Soft | PLA2G6 | 8398 | Soft | LINC00173 | 100287569 | Soft | VNN1 | 8876 | Soft |
| COL6A1 | 1291 | Soft | PLA2R1 | 22925 | Soft | LINC00174 | 285908 | Soft | VPREB3 | 29802 | Soft |
| COL6A2 | 1292 | Soft | PLAG1 | 5324 | Soft | LINC00184 | 100302691 | Soft | VPS37D | 155382 | Soft |
| COL6A4P1 | 344875 | Soft | PLCB1 | 23236 | Soft | LINC00202-1 | 387644 | Soft | VSIG10L | 147645 | Soft |
| COL7A1 | 1294 | Soft | PLCD1 | 5333 | Soft | LINC00202-2 | 731789 | Soft | VWA1 | 64856 | Soft |
| COL9A2 | 1298 | Soft | PLCH2 | 9651 | Soft | LINC00243 | 401247 | Soft | VWA7 | 80737 | Soft |
| COL9A3 | 1299 | Soft | PLCL1 | 5334 | Soft | LINC00324 | 284029 | Soft | VWDE | 221806 | Soft |
| COLCA1 | 399948 | Soft | PLD 1 | 5337 | Soft | LINC00332 | 100874127 | Soft | WASH2P | 375260 | Soft |
| COLEC11 | 78989 | Soft | PLEKHA4 | 57664 | Soft | LINC00339 | 29192 | Soft | WBP1 | 23559 | Soft |
| COLEC12 | 81035 | Soft | PLEKHA6 | 22874 | Soft | LINC00525 | 84847 | Soft | WBP5 | 51186 | Soft |
| COLQ | 8292 | Soft | PLEKHG5 | 57449 | Soft | LINC00548 | 400123 | Soft | WDR31 | 114987 | Soft |
| COPG2IT1 | 53844 | Soft | PLEKHH3 | 79990 | Soft | LINC00565 | 100861555 | Soft | WDR60 | 55112 | Soft |
| CORIN | 10699 | Soft | PLEKHS1 | 79949 | Soft | LINC00592 | 283404 | Soft | WDR63 | 126820 | Soft |
| CORO2A | 7464 | Soft | PLIN1 | 5346 | Soft | LINC00598 | 646982 | Soft | WDR78 | 79819 | Soft |
| CORO2B | 10391 | Soft | PLIN2 | 123 | Soft | LINC00607 | 646324 | Soft | WDR93 | 56964 | Soft |
| CORO6 | 84940 | Soft | PLIN4 | 729359 | Soft | LINC00619 | 414260 | Soft | WDR97 | 340390 | Soft |
| CP | 1356 | Soft | PLOD2 | 5352 | Soft | LINC00622 | 64242 | Soft | WEE2-AS1 | 285962 | Soft |
| CPA3 | 1359 | Soft | PLS3-AS1 | 101927352 | Soft | LINC00632 | 286411 | Soft | WFDC1 | 58189 | Soft |
| CPAMD8 | 27151 | Soft | PLSCR4 | 57088 | Soft | LINC00634 | 339674 | Soft | WFDC3 | 140686 | Soft |
| CPE | 1363 | Soft | PLXDC1 | 57125 | Soft | LINC00638 | 196872 | Soft | WFIKKN1 | 117166 | Soft |
| CPLX1 | 10815 | Soft | PLXDC2 | 84898 | Soft | LINC00648 | 100506433 | Soft | WISP1 | 8840 | Soft |
| CPM | 1368 | Soft | PLXNA3 | 55558 | Soft | LINC00649 | 100506334 | Soft | WISP2 | 8839 | Soft |
| CPQ | 10404 | Soft | PLXNB1 | 5364 | Soft | LINC00663 | 29075 | Soft | WNT2B | 7482 | Soft |
| CPT1C | 126129 | Soft | PLXNB3 | 5365 | Soft | LINC00672 | 284440 | Soft | WNT5A | 7474 | Soft |
| CRAT | 1384 | Soft | PLAND1 | 23129 | Soft | LINC00680-GUSBP4 | 100505576 | Soft | WWC2-AS2 | 152641 | Soft |
| CREBRF | 153222 | Soft | PMEL | 6490 | Soft | LINC00702 | 106660613 | Soft | XAF1 | 54739 | Soft |
| CRELD1 | 78987 | Soft | PMFBP1 | 83449 | Soft | LINC00704 | 100152988 | Soft | XCR1 | 2829 | Soft |
| CRHR1-IT1 | 147081 | Soft | PNMA2 | 10687 | Soft | LINC00706 | 100216001 | Soft | XKR9 | 389668 | Soft |
| CRIP2 | 1397 | Soft | PNPLA7 | 375775 | Soft | LINC00706 | 100652997 | Soft | YJEFN3 | 374887 | Soft |
| CRISP3 | 10321 | Soft | PODNL1 | 79883 | Soft | LINC00840 | 1005(16835 | Soft | YPEL2 | 388403 | Soft |
| CRLF1 | 9244 | Soft | POLD4 | 57804 | Soft | LINC00847 | 729678 | Soft | YPEL3 | 83719 | Soft |
| CROCCP3 | 114819 | Soft | POLI | 11201 | Soft | LINC00853 | 100874253 | Soft | YPEL4 | 219539 | Soft |
| CRTAC1 | 55118 | Soft | POM121L9P | 29774 | Soft | LINC00870 | 100272228 | Soft | YPEL5 | 51646 | Soft |
| CRTC1 | 23373 | Soft | POSTN | 10631 | Soft | LINC00877 | 285286 | Soft | ZBED3-AS1 | 728723 | Soft |
| CRYAB | 1410 | Soft | POU5F1 | 5460 | Soft | LINC00882 | 100302640 | Soft | ZBED5-AS1 | 729013 | Soft |
| CSMD3 | 114788 | Soft | POU5F1P3 | 642559 | Soft | LINC00887 | 100131551 | Soft | ZBED6CL | 113763 | Soft |
| CSRNP3 | 80034 | Soft | POU6F1 | 5463 | Soft | LINC00893 | 100131434 | Soft | ZBEDB | 63920 | Soft |
| CSTA | 1475 | Soft | POU6F2 | 11281 | Soft | LINC00894 | 100272228 | Soft | ZBTB1 | 22890 | Soft |
| CTB-113P19.1 | 101927096 | Soft | PPARA | 5465 | Soft | LINC00898 | 400932 | Soft | ZBTB16 | 7704 | Soft |
| CTBS | 1486 | Soft | PPARGC1A | 10891 | Soft | LINC00899 | 100271722 | Soft | ZBTB22 | 9278 | Soft |
| CTC-338M12.4 | 101928649 | Soft | PPEF1 | 5475 | Soft | LINC00910 | 100130581 | Soft | ZBTB25 | 7597 | Soft |
| CTF1 | 1489 | Soft | PPFIA2 | 8499 | Soft | LINC00920 | 100505865 | Soft | ZC3H12D | 340152 | Soft |
| CTSF | 8722 | Soft | PPFIA4 | 8497 | Soft | LINC00921 | 283876 | Soft | ZC3H6 | 376940 | Soft |
| CTSH | 1512 | Soft | PPIL6 | 285755 | Soft | LINC00942 | 100292680 | Soft | ZC3HAV1L | 92092 | Soft |
| CTSK | 1513 | Soft | PPL | 5493 | Soft | LINC00950 | 92973 | Soft | ZC4H2 | 55906 | Soft |
| CTSO | 1519 | Soft | PPM1L | 151742 | Soft | LINC00957 | 255031 | Soft | ZCCHC24 | 219654 | Soft |
| CUBN | 8029 | Soft | PPM1M | 132160 | Soft | LINC00964 | 157381 | Soft | ZCW PW 1 | 55063 | Soft |
| CUEDC1 | 404093 | Soft | PPM1N | 147699 | Soft | LINC00969 | 440093 | Soft | ZCWPW2 | 152098 | Soft |
| CUL7 | 9820 | Soft | PPP1R13L | 10848 | Soft | LINC01011 | 401232 | Soft | ZDBF2 | 57683 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| CUX1 | 1523 | Soft | PPP1R1C | 151242 | Soft | LINC01024 | 100505636 | Soft | ZDHHC1 | 29800 | Soft |
| CX3CL1 | 6376 | Soft | PPP1R32 | 220004 | Soft | LINC01029 | 101927715 | Soft | ZDHHC11 | 79844 | Soft |
| CXADRP3 | 440224 | Soft | PPP1R3B | 79660 | Soft | LINC01058 | 103724387 | Soft | ZDHHC23 | 254887 | Soft |
| CXCL11 | 6373 | Soft | PPP1R3C | 5507 | Soft | LINC01119 | 100134259 | Soft | ZEB2 | 9839 | Soft |
| CXCL12 | 6387 | Soft | PPP1R3E | 90673 | Soft | LINC01125 | 728537 | Soft | ZEB2-AS1 | 100303491 | Soft |
| CXCL16 | 58191 | Soft | PPP4R1L | 55370 | Soft | LINC01126 | 100129726 | Soft | ZER1 | 10444 | Soft |
| CXCR4 | 7852 | Soft | PRDM1 | 639 | Soft | LINC01137 | 728431 | Soft | ZFHX2 | 85446 | Soft |
| CXXC4 | 80319 | Soft | PRDM2 | 7799 | Soft | LINC01158 | 100506421 | Soft | ZFP14 | 57677 | Soft |
| CXXCS | 51523 | Soft | PRELID2 | 153768 | Soft | LINC01159 | 102682016 | Soft | ZFP90 | 146198 | Soft |
| CYB5D2 | 124936 | Soft | PRICKLE2 | 166336 | Soft | LINC01179 | 101928151 | Soft | ZFYVE1 | 53349 | Soft |
| CYBRD1 | 79901 | Soft | PRICKLE2-AS1 | 100652759 | Soft | LINC 01186 | 101927574 | Soft | ZFWE28 | 57732 | Soft |
| CYHR1 | 50626 | Soft | PRICKLE2-AS3 | 100874243 | Soft | LINC 01219 | 104355220 | Soft | ZG16B | 124220 | Soft |
| CYP11A1 | 1583 | Soft | PRICKLE4 | 29964 | Soft | LINC01260 | 79015 | Soft | ZHX2 | 22882 | Soft |
| CYP17A1 | 1586 | Soft | PRKAA2 | 5563 | Soft | LINC01273 | 101927541 | Soft | ZIC4 | 84107 | Soft |
| CYP19A1 | 1588 | Soft | PRKAB2 | 5565 | Soft | LINC01279 | 100506621 | Soft | ZKSCAN4 | 387032 | Soft |
| CYP27B1 | 1594 | Soft | PRKAG2-AS1 | 100505483 | Soft | LINC01301 | 100506385 | Soft | ZMAT1 | 84460 | Soft |
| CYP2E1 | 1571 | Soft | PRKAR2A-AS1 | 100506637 | Soft | LINC01355 | 100996511 | Soft | ZMIZ1-AS1 | 283050 | Soft |
| CYP39A1 | 51302 | Soft | PRKCE | 5581 | Soft | LINC01410 | 103352539 | Soft | ZMYND10 | 51364 | Soft |
| CYP4B1 | 1580 | Soft | PRKCZ | 5590 | Soft | LINC01426 | 100506385 | Soft | ZMYND8 | 23613 | Soft |
| CYP4F11 | 57834 | Soft | PRKG1 | 5592 | Soft | LINC01443 | 400644 | Soft | ZNF112 | 7771 | Soft |
| CYTH4 | 27128 | Soft | PRKG1-AS1 | 100506939 | Soft | LINC 01512 | 100132354 | Soft | ZNF117 | 51351 | Soft |
| CYTIP | 9595 | Soft | PRKG2 | 5593 | Soft | LINC01518 | 101929397 | Soft | ZNF136 | 7695 | Soft |
| DACT3 | 147906 | Soft | PROB1 | 389333 | Soft | LINC01530 | 729975 | Soft | ZNF137P | 7696 | Soft |
| DARS-AS1 | 101928243 | Soft | PROC | 5624 | Soft | LINC01534 | 101927621 | Soft | ZNF14 | 7561 | Soft |
| DBH | 1621 | Soft | PROCA1 | 147011 | Soft | LINC01537 | 101928555 | Soft | ZNF155 | 7711 | Soft |
| DBH-AS1 | 138948 | Soft | PRODH | 5625 | Soft | LINC01556 | 729583 | Soft | ZNF160 | 90338 | Soft |
| DBNDD1 | 79007 | Soft | PROS1 | 5627 | Soft | LINC01569 | 100507501 | Soft | ZNF165 | 7718 | Soft |
| DBNDD2 | 55861 | Soft | PROX2 | 283571 | Soft | LINC01583 | 101929690 | Soft | ZNF175 | 7728 | Soft |
| DBP | 1628 | Soft | PRR29 | 92340 | Soft | LINC01588 | 283551 | Soft | ZNF192P1 | 651302 | Soft |
| DCHS2 | 54798 | Soft | PRR36 | 80164 | Soft | LING01589 | 100506737 | Soft | ZNF204P | 7754 | Soft |
| DCLK1 | 9201 | Soft | PRR5L | 79899 | Soft | LINC01615 | 101929484 | Soft | ZNF214 | 7761 | Soft |
| DCLK2 | 166614 | Soft | PRRG4 | 79056 | Soft | LINC01619 | 256021 | Soft | ZNF221 | 7638 | Soft |
| DON | 1634 | Soft | PRRT1 | 8086.3 | Soft | LINCR-0002 | 103344926 | Soft | ZNF222 | 7673 | Soft |
| DCST2 | 127579 | Soft | PRRT2 | 112476 | Soft | LINGO2 | 158038 | Soft | ZNF223 | 7766 | Soft |
| DDIT4 | 54541 | Soft | PRRX2 | 51450 | Soft | LINGO3 | 645191 | Soft | ZNF224 | 7767 | Soft |
| DDIT4L | 115265 | Soft | PRSS16 | 10279 | Soft | LIPE-AS1 | 100996307 | Soft | ZNF225 | 7768 | Soft |
| DDO | 8528 | Soft | PRSS27 | 83886 | Soft | LMBR1L | 55716 | Soft | ZNF226 | 7769 | Soft |
| DDR1 | 780 | Soft | PRSS36 | 146547 | Soft | LM BR D 1 | 55788 | Soft | ZNF230 | 7773 | Soft |
| DDR2 | 4921 | Soft | PRSS53 | 339105 | Soft | LMF 1 | 64788 | Soft | ZNF233 | 353355 | Soft |
| DDX60 | 55601 | Soft | PRX | 57716 | Soft | LMNTD2 | 256329 | Soft | ZNF248 | 57209 | Soft |
| DENND3 | 22898 | Soft | PSD | 5662 | Soft | LMO3 | 558285 | Soft | ZNF25 | 219749 | Soft |
| DENND4C | 55667 | Soft | PSG1 | 5669 | Soft | LMOD1 | 25802 | Soft | ZNF 250 | 58500 | Soft |
| DENND6B | 414918 | Soft | PSG4 | 5672 | Soft | LMTK3 | 114783 | Soft | ZNF251 | 90987 | Soft |
| DEPTOR | 64798 | Soft | PSMG3-AS1 | 114796 | Soft | LNX1 | 84708 | Soft | ZNF252P-AS1 | 286103 | Soft |
| DFNB31 | 25861 | Soft | PSORS1C1 | 170679 | Soft | LOC100128288 | 100128288 | Soft | ZNF264 | 9422 | Soft |
| DHRS1 | 115817 | Soft | PSORS1C2 | 170680 | Soft | LOC100129138 | 100129138 | Soft | ZNF280D | 54816 | Soft |
| DHRS13 | 147015 | Soft | PSORS1C3 | 100130889 | Soft | LOC100129534 | 100129534 | Soft | ZNF284 | 342909 | Soft |
| DHRS3 | 9249 | Soft | PSPN | 5623 | Soft | LOC100129603 | 100129603 | Soft | ZNF285 | 26974 | Soft |
| DHX58 | 79132 | Soft | PTCH1 | 5727 | Soft | LOC100129617 | 100129617 | Soft | ZNF292 | 23036 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| DICER1-AS1 | 400242 | Soft | PTCH2 | 8643 | Soft | LOC100129924 | 100129924 | Soft | ZNF311 | 282890 | Soft |
| DISC1 | 27185 | Soft | PTGER2 | 5732 | Soft | LOC100129940 | 100129940 | Soft | ZNF32-AS1 | 414197 | Soft |
| DIXDC1 | 85458 | Soft | PTGES3L | 100885848 | Soft | LOC100129973 | 100129973 | Soft | ZNF337-AS1 | 102724826 | Soft |
| DKFZp434O0226 | 93429 | Soft | PTGFR | 5737 | Soft | LOC100130417 | 100130417 | Soft | ZNF33B | 7582 | Soft |
| DKFZP586I1420 | 222161 | Soft | PTGIR | 5739 | Soft | LOC100130476 | 100130476 | Soft | ZNF345 | 25850 | Soft |
| DLG4 | 1742 | Soft | PTGS1 | 5742 | Soft | LOC100130691 | 100130691 | Soft | ZNF358 | 140467 | Soft |
| DLGAP1-AS1 | 649446 | Soft | PTH1R | 5745 | Soft | LOC100130987 | 100130987 | Soft | ZNF366 | 167465 | Soft |
| DLX4 | 1748 | Soft | PTK6 | 5753 | Soft | LOC100132057 | 100132057 | Soft | ZNF383 | 163087 | Soft |
| DMPK | 1760 | Soft | PTP4A3 | 11156 | Soft | LOC100134368 | 100134368 | Soft | ZNF385A | 25946 | Soft |
| D NAH 1 | 25981 | Soft | PTPRB | 5787 | Soft | LOC100270804 | 100270804 | Soft | ZNF385B | 151126 | Soft |
| DNAH2 | 146754 | Soft | PTPRD | 5789 | Soft | LOC100287036 | 100287036 | Soft | ZNF385C | 201181 | Soft |
| DNAH5 | 1767 | Soft | PTPRH | 5794 | Soft | LOC100288152 | 100288152 | Soft | ZNF391 | 346157 | Soft |
| DNAH6 | 1768 | Soft | PTPRM | 5797 | Soft | LOC100288798 | 100288798 | Soft | ZNF395 | 55893 | Soft |
| DNAH7 | 56171 | Soft | PTPRN | 5798 | Soft | LOC100288911 | 100288911 | Soft | ZNF396 | 252884 | Soft |
| DNAJB2 | 3300 | Soft | PTPRO | 5800 | Soft | LOC100289230 | 100289230 | Soft | ZNF404 | 342908 | Soft |
| DNAJC18 | 202052 | Soft | PTPRR | 5801 | Soft | LOC100289495 | 100289495 | Soft | ZNF419 | 79744 | Soft |
| DNAJC22 | 79962 | Soft | PTPRU | 10076 | Soft | LOC100379224 | 100379224 | Soft | ZNF420 | 147923 | Soft |
| DNAJC28 | 54943 | Soft | PYROXD2 | 84795 | Soft | LOC100421746 | 100421746 | Soft | ZNF436-AS1 | 148898 | Soft |
| DNAJC4 | 3338 | Soft | QPRT | 23475 | Soft | LOC100499484-C9ORF174 | 57653 | Soft | ZNF444 | 55311 | Soft |
| DNAJCSG | 285126 | Soft | RAB11B-AS1 | 100507567 | Soft | LOC100505715 | 100505715 | Soft | ZNF446 | 55663 | Soft |
| DNAL4 | 10126 | Soft | RAB11FIP4 | 84440 | Soft | LOC100505771 | 100505771 | Soft | ZNF461 | 92283 | Soft |
| DNM1P35 | 100128285 | Soft | RAB20 | 55647 | Soft | LOC100505938 | 100505938 | Soft | ZNF467 | 168544 | Soft |
| DNM1P46 | 196968 | Soft | RAB26 | 25837 | Soft | LOC100506022 | 100506022 | Soft | ZNF470 | 388566 | Soft |
| DNM3 | 26052 | Soft | RAB30 | 27314 | Soft | LOC100506127 | 100506127 | Soft | ZNF485 | 220992 | Soft |
| DNM3OS | 100628315 | Soft | RAB33B | 83452 | Soft | LOC100506258 | 100506258 | Soft | ZNF490 | 57474 | Soft |
| DOCK2 | 1794 | Soft | RAB3A | 5864 | Soft | LOC100506271 | 100506271 | Soft | ZNF493 | 284443 | Soft |
| DOCK3 | 1795 | Soft | RAB3D | 9545 | Soft | LOC100506444 | 100506444 | Soft | ZNF501 | 115560 | Soft |
| DOCK6 | 57572 | Soft | RAB40A | 142684 | Soft | LOC100506472 | 100506472 | Soft | ZNF516 | 9658 | Soft |
| DOK4 | 55715 | Soft | RAB40C | 57799 | Soft | LOC100506476 | 100506476 | Soft | ZNF517 | 340385 | Soft |
| DPP4 | 1803 | Soft | RAB6B | 51560 | Soft | LOC100506548 | 100506548 | Soft | ZNF529 | 57711 | Soft |
| DPY19L2P2 | 349152 | Soft | RAB7B | 338382 | Soft | LOC100506679 | 100506679 | Soft | ZNF529-AS1 | 101927599 | Soft |
| DPYD | 1806 | Soft | RAB8B | 51762 | Soft | LOC100506688 | 100506688 | Soft | ZNF546 | 339327 | Soft |
| DPYSL4 | 10570 | Soft | RABGAP1L | 9910 | Soft | LOC100506746 | 100506746 | Soft | ZNF548 | 147694 | Soft |
| DRC3 | 83450 | Soft | RABL2A | 11159 | Soft | LOC100506990 | 100506990 | Soft | ZNF550 | 162972 | Soft |
| DRD4 | 1815 | Soft | RAD51-AS1 | 100506648 | Soft | LOC100507002 | 100507002 | Soft | ZNF554 | 115196 | Soft |
| DTNA | 1837 | Soft | RAET1G | 353091 | Soft | LOC100507053 | 100507053 | Soft | ZNF559 | 84527 | Soft |
| DTX3 | 196403 | Soft | RAG1 | 5896 | Soft | LOC100507156 | 100507156 | Soft | ZNF559-ZNF177 | 100529215 | Soft |
| DTX4 | 23220 | Soft | RALGDS | 5900 | Soft | LOC100507283 | 100507283 | Soft | ZNF572 | 137209 | Soft |
| DUOX1 | 53905 | Soft | RAP2C-AS1 | 1019285778 | Soft | LOC100507291 | 100507291 | Soft | ZNF575 | 284346 | Soft |
| DUSP10 | 11221 | Soft | RAPGEF3 | 10411 | Soft | LOC100507346 | 100507346 | Soft | ZNF577 | 84765 | Soft |
| DUSP19 | 142679 | Soft | RAPGEF4 | 11069 | Soft | LOC100507373 | 100507373 | Soft | ZNF581 | 51545 | Soft |
| DUSP5P1 | 574029 | Soft | RARA-AS1 | 101929693 | Soft | LOC100507477 | 100507477 | Soft | ZNF585A | 199704 | Soft |
| DYRK1B | 9149 | Soft | RARRES2 | 5919 | Soft | LOC100507487 | 100507487 | Soft | ZNF596 | 169270 | Soft |
| EBF1 | 1879 | Soft | RARRES3 | 5920 | Soft | LOC100507547 | 100507547 | Soft | ZNF599 | 148103 | Soft |
| EBF4 | 57593 | Soft | RASA4 | 10156 | Soft | LOC100507642 | 100507642 | Soft | ZNF605 | 100289635 | Soft |
| EBI3 | 10148 | Soft | RASA4B | 100271927 | Soft | LOC100652768 | 100652768 | Soft | ZNF608 | 57507 | Soft |
| EDN1 | 1906 | Soft | RASA4CP | 401331 | Soft | LOC100652999 | 100652999,399 | Soft | ZNF615 | 284370 | Soft |
| EDN2 | 1907 | Soft | RASD2 | 23551 | Soft | LOC100996634 | 221262 | Soft | ZNF630 | 57232 | Soft |

TABLE 2-continued

MeCo genes

| Gene. Symb | gene_id | Status | Gene. Sym | gene_id | Status | Gene. Symbol | gene_id | Status | Gene. Symbol | gene_id | Status |
|---|---|---|---|---|---|---|---|---|---|---|---|
| EDNRA | 1909 | Soft | RASSF2 | 9770 | Soft | LOC100996693 | 100996693 | Soft | ZNF648 | 127665 | Soft |
| EFCAB12 | 90288 | Soft | RASSF4 | 83937 | Soft | LOC101060389 | 101060389 | Soft | ZNF654 | 55279 | Soft |
| EFCAB13 | 124989 | Soft | RASSF5 | 83593 | Soft | LOC101448202 | 101448202 | Soft | ZNF662 | 389114 | Soft |
| EFCAB6 | 64800 | Soft | RASSF9 | 9182 | Soft | LOC101926935 | 101926935 | Soft | ZNF699 | 374879 | Soft |
| EFEMP2 | 30008 | Soft | RBM43 | 375287 | Soft | LOC101927045 | 101927045 | Soft | ZNF713 | 349075 | Soft |
| EFHB | 151651 | Soft | RBM5-AS1 | 100775107 | Soft | LOC101927056 | 101927056 | Soft | ZNF747 | 65988 | Soft |
| EFHC1 | 114327 | Soft | RBMS3 | 27303 | Soft | LOC101927204 | 101927204 | Soft | ZNF775 | 285971 | Soft |
| EFHD1 | 80303 | Soft | RBPS | 83758 | Soft | LOC101927229 | 101927229 | Soft | ZNF789 | 285989 | Soft |
| EFNA3 | 1944 | Soft | RCOR2 | 283248 | Soft | LOC101927282 | 101927282 | Soft | ZNF790 | 388536 | Soft |
| EFNA4 | 1945 | Soft | RDM1 | 201299 | Soft | LOC101927356 | 101927356 | Soft | ZNF808 | 388558 | Soft |
| EFNB3 | 1949 | Soft | RECK | 8434 | Soft | LOC101927365 | 101927365 | Soft | ZNF815P | 401303 | Soft |
| EGF | 1950 | Soft | REEP2 | 51308 | Soft | LOC101927391 | 101927391 | Soft | ZNF821 | 55565 | Soft |
| EGFL8 | 80864 | Soft | REEP6 | 92840 | Soft | LOC101927415 | 101927415 | Soft | ZNF83 | 55769 | Soft |
| EGLN3 | 112399 | Soft | REM2 | 161253 | Soft | LOC101927482 | 101927482 | Soft | ZNF836 | 162962 | Soft |
| EIF3J-AS1 | 645212 | Soft | REPS2 | 9185 | Soft | LOC101927501 | 101927501 | Soft | ZNF837 | 116412 | Soft |
| EIF4E3 | 317649 | Soft | RERG | 85004 | Soft | LOC101927740 | 101927740 | Soft | ZNF84 | 7637 | Soft |
| ELN | 2006 | Soft | RFTN2 | 130132 | Soft | LOC101927759 | 101927759 | Soft | ZNF846 | 162993 | Soft |
| EMILIN3 | 90187 | Soft | RFX2 | 5990 | Soft | LOC101927770 | 101927770 | Soft | ZNF862 | 643641 | Soft |
| EMX2 | 2018 | Soft | RGAG4 | 340526 | Soft | LOC101927780 | 101927780 | Soft | ZP1 | 22917 | Soft |
| ENDOV | 284131 | Soft | RGS11 | 8786 | Soft | LOC101927843 | 101927843 | Soft | ZP3 | 7784 | Soft |
| ENKUR | 219670 | Soft | RGS14 | 10636 | Soft | LOC101927865 | 101927865 | Soft | ZSCAN16-AS1 | 100129195 | Soft |
| ENO2 | 2026 | Soft | RGS3 | 5998 | Soft | LOC101927934 | 101927934 | Soft | ZSCAN2 | 54993 | Soft |
| ENO3 | 2027 | Soft | RHBDL1 | 9028 | Soft | LOC101928034 | 101928034 | Soft | ZSCAN23 | 222696 | Soft |
| ENPP3 | 5169 | Soft | RHBDL2 | 54933 | Soft | LOC101928063 | 101928063 | Soft | ZSCAN30 | 100101467 | Soft |
| EPB41L4A-AS1 | 114915 | Soft | RHOU | 58480 | Soft | LOC101928068 | 101928068 | Soft | ZSCAN31 | 64288 | Soft |
| LOC 101928222 | 101928222 | Soft | ZXDA | 7789 | Soft | LOC101928100 | 101928100 | Soft | ZSWIM4 | 65249 | Soft |
|  |  |  |  |  |  | LOC101928103 | 101928103 | Soft | ZSWIM5 | 57643 | Soft |

TABLE 3

MeCo refined genes

| symbol | gene id | Status | symbol, | gene id | Status | symbol | gene id | Status | symbol | gene id | Status |
|---|---|---|---|---|---|---|---|---|---|---|---|
| ABCF2 | 10061 | Stiff | LZTS1 | 11178 | Stiff | EIF5A2 | 56648 | Stiff | RCL1 | 10171 | Stiff |
| ABCG2 | 9429 | Stiff | MAGOHB | 55110 | Stiff | ELAVL2 | 1993 | Stiff | RECQL4 | 9401 | Stiff |
| ABHD5 | 51099 | Stiff | MAP2K4 | 6416 | Stiff | ELF3 | 1999 | Stiff | RELN | 5649 | Stiff |
| ACOX2 | 8309 | Stiff | MAP3K9 | 4293 | Stiff | ELMO3 | 79767 | Stiff | RFK | 55312 | Stiff |
| ACSL3 | 2181 | Stiff | MARCH3 | 115123 | Stiff | EN2 | 2020 | Stiff | RNASEH1 | 246243 | Stiff |
| ADAM19 | 8728 | Stiff | MCF2 | 4168 | Stiff | ENOX2 | 10495 | Stiff | ROR1 | 4919 | Stiff |
| ADAM23 | 8745 | Stiff | MCF2L | 23263 | Stiff | ENTPD1 | 953 | Stiff | RPGR | 6103 | Stiff |
| ADCY1 | 107 | Stiff | MCM10 | 55388 | Stiff | ENTPD1-AS1 | 728558 | Stiff | RRP12 | 23223 | Stiff |
| ADCY7 | 113 | Stiff | MCM9 | 254394 | Stiff | EPB41L3 | 23136 | Stiff | RRP15 | 51018 | Stiff |
| ADGRG2 | 10149 | Stiff | MDFI | 4188 | Stiff | EPHB2 | 2048 | Stiff | RTEL1 | 51750 | Stiff |
| AJAP1 | 55966 | Stiff | METTL1 | 4234 | Stiff | EPYC | 1833 | Stiff | RXYLT1 | 10329 | Stiff |
| ALCAM | 214 | Stiff | MGLL | 11343 | Stiff | EXOG | 9941 | Stiff | RYR3 | 6263 | Stiff |
| ALDH 161 | 219 | Stiff | MICALL1 | 85377 | Stiff | FAM171A1 | 221061 | Stiff | S1PR1 | 1901 | Stiff |
| ALDH4A1 | 8659 | Stiff | MIS12 | 79003 | Stiff | FAM189A1 | 23359 | Stiff | SCAMPS | 192683 | Stiff |
| AMIGO2 | 347902 | Stiff | MMP1 | 4312 | Stiff | FAM2088 | 54906 | Stiff | SDC1 | 6382 | Stiff |
| ANP32D | 23519 | Stiff | MMP3 | 4314 | Stiff | FAM98A | 25940 | Stiff | SENP3 | 26168 | Stiff |
| ANXA3 | 306 | Stiff | MPP6 | 51678 | Stiff | FANCA | 2175 | Stiff | SERINC2 | 347735 | Stiff |
| AP1M2 | 10053 | Stiff | MRM1 | 79922 | Stiff | FGF1 | 2246 | Stiff | SFMBT1 | 51460 | Stiff |
| AREG | 374 | Stiff | MSLN | 10232 | Stiff | FGF5 | 2250 | Stiff | SFN | 2810 | Stiff |
| ARMCX4 | 100131755 | Stiff | MSR1 | 4481 | Stiff | FHOD3 | 80206 | Stiff | SLC19A1 | 6573 | Stiff |
| ARPCSL | 81873 | Stiff | MSRB1 | 51734 | Stiff | FLAD1 | 80308 | Stiff | SLC25A44 | 9673 | Stiff |
| AT P6VOE2 | 155066 | Stiff | MSX1 | 4487 | Stiff | FOXA1 | 3169 | Stiff | SLC26A2 | 1836 | Stiff |
| BAIAP2L2 | 80115 | Stiff | MUC13 | 56667 | Stiff | FTSJ3 | 117246 | Stiff | SLC3581 | 10237 | Stiff |
| BCAR3 | 8412 | Stiff | MUC6 | 4588 | Stiff | FXN | 2395 | Stiff | SLC36A1 | 206358 | Stiff |
| BMP8A | 353500 | Stiff | MYH10 | 4628 | Stiff | GALNT10 | 55568 | Stiff | SLC4A8 | 9498 | Stiff |
| BNC2 | 54796 | Stiff | MYH15 | 22989 | Stiff | GALNT7 | 51809 | Stiff | SLC7A11 | 23657 | Stiff |
| BORCS8 | 729991 | Stiff | MYT1 | 4661 | Stiff | GCLM | 2730 | Stiff | SLC7A2 | 6542 | Stiff |
| BRIX1 | 55299 | Stiff | NATI | 9 | Stiff | GDPD5 | 81544 | Stiff | SLC9A2 | 6549 | Stiff |
| C12orf4 | 57102 | Stiff | INIPA2 | 81614 | Stiff | GEMIN3 | 50628 | Stiff | SLCO1B3 | 28234 | Stiff |
| C12orf49 | 79794 | Stiff | NKX3-1 | 4824 | Stiff | GEMIN6 | 79833 | Stiff | SLCO3A1 | 28232 | Stiff |
| C3AR1 | 719 | Stiff | NLRP3 | 114548 | Stiff | GFOD1 | 54438 | Stiff | SMCO4 | 56935 | Stiff |
| C3orf52 | 79669 | Stiff | NOC4L | 79050 | Stiff | GFRA1 | 2674 | Stiff | SNAP25 | 6616 | Stiff |
| C7orf43 | 55262 | Stiff | NOL12 | 79159 | Stiff | GINS3 | 64785 | Stiff | SNPH | 9751 | Stiff |
| C9orf78 | 51759 | Stiff | NOP16 | 51491 | Stiff | GIPC1 | 10755 | Stiff | SNRNP25 | 79622 | Stiff |
| CAND2 | 23066 | Stiff | NOVA1 | 4857 | Stiff | GJA3 | 2700 | Stiff | SPP1 | 6696 | Stiff |
| CASZ1 | 54897 | Stiff | NRG1 | 3084 | Stiff | GLRX2 | 51022 | Stiff | SPTB | 6710 | Stiff |
| CCL20 | 6364 | Stiff | NRGN | 4900 | Stiff | GNG4 | 2786 | Stiff | SRP19 | 6728 | Stiff |
| CCNE2 | 9134 | Stiff | NRP2 | 8828 | Stiff | GPR75 | 2825 | Stiff | SRPK3 | 26576 | Stiff |
| CCNO | 10309 | Stiff | NUDT15 | 55270 | Stiff | GPR87 | 10936 | Stiff | SSTR1 | 6751 | Stiff |
| CDC25A | 993 | Stiff | NUFIP1 | 26747 | Stiff | GYG2 | 53836 | Stiff | ST6GALNAC5 | 81849 | Stiff |
| CDC7 | 8317 | Stiff | NUP93 | 9688 | Stiff | HABP4 | 8908 | Stiff | STEAP1 | 26872 | Stiff |
| CDH11 | 1009 | Stiff | OPA3 | 80207 | Stiff | HAPLN1 | 22927 | Stiff | STS | 412 | Stiff |
| CENPN | 55839 | Stiff | ORC6 | 23594 | Stiff | HAUS7 | 1404 | Stiff | STYK1 | 55359 | Stiff |
| CHAD | 1101 | Stiff | OSBP2 | 23762 | Stiff | HBEGF | 55559 | Stiff | SURF2 | 6835 | Stiff |
| CHFR | 55743 | Stiff | OSTM1 | 28962 | Stiff | HEATR3 | 1839 | Stiff | SYT1 | 6857 | Stiff |
| CHUK | 1147 | Stiff | PAK1IP1 | 55003 | Stiff | HGF | 55027 | Stiff | TAF13 | 6884 | Stiff |
| CLDN1 | 9076 | Stiff | PCDH9 | 5101 | Stiff | HHAT | 3082 | Stiff | TBX2 | 6909 | Stiff |
| CLN6 | 54982 | Stiff | PCDHGA10 | 56106 | Stiff | HIST1H2AM | 55733 | Stiff | TDG | 6996 | Stiff |
| CLSPN | 63967 | Stiff | PCDHGA3 | 56112 | Stiff | HIST1H38 | 8336 | Stiff | TEAD4 | 7004 | Stiff |
| CNIH3 | 149811 | Stiff | PCDHGA8 | 9708 | Stiff | HIST1H3G | 8358 | Stiff | TEDC2 | 80178 | Stiff |
| CNTNAP2 | 26047 | Stiff | PCDHGC3 | 5098 | Stiff | HIVEP3 | 8355 | Stiff | TENM3 | 55714 | Stiff |
| COBLL1 | 22837 | Stiff | PCYT2 | 5833 | Stiff | HMGB3 | 59269 | Stiff | TFB2M | 64216 | Stiff |
| COL10A1 | 1300 | Stiff | PDE1C | 5137 | Stiff | HS3ST3A1 | 3149 | Stiff | TGM2 | 7052 | Stiff |
| COL13A1 | 1305 | Stiff | PDSS1 | 23590 | Stiff | HSPBAP1 | 9955 | Stiff | TIGAR | 57103 | Stiff |
| COL17A1 | 1308 | Stiff | PFAS | 5198 | Stiff | HTR7 | 79663 | Stiff | TIMM22 | 29928 | Stiff |
| CREM | 1390 | Stiff | PFDN2 | 5202 | Stiff | IDH3A | 3363 | Stiff | TM EM 104 | 54868 | Stiff |
| CRY1 | 1407 | Stiff | PGP | 283871 | Stiff | IHH | 3419 | Stiff | TMEM177 | 80775 | Stiff |
| CRYBA2 | 1412 | Stiff | PHLDA2 | 7262 | Stiff | ILIA | 3549 | Stiff | TMEM33 | 55161 | Stiff |
| CSF2 | 1437 | Stiff | PHLPP2 | 23035 | Stiff | INAVA | 3552 | Stiff | TNFRSF12A | 51330 | Stiff |
| CSF3 | 1440 | Stiff | PKMYT1 | 9088 | Stiff | INHBA | 55765 | Stiff | TNFRSF21 | 27242 | Stiff |
| CSGALNAC | 55790 | Stiff | PLAT | 5327 | Stiff | ITGAE | 3624 | Stiff | TOE1 | 114034 | Stiff |
| CSTF2 | 1478 | Stiff | PLEK2 | 26499 | Stiff | ITGBL1 | 3682 | Stiff | TOR1A | 1861 | Stiff |
| CTSL | 1514 | Stiff | PLXNA2 | 5362 | Stiff | JAM3 | 9358 | Stiff | TRAPPC10 | 7109 | Stiff |
| CXCLB | 3576 | Stiff | PODXL | 5420 | Stiff | JMJD4 | 83700 | Stiff | TRAPPC13 | 80006 | Stiff |
| CYCS | 54205 | Stiff | POLA2 | 23649 | Stiff | KANK1 | 65094 | Stiff | TRPM2 | 7226 | Stiff |
| DAB2 | 1601 | Stiff | POLR3B | 55703 | Stiff | KCNQ3 | 23189 | Stiff | TSSC4 | 10078 | Stiff |
| DDX10 | 1662 | Stiff | POP1 | 10940 | Stiff | KDM8 | 3786 | Stiff | TTC4 | 7268 | Stiff |
| DDX46 | 9879 | Stiff | POP7 | 10248 | Stiff | KIAA0754 | 79831 | Stiff | TTF2 | 8458 | Stiff |
| DGCR11 | 25786 | Stiff | POU3F2 | 5454 | Stiff | KIAA1549L | 643314 | Stiff | TTN | 7273 | Stiff |
| DGKG | 1608 | Stiff | PPIC | 5480 | Stiff | KLC2 | 25758 | Stiff | TUBB1 | 81027 | Stiff |
| DHRS2 | 10202 | Stiff | PRRX1 | 5396 | Stiff | KLHL18 | 64837 | Stiff | TXNDC9 | 10190 | Stiff |
| DIO2 | 1734 | Stiff | PSMC4 | 5704 | Stiff | KLHL25 | 23276 | Stiff | UCHL3 | 7347 | Stiff |
| DLEU2 | 8847 | Stiff | PTX3 | 5806 | Stiff | KPNA2 | 64410 | Stiff | WDR62 | 284403 | Stiff |
| DLX5 | 1749 | Stiff | PUM3 | 9933 | Stiff | LANCL2 | 3838 | Stiff | WFS1 | 7466 | Stiff |
| DOCK4 | 9732 | Stiff | PWP2 | 5822 | Stiff | LARP4 | 55915 | Stiff | WNT5B | 81029 | Stiff |
| DOCK9 | 23348 | Stiff | RAB27B | 5874 | Stiff | | 113251 | Stiff | WRAP53 | 55135 | Stiff |

TABLE 3-continued

MeCo refined genes

| symbol | gene id | Status | symbol | gene id | Status | symbol | gene id | Status | symbol | gene id | Status |
|---|---|---|---|---|---|---|---|---|---|---|---|
| DOLK | 22845 | Stiff | RABIF | 5877 | Stiff | LETM1 | 3954 | Stiff | YRDC | 79693 | Stiff |
| DOLPP1 | 57171 | Stiff | RAPGEFL1 | 51195 | Stiff | LIF | 3976 | Stiff | ZBTB7C | 201501 | Stiff |
| DYSF | 8291 | Stiff | RBM28 | 55131 | Stiff | LINC01963 | 150967 | Stiff | ZMPSTE24 | 10269 | Stiff |
| EIF4E | 1977 | Stiff | RBP4 | 5950 | Stiff | LRRC59 | 55379 | Stiff | ZNF593 | 51042 | Stiff |
| LUM | 4060 | Stiff | LSG1 | 55341 | Stiff | ZNHIT2 | 741 | Stiff | CYTIP | 9595 | Soft |
| ABCA2 | 20 | Soft | LETMD1 | 25875 | Soft | DBH | 1621 | Soft | RNASET2 | 8635 | Soft |
| ABCB1 | 5243 | Soft | LGALS9 | 3965 | Soft | DBNDD1 | 79007 | Soft | RNF128 | 79589 | Soft |
| ACADL | 33 | Soft | LM BRD 1 | 55788 | Soft | DBP | 1628 | Soft | RNF39 | 80352 | Soft |
| ACAP1 | 9744 | Soft | LPAR1 | 1902 | Soft | DCHS2 | 54798 | Soft | RNF44 | 22838 | Soft |
| ACKR1 | 2532 | Soft | LPAR2 | 9170 | Soft | DCN | 1634 | Soft | RORA | 6095 | Soft |
| ACSM3 | 6296 | Soft | LPAR6 | 10161 | Soft | DDIT4 | 54541 | Soft | ROS1 | 6098 | Soft |
| ACVR2B-AS1 | 100128640 | Soft | LRP1 | 4035 | Soft | DDR2 | 4921 | Soft | RPH3AL | 9501 | Soft |
| ACYP2 | 98 | Soft | LRRC75B | 388886 | Soft | DDX60 | 55601 | Soft | RRAD | 6236 | Soft |
| ADA2 | 51816 | Soft | LSP1 | 4046 | Soft | DENND3 | 22898 | Soft | RRAGB | 10325 | Soft |
| ADAMTS1 | 9510 | Soft | LTF | 4057 | Soft | DEPTOR | 64798 | Soft | RTP4 | 64108 | Soft |
| ADAMTSL2 | 9719 | Soft | LUZP4 | 51213 | Soft | DHRS1 | 115817 | Soft | RUNDC3B | 154661 | Soft |
| ADAP1 | 11033 | Soft | LY75 | 4065 | Soft | DHRS3 | 9249 | Soft | RWDD2A | 112611 | Soft |
| ADCYAP1R1 | 117 | Soft | LYRM9 | 201229 | Soft | DHX58 | 79132 | Soft | RYR1 | 6261 | Soft |
| ADD3 | 120 | Soft | MAGEA11 | 4110 | Soft | DIXDC1 | 85458 | Soft | S1PR2 | 9294 | Soft |
| ADGRB3 | 577 | Soft | MAOA | 4128 | Soft | DNAH6 | 1768 | Soft | S1PR4 | 8698 | Soft |
| ADH6 | 130 | Soft | MAOB | 4129 | Soft | DNAJB2 | 3300 | Soft | S1PR5 | 53637 | Soft |
| ADM2 | 79924 | Soft | MAP1A | 4130 | Soft | DNAJC4 | 3338 | Soft | SALL2 | 6297 | Soft |
| ADRA1B | 147 | Soft | MAP3K13 | 9175 | Soft | DOCK2 | 1794 | Soft | SCN2A | 6326 | Soft |
| AFF1 | 4299 | Soft | MAP3K8 | 1326 | Soft | DOCK3 | 1795 | Soft | SCNN1B | 6338 | Soft |
| AFF2 | 2334 | Soft | MAPRE3 | 22924 | Soft | DOCK6 | 57572 | Soft | SCNN1D | 6339 | Soft |
| AGBL2 | 79841 | Soft | MAPT | 4137 | Soft | DOK4 | 55715 | Soft | SCNN1G | 6340 | Soft |
| AGER | 177 | Soft | MARK4 | 57787 | Soft | DPY19L2P2 | 349152 | Soft | SEC14L5 | 9717 | Soft |
| AIM2 | 9447 | Soft | MASP1 | 5648 | Soft | DPYD | 1806 | Soft | SEC31B | 25956 | Soft |
| AK4 | 205 | Soft | MATN2 | 4147 | Soft | DRD4 | 1815 | Soft | SEMA4A | 64218 | Soft |
| ALDH3A1 | 218 | Soft | MCC | 4163 | Soft | DTX3 | 196403 | Soft | SEMA4G | 57715 | Soft |
| ALPK3 | 57538 | Soft | MDK | 4192 | Soft | DTX4 | 23220 | Soft | SENP7 | 57337 | Soft |
| ALS2CL | 259173 | Soft | MEF2A | 4205 | Soft | DUSP10 | 11221 | Soft | SEPT5-GP1BB | 100526833 | Soft |
| ANK1 | 286 | Soft | MEF2C | 4208 | Soft | EBI3 | 10148 | Soft | SERPINA5 | 5104 | Soft |
| ANXA9 | 8416 | Soft | MEFV | 4210 | Soft | EDN1 | 1906 | Soft | SERPINB1 | 1992 | Soft |
| AP1G2 | 8906 | Soft | MELTF | 4241 | Soft | EEF1AKMT3 | 25895 | Soft | SERPINB9 | 5272 | Soft |
| APC2 | 10297 | Soft | MEOX1 | 4222 | Soft | EFHD1 | 80303 | Soft | SERPINF2 | 5345 | Soft |
| APOA4 | 337 | Soft | METTL7A | 25840 | Soft | EFNA4 | 1945 | Soft | SH2D3A | 10045 | Soft |
| APOBEC3F | 200316 | Soft | MILR1 | 284021 | Soft | EFNB3 | 1949 | Soft | SH3D21 | 79729 | Soft |
| APOBEC3G | 60489 | Soft | MMP24 | 10893 | Soft | ENO3 | 2027 | Soft | SH3PXD2A | 9644 | Soft |
| APOE | 348 | Soft | MMRN2 | 79812 | Soft | EPHX2 | 2053 | Soft | SLAMF8 | 56833 | Soft |
| APOL3 | 80833 | Soft | MORN1 | 79906 | Soft | EPOR | 2057 | Soft | SLC15A3 | 51296 | Soft |
| APPL1 | 26060 | Soft | MOSPD3 | 64598 | Soft | EPS8L1 | 54869 | Soft | SLC17A7 | 57030 | Soft |
| AR | 367 | Soft | MPI | 4351 | Soft | ETV7 | 51513 | Soft | SLC1A4 | 6509 | Soft |
| ARHGAP4 | 393 | Soft | MR1 | 3140 | Soft | EVA1B | 55194 | Soft | SLC22A14 | 9389 | Soft |
| ARHGAP6 | 395 | Soft | MTTP | 4547 | Soft | F10 | 2159 | Soft | SLC22A18AS | 5003 | Soft |
| ARHGEF16 | 27237 | Soft | MTUS1 | 57509 | Soft | FAAH | 2166 | Soft | SLC25A42 | 284439 | Soft |
| ARHGEF17 | 9828 | Soft | MUSK | 4593 | Soft | FAM131B | 9715 | Soft | SLC2A11 | 66035 | Soft |
| ARHGEF6 | 9459 | Soft | MX1 | 4599 | Soft | FAM14981 | 317662 | Soft | SLC43A1 | 8501 | Soft |
| ARL4C | 10123 | Soft | MX2 | 4600 | Soft | FAMSOB | 26240 | Soft | SLC49A3 | 84179 | Soft |
| ARNT2 | 9915 | Soft | MX11 | 4601 | Soft | FAT4 | 2196 | Soft | SLC4A5 | 57835 | Soft |
| ARTN | 9048 | Soft | M YBPC 1 | 4604 | Soft | FBLN1 | 2192 | Soft | SLC6A16 | 28968 | Soft |
| ASS1 | 445 | Soft | MYL5 | 4636 | Soft | FBXO24 | 26261 | Soft | SLC6A3 | 6531 | Soft |
| ASTN2 | 23245 | Soft | MYLK3 | 91807 | Soft | FER1L4 | 80307 | Soft | SLC9A3 | 6550 | Soft |
| ATG14 | 22863 | Soft | MYO15B | 80022 | Soft | FEZ1 | 9638 | Soft | SLCO1A2 | 6579 | Soft |
| ATP2A3 | 489 | Soft | MYO1F | 4542 | Soft | FHIT | 2272 | Soft | SLCO2A1 | 6578 | Soft |
| ATP2C2 | 9914 | Soft | MYRF | 745 | Soft | FLRT1 | 23769 | Soft | SMARCA1 | 6594 | Soft |
| ATP6V1B1 | 525 | Soft | MZF1 | 7593 | Soft | FMO5 | 2330 | Soft | SNTA1 | 6640 | Soft |
| ATP6V1G2 | 534 | Soft | N4BP2L2-IT2 | 116828 | Soft | FN3K | 64122 | Soft | SOX5 | 6660 | Soft |
| AURKC | 6795 | Soft | NACAD | 23148 | Soft | FNDC11 | 79025 | Soft | SPAG4 | 6676 | Soft |
| AZGP1 | 563 | Soft | NCKAP1L | 3071 | Soft | FOXL1 | 2300 | Soft | SPINK5 | 11005 | Soft |
| B3GALT4 | 8705 | Soft | NCKIPSD | 51517 | Soft | FOXO1 | 2308 | Soft | SPINT1 | 6692 | Soft |
| B3GNT4 | 79369 | Soft | NDRG4 | 65009 | Soft | FRK | 2444 | Soft | SRD5A3 | 79644 | Soft |
| BACH2 | 60468 | Soft | NDUFA4L2 | 56901 | Soft | FRMD4B | 23150 | Soft | SSPN | 8082 | Soft |
| BAHCC1 | 57597 | Soft | NEBL | 10529 | Soft | FRMPD4 | 9758 | Soft | ST3GAL5 | 8869 | Soft |
| BCAN | 63827 | Soft | NEK11 | 79858 | Soft | FRS3 | 10817 | Soft | ST6GALNAC2 | 10610 | Soft |
| BCAS3 | 54828 | Soft | NEUROG2 | 63973 | Soft | FUCA1 | 2517 | Soft | ST8SIA1 | 6489 | Soft |
| BCKDHA | 593 | Soft | NFE2L3 | 9603 | Soft | FUT2 | 2524 | Soft | ST8SIA5 | 29906 | Soft |
| BCL11A | 53335 | Soft | NFIL3 | 4783 | Soft | GAA | 2548 | Soft | STAG3 | 10734 | Soft |
| BCL6 | 604 | Soft | NFKBIL1 | 4795 | Soft | GAB1 | 2549 | Soft | STARD5 | 80765 | Soft |
| BDKRB2 | 624 | Soft | NIPAL2 | 79815 | Soft | GAL | 51083 | Soft | STAT4 | 6775 | Soft |
| BEND5 | 79656 | Soft | NIPSNAP1 | 8508 | Soft | GAMT | 2593 | Soft | STOM | 2040 | Soft |
| BEST1 | 7439 | Soft | NIPSNAP3B | 55335 | Soft | GAS8-AS1 | 750 | Soft | STXBP2 | 6813 | Soft |
| BEX1 | 55859 | Soft | NLRP1 | 22861 | Soft | GATD3A | 8209 | Soft | SULT1E1 | 6783 | Soft |
| BEX3 | 27018 | Soft | NMNAT2 | 23057 | Soft | GBP2 | 2634 | Soft | SYNE2 | 23224 | Soft |
| BGN | 633 | Soft | NMRK1 | 54981 | Soft | GEM | 2669 | Soft | SYNGR1 | 9145 | Soft |
| BHLHB9 | 80823 | Soft | NOD2 | 64127 | Soft | GFI1 | 2672 | Soft | SYNGR3 | 9143 | Soft |

TABLE 3-continued

MeCo refined genes

| symbol | gene id | Status | symbol | gene id | Status | symbol | gene id | Status | symbol | gene id | Status |
|---|---|---|---|---|---|---|---|---|---|---|---|
| BHLHE40 | 8553 | Soft | NOTCH3 | 4854 | Soft | GJC2 | 57165 | Soft | SYNPO | 11346 | Soft |
| BLK | 640 | Soft | NPTX1 | 4884 | Soft | GMFG | 9535 | Soft | SYT11 | 23208 | Soft |
| BMP3 | 651 | Soft | NPY2R | 4887 | Soft | GNAZ | 2781 | Soft | SYT12 | 91683 | Soft |
| BMP4 | 652 | Soft | NR1H3 | 10062 | Soft | GOLGA2P5 | 55592 | Soft | SYT13 | 57586 | Soft |
| BMP8B | 656 | Soft | NRTN | 4902 | Soft | GPR173 | 54328 | Soft | SYT17 | 51760 | Soft |
| BOLA1 | 51027 | Soft | NRXN3 | 9369 | Soft | GPR19 | 2842 | Soft | TBC1D17 | 79735 | Soft |
| BTG1 | 694 | Soft | NSG1 | 27065 | Soft | GPT | 2875 | Soft | TBKBP1 | 9755 | Soft |
| BTN2A2 | 10385 | Soft | NT5M | 56953 | Soft | GRB7 | 2886 | Soft | TBXA2R | 6915 | Soft |
| BTN3A1 | 11119 | Soft | NTN3 | 4917 | Soft | GREB1 | 9687 | Soft | TCF7 | 6932 | Soft |
| BTN3A3 | 10384 | Soft | NUDT13 | 25961 | Soft | GRIA1 | 2890 | Soft | TCF7L1 | 83439 | Soft |
| C11orf21 | 29125 | Soft | NUDT7 | 283927 | Soft | GRIK4 | 2900 | Soft | TCIM | 56892 | Soft |
| C14orf93 | 60686 | Soft | OAS1 | 4938 | Soft | GRIK5 | 2901 | Soft | TCL6 | 27004 | Soft |
| C16orf45 | 89927 | Soft | OAS2 | 4939 | Soft | GRIN2A | 2903 | Soft | TDO2 | 6999 | Soft |
| C3orf36 | 80111 | Soft | OASL | 8638 | Soft | GRIN2D | 2906 | Soft | TENM1 | 10178 | Soft |
| C5 | 727 | Soft | OBSL1 | 23363 | Soft | GSN-AS1 | 57000 | Soft | TENT5C | 54855 | Soft |
| C8orf44 | 56260 | Soft | OPLAH | 26873 | Soft | GSTA4 | 2941 | Soft | TES | 26136 | Soft |
| CA11 | 770 | Soft | OR1F1 | 4992 | Soft | GSTM2 | 2946 | Soft | TESK2 | 10420 | Soft |
| CA3 | 761 | Soft | ORM1 | 5004 | Soft | GSTM4 | 2948 | Soft | TESMIN | 9633 | Soft |
| CACNA1B | 774 | Soft | OXR1 | 55074 | Soft | GTF2IRD2B | 389524 | Soft | TFCP2L1 | 29842 | Soft |
| CACNA1G | 8913 | Soft | P2RX7 | 5027 | Soft | GULP1 | 51454 | Soft | TFR2 | 7036 | Soft |
| CADM1 | 23705 | Soft | PACS2 | 23241 | Soft | H6PD | 9563 | Soft | TGFA | 7039 | Soft |
| CADM3 | 57863 | Soft | PADI3 | 51702 | Soft | HBE1 | 3046 | Soft | THEMIS2 | 9473 | Soft |
| CADM3-AS1 | 100131825 | Soft | PAMR1 | 25891 | Soft | HBP1 | 26959 | Soft | THRB | 7068 | Soft |
| CALCOCO1 | 57658 | Soft | PAN2 | 9924 | Soft | HCAR3 | 8843 | Soft | TIMP3 | 7078 | Soft |
| CAMK2B | 816 | Soft | PAPPA | 5069 | Soft | HCFC1R1 | 54985 | Soft | TLE6 | 79816 | Soft |
| CARD14 | 79092 | Soft | PAQR6 | 79957 | Soft | HCG26 | 352961 | Soft | TM7SF2 | 7108 | Soft |
| CARF | 79800 | Soft | PARM1 | 25849 | Soft | HCP5 | 10866 | Soft | TMEM159 | 57146 | Soft |
| CBX7 | 23492 | Soft | PARP3 | 10039 | Soft | HDAC11 | 79885 | Soft | TMEM187 | 8269 | Soft |
| CCDC40 | 55036 | Soft | PATJ | 10207 | Soft | HHLA3 | 11147 | Soft | TMEM80 | 283232 | Soft |
| CCL5 | 6352 | Soft | PAX9 | 5083 | Soft | HLA-DMA | 3108 | Soft | TNFAIP8 | 25816 | Soft |
| CCND2 | 894 | Soft | PBXIP1 | 57326 | Soft | HLA-F | 3134 | Soft | TNFRSF14 | 8764 | Soft |
| CCNG2 | 901 | Soft | PCBP3 | 54039 | Soft | HLA-F-AS1 | 285830 | Soft | TNFRSF25 | 8718 | Soft |
| CCR10 | 2826 | Soft | PCSK1 | 5122 | Soft | HLA-J | 3137 | Soft | TNFSF14 | 8740 | Soft |
| CD180 | 4064 | Soft | PDCD4-AS1 | 282997 | Soft | HLF | 3131 | Soft | TNNT3 | 7140 | Soft |
| CD226 | 10666 | Soft | PDE4DIP | 9659 | Soft | HLTF | 6596 | Soft | TNXB | 7148 | Soft |
| CD24 | 100133941 | Soft | PDE7B | 27115 | Soft | HNF1A | 6927 | Soft | TP53I11 | 9537 | Soft |
| CD27 | 939 | Soft | PDGFB | 5155 | Soft | HNRNPA3P1 | 10151 | Soft | TP63 | 8626 | Soft |
| CD40 | 958 | Soft | PDK1 | 5163 | Soft | HOOK2 | 29911 | Soft | TP73 | 7161 | Soft |
| CD7 | 924 | Soft | PDK4 | 5166 | Soft | HOXA4 | 3201 | Soft | TP73-AS1 | 57212 | Soft |
| CD72 | 971 | Soft | PDZK1IP1 | 10158 | Soft | HOXA6 | 3203 | Soft | TPO | 7173 | Soft |
| CD74 | 972 | Soft | PELI2 | 57161 | Soft | HPCA | 3208 | Soft | TPP1 | 1200 | Soft |
| CD82 | 3732 | Soft | PEX6 | 5190 | Soft | HPD | 3242 | Soft | TRAPPC6A | 79090 | Soft |
| CDH19 | 28513 | Soft | PGAM2 | 5224 | Soft | HPGD | 3248 | Soft | TRIB2 | 28951 | Soft |
| CDH22 | 64405 | Soft | PGAP1 | 80055 | Soft | HR | 55806 | Soft | TRIM22 | 10346 | Soft |
| CDHR5 | 53841 | Soft | PGGHG | 80162 | Soft | HSD11B1 | 3290 | Soft | TRIM29 | 23650 | Soft |
| CDK18 | 5129 | Soft | PGR | 5241 | Soft | HSF4 | 3299 | Soft | TRIM46 | 80128 | Soft |
| CDK19 | 23097 | Soft | PHEX | 5251 | Soft | HSPA1L | 3305 | Soft | TRIOBP | 11078 | Soft |
| CDON | 50937 | Soft | PIEZO2 | 63895 | Soft | HTR2C | 3358 | Soft | TRPS1 | 7227 | Soft |
| CELSR3 | 1951 | Soft | PIGZ | 80235 | Soft | ICAM1 | 3383 | Soft | TSC22D3 | 1831 | Soft |
| CEP68 | 23177 | Soft | PIK3IP1 | 113791 | Soft | ICAM2 | 3384 | Soft | TSHZ2 | 128553 | Soft |
| CES3 | 23491 | Soft | PITPNM3 | 83394 | Soft | ICAM4 | 3386 | Soft | TSPAN15 | 23555 | Soft |
| CFAP44 | 55779 | Soft | PLA2G6 | 8398 | Soft | ICAM5 | 7087 | Soft | TSPAN7 | 7102 | Soft |
| CFB | 629 | Soft | PLCH2 | 9651 | Soft | IFI44 | 10561 | Soft | TTC39A | 22996 | Soft |
| CFI | 3426 | Soft | PLEKHA4 | 57664 | Soft | IFI44L | 10964 | Soft | TTLL1 | 25809 | Soft |
| CHD5 | 26038 | Soft | PLEKHH3 | 79990 | Soft | IFI6 | 2537 | Soft | TUB | 7275 | Soft |
| CHRM3 | 1131 | Soft | PLXNB1 | 5364 | Soft | IFIT1 | 3434 | Soft | TUBA8 | 51807 | Soft |
| CHRNB1 | 1140 | Soft | PLXNB3 | 5365 | Soft | IFIT2 | 3433 | Soft | TUBB2B | 347733 | Soft |
| CHST15 | 51363 | Soft | PMEL | 6490 | Soft | IFIT3 | 3437 | Soft | TXK | 7294 | Soft |
| CIITA | 4261 | Soft | PMFBP1 | 83449 | Soft | IFITM1 | 8519 | Soft | TXNIP | 10628 | Soft |
| CITED2 | 10370 | Soft | PNMA2 | 10687 | Soft | IFT140 | 9742 | Soft | TYMP | 1890 | Soft |
| CLDN18 | 51208 | Soft | PODNL1 | 74883 | Soft | IFT81 | 28981 | Soft | ULBP1 | 80329 | Soft |
| CLDN9 | 9080 | Soft | POLD4 | 57804 | Soft | IGFBP2 | 3485 | Soft | ULK1 | 8408 | Soft |
| CLEC2D | 29121 | Soft | POU5F1P3 | 642559 | Soft | IGFBP3 | 3486 | Soft | VAMP2 | 6844 | Soft |
| CLIP3 | 25999 | Soft | POU6F2 | 11281 | Soft | IGFBP5 | 3488 | Soft | VCAM1 | 7412 | Soft |
| CLUL1 | 27098 | Soft | PPARGC1A | 10891 | Soft | IL13RA2 | 3598 | Soft | VCAN | 1462 | Soft |
| CMKLR1 | 1240 | Soft | PRDM1 | 639 | Soft | IL15 | 3603 | Soft | VPREB3 | 29802 | Soft |
| CNNM2 | 54805 | Soft | PRDM2 | 7799 | Soft | IL16 | 3603 | Soft | VWA7 | 80737 | Soft |
| CNOT8 | 9337 | Soft | PRKAB2 | 5565 | Soft | IL17RC | 84818 | Soft | WHRN | 25861 | Soft |
| CNTN5 | 53942 | Soft | PRKCE | 5581 | Soft | IL1R2 | 7850 | Soft | XAF1 | 54739 | Soft |
| COL11A2 | 1302 | Soft | PRKG2 | 5593 | Soft | IL2RG | 3561 | Soft | XCR1 | 2829 | Soft |
| COL21A1 | 81578 | Soft | PROC | 5624 | Soft | ING4 | 51147 | Soft | ZBTB16 | 7704 | Soft |
| COL4A2 | 1284 | Soft | PRRG4 | 79056 | Soft | INHA | 3623 | Soft | ZBTB25 | 7597 | Soft |
| COL4A3 | 1285 | Soft | PSD | 5662 | Soft | INHBE | 83729 | Soft | ZC4H2 | 55906 | Soft |
| COL4A4 | 1286 | Soft | PSORS1C2 | 170680 | Soft | IRF9 | 10379 | Soft | ZER1 | 10444 | Soft |
| COL9A2 | 1298 | Soft | PSPN | 5623 | Soft | ISG20 | 3669 | Soft | ZFHX2 | 85446 | Soft |
| CORO2A | 7464 | Soft | PTCH1 | 5727 | Soft | ITGA10 | 8515 | Soft | ZHX2 | 22882 | Soft |

TABLE 3-continued

MeCo refined genes

| symbol | gene id | Status | symbol | gene id | Status | symbol | gene id | Status | symbol | gene id | Status |
|---|---|---|---|---|---|---|---|---|---|---|---|
| CP | 1356 | Soft | PTCH2 | 8643 | Soft | ITPR1 | 3708 | Soft | ZNF117 | 51351 | Soft |
| CPM | 1368 | Soft | PTGER2 | 5732 | Soft | IZUMO4 | 113177 | Soft | ZNF136 | 7695 | Soft |
| CPO | 10404 | Soft | PTGFR | 5737 | Soft | JUP | 3728 | Soft | ZNF14 | 7561 | Soft |
| CRELD1 | 78987 | Soft | PTGIR | 5739 | Soft | KCND1 | 3750 | Soft | ZNF155 | 7711 | Soft |
| CRIP2 | 1397 | Soft | PTH1R | 5745 | Soft | KC N H1 | 3756 | Soft | ZNF160 | 90338 | Soft |
| CRISP3 | 10321 | Soft | PTP4A3 | 11156 | Soft | KCNJ9 | 3765 | Soft | ZNF165 | 7718 | Soft |
| C RTC1 | 23373 | Soft | PTPRN | 5798 | Soft | KCNK2 | 3776 | Soft | ZNF175 | 7728 | Soft |
| CTC-338M12.4 | 101928649 | Soft | PTPRO | 5800 | Soft | KCNK3 | 3777 | Soft | ZNF204P | 7754 | Soft |
| CTSH | 1512 | Soft | PTPRR | 5801 | Soft | KCNN1 | 3780 | Soft | ZNF221 | 7638 | Soft |
| CUBN | 8029 | Soft | PTPRU | 10076 | Soft | KCNN4 | 3783 | Soft | ZNF222 | 7673 | Soft |
| CUEDC1 | 404093 | Soft | RAB26 | 25837 | Soft | KDM3A | 55818 | Soft | ZNF225 | 7768 | Soft |
| CULT | 9820 | Soft | RAB40A | 142684 | Soft | KDM4B | 23030 | Soft | ZNF226 | 7769 | Soft |
| CUX1 | 1523 | Soft | RAB6B | 51560 | Soft | KDMSB | 10765 | Soft | ZNF345 | 25850 | Soft |
| CX3CL1 | 6376 | Soft | RALGDS | 5900 | Soft | KIAA1109 | 84162 | Soft | ZNF391 | 346157 | Soft |
| CXCL11 | 6373 | Soft | RARRES3 | 5920 | Soft | KIF5A | 3798 | Soft | ZNF467 | 168544 | Soft |
| CXCR4 | 7852 | Soft | RASSF2 | 9770 | Soft | KLHL24 | 54800 | Soft | ZNF550 | 162972 | Soft |
| CYBRD1 | 79901 | Soft | RASSF4 | 83937 | Soft | KLHL28 | 54813 | Soft | ZNF654 | 55279 | Soft |
| CYP11A1 | 1583 | Soft | RASSF9 | 9182 | Soft | KLRC3 | 3823 | Soft | ZNF747 | 65988 | Soft |
| CYP19A1 | 1588 | Soft | REEP2 | 51308 | Soft | KMO | 8564 | Soft | ZNF821 | 55565 | Soft |
| CYP2E1 | 1571 | Soft | RFX2 | 5990 | Soft | KRTS | 3852 | Soft | ZNF83 | 55769 | Soft |
| CYP39A1 | 51302 | Soft | RGS11 | 8786 | Soft | KRT84 | 3890 | Soft | ZNF862 | 643641 | Soft |
| CYP4B1 | 1580 | Soft | RIOK3 | 8780 | Soft | KYAT1 | 883 | Soft | ZSCAN2 | 54993 | Soft |
| CYTH4 | 27128 | Soft | RIPK4 | 54101 | Soft | LBH | 81606 | Soft | RIPOR2 | 9750 | Soft |

TABLE 4

Proliferation associated genes

| | | |
|---|---|---|
| ALAS2 | PLEK | KLF1 |
| BIRC5 | POLE2 | KIF2C |
| BPGM | PPBP | UBE2C |
| BUB1B | PSMD9 | ADAMTS13 |
| CCNA2 | RFC3 | ZWINT |
| CCNB1 | RFC4 | LSM6 |
| CDK1 | RHAG | SNF8 |
| CDC20 | RHCE | OIP5 |
| CDKN3 | RHD | RPIA |
| CENPA | RPA3 | TPX2 |
| CKS1B | RRM2 | NUP210 |
| CKS2 | SFRS2 | DNAJC9 |
| ARID3A | SNRP8 | NCAPD3 |
| EPB42 | SNRPD1 | ORC6L |
| FECH | SPTA1 | KIF4A |
| FEN1 | AURKA | FBXO7 |
| FOXM1 | TAL1 | TRIM58 |
| GATA1 | TCF3 | FBXO5 |
| GYPA | TPDP1 | KLF15 |
| GYPB | TOP2A | RACGAP1 |
| H3F3A | TYMS | CKLF |
| HMBS | VRK1 | NUSAP1 |
| HMG B2 | WHSC1 | AHSP |
| HMG N2 | CDC45 | GTSE1 |
| KEL | TIMELESS | DTL |
| KIF22 | PRC1 | GINS2 |
| LBR | CCNB2 | C21orf45 |
| LIG1 | AURKB | GTPBP2 |
| LMNB1 | PTTG1 | NCAPG2 |
| LYL1 | APOBEC3B | CDCA4 |
| MAD2L1 | ESPL1 | CDCA8 |
| MCM2 | KIAA0101 | RFWD3 |
| MCM3 | MELK | ASP1B |
| MCM4 | GINS1 | TRMT5 |
| MCM5 | NCAPD2 | NU P37 |
| MCM6 | TROAP | MLP1IP |
| MCM7 | CHAF1A | SHCBP1 |
| MIC8 | SMC4 | CDT1 |
| MK167 | TRIM10 | CDCA3 |
| NUDT1 | KIF20A | TSPO2 |
| NFE2 | DDX39 | RAD51AP1 |
| PCNA | TACC3 | RPP30 |
| PF4 | PPIH | PGD |

TABLE 5

GREAT version   Species assembly: hg19
Association rule: Basal + extension: 5000 bp upstream, 1000 bp downstream, 1000000 bp max extension, curated

| # Ontology | Term Name | Binom Rank | Binom Raw P-Value | Binom FDR Q-Val | Binom Fold Enrich | Binom Obsrvd Region Hits | Binom Region Set Coverag |
|---|---|---|---|---|---|---|---|
| MSigDB Immunologic Signatures | Genes up-regulated in comparison of naive B cells versus unstimulated neutrophils. | 1 | 1.73E−09 | 3.3E−06 | 2.02184 | 87 | 0.0358 |
| Mouse | decreased susceptibility to | 16 | 7.84E−09 | 3.9E−06 | 2.05293 | 77 | 0.03169 |
| MSigDB Perturbation | Genes defining proliferation and self renewal potential of | 9 | 2.78E−08 | 1E−05 | 2.13541 | 65 | 0.02675 |
| Mouse | incomplete cephalic closure | 75 | 3.7E−06 | 0.00039 | 2.24806 | 40 | 0.01646 |
| MSigDB Perturbation | Class II of genes transiently induced by EGF [GeneID | 40 | 4.7E−06 | 0.00039 | 2.28051 | 38 | 0.01564 |
| MSigDB Perturbation | Genes up-regulated in B lymphocytes at 2 h after | 42 | 6.2E−06 | 0.0005 | 2.27985 | 37 | 0.01523 |

TABLE 5-continued

GREAT version   Species assembly: hg19
                  Association rule: Basal + extension: 5000 bp upstream, 1000 bp downstream, 1000000 bp max extension, curated

| # Ontology | Term Name | Binom Rank | Binom Raw P-Value | Binom FDR Q-Val | Binom Fold Enrich | Binom Obsrvd Region Hits | Binom Region Set Coverag |
|---|---|---|---|---|---|---|---|
| MSigDB Perturbation | Cohesin targets identified by ChIP-chip which were up-regulated after knockdown of | 44 | 7.3E−06 | 0.00056 | 2.2078 | 39 | 0.01605 |
| Mouse | altered susceptibility to kidney | 87 | 9.6E−06 | 0.00087 | 2.98302 | 22 | 0.00905 |
| Mouse | abnormal cephalic neural fold | 88 | 1E−05 | 0.00091 | 2.1512 | 40 | 0.01646 |
| GO Biological | UDP-glucuronate metabolic | 25 | 3E−06 | 0.00125 | 7.9595 | 9 | 0.0037 |
| GO Biological | regulation of steroid | 26 | 3.2E−06 | 0.0013 | 2.38102 | 36 | 0.01481 |
| MGI Expression: | TS19_venous system | 8 | 1.5E−06 | 0.00174 | 3.2569 | 23 | 0.00947 |
| GO Biological | positive regulation of myeloid | 38 | 6.7E−06 | 0.00185 | 2.12071 | 43 | 0.0177 |
| Mouse | decreased susceptibility to | 109 | 2.8E−05 | 0.00201 | 2.95096 | 20 | 0.00823 |
| MSigDB Perturbation | Genes down-regulated in blood vessel cells from wound site. | 66 | 4.8E−05 | 0.00245 | 3.0344 | 18 | 0.00741 |
| MGI Expression: | TS15_septum transversum | 10 | 2.8E−06 | 0.00261 | 2.27537 | 40 | 0.01646 |
| MSigDB Perturbation | Genes down-regulated in glioblastoma cell lines displaying spherical growth (cluster-1) compared to those | 72 | 6.4E−05 | 0.00301 | 2.62027 | 22 | 0.00905 |
| MSigDB Perturbation | Genes up-regulated in immunoglobulin light chain amyloidosis plasma cells (ALPC) | 82 | 8.9E−05 | 0.00363 | 2.56162 | 22 | 0.00905 |
| MSigDB Perturbation | Amplification hot spot 27: colocalized fragile sites and | 81 | 8.8E−05 | 0.00365 | 4.21745 | 11 | 0.00453 |
| Mouse Phenotype | abnormal T follicular helper cell | 132 | 7.1E−05 | 0.00428 | 4.73804 | 10 | 0.00412 |
| MSigDB Perturbation | Down-regulated genes in the B lymphocyte developmental signature, based on expression profiling of lymphomas from | 89 | 0.00012 | 0.00472 | 2.03564 | 34 | 0.01399 |
| GO Biological | distal tubule development | 81 | 4.1E−05 | 0.00526 | 3.34252 | 16 | 0.00658 |
| Mouse Phenotype | abnormal alveolocapillary | 142 | 9.6E−05 | 0.00537 | 5.08264 | 9 | 0.0037 |
| GO Biological | regulation of superoxide | 82 | 4.2E−05 | 0.00539 | 4.22246 | 12 | 0.00494 |
| MSigDB Perturbation | Genes identified as hypermethylated in SW48 cells | 94 | 0.00015 | 0.00541 | 2.59719 | 20 | 0.00823 |
| MSigDB Perturbation | Genes whose expression most uniformly correlated with that of MM P14 [GeneI D = 4323] | 98 | 0.00019 | 0.0064 | 2.92242 | 16 | 0.00658 |
| MSigDB Perturbation | Top 40 genes from cluster 15 of acute myeloid leukemia (AML) expression profile; 88% of the samples are FAB M1 or M2 | 105 | 0.00022 | 0.00715 | 2.2487 | 25 | 0.01029 |
| GO Biological | regulation of blood coagulation | 113 | 8.2E−05 | 0.00757 | 2.10952 | 33 | 0.01358 |
| Mouse Phenotype | abnormal lung compliance | 165 | 0.00017 | 0.00828 | 2.3852 | 23 | 0.00947 |
| MGI Expression: | TS20_endocardial cushion | 17 | 1.6E−05 | 0.00904 | 2.29698 | 33 | 0.01358 |
| MSigDB Perturbation | Genes within amplicon 6p24-p22 identified in a copy number | 117 | 0.00033 | 0.00953 | 2.88597 | 15 | 0.00617 |
| MSigDB Perturbation | Genes down-regulated in U2-OS Tet-On cells (osteosarcoma) after induction of ESX1 | 129 | 0.00038 | 0.00979 | 2.13187 | 26 | 0.0107 |
| MSigDB Perturbation | Down-regulated genes that separate angiogenic from non-angiogenic non-small cell lung | 138 | 0.00042 | 0.01024 | 2.2835 | 22 | 0.00905 |
| GO Biological | positive regulation of myeloid | 149 | 0.00015 | 0.01083 | 2.22246 | 27 | 0.01111 |
| Mouse Phenotype | abnormal Peyer's patch size | 186 | 0.00026 | 0.0111 | 2.14853 | 27 | 0.01111 |
| MGI Expression: | TS15_venous system | 25 | 3E−05 | 0.01114 | 2.29413 | 31 | 0.01276 |
| MSigDB Perturbation | Genes down-regulated in AtT20 cells (pituitary cancer) after | 147 | 0.00049 | 0.01132 | 2.30617 | 21 | 0.00864 |
| Mouse Phenotype | increased mast cell number | 194 | 0.0003 | 0.01214 | 2.91644 | 15 | 0.00617 |
| MGI Expression: | TS15_mesenchyme derived | 27 | 3.6E−05 | 0.01241 | 2.27087 | 31 | 0.01276 |
| GO Biological | regulation of macrophage | 160 | 0.00019 | 0.01243 | 3.19354 | 14 | 0.00576 |
| GO Biological | positive regulation of cytokine | 172 | 0.00021 | 0.01299 | 2.10885 | 29 | 0.01193 |
| GO Biological Process | production of molecular mediator involved in | 178 | 0.00024 | 0.01406 | 3.49617 | 12 | 0.00494 |
| MGI Expression: | TS28_rib | 28 | 4.4E−05 | 0.01465 | 3.0558 | 18 | 0.00741 |
| MSigDB Perturbation | Genes up-regulated by tretinoin (ATRA) [PubChem = 444795] in U937 cells (acute promyelocytic leukemia, APL) made resistant to the drug by expression of the | 167 | 0.00076 | 0.01524 | 2.56239 | 16 | 0.00658 |
| MSigDB Perturbation | Genes up-regulated in pilocytic astrocytoma (PA) samples from patients with type 1 neurofibromatosis syndrom | 170 | 0.00078 | 0.01544 | 4.80347 | 7 | 0.00288 |

TABLE 5-continued

GREAT version  Species assembly: hg19
Association rule: Basal + extension: 5000 bp upstream, 1000 bp downstream, 1000000 bp max extension, curated

| # Ontology | Term Name | Binom Rank | Binom Raw P-Value | Binom FDR Q-Val | Binom Fold Enrich | Binom Obsrvd Region Hits | Binom Region Set Coverag |
|---|---|---|---|---|---|---|---|
| MGI Expression: | TS12_future prosencephalon | 29 | 4.9E−05 | 0.01569 | 3.64714 | 14 | 0.00576 |
| Mouse Phenotype | abnormal tricuspid valve | 214 | 0.00044 | 0.01643 | 2.22647 | 23 | 0.00947 |
| MGI Expression: | TS28_pectoral girdle bone | 34 | 6.3E−05 | 0.0172 | 4.04991 | 12 | 0.00494 |
| Mouse Phenotype | decreased cochlear outer hair | 218 | 0.00048 | 0.01733 | 2.03299 | 28 | 0.01152 |
| MGI Expression: | TS22_dorsal aorta | 32 | 6.2E−05 | 0.01796 | 2.17215 | 32 | 0.01317 |
| MSigDB | Genes up-regulated specifically | 183 | 0.00099 | 0.01813 | 2.4969 | 16 | 0.00658 |
| MSigDB Pathway | Genes involved in FRS2- | 15 | 0.00022 | 0.01893 | 2.34785 | 23 | 0.00947 |
| Mouse Phenotype | abnormal cochlear nerve | 232 | 0.00056 | 0.01897 | 2.28489 | 21 | 0.00864 |
| GO Biological | face morphogenesis | 209 | 0.00038 | 0.01914 | 2.12883 | 26 | 0.0107 |
| MSigDB Perturbation | Genes whose expression peaked at 480 min after | 186 | 0.00106 | 0.01919 | 2.0127 | 25 | 0.01029 |
| Mouse Phenotype | decreased interleukin-12 | 234 | 0.00058 | 0.01947 | 2.22879 | 22 | 0.00905 |
| MSigDB Perturbation | Genes up-regulated in hematopoietic precursor cells conditionally expressing HOXA9 | 190 | 0.00111 | 0.01972 | 2.03891 | 24 | 0.00988 |
| GO Biological | negative regulation of steroid | 217 | 0.00042 | 0.02037 | 2.53128 | 18 | 0.00741 |
| Mouse Phenotype | increased circulating | 239 | 0.00062 | 0.02041 | 2.32056 | 20 | 0.00823 |
| Mouse Phenotype | decreased response of heart to | 245 | 0.00069 | 0.02246 | 2.11268 | 24 | 0.00988 |
| GO Biological | negative regulation of steroid | 248 | 0.00054 | 0.02285 | 2.47676 | 18 | 0.00741 |
| MSigDB Perturbation | Genes up-regulated in NI H3T3 cells (fibroblasts) after treatment with Y27632 [PubChem = 123862], an inhibitor of ROCK proteins; the | 225 | 0.00169 | 0.02527 | 2.54069 | 14 | 0.00576 |
| MGI Expression: | TS28_articular cartilage | 45 | 0.00012 | 0.02535 | 3.53138 | 13 | 0.0053 |
| MSigDB Perturbation | Genes in cluster 3: delayed up-regulation in HFW cells | 230 | 0.00183 | 0.02682 | 2.1138 | 20 | 0.00823 |
| GO Biological | positive regulation of DNA- | 266 | 0.00069 | 0.02714 | 3.29551 | 11 | 0.00453 |
| MGI Expression: | TS12_optic sulcus neural | 48 | 0.00014 | 0.02745 | 4.82659 | 9 | 0.0037 |
| MSigDB Perturbation | Up-regulated PDGF targets identified by a gene-trap | 234 | 0.00193 | 0.0278 | 2.20535 | 18 | 0.00741 |
| MSigDB Perturbation | Genes down-regulated during pubertal mammary gland | 237 | 0.00201 | 0.02847 | 2.09706 | 20 | 0.00823 |
| Mouse Phenotype | abnormal mesocardium | 275 | 0.00108 | 0.03099 | 4.0079 | 8 | 0.00329 |
| GO Biological | head morphogenesis | 283 | 0.00085 | 0.03128 | 2.01382 | 26 | 0.0107 |
| GO Biological | regulation of steroid hormone | 292 | 0.00091 | 0.03247 | 2.51716 | 16 | 0.00658 |
| Mouse Phenotype | small second branchial arch | 290 | 0.00124 | 0.03378 | 2.29938 | 18 | 0.00741 |
| MGI Expression: | TS13_septum transversum | 63 | 0.00024 | 0.03562 | 2.32918 | 23 | 0.00947 |
| MSigDB Perturbation | Transcription factors expressed in progenitors of exocrine | 265 | 0.00296 | 0.03754 | 2.23337 | 16 | 0.00658 |
| GO Biological | aorta morphogenesis | 324 | 0.00125 | 0.04016 | 2.1863 | 20 | 0.00823 |
| MGI Expression: | TS28_cartilage | 74 | 0.00033 | 0.04101 | 2.05431 | 29 | 0.01193 |
| MSigDB Perturbation | Selected genes down-regulated in peripheral blood | 291 | 0.00362 | 0.0418 | 2.0294 | 19 | 0.00782 |
| MSigDB Pathway | Genes involved in FGFR ligand | 33 | 0.00106 | 0.0426 | 2.3313 | 18 | 0.00741 |
| MSigDB Pathway | Genes involved in Integrin | 39 | 0.00126 | 0.04281 | 2.5225 | 15 | 0.00617 |
| MGI Expression: | TS15_midgut epithelium | 76 | 0.00037 | 0.04495 | 2.98961 | 14 | 0.00576 |
| GO Biological | regulation of removal of | 342 | 0.00148 | 0.04518 | 5.00961 | 6 | 0.00247 |
| MGI Expression: | TS22_cornea epithelium | 77 | 0.00037 | 0.0454 | 2.13224 | 26 | 0.0107 |
| MGI Expression: | TS24_heart valve | 90 | 0.00044 | 0.04551 | 2.32827 | 21 | 0.00864 |
| MGI Expression: | TS15_primitive ventricle | 87 | 0.00043 | 0.0462 | 2.33177 | 21 | 0.00864 |
| MGI Expression: | TS20_lower respiratory tract | 79 | 0.0004 | 0.0468 | 2.02863 | 29 | 0.01193 |
| MGI Expression: | TS16_trunk dermomyotome | 85 | 0.00043 | 0.0469 | 2.28073 | 22 | 0.00905 |
| GO Biological | histamine transport | 358 | 0.00165 | 0.04823 | 2.94967 | 11 | 0.00453 |
| GO Biological | regulation of glucocorticoid | 369 | 0.00173 | 0.04903 | 2.77341 | 12 | 0.00494 |
| GO Biological | mast cell activation | 370 | 0.00174 | 0.04923 | 2.64092 | 13 | 0.00535 |
| GO Biological Process | signal transduction involved in regulation of gene expression | 375 | 0.00178 | 0.04954 | 2.35381 | 16 | 0.00658 |
| MGI Expression: | TS20_trachea | 97 | 0.00052 | 0.04958 | 2.08586 | 26 | 0.0107 |
| Mouse Phenotype | pancreatic islet hypoplasia | 365 | 0.00229 | 0.04959 | 3.24139 | 9 | 0.0037 |
| MSigDB Immunologic | Genes up-regulated in comparison of naive B cells | 115 | 0.0218 | 1.51928 | 49 | 188 | 0.01583 |
| Mouse Phenotype | decreased susceptibility to | 114 | 3.7E−05 | 2.02938 | 47 | 135 | 0.01519 |
| MSigDB Perturbation | Genes defining proliferation and self renewal potential of | 115 | 0.00027 | 1.92773 | 42 | 127 | 0.01357 |
| Mouse Phenotype | incomplete cephalic closure | 140 | 0.00012 | 2.68138 | 23 | 50 | 0.00743 |
| MSigDB Perturbation | Class II of genes transiently induced by EGF [GeneID | 156 | 0.00121 | 2.42878 | 20 | 48 | 0.00646 |
| MSigDB Perturbation | Genes up-regulated in B lymphocytes at 2 h after | 370 | 0.02692 | 1.98189 | 17 | 50 | 0.00549 |

TABLE 5-continued

GREAT version Species assembly: hg19
Association rule: Basal + extension: 5000 bp upstream, 1000 bp downstream, 1000000 bp max extension, curated

| # Ontology | Term Name | Binom Rank | Binom Raw P-Value | Binom FDR Q-Val | Binom Fold Enrich | Binom Obsrvd Region Hits | Binom Region Set Coverag |
|---|---|---|---|---|---|---|---|
| MSigDB Perturbation | Cohesin targets identified by ChIP-chip which were up-regulated after knockdown of | 44 | 1.51E−07 | 3.66399 | 22 | 35 | 0.00711 |
| Mouse Phenotype | altered susceptibility to kidney | 348 | 0.00507 | 2.91454 | 12 | 24 | 0.00388 |
| Mouse Phenotype | abnormal cephalic neural fold | 165 | 0.00034 | 2.5296 | 23 | 53 | 0.00743 |
| GO Biological | UDP-glucuronate metabolic | 547 | 0.01651 | 5.82908 | 4 | 4 | 0.00129 |
| GO Biological | regulation of steroid | 625 | 0.03003 | 2.06447 | 17 | 48 | 0.00549 |
| MGI Expression: | TS19_venous system | 921 | 0.00462 | 3.27886 | 9 | 16 | 0.00291 |
| GO Biological | positive regulation of myeloid | 327 | 0.00345 | 2.15228 | 24 | 65 | 0.00775 |
| Mouse Phenotype | decreased susceptibility to | 275 | 0.00209 | 3.37473 | 11 | 19 | 0.00355 |
| MSigDB Perturbation | Genes down-regulated in blood vessel cells from wound site. | 300 | 0.01366 | 2.77575 | 10 | 21 | 0.00323 |
| MGI Expression: | TS15_septum transversum | 474 | 7.5E−05 | 3.0967 | 17 | 32 | 0.00549 |
| MSigDB Perturbation | Genes down-regulated in glioblastoma cell lines displaying spherical growth (cluster-1) compared to those | 225 | 0.00541 | 2.79796 | 12 | 25 | 0.00388 |
| MSigDB Perturbation | Genes up-regulated in immunoglobulin light chain amyloidosis plasma cells (ALPC) | 351 | 0.022 | 2.46615 | 11 | 26 | 0.00355 |
| MSigDB Perturbation | Amplification hot spot 27: colocalized fragile sites and | 366 | 0.02606 | 3.49745 | 6 | 10 | 0.00194 |
| Mouse Phenotype | abnormal T follicular helper cell | 848 | 0.04983 | 3.1795 | 6 | 11 | 0.00194 |
| Mouse Phenotype | dilated vasculature | 387 | 0.00809 | 2.55022 | 14 | 32 | 0.00452 |
| MSigDB Perturbation | Down-regulated genes in the B lymphocyte developmental signature, based on expression profiling of lymphomas from | 439 | 0.04016 | 1.73297 | 22 | 74 | 0.00711 |
| GO Biological | distal tubule development | 610 | 0.02631 | 3.4003 | 7 | 12 | 0.00226 |
| Mouse Phenotype | abnormal alveolocapillary | 828 | 0.04824 | 5.82908 | 3 | 3 | 0.00097 |
| GO Biological | regulation of superoxide | 540 | 0.01616 | 3.3309 | 8 | 14 | 0.00258 |
| MSigDB Perturbation | Genes identified as hypermethylated in SW48 cells | 358 | 0.02432 | 2.91454 | 8 | 16 | 0.00258 |
| MSigDB Perturbation | Genes whose expression most uniformly correlated with that of MM P14 [GeneI D = 4323] | 442 | 0.04061 | 3.1795 | 6 | 11 | 0.00194 |
| M Sig DB Perturbation | Top 40 genes from cluster 15 of acute myeloid leukemia (AML) expression profile; 88% of the samples are FAB M1 or M2 | 271 | 0.00882 | 2.52593 | 13 | 30 | 0.0042 |
| GO Biological | regulation of blood coagulation | 539 | 0.01611 | 1.97292 | 22 | 65 | 0.00711 |
| Mouse Phenotype | abnormal lung compliance | 551 | 0.01835 | 2.49818 | 12 | 28 | 0.00388 |
| MGI Expression: | TS20_endocardial cushion | 875 | 0.00333 | 2.70636 | 13 | 28 | 0.0042 |
| MSigDB Perturbation | Genes within amplicon 6p24-p22 identified in a copy number | 149 | 0.00091 | 3.3309 | 12 | 21 | 0.00388 |
| M SigDB Perturbation | Genes down-regulated in U2-OS Tet-On cells (osteosarcoma) after induction of ESX1 | 131 | 0.00056 | 3.01504 | 15 | 29 | 0.00485 |
| MSigDB Perturbation | Down-regulated genes that separate angiogenic from non-angiogenic non-small cell lung | 470 | 0.04652 | 2.04806 | 13 | 37 | 0.0042 |
| GO Biological | positive regulation of | 577 | 0.02295 | 2.24195 | 15 | 39 | 0.00485 |
| Mouse Phenotype | abnormal Peyer's patch size | 813 | 0.04829 | 1.98719 | 15 | 44 | 0.00485 |
| MGI Expression: | TS15_venous system | 561 | 0.00021 | 3.12272 | 15 | 28 | 0.00485 |
| MSigDB Perturbation | Genes down-regulated in AtT20 cells (pituitary cancer) after | 316 | 0.01665 | 2.5648 | 11 | 25 | 0.00355 |
| Mouse Phenotype | increased mast cell number | 801 | 0.04787 | 2.91454 | 7 | 14 | 0.00226 |
| MGI Expression: | TS15_mesenchyme derived | 604 | 0.00035 | 3.2947 | 13 | 23 | 0.0042 |
| GO Biological | regulation of macrophage | 691 | 0.04284 | 3.49745 | 6 | 10 | 0.00194 |
| GO Biological | positive regulation of cytokine | 471 | 0.01127 | 2.07476 | 21 | 59 | 0.00679 |
| GO Biological Process | production of molecular mediator involved in | 698 | 0.04247 | 3.13874 | 7 | 13 | 0.00226 |
| MGI Expression: | TS28_rib | 1173 | 0.01212 | 3.10884 | 8 | 15 | 0.00258 |
| MSigDB Perturbation | Genes up-regulated by tretinoin (ATRA) [PubChem = 444795] in U937 cells (acute promyelocytic leukemia, APL) made resistant to the drug by expression of the | 330 | 0.01929 | 2.64958 | 10 | 22 | 0.00323 |
| MSigDB Perturbation | Genes up-regulated in pilocytic astrocytoma (PA) samples from patients with type 1 neurofibromatosis syndrom | 397 | 0.03162 | 4.66326 | 4 | 5 | 0.00129 |

TABLE 5-continued

GREAT version    Species assembly: hg19
Association rule: Basal + extension: 5000 bp upstream, 1000 bp downstream, 1000000 bp max extension, curated

| # Ontology | Term Name | Binom Rank | Binom Raw P-Value | Binom FDR Q-Val | Binom Fold Enrich | Binom Obsrvd Region Hits | Binom Region Set Coverag |
|---|---|---|---|---|---|---|---|
| MGI Expression: | TS12_future prosencephalon | 1518 | 0.03223 | 3.64317 | 5 | 8 | 0.00162 |
| Mouse Phenotype | abnormal tricuspid valve | 586 | 0.02114 | 2.5648 | 11 | 25 | 0.00355 |
| MGI Expression: | TS28_pectoral girdle bone | 1248 | 0.01712 | 4.16363 | 5 | 7 | 0.00162 |
| Mouse Phenotype | decreased cochlear outer hair | 266 | 0.00199 | 2.91454 | 14 | 28 | 0.00452 |
| MGI Expression: | TS22_dorsal aorta | 476 | 7.5E−05 | 3.21604 | 16 | 29 | 0.00517 |
| MSigDB | Genes up-regulated specifically | 236 | 0.00634 | 3.06794 | 10 | 19 | 0.00323 |
| MSigDB Pathway | Genes involved in FRS2- | 19 | 0.03259 | 2.42878 | 15 | 36 | 0.00485 |
| Mouse Phenotype | abnormal cochlear nerve | 319 | 0.00338 | 3.20599 | 11 | 20 | 0.00355 |
| GO Biological | face morphogenesis | 372 | 0.00482 | 2.72024 | 14 | 30 | 0.00452 |
| MSigDB Perturbation | Genes whose expression peaked at 480 min after | 373 | 0.02695 | 2.08181 | 15 | 42 | 0.00485 |
| Mouse Phenotype | decreased interleukin-12 | 819 | 0.0482 | 2.10495 | 13 | 36 | 0.0042 |
| MSigDB Perturbation | Genes up-regulated in hematopoietic precursor cells conditionally expressing HOXA9 | 409 | 0.03356 | 1.82159 | 20 | 64 | 0.00646 |
| GO Biological | negative regulation of steroid | 597 | 0.02436 | 2.91454 | 9 | 18 | 0.00291 |
| Mouse Phenotype | increased circulating | 837 | 0.04876 | 2.49818 | 9 | 21 | 0.00291 |
| Mouse Phenotype | decreased response of heart to | 786 | 0.04609 | 2.29 | 11 | 28 | 0.00355 |
| GO Biological | negative regulation of steroid | 724 | 0.05 | 2.62309 | 9 | 20 | 0.00291 |
| MSigDB Perturbation | Genes up-regulated in NI H3T3 cells (fibroblasts) after treatment with Y27632 [PubChem = 123862], an inhibitor of ROCK proteins; the | 460 | 0.04567 | 2.21103 | 11 | 29 | 0.00355 |
| MGI Expression: | TS28_articular cartilage | 1179 | 0.01218 | 3.4003 | 7 | 12 | 0.00226 |
| MSigDB Perturbation | Genes in cluster 3: delayed up-regulation in HFW cells | 399 | 0.03176 | 2.16509 | 13 | 35 | 0.0042 |
| GO Biological | positive regulation of DNA- | 654 | 0.03654 | 4.16363 | 5 | 7 | 0.00162 |
| M GI Expression: | TS12_optic sulcus neural | 1071 | 0.00754 | 5.82908 | 4 | 4 | 0.00129 |
| MSigDB Perturbation | Up-regulated PDGF targets identified by a gene-trap | 275 | 0.00921 | 2.91454 | 10 | 20 | 0.00323 |
| MSigDB Perturbation | Genes down-regulated during pubertal mammary gland | 399 | 0.03176 | 2.16509 | 13 | 35 | 0.0042 |
| Mouse Phenotype | abnormal mesocardium | 828 | 0.04824 | 5.82908 | 3 | 3 | 0.00097 |
| GO Biological | head morphogenesis | 536 | 0.01618 | 2.40021 | 14 | 34 | 0.00452 |
| GO Biological | regulation of steroid hormone | 451 | 0.00976 | 3.58713 | 8 | 13 | 0.00258 |
| Mouse Phenotype | small second branchial arch | 484 | 0.01343 | 3.08598 | 9 | 17 | 0.00291 |
| MGI Expression: | TS13_septum transversum | 553 | 0.00019 | 4.16363 | 10 | 14 | 0.00323 |
| MSigDB Perturbation | Transcription factors expressed in progenitors of exocrine | 442 | 0.04061 | 3.1795 | 6 | 11 | 0.00194 |
| GO Biological | aorta morphogenesis | 518 | 0.01518 | 2.91454 | 10 | 20 | 0.00323 |
| MGI Expression: | TS28_cartilage | 738 | 0.00141 | 2.33163 | 20 | 50 | 0.00646 |
| MSigDB Perturbation | Selected genes down-regulated in peripheral blood monocytes (PBMC) of patients with hepatocellular carcinoma (HCC) | 431 | 0.03891 | 2.10495 | 13 | 36 | 0.0042 |
| MSigDB Pathway | Genes involved in FGFR ligand | 14 | 0.03856 | 2.91454 | 11 | 22 | 0.00355 |
| MSigDB Pathway | Genes involved in Integrin | 29 | 0.0393 | 2.5907 | 12 | 27 | 0.00388 |
| MGI Expression: | TS15_midgut epithelium | 1382 | 0.02521 | 4.66326 | 4 | 5 | 0.00129 |
| GO Biological | regulation of removal of | 547 | 0.01651 | 5.82908 | 4 | 4 | 0.00129 |
| MGI Expression: | TS22_cornea epithelium | 604 | 0.00035 | 3.2947 | 13 | 23 | 0.0042 |
| MGI Expression: | TS24_hea rt valve | 659 | 0.00066 | 4.03552 | 9 | 13 | 0.00291 |
| MGI Expression: | TS15_primitive ventricle | 1421 | 0.02734 | 2.7431 | 8 | 17 | 0.00258 |
| MGI Expression: | TS20_lower respiratory tract | 1469 | 0.03083 | 2.18591 | 12 | 32 | 0.00388 |
| MGI Expression: | TS16_trunk dermomyotome | 639 | 0.00053 | 3.56222 | 11 | 18 | 0.00355 |
| GO Biological | histamine transport | 201 | 0.0003 | 5.1814 | 8 | 9 | 0.00258 |
| GO Biological | regulation of glucocorticoid | 654 | 0.03654 | 4.16363 | 5 | 7 | 0.00162 |
| GO Biological | mast cell activation | 343 | 0.00398 | 3.42887 | 10 | 17 | 0.00323 |
| GO Biological Process | signal transduction involved in regulation of gene expression | 530 | 0.01617 | 3.08598 | 9 | 17 | 0.00291 |
| MGI Expression: | TS20_trachea | 1445 | 0.02956 | 2.29 | 11 | 28 | 0.00355 |
| Mouse Phenotype | pancreatic islet hypoplasia | 739 | 0.03998 | 4.66326 | 4 | 5 | 0.00129 |

TABLE 6

GREAT
version 3.0.0    Species assembly: hg19
    Association rule: Basal + extension: 5000 bp upstream, 1000 bp downstream, 1000000 bp max extension, curated regulatory

| # Ontology | Term Name | Binom Rank | Binom Raw P-Value | Binom FDR Q-Val | Binom Fold Enrich | Binom Obsrvd Region Hits | Binom Region Set Coverage |
|---|---|---|---|---|---|---|---|
| MSigDB Perturbation | Genes up-regulated in CD4 + [GeneID = 920] T lymphocytes transduced with FOXP3 [GeneID = 50943]. | 87 | 3.21E−07 | 1.24E−05 | 2.738416 | 34 | 0.004672 |
| MSigDB Perturbation | Genes down-regulated in HeLa cells (cervical carcinoma) 24 h after infection with adenovirus Ad12. | 91 | 4.47E−07 | 1.65E−05 | 2.04296 | 60 | 0.008245 |
| MSigDB Perturbation | Genes up-regulated in DU145-RD cells (prostate cancer) resistant to docetaxel [PubChem = 148124] vs the parental, docetaxel-sensitive cells. | 92 | 4.54E−07 | 1.66E−05 | 2.346385 | 44 | 0.006046 |
| MSigDB Perturbation | Genes up-regulated during prostate cancer progression in mice heterozygotic for both NKX3.1 and PTEN [GeneI D = 4824; 5728]. | 125 | 2.33E−06 | 6.28E−05 | 2.390376 | 37 | 0.005085 |
| MSigDB Perturbation | Genes corresponding to the histamine [PubChem = 774] response network. | 142 | 4.1E−06 | 9.71E−05 | 2.021302 | 51 | 0.007008 |
| MGI Expression: Detected | TS24_chondrocranium | 86 | 1.52E−06 | 0.000165 | 2.509054 | 35 | 0.00481 |
| MSigDB Perturbation | Genes down-regulated after knockdown of RALA or RALB [GeneiD = 5898; 5899], which were also differentially expressed in bladder cancer compared to normal bladder urothelium tissue. | 163 | 9.45E−06 | 0.000195 | 2.241459 | 37 | 0.005085 |
| Mouse Phenotype | disorganized yolk sac vascular plexus | 120 | 3.92E−06 | 0.000259 | 2.075318 | 48 | 0.006596 |
| Mouse Phenotype | abnormal Mullerian duct morphology | 124 | 5.19E−06 | 0.000332 | 2.070606 | 47 | 0.006459 |
| MSigDB Perturbation | Genes up-regulated in RCC4 cells (renal cell carcinoma) engineered to stably express VHL [GeneI D = 7428] off a plasmid vector. | 274 | 0.0001 | 0.001232 | 2.33112 | 26 | 0.003573 |
| Mouse Phenotype | abnormal Langerhans cell physiology | 205 | 6.29E−05 | 0.002429 | 2.066932 | 36 | 0.004947 |
| MGI Expression: Detected | TS12_amnion | 246 | 9.02E−05 | 0.003424 | 2.052029 | 35 | 0.00481 |
| MGI Expression: Detected | T519_external ear | 272 | 0.00012 | 0.004103 | 2.097459 | 32 | 0.004397 |
| MGI Expression: Detected | TS24_basioccipital bone | 278 | 0.000127 | 0.004277 | 2.499719 | 22 | 0.003023 |
| MGI Expression: Detected | TS26_heart valve | 317 | 0.00018 | 0.0053 | 2.243901 | 26 | 0.003573 |
| MGI Expression: Detected | TS23_lower jaw incisor epithelium | 388 | 0.00046 | 0.01107 | 2.690801 | 16 | 0.002199 |
| MSigDB Pathway | Phospholipase C-epsilon pathway | 67 | 0.000706 | 0.013915 | 2.077133 | 25 | 0.003435 |
| Mouse Phenotype | decreased corneal stroma thickness | 380 | 0.000691 | 0.014396 | 2.01573 | 27 | 0.00371 |
| Mouse Phenotype | abnormal bone healing | 388 | 0.000746 | 0.015216 | 2.144297 | 23 | 0.003161 |
| MGI Expression: Detected | TS21_urorectal septum | 457 | 0.000818 | 0.016707 | 2.129113 | 23 | 0.003161 |
| M Sig DB Pathway | Genes involved in Fatty Acyl-CoA Biosynthesis | 86 | 0.001109 | 0.017018 | 2.079229 | 23 | 0.003161 |
| MSigDB Pathway | Genes involved in Synthesis of very long-chain fatty acyl-CoAs | 95 | 0.001438 | 0.019987 | 2.116259 | 21 | 0.002886 |
| M Sig DB Pathway | CBL mediated ligand-induced downregulation of EGF receptors | 100 | 0.001542 | 0.020352 | 2.025521 | 23 | 0.003161 |

TABLE 6-continued

GREAT
version 3.0.0    Species assembly: hg19
    Association rule: Basal + extension: 5000 bp upstream, 1000 bp downstream, 1000000 bp max extension, curated regulatory

| # Ontology | Term Name | Binom Rank | Binom Raw P-Value | Binom FDR Q-Val | Binom Fold Enrich | Binom Obsrvd Region Hits | Binom Region Set Coverage |
|---|---|---|---|---|---|---|---|
| MSigDB Perturbation | Genes down-regulated in tumorous liver tissues from PARK2 [GeneID = 5071] knockout mice compared to the normal, non-tumorous tissue from wild type mice. | 665 | 0.004479 | 0.022657 | 2.583622 | 11 | 0.001512 |
| MGI Expression: Detected | TS20_rest of paramesonephric duct of male | 565 | 0.001593 | 0.02632 | 2.465061 | 15 | 0.002061 |
| GO Cellular Component | spectrin | 66 | 0.0016 | 0.030659 | 2.670339 | 13 | 0.001786 |
| Mouse Phenotype | absent Mullerian ducts | 639 | 0.00392 | 0.048579 | 2.235471 | 15 | 0.002061 |
| MSigDB Perturbation | Genes up-regulated in CD4 + [GeneI D = 920] T lymphocytes transduced with FOXP3 [GeneI D = 50943]. | 674 | 0.029929 | 1.750873 | 15 | 23 | 0.002232 |
| MSigDB Perturbation | Genes down-regulated in HeLa cells (cervical carcinoma) 24 h after infection with adenovirus Ad12. | 618 | 0.023189 | 1.560856 | 25 | 43 | 0.00372 |
| MSigDB Perturbation | Genes up-regulated in DU145-RD cells (prostate cancer) resistant to docetaxel [PubChem = 148124] vs the parental, docetaxel-sensitive cells. | 657 | 0.029468 | 1.666349 | 18 | 29 | 0.002679 |
| MSigDB Perturbation | Genes up-regulated during prostate cancer progression in mice heterozygotic for both NKX3.1 and PTEN [GeneI D = 4824; 5728]. | 660 | 0.029345 | 1.836881 | 13 | 19 | 0.001935 |
| MSigDB Perturbation | Genes corresponding to the histamine [PubChem = 774] response network. | 733 | 0.041269 | 1.594024 | 19 | 32 | 0.002827 |
| MGI Expression: Detected | TS24_chondrocranium | 1076 | 0.001031 | 2.326716 | 13 | 15 | 0.001935 |
| MSigDB Perturbation | Genes down-regulated after knockdown of RALA or RALB [GeneiD = 5898; 5899], which were also differentially expressed in bladder cancer compared to normal bladder urothelium tissue. | 582 | 0.018952 | 1.789782 | 16 | 24 | 0.002381 |
| Mouse Phenotype | disorganized yolk sac vascular plexus | 1075 | 0.023376 | 1.830459 | 15 | 22 | 0.002232 |
| Mouse Phenotype | abnormal Mullerian duct morphology | 1038 | 0.021022 | 1.93893 | 13 | 18 | 0.001935 |
| MSigDB Perturbation | Genes up-regulated in RCC4 cells (renal cell carcinoma) engineered to stably express VHL [GeneI D = 7428] off a plasmid vector. | 434 | 0.007091 | 2.416205 | 9 | 10 | 0.001339 |
| Mouse Phenotype | abnormal Langerhans cell physiology | 1248 | 0.036528 | 1.836881 | 13 | 19 | 0.001935 |
| MGI Expression: Detected | TS12 amnion | 2115 | 0.043962 | 1.917623 | 10 | 14 | 0.001488 |
| MGI Expression: Detected | TS19_external ear | 1593 | 0.013046 | 2.386376 | 8 | 9 | 0.00119 |
| MGI Expression: Detected | T524_basioccipital bone | 1961 | 0.034109 | 2.684673 | 5 | 5 | 0.000744 |
| MGI Expression: Detected | TS26_heart valve | 1857 | 0.02693 | 2.349089 | 7 | 8 | 0.001042 |
| MGI Expression Detected | TS23_lower jaw incisor epithelium | 1857 | 0.02693 | 2.349089 | 7 | 8 | 0.001042 |
| MSigDB Pathway | Phospholipase C-epsilon pathway | 67 | 0.029211 | 2.237227 | 10 | 12 | 0.001488 |
| Mouse Phenotype | decreased corneal stroma thickness | 680 | 0.004339 | 2.440611 | 10 | 11 | 0.001488 |
| Mouse Phenotype | abnormal bone healing | 680 | 0.004339 | 2.440611 | 10 | 11 | 0.001488 |
| MGI Expression: Detected | TS21_urorectal septum | 1641 | 0.015175 | 2.684673 | 6 | 6 | 0.000893 |

TABLE 6-continued

GREAT
version 3.0.0  Species assembly: hg19
Association rule: Basal + extension: 5000 bp upstream, 1000 bp downstream, 1000000 bp max extension, curated regulatory

| # Ontology | Term Name | Binom Rank | Binom Raw P-Value | Binom FDR Q-Val | Binom Fold Enrich | Binom Obsrvd Region Hits | Binom Region Set Coverage |
|---|---|---|---|---|---|---|---|
| MSigDB Pathway | Genes involved in Fatty Acyl-CoA Biosynthesis | 80 | 0.045472 | 1.93893 | 13 | 18 | 0.001935 |
| MSigDB Pathway | Genes involved in Synthesis of very long-chain fatty acyl-CoAs | 73 | 0.036078 | 2.109386 | 11 | 14 | 0.001637 |
| MSigDB Pathway | CBL mediated ligand-induced downregulation of EGF receptors | 49 | 0.017413 | 2.271646 | 11 | 13 | 0.001637 |
| MSigDB Perturbation | Genes down-regulated in tumorous liver tissues from PARK2 [GeneI D = 5071] knockout mice compared to the normal, non-tumorous tissue from wild type mice. | 698 | 0.034525 | 2.684673 | 5 | 5 | 0.000744 |
| MGI Expression: Detected | TS20_rest of paramesonephric duct of male | 1961 | 0.034109 | 2.684673 | 5 | 5 | 0.000744 |
| GO Cellular Component | spectrin | 62 | 0.045415 | 2.386376 | 8 | 9 | 0.00119 |
| Mouse Phenotype | absent Mullerian ducts | 1300 | 0.043632 | 2.684673 | 5 | 5 | 0.000744 |

Example 2

This Example describes further refinement of the MeCo gene score. Breast tumor subtypes Luminal A, Luminal B, Basal, HER2, and Normal-like, characterized based on gene expression data, were analyzed. The following terms are used in Tables 7-12 below and FIGS. 16-22:

BMFS: Bone metastasis-free survival, the duration a breast cancer patient lives after diagnosis without incidence of bone metastasis.

Score: the averaged gene expression of constituent stiff-associated genes subtracted by the averaged gene expression of constituent soft-associated genes.

MeCo genes (also known as "raw MeCo genes"): the original set of differentially-regulated genes in response to stiff vs soft growth in the model system described in Examples 1 and 2; a total of 2,210 genes (711 stiff-associated and 1409 soft-associated).

MeCo-refined genes: an optimized subset of MeCo constituent genes whose score shows a statistically-significant association with BMFS in patients, independent of breast tumor subtype, in two independent cohorts; a set of 1004 total genes (323 stiff-associated and 681 soft-associated); highly predictive of BMFS.

MeCo-refined minimal gene set: a minimal subset of MeCo-refined constituent genes whose score shows a statistically-significant association with BMFS in patients, independent of breast tumor subtype, in two independent cohorts; a set of 28 total genes (6 stiff-associated and 22 soft-associated).

'Luminal A' MeCo minimal gene set: a minimal subset of MeCo constituent genes whose score shows a statistically-significant association with BMFS in 'Luminal A' patients specifically; a set of 100 total genes (37 stiff-associated and 63 soft-associated).

'Luminal B' MeCo minimal gene set: a minimal subset of MeCo constituent genes whose score shows a statistically-significant association with BMFS in 'Luminal B' patients specifically; a set of 100 total genes (27 stiff-associated and 73 soft-associated).

'Basal' MeCo minimal gene set: a minimal subset of MeCo constituent genes whose score shows a statistically-significant association with BMFS in 'Basal' patients specifically; a set of 100 total genes (22 stiff-associated and 78 soft-associated).

'HER2' MeCo minimal gene set: a minimal subset of MeCo constituent genes whose score shows a statistically-significant association with BMFS in 'HER2' patients specifically; a set of 100 total genes (34 stiff-associated and 66 soft-associated).

'Normal-like' MeCo minimal gene set: a minimal subset of MeCo constituent genes whose score shows a statistically-significant association with BMFS in 'Normal-like' patients specifically; a set of 100 total genes (24 stiff-associated and 76 soft-associated).

TABLE 7

MeCo-refined minimal gene set (28 total)

| Entrez ID | Gene Symbol | Association |
|---|---|---|
| 9 | NAT1 | Stiff |
| 55839 | CENPN | Stiff |
| 1300 | COL10A1 | Stiff |
| 5327 | PLAT | Stiff |
| 353500 | BMP8A | Stiff |
| 5480 | PPIC | Stiff |
| 55859 | BEX1 | Soft |
| 6261 | RYR1 | Soft |
| 79885 | HDAC11 | Soft |
| 5920 | RARRES3 | Soft |
| 939 | CD27 | Soft |
| 79056 | PPRG4 | Soft |
| 54739 | XAF1 | Soft |
| 3561 | IL2R | Soft |
| 9170 | LPAR2 | Soft |
| 7161 | TP73 | Soft |
| 3046 | HBEI | Soft |
| 5662 | PSD | Soft |
| 6660 | SOX5 | Soft |
| 9459 | ARHGEF6 | Soft |
| 8638 | OASL | Soft |
| 54798 | DCHS2 | Soft |
| 3780 | KCNN1 | Soft |
| 10666 | CD226 | Soft |

TABLE 7-continued

MeCo-refined minimal gene set (28 total)

| Entrez ID | Gene Symbol | Association |
|---|---|---|
| 8508 | NIPSNAP1 | Soft |
| 6775 | STAT4 | Soft |
| 53637 | S1PR5 | Soft |
| 10817 | FRS3 | Soft |

TABLE 8

'Luminal A' MeCo minimal gene set (100 total)

| Entrez ID | Gene Symbol | Association |
|---|---|---|
| 9 | NAT1 | Stiff |
| 5307 | PITX1 | Stfff |
| 55839 | CENPN | Stiff |
| 9576 | CXCLB | Stiff |
| 8309 | ACOX2 | Stiff |
| 2175 | FANCA | Stiff |
| 6364 | CCL20 | Stiff |
| 993 | CDC25A | Stiff |
| 55388 | MCM10 | Stiff |
| 6696 | SPP1 | Stiff |
| 412 | STS | Stiff |
| 1993 | ELAVL2 | Stiff |
| 86476 | GFM1 | Stiff |
| 63967 | CLSPN | Stiff |
| 79831 | KDM8 | Stiff |
| 5362 | PLXNA2 | Stiff |
| 56667 | MUC13 | Stiff |
| 1999 | ELF3 | Stiff |
| 8828 | NRP2 | Stiff |
| 719 | C3AR1 | Stiff |
| 26168 | SENP3 | Stiff |
| 55379 | LRRC59 | Stiff |
| 23762 | OSBP2 | Stiff |
| 54906 | FAM20 | Stiff |
| 2700 | GJA3 | Stiff |
| 80308 | FLAD1 | Stiff |
| 7866 | IFRD2 | Stiff |
| 55131 | RBM28 | Stiff |
| 79866 | BORA | Stiff |
| 51022 | GLRX2 | Stiff |
| 10755 | GIPC1 | Stiff |
| 192683 | SCAMP | Stiff |
| 10190 | TXNDC | Stiff |
| 1861 | TOR1A | Stiff |
| 55743 | CHFR | Stiff |
| 54897 | CASZ1 | Stiff |
| 57171 | DOLPP1 | Stiff |
| 5190 | PEX6 | Soft |
| 55859 | BEX1 | Soft |
| 347733 | TUBB2B | Soft |
| 79885 | HDAC11 | Soft |
| 79589 | RNF128 | Soft |
| 6236 | RRAD | Soft |
| 286 | ANK1 | Soft |
| 9369 | NRXN3 | Soft |
| 7718 | ZNF165 | Soft |
| 9758 | FRMPD4 | Soft |
| 23150 | FRMD4B | Soft |
| 9715 | FAM131B | Soft |
| 5727 | PTCH1 | Soft |
| 4917 | NTN3 | Soft |
| 349152 | DPY19L2P2 | Soft |
| 57212 | TP73-AS1 | Soft |
| 54762 | GRAMD1C | Soft |
| 7704 | ZBTB16 | Soft |
| 7349 | UCN | Soft |
| 7294 | TXK | Soft |
| 2549 | GAB1 | Soft |
| 57597 | BAHCC1 | Soft |
| 80352 | RNF39 | Soft |
| 10297 | APC2 | Soft |
| 6035 | SLC2A11 | Soft |

TABLE 8-continued

'Luminal A' MeCo minimal gene set (100 total)

| Entrez ID | Gene Symbol | Association |
|---|---|---|
| 352961 | HCG26 | Soft |
| 55592 | GOLGA2P5 | Soft |
| 51208 | CLDN18 | Soft |
| 57000 | GSN-AS1 | Soft |
| 54993 | ZSCAN2 | Soft |
| 1583 | CYP11A1 | Soft |
| 218 | ALDH3A1 | Soft |
| 91683 | SYT12 | Soft |
| 4494 | MT1F | Soft |
| 6340 | SCNN1G | Soft |
| 7161 | TP73 | Soft |
| 55812 | SPATA7 | Soft |
| 6339 | SCNN1D | Soft |
| 3046 | HBE1 | Soft |
| 1326 | MAP3KB | Soft |
| 5662 | PSD | Soft |
| 168544 | ZNF467 | Soft |
| 1806 | DPYD | Soft |
| 345 | APOC3 | Soft |
| 80823 | BHLHB9 | Soft |
| 29842 | TFCP2L1 | Soft |
| 25849 | PARM1 | Soft |
| 9459 | ARHGEF6 | Soft |
| 29121 | CLEC2D | Soft |
| 54769 | ZNF83 | Soft |
| 23373 | CRTC1 | Soft |
| 54798 | DCHS2 | Soft |
| 11201 | POLI | Soft |
| 3780 | KCNN1 | Soft |
| 9719 | ADAMTSL2 | Soft |
| 1992 | SERPINB1 | Soft |
| 1768 | DNAH6 | Soft |
| 10076 | PTPRU | Soft |
| 6490 | PMEL | Soft |
| 8515 | ITGA10 | Soft |
| 54741 | LEPROT | Soft |
| 55777 | MBD5 | Soft |
| 2329 | FMO4 | Soft |

TABLE 9

'Luminal B' MeCo minimal gene set (100 total)

| Entrez ID | Gene Symbol | Association |
|---|---|---|
| 1300 | COL10A1 | Stiff |
| 9498 | SLC4A8 | Stiff |
| 90178 | TEDC2 | Stiff |
| 23223 | RRP12 | Stiff |
| 7262 | PHLDA2 | Stiff |
| 23136 | EPB41L3 | Stiff |
| 5327 | PLAT | Stiff |
| 51018 | RRP15 | Stiff |
| 23348 | DOCK9 | Stiff |
| 5137 | PDE1C | Stiff |
| 353500 | BMP8A | Stiff |
| 4481 | MSR1 | Stiff |
| 28232 | SLCO3A1 | Stiff |
| 10149 | ADGRG2 | Stiff |
| 283871 | PGP | Stiff |
| 79050 | NOC4L | Stiff |
| 115123 | MARCH3 | Stiff |
| 113 | ADCY7 | Stiff |
| 10237 | SLC35B1 | Stiff |
| 55027 | HEATB3 | Stiff |
| 1407 | CRY1 | Stiff |
| 8006 | TRAPPCI3 | Stiff |
| 206358 | SLC36A1 | Stiff |
| 6996 | TDG | Stiff |
| 79003 | MIS12 | Stiff |
| 23590 | PDSS1 | Stiff |
| 1147 | CHUK | Stiff |
| 9687 | GREB1 | Soft |

TABLE 9-continued

'Luminal B' MeCo minimal gene set (100 total)

| Entrez ID | Gene Symbol | Association |
|---|---|---|
| 5364 | PLXNB1 | Soft |
| 55859 | BEX1 | Soft |
| 3708 | ITPR1 | Soft |
| 4604 | MYBPC1 | Soft |
| 3852 | KRTS | Soft |
| 563 | AZGP1 | Soft |
| 4137 | MAPT | Soft |
| 577 | ADGRB3 | Soft |
| 4110 | MAGEA11 | Soft |
| 3823 | KLRC3 | Soft |
| 3488 | IGFBP5 | Soft |
| 23650 | TRI M29 | Soft |
| 8553 | BHLHE40 | Soft |
| 9537 | TP63I11 | Soft |
| 2444 | FRK | Soft |
| 4256 | MGP | Soft |
| 4599 | MX1 | Soft |
| 1397 | CRIP2 | Soft |
| 901 | CCNG2 | Soft |
| 5920 | RARRES3 | Soft |
| 894 | CCND2 | Soft |
| 22996 | TTC9A | Soft |
| 10370 | CITED2 | Soft |
| 2537 | IFI6 | Soft |
| 4130 | MAP1A | Soft |
| 2900 | GRIK4 | Soft |
| 7711 | ZNF155 | Soft |
| 11119 | BTN3A1 | Soft |
| 939 | CD27 | Soft |
| 2696 | GIPR | Soft |
| 54813 | KLHL28 | Soft |
| 80128 | TRIM46 | Soft |
| 7852 | CXCR4 | Soft |
| 80303 | EFHD1 | Soft |
| 2159 | F10 | Soft |
| 20 | ABCA2 | Soft |
| 346157 | ZNF391 | Soft |
| 9651 | PLCH2 | Soft |
| 79056 | PRRG4 | Soft |
| 10297 | APC2 | Soft |
| 54739 | XAF1 | Soft |
| 183 | AGT | Soft |
| 23081 | KDM4C | oft |
| 7773 | ZNF230 | Soft |
| 3437 | IFIT3 | Soft |
| 51807 | TUBA8 | Soft |
| 3561 | IL2RG | Soft |
| 64122 | FN3K | Soft |
| 9170 | LPAR2 | Soft |
| 7161 | TP73 | Soft |
| 3137 | HLA-J | Soft |
| 5662 | PSD | Soft |
| 8519 | IFITM1 | Soft |
| 604 | BCL6 | Soft |
| 3134 | HLA-F | Soft |
| 10039 | PARP3 | Soft |
| 3433 | IFIT2 | Soft |
| 8638 | OASL | Soft |
| 5083 | PAX9 | Soft |
| 694 | BTG1 | Soft |
| 55279 | ZNF654 | Soft |
| 10666 | CD226 | Soft |
| 8209 | GATD3A | Soft |
| 8508 | NIPSNAP1 | Soft |
| 28981 | IFTB1 | Soft |
| 23224 | SYNE2 | Soft |
| 1E+08 | CADM3-AS1 | Soft |
| 4601 | MXI1 | Soft |
| 9389 | SLC22A14 | Soft |
| 83394 | PITPNM3 | Soft |
| 53637 | S1PR5 | Soft |
| 64598 | MOSPD3 | Soft |

TABLE 10

'Basal' MeCo minimal gene set (100 total)

| Entrez ID | Gene Symbol | Association |
|---|---|---|
| 214 | ALCAM | Stiff |
| 10061 | ABCF2 | Stiff |
| 1308 | COL17A1 | Stiff |
| 53836 | GPRB7 | Stiff |
| 1839 | HBEGF | Stiff |
| 347902 | AMIGO2 | Stiff |
| 5327 | PLAT | Stiff |
| 28234 | SLCO1B3 | Stiff |
| 6835 | SURF2 | Stiff |
| 6382 | SDC1 | Stiff |
| 306 | ANXA3 | Stiff |
| 57211 | ADGRG6 | Stiff |
| 10053 | AP1M2 | Stiff |
| 5010 | CLDN11 | Stiff |
| 51099 | ABHD5 | Stiff |
| 3954 | LETM1 | Stiff |
| 4487 | MSX1 | Stiff |
| 3182 | HNRNPAB | Stiff |
| 10755 | GIPC1 | Stiff |
| 29107 | NXT1 | Stiff |
| 246243 | RNASEH1 | Stiff |
| 79693 | YRDC | Stiff |
| 429 | ASCL1 | Soft |
| 9143 | SYNGR3 | Soft |
| 8786 | RGS11 | Soft |
| 28513 | CDH19 | Soft |
| 8825 | LIN7A | Soft |
| 4128 | MAOA | Soft |
| 348 | APOE | Soft |
| 10178 | TENM1 | Soft |
| 284021 | MILR1 | Soft |
| 84440 | RAB11FIP4 | Soft |
| 57804 | POLD4 | Soft |
| 22861 | NLRP1 | Soft |
| 1384 | CRAT | Soft |
| 23363 | OBSL1 | Soft |
| 26959 | HBP1 | Soft |
| 3777 | KCNK3 | Soft |
| 9028 | RHBDL1 | Soft |
| 23150 | FRMD4B | Soft |
| 1757 | SARDH | Soft |
| 10148 | EBI3 | Soft |
| 3696 | ITGB8 | Soft |
| 6927 | HNF1A | Soft |
| 284439 | SLC25A42 | Soft |
| 2906 | GRIN2D | Soft |
| 57326 | PBXIP1 | Soft |
| 147 | ADRA1B | Soft |
| 4208 | MEF2C | Soft |
| 939 | CD27 | Soft |
| 10866 | HCPS | Soft |
| 6676 | SPAG4 | Soft |
| 57835 | SLC4AS | Soft |
| 6999 | TDO2 | Soft |
| 50509 | COL5A3 | Soft |
| 51213 | LUZP4 | Soft |
| 1815 | DRD4 | Soft |
| 1794 | D0CK2 | Soft |
| 148229 | ATP8B3 | Soft |
| 4299 | AFF1 | Soft |
| 60489 | APOBEC3G | Soft |
| 25837 | RAB26 | Soft |
| 51351 | ZNF117 | Soft |
| 10385 | BTN2A2 | Soft |
| 6915 | TBXA2R | Soft |
| 3965 | LGALS9 | Soft |
| 7464 | CORO2A | Soft |
| 639 | PRDM1 | Soft |
| 2745 | GLRX | Soft |
| 3561 | IL2RG | Soft |
| 23097 | CDK19 | Soft |
| 79955 | PDZD7 | Soft |
| 55663 | ZNF446 | Soft |
| 51171 | HSD17B14 | Soft |
| 168544 | ZNF446 | Soft |
| 25961 | NUDT13 | Soft |

TABLE 10-continued

'Basal' MeCo minimal gene set (100 total)

| Entrez ID | Gene Symbol | Association |
|---|---|---|
| 4241 | MELTF | Soft |
| 80055 | PGAP1 | Soft |
| 5800 | PTPRO | Soft |
| 54 | ACP5 | Soft |
| 3603 | IL16 | Soft |
| 23769 | FLRT1 | Soft |
| 7597 | ZBTB25 | Soft |
| 29121 | CLEC2D | Soft |
| 54798 | DCHS2 | Soft |
| 55279 | ZNF654 | Soft |
| 3290 | HSD11B1 | Soft |
| 79729 | SH3D21 | Soft |
| 80765 | STARD5 | Soft |
| 22898 | DENND33 | Soft |
| 10666 | CD226 | Soft |
| 9294 | S1PR2 | Soft |
| 51268 | PIPOX | Soft |
| 534 | ATP6V1G2 | Soft |
| 6775 | STAT4 | Soft |
| 6795 | AURKC | Soft |
| 27237 | ARHGEF16 | Soft |
| 23208 | SYT11 | Soft |
| 53637 | S1PR5 | Soft |
| 10817 | FRS3 | Soft |

TABLE 11

'HER2' MeCo minimal gene set (100 total)

| Entrez ID | Gene Symbol | Association |
|---|---|---|
| 55359 | STYK1 | Stiff |
| 55839 | CENPN | Stiff |
| 10440 | TIMM17A | Stiff |
| 1300 | COL10A1 | Stiff |
| 6549 | SLC9A2 | Stiff |
| 9751 | SNPH | Stiff |
| 1833 | EPYC | Stiff |
| 3084 | NRG1 | Stiff |
| 51531 | TRMD | Stiff |
| 80206 | FHOD3 | Stiff |
| 643314 | KIAA0754 | Stiff |
| 9708 | PCDHGA8 | Stiff |
| 79669 | C3orf52 | Stiff |
| 51809 | GALNT7 | Stiff |
| 1305 | COL13A1 | Stiff |
| 1136 | CHRNA3 | Stiff |
| 7026 | NR2F2 | Stiff |
| 57089 | ENTPD7 | Stiff |
| 7109 | TRAPPC10 | Stiff |
| 9764 | KIAA0513 | Stiff |
| 25758 | KIAA1549L | Stiff |
| 5420 | PODXL | Stiff |
| 5480 | PPIC | Stiff |
| 55027 | HEATR3 | Stiff |
| 55915 | LANCL2 | Stiff |
| 1977 | EIF4E | Stiff |
| 79663 | HSPBAP1 | Stiff |
| 80006 | TRAPPC13 | Stiff |
| 9429 | ABCG2 | Stiff |
| 206358 | SLC36A1 | Stiff |
| 55161 | TMEM33 | Stiff |
| 81614 | NIPA2 | Stiff |
| 54205 | CYCS | Stiff |
| 55703 | POLR3B | Stiff |
| 3669 | ISG20 | Soft |
| 1356 | CP | Soft |
| 5190 | PEX6 | Soft |
| 633 | BGN | Soft |
| 6261 | RYP1 | Soft |
| 5165 | PDK3 | Soft |
| 23650 | TRIM29 | Soft |
| 924 | CD7 | Soft |

TABLE 11-continued

'HER2' MeCo minimal gene set (100 total)

| Entrez ID | Gene Symbol | Association |
|---|---|---|
| 11156 | PTP4A3 | Soft |
| 27202 | C5AR2 | Soft |
| 1240 | CMKLR1 | Soft |
| 7799 | PRDM2 | Soft |
| 64108 | RTP4 | Soft |
| 5920 | RARRES3 | Soft |
| 57572 | DOCK6 | Soft |
| 10370 | CITED2 | Soft |
| 1302 | COL11A2 | Soft |
| 9182 | RASSF9 | Soft |
| 57326 | PBXIP1 | Soft |
| 22983 | MAST1 | Soft |
| 162972 | ZNF550 | Soft |
| 51083 | GAL | Soft |
| 6676 | SPAG4 | Soft |
| 2886 | GRB7 | Soft |
| 83937 | RASSF4 | Soft |
| 101 | ADAM8 | Soft |
| 22924 | MAPRE3 | Soft |
| 2775 | GNAO1 | Soft |
| 4938 | OAS1 | Soft |
| 79015 | LINC01260 | Soft |
| 5163 | PDK1 | Soft |
| 651 | BMP3 | Soft |
| 79056 | PRRG4 | Soft |
| 54739 | XAF1 | Soft |
| 3437 | IFIT3 | Soft |
| 10893 | MMP24 | Soft |
| 3890 | KRT84 | Soft |
| 3600 | IL15 | Soft |
| 3137 | HLA-J | Soft |
| 3383 | ICAM1 | Soft |
| 79816 | TLE6 | Soft |
| 3728 | JUP | Soft |
| 7140 | TNNT3 | Soft |
| 64856 | VWA1 | Soft |
| 2752 | GLUL | Soft |
| 6660 | SOX5 | Soft |
| 79841 | AGBL2 | Soft |
| 54855 | TENT5C | Soft |
| 8635 | RNASET2 | Soft |
| 8638 | OASL | Soft |
| 389524 | GTF2IRD2B | Soft |
| 55074 | OXR1 | Soft |
| 8269 | TMEM187 | Soft |
| 2548 | GAA | Soft |
| 8508 | NIPSNAP1 | Soft |
| 9390 | SLC22A13 | Soft |
| 3623 | INHA | Soft |
| 10379 | IRF9 | Soft |
| 10014 | HDAC5 | Soft |
| 3798 | KIF5A | Soft |
| 22838 | RNF44 | Soft |
| 87715 | SEMA4G | Soft |
| 84805 | CNNM2 | Soft |
| 115817 | DRHS1 | Soft |
| 10817 | FRS3 | Soft |
| 56606 | SLC2A9 | Soft |

TABLE 12

'Normal-like' MeCo minimal gene set (100 total)

| Entrez ID | Gene Symbol | Association |
|---|---|---|
| 1404 | HAPLN1 | Stiff |
| 9498 | SLC4A8 | Stiff |
| 2312 | FLG | Stiff |
| 5101 | PCDH9 | Stiff |
| 9955 | HS3ST3A1 | Stiff |
| 6542 | SLC7A2 | Stiff |
| 6751 | SSTR1 | Stiff |
| 2475 | MTOR | Stiff |

TABLE 12-continued

'Normal-like' MeCo minimal gene set (100 total)

| Entrez ID | Gene Symbol | Association |
|---|---|---|
| 69967 | CLSPN | Stiff |
| 10836 | GPR75 | Stiff |
| 6710 | SPTB | Stiff |
| 149111 | CNIH3 | Stiff |
| 150967 | LINC01963 | Stiff |
| 646 | BNC1 | Stiff |
| 320 | APBA1 | Stiff |
| 7074 | TIAM1 | Stiff |
| 9071 | CLDN10 | Stiff |
| 23066 | CAND2 | Stiff |
| 23198 | PSME4 | Stiff |
| 131566 | DCBLD2 | Stiff |
| 1440 | CSF3 | Stiff |
| 3786 | KCNQ3 | Stiff |
| 8482 | SEMA7A | Stiff |
| 55703 | POLR3B | Stiff |
| 3669 | ISG20 | Soft |
| 5122 | PCSK1 | Soft |
| 347 | APOD | Soft |
| 4604 | MYBPC1 | Soft |
| 563 | AZGP1 | Soft |
| 6373 | CXCL11 | Soft |
| 4316 | MMP7 | Soft |
| 26470 | SEZ6L2 | Soft |
| 56892 | TCIM | Soft |
| 3485 | IGFBP2 | Soft |
| 9537 | TPS3I11 | Soft |
| 1384 | CRAT | Soft |
| 4547 | MTTP | Soft |
| 6376 | CX3CL1 | Soft |
| 25891 | PAMR1 | Soft |
| 4320 | MMP11 | Soft |
| 1906 | EDN1 | Soft |
| 27076 | LYPD3 | Soft |
| 10279 | PRSS16 | Soft |
| 57161 | PELI2 | Soft |
| 7108 | TM7SF2 | Soft |
| 1571 | CYP2E1 | Soft |
| 939 | CD27 | Soft |
| 10866 | HCP5 | Soft |
| 9914 | ATP2C2 | Soft |
| 10158 | PDZK1IP1 | Soft |
| 390616 | ANKRD34C | Soft |
| 5169 | ENPP3 | Soft |
| 10561 | IFI44 | Soft |
| 1.02E+08 | CTC-338M12.4 | Soft |
| 23037 | PDZD2 | Soft |
| 643641 | ZNF862 | Soft |
| 81031 | SLC2A10 | Soft |
| 23254 | KAZN | Soft |
| 20 | ABCA2 | Soft |
| 346157 | ZNF391 | Soft |
| 284443 | ZNF493 | Soft |
| 337 | APOA4 | Soft |
| 651 | BMP3 | Soft |
| 6338 | SCNN1B | Soft |
| 2735 | GLI1 | Soft |
| 10297 | APC2 | Soft |
| 57787 | MARK4 | Soft |
| 6915 | TBXA2R | Soft |
| 1583 | CYP11A1 | Soft |
| 55806 | HR | Soft |
| 5593 | PRKG2 | Soft |
| 9638 | FEZ1 | Soft |
| 23220 | DTX4 | Soft |
| 1588 | CYP19A1 | Soft |
| 656 | BMP8B | Soft |
| 283927 | NUDT7 | Soft |
| 80823 | BHLHB9 | Soft |
| 10252 | SPRY1 | Soft |
| 3732 | CD82 | Soft |
| 54507 | ADAMTSL4 | Soft |
| 3299 | HSF4 | Soft |
| 79369 | B3GNT4 | Soft |
| 8635 | RNASET2 | Soft |
| 201134 | CEP112 | Soft |
| 8368 | OASL | Soft |
| 58500 | ZNF250 | Soft |
| 4854 | NOTCH3 | Soft |
| 80127 | BBOF1 | Soft |
| 53841 | CDHR5 | Soft |
| 1154 | CISH | Soft |
| 2308 | FOXO1 | Soft |
| 28981 | IFT81 | Soft |
| 9866 | TRIM66 | Soft |
| 27237 | ARHGEF16 | Soft |
| 155060 | LOC155060 | Soft |
| 11092 | SPACA9 | Soft |
| 4092 | SMAD7 | Soft |
| 57658 | CALCOCO1 | Soft |
| 80212 | CCDC92 | Soft |
| 10848 | PPP1R13L | Soft |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A composition, kit, or system, comprising:
   a) a plurality of nucleic acid reagents for specifically detecting the level of expression of at least 5 stiff genes;
   b) a plurality of nucleic acid reagents for specifically detecting the level of expression of at least 5 soft genes
   wherein said nucleic acid reagents comprise a label, and wherein said at least 5 stiff genes and said at least 5 soft genes are selected from the group consisting of

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| ABCC9 | 10060 | Stiff | MBL1P | 8512 | Stiff | ELF3 | 1999 | Stiff | RTEL1 | 51750 | Stiff |
| ABCF2 | 10061 | Stiff | MBLAC1 | 255374 | Stiff | ELFN1 | 392617 | Stiff | RTEL1-TNFRSF6B | 100533107 | Stiff |
| ABCG2 | 9429 | Stiff | MCAT | 27349 | Stiff | ELMO3 | 79767 | Stiff | RTN4IP1 | 84816 | Stiff |
| ABHD11 | 83451 | Stiff | MCF2 | 4168 | Stiff | EMC8 | 10328 | Stiff | RTN4R | 65078 | Stiff |
| ABHD13 | 84945 | Stiff | MCF2L | 23263 | Stiff | EMG1 | 10436 | Stiff | RUNX3 | 864 | Stiff |
| ABHD5 | 51099 | Stiff | MCIDAS | 345643 | Stiff | EN2 | 2020 | Stiff | RUVBL1 | 8607 | Stiff |
| ACAN | 176 | Stiff | MCM10 | 55388 | Stiff | ENDOD1 | 23052 | Stiff | RYR3 | 6263 | Stiff |
| ACOX2 | 8309 | Stiff | MCM8 | 84515 | Stiff | ENOX2 | 10495 | Stiff | S1PR1 | 1901 | Stiff |
| ACSL3 | 2181 | Stiff | MCM8-AS1 | 101929225 | Stiff | ENPP1 | 5167 | Stiff | SAC3D1 | 29901 | Stiff |
| ACTL10 | 170487 | Stiff | MCM9 | 254394 | Stiff | ENTPD1 | 953 | Stiff | SACS | 26278 | Stiff |
| ACTL8 | 81569 | Stiff | MCOLN1 | 57192 | Stiff | ENTPD1-AS1 | 728558 | Stiff | SAMD5 | 389432 | Stiff |
| ACTR5 | 79913 | Stiff | MDFI | 4188 | Stiff | ENTPD7 | 57089 | Stiff | SAP30L-AS1 | 386627 | Stiff |
| ADAM19 | 8728 | Stiff | MED27 | 9442 | Stiff | EPB41L3 | 23136 | Stiff | SAPCD2 | 89958 | Stiff |
| ADAM23 | 8745 | Stiff | MEGF10 | 84466 | Stiff | EPB41L4B | 54566 | Stiff | SBDSP1 | 155370 | Stiff |
| ADAMTS12 | 81792 | Stiff | MESDC1 | 59274 | Stiff | EPHB2 | 2048 | Stiff | SCAMP5 | 192683 | Stiff |
| ADAMTS14 | 140766 | Stiff | METTL1 | 4234 | Stiff | EPHB6 | 2051 | Stiff | SCARA3 | 51435 | Stiff |
| ADAT1 | 23536 | Stiff | MFSDZA | 84879 | Stiff | EPHX3 | 79852 | Stiff | SCLY | 51540 | Stiff |
| ADCY1 | 107 | Stiff | MGAT5B | 146664 | Stiff | EPT1 | 85465 | Stiff | SCO1 | 6341 | Stiff |
| ADCY7 | 113 | Stiff | MGC12916 | 84815 | Stiff | ERCC6L | 1833 | Stiff | SCUBE1 | 80274 | Stiff |
| ADD2 | 119 | Stiff | MGLL | 11343 | Stiff | EREG | 54821 | Stiff | SDC1 | 6382 | Stiff |
| ADGRG2 | 10149 | Stiff | MICALL1 | 85377 | Stiff | ESCO2 | 2069 | Stiff | SDF2L1 | 23753 | Stiff |
| ADGRG6 | 57211 | Stiff | MIIP | 60672 | Stiff | EXO1 | 157570 | Stiff | SDSL | 113675 | Stiff |
| ADRM1 | 11047 | Stiff | MIR1237 | 100302280 | Stiff | EXO5 | 9156 | Stiff | SEC11C | 90701 | Stiff |
| AEN | 64782 | Stiff | MIR1306 | 100302197 | Stiff | EXOG | 64789 | Stiff | SEMA3D | 223117 | Stiff |
| AFAP1L2 | 84632 | Stiff | MIR17HG | 407975 | Stiff | EXOSC3 | 9941 | Stiff | SEMA4D | 10507 | Stiff |
| AFP | 174 | Stiff | MIR22HG | 84981 | Stiff | EXOSC4 | 51010 | Stiff | SEMA7A | 8482 | Stiff |
| AIF1L | 83543 | Stiff | MIR3176 | 100423037 | Stiff | EXOSC6 | 54512 | Stiff | SENP3 | 26168 | Stiff |
| AJAP1 | 55966 | Stiff | MIR3658 | 100500832 | Stiff | EXTL3 | 118460 | Stiff | SERHL | 94009 | Stiff |
| ALCAM | 214 | Stiff | MIR589 | 693174 | Stiff | FAM101B | 2137 | Stiff | SERINC2 | 347735 | Stiff |
| ALDH1B1 | 219 | Stiff | MIR600HG | 81571 | Stiff | FAM118B | 359845 | Stiff | SERPINB3 | 6317 | Stiff |
| ALDH4A1 | 8659 | Stiff | MIR664B | 100847052 | Stiff | FAM169A | 79607 | Stiff | SERPINB4 | 6318 | Stiff |
| ALG1 | 56052 | Stiff | MIR6758 | 102465454 | Stiff | FAM171A1 | 26049 | Stiff | SERPINB7 | 8710 | Stiff |
| ALG1L9P | 285407 | Stiff | MIR6776 | 102465465 | Stiff | FAM189A1 | 221061 | Stiff | SFMBT1 | 51460 | Stiff |
| ALYREF | 10189 | Stiff | MIR6804 | 102465428 | Stiff | FAM208B | 23359 | Stiff | SFN | 2810 | Stiff |
| AMD1 | 262 | Stiff | MIS12 | 79003 | Stiff | FAM222A | 54906 | Stiff | SFXN2 | 118980 | Stiff |
| AMICA1 | 120425 | Stiff | MITF | 4286 | Stiff | FAM225A | 84915 | Stiff | SGK223 | 157285 | Stiff |
| AMIGO2 | 347902 | Stiff | MKL1 | 57591 | Stiff | FAM43A | 286333 | Stiff | SGK3 | 23678 | Stiff |
| AMPH | 273 | Stiff | MLP | 90523 | Stiff | FAM58A | 131383 | Stiff | SH2D2A | 9047 | Stiff |
| AMZ1 | 155185 | Stiff | MMP1 | 4312 | Stiff | FAM72C | 92002 | Stiff | SH2D5 | 400745 | Stiff |
| ANAPC7 | 51434 | Stiff | MMP3 | 4314 | Stiff | FAM81A | 554282 | Stiff | SH3RF2 | 153769 | Stiff |
| ANKRD39 | 51239 | Stiff | MON1A | 84315 | Stiff | FAM84A | 145773 | Stiff | SKA3 | 221150 | Stiff |
| ANKRD52 | 283373 | Stiff | MPP6 | 51678 | Stiff | FAM86C1 | 151354 | Stiff | SLC19A1 | 6573 | Stiff |
| ANP32D | 23519 | Stiff | MPV17L2 | 84769 | Stiff | FAM89A | 55199 | Stiff | SLC20A1 | 6574 | Stiff |
| ANXA3 | 306 | Stiff | MPZL3 | 196 | Stiff | FAM98A | 375061 | Stiff | SLC20A2 | 6575 | Stiff |
| AOC1 | 26 | Stiff | MRM1 | 79922 | Stiff | FANCA | 25940 | Stiff | SLC25A10 | 1468 | Stiff |
| AP1M2 | 10053 | Stiff | MROH6 | 642475 | Stiff | FASN | 2194 | Stiff | SLC25A13 | 10165 | Stiff |
| AP4E1 | 23431 | Stiff | MROH7-TTC4 | 100527960 | Stiff | FAXC | 84553 | Stiff | SLC25A18 | 83733 | Stiff |
| AP5B1 | 91056 | Stiff | MRPL20 | 55052 | Stiff | FBF1 | 85302 | Stiff | SLC25A19 | 60386 | Stiff |
| APBA1 | 320 | Stiff | MRPS12 | 6183 | Stiff | FBXL6 | 26233 | Stiff | SLC25A25 | 114789 | Stiff |
| APITD1 | 378708 | Stiff | MRTO4 | 51154 | Stiff | | | | SLC25A32 | 81034 | Stiff |

-continued

| GeneSymbol | gene_id | Status | GeneSymbol | gene_id | Status | GeneSymbol | gene_id | Status |
|---|---|---|---|---|---|---|---|---|
| APTD1-CORT | 100526739 | Stiff | MSLN | 10232 | Stiff | FDX1 | 2230 | Stiff | SLC25A33 | 84275 | Stiff |
| APOO | 79135 | Stiff | MSR1 | 4481 | Stiff | FDXACB1 | 91893 | Stiff | SLC25A44 | 9673 | Stiff |
| APOOP5 | 644649 | Stiff | MSRB1 | 51734 | Stiff | FEM1A | 55527 | Stiff | SLC26A2 | 1836 | Stiff |
| ARAP2 | 116984 | Stiff | MSTO1 | 55154 | Stiff | FGD6 | 55785 | Stiff | SLC27A4 | 10999 | Stiff |
| ARC | 23237 | Stiff | MSTO2P | 100129405 | Stiff | FGF1 | 2246 | Stiff | SLC29A3 | 55315 | Stiff |
| AREG | 374 | Stiff | MSX1 | 4487 | Stiff | FGF5 | 2250 | Stiff | SLC2A6 | 11182 | Stiff |
| ARHGEF4 | 50649 | Stiff | MSX2 | 4488 | Stiff | FHOD3 | 80206 | Stiff | SLC35B1 | 10237 | Stiff |
| ARL14 | 80117 | Stiff | MTFR2 | 113115 | Stiff | FICD | 11153 | Stiff | SLC35G1 | 159371 | Stiff |
| ARMC6 | 93436 | Stiff | MTOR | 2475 | Stiff | FIX1 | 24147 | Stiff | SLC36A1 | 206358 | Stiff |
| ARMC7 | 79637 | Stiff | MTOR-AS1 | 100873935 | Stiff | FLAD1 | 80308 | Stiff | SLC37A1 | 54020 | Stiff |
| ARMCX4 | 100131755 | Stiff | MUC13 | 56667 | Stiff | FLG | 2312 | Stiff | SLC38A3 | 10991 | Stiff |
| ARNTL2 | 56938 | Stiff | MUC5AC | 4586 | Stiff | FLI1 | 2313 | Stiff | SLC39A3 | 29985 | Stiff |
| ARNTL2-AS1 | 101928646 | Stiff | MUC6 | 4588 | Stiff | FOXA1 | 3169 | Stiff | SLC43A2 | 124935 | Stiff |
| ARPC5L | 81873 | Stiff | MVB12B | 89853 | Stiff | FOXC1 | 2296 | Stiff | SLC45A3 | 85414 | Stiff |
| ARRDC1-AS1 | 85026 | Stiff | MYBBP1A | 10514 | Stiff | FPR1 | 2357 | Stiff | SLC45A4 | 57210 | Stiff |
| ARSB | 411 | Stiff | MYEOV2 | 150678 | Stiff | FSIP2 | 401024 | Stiff | SLC4A11 | 83959 | Stiff |
| ASRGL1 | 80150 | Stiff | MYH10 | 4628 | Stiff | FTSJ3 | 117246 | Stiff | SLC4A8 | 9498 | Stiff |
| ATAD3A | 55210 | Stiff | MYH15 | 22989 | Stiff | FXN | 2395 | Stiff | SLC52A2 | 79581 | Stiff |
| ATAD3B | 83858 | Stiff | MYLK2 | 85366 | Stiff | FZD9 | 8326 | Stiff | SLC5A6 | 8884 | Stiff |
| ATF5 | 22809 | Stiff | MYO5B | 4645 | Stiff | GAB3 | 139716 | Stiff | SLC7A11 | 23657 | Stiff |
| ATF7IP2 | 80063 | Stiff | MYT1 | 4661 | Stiff | GALNT10 | 55568 | Stiff | SLC7A2 | 6542 | Stiff |
| ATG101 | 60673 | Stiff | MYZAP | 100820829 | Stiff | GALNT14 | 79623 | Stiff | SLC9A2 | 6549 | Stiff |
| ATP2A1-AS1 | 100289092 | Stiff | NAA15 | 80155 | Stiff | GALNT7 | 51809 | Stiff | SLCO1B3 | 28234 | Stiff |
| ATP6V0A2 | 23545 | Stiff | NAPRT | 93100 | Stiff | GALR2 | 8811 | Stiff | SLCO3A1 | 28232 | Stiff |
| ATP6V0D2 | 245972 | Stiff | NAT1 | 9 | Stiff | GAR1 | 54433 | Stiff | SLFN12L | 100506736 | Stiff |
| ATP6V0E2 | 155066 | Stiff | NBPF20 | 100288142 | Stiff | GATAD2A | 54815 | Stiff | SMAGP | 57228 | Stiff |
| ATP6V0E2-AS1 | 401431 | Stiff | NCEH1 | 57552 | Stiff | GCH1 | 2643 | Stiff | SMCO4 | 56935 | Stiff |
| ATP6V1B1-AS1 | 101927750 | Stiff | NDOR1 | 27158 | Stiff | GCLM | 2730 | Stiff | SNAP25 | 6616 | Stiff |
| ATR | 545 | Stiff | NDUFAF4 | 29078 | Stiff | GDA | 9615 | Stiff | SNHG9 | 735301 | Stiff |
| AUNIP | 79000 | Stiff | NDUFAF6 | 137682 | Stiff | GDAP1 | 54332 | Stiff | SNORA10 | 574042 | Stiff |
| B3GALNT1 | 8706 | Stiff | NETO2 | 81831 | Stiff | GDPD5 | 81544 | Stiff | SNORA17A | 677804 | Stiff |
| B3GALT1 | 8708 | Stiff | NFKBIB | 4793 | Stiff | GEMIN4 | 50628 | Stiff | SNORA22 | 677807 | Stiff |
| B3GLCT | 145173 | Stiff | NIP7 | 51388 | Stiff | GEMIN6 | 79833 | Stiff | SNORA3B | 677826 | Stiff |
| B3GNT2 | 10678 | Stiff | NIPA2 | 81614 | Stiff | GFM1 | 85476 | Stiff | SNORA48 | 652965 | Stiff |
| B4GALT6 | 9331 | Stiff | NKX3-1 | 4824 | Stiff | GFOD1 | 54438 | Stiff | SNORA51 | 677831 | Stiff |
| BAIAP2L2 | 80115 | Stiff | NLK | 51701 | Stiff | GFRA1 | 2674 | Stiff | SNORA52 | 619565 | Stiff |
| BAMBI | 25805 | Stiff | NLRP2 | 55655 | Stiff | GINS3 | 64785 | Stiff | SNORA55 | 677834 | Stiff |
| BATF3 | 55509 | Stiff | NLRP3 | 114548 | Stiff | GINS4 | 84296 | Stiff | SNORA6 | 574040 | Stiff |
| BCAR3 | 8412 | Stiff | NOC4L | 79050 | Stiff | GIPC1 | 10755 | Stiff | SNORA65 | 26783 | Stiff |
| BCCIP | 56647 | Stiff | NOL12 | 79159 | Stiff | GJA3 | 2700 | Stiff | SNORA71G | 677839 | Stiff |
| BCR | 613 | Stiff | NOL6 | 65083 | Stiff | GLB1L3 | 112937 | Stiff | SNORD101 | 594837 | Stiff |
| BDKRB1 | 623 | Stiff | NOLC1 | 9221 | Stiff | GLDC | 2731 | Stiff | SNORD110 | 692213 | Stiff |
| BEND3 | 57673 | Stiff | NOP16 | 51491 | Stiff | GLMN | 11146 | Stiff | SNORD119 | 100113378 | Stiff |
| BEND7 | 222389 | Stiff | NOP2 | 4839 | Stiff | GLRX2 | 51022 | Stiff | SNORD12C | 26765 | Stiff |
| BEST3 | 144453 | Stiff | NOP56 | 10528 | Stiff | GLYCTK | 132158 | Stiff | SNORD14C | 85389 | Stiff |
| BLM | 641 | Stiff | NOS1AP | 9722 | Stiff | GMPPB | 29925 | Stiff | SNORD14D | 85390 | Stiff |
| BMP8A | 353500 | Stiff | NOVA1 | 4857 | Stiff | GNAS-AS1 | 149775 | Stiff | SNORD17 | 692086 | Stiff |
| BMS1P21 | 100288974 | Stiff | NOX01 | 124056 | Stiff | GNG4 | 2786 | Stiff | SNORD2 | 619567 | Stiff |
| BNC1 | 646 | Stiff | NPB | 256933 | Stiff | GNLY | 10578 | Stiff | SNORD26 | 9302 | Stiff |
| BNC2 | 54796 | Stiff | NPLOC4 | 55666 | Stiff | GPAT3 | 84803 | Stiff | SNORD27 | 9301 | Stiff |
| BORA | 79866 | Stiff | INPR3 | 4883 | Stiff | GPATCH4 | 54865 | Stiff | SNORD28 | 9300 | Stiff |

-continued

| GeneSymbol | gene_id | Status | GeneSymbol | gene_id | Status | GeneSymbol | gene_id | Status |
|---|---|---|---|---|---|---|---|---|
| BORCS8 | 91 | Stiff | NR1I3 | 9970 | Stiff | GPR1 | 2825 | Stiff | SNORD29 | 9297 | Stiff |
| BRIX1 | 55299 | Stiff | NR2F2 | 7026 | Stiff | GPR3 | 2827 | Stiff | SNORD30 | 9299 | Stiff |
| BRMS1 | 25855 | Stiff | NRADDP | 100129354 | Stiff | GPR75 | 10936 | Stiff | SNORD45A | 26805 | Stiff |
| BYSL | 705 | Stiff | NRG1 | 3084 | Stiff | GPR87 | 53836 | Stiff | SNORD48 | 26801 | Stiff |
| C10orf128 | 170371 | Stiff | NRGN | 4900 | Stiff | GPRIN1 | 114787 | Stiff | SNORD57 | 26792 | Stiff |
| C10orf2 | 2 | Stiff | NRP2 | 8828 | Stiff | GRHL1 | 29841 | Stiff | SNORD83A | 116937 | Stiff |
| C11orf91 | 100131378 | Stiff | NRROS | 375387 | Stiff | GRWD1 | 83743 | Stiff | SNORD83B | 116938 | Stiff |
| C11orf96 | 387763 | Stiff | NSUN2 | 54888 | Stiff | GSDMC | 56169 | Stiff | SNORD86 | 692201 | Stiff |
| C1orf98 | 102288414 | Stiff | NTMT1 | 28989 | Stiff | GSG2 | 83903 | Stiff | SNPH | 9751 | Stiff |
| C12orf4 | 57102 | Stiff | NTN4 | 59277 | Stiff | GTF2H2 | 2966 | Stiff | SNRNP25 | 79622 | Stiff |
| C12orf43 | 64897 | Stiff | NUDT15 | 55270 | Stiff | GTF2H2B | 653238 | Stiff | SNRNP40 | 9410 | Stiff |
| C12orf49 | 79794 | Stiff | NUDT16 | 131870 | Stiff | GTF2H2C | 728340 | Stiff | SOGA3 | 387104 | Stiff |
| C14orf169 | 79697 | Stiff | NUFIP1 | 26747 | Stiff | GTF2H2C | 730394 | Stiff | SOX7 | 83595 | Stiff |
| C14orf80 | 283643 | Stiff | NUP93 | 9688 | Stiff | GTF3C6 | 112495 | Stiff | SOX9 | 6662 | Stiff |
| C16orf159 | 80178 | Stiff | NXT1 | 29107 | Stiff | GTPBP4 | 23560 | Stiff | SP6 | 80320 | Stiff |
| C17orf51 | 339263 | Stiff | ODC1 | 4953 | Stiff | GXYLT1 | 3464 | Stiff | SP7 | 121340 | Stiff |
| C17orf89 | 284184 | Stiff | OGFOD1 | 55239 | Stiff | GYG1 | 8908 | Stiff | SPAG1 | 6674 | Stiff |
| C19orf47 | 126526 | Stiff | OGFRP1 | 388906 | Stiff | HABP4 | 22927 | Stiff | SPATA5 | 166378 | Stiff |
| C19orf173 | 55150 | Stiff | OLAH | 5301 | Stiff | HAPLN1 | 1404 | Stiff | SPECC1 | 92521 | Stiff |
| C1orf106 | 55765 | Stiff | ONECUT2 | 9480 | Stiff | HARBI1 | 283254 | Stiff | SPNS2 | 124976 | Stiff |
| C1orf109 | 54955 | Stiff | OPA3 | 80207 | Stiff | HAS3 | 3038 | Stiff | SPP1 | 6696 | Stiff |
| Ctorf226 | 400793 | Stiff | OR2W3 | 343171 | Stiff | HAUS7 | 55559 | Stiff | SPRR2D | 6703 | Stiff |
| C20orf24 | 55969 | Stiff | ORAI1 | 84876 | Stiff | HBEGF | 1839 | Stiff | SPRTN | 83932 | Stiff |
| C2CD2L | 9854 | Stiff | ORC6 | 23594 | Stiff | HEATR3 | 55027 | Stiff | SPTB | 6710 | Stiff |
| C3AR1 | 719 | Stiff | OSBP2 | 23762 | Stiff | HGF | 3082 | Stiff | SPX | 80763 | Stiff |
| C3orf52 | 79669 | Stiff | OSBPL6 | 114880 | Stiff | HGH1 | 51236 | Stiff | SRP19 | 6728 | Stiff |
| C6orf158 | 52999 | Stiff | OSTM1 | 28962 | Stiff | HHAT | 55733 | Stiff | SRPK3 | 26576 | Stiff |
| C7orf26 | 79034 | Stiff | OTUD6B | 51633 | Stiff | HHIP | 64399 | Stiff | SSSCA1 | 10534 | Stiff |
| C7orf43 | 55262 | Stiff | P2RY2 | 5029 | Stiff | HHIP-AS1 | 283254 | Stiff | SSTR1 | 6751 | Stiff |
| C9orf78 | 51759 | Stiff | PAEP | 5047 | Stiff | HHIPL2 | 646576 | Stiff | ST6GALNAC5 | 81849 | Stiff |
| CA2 | 760 | Stiff | PAK1IP1 | 55003 | Stiff | HIRA | 7290 | Stiff | STEAP1 | 26872 | Stiff |
| CABLES1 | 91768 | Stiff | PALM2 | 114299 | Stiff | HIST1H2AE | 3012 | Stiff | STK10 | 6793 | Stiff |
| CAMK2N2 | 94032 | Stiff | PAQR9 | 344838 | Stiff | HIST1H2AG | 8969 | Stiff | STON2 | 85439 | Stiff |
| CAND2 | 23066 | Stiff | PCAT7 | 101928099 | Stiff | HIST1H2AH | 85235 | Stiff | STOX2 | 56977 | Stiff |
| CARD11 | 84433 | Stiff | PCDH9 | 5101 | Stiff | HIST1H2AM | 8336 | Stiff | STRBP | 55342 | Stiff |
| CARD8-AS1 | 100505812 | Stiff | PCDHGA1 | 56114 | Stiff | HIST1H2BC | 8347 | Stiff | STRIP2 | 57464 | Stiff |
| CARD9 | 64170 | Stiff | PCDHGA10 | 56106 | Stiff | HIST1H2BF | 8343 | Stiff | STS | 412 | Stiff |
| CASZ1 | 54897 | Stiff | PCDHGA11 | 56105 | Stiff | HIST1H2BG | 8339 | Stiff | STX11 | 8676 | Stiff |
| CBBE1 | 147372 | Stiff | PCDHGA12 | 26025 | Stiff | HIST1H2BI | 8346 | Stiff | STXBP5L | 9515 | Stiff |
| CCDC137 | 339230 | Stiff | PCDHGA2 | 56113 | Stiff | HIST1H2BJ | 8970 | Stiff | STYK1 | 55359 | Stiff |
| CCDC168 | 643677 | Stiff | PCDHGA3 | 56112 | Stiff | HIST1H2BM | 8342 | Stiff | SURF2 | 6835 | Stiff |
| CCDC86 | 79080 | Stiff | PCDHGA4 | 56111 | Stiff | HIST1H2BO | 8348 | Stiff | SUSD4 | 55061 | Stiff |
| CCDC96 | 257236 | Stiff | PCDHGA5 | 56110 | Stiff | HIST1H3B | 8358 | Stiff | SUV39H1 | 6839 | Stiff |
| CCL20 | 6364 | Stiff | PCDHGA7 | 56108 | Stiff | HIST1H3D | 8351 | Stiff | SVIP | 258010 | Stiff |
| CCNE1 | 898 | Stiff | PCDHGA8 | 9708 | Stiff | HIST1H3F | 8968 | Stiff | SWSAP1 | 126074 | Stiff |
| CCNE2 | 9134 | Stiff | PCDHGA9 | 56107 | Stiff | HIST1H3G | 8355 | Stiff | SYNPO2L | 79933 | Stiff |
| CCNF | 899 | Stiff | PCDHGB1 | 56104 | Stiff | HIST1H4A | 8359 | Stiff | SYT1 | 6857 | Stiff |
| CCNJ | 54619 | Stiff | PCDHGB2 | 56103 | Stiff | HIST1H4B | 8366 | Stiff | TACC2 | 10579 | Stiff |
| CCNO | 10309 | Stiff | PCDHGB3 | 56102 | Stiff | HIST1H4C | 8364 | Stiff | TACO1 | 51204 | Stiff |
| CCNYL1 | 151195 | Stiff | PCDHGB4 | 8641 | Stiff | HIST2H2AC | 8338 | Stiff | TAF13 | 6884 | Stiff |
| CD101 | 9398 | Stiff | PCDHGB5 | 56101 | Stiff | HIST2H2BF | 440689 | Stiff | TAF5 | 6877 | Stiff |

| GeneSymbol | gene_id | Status | GeneSymbol | gene_id | Status | GeneSymbol | gene_id | Status |
|---|---|---|---|---|---|---|---|---|
| CD274 | 29126 | Stiff | PCDHGB6 | 56100 | Stiff | HIVEP3 | 59269 | Stiff | TAF5L | 27097 | Stiff |
| CD300C | 10871 | Stiff | PCDHGB7 | 56099 | Stiff | HMGB3 | 3149 | Stiff | TBC1D4 | 9882 | Stiff |
| CD70 | 970 | Stiff | PCDHGC3 | 5098 | Stiff | HNRNPAB | 3182 | Stiff | TBX2 | 6909 | Stiff |
| CDC25A | 993 | Stiff | PCDHGC4 | 56098 | Stiff | HOXB3 | 3213 | Stiff | TCHH | 84260 | Stiff |
| CDC42EP2 | 10435 | Stiff | PCDHGC5 | 56097 | Stiff | HOXD8 | 3234 | Stiff | TCOF1 | 6949 | Stiff |
| CDC6 | 990 | Stiff | PONXL3 | 399909 | Stiff | HRK | 8739 | Stiff | TDG | 6996 | Stiff |
| CDC7 | 8317 | Stiff | PCSK7 | 9159 | Stiff | HS3ST1 | 9957 | Stiff | TEAD4 | 7004 | Stiff |
| CDCA7 | 83879 | Stiff | PCYT2 | 5833 | Stiff | HS3ST3A1 | 9955 | Stiff | TELO2 | 9894 | Stiff |
| CDH11 | 1009 | Stiff | PDCD2L | 84306 | Stiff | HSH2D | 84941 | Stiff | TENM3 | 55714 | Stiff |
| CDH15 | 1013 | Stiff | PDCD6IPP2 | 646278 | Stiff | HSPA14 | 51182 | Stiff | TEX2 | 55852 | Stiff |
| CELF5 | 60680 | Stiff | PDCL3 | 79031 | Stiff | HSPA1B | 3304 | Stiff | TEX30 | 93081 | Stiff |
| CENPM | 79019 | Stiff | PDE12 | 201626 | Stiff | HSPA6 | 3310 | Stiff | TFB2M | 64216 | Stiff |
| CENPN | 55839 | Stiff | PDE1C | 5137 | Stiff | HSPBAP1 | 79663 | Stiff | TFRC | 7037 | Stiff |
| CENPP | 401541 | Stiff | PDSS1 | 23590 | Stiff | HSPH1 | 10808 | Stiff | TGM2 | 7052 | Stiff |
| CENPV | 201161 | Stiff | PFAS | 5198 | Stiff | HTR7 | 3363 | Stiff | THAP7 | 80764 | Stiff |
| CEP78 | 84131 | Stiff | PFDN2 | 5202 | Stiff | HYAL2 | 8692 | Stiff | THBD | 7056 | Stiff |
| CES1P2 | 390732 | Stiff | PGAM5 | 192111 | Stiff | HYOU1 | 10525 | Stiff | TIAM1 | 7074 | Stiff |
| CFAP157 | 286207 | Stiff | PGP | 283871 | Stiff | IDH3A | 3419 | Stiff | TIGAR | 57103 | Stiff |
| CGNL1 | 84952 | Stiff | PHF19 | 26147 | Stiff | IFRD2 | 7866 | Stiff | TIMM10 | 26519 | Stiff |
| CHAC2 | 494143 | Stiff | PHF5A | 84844 | Stiff | IGF2BP3 | 10643 | Stiff | TIMM17A | 10440 | Stiff |
| CHAD | 1101 | Stiff | PHLDA2 | 7262 | Stiff | IGFN1 | 91156 | Stiff | TIMM22 | 29928 | Stiff |
| CHFR | 55743 | Stiff | PHLPP2 | 23035 | Stiff | IHH | 3549 | Stiff | TIMM23 | 100287932 | Stiff |
| CHL1 | 10752 | Stiff | PHOSPHO1 | 162466 | Stiff | IL12A | 3592 | Stiff | TIMM23B | 100652748 | Stiff |
| CHORDC1 | 26973 | Stiff | PI3 | 5266 | Stiff | IL1A | 3552 | Stiff | TIMM8A | 1678 | Stiff |
| CHRNA3 | 1136 | Stiff | PIGW | 284098 | Stiff | IL1B | 3553 | Stiff | TIPIN | 54962 | Stiff |
| CHRNA5 | 1138 | Stiff | PIK3R4 | 30849 | Stiff | IL6 | 3569 | Stiff | TJP1 | 7082 | Stiff |
| CHUK | 1147 | Stiff | PITX1 | 54984 | Stiff | ILDR2 | 387597 | Stiff | TMC7 | 79905 | Stiff |
| CLCN5 | 1184 | Stiff | PKNX1 | 5307 | Stiff | INHBA | 3624 | Stiff | TMEFF2 | 23671 | Stiff |
| CLDN1 | 9076 | Stiff | PKI55 | 150967 | Stiff | INSC | 387755 | Stiff | TMEM104 | 54868 | Stiff |
| CLDN10 | 9071 | Stiff | PKMYT1 | 9088 | Stiff | IPO13 | 9670 | Stiff | TMEM110-MUSTN1 | 100526772 | Stiff |
| CLDN11 | 5010 | Stiff | PLAT | 5327 | Stiff | IPOSP1 | 100132815 | Stiff | TMEM138 | 51524 | Stiff |
| CLN6 | 54982 | Stiff | PLCD4 | 84812 | Stiff | IPPK | 64768 | Stiff | ITMEM154 | 201799 | Stiff |
| CLSPN | 63967 | Stiff | PLCE1 | 51196 | Stiff | ISG20L2 | 81875 | Stiff | TMEM177 | 80775 | Stiff |
| CLTB | 1212 | Stiff | PLCE1-AS1 | 100128054 | Stiff | ISM1 | 140862 | Stiff | TMEM199 | 147007 | Stiff |
| CLUH | 23277 | Stiff | PLD5 | 200150 | Stiff | ISOC1 | 51015 | Stiff | TMEM201 | 199953 | Stiff |
| CMTM7 | 112616 | Stiff | PLEK2 | 26499 | Stiff | ISOC2 | 79763 | Stiff | TMEM206 | 55248 | Stiff |
| CNIH3 | 149111 | Stiff | PLK3 | 1263 | Stiff | ITGA6 | 3655 | Stiff | TMEM236 | 653567 | Stiff |
| CNN3 | 1266 | Stiff | PLXNA2 | 5362 | Stiff | ITGAE | 3682 | Stiff | TMEM249 | 340393 | Stiff |
| CNTF | 1270 | Stiff | PLXNA4 | 91584 | Stiff | ITGB1BP2 | 26548 | Stiff | TMEM251 | 26175 | Stiff |
| CNTNAP2 | 26047 | Stiff | PNO1 | 56902 | Stiff | ITGBL1 | 9358 | Stiff | TMEM33 | 55161 | Stiff |
| COA7 | 65260 | Stiff | PNP | 4860 | Stiff | JADE2 | 23338 | Stiff | TMEM5 | 10329 | Stiff |
| COBLL1 | 22837 | Stiff | PNPT1 | 87178 | Stiff | JAM3 | 83700 | Stiff | TMPO | 7112 | Stiff |
| COL10A1 | 1300 | Stiff | PODXL | 5420 | Stiff | JMJD4 | 65094 | Stiff | TNF | 7124 | Stiff |
| COL13A1 | 1305 | Stiff | PODXL2 | 50512 | Stiff | KANK1 | 23189 | Stiff | TNFRSF12A | 51330 | Stiff |
| COL17A1 | 1308 | Stiff | POLA2 | 23649 | Stiff | KBTBD8 | 84541 | Stiff | TNFRSF21 | 27242 | Stiff |
| COL20A1 | 57642 | Stiff | POLE3 | 54107 | Stiff | KCNH2 | 3757 | Stiff | TNFRSF8 | 943 | Stiff |
| CREB5 | 9586 | Stiff | POLR1A | 25885 | Stiff | KCNQ3 | 3786 | Stiff | TNS4 | 84951 | Stiff |
| CREG2 | 200407 | Stiff | POLR3B | 55703 | Stiff | KDM8 | 79831 | Stiff | TOE1 | 114034 | Stiff |
| CREM | 1390 | Stiff | POUR3E | 55718 | Stiff | KIAA0513 | 9764 | Stiff | TOMM40 | 10452 | Stiff |
| CRSP8P | 441089 | Stiff | POLR3G | 10622 | Stiff | KIAA0754 | 643314 | Stiff | TOMM40L | 84134 | Stiff |
| CRY1 | 1407 | Stiff | POLR3K | 51728 | Stiff | KIAA1524 | 57650 | Stiff | TONSL | 4796 | Stiff |

| GeneSymbol | gene_id | Status | GeneSymbol | gene_id | Status | GeneSymbol | gene_id | Status |
|---|---|---|---|---|---|---|---|---|
| CRYBA2 | 1412 | Stiff | POMGNT2 | 84892 | Stiff | KIAA1549L | 25758 | Stiff | TONSL-AS1 | 100287098 | Stiff |
| CSF2 | 1437 | Stiff | POP1 | 10940 | Stiff | KIF21B | 23046 | Stiff | TOR1A | 1861 | Stiff |
| CSF2RB | 1439 | Stiff | POP5 | 51367 | Stiff | KLC2 | 64837 | Stiff | TOR3A | 64222 | Stiff |
| CSF3 | 1440 | Stiff | POP7 | 10248 | Stiff | KLF5 | 688 | Stiff | TP53RK | 112858 | Stiff |
| CSGALNACT1 | 55790 | Stiff | POU3F2 | 5454 | Stiff | KLHL18 | 23276 | Stiff | TRAPPC10 | 7109 | Stiff |
| CST7 | 8530 | Stiff | PPARGC1B | 133522 | Stiff | KLHL25 | 64410 | Stiff | TRAPPC13 | 80006 | Stiff |
| GSTF2 | 1478 | Stiff | PPIC | 5480 | Stiff | KLHL9 | 55958 | Stiff | TREX2 | 11219 | Stiff |
| CTNND2 | 1501 | Stiff | PPIF | 10105 | Stiff | KLK4 | 9622 | Stiff | TRHDE-AS1 | 283392 | Stiff |
| CTPS1 | 1503 | Stiff | PPIL1 | 51645 | Stiff | KNOP1 | 400506 | Stiff | TRMO | 51531 | Stiff |
| CTSL | 1514 | Stiff | PPRC1 | 23082 | Stiff | KPNA2 | 3838 | Stiff | TRMT12 | 55039 | Stiff |
| CTSV | 1515 | Stiff | PRADC1 | 84279 | Stiff | KPNA3 | 3839 | Stiff | TRMT6 | 51605 | Stiff |
| CTSW | 1521 | Stiff | PROM16 | 63976 | Stiff | KRT1 | 3848 | Stiff | TRMT61A | 115708 | Stiff |
| CTU2 | 348180 | Stiff | PREB | 10113 | Stiff | KRT15 | 3866 | Stiff | TRPM2 | 7226 | Stiff |
| CXCL1 | 2919 | Stiff | PRF1 | 5551 | Stiff | KRT3 | 3850 | Stiff | TRPV4 | 59341 | Stiff |
| CXCL2 | 2920 | Stiff | PRKCQ-AS1 | 439949 | Stiff | KRT34 | 3885 | Stiff | TSC22D2 | 9819 | Stiff |
| CXCL3 | 2921 | Stiff | PRLR | 5618 | Stiff | KRT81 | 3887 | Stiff | TSEN54 | 283989 | Stiff |
| CXCL8 | 3576 | Stiff | PRMT6 | 55170 | Stiff | KSR1 | 8844 | Stiff | TSHZ3 | 57616 | Stiff |
| CYB5R2 | 51700 | Stiff | PROSER2 | 254427 | Stiff | L3MBTL2 | 83746 | Stiff | TSPAN17 | 26262 | Stiff |
| CYCS | 54205 | Stiff | PRR22 | 163154 | Stiff | LANCL2 | 55915 | Stiff | TSSC4 | 10078 | Stiff |
| DAB2 | 1601 | Stiff | PRR5 | 55615 | Stiff | LARP4 | 113251 | Stiff | TTC4 | 7268 | Stiff |
| DAW1 | 164781 | Stiff | PRRX1 | 5396 | Stiff | LCMT2 | 9836 | Stiff | TTF2 | 8458 | Stiff |
| DBF4 | 10926 | Stiff | PSEN2 | 5664 | Stiff | LCTL | 197021 | Stiff | TTLL11 | 158135 | Stiff |
| DBF4B | 80174 | Stiff | PSMC4 | 5704 | Stiff | LDLRAP1 | 26119 | Stiff | TTN | 7273 | Stiff |
| DCBLD2 | 131566 | Stiff | PSMD1 | 5707 | Stiff | LETM1 | 3954 | Stiff | TUBB1 | 81027 | Stiff |
| DCTPP1 | 79077 | Stiff | PSMD11 | 5717 | Stiff | LETM2 | 137994 | Stiff | TUBGCP5 | 114791 | Stiff |
| DDIAS | 220042 | Stiff | PSME3 | 10197 | Stiff | LIF | 3976 | Stiff | TXNDC9 | 10190 | Stiff |
| DDX10 | 1662 | Stiff | PSME4 | 23198 | Stiff | LIG3 | 3980 | Stiff | UBASH3B | 84959 | Stiff |
| DDX19A | 55308 | Stiff | PSPC1 | 55269 | Stiff | LINC00311 | 197196 | Stiff | UBE2F-SCLY | 100533179 | Stiff |
| DDX21 | 9188 | Stiff | PTGDR | 11251 | Stiff | LINC00346 | 283487 | Stiff | UBIAD1 | 29914 | Stiff |
| DDX28 | 55794 | Stiff | PTRH1 | 138428 | Stiff | LINC00707 | 100507127 | Stiff | UCA1 | 652995 | Stiff |
| DDX46 | 9879 | Stiff | PTS | 5805 | Stiff | LINC00857 | 439990 | Stiff | UCHL3 | 7347 | Stiff |
| DDX51 | 317781 | Stiff | PTX3 | 5806 | Stiff | LINC00880 | 339894 | Stiff | UFSP1 | 402682 | Stiff |
| DDX52 | 11056 | Stiff | PUM3 | 9933 | Stiff | LINC00941 | 100287314 | Stiff | UHRF1 | 29128 | Stiff |
| DENND5B | 160518 | Stiff | PUS1 | 80324 | Stiff | LINC01117 | 102724224 | Stiff | URB2 | 9816 | Stiff |
| DEPDC1-AS1 | 101927220 | Stiff | PUSL1 | 126789 | Stiff | LINC01224 | 104472717 | Stiff | UTP15 | 84135 | Stiff |
| DGCR11 | 25786 | Stiff | PVR | 5817 | Stiff | LINC01287 | 103724390 | Stiff | UTP20 | 27340 | Stiff |
| DGCR5 | 26220 | Stiff | PVRL1 | 5818 | Stiff | LINC01322 | 103695433 | Stiff | UTP3 | 57050 | Stiff |
| DGKG | 1608 | Stiff | PWP2 | 5822 | Stiff | LINC01468 | 101928687 | Stiff | VEPH1 | 79674 | Stiff |
| DHCR24 | 1718 | Stiff | PYCRL | 65263 | Stiff | LINC01605 | 100507420 | Stiff | VGF | 7425 | Stiff |
| DHRS11 | 79154 | Stiff | PZP | 5858 | Stiff | LIPG | 9388 | Stiff | VPS53 | 55275 | Stiff |
| DHRS2 | 10202 | Stiff | RAB27B | 5874 | Stiff | LIPH | 200879 | Stiff | VPS9D1-AS1 | 100128881 | Stiff |
| DHRS9 | 10170 | Stiff | RAB3B | 5865 | Stiff | LMO7-AS1 | 101927155 | Stiff | VWA2 | 340706 | Stiff |
| DHX34 | 9704 | Stiff | RABEP1 | 9135 | Stiff | LOC100128361 | 100128361 | Stiff | WDR4 | 10785 | Stiff |
| DHX37 | 57647 | Stiff | RABIF | 5877 | Stiff | LOC100129046 | 100129046 | Stiff | WDR46 | 9277 | Stiff |
| DIO2 | 1734 | Stiff | RANGAP1 | 5905 | Stiff | LOC100013038 | 100130238 | Stiff | WDR62 | 284403 | Stiff |
| DIO2-AS1 | 100628307 | Stiff | RAPGEFL1 | 51195 | Stiff | LOC100287042 | 100287042 | Stiff | WDR77 | 79084 | Stiff |
| DKC1 | 1736 | Stiff | RASGEF1B | 153020 | Stiff | LOC100049489 | 1004994 | Stiff | NFS1 | 7466 | Stiff |
| DLEU2 | 8847 | Stiff | RASGRP1 | 10125 | Stiff | LOC100050302 | 100506 | Stiff | WNT5B | 81029 | Stiff |
| DLEU2L | 79469 | Stiff | RBM24 | 221662 | Stiff | LOC100507634 | 100507 | Stiff | WNT9A | 7483 | Stiff |
| DLX3 | 1747 | Stiff | RBM28 | 55131 | Stiff | LOC101926940 | 101926940 | Stiff | WRAP53 | 55135 | Stiff |
| DLX5 | 1749 | Stiff | RBP4 | 5950 | Stiff | LOC101927267 | 101927267 | Stiff | WTAPP1 | 100288077 | Stiff |

| GeneSymbol | gene_id | Status | GeneSymbol | gene_id | Status | GeneSymbol | gene_id | Status |
|---|---|---|---|---|---|---|---|---|
| DMRTA2 | 63950 | Stiff | RBPMS2 | 348093 | Stiff | LOC101927746 | 101927746 | Stiff | XIRP2 | 129446 | Stiff |
| DNAJB11 | 51726 | Stiff | RCL1 | 10171 | Stiff | LOC101928163 | 101928163 | Stiff | XPO4 | 64328 | Stiff |
| DNLZ | 728489 | Stiff | RDH10 | 157506 | Stiff | LOC102723729 | 102723729 | Stiff | XRCC2 | 7516 | Stiff |
| DOCK4 | 9732 | Stiff | RECQL4 | 9401 | Stiff | LOC102724434 | 102724434 | Stiff | YRDC | 79693 | Stiff |
| DOCK9 | 23348 | Stiff | RELN | 5649 | Stiff | LOC105370333 | 105370333 | Stiff | ZBTB2 | 57621 | Stiff |
| DOHH | 83475 | Stiff | RFK | 55312 | Stiff | LOC339166 | 339166 | Stiff | ZBTB7C | 201501 | Stiff |
| DOLK | 22845 | Stiff | RFX8 | 731220 | Stiff | LOC341056 | 341056 | Stiff | ZBTB9 | 221504 | Stiff |
| DOLPP1 | 57171 | Stiff | RIMS2 | 9699 | Stiff | LOC541472 | 541472 | Stiff | ZDHHC14 | 79683 | Stiff |
| DPF3 | 8110 | Stiff | RIOK1 | 83732 | Stiff | LOC646762 | 646762 | Stiff | ZFAND4 | 93550 | Stiff |
| DPH2 | 1802 | Stiff | RNASEH1 | 246243 | Stiff | LRP8 | 7804 | Stiff | ZFP69B | 65243 | Stiff |
| DPH3 | 285381 | Stiff | RNASEH1-AS1 | 100506054 | Stiff | LRR1 | 122769 | Stiff | ZIC5 | 85416 | Stiff |
| DSP | 1832 | Stiff | RNF219 | 79596 | Stiff | LRRC59 | 55379 | Stiff | ZIK1 | 284307 | Stiff |
| DUSIL | 64118 | Stiff | RNF219-AS1 | 100874222 | Stiff | LRWD1 | 222229 | Stiff | ZMPSTE24 | 10269 | Stiff |
| DUS3L | 56931 | Stiff | RNMTL1 | 55178 | Stiff | LSG1 | 55341 | Stiff | ZMYND19 | 116225 | Stiff |
| DUSP5 | 1847 | Stiff | ROR1 | 4919 | Stiff | LSM10 | 84967 | Stiff | ZNF30 | 90075 | Stiff |
| DUSP8 | 1850 | Stiff | RPGR | 6103 | Stiff | LSMEM2 | 132228 | Stiff | ZNF300 | 91975 | Stiff |
| DUSP9 | 1852 | Stiff | RPP40 | 10799 | Stiff | LTV1 | 84946 | Stiff | ZNF35 | 7584 | Stiff |
| DYSF | 8291 | Stiff | RPS16P5 | 647190 | Stiff | LUM | 4060 | Stiff | ZNF365 | 22891 | Stiff |
| E2F6 | 1876 | Stiff | RPS26 | 6231 | Stiff | LYAR | 55646 | Stiff | ZNF43 | 7594 | Stiff |
| E2F7 | 144455 | Stiff | RPS6KA4 | 8986 | Stiff | LZTS1 | 11178 | Stiff | ZNF469 | 84627 | Stiff |
| EBNA1BP2 | 10969 | Stiff | RPUSD1 | 113000 | Stiff | MAGEA3 | 4102 | Stiff | ZNF488 | 118738 | Stiff |
| ECE2 | 110599564 | Stiff | RPUSD2 | 27079 | Stiff | MAGEA6 | 4105 | Stiff | ZNF583 | 147949 | Stiff |
| ECE2 | 110599583 | Stiff | RRP1 | 8568 | Stiff | MAGI2-AS3 | 100505881 | Stiff | ZNF593 | 51042 | Stiff |
| EDEM3 | 80267 | Stiff | RRP12 | 232 | Stiff | MAGOHB | 55110 | Stiff | ZNF681 | 148213 | Stiff |
| EEF1E1 | 9521 | Stiff | RRP15 | 51018 | Stiff | MAK16 | 84549 | Stiff | ZNF689 | 115509 | Stiff |
| EEF2KMT | 196483 | Stiff | RRP1B | 23076 | Stiff | MAP2K4 | 6416 | Stiff | ZNF736 | 728927 | Stiff |
| EFR3B | 22979 | Stiff | RRP36 | 88745 | Stiff | MAP3K9 | 4293 | Stiff | ZNF778 | 197320 | Stiff |
| EID2 | 163126 | Stiff | RRP7A | 27341 | Stiff | MAP6D1 | 79929 | Stiff | ZNF786 | 136051 | Stiff |
| EIF4E | 1977 | Stiff | RRP7BP | 91695 | Stiff | MARCH3 | 115123 | Stiff | ZNF85 | 7639 | Stiff |
| EIF5A2 | 56648 | Stiff | RRP9 | 9136 | Stiff | MARCH4 | 57574 | Stiff | ZNHIT2 | 741 | Stiff |
| ELAC2 | 60528 | Stiff | RRS1 | 23212 | Stiff | MARS2 | 92935 | Stiff | ZWILCH | 55055 | Stiff |
| ELAVL2 | 1993 | Stiff | RSPH4A | 345895 | Stiff | MB | 4151 | Stiff | LOC101928414 | 101928414 | Soft |
| A1BG | 1 | Soft | LOC101928453 | 101928453 | Soft | EPHA5 | 2044 | Soft | RHPN1 | 114822 | Soft |
| AATBC | 284137 | Soft | LOC101928489 | 101928489 | Soft | EPHA5-AS1 | 100144602 | Soft | RIBC1 | 158787 | Soft |
| AATK | 96 | Soft | LOC101928673 | 101928673 | Soft | EPHA7 | 2045 | Soft | RIMS3 | 9783 | Soft |
| ABAT | 18 | Soft | LOC101928710 | 101928710 | Soft | EPHX2 | 2053 | Soft | RIMS4 | 140730 | Soft |
| ABCA2 | 20 | Soft | LOC101928718 | 101928718 | Soft | EPOR | 2057 | Soft | RIOK3 | 8780 | Soft |
| ABCA3 | 21 | Soft | LOC101928767 | 101928767 | Soft | EPPK1 | 83481 | Soft | RIPK4 | 54101 | Soft |
| ABCA4 | 24 | Soft | LOC101928978 | 101928978 | Soft | EPS8L1 | 54869 | Soft | RLN3 | 117579 | Soft |
| ABCA6 | 23460 | Soft | LOC101929140 | 101929140 | Soft | EPS8L2 | 64787 | Soft | RMDN2 | 151393 | Soft |
| ABCA8 | 10351 | Soft | LOC101929371 | 101929371 | Soft | EPSTI1 | 94240 | Soft | RNASE4 | 6038 | Soft |
| ABCA9 | 10350 | Soft | LOC101929378 | 101929378 | Soft | ERICH2 | 285141 | Soft | RNASET2 | 8635 | Soft |
| ABCB1 | 5243 | Soft | LOC101929532 | 101929532 | Soft | ERMN | 57471 | Soft | RNF122 | 79845 | Soft |
| ABCC3 | 8714 | Soft | LOC101929709 | 101929709 | Soft | ERV3-1 | 2086 | Soft | RNF128 | 79589 | Soft |
| ABHD1 | 84696 | Soft | LOC101929710 | 101929710 | Soft | ESPNL | 339768 | Soft | RNF150 | 57484 | Soft |
| ABHD4 | 63874 | Soft | LOC101929767 | 101929767 | Soft | ETV7 | 51513 | Soft | RNF165 | 494470 | Soft |
| ABHD8 | 79575 | Soft | LOC102477328 | 102477328 | Soft | EVA1B | 55194 | Soft | RNF180 | 285671 | Soft |
| ABLIM2 | 84448 | Soft | LOC102503427 | 102503427 | Soft | EVA1C | 59271 | Soft | RNF212B | 100507650 | Soft |
| ABTB1 | 80325 | Soft | LOC102723809 | 102723809 | Soft | EXD3 | 54932 | Soft | RNF215 | 200312 | Soft |
| ACAD11 | 84129 | Soft | LOC102724050 | 102724050 | Soft | EXOC3L1 | 283849 | Soft | RNF217 | 154214 | Soft |
| ACADL | 33 | Soft | LOC102724190 | 102724190 | Soft | EYA1 | 2138 | Soft | RNF24 | 11237 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| ACADS | 35 | Soft | LOC102724467 | 102724467 | Soft | EYA2 | 2139 | Soft | RNF32 | 140545 | Soft |
| ACAP1 | 9744 | Soft | LOC102724814 | 102724814 | Soft | EYS | 346007 | Soft | RNF39 | 80352 | Soft |
| ACBD4 | 79777 | Soft | LOC102724927 | 102724927 | Soft | F10 | 2159 | Soft | RNF44 | 22838 | Soft |
| ACCS | 84680 | Soft | LOC103021296 | 103021296 | Soft | F11R | 50848 | Soft | RNPC3 | 55599 | Soft |
| ACKR1 | 2532 | Soft | LOC103091866 | 103091866 | Soft | F2RL2 | 2151 | Soft | ROPN1L | 83853 | Soft |
| ACKR3 | 57007 | Soft | LOC105372795 | 105372795 | Soft | F8 | 2157 | Soft | RORA | 6095 | Soft |
| ACOT4 | 122970 | Soft | LOC105447645 | 105447645 | Soft | FAAH | 2166 | Soft | RORC | 6097 | Soft |
| ACP5 | 54 | Soft | LOC105747689 | 105747689 | Soft | FAM102B | 284611 | Soft | ROS1 | 6098 | Soft |
| ACP6 | 51205 | Soft | LOC113230 | 113230 | Soft- | FAM114A1 | 92689 | Soft | RPH3AL | 9501 | Soft |
| ACPP | 55 | Soft | LOC115110 | 115110 | Soft | FAM122C | 159091 | Soft | RPL32P3 | 132241 | Soft |
| ACRC | 93953 | Soft | LOC143666 | 143666 | Soft | FAM131B | 9715 | Soft | RPL34-AS1 | 285456 | Soft |
| ACSF2 | 80221 | Soft | LOC145783 | 145783 | Soft | FAM131C | 348487 | Soft | RPLP0P2 | 113157 | Soft |
| ACSM3 | 6296 | Soft | LOC148696 | 148696 | Soft | FAM134B | 54463 | Soft | RPS10P7 | 376693 | Soft |
| ACSM4 | 341392 | Soft | LOC154761 | 154761 | Soft | FAM13A | 10144 | Soft | RPS15AP10 | 728963 | Soft |
| ACSM5 | 54988 | Soft | LOC155060 | 155060 | Soft | FAM13A-AS1 | 285512 | Soft | RPS29 | 6235 | Soft |
| ACTA2 | 59 | Soft | LOC171391 | 171391 | Soft | FAM149B1 | 317662 | Soft | RRAD | 6236 | Soft |
| ACTA2-AS1 | 100132116 | Soft | LOC202181 | 202181 | Soft | FAM160A1 | 729830 | Soft | RRAGB | 10325 | Soft |
| ACTBL2 | 345651 | Soft | LOC254896 | 254896 | Soft | FAM161B | 145483 | Soft | RRAGD | 58528 | Soft |
| ACVR2B-AS1 | 100128640 | Soft | LOC283038 | 283038 | Soft | FAM162A | 26355 | Soft | RRNAD1 | 51093 | Soft |
| ACYP2 | 98 | Soft | LOC283335 | 283335 | Soft | FAM167A | 83648 | Soft | RSBN1 | 54665 | Soft |
| ADAM8 | 101 | Soft | LOC283575 | 283575 | Soft | FAM167B | 84734 | Soft | RSPH3 | 83861 | Soft |
| ADAMTS1 | 9510 | Soft | LOC284080 | 284080 | Soft | FAM168A | 23201 | Soft | RSRP1 | 57035 | Soft |
| ADAMTS10 | 81794 | Soft | LOC284454 | 284454 | Soft | FAM171A2 | 284069 | Soft | RTN4RL2 | 349667 | Soft |
| ADAMTS2 | 9509 | Soft | LOC284930 | 284930 | Soft | FAM179A | 165186 | Soft | RTP4 | 64108 | Soft |
| ADAMTS5 | 11096 | Soft | LOC285819 | 285819 | Soft | FAM183A | 440585 | Soft | RUNDC38 | 154661 | Soft |
| ADAMTS7 | 11173 | Soft | LOC285847 | 285847 | Soft | FAM184B | 27146 | Soft | RUNX1T1 | 862 | Soft |
| ADAMTS7P1 | 390660 | Soft | LOC374443 | 374443 | Soft | FAM198A | 29085 | Soft | RWDD2A | 112611 | Soft |
| ADAMTS9-AS2 | 100507098 | Soft | LOC388813 | 388813 | Soft | FAM20G | 56975 | Soft | RXFP1 | 59350 | Soft |
| ADAMTSL2 | 9719 | Soft | LOC400706 | 400706 | Soft | FAM212B | 55924 | Soft | RYR1 | 6261 | Soft |
| ADAMTSL4 | 54507 | Soft | LOC401320 | 401320 | Soft | FAM212B-AS1 | 100506343 | Soft | RYR2 | 6262 | Soft |
| ADAP1 | 11033 | Soft | LOC440028 | 440028 | Soft | FAM213A | 84293 | Soft | S100A3 | 6274 | Soft |
| ADCYAP1R1 | 117 | Soft | LOC440173 | 440173 | Soft | FAM214A | 56204 | Soft | S1PR2 | 9294 | Soft |
| ADD3 | 120 | Soft | LOC441081 | 441081 | Soft | FAM214B | 80256 | Soft | S1PR4 | 8698 | Soft |
| ADGRA2 | 25960 | Soft | LOC554206 | 554206 | Soft | FAM227A | 646851 | Soft | S1PR5 | 53637 | Soft |
| ADGRB3 | 577 | Soft | LOC554223 | 554223 | Soft | FAM227B | 195951 | Soft | SAA2-SAA4 | 100528017 | Soft |
| ADGRG1 | 9289 | Soft | LOC642852 | 642852 | Soft | FAM228B | 375190 | Soft | SAA4 | 6291 | Soft |
| ADGRL1 | 22859 | Soft | LOC644285 | 644285 | Soft | FAM229A | 100128071 | Soft | SALL2 | 6297 | Soft |
| ADGRL2 | 23266 | Soft | LOC644919 | 644919 | Soft | FAM26E | 254228 | Soft | SALL4 | 57167 | Soft |
| ADGRL3 | 23284 | Soft | LOC646471 | 646471 | Soft | FAM46A | 55603 | Soft | SAMD14 | 201191 | Soft |
| ADH6 | 130 | Soft | LOC648987 | 648987 | Soft | FAM46C | 115572 | Soft | SAMD9L | 219285 | Soft |
| ADM | 133 | Soft | LOC653160 | 653160 | Soft | FAM47E | 54855 | Soft | SARDH | 1757 | Soft |
| ADM2 | 79924 | Soft | LOC654841 | 654841 | Soft | FAM47E-STBD1 | 100129583 | Soft | SASH1 | 23328 | Soft |
| ADORA2A-AS1 | 646023 | Soft | LOC728392 | 728392 | Soft | FAM50B | 100631383 | Soft | SATB1 | 6304 | Soft |
| ADPRHL1 | 113622 | Soft | LOC728613 | 728613 | Soft | FAM63A | 26240 | Soft | SBF2-AS1 | 283104 | Soft |
| ADRA1B | 147 | Soft | LOC728730 | 728730 | Soft | FAM65B | 55793 | Soft | SCARA5 | 286133 | Soft |
| ADRB2 | 154 | Soft | LOC728743 | 728743 | Soft | FAM71C | 9750 | Soft | SCARF1 | 8578 | Soft |
| ADSSL1 | 122622 | Soft | LOC729603 | 729603 | Soft | FAM83H-AS1 | 196472 | Soft | SCARF2 | 91179 | Soft |
| AFF1 | 4299 | Soft | LOG730668 | 730668 | Soft | FAM86B3P | 100128338 | Soft | SCARNA8 | 677776 | Soft |
| AFF2 | 2334 | Soft | LOC90246 | 90246 | Soft | FAM8A1 | 286042 | Soft | SCARNA9 | 619383 | Soft |
| AGBL2 | 79841 | Soft | LOH12CR2 | 503693 | Soft | FANK1 | 51439 | Soft | SCART1 | 619207 | Soft |
| AGER | 177 | Soft | LOX | 4015 | Soft |  | 92565 | Soft | SCD5 | 79966 | Soft |

-continued

| GeneSymbol | gene_id | Status | GeneSymbol | gene_id | Status | GeneSymbol | gene_id | Status |
|---|---|---|---|---|---|---|---|---|
| AGPAT4-IT1 | 79992 | Soft | LOXL1 | 4016 | Soft | FAP | 2191 | Soft | SCN2A | 6326 | Soft |
| AGT | 183 | Soft | LOXL1-AS1 | 100287616 | Soft | FAS-AS1 | 100302740 | Soft | SCNN1B | 6338 | Soft |
| AHNAK2 | 113146 | Soft | LOXL2 | 4017 | Soft | FAT2 | 2196 | Soft | SCNN1D | 633 | Soft |
| AHRR | 57491 | Soft | LPAR1 | 1902 | Soft | FAXDC2 | 10826 | Soft | SCNN1G | 6340 | Soft |
| AHSA2 | 130872 | Soft | LPAR2 | 9170 | Soft | FBLIM1 | 54751 | Soft | SCX | 642658 | Soft |
| AIFM3 | 150209 | Soft | LPAR6 | 10161 | Soft | FBLN1 | 2192 | Soft | SDCBP2 | 27111 | Soft |
| AIM2 | 9447 | Soft | LPIN3 | 64900 | Soft | FBLN2 | 2199 | Soft | SDHAP3 | 728609 | Soft |
| AK4 | 205 | Soft | LPP | 4026 | Soft | FBXL16 | 146330 | Soft | SEC14L5 | 9717 | Soft |
| AK7 | 122481 | Soft | LRCH2 | 57631 | Soft | FBXL8 | 55336 | Soft | SEC16B | 89866 | Soft |
| AK8 | 158067 | Soft | LRG1 | 116844 | Soft | FBXO15 | 201456 | Soft | SEC1P | 653677 | Soft |
| AK9 | 221264 | Soft | LRGUK | 136332 | Soft | FBXO24 | 26261 | Soft | SEC31B | 25956 | Soft |
| AKAP3 | 10566 | Soft | LRP1 | 4035 | Soft | FBXO32 | 114907 | Soft | SELENBP1 | 8991 | Soft |
| AKR1B15 | 441282 | Soft | ILRP1-AS | 105751187 | Soft | FBXO41 | 150726 | Soft | SEMA3B | 7869 | Soft |
| AKR7A3 | 22977 | Soft | LRP1B | 53353 | Soft | FBXO42 | 54455 | Soft | SEMA4A | 64218 | Soft |
| AKR7L | 246181 | Soft | LRP4 | 4038 | Soft | FBXO44 | 93611 | Soft | SEMA4B | 10509 | Soft |
| AKT3 | 10000 | Soft | LRP4-AS1 | 100507401 | Soft | FBXO6 | 26270 | Soft | SEMA4G | 57715 | Soft |
| ALDH1L1 | 10840 | Soft | LRRC27 | 80313 | Soft | FCGBP | 8857 | Soft | SEMA6B | 10501 | Soft |
| ALDH1L2 | 160428 | Soft | LRRC29 | 231 | Soft | FCGR2A | 2212 | Soft | SENP7 | 57337 | Soft |
| ALDH2 | 217 | Soft | LRRC37A3 | 374819 | Soft | FCGRT | 2217 | Soft | SEPP1 | 6414 | Soft |
| ALDH3A1 | 218 | Soft | LRRC37A6P | 387646 | Soft | FCHO1 | 23149 | Soft | SEPT1 | 1731 | Soft |
| ALDH3B1 | 221 | Soft | LRRC37A8P | 100533789 | Soft | FER1L4 | 80307 | Soft | SEPT5 | 5413 | Soft |
| ALDH6A1 | 4329 | Soft | LRRC37B | 114659 | Soft | FEZ1 | 9638 | Soft | SEPT5-GP1BB | 100526833 | Soft |
| ALDH8A1 | 64577 | Soft | LRRC56 | 115399 | Soft | FGF11 | 2256 | Soft | SEPT7-AS1 | 101928545 | Soft |
| ALDOC | 230 | Soft | LRRC6 | 23639 | Soft | FGGY | 55277 | Soft | SERING4 | 619189 | Soft |
| ALOX12 | 239 | Soft | LRRC61 | 65999 | Soft | FHAD1 | 114827 | Soft | SERPINA5 | 5104 | Soft |
| ALPK1 | 80216 | Soft | LRRC66 | 339977 | Soft | FHIT | 2272 | Soft | SERPINB1 | 1992 | Soft |
| ALPK3 | 115701 | Soft | LRRG7 | 57554 | Soft | FIBCD1 | 84929 | Soft | SERPINB9 | 5272 | Soft |
| ALS2CL | 259173 | Soft | LRRC73 | 221424 | Soft | FIBIN | 387758 | Soft | SERPINE2 | 5270 | Soft |
| AMT | 275 | Soft | LRRC758 | 388886 | Soft | FLJ31356 | 403150 | Soft | SERPINF1 | 5176 | Soft |
| AMY2B | 280 | Soft | LRRK2 | 120892 | Soft | FLJ37035 | 399821 | Soft | SERPINF2 | 5345 | Soft |
| ANG | 283 | Soft | LRSAM1 | 90678 | Soft | FLJ37453 | 729614 | Soft | SERPING1 | 710 | Soft |
| ANGPT1 | 284 | Soft | LSP1 | 4046 | Soft | FLJ43879 | 401039 | Soft | SESN1 | 27244 | Soft |
| ANGPTL4 | 51129 | Soft | LTBP2 | 4053 | Soft | FLJ45079 | 400624 | Soft | SESN3 | 143686 | Soft |
| ANK1 | 286 | Soft | LTBP3 | 4054 | Soft | FLJ46906 | 441172 | Soft | SETBP1 | 26040 | Soft |
| ANKAR | 150709 | Soft | LTBP4 | 8425 | Soft | FLRT1 | 23769 | Soft | SEZ6L2 | 26470 | Soft |
| ANKDD1A | 348094 | Soft | LTF | 4057 | Soft | FMO3 | 2328 | Soft | SGPP2 | 130367 | Soft |
| ANKFN1 | 162282 | Soft | LUADT1 | 106182249 | Soft | FMO4 | 2329 | Soft | SGSM2 | 9905 | Soft |
| ANKLE1 | 126549 | Soft | LUCAT1 | 100505994 | Soft | FMO5 | 2330 | Soft | SH2B2 | 10603 | Soft |
| ANKRAP1 | 57037 | Soft | LURAP1 | 541468 | Soft | FN1 | 2335 | Soft | SH2D3A | 10045 | Soft |
| ANKMY2 | 57763 | Soft | LUZP4 | 51213 | Soft | FN3K | 64122 | Soft | SH3BGR | 6450 | Soft |
| ANKRA2 | 57763 | Soft | LVCAT1 | 100506827 | Soft | FNBP1L | 54874 | Soft | SH3BP2 | 6452 | Soft |
| ANKRD2 | 26287 | Soft | LVCAT5 | 105375475 | Soft | FOS | 2353 | Soft | SH3D21 | 79729 | Soft |
| ANKRD24 | 170961 | Soft | LY75 | 4065 | Soft | FOSB | 2354 | Soft | SH3PXD2A | 9644 | Soft |
| ANKRD30B | 374860 | Soft | LY75-CD302 | 10052664 | Soft | FOXD1 | 2297 | Soft | SH3YL1 | 26751 | Soft |
| ANKRD34C | 390616 | Soft | LY96 | 23643 | Soft | FOXL1 | 2300 | Soft | SHC2 | 25759 | Soft |
| ANKRD36C | 400986 | Soft | LYPD1 | 116372 | Soft | FOXO1 | 2308 | Soft | SHC3 | 53358 | Soft |
| ANKRD37 | 353322 | Soft | LYPD3 | 27076 | Soft | FOXO4 | 4303 | Soft | SHF | 90525 | Soft |
| ANKZF1 | 55139 | Soft | LYRM9 | 201229 | Soft | FOXP1 | 27086 | Soft | SKIDA1 | 387640 | Soft |
| ANO9 | 338440 | Soft | MAATS1 | 89876 | Soft | FOXP2 | 93986 | Soft | SKINTL | 391037 | Soft |
| ANXA2R | 389289 | Soft | MAB21L3 | 126868 | Soft | FOXP4-AS1 | 101060264 | Soft | SKOR1 | 390598 | Soft |
| ANXA8L1 | 728113 | Soft | MACROD1 | 28992 | Soft | FRG1DP | 102273316 | Soft | SLAMF8 | 56833 | Soft |

-continued

| GeneSymbol | gene_id | Status | GeneSymbol | gene_id | Status | GeneSymbol | gene_id | Status |
|---|---|---|---|---|---|---|---|---|
| ANXA9 | 8416 | Soft | MAF | 4094 | Soft | SLAMF9 | 89886 | Soft |
| AOC3 | 8639 | Soft | MAFB | 9935 | Soft | SLC12A5 | 57468 | Soft |
| AP1G2 | 8906 | Soft | MAGEA11 | 4110 | Soft | SLC12A7 | 10723 | Soft |
| APBB3 | 10307 | Soft | MAMDC2 | 256691 | Soft | SLC12A8 | 84561 | Soft |
| APC2 | 10297 | Soft | MAML2 | 84441 | Soft | SLC13A4 | 26266 | Soft |
| APCDD1 | 147495 | Soft | MAN1B1-AS1 | 100289341 | Soft | SLC14A1 | 6563 | Soft |
| APH1B | 83464 | Soft | MANEA-AS1 | 101927288 | Soft | SLC15A3 | 51296 | Soft |
| APLN | 8862 | Soft | MAOA | 4128 | Soft | SLC16A2 | 6567 | Soft |
| APOA4 | 337 | Soft | MAOB | 4129 | Soft | SLC17A5 | 26503 | Soft |
| APOBEC3D | 140564 | Soft | MAP1A | 4130 | Soft | SLC17A7 | 57030 | Soft |
| APOBEC3F | 200316 | Soft | MAP1LC3A | 84557 | Soft | SLC1A4 | 6509 | Soft |
| APOBEC3G | 60489 | Soft | MAP3K12 | 7786 | Soft | SLC22A13 | 9390 | Soft |
| APOC1 | 341 | Soft | MAP3K13 | 9175 | Soft | SLC22A14 | 9389 | Soft |
| APOC3 | 345 | Soft | MAP3K8 | 1326 | Soft | SLC22A18 | 5002 | Soft |
| APOD | 347 | Soft | MAP7D2 | 256714 | Soft | SLC22A18AS | 5003 | Soft |
| APOE | 348 | Soft | MAPK10 | 5602 | Soft | SLC22A23 | 63027 | Soft |
| APOL3 | 80833 | Soft | MAPK3 | 5595 | Soft | SLC23A3 | 151295 | Soft |
| APOLD1 | 81575 | Soft | MAPRE3 | 22924 | Soft | SLC25A27 | 9481 | Soft |
| APPL1 | 26060 | Soft | MAPT | 4137 | Soft | SLC25A42 | 284439 | Soft |
| AQP1 | 358 | Soft | MARCH9 | 92979 | Soft | SLC25A45 | 283130 | Soft |
| AQP3 | 360 | Soft | MARK4 | 57787 | Soft | SLC26A6 | 65010 | Soft |
| AR | 367 | Soft | MASP1 | 5648 | Soft | SLC27A1 | 115019 | Soft |
| ARFGEF3 | 57221 | Soft | MAST1 | 22983 | Soft | SLC29A2 | 376497 | Soft |
| ARHGAP20 | 57569 | Soft | MATN1-AS1 | 100129196 | Soft | SLC29A4 | 3177 | Soft |
| ARHGAP24 | 83478 | Soft | MATN2 | 4147 | Soft | SLC2A1-AS1 | 222962 | Soft |
| ARHGAP4 | 393 | Soft | MBD5 | 55777 | Soft | SLC2A10 | 440584 | Soft |
| ARHGAP44 | 9912 | Soft | MCC | 4163 | Soft | SLC2A11 | 81031 | Soft |
| ARHGAP6 | 395 | Soft | MCOLN2 | 255231 | Soft | SLC2A14 | 66035 | Soft |
| ARHGAP8 | 23779 | Soft | MDGA1 | 266727 | Soft | SLO2A3 | 144195 | Soft |
| ARHGEF10L | 55160 | Soft | MDH1B | 130752 | Soft | SLC2A4 | 6515 | Soft |
| ARHGEF16 | 27237 | Soft | MDK | 4192 | Soft | SLC2A5 | 6517 | Soft |
| ARHGEF17 | 9828 | Soft | MEF2A | 4205 | Soft | SLC2A9 | 6518 | Soft |
| ARHGEF19 | 128272 | Soft | MEF2C | 4208 | Soft | SLC35E2 | 56606 | Soft |
| ARHGEF25 | 115557 | Soft | MEFV | 4210 | Soft | SLC38A5 | 9906 | Soft |
| ARHGEF37 | 389937 | Soft | MEGF6 | 1953 | Soft | SLC40A1 | 92745 | Soft |
| ARHGEF40 | 55701 | Soft | MEGF8 | 1954 | Soft | SLC41A2 | 30061 | Soft |
| ARHGEF6 | 9459 | Soft | MEIS1 | 4211 | Soft | SLC43A1 | 84102 | Soft |
| ARID4A | 5926 | Soft | MEIS1-AS2 | 100873998 | Soft | SLC44A5 | 8501 | Soft |
| ARL4C | 10123 | Soft | MEIS3 | 56917 | Soft | SLC45A1 | 204962 | Soft |
| ARMC12 | 221481 | Soft | MEOX1 | 4222 | Soft | SLC47A2 | 50651 | Soft |
| ARNT2 | 9915 | Soft | METTL20 | 254013 | Soft | SLC4A5 | 146802 | Soft |
| ARRB1 | 408 | Soft | METTL21B | 25895 | Soft | SLC5A9 | 57835 | Soft |
| ARRDC2 | 27106 | Soft | METTL7A | 25840 | Soft | SLC6A1 | 200010 | Soft |
| ARRDC3 | 57561 | Soft | MEX3A | 92312 | Soft | SLC6A16 | 6529 | Soft |
| ARRDC3-AS1 | 100129716 | Soft | MEX3B | 84206 | Soft | SLO6A3 | 28968 | Soft |
| ARRDC4 | 91947 | Soft | MFAP4 | 4239 | Soft | SLC9A3 | 6531 | Soft |
| ARSG | 22901 | Soft | MFI2 | 4241 | Soft | SLCO1A2 | 6550 | Soft |
| ARTN | 9048 | Soft | MFI2-AS1 | 100507057 | Soft | SLCO2A1 | 6579 | Soft |
| AS3MT | 57412 | Soft | MFSD7 | 84179 | Soft | SLITRK | 6578 | Soft |
| ASAP3 | 55616 | Soft | MGC16275 | 85001 | Soft | SLITRKA | 84631 | Soft |
| ASCL1 | 429 | Soft | MGP | 4256 | Soft | | 139065 | Soft |

-continued

| GeneSymbol | gene_id | Status | GeneSymbol | gene_id | Status | GeneSymbol | gene_id | Status |
|---|---|---|---|---|---|---|---|---|
| ASIC1 | 41 | Soft | MIAT | 440823 | Soft | GLRX | 2745 | Soft | SLITRK6 | 84189 | Soft |
| ASIC3 | 9311 | Soft | MIATNB | 102724827 | Soft | GLT8D2 | 83468 | Soft | SMAD6 | 4091 | Soft |
| ASIP | 434 | Soft | MIB2 | 142678 | Soft | GLTSCR2-AS1 | 106144593 | Soft | SMAD7 | 4092 | Soft |
| ASPG | 374569 | Soft | MIEF2 | 125170 | Soft | GLUL | 2752 | Soft | SMAD9 | 4093 | Soft |
| ASPRV1 | 151516 | Soft | MILR1 | 284021 | Soft | GLYATL2 | 219970 | Soft | SMARCA1 | 6594 | Soft |
| ASS1 | 445 | Soft | MIR1228 | 100302201 | Soft | GMDS-AS1 | 100508120 | Soft | SMARCD3 | 6604 | Soft |
| ASTN2 | 23245 | Soft | MIR1260B | 100422991 | Soft | GMFG | 9535 | Soft | SMC2-AS1 | 101928550 | Soft |
| ATG14 | 22863 | Soft | MIR1287 | 100302133 | Soft | GNAM1 | 2770 | Soft | SMCO3 | 440087 | Soft |
| ATG16L2 | 89849 | Soft | MIR155HG | 114614 | Soft | GNAO1 | 2775 | Soft | SMIM1 | 388588 | Soft |
| ATHL1 | 80162 | Soft | MIR181A2HG | 100379345 | Soft | GNAZ | 2781 | Soft | SMIM3 | 85027 | Soft |
| ATOH8 | 84913 | Soft | MIR193BHG | 100129781 | Soft | GNG2 | 54331 | Soft | SMTNL1 | 219537 | Soft |
| ATP1A1-AS1 | 84852 | Soft | MIR199A2 | 406977 | Soft | GNGT | 2788 | Soft | SNCA | 6622 | Soft |
| ATP1A2 | 477 | Soft | MIR210 | 406992 | Soft | GNRH1 | 2796 | Soft | SNED1 | 25992 | Soft |
| ATP2A3 | 489 | Soft | MIR210HG | 100506211 | Soft | GOLGA2P5 | 55592 | Soft | SNHG18 | 100505806 | Soft |
| ATP2B2 | 491 | Soft | MIR214 | 406996 | Soft | GOLGA7B | 401647 | Soft | SNTA1 | 6640 | Soft |
| ATP2C2 | 9914 | Soft | MIR23A | 407010 | Soft | GOLGA8B | 440270 | Soft | SNTB1 | 6641 | Soft |
| ATP6AP1L | 92270 | Soft | MIR24-2 | 407013 | Soft | GP1BB | 2812 | Soft | SNX21 | 90203 | Soft |
| ATP6V1B1 | 525 | Soft | MIR27A | 407018 | Soft | GPM6B | 2824 | Soft | SNX32 | 254122 | Soft |
| ATP6V1G2 | 534 | Soft | MIR29C | 407026 | Soft | GPNMB | 10457 | Soft | SNX33 | 257364 | Soft |
| ATP7A | 538 | Soft | MIR3120 | 100422882 | Soft | GPR146 | 115330 | Soft | SOD3 | 6649 | Soft |
| ATP8B3 | 148229 | Soft | MIR324 | 442898 | Soft | GPR155 | 151556 | Soft | SOHLH2 | 54937 | Soft |
| ATXN3 | 4287 | Soft | MIR34AHG | 106614088 | Soft | GPR162 | 27239 | Soft | SORBS1 | 10580 | Soft |
| AURKC | 6795 | Soft | MIR3681HG | 100506457 | Soft | GPR173 | 5432 | Soft | SORCS2 | 57537 | Soft |
| AZGP1 | 563 | Soft | MIR4635 | 100616479 | Soft | GPR19 | 2842 | Soft | SOX4 | 6659 | Soft |
| AZIN2 | 113451 | Soft | MIR4680 | 100616113 | Soft | GPR35 | 2859 | Soft | SOX5 | 6660 | Soft |
| B3GALT4 | 8705 | Soft | MIR4712 | 100616396 | Soft | GPR37 | 86 | Soft | SPS | 038958 | Soft |
| B3GNT4 | 79369 | Soft | MIR4800 | 100616358 | Soft | GPR39 | 28639 | Soft | SPACA6P-AS | 102238594 | Soft |
| B3GNT7 | 93010 | Soft | MIR5193 | 100847079 | Soft | GPR62 | 118442 | Soft | SPAG4 | 6676 | Soft |
| B4GALNT2 | 124872 | Soft | MIR548AR | 100847035 | Soft | GPRASP1 | 9737 | Soft | SPAG8 | 26206 | Soft |
| B4GALNT4 | 338707 | Soft | MIR612 | 693197 | Soft | GPRIN3 | 285513 | Soft | SPATA12 | 353324 | Soft |
| BACE1-AS | 100379571 | Soft | MIR641 | 693226 | Soft | GPT | 2875 | Soft | SPATA17 | 128153 | Soft |
| BACH1 | 571 | Soft | MIR675 | 100033819 | Soft | GRAMD1C | 54762 | Soft | SPATA17-AS1 | 103752555 | Soft |
| BACH2 | 60468 | Soft | MIR6757 | 102466193 | Soft | GRAMD3 | 65983 | Soft | SPATA18 | 132671 | Soft |
| BAHCC1 | 57597 | Soft | MIR6891 | 102465537 | Soft | GRB7 | 2886 | Soft | SPATA25 | 128497 | Soft |
| BAIAP2-AS1 | 440465 | Soft | MIR711 | 100313843 | Soft | GREB1 | 9687 | Soft | SPATA6 | 54558 | Soft |
| BAIAP3 | 8938 | Soft | MIR7847 | 102465993 | Soft | GREM1 | 6585 | Soft | SPATA6L | 55064 | Soft |
| BASP1P1 | 646201 | Soft | MIR99AHG | 388815 | Soft | GRIA1 | 2890 | Soft | SPATA7 | 55812 | Soft |
| BBC3 | 54828 | Soft | MKLN1-AS | 100506881 | Soft | GRIK1-AS2 | 100289187 | Soft | SPATC1 | 375686 | Soft |
| BBOF1 | 27113 | Soft | MLXIPL | 4316 | Soft | GRIK2 | 54103 | Soft | SPEF1 | 25876 | Soft |
| BBS1 | 80127 | Soft | MME | 4311 | Soft | GRIK4 | 55876 | Soft | SPEG | 10290 | Soft |
| BBS12 | 166379 | Soft | MMP11 | 4320 | Soft | GRIK5 | 2897 | Soft | SPIN2B | 474343 | Soft |
| BBS2 | 583 | Soft | MMP17 | 4326 | Soft | GRIN2A | 2903 | Soft | SPIN3 | 169981 | Soft |
| BBS9 | 27241 | Soft | MMP19 | 4327 | Soft | GRIN2D | 2906 | Soft | SPINK5 | 11005 | oft |
| BCAN | 63827 | Soft | MMP24 | 10893 | Soft | GS1-259H13.2 | 100289187 | Soft | SPINT1 | 6692 | Soft |
| BCAS3 | 54828 | Soft | MMP25-AS1 | 100507419 | Soft | GSAP | 54103 | Soft | SPRY1 | 10252 | Soft |
| BCHE | 590 | Soft | MMP7 | 4316 | Soft | GSDMB | 55876 | Soft | SRCIN1 | 80725 | Soft |
| BCKDHA | 593 | Soft | MMRN2 | 79812 | Soft | GSN | 2934 | Soft | SRD5A3 | 79644 | Soft |
| BCL11A | 53335 | Soft | MORN1 | 79906 | Soft | GSN-AS1 | 57000 | Soft | SRGAP3 | 9901 | oft |
| BCL11B | 64919 | Soft | MOSPD3 | 64598 | Soft | GSTA4 | 2941 | Soft | SRP14-AS1 | 100131089 | Soft |
| BCL6 | 604 | Soft | MPI | 4351 | Soft | GSTM2 | 2946 | Soft | SRRM3 | 222183 | Soft |
| BCORL1 | 63035 | Soft | MR1 | 3140 | Soft | GSTM4 | 2948 | Soft | SSBP2 | 23635 | Soft |

-continued

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| BDKRB2 | 624 | Soft | MRAP2 | 112609 | Soft | GTF2IRD2 | 84163 | Soft | SSBP3-AS1 | 619518 | Soft |
| BDNF-AS | 497258 | Soft | MRC2 | 9902 | Soft | GTF2IRD2B | 389524 | Soft | SSC4D | 136853 | Soft |
| BEAN1 | 146227 | Soft | MROH2A | 339766 | Soft | GUCY1B3 | 2983 | Soft | SSC5D | 284297 | Soft |
| BEND5 | 79656 | Soft | MRPL23-AS1 | 100133545 | Soft | GULP1 | 51454 | Soft | SSH3 | 54961 | Soft |
| BEST1 | 7439 | Soft | MRVI1 | 10335 | Soft | GUSBP4 | 375513 | Soft | SSPN | 8082 | oft |
| BEX1 | 55859 | Soft | MSC-AS1 | 100132891 | Soft | GXYLT2 | 727936 | Soft | SSR4P1 | 728039 | Soft |
| BFSP1 | 631 | Soft | MSRB2 | 22921 | Soft | GYPC | 2995 | Soft | ST3GAL3 | 6487 | Soft |
| BGN | 633 | Soft | MST1 | 4485 | Soft | H19 | 283120 | Soft | ST3GAL4-AS1 | 399972 | Soft |
| BHLHB9 | 80823 | Soft | MST1L | 11223 | Soft | H6PD | 95 | Soft | ST3GAL5 | 8869 | Soft |
| BHLHE40 | 8553 | Soft | MST1P2 | 11209 | Soft | HAL | 3034 | Soft | ST6GALNAC2 | 10610 | Soft |
| BHLHE41 | 79365 | Soft | MT1F | 4494 | Soft | HAR1A | 768096 | Soft | ST8SIA1 | 6489 | Soft |
| BISPR | 105221694 | Soft | MTA3 | 57504 | Soft | HAS2 | 3037 | Soft | ST8SIA5 | 29906 | Soft |
| BLK | 640 | Soft | MTHFD2P1 | 100287639 | Soft | HAS2-AS1 | 594842 | Soft | STAC2 | 342667 | Soft |
| BMF | 90427 | Soft | MTL5 | 9633 | Soft | HBE1 | 3046 | Soft | STAG3 | 10734 | Soft |
| BMP3 | 651 | Soft | MTMR11 | 10903 | Soft | HBG2 | 3048 | Soft | STAP2 | 55620 | Soft |
| BMP4 | 652 | Soft | MTMR9LP | 339483 | Soft | HBP1 | 26959 | Soft | STARD13-AS | 100874241 | Soft |
| BMP8B | 656 | Soft | MTTP | 4547 | Soft | HCAR2 | 8843 | Soft | STARD5 | 80765 | Soft |
| BMPR1B | 658 | Soft | MTUS1 | 57509 | Soft | HCAR3 | 54985 | Soft | STARD9 | 57519 | Soft |
| BNIP3 | 664 | Soft | MTUS2 | 23281 | Soft | HCFC1R1 | 352961 | Soft | STAT2 | 6773 | Soft |
| BNIP3L | 665 | Soft | MUC1 | 4582 | Soft | HCG26 | 253018 | Soft | STAT4 | 6775 | Soft |
| BOC | 91653 | Soft | MUC12 | 10071 | Soft | HCG27 | 54435 | Soft | STBD1 | 8987 | Soft |
| BOLA1 | 51027 | Soft | MUC15 | 143662 | Soft | HCG8 | 80862 | Soft | STK32A | 202374 | Soft |
| BOLA3-AS1 | 100507171 | Soft | MUC20 | 200958 | Soft | HCPS | 10866 | Soft | STOM | 2040 | Soft |
| BORCS7-ASMT | 100528007 | Soft | MUM1L1 | 139221 | Soft | HDAC11 | 79885 | Soft | STON1 | 11037 | Soft |
| BPIFB4 | 149954 | Soft | MUSK | 4593 | Soft | HDAC5 | 10014 | Soft | STON1-GTF2A1L | 286749 | Soft |
| BRSK1 | 84446 | Soft | MX1 | 4599 | Soft | HDGFL1 | 154150 | Soft | STOX1 | 219736 | Soft |
| BTBD16 | 118663 | Soft | MX2 | 4600 | Soft | HECW2 | 57520 | Soft | STRA6 | 64220 | Soft |
| BTBD19 | 149478 | Soft | MXD4 | 10608 | Soft | HEPH | 9843 | Soft | STX1B | 112755 | Soft |
| BTBD8 | 284697 | Soft | MXI1 | 4601 | Soft | HEXDC | 284004 | Soft | STXBP2 | 6813 | Soft |
| BTG1 | 694 | Soft | MYBPC1 | 4604 | Soft | HEXIM2 | 124790 | Soft | SUGCT | 79783 | Soft |
| BTN2A2 | 10385 | Soft | MYCBPAP | 84073 | Soft | HHLA3 | 11147 | Soft | SUGT1P1 | 441394 | Soft |
| BTN2A3P | 54718 | Soft | MYL5 | 10398 | Soft | HILPDA | 29923 | Soft | SULF1 | 23213 | Soft |
| BTN3A1 | 11119 | Soft | MYL9 | 10398 | Soft | HIST1H3E | 8353 | Soft | SULF2 | 55959 | Soft |
| BTN3A3 | 10384 | Soft | MYLK3 | 91807 | Soft | HIST1H3E | 8353 | Soft | SULT1E1 | 6783 | Soft |
| BTNL9 | 153579 | Soft | MYLK4 | 340156 | Soft | HIST2H2BC | 337873 | Soft | SVEP1 | 79987 | Soft |
| C10orf10 | 11067 | Soft | MYO15A | 51168 | Soft | HIST3H2A | 92815 | Soft | SYN2 | 6854 | Soft |
| C10orf11 | 83938 | Soft | MYO15B | 80022 | Soft | HKR1 | 284459 | Soft | SYNE2 | 23224 | Soft |
| C10orf125 | 220979 | Soft | MYO16 | 23026 | Soft | HLA-DMA | 3108 | Soft | SYNE4 | 163183 | Soft |
| C11orf54 | 64115 | Soft | MYO1F | 4542 | Soft | HLA-F | 3134 | Soft | SYNGAP1 | 8831 | Soft |
| C11orf21 | 29125 | Soft | MYO3B | 140469 | Soft | HLA-F-AS1 | 285830 | Soft | SYNGR1 | 9145 | Soft |
| C11orf54 | 28970 | Soft | MYOM1 | 8736 | Soft | HLA-J | 3137 | Soft | SYNGR3 | 9143 | Soft |
| C11orf70 | 85016 | Soft | MYOZ2 | 51778 | Soft | HLF | 3131 | Soft | SYNPO | 11346 | Soft |
| C12orf60 | 144608 | Soft | MYRF | 745 | Soft | HLTF | 6596 | Soft | SYNPOZ | 171024 | Soft |
| C12orf76 | 400073 | Soft | MZF1 | 7593 | Soft | HLTF-AS1 | 100873945 | Soft | SYS1-OBNDD2 | 767557 | Soft |
| C14orf132 | 56967 | Soft | MZF1-AS1 | 100131691 | Soft | HMBOX1 | 79618 | Soft | SYT11 | 23208 | Soft |
| C14orf93 | 60686 | Soft | N4BP2L1 | 90634 | Soft | HMCN1 | 83872 | Soft | SYT12 | 91683 | Soft |
| C15orf62 | 643338 | Soft | N4BP2L2-IT2 | 116828 | Soft | HMGCL | 3155 | Soft | SYT13 | 57586 | Soft |
| C16orf45 | 89927 | Soft | N4BP3 | 23138 | Soft | HNF1A | 6927 | Soft | SYT17 | 51760 | Soft |
| C16orf74 | 404550 | Soft | NAALADL2 | 254827 | Soft | HNRNPA3P1 | 10151 | Soft | SYT8 | 9066 | Soft |
| C16orf189 | 146556 | Soft | NACAD | 23148 | Soft | HOGA1 | 112817 | Soft | SYTL1 | 90019 | Soft |
| C17orf100 | 388327 | Soft | NALT1 | 101928483 | Soft | HOME4 | 57594 | Soft | SYTL1 | 84958 | Soft |

| GeneSymbol | gene_id | Status | GeneSymbol | gene_id | Status | GeneSymbol | gene_id | Status |
|---|---|---|---|---|---|---|---|---|
| C18orf65 | 400658 | Soft | NANOS1 | 340719 | Soft | HOOK2 | 29911 | Soft | SYTL2 | 54843 | Soft |
| C19orf54 | 284325 | Soft | NAP1L6 | 645996 | Soft | HOTAIR | 100124700 | Soft | TAF1A-AS1 | 100506161 | Soft |
| C19orf157 | 79173 | Soft | NAPSA | 9476 | Soft | HOTS | 103344718 | Soft | TAGLN | 6876 | Soft |
| C9orf162 | 128346 | Soft | NATD1 | 256302 | Soft | HOXA-AS2 | 285943 | Soft | TAS2R4 | 50832 | Soft |
| C9orf167 | 284498 | Soft | NBEA | 26960 | Soft | HOXA11-AS | 221883 | Soft | TAS2R5 | 54429 | Soft |
| C1orf204 | 284677 | Soft | NCK1-AS1 | 101927597 | Soft | HOXA13 | 3209 | Soft | TBC1D10A | 83874 | Soft |
| C1orf21 | 81563 | Soft | NCKAP1L | 3071 | Soft | HOXA4 | 3201 | Soft | TBC1D17 | 79735 | Soft |
| C1orf220 | 400798 | Soft | NCKIPSD | 51517 | Soft | HOXA5 | 3202 | Soft | TBC1D32 | 221322 | Soft |
| C1orf228 | 339541 | Soft | NDN | 79625 | Soft | HOXA6 | 3203 | Soft | TBC1D3H | 729877 | Soft |
| C1orf54 | 79630 | Soft | NDRG1 | 10397 | Soft | HOXC-AS1 | 100874363 | Soft | TBC1D3I | 102724862 | Soft |
| C1QL1 | 10882 | Soft | NDRG4 | 65009 | Soft | HOXC-AS2 | 100874364 | Soft | TBC1D3L | 101060376 | Soft |
| C1QTNF1 | 114897 | Soft | NDUFA4L2 | 56901 | Soft | HPCA | 3208 | Soft | TBC1D8B | 54885 | Soft |
| C1QTNF1-AS1 | 100507410 | Soft | NEAT1 | 283131 | Soft | HPD | 3242 | Soft | TBKBP1 | 9755 | Soft |
| C1QTNF3 | 114899 | Soft | NEBL | 10529 | Soft | HPGD | 3248 | Soft | TBX19 | 9095 | Soft |
| C1QTNF6 | 114904 | Soft | NEBL-AS1 | 100128511 | Soft | HR | 55806 | Soft | TBX6 | 6911 | Soft |
| C1R | 715 | Soft | NEDD9 | 4739 | Soft | HRAT17 | 101928036 | Soft | TBXA2R | 6915 | Soft |
| C1RL | 51279 | Soft | NEIL1 | 79661 | Soft | HRAT5 | 102467073 | Soft | TBXAS1 | 6916 | Soft |
| C1RL-AS1 | 283314 | Soft | NEK11 | 79858 | Soft | HRAT92 | 441307 | Soft | TC2N | 123036 | Soft |
| C1S | 716 | Soft | NEU4 | 129807 | Soft | HRCT1 | 646962 | Soft | TCAF1 | 285966 | Soft |
| C2 | 717 | Soft | NEURL1B | 54492 | Soft | HRNR | 388617 | Soft | TCAF3 | 6920 | Soft |
| C20orf194 | 2594 | Soft | NEURL2 | 140825 | Soft | HS6ST3 | 266722 | Soft | TCF4 | 6925 | Soft |
| C20orf195 | 79025 | Soft | NEUROG2 | 63973 | Soft | HSBP1L1 | 440498 | Soft | TCE1 | 6932 | Soft |
| C21orf33 | 8209 | Soft | NFATC4 | 4776 | Soft | HSD11B1 | 3290 | Soft | TCF7L1 | 83439 | Soft |
| C22orf34 | 348645 | Soft | NFE2L3 | 9603 | Soft | HSD11B1L | 374875 | Soft | TCL6 | 27004 | Soft |
| C2orf15 | 150590 | Soft | NFE4 | 58160 | Soft | HSD17B14 | 51171 | Soft | TCP11L2 | 255394 | Soft |
| C2orf81 | 388963 | Soft | NFIL3 | 4783 | Soft | HSD17B6 | 8630 | Soft | TCTE1 | 202500 | Soft |
| C3 | 718 | Soft | NFKBIL1 | 4795 | Soft | HSD17B7P2 | 158160 | Soft | TCTN1 | 79600 | Soft |
| C3orf18 | 51161 | Soft | NGFRAP1 | 27018 | Soft | HSD387 | 80270 | Soft | TDO2 | 6999 | Soft |
| C3orf36 | 80111 | Soft | NHLRC3 | 387921 | Soft | HSF4 | 3299 | Soft | TDRD9 | 122402 | Soft |
| C3orf67 | 200844 | Soft | NHLRC4 | 283948 | Soft | HSPA1L | 3305 | Soft | TENM1 | 10178 | Soft |
| C4A | 720 | Soft | NHS | 4810 | Soft | HSPB7 | 27129 | Soft | TENM2 | 57451 | Soft |
| C4B | 721 | Soft | NHSL2 | 340527 | Soft | HSPG2 | 3339 | Soft | TES | 26136 | Soft |
| C4B_2 | 100293534 | Soft | NICN1 | 84276 | Soft | HTR2C | 3358 | Soft | TESK2 | 10420 | Soft |
| C4orf3 | 401152 | Soft | NID2 | 22795 | Soft | HTRA1 | 5654 | Soft | TET1 | 80312 | Soft |
| C4orf47 | 441054 | Soft | NIFK-AS1 | 254128 | Soft | ICAM1 | 3383 | Soft | TEX9 | 374618 | Soft |
| C5 | 727 | Soft | NIM1K | 167359 | Soft | ICAM2 | 3384 | Soft | TFCP2L1 | 29842 | Soft |
| C5AR1 | 728 | Soft | NIPAL2 | 79815 | Soft | ICAM4 | 3386 | Soft | TFDP2 | 7029 | Soft |
| C5AR2 | 27202 | Soft | NIPAL4 | 348938 | Soft | ICAM5 | 7087 | Soft | TFP1 | 7035 | Soft |
| C5orf46 | 389336 | Soft | NIPSNAP1 | 8508 | Soft | ID2-AS1 | 100506299 | Soft | TFR2 | 7036 | Soft |
| C6orf223 | 221416 | Soft | NIPSNAP3B | 55335 | Soft | IDUA | 3425 | Soft | TG | 7038 | Soft |
| CZorf13 | 100506380 | Soft | NKD1 | 85407 | Soft | IF144 | 10561 | Soft | TGFA | 7039 | Soft |
| C7orf61 | 402573 | Soft | NKD2 | 85409 | Soft | IF144L | 10964 | Soft | TGFB1I1 | 7041 | Soft |
| C8orf31 | 286122 | Soft | NLGN2 | 57555 | Soft | IF16 | 2537 | Soft | TGFBR3 | 7049 | Soft |
| C8orf34 | 116328 | Soft | NLGN3 | 54413 | Soft | IFIH1 | 64135 | Soft | TGFBR3L | 100507588 | Soft |
| C8orf4 | 56892 | Soft | NLRC3 | 197358 | Soft | IFIT1 | 3434 | Soft | THAP2 | 83591 | Soft |
| C8orf44 | 56260 | Soft | NLRP1 | 22861 | Soft | IFIT2 | 3433 | Soft | THAP7-AS1 | 439931 | Soft |
| C8orf48 | 157773 | Soft | NMNAT2 | 23057 | Soft | IFIT3 | 3437 | Soft | THAP8 | 199745 | Soft |
| C8orf58 | 541565 | Soft | NMNAT3 | 349565 | Soft | IFITM1 | 8519S | Soft | THBS2 | 7058 | Soft |
| C9orf173 | 441476 | Soft | NMRK1 | 54981 | Soft | IFITM10 | 402778 | Soft | THBS3 | 7059 | Soft |
| C9orf173-AS1 | 100129722 | Soft | INMU | 10874 | Soft | IFITM4P | 340198 | Soft | THBS4 | 7060- | Soft |
| C9orf3 | 84909 | Soft | NOD2 | 64127 | Soft | IFT140 | 9742 | Soft | THEMIS2 | 9473 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| C9orf9 | 11092 | Soft | NOL3 | 8996 | Soft | IFT80 | 57560 | Soft | THRA | 7067 | Soft |
| CA11 | 770 | Soft | NOLAL | 140688 | Soft | IFT81 | 28981 | Soft | THRB | 7068 | Soft |
| CA3 | 761 | Soft | NOTCH3 | 4854 | Soft | IGBP1P1 | 280655 | Soft | TIMP3 | 7078 | Soft |
| CA5B | 11238 | Soft | NOTUM | 147111 | Soft | IGF2BP1 | 10642 | Soft | TLCD2 | 727910 | Soft |
| CA9 | 768 | Soft | NOXA1 | 10811 | Soft | IGFBP2 | 3485 | Soft | TLE2 | 7089 | Soft |
| CACFD1 | 11094 | Soft | NOXRED1 | 122945 | Soft | IGFBP3 | 3486 | Soft | TLE6 | 79816 | Soft |
| CACNA1B | 774 | Soft | NPAS1 | 4861 | Soft | IGFBP5 | 3488 | Soft | TLR1 | 7096 | Soft |
| CACNA1C | 775 | Soft | NPAS2 | 4862 | Soft | IGFBP7-AS1 | 255130 | Soft | TLR9 | 54106 | Soft |
| CACNA1G | 8913 | Soft | NPC1L1 | 29881 | Soft | IGIP | 492311 | Soft | TM4SF1-AS1 | 100874091 | Soft |
| CACNA1H | 8912 | Soft | NPHP1 | 4867 | Soft | IGSF10 | 285313 | Soft | TM7SF2 | 7108 | Soft |
| CACNA1I | 8911 | Soft | NPHP3 | 27031 | Soft | IGSF22 | 283284 | Soft | TMCC1-AS1 | 100507032 | Soft |
| CACNA2D2 | 9254 | Soft | NPHP3-ACAD11 | 100532724 | Soft | IGSF8 | 93185 | Soft | TMEM100 | 55273 | Soft |
| CACNA2D3 | 55799 | Soft | NPM2 | 10361 | Soft | IGSF9 | 57549 | Soft | TMEM102 | 284114 | Soft |
| CACNB1 | 782 | Soft | NPTN-IT1 | 101241892 | Soft | IL11RA | 3590 | Soft | TMEM107 | 84314 | Soft |
| CACNB3 | 784 | Soft | NPTX1 | 4884 | Soft | IL13RA2 | 3598 | Soft | TMEM116 | 89894 | Soft |
| CADM1 | 23705 | Soft | NPW | 283869 | Soft | IL15 | 3600 | Soft | TMEM130 | 222865 | Soft |
| CADM3 | 57863 | Soft | NPY2R | 4887 | Soft | IL16 | 3603 | Soft | TMEM132B | 114795 | Soft |
| CADM3-AS1 | 100131825 | Soft | NR1D1 | 9572 | Soft | IL17B | 27190 | Soft | TMEM136 | 219902 | Soft |
| CADM4 | 199731 | Soft | NR1H3 | 10062 | Soft | IL17RC | 84818 | Soft | TMEM143 | 55260 | Soft |
| CAHM | 100526820 | Soft | NR2F1-AS1 | 441094 | Soft | IL17RE | 132014 | Soft | TMEM145 | 284339 | Soft |
| CALCOCO1 | 57658 | Soft | NRBP2 | 340371 | Soft | IL18BP | 10068 | Soft | TMEM159 | 57146 | Soft |
| CALHM3 | 119395 | Soft | NRN1 | 51299 | Soft | IL1R2 | 7850 | Soft | TMEM173 | 340061 | Soft |
| CAMK2B | 816 | Soft | NRN1L | 123904 | Soft | IL23R | 149233 | Soft | TMEM178B | 100507421 | Soft |
| CAMKV | 79012 | Soft | NRSN2-AS1 | 100507459 | Soft | ILZRG | 3561 | Soft | TMEM187 | 8269 | Soft |
| CAND1.11 | 100130460 | Soft | NRTN | 4902 | Soft | IL34 | 146433 | Soft | TMEM198B | 440104 | Soft |
| CAPN3 | 825 | Soft | NRXN2 | 9379 | Soft | IMPG2 | 50939 | Soft | TMEM25 | 84866 | Soft |
| CAPS | 828 | Soft | NRXN3 | 9369 | Soft | NADL | 10207 | Soft | TMEM255A | 5502 | Soft |
| CARD14 | 79092 | Soft | NSG1 | 27065 | Soft | NAFM1 | 255783 | Soft | TMEM27 | 57393 | Soft |
| CARF | 79800 | Soft | NT5M | 56953 | Soft | INE2 | 8551 | Soft | TMEM37 | 140738 | Soft |
| CARMN | 728264 | Soft | NTN3 | 4917 | Soft | ING4 | 51147 | Soft | TMEM38A | 79041 | Soft |
| CARNS1 | 57571 | Soft | NTN5 | 126147 | Soft | INHA | 3623 | Soft | TMEM42 | 131616 | Soft |
| CASC10 | 26 | Soft | NUDT13 | 25961 | Soft | INHBE | 83729 | Soft | TMEM45A | 55076 | Soft |
| CASC2 | 508 | Soft | NUDT14 | 256281 | Soft | INMT | 11185 | Soft | TMEM47 | 83604 | Soft |
| CASC9 | 101805492 | Soft | NUD17 | 283927 | Soft | INSIG2 | 51141 | Soft | TMEM51-AS1 | 200197 | Soft |
| CATSPER2P1 | 440278 | Soft | NUGGC | 389643 | Soft | INTS6-AS1 | 100507398 | Soft | TMEM59L | 25789 | Soft |
| CBLN3 | 643866 | Soft | NUPR1 | 26471 | Soft | IP6K2 | 51447 | Soft | TMEM63C | 57156 | Soft |
| CBS | 875 | Soft | NXNL2 | 158046 | Soft | IP6K3 | 117283 | Soft | TMEM67 | 91147 | Soft |
| CBX7 | 23492 | Soft | NXPH4 | 11247 | Soft | IPMK | 253430 | Soft | TMEM74B | 55321 | Soft |
| CCBL1 | 883 | Soft | NYAP1 | 222926 | Soft | IQCD | 115811 | Soft | TMEM80 | 283232 | Soft |
| CCDC102A | 92922 | Soft | NYNRIN | 57523 | Soft | IQCH-AS1 | 100506686 | Soft | TMEM8B | 51754 | Soft |
| CCDC102B | 79839 | Soft | OAS1 | 4938 | Soft | IQGAP2 | 10788 | Soft | TMEM91 | 641649 | Soft |
| CCDC103 | 388389 | Soft | OAS2 | 4939 | Soft | IQUB | 154865 | Soft | TMEM92 | 162461 | Soft |
| CCDC110 | 256309 | Soft | OASL | 8638 | Soft | IRAK3 | 11213 | Soft | TMEM92-AS1 | 103752589 | Soft |
| CCDC146 | 57639 | Soft | OBSCN | 84033 | Soft | IRF6 | 3664 | Soft | TMEM98-AS1 | 493900 | Soft |
| CCDC148 | 130940 | Soft | OBSL1 | 23363 | Soft | IRF9 | 10379 | Soft | TNFAIP8 | 25816 | Soft |
| CCDC151 | 115948 | Soft | OCEL1 | 79629 | Soft | IRX3 | 79191 | Soft | TNFRSF10C | 8794 | Soft |
| CCDC152 | 100129792 | Soft | ODF3B | 440836 | Soft | ISG20 | 3669 | Soft | TNFRSF14 | 8764 | Soft |
| CCDC158 | 339965 | Soft | ODF3L1 | 161753 | Soft | ISLR | 3671 | Soft | TNFRSF25 | 8718 | Soft |
| CCDC17 | 149483 | Soft | OGFR-AS1 | 101409261 | Soft | ISLR2 | 57611 | Soft | TNFSF13B | 10673 | Soft |
| CCDC18-AS1 | 100131564 | Soft | OLFM2 | 93145 | Soft | ITGA1 | 3672 | Soft | TNFSF14 | 8740 | Soft |
| CCDC180 | 100499483 | Soft | OLFML2A | 169611 | Soft | ITGA10 | 8515 | Soft | TNFSF4 | 7292 | Soft |

-continued

| GeneSymbol | gene_id | Status | GeneSymbol | gene_id | Status | GeneSymbol | gene_id | Status |
|---|---|---|---|---|---|---|---|---|
| CCDC183 | 84960 | Soft | OLFML2B | 25903 | Soft | ITGA11 | 22801 | Soft | TNK1 | 8711 | Soft |
| CCDC184 | 387856 | Soft | OLFML3 | 56944 | Soft | ITGA2B | 3674 | Soft | TNNI2 | 7136 | Soft |
| CCDC191 | 57577 | Soft | OLMALINC | 90271 | Soft | ITGAX | 3687 | Soft | TNNI3K | 51086 | Soft |
| CCDC40 | 55036 | Soft | OOEP | 441161 | Soft | ITGB2 | 3689 | Soft | TNNT1 | 7138 | Soft |
| CCDC64B | 146439 | Soft | OPLAH | 26873 | Soft | ITGB2-AS1 | 100505746 | Soft | TNNT3 | 7140 | Soft |
| CCDC65 | 85478 | Soft | OPN3 | 23596 | Soft | ITGB4 | 3691 | Soft | TNS1 | 7145 | Soft |
| CCDC74A | 90557 | Soft | OPRL1 | 4987 | Soft | ITGB8 | 3696 | Soft | TNXB | 7148 | Soft |
| CCDC80 | 151887 | Soft | OR10V2P | 81343 | Soft | ITIH4 | 3700 | Soft | TOB1-AS1 | 400604 | Soft |
| CCDC92 | 80212 | Soft | OR1F1 | 4992 | Soft | ITIH4-AS1 | 100873993 | Soft | TOB2P1 | 222699 | Soft |
| CCL26 | 10344 | Soft | OR51B4 | 79339 | Soft | ITPR1 | 3708 | Soft | TOLLIP-AS1 | 255512 | Soft |
| CCL5 | 6352 | Soft | OR51B5 | 282763 | Soft | ITPR1-AS1 | 100996539 | Soft | TP53I11 | 9537 | Soft |
| COND2 | 894 | Soft | ORAI3 | 93129 | Soft | IZUMO4 | 113177 | Soft | TP53INP1 | 94241 | Soft |
| COND2-AS1 | 1037525 | Soft | ORM1 | 5004 | Soft | JAG2 | 3714 | Soft | TP53INP2 | 58476 | Soft |
| CONG2 | 901 | Soft | OSBPL5 | 114879 | Soft | JAK3 | 3718 | Soft | TP53TG1 | 11257 | Soft |
| CCNYL2 | 414194 | Soft | OSCAR | 126014 | Soft | JAM2 | 58494 | Soft | TP63 | 8626 | Soft |
| CCR10 | 2826 | Soft | OSCP1 | 127700 | Soft | JPH2 | 57158 | Soft | TP73 | 7161 | Soft |
| CCT6B | 10693 | Soft | OSER1-AS1 | 100505783 | Soft | JUP | 3728 | Soft | TP73-AS1 | 57212 | Soft |
| CD180 | 4064 | Soft | OSR2 | 116039 | Soft | KALRN | 8997 | Soft | TPO | 7173 | Soft |
| CD226 | 10666 | Soft | OVCH1 | 341350 | Soft | KATNAL2 | 83473 | Soft | TPP1 | 1200 | Soft |
| CD24 | 100133941 | Soft | OXR1 | 55074 | Soft | KAZALD1 | 81621 | Soft | TPPP | 11076 | Soft |
| CD27 | 939 | Soft | P2RX6 | 9127 | Soft | KAZN | 23254 | Soft | TPPP3 | 51673 | Soft |
| CD27-AS1 | 678655 | Soft | P2RX7 | 5027 | Soft | KBTBD3 | 143879 | Soft | TPRG1 | 285386 | Soft |
| CD36 | 948 | Soft | P4HA1 | 5033 | Soft | KBTBD7 | 84078 | Soft | TPRG1-AS1 | 100874043 | Soft |
| CD40 | 958 | Soft | P4HA2-AS1 | 100861518 | Soft | KC6 | 641516 | Soft | TPSG1 | 25823 | Soft |
| CD68 | 968 | Soft | P4HTM | 54681 | Soft | KCCAT211 | 102724550 | Soft | TPT1-AS1 | 100190939 | Soft |
| CD7 | 924 | Soft | PACS2 | 23241 | Soft | KCNAB2 | 8514 | Soft | TRABD2B | 388630 | Soft |
| CD72 | 971 | Soft | PADI3 | 51702 | Soft | KCND1 | 3750 | Soft | TRAPPC6A | 79090 | Soft |
| CD74 | 972 | Soft | PAGE2 | 203569 | Soft | KCNE3 | 10008 | Soft | TREML1 | 54210 | Soft |
| CD82 | 3732 | Soft | PAGE2B | 389860 | Soft | KCNE4 | 23704 | Soft | TRIB2 | 28951 | Soft |
| CDC42EP5 | 148170 | Soft | PAGE3 | 139793 | Soft | KCNH1 | 3756 | Soft | TRIM17 | 51127 | Soft |
| CDH13 | 1012 | Soft | PAIP2B | 400961 | Soft | KCNH3 | 23416 | Soft | TRIM22 | 10346 | Soft |
| CDH19 | 28513 | Soft | PALD1 | 27143 | Soft | KCNH5 | 27133 | Soft | TRIM29 | 23650 | Soft |
| CDH22 | 64405 | Soft | PAMR1 | 25891 | Soft | KCNH8 | 131096 | Soft | TRIM34 | 53840 | Soft |
| CDHR5 | 53841 | Soft | PAN2 | 9924 | Soft | KCNIP2 | 30819 | Soft | TRIM4 | 89122 | Soft |
| CDK18 | 5129 | Soft | PAPLN | 89932 | Soft | KCNJ9 | 3765 | Soft | TRIM46 | 80128 | Soft |
| CDK19 | 23097 | Soft | PAPPA | 5069 | Soft | KCNK15-AS1 | 106144538 | Soft | TRIM52 | 84851 | Soft |
| CDKL2 | 8999 | Soft | PAPPA-AS1 | 493913 | Soft | KCNK2 | 3776 | Soft | TRIM54 | 57159 | Soft |
| CDKN1B | 1027 | Soft | PAPPA2 | 60676 | Soft | KCNK3 | 3777 | Soft | TRIM6-TRIM34 | 445372 | Soft |
| CDNF | 441549 | Soft | PAQR6 | 79957 | Soft | KCNMB2-AS1 | 104797538 | Soft | TRIM63 | 84676 | Soft |
| CDON | 50937 | Soft | PAQR8 | 85315 | Soft | KCNN1 | 3780 | Soft | TRIM66 | 9866 | Soft |
| CDR1 | 1038 | Soft | PARD6G-AS1 | 100130522 | Soft | KCNN4 | 3783 | Soft | TRIM69 | 140691 | Soft |
| CECR1 | 51816 | Soft | PARK2 | 5071 | Soft | KCNT2 | 343450 | Soft | TRIML1 | 339976 | Soft |
| CECR2 | 27443 | Soft | PARM1 | 25849 | Soft | KCNK3 | 147040 | Soft | TRIOBP | 11078 | Soft |
| CECR5-AS1 | 100130717 | Soft | PARP10 | 84875 | Soft | KCTD11 | 57528 | Soft | TRIOK | 286144 | Soft |
| CELF6 | 60677 | Soft | PARP16 | 54956 | Soft | KCTD16 | 146212 | Soft | TRO | 7216 | Soft |
| CELSR3 | 1951 | Soft | PARP3 | 10039 | Soft | KCTD19 | 126695 | Soft | ITRPC1 | 7220 | Soft |
| CEMIP | 57214 | Soft | PAX9 | 5083 | Soft | KDF1 | 55818 | Soft | TRPM4 | 54795 | Soft |
| CEP112 | 201134 | Soft | PBXIP1 | 57326 | Soft | KDM3A | 23030 | Soft | TRPS1 | 7227 | Soft |
| CEP126 | 57562 | Soft | PCAT2 | 103164619 | Soft | KDM4B | 23081 | Soft | TRPT1 | 83707 | Soft |
| CEP68 | 23177 | Soft | PCAT5 | 102578074 | Soft | KDM4C | 10765 | Soft | TRPV1 | 7442 | Soft |
| CERS1 | 10715 | Soft | PCAT6 | 100506696 | Soft | KDM5B | 3791 | Soft | TSC22D3 | 1831 | Soft |

-continued

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| CERS4 | 79603 | Soft | PCBP1-AS1 | 400960 | Soft | KIAA0825 | 285600 | Soft | TSHZ2 | 128553 | Soft |
| CES3 | 23491 | Soft | PCBP3 | 54039 | Soft | KIAA0895L | 653319 | Soft | TSLP | 85480 | Soft |
| CFAP126 | 257177 | Soft | PCDH18 | 54510 | Soft | KIAA1107 | 23285 | Soft | TSNARE1 | 203062 | Soft |
| CFAP206 | 154313 | Soft | PCDH20 | 64881 | Soft | KIAA1109 | 84162 | Soft | TSNAXIP1 | 55815 | Soft |
| CFAP221 | 200373 | Soft | PCDH7 | 5099 | Soft | KIAA1462 | 57608 | Soft | TSPAN1 | 10103 | Soft |
| CFAP43 | 80217 | Soft | PCDHB5 | 26167 | Soft | KIAA1683 | 80726 | Soft | TSPAN15 | 23555 | Soft |
| CFAP44 | 55779 | Soft | PCDHB9 | 56127 | Soft | KIAA1958 | 158405 | Soft | TSPAN18 | 90139 | Soft |
| CFAP47 | 286464 | Soft | PCED1A | 64773 | Soft | KIF26A | 26153 | Soft | TSPAN19 | 144448 | Soft |
| CFAP53 | 220136 | Soft | PCMTD1 | 115294 | Soft | KIF3C | 3797 | Soft | TSPAN31 | 6302 | Soft |
| CFAP54 | 144535 | Soft | PCOLCE | 5118 | Soft | KIFSA | 3798 | Soft | TSPAN7 | 7102 | Soft |
| CFAP57 | 149465 | Soft | PCOLCE-AS1 | 100129845 | Soft | KIF50 | 3800 | Soft | TSPAN8 | 7103 | Soft |
| CFAP58-AS1 | 100505869 | Soft | PCP2 | 126006 | Soft | KIFC2 | 90990 | Soft | TSSK3 | 81629 | Soft |
| CFAP70 | 118491 | Soft | PCSK1 | 5122 | Soft | KISS1R | 84634 | Soft | TSSK6 | 83983 | Soft |
| CFB | 629 | Soft | PCSK4 | 54760 | Soft | KIZ | 55857 | Soft | TTBK2 | 146057 | Soft |
| CFD | 1675 | Soft | PDCD4 | 27250 | Soft | KIZ-AS1 | 101929591 | Soft | TTC21A | 199223 | Soft |
| CFH | 3075 | Soft | PDCD4-AS1 | 282997 | Soft | KLC4 | 3995 | Soft | TTC25 | 83538 | Soft |
| CFHR3 | 10878 | Soft | PDE2A | 5138 | Soft | KLF2 | 10365 | Soft | TTC30A | 92104 | Soft |
| CFI | 3426 | Soft | PDE4C | 5143 | Soft | KLF7 | 8609 | Soft | TTO39A | 29 | Soft |
| CHD5 | 26038 | Soft | PDE4DIP | 9659 | Soft | KLF8 | 11279 | Soft | TTC39B | 158219 | Soft |
| CHD6 | 84181 | Soft | PDE5A | 8654 | Soft | KLHDC1 | 122773 | Soft | TTLL1 | 25809 | Soft |
| CHRM3 | 1131 | Soft | PDE7B | 27115 | Soft | KLHDC8B | 200942 | Soft | TTLL3 | 26140 | Soft |
| CHRNB1 | 1140 | Soft | PDE8B | 8622 | Soft | KLHL24 | 54800 | Soft | TTYH2 | 94015 | Soft |
| CHST1 | 8534 | Soft | PDGFB | 5155 | Soft | KLHL28 | 54813 | Soft | TUB | 7275 | Soft |
| CHST15 | 51363 | Soft | PDGFD | 80310 | Soft | KLHL3 | 26249 | Soft | TUBA3FP | 113691 | Soft |
| CIART | 148523 | Soft | PDGFRA | 5156 | Soft | KLHL30 | 377007 | Soft | TUBA8 | 51807 | Soft |
| CITA | 4261 | Soft | PDGFRB | 5159 | Soft | KLHL31 | 401265 | Soft | TUBAL3 | 79861 | Soft |
| CISH | 1154 | Soft | PDK1 | 5163 | Soft | KLHL36 | 79786 | Soft | TUBB2B | 347733 | Soft |
| CITED2 | 10370 | Soft | PDK3 | 5165 | Soft | KLHL38 | 340359 | Soft | TWIST1 | 7291 | Soft |
| CKB | 1152 | Soft | PDK4 | 5166 | Soft | KLHL7-AS1 | 100775104 | Soft | IXK | 7294 | Soft |
| CLCNKA | 1187 | Soft | PDLIM2 | 64236 | Soft | KLRC2 | 3822 | Soft | TXLNB | 167838 | Soft |
| CLCN16 | 10686 | Soft | PDZD2 | 23037 | Soft | KLRC3 | 3823 | Soft | TXNIP | 10628 | Soft |
| CLDN18 | 51208 | Soft | PDZD7 | 79955 | Soft | KLRC4-KLRK1 | 100528032 | Soft | TYMP | 1890 | Soft |
| CLDN9 | 9080 | Soft | PDZK11P1 | 10158 | Soft | KLRK1 | 22914 | Soft | TYRP1 | 7306 | Soft |
| CLDND2 | 125875 | Soft | PEAR1 | 375033 | Soft | KMO | 8564 | Soft | UBA6-AS1 | 550112 | Soft |
| CLEC11A | 6320 | Soft | PELI2 | 57161 | Soft | KMT2E-AS1 | 100216545 | Soft | UBA7 | 7318 | Soft |
| CLEC2B | 9976 | Soft | PEX11A | 8800 | Soft | KRBA2 | 124751 | Soft | UBAP1L | 390595 | Soft |
| CLEC2D | 29121 | Soft | PEX11G | 92960 | Soft | KRCC1 | 51315 | Soft | UBE2Q2P1 | 388165 | Soft |
| CLEC3B | 7123 | Soft | PEX5L | 51555 | Soft | KREMEN1 | 83999 | Soft | UCN | 7349 | Soft |
| CLHC1 | 130162 | Soft | PEX6 | 5190 | Soft | KREMEN2 | 79412 | Soft | UCN2 | 90226 | Soft |
| CLIC2 | 1193 | Soft | PFKFB4 | 5210 | Soft | KRT17 | 3872 | Soft | UGDH-AS1 | 100885776 | Soft |
| CLIC5 | 53405 | Soft | PFN1P2 | 767846 | Soft | KRT5 | 3852 | Soft | UGT1A1 | 54658 | Soft |
| CLIP1-AS1 | 100507066 | Soft | PGAM2 | 5224 | Soft | KRT79 | 338785 | Soft | UGT1A10 | 54575 | Soft |
| CLIP3 | 25999 | Soft | PGAP1 | 80055 | Soft | KRT84 | 3890 | Soft | UGT1A3 | 54659 | Soft |
| CLK1 | 1195 | Soft | PGF | 5228 | Soft | KRTAP1-5 | 83895 | Soft | UGT1A4 | 54657 | Soft |
| CLK4 | 57396 | Soft | PGPEP1 | 54858 | Soft | KY | 339855 | Soft | UGT1A5 | 54579 | Soft |
| CLMN | 79789 | Soft | PGR | 5241 | Soft | L1CAM | 3897 | Soft | UGT1A6 | 54578 | Soft |
| CLSTN3 | 9746 | Soft | PHEX | 5251 | Soft | L3MBTL1 | 26013 | Soft | UGT1A7 | 54577 | Soft |
| CLUL1 | 27098 | Soft | PHF21A | 51317 | Soft | L3MBTL4 | 91133 | Soft | UGT1A8 | 54576 | Soft |
| CLYBL | 171425 | Soft | PHLDB3 | 653583 | Soft | LAMB2 | 3913 | Soft | UGT1A9 | 54600 | Soft |
| CMKLR1 | 1240 | Soft | PHYHD1 | 254295 | Soft | LAMB2P1 | 22973 | Soft | UGT2A1 | 10941 | Soft |
| CNBD1 | 168975 | Soft | PHYKPL | 85007 | Soft | LAPTM5 | 7805 | Soft | UGT2A2 | 574537 | Soft |

-continued

| GeneSymbol | gene_id | Status | GeneSymbol | gene_id | Status | GeneSymbol | gene_id | Status |
|---|---|---|---|---|---|---|---|---|
| CNNM2 | 54805 | Soft | PIEZO2 | 63895 | Soft | LBH | 81606 | Soft | ULBP1 | 80329 | Soft |
| CNOT8 | 9337 | Soft | PIGV | 55650 | Soft | LBX2 | 85474 | Soft | ULK1 | 8408 | Soft |
| CNR1 | 1268 | Soft | PIGZ | 80235 | Soft | LBX2-AS1 | 151534 | Soft | UNG13C | 440279 | Soft |
| CNRIP1 | 25927 | Soft | PIH1D2 | 120379 | Soft | LCA5 | 167691 | Soft | UNC5B | 219699 | Soft |
| CNTN3 | 5067 | Soft | PIK3C2B | 5287 | Soft | LDB3 | 11155 | Soft | UNC5B-AS1 | 728978 | Soft |
| CNTN5 | 53942 | Soft | PIK3CD-AS2 | 101929074 | Soft | LDHD | 197257 | Soft | URAHP | 100130015 | Soft |
| CNTNAP4 | 85445 | Soft | PIK3IP1 | 113791 | Soft | LDLRAD2 | 401944 | Soft | USP27X-AS1 | 158572 | Soft |
| COL11A2 | 1302 | Soft | PIM1 | 5292 | Soft | LENG8-AS1 | 104355426 | Soft | USP30 | 84749 | Soft |
| COL14A1 | 7373 | Soft | PIP5KL1 | 138429 | Soft | LEPR | 3953 | Soft | VAMP1 | 6843 | Soft |
| COL18A1 | 80781 | Soft | PIPOX | 51268 | Soft | LEPROT | 54741 | Soft | VAMP2 | 6844 | Soft |
| COL21A1 | 81578 | Soft | PITPNM3 | 83394 | Soft | LETMD1 | 25875 | Soft | VASN | 114990 | Soft |
| COL28A1 | 340267 | Soft | PIWIL4 | 143689 | Soft | LGALS9 | 3965 | Soft | VCAM1 | 7412 | Soft |
| COL3A1 | 1281 | Soft | PKD1 | 5310 | Soft | LGI4 | 163175 | Soft | VCAN | 1462 | Soft |
| COL4A2 | 1284 | Soft | PKD1L2 | 114780 | Soft | LHPP | 64077 | Soft | VEGFA | 7422 | Soft |
| COL4A2-AS1 | 100874203 | Soft | PKDCC | 91461 | Soft | LHX9 | 56956 | Soft | VIM-AS1 | 100507347 | Soft |
| COL4A3 | 1285 | Soft | PKDREJ | 10343 | Soft | LIN7A | 8825 | Soft | VLDLR | 7436 | Soft |
| COL4A4 | 1286 | Soft | PKHD1 | 5314 | Soft | LINC-PINT | 378805 | Soft | VLDLR-AS1 | 401491 | Soft |
| COL5A1 | 1289 | Soft | PKHD1L1 | 93035 | Soft | LINC00163 | 727699 | Soft | VMAC | 400673 | Soft |
| COL5A3 | 50509 | Soft | PLA2G6 | 8398 | Soft | LINC00173 | 100287569 | Soft | VNN1 | 8876 | Soft |
| COL6A1 | 1291 | Soft | PLA2R1 | 22925 | Soft | LINC00174 | 285908 | Soft | VPREB3 | 29802 | Soft |
| COL6A2 | 1292 | Soft | PLAG1 | 5324 | Soft | LINC00184 | 100302691 | Soft | VPS37D | 155382 | Soft |
| COL6A4P1 | 344875 | Soft | PLCB1 | 23236 | Soft | LINC00202-1 | 387644 | Soft | VSIG10L | 147645 | Soft |
| COL7A1 | 1294 | Soft | PLCD1 | 5333 | Soft | LINC00202-2 | 731789 | Soft | VWA1 | 64856 | Soft |
| COL9A2 | 1298 | Soft | PLCH2 | 9651 | Soft | LINC00243 | 401247 | Soft | VWA7 | 80737 | Soft |
| COL9A3 | 1299 | Soft | PLCL1 | 5334 | Soft | LINC00324 | 284029 | Soft | VWDE | 221806 | Soft |
| COLCA1 | 399948 | Soft | PLD1 | 5337 | Soft | LINC00332 | 100874127 | Soft | WASH2P | 375260 | Soft |
| COLEC11 | 78989 | Soft | PLEKHA4 | 57664 | Soft | LINC00339 | 29092 | Soft | WBP1 | 23559 | Soft |
| COLEC12 | 81035 | Soft | PLEKHA6 | 22874 | Soft | LINC00525 | 84847 | Soft | WBP5 | 51186 | Soft |
| COLQ | 8292 | Soft | PLEKHG5 | 57449 | Soft | LINC00548 | 400123 | Soft | WDR31 | 114987 | Soft |
| COPG2IT1 | 53844 | Soft | PLEKHH3 | 79990 | Soft | LINC00565 | 100861555 | Soft | WDR60 | 55112 | Soft |
| CORIN | 10699 | Soft | PLEKHS1 | 79949 | Soft | LINC00592 | 283404 | Soft | WDR63 | 126820 | Soft |
| CORO2A | 7464 | Soft | PLIN1 | 5346 | Soft | LINC00598 | 646982 | Soft | WDR78 | 79819 | Soft |
| CORO2B | 10391 | Soft | PLIN2 | 123 | Soft | LINC00607 | 64632 | Soft | WDR93 | 56964 | Soft |
| CORO6 | 84940 | Soft | PLIN4 | 729359 | Soft | LINC00619 | 414260 | Soft | WDR97 | 340390 | Soft |
| CP | 1356 | Soft | PLOD2 | 5352 | Soft | LINC00622 | 644242 | Soft | WEE2-AS1 | 28596 | Soft |
| CPA3 | 1359 | Soft | PLS3-AS1 | 101927352 | Soft | LINC00632 | 286411 | Soft | WFDC1 | 58189 | Soft |
| CPAMD8 | 27151 | Soft | PLSCR4 | 57088 | Soft | LINC00634 | 339674 | Soft | WFDC3 | 140686 | Soft |
| CPE | 1363 | Soft | PLXDC1 | 57125 | Soft | LINC00638 | 196872 | Soft | WFIKKN1 | 117166 | Soft |
| CPLX1 | 10815 | Soft | PLXDC2 | 84898 | Soft | LINC00648 | 100506433 | Soft | WISP1 | 8840 | Soft |
| CPM | 1368 | Soft | PLXNA3 | 55558 | Soft | LINC00649 | 100506334 | Soft | WISP2 | 8839 | Soft |
| CPQ | 10404 | Soft | PLXNB1 | 5364 | Soft | LINC00652 | 29075 | Soft | WNT2B | 7482 | Soft |
| CPT1C | 126129 | Soft | PLXNB3 | 5365 | Soft | LINC00663 | 284440 | Soft | WNT5A | 7474 | Soft |
| CRAT | 1384 | Soft | PLXND1 | 23129 | Soft | LINC00672 | 100505576 | Soft | WWC2-AS2 | 152641 | Soft |
| CREBRF | 153222 | Soft | PMEL | 6490 | Soft | LINC00680-GUSBP4 | 106660613 | Soft | XAF1 | 54739 | Soft |
| CRELD1 | 78987 | Soft | PMFBP1 | 83449 | Soft | LINC00702 | 100688 | Soft | XCR1 | 2829 | Soft |
| CRHR1-IT1 | 147081 | Soft | PNMA2 | 10687 | Soft | LINC00704 | 100216001 | Soft | XKR9 | 389668 | Soft |
| CRIP2 | 13979 | Soft | PNPLA7 | 375775 | Soft | LINC00706 | 100652997 | Soft | YJEFN3 | 374887 | Soft |
| CRISP3 | 10321 | Soft | PODNL1 | 79883 | Soft | LINC00840 | 100506835 | Soft | YPEL2 | 388403 | Soft |
| CRLF1 | 9244 | Soft | POLD4 | 57804 | Soft | LINC00847 | 729678 | Soft | YPEL3 | 83719 | Soft |
| CROCCP3 | 114819 | Soft | POLI | 11201 | Soft | LINC00853 | 100874253 | Soft | YPEL4 | 219539 | Soft |
| CRTAC1 | 55118 | Soft | POM121L9P | 29774 | Soft | LINC00870 | 201617 | Soft | YPEL5 | 51646 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| CRTC1 | 23373 | Soft | POSTN | 10631 | Soft | LINC00877 | 285286 | Soft | ZBED3-AS1 | 728723 | Soft |
| CRYAB | 1410 | Soft | POU5F1 | 5460 | Soft | LINC00882 | 100302640 | Soft | ZBED5-AS1 | 729013 | Soft |
| CSMD3 | 114788 | Soft | POU5F1P3 | 642559 | Soft | LINC00887 | 100131551 | Soft | ZBED6CL | 113763 | Soft |
| CSRNP3 | 80034 | Soft | POU6F1 | 5463 | Soft | LINC00893 | 100131434 | Soft | ZBED8 | 63920 | Soft |
| CSTA | 1475 | Soft | POU6F2 | 11281 | Soft | LINC00894 | 100272228 | Soft | ZBTB1 | 22890 | Soft |
| CTB-113P19.1 | 101927096 | Soft | PPARA | 5465 | Soft | LINC00898 | 400932 | Soft | ZBTB16 | 7704 | Soft |
| CTBS | 1486 | Soft | PPARGC1A | 10891 | Soft | LINC00899 | 100271722 | Soft | ZBTB22 | 9278 | Soft |
| CTC-338M12.4 | 101928649 | Soft | PPEF1 | 5475 | Soft | LINC00910 | 100130581 | Soft | ZBTB25 | 7597 | Soft |
| CTF1 | 1489 | Soft | PPFIA2 | 8499 | Soft | LINC00920 | 100505865 | Soft | ZC3H12D | 340152 | Soft |
| CTSF | 8722 | Soft | PPFIA4 | 8497 | Soft | LINC00921 | 283876 | Soft | ZC3H6 | 376940 | Soft |
| CTSH | 1512 | Soft | PPIL6 | 285755 | Soft | LINC00942 | 100292680 | Soft | ZC3HAV1L | 92092 | Soft |
| CTSK | 1513 | Soft | PPL | 5493 | Soft | LINC00950 | 92973 | Soft | ZC4H2 | 55906 | Soft |
| CTSO | 1519 | Soft | PPM1L | 151742 | Soft | LINC00957 | 255031 | Soft | ZCCHC24 | 219654 | Soft |
| CUBN | 8029 | Soft | PPM1M | 132160 | Soft | LINC00964 | 157381 | Soft | ZCWPW1 | 55063 | Soft |
| CUEDC1 | 404093 | Soft | PPM1N | 147699 | Soft | LINC00969 | 440993 | Soft | ZCWPW2 | 152098 | Soft |
| CUL7 | 9820 | Soft | PPP1R13L | 10848 | Soft | LINC01011 | 401232 | Soft | ZDBF2 | 57683 | Soft |
| CUX1 | 1523 | Soft | PPP1R1C | 151242 | Soft | LINC01024 | 100505636 | Soft | ZDHHC1 | 29800 | Soft |
| CX3CL1 | 6376 | Soft | PPP1R32 | 220004 | Soft | LINC01029 | 101927715 | Soft | ZDHHC11 | 79844 | Soft |
| CXADRP3 | 440224 | Soft | PPP1R3B | 79660 | Soft | LINC01058 | 103724387 | Soft | ZDHHC23 | 254887 | Soft |
| CXCL11 | 6373 | Soft | PPP1R3C | 5507 | Soft | LINC01119 | 100134259 | Soft | IZEB2 | 9839 | Soft |
| CXCL12 | 6387 | Soft | PPP1R3E | 90673 | Soft | LINC01125 | 728537 | Soft | ZEB2-AS1 | 100303491 | Soft |
| CXCL16 | 58191 | Soft | PPP4R1L | 55370 | Soft | LINC01126 | 100129726 | Soft | ZER1 | 10444 | Soft |
| CXCR4 | 7852 | Soft | PRDM1 | 639 | Soft | LINC01137 | 728431 | Soft | ZFHX2 | 85446 | Soft |
| CXXC4 | 80319 | Soft | PRDM2 | 7799 | Soft | LINC01158 | 100506421 | Soft | ZFP14 | 57677 | Soft |
| CXXC5 | 51523 | Soft | PRELID2 | 153768 | Soft | LINC01159 | 102682016 | Soft | ZFP90 | 146198 | Soft |
| CYB5D2 | 124936 | Soft | PRICKLE2 | 166336 | Soft | LINC01179 | 101928151- | Soft | ZFYVE1 | 53349 | Soft |
| CYBRD1 | 79901 | Soft | PRICKLE2-AS1 | 100652759 | Soft | LINC01186 | 101927574 | Soft | ZFYVE28 | 57732 | Soft |
| CYHR1 | 50626 | Soft | PRICKLE2-AS3 | 100874243 | Soft | LINC01219 | 104355220 | Soft | ZG16E | 124220 | Soft |
| CYP11A1 | 1583 | Soft | PRICKLE4 | 29964 | Soft | LINC01260 | 79015 | Soft | ZHX2 | 22882 | Soft |
| CYP17A1 | 1586 | Soft | PRKAA2 | 5563 | Soft | LINC01273 | 101927541 | Soft | ZIC4 | 84107 | Soft |
| CYP19A1 | 1588 | Soft | PRKAB2 | 5565 | Soft | LINC01279 | 100506621 | Soft | ZKSCAN4 | 387032 | Soft |
| CYP27B1 | 1594 | Soft | PRKAG2-AS1 | 100505483 | Soft | LINC01301 | 100505532 | Soft | ZMAT1 | 84460 | Soft |
| CYP2E1 | 1571 | Soft | PRKAR2A-AS1 | 100506637 | Soft | LINC01355 | 100996517 | Soft | ZMIZ1-AS1 | 283050 | Soft |
| CYP39A1 | 51302 | Soft | PRKCE | 5581 | Soft | LINC01410 | 1033 | Soft | ZMYND10 | 51364 | Soft |
| CYP4B1 | 1580 | Soft | PRKCZ | 5590 | Soft | LINC01426 | 100506385 | Soft | ZMYND8 | 23613 | Soft |
| CYP4F11 | 57834 | Soft | PRKG1 | 5592 | Soft | LINC01443 | 400644 | Soft | ZNF112 | 7771 | Soft |
| CYTH4 | 27128 | Soft | PRKG1-AS1 | 100506385 | Soft | LINC01512 | 100132354 | Soft | ZNF117 | 51351 | Soft |
| CYTIP | 9595 | Soft | PRKG2 | 5593 | Soft | LINC01518 | 101929397 | Soft | ZNF136 | 7695 | Soft |
| DACT3 | 147906 | Soft | PROB1 | 389333 | Soft | LINC01530 | 729975 | Soft | ZNF137P | 7696 | Soft |
| DARS-AS1 | 101928243 | Soft | PROC | 147011 | Soft | LINC01534 | 101927621 | Soft | ZNF14 | 7561 | Soft |
| DBH | 1621 | Soft | PROCA1 | 5625 | Soft | LINC01537 | 101928555 | Soft | ZNF155 | 7711 | Soft |
| DBH-AS1 | 138948 | Soft | PRODH | 5625 | Soft | LINC01556 | 729583 | Soft | ZNF160 | 90338 | Soft |
| DBNDD1 | 79007 | Soft | PROS1 | 5627 | Soft | LINC01569 | 100507501 | Soft | ZNF165 | 7718 | Soft |
| DBNDD2 | 55861 | Soft | PROX2 | 283571 | Soft | LINC01583 | 101929690 | Soft | ZNF175 | 7728 | Soft |
| DBP | 1628 | Soft | PRR29 | 92340 | Soft | LINC01588 | 283551 | Soft | ZNF192P1 | 651302 | Soft |
| DCHS2 | 54798 | Soft | PRR36 | 80164 | Soft | LING01589 | 100506737 | Soft | ZNF204P | 7754 | Soft |
| DCLK1 | 9201 | Soft | PRR5L | 79899 | Soft | LINC01615 | 101929484 | Soft | ZNF214 | 7761 | Soft |
| DCLK2 | 166614 | Soft | PRRG4 | 79056 | Soft | LINC01619 | 256021 | Soft | ZNF221 | 7638 | Soft |
| DON | 1634 | Soft | PRRT1 | 80863 | Soft | LINCR-0002 | 103344926 | Soft | ZNF222 | 7673 | Soft |
| DCST2 | 27579 | Soft | PRRT2 | 112476 | Soft | LINGO2 | 158038 | Soft | ZNF223 | 7766 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| DDIT4 | 54541 | Soft | PRRX2 | 51450 | Soft | LINGO3 | 645191 | Soft | ZNF224 | 7767 | Soft |
| DDIT4L | 115265 | Soft | PRSS16 | 10279 | Soft | LIPE-AS1 | 100996307 | Soft | ZNF225 | 7768 | Soft |
| DDO | 8528 | Soft | PRSS27 | 83886 | Soft | LMBR1L | 55716 | Soft | ZNF226 | 7769 | Soft |
| DDR1 | 780 | Soft | PRSS36 | 146547 | Soft | LMBRD1 | 55788 | Soft | ZNF230 | 7773 | Soft |
| DDR2 | 4921 | Soft | PRSS5 | 339105 | Soft | LMF1 | 56788 | Soft | ZNF233 | 353355 | Soft |
| DDX60 | 55601 | Soft | PRX | 57716 | Soft | LMNTD2 | 256329 | Soft | ZNF248 | 57209 | Soft |
| DENND3 | 22898 | Soft | PSD | 5662 | Soft | LMO3 | 55885 | Soft | ZNF25 | 219749 | Soft |
| DENND4C | 55667 | Soft | PSG1 | 5669 | Soft | LMOD1 | 25802 | Soft | ZNF250 | 58500 | Soft |
| DENND6B | 414918 | Soft | PSG4 | 5672 | Soft | LMTK3 | 114783 | Soft | ZNF251 | 90987 | Soft |
| DEPTOR | 64798 | Soft | PSMG3-AS1 | 114796 | Soft | LNX1 | 84708 | Soft | ZNF252P-AS1 | 286103 | Soft |
| DFNB31 | 25861 | Soft | PSORSIC1 | 170679 | Soft | LOC100128288 | 100128288 | Soft | ZNF264 | 9422 | Soft |
| DHRS1 | 115817 | Soft | PSORSIC2 | 170680 | Soft | LOC100129138 | 100129138 | Soft | ZNF280D | 54816 | Soft |
| DHRS13 | 147015 | Soft | PSORSIC3 | 100130889 | Soft | LOC100129534 | 100129534 | Soft | ZNF284 | 342 | Soft |
| DHRS3 | 9249 | Soft | PSPN | 5623 | Soft | LOC100129603 | 100129603 | Soft | ZNF285 | | Soft |
| DHX58 | 79132 | Soft | PTCH1 | 5727 | Soft | LOC100129617 | 100129617 | Soft | ZNF292 | 23 | Soft |
| DIGER1-AS1 | 400242 | Soft | PTCH2 | 8643 | Soft | LOC100129924 | 100129924 | Soft | ZNF311 | 328 | Soft |
| DISC1 | 27185 | Soft | PTGER2 | 5732 | Soft | LOC100129940 | 100129940 | Soft | ZNF32-AS1 | 414197 | Soft |
| DXDC1 | 85458 | Soft | PTGES3L | 100885848 | Soft | LOC100129973 | 100129973 | Soft | ZNF337-AS1 | 102724826 | Soft |
| DKFZp4340226 | 93429 | Soft | PTGFR | 5737 | Soft | LOC100130417 | 100130417 | Soft | ZNF33B | 7582 | Soft |
| DKFZP586I1420 | 222161 | Soft | PTGIR | 5739 | Soft | LOC100130476 | 100130476 | Soft | ZNF345 | 350 | Soft |
| DLG4 | 1742 | Soft | PTGS1 | 5742 | Soft | LOC100130691 | 100130691 | Soft | ZNF358 | 140467 | Soft |
| DLGAP1-AS1 | 649446 | Soft | PTH1R | 5745 | Soft | LOC100130987 | 100130987 | Soft | ZNF366 | 167465 | Soft |
| DLX4 | 1748 | Soft | PTK6 | 5753 | Soft | LOC100132057 | 100132057 | Soft | ZNF383 | 163087 | Soft |
| DMPK | 1760 | Soft | PTP4A3 | 11156 | Soft | LOC100134368 | 100134368 | Soft | ZNF385A | 25946 | Soft |
| DNAH1 | 25981 | Soft | PTPRB | 5787 | Soft | LOC100270804 | 100270804 | Soft | ZNF385B | 151126 | Soft |
| DNAH2 | 146754 | Soft | PTPRD | 5789 | Soft | LOC100287036 | 100287036 | Soft | ZNF385C | 201181 | Soft |
| DNAH5 | 1767 | Soft | PTPRH | 5794 | Soft | LOC100288152 | 100288152 | Soft | ZNF391 | 346157 | Soft |
| DNAH6 | 1768 | Soft | PTPRM | 5797 | Soft | LOC100288798 | 100288798 | Soft | ZNF395 | 5893 | Soft |
| DNAH7 | 56171 | Soft | PTPRN | 5798 | Soft | LOC100288911 | 100288911 | Soft | ZNF396 | 252884 | Soft |
| DNAJB2 | 3300 | Soft | PTPRO | 5800 | Soft | LOC100289230 | 100289230 | Soft | ZNF404 | 342908 | Soft |
| DNAJC18 | 202052 | Soft | PTPRR | 5801 | Soft | LOC100289495 | 100289495 | Soft | ZNF419 | 79744 | Soft |
| DNAJC22 | 79962 | Soft | PTPRU | 10076 | Soft | LOC100379224 | 100379224 | Soft | ZNF420 | 147923 | Soft |
| DNAJC28 | 54943 | Soft | PYROXD2 | 84795 | Soft | LOC100421746 | 100421746 | Soft | ZNF436-AS1 | 148898 | Soft |
| DNAJC4 | 3338 | Soft | QPRT | 23475 | Soft | LOC100494484-C9ORF174 | 57653 | Soft | ZNF444 | 55311 | Soft |
| DNAJC5G | 285126 | Soft | RAB11B-AS1 | 100507567 | Soft | LOG100505715 | 100505715 | Soft | ZNF446 | 55663 | Soft |
| DNAL4 | 10126 | Soft | RAB11FIP4 | 84440 | Soft | LOC100505771 | 100505771 | Soft | ZNF461 | 92283 | Soft |
| DNM1P35 | 100128285 | Soft | RAB20 | 55647 | Soft | LOC100505938 | 100505938 | Soft | ZNF467 | 163544 | Soft |
| DNM1P46 | 196968 | Soft | RAB26 | 25837 | Soft | LOC100506022 | 100506022 | Soft | ZNF470 | 388566 | Soft |
| DNM3 | 26052 | Soft | RAB30 | 27314 | Soft | LOC100506127 | 100506127 | Soft | ZNF485 | 220992 | Soft |
| DNM3OS | 100628315 | Soft | RAB33B | 83452 | Soft | LOC100506258 | 100506258 | Soft | ZNF490 | 57474 | Soft |
| DOCK2 | 1794 | Soft | RAB3A | 5864 | Soft | LOC100506271 | 100506271 | Soft | ZNF493 | 284443 | Soft |
| DOCK3 | 1795 | Soft | RAB3D | 9545 | Soft | LOC100506444 | 100506444 | Soft | ZNF501 | 115560 | Soft |
| DOCK6 | 57572 | Soft | RAB40A | 142684 | Soft | LOC100506472 | 100506472 | Soft | ZNF516 | 9658 | Soft |
| DOK4 | 55715 | Soft | RAB400 | 57799 | Soft | LOC100506476 | 100506476 | Soft | ZNF517 | 340385 | Soft |
| DPP4 | 1803 | Soft | RAB6B | 51560 | Soft | LOC100506548 | 100506548 | Soft | ZNF529 | 57711 | Soft |
| DPY19L2P2 | 349152 | Soft | RAB7B | 338382 | Soft | LOC100506679 | 100506679 | Soft | ZNF529-AS1 | 101927599 | Soft |
| DPYD | 1806 | Soft | RAB8B | 51762 | Soft | LOC100506688 | 100506688 | Soft | ZNF546 | 339327 | Soft |
| DPYSL4 | 10570 | Soft | RABGAP1L | 9910 | Soft | LOC100506746 | 100506746 | Soft | ZNF548 | 147694 | Soft |
| DRC3 | 83450 | Soft | RABLZA | 11159 | Soft | LOC100506990 | 100506990 | Soft | ZNF550 | 162972 | Soft |
| DRD4 | 1815 | Soft | RAD51-AS1 | 100505648 | Soft | LOC100507002 | 100507002 | Soft | ZNF554 | 115196 | Soft |

-continued

| GeneSymbol | gene_id | Status | GeneSymbol | gene_id | Status | GeneSymbol | gene_id | Status |
|---|---|---|---|---|---|---|---|---|
| DTNA | 1837 | Soft | RAET1G | 353091 | Soft | LOC100507053 | 100507053 | Soft | ZNF559 | 84527 | Soft |
| DTX3 | 196403 | Soft | RAG1 | 5896 | Soft | LOC100507156 | 100507156 | Soft | ZNF559-ZNF177 | 100529215 | Soft |
| DTX4 | 23220 | Soft | RALGDS | 5900 | Soft | LOC100507283 | 100507283 | Soft | ZNF572 | 137209 | Soft |
| DUOX1 | 53905 | Soft | RAP2C-AS1 | 101928578 | Soft | LOC100507291 | 100507291 | Soft | ZNF575 | 284346 | Soft |
| DUSP10 | 11221 | Soft | RAPGEF3 | 10411 | Soft | LOC100507346 | 100507346 | Soft | ZNF577 | 84765 | Soft |
| DUSP19 | 142679 | Soft | RAPGEF4 | 11069 | Soft | LOC100507373 | 100507373 | Soft | ZNF581 | 51545 | Soft |
| DUSP5P1 | 574029 | Soft | RARA-AS1 | 101929693 | Soft | LOC100507477 | 100507477 | Soft | ZNF585A | 199704 | Soft |
| DYRK1B | 9149 | Soft | RARRES2 | 5919 | Soft | LOC100507487 | 100507487 | Soft | ZNF596 | 169270 | Soft |
| EBF1 | 1879 | Soft | RARRES3 | 5920 | Soft | LOC100507547 | 100507547 | Soft | ZNF599 | 148103 | Soft |
| EBF4 | 57593 | Soft | RASA4 | 10156 | Soft | LOC100507642 | 100507642 | Soft | ZNF605 | 100288635 | Soft |
| EBI3 | 10148 | Soft | RASA4B | 100271927 | Soft | LOC100652768 | 100652768 | Soft | ZNF608 | 57507 | Soft |
| EDN1 | 1906 | Soft | RASA4CP | 401331 | Soft | LOC100652999 | 100652999 | Soft | ZNF615 | 284370 | Soft |
| EDN2 | 1907 | Soft | RASD2 | 23551 | Soft | LOC100996634 | 100996634 | Soft | ZNF630 | 57232 | Soft |
| EDNRA | 1909 | Soft | RASSF2 | 9770 | Soft | LOC100996693 | 100996693 | Soft | ZNF648 | 127665 | Soft |
| EFCAB12 | 90288 | Soft | RASSF4 | 83937 | Soft | LOC101060389 | 101060389 | Soft | ZNF654 | 55279 | Soft |
| EFCAB13 | 124989 | Soft | RASSF5 | 83593 | Soft | LOC101448202 | 101448202 | Soft | ZNF662 | 389114 | Soft |
| EFCAB6 | 64800 | Soft | RASSF9 | 9182 | Soft | LOC101926935 | 101926935 | Soft | ZNF699 | 374879 | Soft |
| EFEMP2 | 30008 | Soft | RBM43 | 375287 | Soft | LOC101927045 | 101927045 | Soft | ZNF713 | 349075 | Soft |
| EFHB | 151651 | Soft | RBM5-AS1 | 100775107 | Soft | LOC101927056 | 101927056 | Soft | ZNF747 | 65988 | Soft |
| EFHC1 | 114327 | Soft | RBMS3 | 27303 | Soft | LOC101927204 | 101927204 | Soft | ZNF775 | 285971 | Soft |
| EFHD1 | 80303 | Soft | RBP5 | 83758 | Soft | LOC101927229 | 101927229 | Soft | ZNF789 | 285989 | Soft |
| EFNA3 | 1944 | Soft | RCOR2 | 283248 | Soft | LOC101927282 | 101927282 | Soft | ZNF790 | 388536 | Soft |
| EFNA4 | 1945 | Soft | RDM1 | 201299 | Soft | LOC101927356 | 101927356 | Soft | ZNF808 | 388558 | Soft |
| EFNB3 | 1949 | Soft | RECK | 8434 | Soft | LOC101927365 | 101927365 | Soft | ZNF815P | 401303 | Soft |
| EGF | 1950 | Soft | REEPZ | 51308 | Soft | LOC101927391 | 101927391 | Soft | ZNF821 | 55565 | Soft |
| EGFL8 | 80864 | Soft | REEP6 | 92840 | Soft | LOC101927415 | 101927415 | Soft | ZNF83 | 55769 | Soft |
| EGLN3 | 112399 | Soft | REM2 | 161253 | Soft | LOC101927482 | 101927482 | Soft | ZNF836 | 162962 | Soft |
| EIF3J-AS1 | 645212 | Soft | REPS2 | 9185 | Soft | LOC101927501 | 101927501 | Soft | ZNF837 | 116412 | Soft |
| EIF4E3 | 317649 | Soft | RERG | 85004 | Soft | LOC101927740 | 101927740 | Soft | ZNF84 | 7637 | Soft |
| ELN | 2006 | Soft | RFTN2 | 130132 | Soft | LOC101927759 | 101927759 | Soft | ZNF846 | 162993 | Soft |
| EMILIN3 | 90187 | Soft | RFX2 | 5990 | Soft | LOC101927770- | 101927770- | Soft | ZNF862 | 643641 | Soft |
| EMX2 | 2018 | Soft | RGAG4 | 340526 | Soft | LOC101927780 | 101927780 | Soft | ZP1 | 22917 | Soft |
| ENDOV | 284131 | Soft | RGS11 | 8786 | Soft | LOC101927843 | 101927843 | Soft | ZP3 | 7784 | Soft |
| ENKUR | 219670 | Soft | RGS14 | 10636 | Soft | LOC101927865 | 101927865 | Soft | ZSCAN16-AS1 | 100129195 | Soft |
| ENO2 | 2026 | Soft | RGS3 | 5998 | Soft | LOC101927934 | 101927934 | Soft | ZSCAN2 | 54993 | Soft |
| ENO3 | 2027 | Soft | RHBDL1 | 9028 | Soft | LOC101928034 | 101928034 | Soft | ZSCAN23 | 222696 | Soft |
| ENPP3 | 5169 | Soft | RHBDL2 | 54933 | Soft | LOC101928063 | 101928063 | Soft | ZSCAN30 | 100101467 | Soft |
| EPB41L4A-AS1 | 114915 | Soft | RHOU | 58480 | Soft | LOC101928068 | 101928068 | Soft | ZSCAN31 | 64288 | Soft |
| LOC101928222 | 101928222 | Soft | ZXDA | 7789 | Soft | LOC101928100 | 101928100 | Soft | ZSWIM4 | 65249 | Soft |
| | | | | | | LOC101928103 | 101928103 | Soft | and ZSWIM5 | 57643 | Soft |

2. The composition, kit, or system of claim 1, wherein said nucleic acid reagents are selected from the group consisting of a plurality of nucleic acid probes, a plurality of nucleic acid primers, and a plurality of pairs of nucleic acid primers.

3. A composition, kit, or system, comprising:
 a plurality of labeled nucleic acid reagents for specifically detecting the level of expression of all of the following genes:

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| ABCC9 | 10060 | Stiff | MBL1P | 8512 | Stiff | ELF3 | 1999 | Stiff | RTEL1 | 51750 | Stiff |
| ABCF2 | 10061 | Stiff | MBLAC1 | 255374 | Stiff | ELFN1 | 392617 | Stiff | RTEL1-TNFRSF6B | 100533107 | Stiff |
| ABCG2 | 9429 | Stiff | MCAT | 27349 | Stiff | ELMO3 | 79767 | Stiff | RTN4IP1 | 84816 | Stiff |
| ABHD11 | 83451 | Stiff | MCF2 | 4168 | Stiff | EMC8 | 10328 | Stiff | RTN4R | 65078 | Stiff |
| ABHD13 | 84945 | Stiff | MCF2L | 23263 | Stiff | EMG1 | 10436 | Stiff | RUNX3 | 864 | Stiff |
| ABHD5 | 51099 | Stiff | MCIDAS | 345643 | Stiff | EN2 | 2020 | Stiff | RUVBL1 | 8607 | Stiff |
| ACAN | 176 | Stiff | MCM10 | 55388 | Stiff | ENDOD1 | 23052 | Stiff | RYR3 | 6263 | Stiff |
| ACOX2 | 8309 | Stiff | MCM8 | 84515 | Stiff | ENOX2 | 10495 | Stiff | S1PR1 | 1901 | Stiff |
| ACSL3 | 2181 | Stiff | MCM8-AS1 | 101929225 | Stiff | ENPP1 | 5167 | Stiff | SAC3D1 | 29901 | Stiff |
| ACTL10 | 170487 | Stiff | MCM9 | 254394 | Stiff | ENTPD1 | 953 | Stiff | SACS | 26278 | Stiff |
| ACTL8 | 81569 | Stiff | MCOLN1 | 57192 | Stiff | ENTPD1-AS1 | 728558 | Stiff | SAMD5 | 389432 | Stiff |
| ACTR5 | 79913 | Stiff | MDFI | 4188 | Stiff | ENTPD7 | 57089 | Stiff | SAP30L-AS1 | 386627 | Stiff |
| ADAM19 | 8728 | Stiff | MED27 | 9442 | Stiff | EPB41L3 | 23136 | Stiff | SAPCD2 | 89958 | Stiff |
| ADAM23 | 8745 | Stiff | MEGF10 | 84466 | Stiff | EPB41L4B | 54566 | Stiff | SBDSP1 | 155370 | Stiff |
| ADAMTS12 | 81792 | Stiff | MESDC1 | 59274 | Stiff | EPHB2 | 2048 | Stiff | SCAMP5 | 192683 | Stiff |
| ADAMTS14 | 140766 | Stiff | METTL1 | 4234 | Stiff | EPHB6 | 2051 | Stiff | SCARA3 | 51435 | Stiff |
| ADAT1 | 23536 | Stiff | MFSD2A | 84879 | Stiff | EPHX3 | 79852 | Stiff | SCLY | 51540 | Stiff |
| ADCY1 | 107 | Stiff | MGAT5B | 146664 | Stiff | EPT1 | 85465 | Stiff | SCO1 | 6341 | Stiff |
| ADCY7 | 113 | Stiff | MGC12916 | 84815 | Stiff | ERCC6L | 1833 | Stiff | SCUBE1 | 80274 | Stiff |
| ADD2 | 119 | Stiff | MGLL | 11343 | Stiff | EREG | 2069 | Stiff | SDC1 | 6382 | Stiff |
| ADGRG2 | 10149 | Stiff | MICALL1 | 85377 | Stiff | ESCO2 | 157570 | Stiff | SDF2L1 | 23753 | Stiff |
| ADGRG6 | 57211 | Stiff | MIIP | 60672 | Stiff | EXO1 | 9156 | Stiff | SDSL | 113675 | Stiff |
| ADRM1 | 11047 | Stiff | MIR1237 | 100302280 | Stiff | EXO5 | 64789 | Stiff | SEC11C | 90701 | Stiff |
| AEN | 64782 | Stiff | MIR1306 | 100302197 | Stiff | EXOG | 9941 | Stiff | SEMA3D | 22117 | Stiff |
| AFAP1L2 | 84632 | Stiff | MIR17HG | 407975 | Stiff | EXOSC3 | 51010 | Stiff | SEMA4D | 10507 | Stiff |
| AFP | 174 | Stiff | MIR22HG | 84981 | Stiff | EXOSC4 | 54512 | Stiff | SEMA7A | 8482 | Stiff |
| AIF1L | 83543 | Stiff | MIR3176 | 100423037 | Stiff | EXOSC6 | 118460 | Stiff | SENP3 | 26168 | Stiff |
| AJAP1 | 55966 | Stiff | MIR3658 | 100500832 | Stiff | EXTL3 | 2137 | Stiff | SERHL | 94009 | Stiff |
| ALCAM | 214 | Stiff | MIR589 | 693174 | Stiff | FAM101B | 359845 | Stiff | SERINC2 | 347735 | Stiff |
| ALDH1B1 | 219 | Stiff | MIR600HG | 81571 | Stiff | FAM118B | 79607 | Stiff | SERPINB3 | 6317 | Stiff |
| ALDH4A1 | 8659 | Stiff | MIR664B | 100847052 | Stiff | FAM169A | 26049 | Stiff | SERPINB4 | 6318 | Stiff |
| ALG1 | 56052 | Stiff | MIR6758 | 102465454 | Stiff | FAM171A1 | 221061 | Stiff | SERPINB7 | 8710 | Stiff |
| ALG1L9P | 285407 | Stiff | MIR6776 | 102465465 | Stiff | FAM189A1 | 23359 | Stiff | SFMBT1 | 51460 | Stiff |
| ALYREF | 10189 | Stiff | MIR6804 | 102465482 | Stiff | FAM208B | 54906 | Stiff | SFN | 2810 | Stiff |
| AMD1 | 262 | Stiff | MIS12 | 79003 | Stiff | FAM222A | 84915 | Stiff | SFXN2 | 118980 | Stiff |
| AMICA1 | 120425 | Stiff | MITF | 4286 | Stiff | FAM225A | 286333 | Stiff | SGK223 | 157285 | Stiff |
| AMIGO2 | 347902 | Stiff | MKL1 | 57591 | Stiff | FAM43A | 131583 | Stiff | SGK3 | 23678 | Stiff |
| AMPH | 273 | Stiff | MLP | 90523 | Stiff | FAM58A | 92002 | Stiff | SH2D2A | 9047 | Stiff |
| AMZ1 | 155185 | Stiff | MMP1 | 4312 | Stiff | FAM72C | 554282 | Stiff | SH2D5 | 400745 | Stiff |
| ANAPC7 | 51434 | Stiff | MMP3 | 4314 | Stiff | FAM81A | 145773 | Stiff | SH3RF2 | 153769 | Stiff |
| ANKRD39 | 51239 | Stiff | MON1A | 84315 | Stiff | FAM84A | 151354 | Stiff | SKA3 | 221150 | Stiff |
| ANKRD52 | 283373 | Stiff | MPP6 | 51678 | Stiff | FAM86C1 | 55199 | Stiff | SLC19A1 | 6573 | Stiff |
| ANP32D | 23519 | Stiff | MPV17L2 | 84769 | Stiff | FAM89A | 375061 | Stiff | SLC20A1 | 6574 | Stiff |
| ANXA3 | 306 | Stiff | MPZL3 | 196264 | Stiff | FAM98A | 25940 | Stiff | SLC20A2 | 6575 | Stiff |
| AOC1 | 26 | Stiff | MRM1 | 79922 | Stiff | FANCA | 2175 | Stiff | SLC25A10 | 1468 | Stiff |
| AP1M2 | 10053 | Stiff | MROH6 | 642475 | Stiff | FASN | 2194 | Stiff | SLC25A13 | 10165 | Stiff |
| AP4E1 | 23431 | Stiff | MROH7-TTC4 | 100527960 | Stiff | FAXC | 84553 | Stiff | SLC25A18 | 83733 | Stiff |
| AP5B1 | 91056 | Stiff | MRPL20 | 55052 | Stiff | FBF1 | 85302 | Stiff | SLC25A19 | 60386 | Stiff |
| APBA1 | 320 | Stiff | MRPS12 | 6183 | Stiff | FBXL6 | 26233 | Stiff | SLC25A25 | 114789 | Stiff |
| APITD1 | 378708 | Stiff | MRTO4 | 51154 | Stiff | | | | SLC25A32 | 81034 | Stiff |

-continued

| GeneSymbol | gene_id | GeneSymbol | gene_id | Status | GeneSymbol | gene_id | Status | GeneSymbol | gene_id | Status |
|---|---|---|---|---|---|---|---|---|---|---|
| APTTD1-CORT | 100526739 | MSLN | 10232 | Stiff | FDX1 | 2230 | Stiff | SLC25A33 | 84275 | Stiff |
| APOO | 79135 | MSR1 | 4481 | Stiff | FDXACB1 | 91893 | Stiff | SLC25A44 | 9673 | Stiff |
| APOOP5 | 644649 | MSRB1 | 51734 | Stiff | FEM1A | 55527 | Stiff | SLC26A2 | 1836 | Stiff |
| ARAP2 | 116984 | MSTO1 | 55154 | Stiff | FGD6 | 55785 | Stiff | SLC27A4 | 10999 | Stiff |
| ARC | 23237 | MSTO2P | 100129405 | Stiff | FGF1 | 2246 | Stiff | SLC29A3 | 55315 | Stiff |
| AREG | 374 | MSX1 | 4487 | Stiff | FGF5 | 2250 | Stiff | SLC2A6 | 11182 | Stiff |
| ARHGEF4 | 50649 | MSX2 | 4488 | Stiff | FHOD3 | 80206 | Stiff | SLC35B1 | 10237 | Stiff |
| ARL14 | 80117 | MTFR2 | 113115 | Stiff | FICD | 11153 | Stiff | SLC35G1 | 159371 | Stiff |
| ARMC6 | 93436 | MTOR | 2475 | Stiff | FIX1 | 24147 | Stiff | SLC36A1 | 206358 | Stiff |
| ARMC7 | 79637 | MTOR-AS1 | 100873935 | Stiff | FLAD1 | 80308 | Stiff | SLC37A1 | 54020 | Stiff |
| ARMCX4 | 100131755 | MUC13 | 56667 | Stiff | FLG | 2312 | Stiff | SLC38A3 | 10991 | Stiff |
| ARNTL2 | 56938 | MUC5AC | 4586 | Stiff | FLI1 | 2313 | Stiff | SLC39A3 | 29985 | Stiff |
| ARNTL2-AS1 | 101928646 | MUC6 | 4588 | Stiff | FOXA1 | 3169 | Stiff | SLC43A2 | 124935 | Stiff |
| ARPC5L | 81873 | MVB12B | 89853 | Stiff | FOXC1 | 2296 | Stiff | SLC45A3 | 85414 | Stiff |
| ARRDC1-AS1 | 85026 | MYBBP1A | 10514 | Stiff | FPR1 | 2357 | Stiff | SLC45A4 | 57210 | Stiff |
| ARSB | 411 | MYEOV2 | 150678 | Stiff | FSIP2 | 401024 | Stiff | SLC4A11 | 83959 | Stiff |
| ASRGL1 | 80150 | MYH10 | 4628 | Stiff | FTSJ3 | 117246 | Stiff | SLC4A8 | 9498 | Stiff |
| ATAD3A | 55210 | MYH15 | 22989 | Stiff | FXN | 2395 | Stiff | SLC52A2 | 79581 | Stiff |
| ATAD3B | 83858 | MYLK2 | 85366 | Stiff | FZD9 | 8326 | Stiff | SLC5A6 | 8884 | Stiff |
| ATF5 | 22809 | MYO5B | 4645 | Stiff | GAB3 | 139716 | Stiff | SLC7A11 | 23657 | Stiff |
| ATF7IP2 | 80063 | MYT1 | 4661 | Stiff | GALNT10 | 55568 | Stiff | SLC7A2 | 6542 | Stiff |
| ATG101 | 60673 | MYZAP | 100820829 | Stiff | GALNT14 | 79623 | Stiff | SLC9A2 | 6549 | Stiff |
| ATP2A1-AS1 | 100289092 | NAA15 | 80155 | Stiff | GALNT7 | 51809 | Stiff | SLCO1B3 | 28234 | Stiff |
| ATP6V0A2 | 23545 | NAPRT | 93100 | Stiff | GALR2 | 8811 | Stiff | SLCO3A1 | 28232 | Stiff |
| ATP6V0D2 | 245972 | NAT1 | 9 | Stiff | GAR1 | 54433 | Stiff | SLFN12L | 100506736 | Stiff |
| ATP6V0E2 | 155066 | NBPF20 | 100288142 | Stiff | GATAD2A | 54815 | Stiff | SMAGP | 57228 | Stiff |
| ATP6V0E2-AS1 | 401431 | NCEH1 | 57552 | Stiff | GCH1 | 2643 | Stiff | SMCO4 | 56935 | Stiff |
| ATP6V1B1-AS1 | 101927750 | NDOR1 | 27158 | Stiff | GCLM | 2730 | Stiff | SNAP25 | 6616 | Stiff |
| ATR | 545 | NDUFAF4 | 29078 | Stiff | GDA | 9615 | Stiff | SNHG9 | 735301 | Stiff |
| AUNIP | 79000 | NDUFAF6 | 137682 | Stiff | GDAP1 | 54332 | Stiff | SNORA10 | 574042 | Stiff |
| B3GALNT1 | 8706 | NETO2 | 81831 | Stiff | GDPD5 | 81544 | Stiff | SNORA17A | 677804 | Stiff |
| B3GALT1 | 8708 | NFKBIB | 4793 | Stiff | GEMIN4 | 50628 | Stiff | SNORA22 | 677807 | Stiff |
| B3GLCT | 145173 | NIP7 | 51388 | Stiff | GEMIN6 | 79833 | Stiff | SNORA3B | 677826 | Stiff |
| B3GNT2 | 10678 | NIPA2 | 81614 | Stiff | GFM1 | 85476 | Stiff | SNORA48 | 652965 | Stiff |
| B4GALT6 | 9331 | NKX3-1 | 4824 | Stiff | GFOD1 | 54438 | Stiff | SNORA51 | 677831 | Stiff |
| BAIAP2L2 | 80115 | NLK | 51701 | Stiff | GFRA1 | 2674 | Stiff | SNORA52 | 619565 | Stiff |
| BAMBI | 25805 | NLRP2 | 55655 | Stiff | GINS3 | 64785 | Stiff | SNORA55 | 677834 | Stiff |
| BATF3 | 55509 | NLRP3 | 114548 | Stiff | GINS4 | 84296 | Stiff | SNORA6 | 574040 | Stiff |
| BCAR3 | 8412 | NOC4L | 79050 | Stiff | GIPC1 | 10755 | Stiff | SNORA65 | 26783 | Stiff |
| BCCIP | 56647 | NOL12 | 79159 | Stiff | GJA3 | 2700 | Stiff | SNORA71G | 677839 | Stiff |
| BCR | 613 | NOL6 | 65083 | Stiff | GLB1L3 | 112937 | Stiff | SNORD101 | 594837 | Stiff |
| BDKRB1 | 623 | NOLC1 | 9221 | Stiff | GLDC | 2731 | Stiff | SNORD110 | 692213 | Stiff |
| BEND3 | 57673 | NOP16 | 51491 | Stiff | GLMN | 11146 | Stiff | SNORD119 | 100113378 | Stiff |
| BEND7 | 222389 | NOP2 | 4839 | Stiff | GLRX2 | 51022 | Stiff | SNORD120 | 26765 | Stiff |
| BEST3 | 144453 | NOP56 | 10528 | Stiff | GLYCTK | 132158 | Stiff | SNORD14C | 85389 | Stiff |
| BLM | 641 | NOS1AP | 9722 | Stiff | GMPPB | 29925 | Stiff | SNORD14D | 85390 | Stiff |
| BMP8A | 353500 | NOVA1 | 4857 | Stiff | GNAS-AS1 | 149775 | Stiff | SNORD17 | 692086 | Stiff |
| BMS1P21 | 100288974 | NOXO1 | 124056 | Stiff | GNG4 | 2786 | Stiff | SNORD2 | 619567 | Stiff |
| BNC1 | 646 | NPB | 25933 | Stiff | GNLY | 10578 | Stiff | SNORD26 | 9302 | Stiff |
| BNC2 | 54796 | NPLOC4 | 55666 | Stiff | GPAT3 | 84803 | Stiff | SNORD27 | 9301 | Stiff |
| BORA | 79866 | NPR3 | 4883 | Stiff | GPATCH4 | 54865 | Stiff | SNORD28 | 9300 | Stiff |

-continued

| GeneSymbol | gene_id | Status | GeneSymbol | gene_id | Status | GeneSymbol | gene_id | Status |
|---|---|---|---|---|---|---|---|---|
| BORCS8 | 729991 | Stiff | NR1I3 | 9970 | Stiff | GPR1 | 2825 | Stiff | SNORD29 | 9297 | Stiff |
| BRIX1 | 55299 | Stiff | NR2F2 | 7026 | Stiff | GPR3 | 2827 | Stiff | SNORD30 | 9299 | Stiff |
| BRMS1 | 25855 | Stiff | NRADDP | 100129354 | Stiff | GPR75 | 10936 | Stiff | SNORD45A | 26805 | Stiff |
| BYSL | 705 | Stiff | NRG1 | 3084 | Stiff | GPR87 | 53836 | Stiff | SNORD48 | 26801 | Stiff |
| C10orf128 | 170371 | Stiff | NRGN | 4900 | Stiff | GPRIN1 | 114787 | Stiff | SNORD57 | 26792 | Stiff |
| C10orf2 | 56652 | Stiff | NRP2 | 8828 | Stiff | GRHL1 | 29841 | Stiff | SNORD83A | 116937 | Stiff |
| C11orf91 | 100131378 | Stiff | NRROS | 375387 | Stiff | GRWD1 | 83743 | Stiff | SNORD83B | 116938 | Stiff |
| C11orf96 | 387763 | Stiff | NSUN2 | 54888 | Stiff | GSDMC | 56169 | Stiff | SNORD86 | 692201 | Stiff |
| C11orf98 | 102288414 | Stiff | NTMT1 | 28989 | Stiff | GSG2 | 3903 | Stiff | SNPH | 9751 | Stiff |
| C12orf4 | 57102 | Stiff | NTN4 | 59277 | Stiff | GTF2H2 | 2966 | Stiff | SNRNP25 | 79622 | Stiff |
| C12orf43 | 64897 | Stiff | NUDT15 | 55270 | Stiff | GTF2H2B | 653238 | Stiff | SNRNP40 | 9410 | Stiff |
| C12orf49 | 79794 | Stiff | NUDT16 | 131870 | Stiff | GTF2H2C | 728340 | Stiff | SOGA3 | 387104 | Stiff |
| C14orf169 | 79697 | Stiff | NUFIP1 | 26747 | Stiff | GTF2H2C_2 | 730394 | Stiff | SOX7 | 83595 | Stiff |
| C14orf80 | 28364 | Stiff | NUP93 | 9688 | Stiff | GTF3C6 | 112495 | Stiff | SOX9 | 6662 | Stiff |
| C16orf59 | 80178 | Stiff | NXT1 | 29107 | Stiff | GTPBP4 | 60 | Stiff | SP6 | 80320 | Stiff |
| C17orf51 | 339263 | Stiff | ODC1 | 4953 | Stiff | GXYLT1 | 283464 | Stiff | SP7 | 121340 | Stiff |
| C17orf89 | 284184 | Stiff | OGFOD1 | 55239 | Stiff | GYG2 | 8908 | Stiff | SPAG1 | 6674 | Stiff |
| C19orf147 | 126526 | Stiff | OGFRP1 | 388906 | Stiff | HABP4 | 22927 | Stiff | SPATA5 | 166378 | Stiff |
| C19orf73 | 55150 | Stiff | OLAH | 55301 | Stiff | HAPLN1 | 1404 | Stiff | SPECC1 | 92521 | Stiff |
| C1orf106 | 55765 | Stiff | ONECUT2 | 9480 | Stiff | HARBI1 | 283254 | Stiff | SPNS2 | 124976 | Stiff |
| C1orf109 | 54956 | Stiff | OPA3 | 80207 | Stiff | HAS3 | 3038 | Stiff | SPP1 | 6696 | Stiff |
| C1orf226 | 400793 | Stiff | OR2W3 | 343171 | Stiff | HAUS7 | 55559 | Stiff | SPRR2D | 6703 | Stiff |
| C20orf24 | 55969 | Stiff | ORAI1 | 84876 | Stiff | HBEGF | 1839 | Stiff | SPRTN | 83932 | Stiff |
| C2CD2L | 9854 | Stiff | ORC6 | 23594 | Stiff | HEATR3 | 55027 | Stiff | SPTB | 6710 | Stiff |
| C3AR1 | 719 | Stiff | OSBP2 | 23762 | Stiff | HGF | 3082 | Stiff | SPX | 80763 | Stiff |
| C3orf52 | 79669 | Stiff | OSBPL6 | 114880 | Stiff | HGH1 | 51236 | Stiff | SRP19 | 6728 | Stiff |
| C6orf58 | 3529999 | Stiff | OSTM1 | 28962 | Stiff | HHAT | 55733 | Stiff | SRPK3 | 26576 | Stiff |
| C7orf26 | 79034 | Stiff | OTUD6B | 51633 | Stiff | HHIP | 64399 | Stiff | SSSCA1 | 10534 | Stiff |
| C7orf43 | 55262 | Stiff | P2RY2 | 5029 | Stiff | HHIP-AS1 | 646576 | Stiff | SSTR1 | 6751 | Stiff |
| C9orf78 | 51759 | Stiff | PAEP | 5047 | Stiff | HHIPL2 | 79802 | Stiff | ST6GALNAC5 | 81849 | Stiff |
| CA2 | 760 | Stiff | PAK1IP1 | 55003 | Stiff | HIRA | 7290 | Stiff | STEAP1 | 26872 | Stiff |
| CABLES1 | 91768 | Stiff | PALM2 | 114299 | Stiff | HIST1H2AE | 3012 | Stiff | STK10 | 6793 | Stiff |
| CAMK2N2 | 94032 | Stiff | PAQR9 | 344838 | Stiff | HIST1H2AG | 8969 | Stiff | STON2 | 85439 | Stiff |
| CAND2 | 23066 | Stiff | PCAT7 | 101928099 | Stiff | HIST1H2AH | 85235 | Stiff | STOX2 | 56977 | Stiff |
| CARD11 | 84433 | Stiff | PCDH9 | 5101 | Stiff | HIST1H2AM | 8336 | Stiff | STRBP | 55342 | Stiff |
| CARD8-AS1 | 100505812 | Stiff | PCDHGA1 | 56114 | Stiff | HIST1H2BC | 8347 | Stiff | STRIP2 | 57464 | Stiff |
| CARD9 | 64170 | Stiff | PCDHGA10 | 56106 | Stiff | HIST1H2BF | 8343 | Stiff | STS | 412 | Stiff |
| CASZ1 | 54897 | Stiff | PCDHGA11 | 56105 | Stiff | HIST1H2BG | 8339 | Stiff | STX11 | 8676 | Stiff |
| CCBE1 | 147372 | Stiff | PCDHGA12 | 26025 | Stiff | HIST1H2BI | 8346 | Stiff | STXBP5L | 9515 | Stiff |
| CCDC137 | 339230 | Stiff | PCDHGA2 | 56113 | Stiff | HIST1H2BJ | 8970 | Stiff | STYK1 | 55359 | Stiff |
| CCDC168 | 643677 | Stiff | PCDHGA3 | 56112 | Stiff | HIST1H2BM | 8342 | Stiff | SURF2 | 6835 | Stiff |
| CCDC86 | 79080 | Stiff | PCDHGA4 | 56111 | Stiff | HIST1H2BO | 8348 | Stiff | SUSD4 | 55061 | Stiff |
| CCDC96 | 257236 | Stiff | PCDHGA5 | 56110 | Stiff | HIST1H3B | 8358 | Stiff | SUV39H1 | 6839 | Stiff |
| CCL20 | 6364 | Stiff | PCDHGA7 | 56108 | Stiff | HIST1H3D | 8351 | Stiff | SVIP | 258010 | Stiff |
| CCNE1 | 898 | Stiff | PCDHGA8 | 9708 | Stiff | HIST1H3F | 8968 | Stiff | SWSAP1 | 126074 | Stiff |
| CCNE2 | 9134 | Stiff | PCDHGA9 | 56107 | Stiff | HIST1H3G | 8355 | Stiff | SYNPO2L | 79933 | Stiff |
| CCNF | 899 | Stiff | PCDHGB1 | 56104 | Stiff | HIST1H4A | 8359 | Stiff | SYT1 | 6857 | Stiff |
| CCNJ | 54619 | Stiff | PCDHGB2 | 56103 | Stiff | HIST1H4B | 8366 | Stiff | TACC2 | 10579 | Stiff |
| CCNO | 10309 | Stiff | PCDHGB3 | 56102 | Stiff | HIST1H4C | 8364 | Stiff | TACO1 | 51204 | Stiff |
| CCNYL1 | 151195 | Stiff | PCDHGB4 | 8641 | Stiff | HIST2H2AC | 8338 | Stiff | TAF13 | 6884 | Stiff |
| CD101 | 9398 | Stiff | PCDHGB5 | 56101 | Stiff | HIST2H2BF | 440689 | Stiff | TAF5 | 6877 | Stiff |

| GeneSymbol | gene_id | Status | GeneSymbol | gene_id | Status | GeneSymbol | gene_id | Status |
|---|---|---|---|---|---|---|---|---|
| CD274 | 29126 | Stiff | PCDHGB6 | 56100 | Stiff | HIVEP3 | 59269 | Stiff |
| CD300C | 10871 | Stiff | PCDHGB7 | 56099 | Stiff | HMGB3 | 3149 | Stiff |
| CD70 | 970 | Stiff | PCDHGC3 | 5098 | Stiff | HNRNPAB | 3182 | Stiff |
| CDC25A | 993 | Stiff | PCDHGC4 | 56098 | Stiff | HOXB3 | 3213 | Stiff |
| CDC42EP2 | 10435 | Stiff | PCDHGC5 | 56097 | Stiff | HOXD8 | 3234 | Stiff |
| CDC6 | 990 | Stiff | PCNXL3 | 399909 | Stiff | HRK | 8739 | Stiff |
| CDC7 | 8317 | Stiff | PCSK7 | 9159 | Stiff | HS3ST1 | 9957 | Stiff |
| CDCA7 | 83879 | Stiff | PCYT2 | 5833 | Stiff | HS3ST3A1 | 9955 | Stiff |
| CDH11 | 1009 | Stiff | PDCD2L | 84306 | Stiff | HSH2D | 84941 | Stiff |
| CDH15 | 1013 | Stiff | PDCD6IPP2 | 646278 | Stiff | HSPA14 | 51182 | Stiff |
| CELF5 | 60680 | Stiff | PDCL3 | 79031 | Stiff | HSPA1B | 3304 | Stiff |
| CENPM | 79019 | Stiff | PDE12 | 201626 | Stiff | HSPA6 | 3310 | Stiff |
| CENPN | 55839 | Stiff | PDE1C | 5137 | Stiff | HSPBAP1 | 79663 | Stiff |
| CENPP | 401541 | Stiff | PDSS1 | 23590 | Stiff | HSPH1 | 10808 | Stiff |
| CENPV | 201161 | Stiff | PFAS | 5198 | Stiff | HTR7 | 3363 | Stiff |
| CEP78 | 84131 | Stiff | PFDN2 | 5202 | Stiff | HYAL2 | 8692 | Stiff |
| CES1P2 | 390732 | Stiff | PGAM5 | 192111 | Stiff | HYOU1 | 10525 | Stiff |
| CFAP157 | 286207 | Stiff | PGP | 283871 | Stiff | IDH3A | 3419 | Stiff |
| CGNL1 | 84952 | Stiff | PHF19 | 26147 | Stiff | IFRD2 | 7866 | Stiff |
| CHAC2 | 494143 | Stiff | PHF5A | 84844 | Stiff | IGF2BP3 | 10643 | Stiff |
| CHAD | 1101 | Stiff | PHLDA2 | 7262 | Stiff | IGFN1 | 91156 | Stiff |
| CHFR | 55743 | Stiff | PHLPP2 | 23035 | Stiff | IHH | 3549 | Stiff |
| CHL1 | 10752 | Stiff | PHOSPHO1 | 162466 | Stiff | IL12A | 3592 | Stiff |
| CHORDC1 | 26973 | Stiff | P13 | 5266 | Stiff | IL1A | 3552 | Stiff |
| CHRNA3 | 1136 | Stiff | PIGW | 284098 | Stiff | IL1B | 3553 | Stiff |
| CHRNA5 | 1138 | Stiff | PIK3R4 | 30849 | Stiff | IL6 | 3569 | Stiff |
| CHUK | 1147 | Stiff | PINX1 | 54984 | Stiff | ILDR2 | 387597 | Stiff |
| CLCN5 | 1184 | Stiff | PITX1 | 5307 | Stiff | INHBA | 3624 | Stiff |
| CLDN1 | 9076 | Stiff | PKI55 | 150967 | Stiff | INSC | 387755 | Stiff |
| CLDN10 | 9071 | Stiff | PKMYT1 | 9088 | Stiff | IPO13 | 9670 | Stiff |
| CLDN11 | 5010 | Stiff | PLAT | 5327 | Stiff | IPO5P1 | 100132815 | Stiff |
| CLN6 | 54982 | Stiff | PLCD4 | 84812 | Stiff | ISG20L2 | 64768 | Stiff |
| CLSPN | 63967 | Stiff | PLCE1 | 51196 | Stiff | ISM1 | 81875 | Stiff |
| CLTB | 1212 | Stiff | PLCE1-AS1 | 100128054 | Stiff | ISOC1 | 140862 | Stiff |
| CLUH | 23277 | Stiff | PLD5 | 200150 | Stiff | ISOC2 | 51015 | Stiff |
| CMTM7 | 112616 | Stiff | PLEK2 | 26499 | Stiff | ITGA6 | 79763 | Stiff |
| CNIH3 | 149111 | Stiff | PLK3 | 1263 | Stiff | ITGAE | 3655 | Stiff |
| CNN3 | 1266 | Stiff | PLXNA2 | 5362 | Stiff | ITGB1BP2 | 3682 | Stiff |
| CNTF | 1270 | Stiff | PLXNA4 | 91584 | Stiff | JADE2 | 26548 | Stiff |
| CNTNAP2 | 26047 | Stiff | PNO1 | 56902 | Stiff | JAM3 | 9358 | Stiff |
| COA7 | 65260 | Stiff | PNP | 4860 | Stiff | JMJD4 | 23338 | Stiff |
| COBLL1 | 22837 | Stiff | PNPT1 | 87178 | Stiff | KANK1 | 83700 | Stiff |
| COL10A1 | 1300 | Stiff | PODXL | 5420 | Stiff | KBTBD8 | 65094 | Stiff |
| COL13A1 | 1305 | Stiff | PODXL2 | 50512 | Stiff | KCNH2 | 23189 | Stiff |
| COL17A1 | 1308 | Stiff | POLA2 | 23649 | Stiff | KCNQ3 | 84541 | Stiff |
| COL20A1 | 57642 | Stiff | POLE3 | 54107 | Stiff | KDM8 | 3757 | Stiff |
| CREB5 | 9586 | Stiff | POLR1A | 25885 | Stiff | KIAA0513 | 3786 | Stiff |
| CREG2 | 200407 | Stiff | POLR3B | 55703 | Stiff | KIAA0754 | 79831 | Stiff |
| CREM | 1390 | Stiff | POLR3E | 55718 | Stiff | KIAA1524 | 57650 | Stiff |
| CRSP8P | 441089 | Stiff | POLR3G | 10622 | Stiff | | | |
| CRY1 | 1407 | Stiff | POLR3K | 51728 | Stiff | | | |

| GeneSymbol | gene_id | Status |
|---|---|---|
| TAF5L | 27097 | Stiff |
| TBC1D4 | 9882 | Stiff |
| TBX2 | 6909 | Stiff |
| TCHP | 84260 | Stiff |
| TCOF | 6949 | Stiff |
| TDG | 6996 | Stiff |
| TEAD4 | 7004 | Stiff |
| TELO2 | 9894 | Stiff |
| TENM3 | 55714 | Stiff |
| TEX2 | 55852 | Stiff |
| TEX30 | 93081 | Stiff |
| TFB2M | 64216 | Stiff |
| TFRC | 7037 | Stiff |
| TGM2 | 7052 | Stiff |
| THAP7 | 80764 | Stiff |
| THBD | 7056 | Stiff |
| TIAM1 | 7074 | Stiff |
| TIGAR | 57103 | Stiff |
| TIMM10 | 26519 | Stiff |
| TIMM17A | 10440 | Stiff |
| TIMM22 | 29928 | Stiff |
| TIMM23 | 100287932 | Stiff |
| TIMM23B | 100652748 | Stiff |
| TIMM8A | 1678 | Stiff |
| TIPIN | 54962 | Stiff |
| TIP1 | 7082 | Stiff |
| TMC7 | 79905 | Stiff |
| TMEFF2 | 23671 | Stiff |
| TMEM104 | 54868 | Stiff |
| TMEM110-MUSTN1 | 100526772 | Stiff |
| TMEM138 | 51524 | Stiff |
| TMEM154 | 201799 | Stiff |
| TMEM177 | 80775 | Stiff |
| TMEM199 | 147007 | Stiff |
| TMEM201 | 199953 | Stiff |
| TMEM206 | 55248 | Stiff |
| TMEM236 | 653567 | Stiff |
| TMEM249 | 340393 | Stiff |
| TMEM251 | 26175 | Stiff |
| TMEM33 | 55161 | Stiff |
| TMEM5 | 10329 | Stiff |
| TMPO | 7112 | Stiff |
| TNF | 7124 | Stiff |
| TNFRSF12A | 51330 | Stiff |
| TNFRSF21 | 27242 | Stiff |
| TNFRSF8 | 943 | Stiff |
| TNS4 | 84951 | Stiff |
| TOE1 | 114034 | Stiff |
| TOMM40 | 10452 | Stiff |
| TOMM40L | 84134 | Stiff |
| TONSL | 4796 | Stiff |

| GeneSymbol | gene_id | Status | GeneSymbol | gene_id | Status | GeneSymbol | gene_id | Status |
|---|---|---|---|---|---|---|---|---|
| CRYBA2 | 1412 | Stiff | POMGNT2 | 84892 | Stiff | KIAA1549L | 25758 | Stiff |
| CSF2 | 1437 | Stiff | POP1 | 10940 | Stiff | KIF21B | 23046 | Stiff |
| CSF2RB | 1439 | Stiff | POP5 | 51367 | Stiff | KLG2 | 64837 | Stiff |
| CSF3 | 1440 | Stiff | POP7 | 10248 | Stiff | KLF5 | 688 | Stiff |
| CSGALNACT1 | 55790 | Stiff | POU3F2 | 5454 | Stiff | KLHL18 | 23276 | Stiff |
| CST7 | 8530 | Stiff | PPARGC1B | 133522 | Stiff | KLHL25 | 64410 | Stiff |
| CSTF2 | 1478 | Stiff | PPIC | 5480 | Stiff | KLHL9 | 55958 | Stiff |
| CTNND2 | 1501 | Stiff | PPIF | 10105 | Stiff | KLK4 | 9622 | Stiff |
| CTPS1 | 1503 | Stiff | PPIL1 | 51645 | Stiff | KNOP1 | 400506 | Stiff |
| CTSL | 1514 | Stiff | PPRC1 | 23082 | Stiff | KPNA2 | 3838 | Stiff |
| CTSV | 1515 | Stiff | PRADC1 | 84279 | Stiff | KPNA3 | 3839 | Stiff |
| CTSW | 1521 | Stiff | PRDM16 | 63976 | Stiff | KRT1 | 3848 | Stiff |
| CTU2 | 348180 | Stiff | PREB | 10113 | Stiff | KRT15 | 3866 | Stiff |
| CXCL1 | 2919 | Stiff | PRF1 | 5551 | Stiff | KRT3 | 3850 | Stiff |
| CXCL2 | 2920 | Stiff | PRKCQ-AS1 | 439949 | Stiff | KRT34 | 3885 | Stiff |
| CXCL3 | 2921 | Stiff | PRLR | 5618 | Stiff | KRT81 | 3887 | Stiff |
| CXCL8 | 3576 | Stiff | PRMT6 | 55170 | Stiff | KSR1 | 8844 | Stiff |
| CYB5R2 | 51700 | Stiff | PROSER2 | 254427 | Stiff | L3MBTL2 | 83746 | Stiff |
| CYCS | 54205 | Stiff | PRR22 | 163154 | Stiff | LANCL2 | 55915 | Stiff |
| DAB2 | 1601 | Stiff | PRR5 | 55615 | Stiff | LARP4 | 113251 | Stiff |
| DAW1 | 164781 | Stiff | PRRX1 | 5396 | Stiff | LCMT2 | 9836 | Stiff |
| DBF4 | 10926 | Stiff | PSEN2 | 5664 | Stiff | LCTL | 197021 | Stiff |
| DBF4B | 80174 | Stiff | PSMC4 | 5704 | Stiff | LDLRAP1 | 26119 | Stiff |
| DCBLD2 | 131566 | Stiff | PSMD1 | 5707 | Stiff | LETM1 | 3954 | Stiff |
| DCTPP1 | 79077 | Stiff | PSMD11 | 5717 | Stiff | LETM2 | 137994 | Stiff |
| DDIAS | 220042 | Stiff | PSME3 | 10197 | Stiff | LIF | 3976 | Stiff |
| DDX10 | 1662 | Stiff | PSME4 | 23198 | Stiff | LIG3 | 3980 | Stiff |
| DDX19A | 55308 | Stiff | PSPC1 | 55269 | Stiff | LINC00311 | 197196 | Stiff |
| DDX21 | 9188 | Stiff | PTGDR2 | 11251 | Stiff | LINC00346 | 283487 | Stiff |
| DDX28 | 55794 | Stiff | PTRH1 | 138428 | Stiff | LING00707 | 100507127 | Stiff |
| DDX46 | 9879 | Stiff | PTS | 5805 | Stiff | LINC00857 | 439990 | Stiff |
| DDX51 | 317781 | Stiff | PTX3 | 5806 | Stiff | LINC00880 | 339894 | Stiff |
| DDX52 | 11056 | Stiff | PUM3 | 9933 | Stiff | LINC00941 | 100287314 | Stiff |
| DENND5B | 160518 | Stiff | PUS1 | 80324 | Stiff | LINC01117 | 1027224 | Stiff |
| DEPDC1-AS1 | 101927220 | Stiff | PUSL1 | 126789 | Stiff | LINC01224 | 104472717 | Stiff |
| DGCR11 | 25786 | Stiff | PVR | 5817 | Stiff | LINC01287 | 103724390 | Stiff |
| DGCR5 | 26220 | Stiff | PVRL1 | 5818 | Stiff | LINC01322 | 103695433 | Stiff |
| DGKG | 1608 | Stiff | PWP2 | 5822 | Stiff | LINC01468 | 101928687 | Stiff |
| DHCR24 | 1718 | Stiff | PYCRL | 65263 | Stiff | LINC01605 | 100507420 | Stiff |
| DHRS11 | 79154 | Stiff | PZP | 5858 | Stiff | LIPG | 9388 | Stiff |
| DHRS2 | 10202 | Stiff | RAB27B | 5874 | Stiff | LIPH | 200879 | Stiff |
| DHRS9 | 10170 | Stiff | RAB3B | 5865 | Stiff | LMO7-AS1 | 101927155 | Stiff |
| DHX34 | 9704 | Stiff | RABEP1 | 9135 | Stiff | LOC100128361 | 100128361 | Stiff |
| DHX37 | 57647 | Stiff | RABIF | 5877 | Stiff | LOC100129046 | 100129046 | Stiff |
| DIO2 | 1734 | Stiff | RANGAP1 | 5905 | Stiff | LOC100130238 | 100130238 | Stiff |
| DIO2-AS1 | 100628307 | Stiff | RAPGEFL1 | 51195 | Stiff | LOC100287042 | 100287042 | Stiff |
| DKC1 | 1736 | Stiff | RASGEF1B | 153020 | Stiff | LOC100499489 | 100499489 | Stiff |
| DLEU2 | 8847 | Stiff | RASGRP1 | 10125 | Stiff | LOC100506302 | 100506302 | Stiff |
| DLEU2L | 79469 | Stiff | RBM24 | 221662 | Stiff | LOC100507634 | 100507634 | Stiff |
| DLX3 | 1747 | Stiff | RBM28 | 55131 | Stiff | LOC101926940 | 101926940 | Stiff |
| DLX5 | 1749 | Stiff | RBP4 | 5950 | Stiff | LOC101927267 | 101927267 | Stiff |

| GeneSymbol | gene_id | Status |
|---|---|---|
| TONSL-AS1 | 100287098 | Stiff |
| TOR1A | 1861 | Stiff |
| TOR3A | 64222 | Stiff |
| TP53RK | 112858 | Stiff |
| TRAPPC10 | 7109 | Stiff |
| TRAPPC13 | 80006 | Stiff |
| TREX2 | 11219 | Stiff |
| TRHDE-AS1 | 283392 | Stiff |
| TRMO | 51531 | Stiff |
| TRMT12 | 55039 | Stiff |
| TRMT6 | 51605 | Stiff |
| TRMT61A | 115708 | Stiff |
| TRPM2 | 7226 | Stiff |
| TRPV4 | 59341 | Stiff |
| TSC22D2 | 9819 | Stiff |
| TSEN54 | 283989 | Stiff |
| TSHZ3 | 57616 | Stiff |
| TSPAN17 | 26262 | Stiff |
| TSSC4 | 10078 | Stiff |
| TTC4 | 7268 | Stiff |
| TTF2 | 8458 | Stiff |
| TTLL11 | 158135 | Stiff |
| TTN | 7273 | Stiff |
| TUBB1 | 81027 | Stiff |
| TUBGCP5 | 114791 | Stiff |
| TXNDC9 | 10190 | Stiff |
| UBASH3B | 84959 | Stiff |
| UBE2F-SCLY | 100533179 | Stiff |
| UBIAD1 | 914 | Stiff |
| UCA1 | 652995 | Stiff |
| UCHL3 | 7347 | Stiff |
| UFSP1 | 402682 | Stiff |
| UHRF1 | 29128 | Stiff |
| URB2 | 9816 | Stiff |
| UTP15 | 84135 | Stiff |
| UTP20 | 27340 | Stiff |
| UTP3 | 57050 | Stiff |
| VEPH1 | 79674 | Stiff |
| VGF | 7425 | Stiff |
| VPS53 | 55275 | Stiff |
| VPS9D1-AS1 | 100128881 | Stiff |
| VWA2 | 340706 | Stiff |
| WDR4 | 10785 | Stiff |
| WDR46 | 9277 | Stiff |
| WDR62 | 284403 | Stiff |
| WDR77 | 79084 | Stiff |
| WFS1 | 7466 | Stiff |
| WNT5B | 81029 | Stiff |
| WNT9A | 7483 | Stiff |
| WRAP53 | 55135 | Stiff |
| WTAPP1 | 100288077 | Stiff |

| GeneSymbol | gene_id | Status | GeneSymbol | gene_id | Status | GeneSymbol | gene_id | Status |
|---|---|---|---|---|---|---|---|---|
| DMRTA2 | 63950 | Stiff | RBPMS2 | 348093 | Stiff | LOC101927746 | 101927746 | Stiff | XIRP2 | 129446 | Stiff |
| DNAJB11 | 51726 | Stiff | RCL1 | 10171 | Stiff | LOC101928163 | 10192 8163 | Stiff | XPO4 | 64328 | Stiff |
| DNLZ | 728489 | Stiff | RDH10 | 157506 | Stiff | LOC102723729 | 102723729 | Stiff | XRCC2 | 7516 | Stiff |
| DOCK4 | 9732 | Stiff | RECQL4 | 9401 | Stiff | LOC102724434 | 102724434 | Stiff | YRDC | 79693 | Stiff |
| DOCK9 | 23348 | Stiff | RELN | 5649 | Stiff | LOC105370333 | 105370333 | Stiff | ZBTB2 | 57621 | Stiff |
| DOHH | 83475 | Stiff | RFK | 55312 | Stiff | 339166 | 339166 | Stiff | ZBTB7C | 201501 | Stiff |
| DOLK | 22845 | Stiff | RFX8 | 731220 | Stiff | 341056 | 341056 | Stiff | ZBTB9 | 221504 | Stiff |
| DOLPP1 | 57171 | Stiff | RIMS2 | 9699 | Stiff | LOC341472 | 541472 | Stiff | ZDHHC14 | 79683 | Stiff |
| DPF3 | 8110 | Stiff | RIOK | 83732 | Stiff | LOC646762 | 646762 | Stiff | ZFAND4 | 93550 | Stiff |
| DPH2 | 1802 | Stiff | RNASEH1 | 246243 | Stiff | LRP8 | 7804 | Stiff | ZFP69B | 65243 | Stiff |
| DPH3 | 285381 | Stiff | RNASEH1-AS1 | 100506054 | Stiff | LRR1 | 122769 | Stiff | ZIC5 | 85416 | Stiff |
| DSP | 1832 | Stiff | RNF219 | 79596 | Stiff | LRRC59 | 55379 | Stiff | ZIK1 | 284307 | Stiff |
| DUS1L | 64118 | Stiff | RNF219-AS1 | 100874222 | Stiff | LRWD1 | 225559 | Stiff | ZMPSTE24 | 10269 | Stiff |
| DUS3L | 56931 | Stiff | RNMTL1 | 55178 | Stiff | LSG1 | 5341 | Stiff | ZMYND19 | 116225 | Stiff |
| DUSP5 | 1847 | Stiff | ROR1 | 4919 | Stiff | LSM10 | 84967 | Stiff | ZNF30 | 90075 | Stiff |
| DUSP8 | 1850 | Stiff | RPGR | 6103 | Stiff | LSMEM2 | 132228 | Stiff | ZNF300 | 91975 | Stiff |
| DUSP9 | 1852 | Stiff | RPP40 | 10799 | Stiff | LITV1 | 84946 | Stiff | ZNF35 | 7584 | Stiff |
| DYSF | 8291 | Stiff | RPS16P5 | 647190 | Stiff | LUM | 4060 | Stiff | ZNF365 | 22891 | Stiff |
| E2F6 | 1876 | Stiff | RPS26 | 6231 | Stiff | LYAR | 55646 | Stiff | ZNF43 | 7594 | Stiff |
| E2F7 | 144455 | Stiff | RPS6KA4 | 8986 | Stiff | LZTS1 | 11178 | Stiff | ZNF469 | 84627 | Stiff |
| BBNA1BP2 | 10969 | Stiff | RPUSD1 | 113000 | Stiff | MAGEA3 | 4102 | Stiff | ZNF488 | 118738 | Stiff |
| ECE2 | 110599564 | Stiff | RPUSD2 | 27079 | Stiff | MAGEA6 | 4105 | Stiff | ZNF583 | 147949 | Stiff |
| ECE2 | 110599583 | Stiff | RRP1 | 8568 | Stiff | MAGI2-AS3 | 100505881 | Stiff | ZNF593 | 51042 | Stiff |
| EDEM3 | 80267 | Stiff | RRP12 | 23223 | Stiff | MAGOHB | 55110 | Stiff | ZNF681 | 148213 | Stiff |
| EEF1E1 | 9521 | Stiff | RRP15 | 51018 | Stiff | MAK16 | 84549 | Stiff | ZNF689 | 115509 | Stiff |
| EEF2KMT | 196483 | Stiff | RRP1B | 23076 | Stiff | MAP2K4 | 6416 | Stiff | ZNF736 | 728927 | Stiff |
| EFR3B | 22979 | Stiff | RRP36 | 88745 | Stiff | MAP3K9 | 4293 | Stiff | ZNF778 | 197320 | Stiff |
| EID2 | 163126 | Stiff | RRP7A | 27341 | Stiff | MAP6D1 | 79929 | Stiff | ZNF786 | 136051 | Stiff |
| EIF4E | 1977 | Stiff | RRP7BP | 91695 | Stiff | MARCH3 | 115123 | Stiff | ZNF85 | 7639 | Stiff |
| EIF5A2 | 56648 | Stiff | RRP9 | 9136 | Stiff | MARCH4 | 57574 | Stiff | ZNHIT2 | 741 | Stiff |
| ELAC2 | 60528 | Stiff | RRS1 | 23212 | Stiff | MARS2 | 92935 | Stiff | ZWILCH | 55055 | Stiff |
| ELAVL2 | 1993 | Stiff | RSPH4A | 345895 | Stiff | MB | 4151 | Stiff | LOC101928414 | 101928414 | Soft |
| A1BG | 1 | Soft | LOC101928453 | 101928453 | Soft | EPHA5 | 2044 | Soft | RHPN1 | 114822 | Soft |
| AATBC | 284837 | Soft | LOC101928489 | 101928489 | Soft | EPHA5-AS1 | 100144602 | Soft | RIBC1 | 158787 | Soft |
| AATK | 9625 | Soft | LOC101928673 | 101928673 | Soft | EPHA7 | 2045 | Soft | RIMS3 | 9783 | Soft |
| ABAT | 18 | Soft | LOC101928710 | 101928710 | Soft | EPHX2 | 2053 | Soft | RIMS4 | 140730 | Soft |
| ABCA2 | 20 | Soft | LOC101928718 | 101928718 | Soft | EPOR | 2057 | Soft | RIOK3 | 8780 | Soft |
| ABCA3 | 21 | Soft | LOC101928767 | 101928767 | Soft | EPPK1 | 83481 | Soft | RIPK4 | 54101 | Soft |
| ABCA4 | 24 | Soft | LOC101928978 | 101928978 | Soft | EPS8L1 | 54869 | Soft | RLN3 | 117579 | Soft |
| ABCA6 | 23460 | Soft | LOC101929140 | 101929140 | Soft | EPS8L2 | 64787 | Soft | RMDN2 | 151393 | Soft |
| ABCA8 | 10351 | Soft | LOC101929371 | 101929371 | Soft | EPSTI1 | 94240 | Soft | RNASE4 | 6038 | Soft |
| ABCA9 | 10350 | Soft | LOC101929378 | 101929378 | Soft | ERICH2 | 285141 | Soft | RNASET2 | 8635 | Soft |
| ABCB1 | 5243 | Soft | LOC101929532 | 101929532 | Soft | ERMN | 57471 | Soft | RNF122 | 79845 | Soft |
| ABCC3 | 8714 | Soft | LOC101929709 | 101929709 | Soft | ERV3-1 | 2086 | Soft | RNF128 | 79589 | Soft |
| ABHD1 | 84696 | Soft | LOC101929710 | 101929710 | Soft | ESPNL | 339768 | Soft | RNF150 | 57484 | Soft |
| ABHD4 | 63874 | Soft | LOC101929767 | 101929767 | Soft | ETV7 | 51513 | Soft | RNF165 | 494470 | Soft |
| ABHD8 | 79575 | Soft | LOC102477328 | 102477328 | Soft | EVA1B | 55194 | Soft | RNF180 | 285671 | Soft |
| ABLIM2 | 84448 | Soft | LOC102503427 | 102503427 | Soft | EVA1C | 59271 | Soft | RNF212B | 100507650 | Soft |
| ABTB1 | 80325 | Soft | LOC102723809 | 102723809 | Soft | EXD3 | 54932 | Soft | RNF215 | 200312 | Soft |
| ACAD11 | 84129 | Soft | LOC102724050 | 102724050 | Soft | EXOC3L1 | 283849 | Soft | RNF217 | 154214 | Soft |
| ACADL | 33 | Soft | LOC102724190 | 102724190 | Soft | EYA1 | 2138 | Soft | RNF24 | 11237 | Soft |

-continued

| GeneSymbol | gene_id | Status | GeneSymbol | gene_id | Status | GeneSymbol | gene_id | Status |
|---|---|---|---|---|---|---|---|---|
| ACADS | 35 | Soft | LOC102724467 | 102724467 | Soft | EYA2 | 2139 | Soft | RNF32 | 140545 | Soft |
| ACAP1 | 9744 | Soft | LOC102724814 | 102724814 | Soft | EYS | 346007 | Soft | RNF39 | 80352 | Soft |
| ACBD4 | 79777 | Soft | LOC102724927 | 102724927 | Soft | F10 | 2159 | Soft | RNF44 | 2838 | Soft |
| ACCS | 84680 | Soft | LOC103021296 | 103021296 | Soft | F11R | 50848 | Soft | RNPC3 | 55599 | Soft |
| ACKR1 | 2532 | Soft | LOC103091866 | 103091866 | Soft | F2RL2 | 2151 | Soft | ROPN1L | 83853 | Soft |
| ACKR3 | 57007 | Soft | LOC105372795 | 105372795 | Soft | F8 | 2157 | Soft | RORA | 6095 | Soft |
| ACOT4 | 122970 | Soft | LOC105447645 | 105447645 | Soft | FAAH | 2166 | Soft | RORC | 6097 | Soft |
| ACP5 | 54 | Soft | LOC105747689 | 105747689 | Soft | FAM102B | 284611 | Soft | ROS1 | 6098 | Soft |
| ACP6 | 51205 | Soft | LOC113230 | 113230 | Soft | FAM114A1 | 92689 | Soft | RPH3AL | 9501 | Soft |
| ACPP | 55 | Soft | LOC115110 | 115110 | Soft | FAM122C | 159091 | Soft | RPL32P3 | 132241 | Soft |
| ACRC | 93953 | Soft | LOC143666 | 143666 | Soft | FAM131B | 9715 | Soft | RPL34-AS1 | 285456 | Soft |
| ACSF2 | 80221 | Soft | LOC145783 | 145783 | Soft | FAM131C | 348487 | Soft | RPLP0P2 | 113157 | Soft |
| ACSM3 | 6296 | Soft | LOC148696 | 148696 | Soft | FAM134B | 54463 | Soft | RPS10P7 | 376693 | Soft |
| ACSM4 | 34139 | Soft | LOC154761 | 154761 | Soft | FAM13A | 10144 | Soft | RPS15AP10 | 728963 | Soft |
| ACSM5 | 54988 | Soft | LOC155060 | 155060 | Soft | FAM13A-AS1 | 285512 | Soft | RPS29 | 6235 | Soft |
| ACTA2 | 59 | Soft | LOC171391 | 171391 | Soft | FAM149B1 | 317662 | Soft | RRAD | 6236 | Soft |
| ACTA2-AS1 | 100132116 | Soft | LOC202181 | 202181 | Soft | FAM160A1 | 729830 | Soft | RRAGB | 10325 | Soft |
| ACTBL2 | 345651 | Soft | LOC254896 | 254896 | Soft | FAM161B | 145483 | Soft | RRAGD | 58528 | Soft |
| ACVR2B-AS1 | 100128640 | Soft | LOC283038 | 283038 | Soft | FAM162A | 26355 | Soft | RRNAD1 | 51093 | Soft |
| ACYP2 | 98 | Soft | OC335 | 283335 | Soft | FAM167A | 83648 | Soft | RSBN1 | 54665 | Soft |
| ADAM8 | 101 | Soft | LOC283575 | 283575 | Soft | FAM167B | 84734 | Soft | RSPH3 | 83861 | Soft |
| ADAMTS1 | 9510 | Soft | LOC284080 | 284080 | Soft | FAM168A | 23201 | Soft | RSRP | 57035 | Soft |
| ADAMTS10 | 8179 | Soft | LOC284454 | 284454 | Soft | FAM171A2 | 284069 | Soft | RTN4RL2 | 349667 | Soft |
| ADAMTS2 | 9509 | Soft | LOC284930 | 284930 | Soft | FAM179A | 165186 | Soft | RTP4 | 64108 | Soft |
| ADAMTS5 | 11096 | Soft | LOC285819 | 285819 | Soft | FAM183A | 440585 | Soft | RUNDC38 | 154661 | Soft |
| ADAMTS7 | 11173 | Soft | LOC285847 | 285847 | Soft | FAM184B | 27146 | Soft | RUNX1T1 | 862 | Soft |
| ADAMTS7P1 | 390660 | Soft | LOC374443 | 374443 | Soft | FAM198A | 729085 | Soft | RWDD2A | 112611 | Soft |
| ADAMTS9-AS2 | 100507098 | Soft | LOC388813 | 388813 | Soft | FAM20C | 56975 | Soft | RXFP1 | 59350 | Soft |
| ADAMTSL2 | 9719 | Soft | LOC400706 | 400706 | Soft | FAM212B | 55924 | Soft | RYR1 | 6261 | Soft |
| ADAMTSL4 | 54507 | Soft | LOC401320 | 401320 | Soft | FAM212B-AS1 | 100506343 | Soft | RYR2 | 6262 | Soft |
| ADAP1 | 11033 | Soft | LOC440028 | 440028 | Soft | FAM213A | 84293 | Soft | S100A3 | 6274 | Soft |
| ADCYAP1R1 | 117 | Soft | LOC440173 | 440173 | Soft | FAM214A | 56204 | Soft | S1PR2 | 9294 | Soft |
| ADD3 | 120 | Soft | LOC441081 | 441081 | Soft | FAM214B | 80256 | Soft | S1PR4 | 698 | Soft |
| ADGRA2 | 25960 | Soft | LOC554206 | 554206 | Soft | FAM227A | 646851 | Soft | S1PR5 | 53637 | Soft |
| ADGRB3 | 577 | Soft | LOC55423 | 55423 | Soft | FAM227B | 196951 | Soft | SAA2-SAA4 | 100528017 | Soft |
| ADGRG1 | 9289 | Soft | LOC642852 | 642852 | Soft | FAM228B | 375190 | Soft | SAA4 | 6291 | Soft |
| ADGRL1 | 22859 | Soft | LOC644285 | 644285 | Soft | FAM229A | 100128071 | Soft | SALL2 | 6297 | Soft |
| ADGRL2 | 23266 | Soft | LOC644919 | 644919 | Soft | FAM26E | 254228 | Soft | SALL4 | 57167 | Soft |
| ADGRL3 | 23284 | Soft | LOC646471 | 646471 | Soft | FAM46A | 55603 | Soft | SAMD14 | 201191 | Soft |
| ADH6 | 30 | Soft | LOC648987 | 648987 | Soft | FAM46B | 115572 | Soft | SAMD9L | 219285 | Soft |
| ADM | 133 | Soft | LOC653160 | 653160 | Soft | FAM46C | 54855 | Soft | SARDH | 1757 | Soft |
| ADM2 | 79924 | Soft | LOC654841 | 654841 | Soft | FAM47E | 100129583 | Soft | SASH1 | 23328 | Soft |
| ADORA2A-AS1 | 646023 | Soft | LOC728392 | 728392 | Soft | FAM47E-STBD1 | 100631383 | Soft | SATB1 | 6304 | Soft |
| ADPRHL1 | 113622 | Soft | LOC728613 | 728613 | Soft | FAM50B | 26240 | Soft | SBF2-AS1 | 283104 | Soft |
| ADRA1B | 147 | Soft | LOC728730 | 728730 | Soft | FAM63A | 55793 | Soft | SCARA5 | 286133 | Soft |
| ADRB2 | 154 | Soft | LOC728743 | 728743 | Soft | FAM65B | 9750 | Soft | SCARF1 | 8578 | Soft |
| ADSSL1 | 122622 | Soft | LOG729603 | 729603 | Soft | FAM71C | 196472 | Soft | SCARF2 | 91179 | Soft |
| AFF1 | 4299 | Soft | LOG730668 | 730668 | Soft | FAM83H-AS1 | 100128338 | Soft | SCARNAS | 677776 | Soft |
| AFF2 | 2334 | Soft | LOC90246 | 90246 | Soft | FAM86B3P | 286042 | Soft | SCARNA9 | 619383 | Soft |
| AGBL2 | 79841 | Soft | LOH12CR2 | 503693 | Soft | FAM8A1 | 51439 | Soft | SCART1 | 619207 | Soft |
| AGER | 177 | Soft | LOX | 4015 | Soft | FANK1 | 92565 | Soft | SCD5 | 79966 | Soft |

| GeneSymbol | gene_id | Status | GeneSymbol | gene_id | Status | GeneSymbol | gene_id | Status |
|---|---|---|---|---|---|---|---|---|
| AGPAT4-IT1 | 79992 | Soft | LOXL1 | 4016 | Soft | FAP | 2191 | Soft | SCN2A | 6326 | Soft |
| AGT | 183 | Soft | LOXL1-AS1 | 100287616 | Soft | FAS-AS1 | 100302740 | Soft | SCNN1B | 6338 | Soft |
| AHNAK2 | 113146 | Soft | LOXL2 | 4017 | Soft | FAT2 | 2196 | Soft | SCNN1D | 6339 | Soft |
| AHRR | 57491 | Soft | LPAR1 | 1902 | Soft | FAXDC2 | 10826 | Soft | SCNN1G | 6340 | Soft |
| AHSA2 | 130872 | Soft | LPAR2 | 9170 | Soft | FBLIM1 | 54751 | Soft | SCX | 642658 | Soft |
| AIFM3 | 150209 | Soft | LPAR6 | 10161 | Soft | FBLN1 | 2192 | Soft | SDCBP2 | 27111 | Soft |
| AIM2 | 9447 | Soft | LPIN3 | 64900 | Soft | FBLN2 | 2199 | Soft | SDHAP3 | 728609 | Soft |
| AK4 | 205 | Soft | LPP | 4026 | Soft | FBXL16 | 146330 | Soft | SEC14L5 | 9717 | Soft |
| AK7 | 122481 | Soft | LRCH2 | 57631 | Soft | FBXL8 | 55336 | Soft | SEC16B | 89866 | Soft |
| AK8 | 158067 | Soft | LRG1 | 116844 | Soft | FBXO15 | 201456 | Soft | SEC1P | 653677 | Soft |
| AK9 | 221264 | Soft | LRGUK | 13633 | Soft | FBXO24 | 26261 | Soft | SESEC31B | 25956 | Soft |
| AKAP3 | 10566 | Soft | LRP1 | 4035 | Soft | FBXO32 | 114907 | Soft | SELENBP1 | 8991 | Soft |
| AKR1B15 | 441282 | Soft | LRP1-AS | 105751187 | Soft | FBXO41 | 150726 | Soft | SEMA3B | 7869 | Soft |
| AKR7A3 | 22977 | Soft | LRP1B | 53353 | Soft | FBXO42 | 54455 | Soft | SEMA4A | 64218 | Soft |
| AKR7L | 246181 | Soft | LRP4 | 40138 | Soft | FBXO44 | 93611 | Soft | SEMA4B | 10509 | Soft |
| AKT3 | 10000 | Soft | LRP4-AS1 | 100507401 | Soft | FBXO6 | 26270 | Soft | SEMA4G | 57715 | Soft |
| ALDH1L1 | 10840 | Soft | LRRC27 | 80313 | Soft | FCGBP | 8857 | Soft | SEMA6B | 10501 | Soft |
| ALDH1L2 | 160428 | Soft | LRRC29 | 26231 | Soft | FCGR2A | 2212 | Soft | SENP7 | 57337 | Soft |
| ALDH2 | 217 | Soft | LRRC37A3 | 374819 | Soft | FCGRT | 2217 | Soft | SEPP1 | 6414 | Soft |
| ALDH3A1 | 218 | Soft | RRC37A6P | 387646 | Soft | FCHO1 | 23149 | Soft | SEPT1 | 1731 | Soft |
| ALDH3B1 | 221 | Soft | LRRC37A8P | 100533789 | Soft | FERIL4 | 80307 | Soft | SEPT5 | 5413 | Soft |
| ALDH6A1 | 4329 | Soft | LRRC37B | 114659 | Soft | FEZ1 | 9638 | Soft | SEPT5-GP1BB | 100526833 | Soft |
| ALDH8A1 | 64577 | Soft | LRRC56 | 115399 | Soft | FGF11 | 2256 | Soft | SEPT7-AS1 | 101928545 | Soft |
| ALDOC | 230 | Soft | LRRC6 | 2363 | Soft | FGGY | 55277 | Soft | SERINC4 | 619189 | Soft |
| ALOX12 | 239 | Soft | LRRC61 | 65999 | Soft | FHAD1 | 114827 | Soft | SERPINA5 | 5104 | Soft |
| ALPK1 | 80216 | Soft | LRRC66 | 39977 | Soft | FHIT | 2272 | Soft | SERPINB1 | 1992 | Soft |
| ALPK2 | 115701 | Soft | LRRC7 | 57554 | Soft | FIBCD1 | 84929 | Soft | SERPINB9 | 5272 | Soft |
| ALPK3 | 57538 | Soft | LRRC73 | 221424 | Soft | FIBIN | 387758 | Soft | SERPINE2 | 5270 | Soft |
| ALS2CL | 259173 | Soft | LRRC75B | 388886 | Soft | FLJ31356 | 403150 | Soft | SERPINF1 | 5176 | Soft |
| AMT | 275 | Soft | LRRK2 | 120892 | Soft | FLJ37035 | 399821 | Soft | SERPINF2 | 5345 | Soft |
| AMY2B | 280 | Soft | LRSAM1 | 90678 | Soft | FLJ37453 | 729614 | Soft | SERPING1 | 710 | Soft |
| ANG | 283 | Soft | LSP1 | 4046 | Soft | FLJ43879 | 401039 | Soft | SESN3 | 143686 | Soft |
| ANGPT1 | 284 | Soft | LTBP2 | 4053 | Soft | FLJ45079 | 400624 | Soft | SETBP1 | 26040 | Soft |
| ANGPTL4 | 51129 | Soft | LTBP3 | 4054 | Soft | FLJ46906 | 441172 | Soft | SEZ6L2 | 26470 | Soft |
| ANK1 | 286 | Soft | LTBP4 | 8425 | Soft | FLRT1 | 23769 | Soft | SGPP2 | 130367 | Soft |
| ANKAR | 150709 | Soft | LTF | 4057 | Soft | FMO3 | 2328 | Soft | SGSM2 | 9905 | Soft |
| ANKDD1A | 348094 | Soft | LUADT1 | 106182249 | Soft | FMO4 | 2329 | Soft | SH2D3A | 10603 | Soft |
| ANKFN1 | 16228 | Soft | LUCAT1 | 100505994 | Soft | FMO5 | 2330 | Soft | SH282 | 10045 | Soft |
| ANKLE1 | 12549 | Soft | LURAP1 | 541468 | Soft | FN1 | 2335 | Soft | SH3BGR | 6450 | Soft |
| ANKMY2 | 57037 | Soft | LUZP4 | 51213 | Soft | FN3K | 64122 | Soft | SH3BP2 | 6452 | Soft |
| ANKRA2 | 57763 | Soft | LVCAT1 | 100506827 | Soft | FNBP1L | 54874 | Soft | SH3D21 | 79729 | Soft |
| ANKRD2 | 26287 | Soft | LVCAT5 | 1053754775 | Soft | FOS | 2353 | Soft | SH3PXD2A | 9644 | Soft |
| ANKRD24 | 170961 | Soft | LY75 | 4065 | Soft | FOSB | 2354 | Soft | SH3YL1 | 26751 | Soft |
| ANKRD30B | 374860 | Soft | LY75-CD302 | 100526664 | Soft | FOXD1 | 2297 | Soft | SHC2 | 25759 | Soft |
| ANKRD34C | 390616 | Soft | LY96 | 23643 | Soft | FOXLI | 2300 | Soft | SHC3 | 53358 | Soft |
| ANKRD36G | 400986 | Soft | LYPD1 | 116372 | Soft | FOXO1 | 2308 | Soft | SHF | 90525 | Soft |
| ANKRD37 | 353322 | Soft | LYPD3 | 27076 | Soft | FOXO4 | 4303 | Soft | SKIDA1 | 387640 | Soft |
| ANKZF1 | 55139 | Soft | LYRM9 | 201229 | Soft | FOXP1 | 27086 | Soft | SKINTL | 391037 | Soft |
| ANO9 | 338440 | Soft | MAATS1 | 89876 | Soft | FOXP2 | 93986 | Soft | SKOR1 | 390598 | Soft |
| ANXA2R | 389289 | Soft | MAB21L3 | 126868 | Soft | FOXP4-AS1 | 101060264 | Soft | SLAMF8 | 56833 | Soft |
| ANXA8L1 | 728113 | Soft | MACROD1 | 28992 | Soft | FRG1DP | 102723316 | Soft | | | |

| GeneSymbol | gene_id | Status | GeneSymbol | gene_id | Status | GeneSymbol | gene_id | Status |
|---|---|---|---|---|---|---|---|---|
| ANXA9 | 8416 | Soft | MAF | 4094 | Soft | SLAMF9 | 89886 | Soft |
| AOC3 | 8639 | Soft | MAFB | 9935 | Soft | SLC12A5 | 57468 | Soft |
| AP1G2 | 8906 | Soft | MAGEA11 | 4110 | Soft | SLC12A7 | 10723 | Soft |
| APBB3 | 10307 | Soft | MAMDC2 | 256691 | Soft | SLC12A8 | 84561 | Soft |
| APC2 | 10297 | Soft | MAML2 | 84441 | Soft | SLC13A4 | 26266 | Soft |
| APCDD1 | 147495 | Soft | MAN1B1-AS1 | 100289341 | Soft | SLC14A1 | 6563 | Soft |
| APH1B | 83464 | Soft | MANEA-AS1 | 101927288 | Soft | SLC15A3 | 51296 | Soft |
| APLN | 8862 | Soft | MAOA | 4128 | Soft | SLC16A2 | 6567 | Soft |
| APOA4 | 337 | Soft | MAOB | 4129 | Soft | SLC17A5 | 26503 | Soft |
| APOBEC3D | 140564 | Soft | MAP1A | 4130 | Soft | SLC17A7 | 57030 | Soft |
| APOBEC3F | 200316 | Soft | MAP1LC3A | 84557 | Soft | SLC1A4 | 6509 | Soft |
| APOBEC3G | 60489 | Soft | MAP3K12 | 7786 | Soft | SLC22A13 | 9390 | Soft |
| APOC1 | 341 | Soft | MAP3K13 | 9175 | Soft | SLC22A14 | 9389 | Soft |
| APOC3 | 345 | Soft | MAP3K8 | 1326 | Soft | SLC22A18 | 5002 | Soft |
| APOD | 347 | Soft | MAP7D2 | 256714 | Soft | SLC22A18AS | 5003 | Soft |
| APOE | 348 | Soft | MAPK10 | 5602 | Soft | SLC22A23 | 63027 | Soft |
| APOL3 | 80833 | Soft | MAPK3 | 5595 | Soft | SLC23A3 | 151295 | Soft |
| APOLD1 | 81575 | Soft | MAPRE3 | 22924 | Soft | SLC25A27 | 9481 | Soft |
| APPL1 | 26060 | Soft | MAPT | 4137 | Soft | SLC25A42 | 284439 | Soft |
| AQP1 | 358 | Soft | MARCH9 | 92979 | Soft | SLC25A45 | 283130 | Soft |
| AQP3 | 360 | Soft | MARK4 | 57787 | Soft | SLC26A6 | 65010 | Soft |
| AR | 367 | Soft | MASP1 | 5648 | Soft | SLC26A9 | 115019 | Soft |
| ARFGEF3 | 57221 | Soft | MAST1 | 22983 | Soft | SLC27A1 | 376497 | Soft |
| ARHGAP20 | 57569 | Soft | MATN1-AS1 | 100129196 | Soft | SLC29A2 | 3177 | Soft |
| ARHGAP24 | 83478 | Soft | MATN2 | 4147 | Soft | SLC29A4 | 222962 | Soft |
| ARHGAP4 | 393 | Soft | MBD5 | 55777 | Soft | SLC2A1-AS1 | 440584 | Soft |
| ARHGAP44 | 9912 | Soft | MCC | 4163 | Soft | SLC2A10 | 81031 | Soft |
| ARHGAP6 | 395 | Soft | MCOLN2 | 255231 | Soft | SLC2A11 | 66035 | Soft |
| ARHGAP8 | 23779 | Soft | MDGA1 | 266727 | Soft | SLC2A14 | 144195 | Soft |
| ARHGEF10L | 55160 | Soft | MDH1B | 130752 | Soft | SLC2A3 | 6515 | Soft |
| ARHGEF16 | 27237 | Soft | MDK | 4192 | Soft | SLC2A4 | 6517 | Soft |
| ARHGEF17 | 9828 | Soft | MEF2A | 4205 | Soft | SLC2A5 | 6518 | Soft |
| ARHGEF19 | 128272 | Soft | MEF2C | 4208 | Soft | SLC2A9 | 56606 | Soft |
| ARHGEF25 | 115557 | Soft | MEFV | 4210 | Soft | SLC35E2 | 9906 | Soft |
| ARHGEF37 | 389337 | Soft | MEGF6 | 1953 | Soft | SLC38A5 | 92745 | Soft |
| ARHGEF40 | 27106 | Soft | MEGF8 | 1954 | Soft | SLC40A1 | 30061 | Soft |
| ARHGEF6 | 55701 | Soft | MEIS1 | 4211 | Soft | SLC41A2 | 84102 | Soft |
| ARID4A | 9459 | Soft | MEIS1-AS2 | 100873998 | Soft | SLC43A1 | 8501 | Soft |
| ARL4C | 5926 | Soft | MEIS3 | 56917 | Soft | SLC44A5 | 204962 | Soft |
| ARMC12 | 10123 | Soft | MEOX1 | 4222 | Soft | SLC45A1 | 50651 | Soft |
| ARNT2 | 221481 | Soft | METTL20 | 254013 | Soft | SLC47A2 | 146802 | Soft |
| ARRB1 | 9915 | Soft | METTL21B | 25895 | Soft | SLC5A5 | 57835 | Soft |
| ARRDC2 | 408 | Soft | METTL7A | 25840 | Soft | SLC5A9 | 200010 | Soft |
| ARRDC3 | 57561 | Soft | MEX3A | 92312 | Soft | SLC6A1 | 6529 | Soft |
| ARRDC3-AS1 | 100129716 | Soft | MEX3B | 84206 | Soft | SLC6A16 | 28968 | Soft |
| ARRDC4 | 91947 | Soft | MFAP4 | 4239 | Soft | SLC6A3 | 6531 | Soft |
| ARSG | 22901 | Soft | MFI2 | 4241 | Soft | SLC9A3 | 6550 | Soft |
| ARTN | 9048 | Soft | MF12-AS1 | 100507057 | Soft | SLCO1A2 | 6579 | Soft |
| AS3MT | 57412 | Soft | MFSD7 | 84179 | Soft | SLCO2A1 | 6578 | Soft |
| ASAP3 | 55616 | Soft | MGC16275 | 85001 | Soft | SLITRK2 | 84631 | Soft |
| ASCL1 | 429 | Soft | MGP | 4256 | Soft | SLITRK4 | 139065 | Soft |

-continued

| GeneSymbol | gene_id | Status | GeneSymbol | gene_id | Status | GeneSymbol | gene_id | Status |
|---|---|---|---|---|---|---|---|---|
| ASIC1 | 41 | Soft | MIAT | 440823 | Soft | SLITRK6 | 84189 | Soft |
| ASIC3 | 9311 | Soft | MIATNB | 102724827 | Soft | SMAD6 | 4091 | Soft |
| ASIP | 434 | Soft | MIB2 | 142678 | Soft | SMAD7 | 4092 | Soft |
| ASPG | 374569 | Soft | MIEF2 | 125170 | Soft | SMAD9 | 4093 | Soft |
| ASPRV1 | 151516 | Soft | MILR1 | 284021 | Soft | SMARCA1 | 6594 | Soft |
| ASS1 | 445 | Soft | MIR1228 | 100302201 | Soft | SMARCD3 | 6604 | Soft |
| ASTN2 | 23245 | Soft | MIR1260B | 100422991 | Soft | SMC2-AS1 | 101928550 | Soft |
| ATG14 | 22863 | Soft | MIR1287 | 100302133 | Soft | SMCO3 | 440087 | Soft |
| ATG16L2 | 89849 | Soft | MIR155HG | 114614 | Soft | SMIM1 | 388588 | Soft |
| ATHL1 | 80162 | Soft | MIR181A2HG | 100379345 | Soft | SMIM3 | 85027 | Soft |
| ATOH8 | 84913 | Soft | MIR193BHG | 100129781 | Soft | SMTNL1 | 219537 | Soft |
| ATP1A1-AS1 | 84852 | Soft | MIR199A2 | 406977 | Soft | SNCA | 6622 | Soft |
| ATP1A2 | 477 | Soft | MIR210 | 406992 | Soft | SNED1 | 5992 | Soft |
| ATP2A3 | 489 | Soft | MIR210HG | 100506211 | Soft | SNHG18 | 100505806 | Soft |
| ATP2B2 | 491 | Soft | MIR214 | 406996 | Soft | SNTA1 | 6640 | Soft |
| ATP2C2 | 9914 | Soft | MIR23A | 407010 | Soft | SNTB1 | 6641 | Soft |
| ATP6AP1L | 92270 | Soft | MIR24-2 | 407013 | Soft | SNX21 | 90203 | Soft |
| ATP6V1B1 | 525 | Soft | MIR27A | 407018 | Soft | SNX32 | 254122 | Soft |
| ATP6V1G2 | 534 | Soft | MIR29C | 407026 | Soft | SNX33 | 257364 | Soft |
| ATP7A | 538 | Soft | MIR3120 | 100422882 | Soft | SOD3 | 6649 | Soft |
| ATP8B3 | 148229 | Soft | MIR324 | 442898 | Soft | SOHLH2 | 54937 | Soft |
| ATXN3 | 4287 | Soft | MIR34AHG | 106614088 | Soft | SORBS1 | 10580 | Soft |
| AURKC | 6795 | Soft | MIR3681HG | 100506457 | Soft | SORCS2 | 57537 | Soft |
| AZGP1 | 563 | Soft | MIR4635 | 100616479 | Soft | SOX4 | 6659 | Soft |
| AZIN2 | 113451 | Soft | MIR4680 | 100616396 | Soft | SOX5 | 6660 | Soft |
| B3GALT4 | 8705 | Soft | MIR4712 | 100616358 | Soft | SP5 | 389058 | Soft |
| B3GNT4 | 79369 | Soft | MIR4800 | 100847079 | Soft | SPACA6P-AS | 102238594 | Soft |
| B3GNT7 | 93010 | Soft | MIR5193 | 100847035 | Soft | SPAG4 | 6676 | Soft |
| B4GALNT2 | 124872 | Soft | MIR548AR | 693197 | Soft | SPAG8 | 26206 | Soft |
| B4GALNT4 | 338707 | Soft | MIR612 | 693226 | Soft | SPATA12 | 353324 | Soft |
| BACE1-AS | 100379571 | Soft | MIR641 | 100033819 | Soft | SPATA17 | 128153 | Soft |
| BACH1 | 571 | Soft | MIR675 | 102466193 | Soft | SPATA17-AS1 | 103752555 | Soft |
| BACH2 | 60468 | Soft | MIR6757 | 102465537 | Soft | SPATA18 | 132671 | Soft |
| BAHCC1 | 57597 | Soft | MIR6891 | 100313843 | Soft | SPATA25 | 128497 | Soft |
| BAIAP2-AS1 | 440465 | Soft | MIR711 | 102465993 | Soft | SPATA6 | 54558 | Soft |
| BAIAP3 | 8938 | Soft | MIR7847 | 388815 | Soft | SPATA6L | 55064 | Soft |
| BASP1P1 | 646201 | Soft | MIR99AHG | 100507419 | Soft | SPATA7 | 55812 | Soft |
| BBC3 | 4828 | Soft | MKLN1-AS | 100506881 | Soft | SPATG1 | 375686 | Soft |
| BBOF1 | 27113 | Soft | MLXIPL | 4316 | Soft | SPEF1 | 25876 | Soft |
| BBS1 | 80127 | Soft | MME | 51085 | Soft | SPEG | 10290 | Soft |
| BBS12 | 166379 | Soft | MMP11 | 4311 | Soft | SPIN2B | 474343 | Soft |
| BBS2 | 583 | Soft | MMP17 | 4320 | Soft | SPIN3 | 169981 | Soft |
| BBS9 | 27241 | Soft | MMP19 | 4327 | Soft | SPINKS | 11005 | Soft |
| BCAN | 63827 | Soft | MMP24 | 10893 | Soft | SPINT1 | 6692 | Soft |
| BCAS3 | 4828 | Soft | MMP25-AS1 | 100507419 | Soft | SPRY1 | 10252 | Soft |
| BCHE | 590 | Soft | MMP7 | 4316 | Soft | SRCIN1 | 80725 | Soft |
| BCKDHA | 593 | Soft | MMRN2 | 79812 | Soft | SRD5A3 | 79644 | Soft |
| BCL11A | 53335 | Soft | MORN1 | 79906 | Soft | SRGAP3 | 9901 | Soft |
| BCL11B | 64919 | Soft | MOSPD3 | 64598 | Soft | SRP14-AS1 | 100131089 | Soft |
| BCL6 | 604 | Soft | MPI | 4351 | Soft | SRRM3 | 222183 | Soft |
| BCORL1 | 63035 | Soft | MR1 | 3140 | Soft | SSBP2 | 23635 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| BDKRB2 | 624 | Soft | MRAP2 | 112609 | Soft | GTF2IRD2 | 84163 | Soft | SSBP3-AS1 | 619518 | Soft |
| BDNF-AS | 497258 | Soft | MRC2 | 9902 | Soft | GTF2IRD2B | 389524 | Soft | SSC4D | 136853 | Soft |
| BEAN1 | 146227 | Soft | MROH2A | 339766 | Soft | GUCY1B3 | 2983 | Soft | SSC5D | 284297 | Soft |
| BEND5 | 79656 | Soft | MRPL23-AS1 | 100133545 | Soft | GULP1 | 51454 | Soft | SSH3 | 54961 | Soft |
| BEST1 | 7439 | Soft | MRVI1 | 10335 | Soft | GUSBP4 | 375513 | Soft | SSPN | 8082 | Soft |
| BEX1 | 55859 | Soft | MSC-AS1 | 100132891 | Soft | GXYLT2 | 727936 | Soft | SSR4P1 | 728039 | Soft |
| BFSP1 | 631 | Soft | MSRB2 | 22921 | Soft | GYPC | 2995 | Soft | ST3GAL3 | 6487 | Soft |
| BGN | 633 | Soft | MST1 | 4485 | Soft | H19 | 283120 | Soft | ST3GAL4-AS1 | 399972 | Soft |
| BHLHB9 | 80823 | Soft | MST1L | 11223 | Soft | H6PD | 9563 | Soft | ST3GAL5 | 8869 | Soft |
| BHLHE40 | 8553 | Soft | MST1P2 | 11209 | Soft | HAL | 3034 | Soft | ST6GALNAC2 | 10610 | Soft |
| BHLHE41 | 79365 | Soft | MT1F | 4494 | Soft | HAR1A | 768096 | Soft | ST8SIA1 | 6489 | Soft |
| BISPR | 105221694 | Soft | MTA3 | 57504 | Soft | HAS2 | 3037 | Soft | ST8SIA5 | 29906 | Soft |
| BLK | 640 | Soft | MTHFD2P1 | 100287639 | Soft | HAS2-AS1 | 594842 | Soft | STAC2 | 3466 | Soft |
| BMF | 90427 | Soft | MTL5 | 9633 | Soft | HBE1 | 3046 | Soft | STAG3 | 1073 | Soft |
| BMP3 | 651 | Soft | MTMR11 | 10903 | Soft | HBG2 | 3048 | Soft | STAP2 | 5620 | Soft |
| BMP4 | 652 | Soft | MTMR9LP | 339483 | Soft | HBP1 | 26959 | Soft | STARD13-AS | 100874241 | Soft |
| BMP8B | 656 | Soft | MTTP | 4547 | Soft | HCAR2 | 338442 | Soft | STARD5 | 80765 | Soft |
| BMPR1B | 658 | Soft | MTUS1 | 57509 | Soft | HCAR3 | 8843 | Soft | STARD9 | 57519 | Soft |
| BNIP3 | 664 | Soft | MTUS2 | 23281 | Soft | HCFC1R1 | 54985 | Soft | STAT2 | 6773 | Soft |
| BNIP3L | 665 | Soft | MUC1 | 4582 | Soft | HCG26 | 352961 | Soft | STAT4 | 6775 | Soft |
| BOC | 91653 | Soft | MUC12 | 10071 | Soft | HCG27 | 253018 | Soft | STBD1 | 8987 | Soft |
| BOLA1 | 51027 | Soft | MUC15 | 143662 | Soft | HCG4 | 54435 | Soft | STK32A | 202374 | Soft |
| BOLA3-AS1 | 100507171 | Soft | MUC20 | 200958 | Soft | HCG8 | 80862 | Soft | STOM | 2040 | Soft |
| BORCS7-ASMT | 100528807 | Soft | MUM1L1 | 139221 | Soft | HCP5 | 1086 | Soft | STON1 | 11037 | Soft |
| BPIFB4 | 149954 | Soft | MUSK | 4593 | Soft | HDAC11 | 79885 | Soft | STON1-GTF2A1L | 286749 | Soft |
| BRSK1 | 84446 | Soft | MX1 | 4599 | Soft | HDAC5 | 10014 | Soft | STOX1 | 219736 | Soft |
| BTBD16 | 118663 | Soft | MX2 | 4600 | Soft | HDGFL1 | 154150 | Soft | STRA6 | 64220 | Soft |
| BTBD19 | 149478 | Soft | MXD4 | 10608 | Soft | HECW2 | 57520 | Soft | STX1B | 112755 | Soft |
| BTBD8 | 284697 | Soft | MXI1 | 4601 | Soft | HEPH | 9843 | Soft | STXBP2 | 6813 | Soft |
| BTG1 | 694 | Soft | MYBPC1 | 4604 | Soft | HEXDC | 284004 | Soft | SUGCT | 79783 | Soft |
| BTN2A2 | 10385 | Soft | MYCBPAP | 84073 | Soft | HEXIM2 | 124790 | Soft | SUGT1P1 | 441394 | Soft |
| BTN2A3P | 54718 | Soft | MYL5 | 463 | Soft | HHLA3 | 11147 | Soft | SULF1 | 23213 | Soft |
| BTN3A1 | 11119 | Soft | MYL9 | 10398 | Soft | HILPDA | 29923 | Soft | SULF2 | 55959 | Soft |
| BTN3A3 | 10384 | Soft | MYLK3 | 91807 | Soft | HIST1H3E | 8353 | Soft | SULT1E1 | 6783 | Soft |
| BTNL9 | 153579 | Soft | MYLK4 | 340156 | Soft | HIST2H2BC | 337873 | Soft | SVEP1 | 79987 | Soft |
| C10orf10 | 11067 | Soft | MYO15A | 51168 | Soft | HIST3H2A | 92815 | Soft | SYN2 | 6854 | Soft |
| C10orf11 | 83938 | Soft | MYO15B | 80022 | Soft | HKR1 | 284459 | Soft | SYNE2 | 23224 | Soft |
| C10orf25 | 118663 | Soft | MYO16 | 2302 | Soft | HLA-DMA | 3108 | Soft | SYNE4 | 163183 | Soft |
| C10orf54 | 220979 | Soft | MYO1F | 4542 | Soft | HLA-F | 3134 | Soft | SYNGAP1 | 8831 | Soft |
| C11orf21 | 64115 | Soft | MYO3B | 140469 | Soft | HLA-F-AS1 | 285830 | Soft | SYNGR1 | 9145 | Soft |
| C11orf54 | 29125 | Soft | MYOM1 | 8736 | Soft | HLA-J | 3137 | Soft | SYNGR3 | 9143 | Soft |
| C11orf70 | 28970 | Soft | MYOZ2 | 51778 | Soft | HLF | 3131 | Soft | SYNPO | 11346 | Soft |
| C12orf60 | 85016 | Soft | MYRF | 745 | Soft | HLTF | 6596 | Soft | SYNPO2 | 171024 | Soft |
| C12orf76 | 144608 | Soft | MZF1 | 7593 | Soft | HLTF-AS1 | 100873945 | Soft | SYS1-OBNDD2 | 767557 | Soft |
| C14orf132 | 400073 | Soft | MZF1-AS1 | 100131691 | Soft | HMBOX1 | 79618 | Soft | SYT11 | 23208 | Soft |
| C14orf93 | 56967 | Soft | N4BP2L1 | 90634 | Soft | HMCN1 | 83872 | Soft | SYT12 | 91683 | Soft |
| C15orf62 | 60686 | Soft | N4BP2L2-IT2 | 116828 | Soft | HMGCL | 3155 | Soft | SYT13 | 57586 | Soft |
| C16orf45 | 643338 | Soft | NAALADL2 | 23138 | Soft | HNF1A | 6927 | Soft | SYT17 | 51760 | Soft |
| C16orf74 | 89927 | Soft | NAALADL2 | 254827 | Soft | HNRNPA3P1 | 10151 | Soft | SYT7 | 9066 | Soft |
| C16orf89 | 404550 | Soft | NACAD | 23148 | Soft | HOGA1 | 112817 | Soft | SYT8 | 90019 | Soft |
| C17orf100 | 146556 | Soft | NALT1 | 101928483 | Soft | HOMEZ | 57594 | Soft | SYTL1 | 84958 | Soft |

| GeneSymbol | gene_id | Status | GeneSymbol | gene_id | Status | GeneSymbol | gene_id | Status |
|---|---|---|---|---|---|---|---|---|
| C18orf65 | 400658 | Soft | NANOS1 | 340719 | Soft | HOOK2 | 29911 | Soft | SYTL2 | 54843 | Soft |
| C19orf54 | 284325 | Soft | NAP1L6 | 64599 | Soft | HOTAIR | 100124700 | Soft | TAF1A-AS1 | 100506161 | Soft |
| C19orf57 | 79173 | Soft | NAPSA | 9476 | Soft | HOTS | 103344718 | Soft | TAGLN | 6876 | Soft |
| C1orf162 | 128346 | Soft | NATD1 | 256302 | Soft | HOXA-AS2 | 285943 | Soft | TAS2R4 | 50832 | Soft |
| C1orf167 | 284498 | Soft | NBEA | 26960 | Soft | HOXA11-AS | 221883 | Soft | TAS2R5 | 54429 | Soft |
| C1orf204 | 284677 | Soft | NCK1-AS1 | 101927597 | Soft | HOXA13 | 3209 | Soft | TBC1D10A | 83874 | Soft |
| C1orf21 | 81563 | Soft | NCKAP1L | 3071 | Soft | HOXA4 | 3201 | Soft | TBC1D17 | 79735 | Soft |
| C1orf220 | 400798 | Soft | NCKIPSD | 51517 | Soft | HOXA5 | 3202 | Soft | TBC1D32 | 221322 | Soft |
| C1orf228 | 339541 | Soft | NDNF | 79625 | Soft | HOXA6 | 3203 | Soft | TBC1D3H | 729877 | Soft |
| C1orf54 | 79630 | Soft | NDRG1 | 10397 | Soft | HOXC-AS1 | 100874363 | Soft | TBC1D31 | 102724862 | Soft |
| C1QL1 | 10882 | Soft | NDRG4 | 65009 | Soft | HOXC-AS2 | 100874364 | Soft | TBC1D3L | 101060376 | Soft |
| C1QTNF1 | 114897 | Soft | NDUFA4L2 | 56901 | Soft | HPCA | 3208 | Soft | TBC1D8B | 54885 | Soft |
| C1QTNF1-AS1 | 100507410 | Soft | NEAT1 | 28313 | Soft | HPD | 3242 | Soft | TBKBP1 | 9755 | Soft |
| C1QTNF3 | 114899 | Soft | NEBL | 10529 | Soft | HPGD | 3248 | Soft | TBX19 | 9095 | Soft |
| C1QTNF6 | 114904 | Soft | NEBL-AS1 | 100128511 | Soft | HR | 55806 | Soft | TBX6 | 6911 | Soft |
| C1R | 715 | Soft | NEDD9 | 4739 | Soft | HRAT17 | 101928036 | Soft | TBXA2R | 6915 | Soft |
| C1RL | 51279 | Soft | NEIL1 | 79661 | Soft | HRAT5 | 102467073 | Soft | TBXAS1 | 6916 | Soft |
| C1RL-AS1 | 283314 | Soft | NEK11 | 79858 | Soft | HRAT92 | 441307 | Soft | TC2N | 23036 | Soft |
| C1S | 716 | Soft | NEU4 | 129807 | Soft | HRCT1 | 646962 | Soft | TCAF2 | 285966 | Soft |
| C2 | 717 | Soft | NEURL1B | 54492 | Soft | HRNR | 88697 | Soft | TCEA3 | 6920 | Soft |
| C20orf194 | 25943 | Soft | NEURL2 | 140825 | Soft | HS6ST3 | 26672 | Soft | TCF4 | 6925 | Soft |
| C20orf195 | 79025 | Soft | NEUROG2 | 63973 | Soft | HSBP1L1 | 440498 | Soft | TCF7 | 6932 | Soft |
| C21orf33 | 8209 | Soft | NFATC4 | 4776 | Soft | HSD11B1 | 3290 | Soft | TCF7L1 | 83439 | Soft |
| C22orf34 | 348645 | Soft | NFE2L3 | 9603 | Soft | HSD11B1L | 374875 | Soft | TCL6 | 27004 | Soft |
| C2orf15 | 150590 | Soft | NFE4 | 58160 | Soft | HSD17B6 | 51171 | Soft | TCP11L2 | 255394 | Soft |
| C2orf81 | 388963 | Soft | NFIL3 | 4783 | Soft | HSD17B14 | 8630 | Soft | TCTE1 | 202500 | Soft |
| C3 | 718 | Soft | NFKBIL1 | 4795 | Soft | HSD17B7P2 | 158160 | Soft | TCTN1 | 79600 | Soft |
| C3orf18 | 51161 | Soft | NGFRAP1 | 27018 | Soft | HSD387 | 80270 | Soft | TDO2 | 6999 | Soft |
| C3orf36 | 80111 | Soft | NHLRC3 | 387921 | Soft | HSF4 | 3299 | Soft | TDRD9 | 122402 | Soft |
| C3orf67 | 200844 | Soft | NHLRC4 | 283948 | Soft | HSPA1L | 3305 | Soft | TENM1 | 10178 | Soft |
| C4A | 720 | Soft | NHS | 4810 | Soft | HSPB7 | 27129 | Soft | TENM2 | 57451 | Soft |
| C4B | 721 | Soft | NHSL2 | 340527 | Soft | HSPG2 | 3339 | Soft | TES | 26136 | Soft |
| C4B_2 | 100293534 | Soft | NICN1 | 84276 | Soft | HTR2C | 3358 | Soft | TESK2 | 10420 | Soft |
| C4orf3 | 401152 | Soft | NID2 | 22795 | Soft | HTRA1 | 5654 | Soft | TET1 | 80312 | Soft |
| C4orf47 | 441054 | Soft | NIFK-AS1 | 254128 | Soft | ICAM1 | 3383 | Soft | TEX9 | 374618 | Soft |
| C5 | 727 | Soft | NIM1K | 167359 | Soft | ICAM2 | 338 | Soft | TFCP2L1 | 29842 | Soft |
| C5AR1 | 728 | Soft | NIPAL2 | 79815 | Soft | ICAM4 | 33186oft | Soft | TFDP2 | 7029 | Soft |
| C5AR2 | 27202 | Soft | NIPAL4 | 348938 | Soft | ICAM5 | 7087 | Soft | TFPI | 7035 | Soft |
| C5orf46 | 389336 | Soft | NIPSNAP1 | 8508 | Soft | ID2-AS1 | 100506299 | Soft | TFR2 | 7036 | Soft |
| C6orf223 | 221416 | Soft | NIPSNAP3B | 55335 | Soft | IDUA | 3425 | Soft | TG | 7038 | Soft |
| C7orf13 | 100506380 | Soft | NKD1 | 85407 | Soft | IF144 | 10561 | Soft | TGFA | 7039 | Soft |
| C7orf61 | 402573 | Soft | NKD2 | 85409 | Soft | IF144L | 10964 | Soft | TGFB1I1 | 7041 | Soft |
| C8orf31 | 286122 | Soft | NLGN2 | 57555 | Soft | IF16 | 2537 | Soft | TGFBR3 | 7049 | Soft |
| C8orf34 | 116328 | Soft | NLGN3 | 54413 | Soft | IFIH1 | 64135 | Soft | TGFBR3L | 100507588 | Soft |
| C8orf4 | 56892 | Soft | NLRC3 | 197358 | Soft | IFIT1 | -3434 | Soft | THAP2 | 83591 | Soft |
| C8orf44 | 6260 | Soft | NLRP1 | 22861 | Soft | IFIT2 | 3433 | Soft | THAP7-AS1 | 439931 | Soft |
| C8orf48 | 157773 | Soft | NMNAT2 | 23057 | Soft | IFIT3 | 3437 | Soft | THAP8 | 199745 | Soft |
| C8orf58 | 541565 | Soft | NMNAT3 | 349565 | Soft | IFITM1 | 8519 | Soft | THBS2 | 7058 | Soft |
| C9orf173 | 441476 | Soft | NMRK1 | 54981 | Soft | IFITM10 | 402778 | Soft | THBS3 | 7059 | Soft |
| C9orf173-AS1 | 100129722 | Soft | NMU | 10874 | Soft | IFITM4P | 340198 | Soft | THBS4 | 7060 | Soft |
| C9orf3 | 84909 | Soft | NOD2 | 64127 | Soft | IFT140 | 9742 | Soft | THEMIS2 | 9473 | Soft |

| GeneSymbol | gene_id | Status | GeneSymbol | gene_id | Status | GeneSymbol | gene_id | Status |
|---|---|---|---|---|---|---|---|---|
| C9orf9 | 11092 | Soft | NOL3 | 8996 | Soft | IFT80 | 57560 | Soft | THRA | 7067 | Soft |
| CA11 | 770 | Soft | NOL4L | 140688 | Soft | IFT81 | 28981 | Soft | THRB | 7068 | Soft |
| CA3 | 761 | Soft | NOTCH3 | 4854 | Soft | IGBP1P1 | 280655 | Soft | TIMP3 | 7078 | Soft |
| CA5B | 11238 | Soft | NOTUM | 147111 | Soft | IGF2BP1 | 10642 | Soft | TLCD2 | 727910 | Soft |
| CA9 | 768 | Soft | NOXA1 | 10811 | Soft | IGFBP2 | 3485 | Soft | TLE2 | 7089 | Soft |
| CACFD1 | 11094 | Soft | NOXRED1 | 122945 | Soft | IGFBP3 | 3486 | Soft | TLE6 | 79816 | Soft |
| CACNA1B | 774 | Soft | NPAS1 | 4861 | Soft | IGFBP5 | 3488 | Soft | TLR1 | 7096 | Soft |
| CACNA1C | 775 | Soft | NPAS2 | 4862 | Soft | IGFBP7-AS1 | 255130 | Soft | TLR9 | 54106 | Soft |
| CACNA1G | 8913 | Soft | NPC1L1 | 29881 | Soft | IGIP | 492311 | Soft | TM4SF1-AS1 | 100874091 | Soft |
| CACNA1H | 8912 | Soft | NPHP1 | 4867 | Soft | IGSF10 | 285313 | Soft | TM7SF2 | 7108 | Soft |
| CACNA1I | 8911 | Soft | NPHP3 | 27031 | Soft | IGSF22 | 283284 | Soft | TMCC1-AS1 | 100507032 | Soft |
| CACNA2D2 | 9254 | Soft | NPHP3-ACAD11 | 100532724 | Soft | IGSF8 | 93185 | Soft | TMEM100 | 55273 | Soft |
| CACNA2D3 | 55799 | Soft | NPM2 | 10361 | Soft | IGSF9 | 57549 | Soft | TMEM102 | 284114 | Soft |
| CACNB1 | 782 | Soft | NPTN-IT1 | 101241892 | Soft | IL11RA | 3590 | Soft | TMEM107 | 84314 | Soft |
| CACNB3 | 784 | Soft | NPTX1 | 4884 | Soft | IL13RA2 | 3598 | Soft | TMEM116 | 89894 | Soft |
| CADM1 | 23705 | Soft | NPW | 283869 | Soft | IL15 | 3600 | Soft | TMEM130 | 222865 | Soft |
| CADM3 | 57863 | Soft | NPY2R | 4887 | Soft | IL17B | 27190 | Soft | TMEM132B | 114795 | Soft |
| CADM3-AS1 | 100131825 | Soft | NR1D1 | 9572 | Soft | IL17B | 27190 | Soft | TMEM136 | 219902 | Soft |
| CADM4 | 199731 | Soft | NR1H3 | 10062 | Soft | IL17RC | 84818 | Soft | TMEM143 | 55260 | Soft |
| CAHM | 100526820 | Soft | NR2F1-AS1 | 441094 | Soft | IL17RE | 132014 | Soft | TMEM145 | 284339 | Soft |
| CALCOCO1 | 57658 | Soft | NRBP2 | 340713 | Soft | IL18BP | 10068 | Soft | TMEM159 | 57146 | Soft |
| CALHM3 | 119395 | Soft | NRN1 | 51299 | Soft | IL1R2 | 7850 | Soft | TMEM173 | 340061 | Soft |
| CAMK2B | 816 | Soft | NRN1L | 123904 | Soft | IL23R | 149233 | Soft | TMEM178B | 100507421 | Soft |
| CAMKV | 79012 | Soft | NRSN2-AS1 | 100507459 | Soft | IL2RG | 3561 | Soft | TMEM187 | 8269 | Soft |
| CAND1.11 | 100130460 | Soft | NRTN | 4902 | Soft | IL34 | 146433 | Soft | TMEM198B | 440104 | Soft |
| CAPN3 | 825 | Soft | NRXN2 | 9379 | Soft | IMPG2 | 50939 | Soft | TMEM25 | 84866 | Soft |
| CAPS | 828 | Soft | NRXN3 | 9369 | Soft | INADL | 10207 | Soft | TMEM255A | 55026 | Soft |
| CARD14 | 79092 | Soft | NSG1 | 27065 | Soft | INAFM1 | 255783 | Soft | TMEM27 | 57393 | Soft |
| CARF | 79800 | Soft | NT5M | 56953 | Soft | INE2 | 8551 | Soft | TMEM37 | 1407 | Soft |
| CARMN | 728264 | Soft | NTN3 | 4917 | Soft | ING4 | 51147 | Soft | TMEM38A | 79041 | Soft |
| CARNS1 | 57571 | Soft | NTN5 | 126147 | Soft | INHA | 3623 | Soft | TMEM42 | 131616 | Soft |
| CASC10 | 99726 | Soft | NUDT13 | 25961 | Soft | INHBE | 83729 | Soft | TMEM45A | 55076 | Soft |
| CASC2 | 55082 | Soft | NUDT14 | 5628 | Soft | INMT | 11185 | Soft | TMEM47 | 83604 | Soft |
| CASC9 | 101805492 | Soft | NUDT7 | 283927 | Soft | INSIG2 | 51141 | Soft | TMEM51-AS1 | 200197 | Soft |
| CATSPER2P1 | 440278 | Soft | NUGGC | 389643 | Soft | INTS6-AS1 | 100507398 | Soft | TMEM59L | 25789 | Soft |
| CBLN3 | 3866 | Soft | NUPR1 | 26471 | Soft | IP6K2 | 51447 | Soft | TMEM63C | 57156 | Soft |
| CBS | 875 | Soft | NXNL2 | 158046 | Soft | IP6K3 | 117283 | Soft | TMEM67 | 91147 | Soft |
| CBX7 | 23492 | Soft | NXPH4 | 11247 | Soft | IPMK | 253430 | Soft | TMEM74B | 55321 | Soft |
| CCBL1 | 883 | Soft | NYAP1 | 222950 | Soft | IQCD | 115811 | Soft | TMEM80 | 283232 | Soft |
| CCDC102A | 92922 | Soft | NYNRIN | 57523 | Soft | IQCH-AS1 | 100506686 | Soft | TMEM8B | 5175 | Soft |
| CCDC102B | 79839 | Soft | OAS1 | 4938 | Soft | IQGAP2 | 10788 | Soft | TMEM91 | 641649 | Soft |
| CCDC103 | 388389 | Soft | OAS2 | 4939 | Soft | IQUB | 154865 | Soft | TMEM92 | 162461 | Soft |
| CCDC110 | 256309 | Soft | OASL | 8638 | Soft | IRAK3 | 11213 | Soft | TMEM92-AS1 | 103752589 | Soft |
| CCDC146 | 57639 | Soft | OBSCN | 84033 | Soft | IRF6 | 3664 | Soft | TMEM9B-AS1 | 493900 | Soft |
| CCDC148 | 130940 | Soft | OBSL1 | 23363 | Soft | IRF9 | 10379 | Soft | TNFAIP8 | 25816 | Soft |
| CCDC151 | 115948 | Soft | OCEL1 | 79629 | Soft | IRX3 | 79191 | Soft | TNFRSF10C | 8794 | Soft |
| CCDC152 | 100129792 | Soft | ODF3B | 44083 | Soft | ISG20 | 3669 | Soft | TNFRSF14 | 8764 | Soft |
| CCDC158 | 339965 | Soft | ODF3L1 | 16175 | Soft | ISLR | 3671 | Soft | TNFRSF25 | 8718 | Soft |
| CCDC17 | 49483 | Soft | OGFR-AS1 | 101409261 | Soft | ISLR2 | 57611 | Soft | TNFSF13B | 10673 | Soft |
| CCDC18-AS1 | 10013156 | Soft | OLFM2 | 93145 | Soft | ITGA1 | 3672 | Soft | TNFSF14 | 8740 | Soft |
| CCDC180 | 10049 | Soft | OLFML2A | 169611 | Soft | ITGA10 | 8515 | Soft | TNFSF4 | 7292 | Soft |

| GeneSymbol | gene_id | Status | GeneSymbol | gene_id | Status | GeneSymbol | gene_id | Status | GeneSymbol | gene_id | Status |
|---|---|---|---|---|---|---|---|---|---|---|---|
| CCDC183 | 84960 | Soft | OLFML2B | 25903 | Soft | ITGA11 | 22801 | Soft | TNK1 | 8711 | Soft |
| CCDC184 | 387856 | Soft | OLFML3 | 56944 | Soft | ITGA2B | 3674 | Soft | TNN12 | 7136 | Soft |
| CCDC191 | 57577 | Soft | OLMALINC | 90271 | Soft | ITGAX | 3687 | Soft | TNNI3K | 51086 | Soft |
| CCDC40 | 55036 | Soft | OOEP | 441161 | Soft | ITGB2 | 3689 | Soft | TNNT1 | 7138 | Soft |
| CCDC64B | 146439 | Soft | OPLAH | 26873 | Soft | ITGB2-AS1 | 100505746 | Soft | TNNT3 | 7140 | Soft |
| CCDC65 | 85478 | Soft | OPN3 | 23596 | Soft | ITGB4 | 3691 | Soft | TNS1 | 7145 | Soft |
| CCDC74A | 90557 | Soft | OPRL1 | 4987 | Soft | ITGB8 | 3696 | Soft | TNXB | 7148 | Soft |
| CCDC80 | 151887 | Soft | OR10V2P | 813 | Soft | ITH4 | 3700 | Soft | TOB1-AS1 | 400604 | Soft |
| CCDC92 | 80212 | Soft | OR1F1 | 4992 | Soft | ITIH4-AS1 | 100873993 | Soft | TOB2P1 | 699 | Soft |
| CCL26 | 10344 | Soft | OR51B4 | 79339 | Soft | ITPR1 | 3708 | Soft | TOLLIP-AS1 | 255512 | Soft |
| CCL5 | 6352 | Soft | OR51B5 | 282763 | Soft | ITPR1-AS1 | 100996539 | Soft | TP53I11 | 9537 | Soft |
| CCND2 | 894 | Soft | ORAI3 | 93129 | Soft | IZUMO4 | 113177 | Soft | TP53INP1 | 94241 | Soft |
| CCND2-AS1 | 103752584 | Soft | ORM1 | 5004 | Soft | JAG2 | 3714 | Soft | TP53INP2 | 58476 | Soft |
| CCNG2 | 901 | Soft | OSBPL5 | 114879 | Soft | JAK3 | 3718 | Soft | TP53TG1 | 11257 | Soft |
| CCNYL2 | 414194 | Soft | OSCAR | 126014 | Soft | JAM2 | 58494 | Soft | TP63 | 8626 | Soft |
| CCR10 | 2826 | Soft | OSCP1 | 127700 | Soft | JPH2 | 57158 | Soft | TP73 | 7161 | Soft |
| CCT6B | 10693 | Soft | OSER1-AS1 | 100505783 | Soft | JUP | 3728 | Soft | TP73-AS1 | 57212 | Soft |
| CD180 | 4064 | Soft | OSR2 | 116039 | Soft | KALRN | 8997 | Soft | TPO | 7173 | Soft |
| CD226 | 10666 | Soft | OVCH1 | 341350 | Soft | KATNAL2 | 83473 | Soft | TPP1 | 1200 | Soft |
| CD24 | 100133941 | Soft | OXR1 | 55074 | Soft | KAZALD1 | 81621 | Soft | TPPP | 11076 | Soft |
| CD27 | 939 | Soft | P2RX6 | 9127 | Soft | KAZN | 23254 | Soft | TPPP3 | 51673 | Soft |
| CD27-AS1 | 678655 | Soft | P2RX7 | 5027 | Soft | KBTBD3 | 143879 | Soft | TPRG1 | 285386 | Soft |
| CD36 | 948 | Soft | P4HA1 | 5033 | Soft | KBTBD7 | 84078 | Soft | TPRG1-AS1 | 100874043 | Soft |
| CD40 | 958 | Soft | P4HA2-AS1 | 100861518 | Soft | KCCAT211 | 641516 | Soft | TPSG1 | 25823 | Soft |
| CD68 | 968 | Soft | P4HTM | 54681 | Soft | KCNAB2 | 102724550 | Soft | TPT1-AS1 | 100190939 | Soft |
| CD7 | 924 | Soft | PACS2 | 23241 | Soft | KCND1 | 8514 | Soft | TRABD2B | 388630 | Soft |
| CD72 | 971 | Soft | PADI3 | 51702 | Soft | KCNE3 | 3750 | Soft | TRAPPC6A | 79090 | Soft |
| CD74 | 972 | Soft | PAGE2 | 20 | Soft | KCNE4 | 10008 | Soft | TREM1 | 54210 | Soft |
| CD82 | 3732 | Soft | PAGE2B | 389860 | Soft | KCNH1 | 23704 | Soft | TRIB2 | 28951 | Soft |
| CDC42EP5 | 148170 | Soft | PAGE3 | 139793 | Soft | KCNH3 | 3756 | Soft | TRIM17 | 51127 | Soft |
| CDH13 | 1012 | Soft | PAIP2B | 400961 | Soft | KCNH5 | 23416 | Soft | TRIM22 | 10346 | Soft |
| CDH19 | 28513 | Soft | PALD1 | 27143 | Soft | KCNH8 | 27133 | Soft | TRIM29 | 23650 | Soft |
| CDH22 | 64405 | Soft | PAMR1 | 25891 | Soft | KCNIP2 | 131096 | Soft | TRIM34 | 53840 | Soft |
| CDHR5 | 53841 | Soft | PAN2 | 9924 | Soft | KCNJ9 | 30819 | Soft | TRIM4 | 89122 | Soft |
| CDK18 | 5129 | Soft | PAPLN | 89932 | Soft | KCNK15-AS1 | 5069 | Soft | TRIM46 | 80128 | Soft |
| CDK19 | 23097 | Soft | PAPPA | 5069 | Soft | KCNK2 | 106144538 | Soft | TRIM52 | 84851 | Soft |
| CDKL2 | 8999 | Soft | PAPPA-AS1 | 493913 | Soft | KCNK3 | 3776 | Soft | TRIM54 | 57159 | Soft |
| CDKN1B | 1027 | Soft | PAPPA2 | 60676 | Soft | KCNMB2-AS1 | 3777 | Soft | TRIM6-TRIM34 | 445372 | Soft |
| CDNF | 441549 | Soft | PAQR6 | 79957 | Soft | KCNN1 | 104797538 | Soft | TRIM63 | 84676 | Soft |
| CDON | 50937 | Soft | PAQR8 | 85315 | Soft | KCNN4 | 3780 | Soft | TRIM66 | 9866 | Soft |
| CDR1 | 1038 | Soft | PARD6G-AS1 | 100130522 | Soft | KCNT2 | 3783 | Soft | TRIM69 | 140691 | Soft |
| CECR1 | 51816 | Soft | PARK2 | 5071 | Soft | KCTD11 | 343450 | Soft | TRIML1 | 339976 | Soft |
| CECR2 | 27443 | Soft | PARM1 | 25849 | Soft | KCTD16 | 147040 | Soft | TRIOBP | 11078 | Soft |
| CECR5-AS1 | 100130717 | Soft | PARP10 | 84875 | Soft | KCTD19 | 57528 | Soft | TRIQK | 286144 | Soft |
| CELF6 | 60677 | Soft | PARP16 | 54956 | Soft | KDF1 | 146212 | Soft | TRO | 7216 | Soft |
| CELSR3 | 1951 | Soft | PARP3 | 10039 | Soft | KDM3A | 126695 | Soft | TRPC1 | 7220 | Soft |
| CEMIP | 57214 | Soft | PAX9 | 5083 | Soft | KDM4B | 55818 | Soft | TRPM4 | 54795 | Soft |
| CEP112 | 201134 | Soft | PBXIP1 | 57326 | Soft | KDM4C | 23030 | Soft | TRPS1 | 7227 | Soft |
| CEP126 | 57562 | Soft | PCAT2 | 103164619 | Soft | KDM5B | 23081 | Soft | TRPT1 | 83707 | Soft |
| CEP68 | 23177 | Soft | PCAT5 | 102578074 | Soft | KDR | 3791 | Soft | TRPV1 | 7442 | Soft |
| CERS1 | 10715 | Soft | PCAT6 | 100506696 | Soft | | | | TSC22D3 | 1831 | Soft |

-continued

| GeneSymbol | gene_id | Status | GeneSymbol | gene_id | Status | GeneSymbol | gene_id | Status |
|---|---|---|---|---|---|---|---|---|
| CERS4 | 79603 | Soft | PCBP1-AS1 | 400960 | Soft | KIAA0825 | 285600 | Soft | TSHZ2 | 128553 | Soft |
| CES3 | 23491 | Soft | PCBP3 | 54039 | Soft | KIAA0895L | 653319 | Soft | TSLP | 85480 | Soft |
| CFAP126 | 257177 | Soft | PCDH18 | 54510 | Soft | KIAA1107 | 23285 | Soft | TSNARE1 | 203062 | Soft |
| CFAP206 | 154313 | Soft | PCDH20 | 64881 | Soft | KIAA1109 | 84162 | Soft | TSNAXIP1 | 55815 | Soft |
| CFAP221 | 200373 | Soft | PCDH7 | 5099 | Soft | KIAA1462 | 57608 | Soft | TSPAN1 | 10103 | Soft |
| CFAP43 | 80217 | Soft | PCDHB5 | 26167 | Soft | KIAA1683 | 80726 | Soft | TSPAN15 | 23555 | Soft |
| CFAP44 | 55779 | Soft | PCDHB9 | 56127 | Soft | KIAA1958 | 158405 | Soft | TSPAN18 | 90139 | Soft |
| CFAP47 | 286464 | Soft | PCED1A | 64773 | Soft | KIF26A | 26153 | Soft | TSPAN19 | 144448 | Soft |
| CFAP53 | 220136 | Soft | PCMTD1 | 115294 | Soft | KIF3G | 3797 | Soft | TSPAN31 | 6302 | Soft |
| CFAP54 | 144535 | Soft | PCOLCE | 5118 | Soft | KIF5A | 3798 | Soft | TSPAN7 | 7102 | Soft |
| CFAP57 | 149465 | Soft | PCOLCE-AS1 | 100129845 | Soft | KIF5C | 3800 | Soft | TSPAN8 | 7103 | Soft |
| CFAP58-AS1 | 100505869 | Soft | PCP2 | 126006 | Soft | KIFC2 | 90990 | Soft | TSSK3 | 81629 | Soft |
| CFAP70 | 118491 | Soft | PCSK1 | 5122 | Soft | KISS1R | 84634 | Soft | TSSK6 | 83983 | Soft |
| CFB | 629 | Soft | PCSK4 | 54760 | Soft | KIZ | 55857 | Soft | TTBK2 | 146057 | Soft |
| CFD | 1675 | Soft | PDCD4 | 27250 | Soft | KIZ-AS1 | 101929591 | Soft | TTC21A | 199223 | Soft |
| CFH | 3075 | Soft | PDCD4-AS1 | 282997 | Soft | KLC4 | 89953 | Soft | TTC25 | 83538 | Soft |
| CFHR3 | 10878 | Soft | PDE2A | 5138 | Soft | KLF2 | 10365 | Soft | TTC30A | 92104 | Soft |
| CFI | 3426 | Soft | PDE4C | 5143 | Soft | KLF7 | 8609 | Soft | TTC39A | 22996 | Soft |
| CHD5 | 26038 | Soft | PDEDIP | 9659 | Soft | KLF8 | 11279 | Soft | TTC398 | 158219 | Soft |
| CHD6 | 84181 | Soft | PDE5A | 8654 | Soft | KLHDC1 | 122773 | Soft | TTLL1 | 25809 | Soft |
| CHRM3 | 1131 | Soft | PDE7B | 27115 | Soft | KLHDC8B | 200942 | Soft | TTLL3 | 26140 | Soft |
| CHRNB1 | 1140 | Soft | PDE8B | 8622 | Soft | KLHL24 | 54800 | Soft | TTYH2 | 94015 | Soft |
| CHST1 | 8534 | Soft | PDGFB | 5155 | Soft | KLHL28 | 54813 | Soft | TUB | 7275 | Soft |
| CHST15 | 51363 | Soft | PDGFD | 80310 | Soft | KLHL3 | 26249 | Soft | TUBA3FP | 113691 | Soft |
| CIART | 148523 | Soft | PDGFRA | 5156 | Soft | KLHL30 | 377007 | Soft | TUBA8 | 51807 | Soft |
| CITA | 4261 | Soft | PDGFRB | 5159 | Soft | KLHL31 | 401265 | Soft | TUBAL3 | 79861 | Soft |
| CISH | 1154 | Soft | PDK1 | 5163 | Soft | KLHL36 | 79786 | Soft | TUBB2B | 347733 | Soft |
| CITED2 | 10370 | Soft | PDK3 | 5165 | Soft | KLHL38 | 340359 | Soft | TWIST1 | 7291 | Soft |
| CKB | 1152 | Soft | PDK4 | 5166 | Soft | KLHL7-AS1 | 100775104 | Soft | TXK | 7294 | Soft |
| CLCNKA | 1187 | Soft | PDLIM2 | 64236 | Soft | KLRC2 | 3822 | Soft | TXLNB | 167838 | Soft |
| CLDN16 | 10686 | Soft | PDZD2 | 23037 | Soft | KLRC3 | 3823 | Soft | TXNIP | 10628 | Soft |
| CLDN18 | 51208 | Soft | PDZD7 | 79955 | Soft | KLRC4-KLRK1 | 100528032 | Soft | TYMP | 1890 | Soft |
| CLDN9 | 9080 | Soft | PDZK1IP1 | 10158 | Soft | KLRK1 | 22914 | Soft | TYRP1 | 7306 | Soft |
| CLDND2 | 125875 | Soft | PEAR1 | 375033 | Soft | KMO | 8564 | Soft | UBA6-AS1 | 550112 | Soft |
| CLEC11A | 6320 | Soft | PELI2 | 57161 | Soft | KMT2E-AS1 | 100216545 | Soft | UBA7 | 7318 | Soft |
| CLEC2B | 9976 | Soft | PEX11A | 8800 | Soft | KRBA2 | 124751 | Soft | UBAP1L | 390595 | Soft |
| CLEC2D | 29121 | Soft | PEX11G | 92960 | Soft | KRCC1 | 51315 | Soft | UBE2Q2P1 | 388165 | Soft |
| CLEC38 | 7123 | Soft | PEX5L | 51555 | Soft | KREMEN1 | 83999 | Soft | UCN | 7349 | Soft |
| CLHC1 | 130162 | Soft | PEX6 | 5190 | Soft | KREMEN2 | 79412 | Soft | UCN2 | 90226 | Soft |
| CLIC2 | 1193 | Soft | PFKFB4 | 5210 | Soft | KRT17 | 3872oft | Soft | UGDH-AS1 | 100885776 | Soft |
| CLIC5 | 53405 | Soft | PFN1P2 | 767846 | Soft | KRT5 | 3852 | Soft | UGT1A1 | 54658 | Soft |
| CLIP1-AS1 | 100507066 | Soft | IPGAM2 | 5224 | Soft | KRT79 | 338785 | Soft | UGT1A10 | 54575 | Soft |
| CLIP3 | 25999 | Soft | PGAP1 | 80055 | Soft | KRT84 | 3890 | Soft | UGT1A3 | 54659 | Soft |
| CLK1 | 1195 | Soft | PGF | 5228 | Soft | KRTAP1-5 | 83895 | Soft | UGT1A4 | 54657 | Soft |
| CLK4 | 57396 | Soft | PGPEP1 | 54858 | Soft | KY | 339855 | Soft | UGT1A5 | 54579 | Soft |
| CLMN | 79789 | Soft | PGR | 5241 | Soft | L1CAM | 3897 | Soft | UGT1A6 | 54578 | Soft |
| CLSTN3 | 9746 | Soft | PHEX | 5251 | Soft | L3MBTL1 | 26013 | Soft | UGT1A7 | 54577 | Soft |
| CUL1 | 27098 | Soft | PHF21A | 51317 | Soft | L3MBTL4 | 91133 | Soft | UGT1A8 | 54576 | Soft |
| CLYBL | 171425 | Soft | PHLDB3 | 653583 | Soft | LAMB2 | 3913 | Soft | UGT1A9 | 54600 | Soft |
| CMKLR1 | 1240 | Soft | PHYHD1 | 254295 | Soft | LAMB2P1 | 22973 | Soft | UGT2A1 | 10941 | Soft |
| CNBD1 | 168975 | Soft | PHYKPL | 85007 | Soft | LAPTM5 | 7805 | Soft | UGT2A2 | 574537 | Soft |

-continued

| GeneSymbol | gene_id | Status | GeneSymbol | gene_id | Status | GeneSymbol | gene_id | Status |
|---|---|---|---|---|---|---|---|---|
| CNNM2 | 54805 | Soft | PIEZO2 | 63895 | Soft | LBH | 81606 | Soft | ULBP1 | 80329 | Soft |
| CNOT8 | 9337 | Soft | PIGV | 55650 | Soft | LBX2 | 85474 | Soft | ULK1 | 8408 | Soft |
| CNR1 | 1268 | Soft | PIGZ | 80235 | Soft | LBX2-AS1 | 151534 | Soft | UNC13C | 440279 | Soft |
| CNRIP1 | 25927 | Soft | PIH1D2 | 120379 | Soft | LCA5 | 167691 | Soft | UNC5B | 219699 | Soft |
| CNTN3 | 5067 | Soft | PIK3C28 | 5287 | Soft | LDB3 | 11155 | Soft | UNC5B-AS1 | 728978 | Soft |
| CNTN5 | 53942 | Soft | PIK3CD-AS2 | 101929074 | Soft | LDHD | 197257 | Soft | URAHP | 100130015 | Soft |
| CNTNAP4 | 85445 | Soft | PIK3IP1 | 113791 | Soft | LDLRAD2 | 401944 | Soft | USP27X-AS1 | 158572 | Soft |
| COL11A2 | 1302 | Soft | PIM1 | 5292 | Soft | LENG8-AS1 | 104355426 | Soft | USP30 | 84749 | Soft |
| COL14A1 | 7373 | Soft | PIP5KL1 | 138429 | Soft | LEPR | 3953 | Soft | VAMP1 | 6843 | Soft |
| COL18A1 | 80781 | Soft | PIPOX | 51268 | Soft | LEPROT | 54741 | Soft | VAMP2 | 6844 | Soft |
| COL21A1 | 81578 | Soft | PITPNM3 | 83394 | Soft | LETMD1 | 25875 | Soft | VASN | 114990 | Soft |
| COL28A1 | 340267 | Soft | PIWIL4 | 143689 | Soft | LGALS9 | 3965 | Soft | VCAM1 | 7412 | Soft |
| COL3A1 | 1281 | Soft | PKD1 | 5310 | Soft | LGI4 | 163175 | Soft | VCAN | 1462 | Soft |
| COL4A2 | 1284 | Soft | PKD1L2 | 114780 | Soft | LHPP | 64077 | Soft | VEGFA | 7422 | Soft |
| COL4A2-AS1 | 10087420 | Soft | PKDCC | 91461 | Soft | LHX9 | 56956 | Soft | VIM-AS1 | 100507347 | Soft |
| COL4A3 | 1285 | Soft | PKDREJ | 10343 | Soft | LIN7A | 8825 | Soft | VLDLR | 7436 | Soft |
| COL4A4 | 1286 | Soft | PKHD1 | 5314 | Soft | LINC-PINT | 378805 | Soft | VLDLR-AS1 | 401491 | Soft |
| COL5A1 | 1289 | Soft | PKHD1L1 | 93035 | Soft | LINC00163 | 727699 | Soft | VMAC | 400673 | Soft |
| COL5A3 | 50509 | Soft | PLA2G6 | 8398 | Soft | LINC00173 | 100287569 | Soft | VNN1 | 8876 | Soft |
| COL6A1 | 1291 | Soft | PLA2R1 | 22925 | Soft | LINC00174 | 285908 | Soft | VPREB3 | 29802 | Soft |
| COL6A2 | 1292 | Soft | PLAG1 | 5324 | Soft | LINC00184 | 100302691 | Soft | VPS37D | 155382 | Soft |
| COL6A4P1 | 344875 | Soft | PLCB1 | 23236 | Soft | LINC00202-1 | 387644 | Soft | VSIG10L | 147645 | Soft |
| COL7A1 | 1294 | Soft | PLCD1 | 5333 | Soft | LINC00202-2 | 731789 | Soft | VWA1 | 64856 | Soft |
| COL9A2 | 1298 | Soft | PLCH2 | 9651 | Soft | LINC00243 | 401247 | Soft | VWA7 | 80737 | Soft |
| COL9A3 | 1299 | Soft | PLCL1 | 5334 | Soft | LINC00324 | 284029 | Soft | VWDE | 221806 | Soft |
| COLCA1 | 399948 | Soft | PLD1 | 5337 | Soft | LINC00332 | 100874127 | Soft | WASH2 | 375260 | Soft |
| COLEC11 | 78989 | Soft | PLEKHA4 | 57664 | Soft | LINC00339 | 29092 | Soft | WBP1 | 23559 | Soft |
| COLEC12 | 81035 | Soft | PLEKHA6 | 22874 | Soft | LINC00525 | 84847 | Soft | WBP5 | 51186 | Soft |
| COLQ | 8292 | Soft | PLEKHG5 | 57449 | Soft | LINC00548 | 400123 | Soft | WDR31 | 114987 | Soft |
| COPG2IT1 | 53844 | Soft | PLEKHH3 | 79990 | Soft | LINC00565 | 100861555 | Soft | WDR60 | 55112 | Soft |
| CORIN | 10699 | Soft | PLEKHS1 | 79949 | Soft | LINC00592 | 283404 | Soft | WDR63 | 126820 | Soft |
| CORO2A | 7464 | Soft | PLIN1 | 5346 | Soft | LINC00598 | 646982 | Soft | WDR78 | 79819 | Soft |
| CORO2B | 10391 | Soft | PLIN2 | 123 | Soft | LINC00607 | 646324 | Soft | WDR93 | 56964 | Soft |
| CORO6 | 84940 | Soft | PLIN4 | 729359 | Soft | LINC00619 | 414260 | Soft | WDR97 | 340390 | Soft |
| CP | 1356 | Soft | PLOD2 | 5352 | Soft | LINC00622 | 644242 | Soft | WEE2-AS1 | 285962 | Soft |
| CPA3 | 1359 | Soft | PLS3-AS1 | 101927352 | Soft | LINC00632 | 286411 | Soft | WFDC1 | 58189 | Soft |
| CPAMD8 | 27151 | Soft | PLSCR4 | 57088 | Soft | LINC00634 | 339674 | Soft | WFDC3 | 140686 | Soft |
| CPE | 1363 | Soft | PLXDC1 | 57125 | Soft | LINC00638 | 196872 | Soft | WFIKKN1 | 117166 | Soft |
| CPLX1 | 10815 | Soft | PLXDC2 | 84898 | Soft | LINC00648 | 100506433 | Soft | WISP1 | 8840 | Soft |
| CPM | 1368 | Soft | PLXNA3 | 55558 | Soft | LINC00649 | 100506334 | Soft | WISP2 | 8839 | Soft |
| CPQ | 10404 | Soft | PLXNB1 | 5364 | Soft | LINC00652 | 29075 | Soft | WNT2B | 7482 | Soft |
| CPT1C | 126129 | Soft | PLXNB3 | 5365 | Soft | LINC00663 | 284440 | Soft | WNT5A | 7474 | Soft |
| CRAT | 1384 | Soft | PLXND1 | 23129 | Soft | LINC00672 | 100505576 | Soft | WWC2-AS | 152641 | Soft |
| CREBRF | 153222 | Soft | PMEL | 6490 | Soft | LINC00680-GUSBP4 | 106660613 | Soft | XAF1 | 54739 | Soft |
| CRELD1 | 78987 | Soft | PMFBP1 | 83449 | Soft | LINC00702 | 100652988 | Soft | XCR1 | 2829 | Soft |
| CRHR1-IT1 | 147081 | Soft | PNMA2 | 10687 | Soft | LINC00704 | 100216001 | Soft | XKR9 | 389668 | Soft |
| CRIP2 | 1397 | Soft | PNPLA7 | 375775 | Soft | LINC00706 | 100652997 | Soft | YJEFN5 | 374887 | Soft |
| CRISP3 | 10321 | Soft | PODNL1 | 79883 | Soft | LINC00840 | 100506835 | Soft | YPEL2 | 388403 | Soft |
| CRLF1 | 9244 | Soft | POLD4 | 57804 | Soft | LINC00847 | 729678 | Soft | YPEL3 | 83719 | Soft |
| CROCC2 | 728979 | Soft | | | | | | | | | |
| CROCCP3 | 114819 | Soft | POLI | 11201 | Soft | LINC00853 | 100874253 | Soft | YPEL4 | 219539 | Soft |
| CRTAC1 | 55118 | Soft | POM121L9P | 29774 | Soft | LINC00870 | 201617 | Soft | YPEL5 | 51646 | Soft |

| GeneSymbol | gene_id | Status | GeneSymbol | gene_id | Status | GeneSymbol | gene_id | Status |
|---|---|---|---|---|---|---|---|---|
| CRTC1 | 23373 | Soft | POSTN | 10631 | Soft | LINC00877 | 285286 | Soft | ZBED3-AS1 | 728723 | Soft |
| CRYAB | 1410 | Soft | POU5F1 | 5460 | Soft | LINC00882 | 100302640 | Soft | ZBED5-AS1 | 729013 | Soft |
| CSMD3 | 114788 | Soft | POU5F1P3 | 642559 | Soft | LINC00887 | 100131551 | Soft | ZBED6CL | 113763 | Soft |
| CSRNP3 | 80034 | Soft | POU6F1 | 5463 | Soft | LINC00893 | 100131434 | Soft | ZBED8 | 63920 | Soft |
| CSTA | 1475 | Soft | POU6F2 | 11281 | Soft | LINC00894 | 100272228 | Soft | ZBTB1 | 22890 | Soft |
| CTB-113P19.1 | 101927096 | Soft | PPARA | 5465 | Soft | LINC00898 | 400932 | Soft | ZBTB16 | 7704 | Soft |
| CTBS | 1486 | Soft | PPARCC1A | 10891 | Soft | LINC00899 | 100271722 | Soft | ZBTB22 | 9278 | Soft |
| CTC-338M124 | 101928649 | Soft | PPEF1 | 5475 | Soft | LINC00910 | 100130581 | Soft | ZBTB25 | 7597 | Soft |
| CTF1 | 1489 | Soft | PPFIA2 | 8499 | Soft | LINC00920 | 100505865 | Soft | ZC3H12D | 340152 | Soft |
| CTSF | 8722 | Soft | PPFIA4 | 8497 | Soft | LINC00921 | 283876 | Soft | ZC3H6 | 376940 | Soft |
| CTSH | 1512 | Soft | PPIL6 | 285755 | Soft | LINC00942 | 100292680 | Soft | ZC3HAV1L | 92092 | Soft |
| CTSK | 1513 | Soft | PPL | 5493 | Soft | LINC00950 | 92973 | Soft | ZC4H2 | 55906 | Soft |
| CTSO | 1519 | Soft | PPM1L | 151742 | Soft | LINC00957 | 255031 | Soft | ZCCHC24 | 219654 | Soft |
| CUBN | 8029 | Soft | PPM1M | 132160 | Soft | LINC00964 | 157381 | Soft | ZCWPW1 | 55063 | Soft |
| CUEDC1 | 404093 | Soft | PPM1N | 147699 | Soft | LINC00969 | 440993 | Soft | ZCWPW2 | 152098 | Soft |
| CUL7 | 9820 | Soft | PPP1R13L | 10848 | Soft | LINC01011 | 401232 | Soft | ZDBF2 | 57683 | Soft |
| CUX1 | 1523 | Soft | PPP1R1C | 151242 | Soft | LINC01024 | 100505636 | Soft | ZDHHC1 | 29800 | Soft |
| CX3CL1 | 6376 | Soft | PPP1R32 | 220004 | Soft | LINC01029 | 101927715 | Soft | ZDHHC11 | 79844 | Soft |
| CXADRP3 | 440224 | Soft | PPP1R3B | 79660 | Soft | LINC01058 | 103724387 | Soft | ZDHHC23 | 254887 | Soft |
| CXCL11 | 6373 | Soft | PPP1R3C | 5507 | Soft | LINC01119 | 100134259 | Soft | ZEB2 | 9839 | Soft |
| CXCL12 | 6387 | Soft | PPP1R3E | 90673 | Soft | LINC01125 | 728537 | Soft | ZEB2-AS1 | 100303491 | Soft |
| CXCL16 | 58191 | Soft | PPP4R1L | 55370 | Soft | LINC01126 | 100129726 | Soft | ZER1 | 10444 | Soft |
| CXCR4 | 7852 | Soft | PRDM1 | 639 | Soft | LINC01137 | 728431 | Soft | ZFHX2 | 85446 | Soft |
| CXXC4 | 80319 | Soft | PRDM2 | 7799 | Soft | LINC01158 | 100506421 | Soft | ZFP14 | 57677 | Soft |
| CXXC5 | 51523 | Soft | PRELID2 | 15376 | Soft | LINC01159 | 102682016 | Soft | ZFP90 | 146198 | Soft |
| CYB5D2 | 124936 | Soft | PRICKLE2 | 166336 | Soft | LINC01179 | 101928151 | Soft | ZFYVE1 | 53349 | Soft |
| CYBRD1 | 79901 | Soft | PRICKLE2-AS1 | 100652759 | Soft | LINC01186 | 101927574 | Soft | ZFYVE28 | 57732 | Soft |
| CYHR1 | 50626 | Soft | PRICKLE2-AS3 | 100874243 | Soft | LINC01219 | 104355220 | Soft | ZG16B | 124220 | Soft |
| CYP11A1 | 1583 | Soft | PRICKLE4 | 29964 | Soft | LINC01260 | 79015 | Soft | ZHX2 | 2882 | Soft |
| CYP17A1 | 1586 | Soft | PRKAA2 | 5563 | Soft | LINC01273 | 101927541 | Soft | ZIC4 | 84107 | Soft |
| CYP19A1 | 1588 | Soft | PRKAB2 | 5565 | Soft | LINC01279 | 100506621 | Soft | ZKSCAN4 | 387032 | Soft |
| GYP27B1 | 1594 | Soft | PRKAG2-AS1 | 100505483 | Soft | LINC01301 | 100505532 | Soft | ZMAT1 | 84460 | Soft |
| CYP2E1 | 1571 | Soft | PRKAR2A-AS1 | 100506637 | Soft | LINC01355 | 100996511 | Soft | ZMIZ1-AS1 | 283050 | Soft |
| CYP39A1 | 51302 | Soft | PRKCE | 5581 | Soft | LINC01410 | 103352539 | Soft | ZMYND10 | 51364 | Soft |
| CYP4B1 | 1580 | Soft | PRKCZ | 590 | Soft | LINC01426 | 100506385 | Soft | ZMYND8 | 23613 | Soft |
| CYP4F11 | 57834 | Soft | PRKG1 | 592 | Soft | LINC01443 | 400644 | Soft | ZNF112 | 7771 | Soft |
| CYTH4 | 27128 | Soft | PRKG1-AS1 | 100506939 | Soft | LINC01512 | 100132354 | Soft | ZNF117 | 51351 | Soft |
| CYTIP | 9595 | Soft | PRKG2 | 5593 | Soft | LINC01518 | 101929397 | Soft | ZNF136 | 7695 | Soft |
| DACT3 | 147906 | Soft | PROB1 | 389333 | Soft | LINC01530 | 729975 | Soft | ZNF137P | 7696 | Soft |
| DARS-AS1 | 10192 | Soft | PROC | 5624 | Soft | LINC01534 | 101927621 | Soft | ZNF14 | 7561 | Soft |
| DBH | 1621 | Soft | PROCA1 | 147011 | Soft | LINC01537 | 101928555 | Soft | ZNF155 | 7711 | Soft |
| DBH-AS1 | 138948 | Soft | PRODH | 5625 | Soft | LINC01556 | 729583 | Soft | ZNF160 | 90338 | Soft |
| DBNDD1 | 79007 | Soft | PROS1 | 5627 | Soft | UNC01569 | 100507501 | Soft | ZNF165 | 7718 | Soft |
| DBNDD2 | 5586 | Soft | PROX2 | 28351 | Soft | LING01583 | 10192990 | Soft | ZNF175 | 7728 | Soft |
| DBP | 1628 | Soft | PRR29 | 92340 | Soft | LINC01588 | 283551 | Soft | ZNF192P1 | 651302 | Soft |
| DCHS2 | 54798 | Soft | PRR36 | 80164 | Soft | LING01589 | 100506737 | Soft | ZNF204P | 7754 | Soft |
| DCLK1 | 9201 | Soft | PRR5L | 79899 | Soft | LINC01615 | 101929484 | Soft | ZNF214 | 7761 | Soft |
| DCLK2 | 166614 | Soft | PRRG4 | 79056 | Soft | LINC01619 | 256021 | Soft | ZNF221 | 7638 | Soft |
| DCN | 1634 | Soft | PRRT1 | 80863 | Soft | LINCR-0002 | 10334926 | Soft | ZNF222 | 7673 | Soft |
| DCST2 | 127579 | Soft | PRRT2 | 112476 | Soft | LINGO2 | 158038 | Soft | ZNF223 | 7766 | Soft |
| DDIT4 | 54541 | Soft | PRRX2 | 51450 | Soft | LINGO3 | 645191 | Soft | ZNF224 | 7767 | Soft |

| GeneSymbol | gene_id | Status | GeneSymbol | gene_id | Status | GeneSymbol | gene_id | Status |
|---|---|---|---|---|---|---|---|---|
| DDIT4L | 115265 | Soft | PRSS16 | 10279 | Soft | LIPE-AS1 | 100996307 | Soft | ZNF225 | 7768 | Soft |
| DDO | 8528 | Soft | PRSS27 | 83886 | Soft | LMBR1L | 6716 | Soft | ZNF226 | 7769 | Soft |
| DDR1 | 780 | Soft | PRSS36 | 146547 | Soft | LMBRD1 | 55788 | Soft | ZNF230 | 7773 | Soft |
| DDR2 | 4921 | Soft | PRSS53 | 339105 | Soft | LMF1 | 6478 | Soft | ZNF233 | 353355 | Soft |
| DDX60 | 55601 | Soft | PRX | 57716 | Soft | LMNTD2 | 256329 | Soft | ZNF248 | 57209 | Soft |
| DENND3 | 22898 | Soft | PSD | 5662 | Soft | LMO3 | 5885 | Soft | ZNF25 | 219749 | Soft |
| DENND4C | 5566 | Soft | PSG1 | 5669 | Soft | LMOD1 | 5802 | Soft | ZNF250 | 58500 | Soft |
| DENND6B | 414918 | Soft | PSG4 | 5672 | Soft | LMTK3 | 114783 | Soft | ZNF251 | 90987 | Soft |
| DEPTOR | 64798 | Soft | PSMG3-AS1 | 114796 | Soft | LNX1 | 84708 | Soft | ZNF252P-AS1 | 286103 | Soft |
| DFNB31 | 25861 | Soft | PSORS1C1 | 170679 | Soft | LOC100128288 | 100128288 | Soft | ZNF264 | 9422 | Soft |
| DHRS1 | 115817 | Soft | PSORS1C2 | 170680 | Soft | LOC100129138 | 100129138 | Soft | ZNF280D | 54816 | Soft |
| DHRS13 | 147015 | Soft | PSORS1C3 | 100130889 | Soft | LOC100129534 | 100129534 | Soft | ZNF284 | 342909 | Soft |
| DHRS3 | 9249 | Soft | PSPN | 5623 | Soft | LOC100129603 | 100129603 | Soft | ZNF285 | 26974 | Soft |
| DHX58 | 79132 | Soft | PTCH1 | 5727 | Soft | LOC100129617 | 100129617 | Soft | ZNF292 | 23036 | Soft |
| DICER1-AS1 | 400242 | Soft | PTCH2 | 8643 | Soft | LOC100129924 | 100129924 | Soft | ZNF311 | 282890 | Soft |
| DISC1 | 27185 | Soft | PTGER2 | 5732 | Soft | LOC100129940 | 100129940 | Soft | ZNF32-AS1 | 414197 | Soft |
| DIXDC1 | 85458 | Soft | PTGES3L | 885848 | Soft | LOC100129973 | 100129973 | Soft | ZNF337-AS | 102724826 | Soft |
| DKFZp434J0226 | 93429 | Soft | PTGFR | 5737 | Soft | LOC100130417 | 100130417 | Soft | ZNF33B | 7582 | Soft |
| DKFZP586I1420 | 222161 | Soft | PTGIR | 5739 | Soft | LOC100130476 | 100130476 | Soft | ZNF345 | 25850 | Soft |
| DLG4 | 1742 | Soft | PTGS1 | -5742 | Soft | LOC100130691 | 100130691 | Soft | ZNF358 | 140467 | Soft |
| DLGAP1-AS1 | 649446 | Soft | PTHIR | 5745 | Soft | LOC100130987 | 100130987 | Soft | ZNF366 | 167465 | Soft |
| DLX4 | 1748 | Soft | PTK6 | 5753 | Soft | LOC100132057 | 100132057 | Soft | ZNF383 | 163087 | Soft |
| DMPK | 1760 | Soft | PTP4A3 | 11156 | Soft | LOC100134368 | 100134368 | Soft | ZNF385A | 25946 | Soft |
| DNAH1 | 25981 | Soft | PTPRB | 5787 | Soft | LOC100270804 | 100270804 | Soft | ZNF385B | 151126 | Soft |
| DNAH2 | 146754 | Soft | PTPRD | 5789 | Soft | LOC100287036 | 100287036 | Soft | ZNF385G | 201181 | Soft |
| DNAH5 | 1767 | Soft | PTPRH | 5794 | Soft | LOC100288152 | 100288152 | Soft | ZNF391 | 346157 | Soft |
| DNAH6 | 1768 | Soft | PTPRM | 5797 | Soft | LOC10028798 | 10028798 | Soft | ZNF395 | 55893 | Soft |
| DNAH7 | 56171 | Soft | PTPRN | 5798 | Soft | LOC10028911 | 10028911 | Soft | ZNF396 | 252884 | Soft |
| DNAJB2 | 3300 | Soft | PTPRO | 5800 | Soft | LOC100289230 | 100289230 | Soft | ZNF404 | 342908 | Soft |
| DNAJC18 | 202052 | Soft | PTPRR | 5801 | Soft | LOC100289495 | 100289495 | Soft | ZNF419 | 79744 | Soft |
| DNAJC22 | 79962 | Soft | PTPRU | 10076 | Soft | LOC100379224 | 100379224 | Soft | ZNF420 | 147923 | Soft |
| DNAJC28 | 54943 | Soft | PYROXD2 | 84795 | Soft | LOC100421746 | 100421746 | Soft | ZNF436-AS1 | 148898 | Soft |
| DNAJC4 | 3338 | Soft | QPRT | 23475 | Soft | LOC100499484-C9ORF174 | 57653 | Soft | ZNF444 | 55311 | Soft |
| DNAJC5G | 285126 | Soft | RAB11B-AS1 | 100507567 | Soft | LOC100505715 | 100505715 | Soft | ZNF446 | 55663 | Soft |
| DNAL4 | 10126 | Soft | RAB11FIP4 | 84440 | Soft | LOC100505771 | 100505771 | Soft | ZNF461 | 92283 | Soft |
| DNM1P35 | 100128285 | Soft | RAB20 | 55647 | Soft | LOC100505938 | 100505938 | Soft | ZNF467 | 168544 | Soft |
| DNM1P46 | 196968 | Soft | RAB26 | 2587 | Soft | LOC100506022 | 100506022 | Soft | ZNF470 | 388566 | Soft |
| DNM3 | 26052 | Soft | RAB30 | 27314 | Soft | LOC100506127 | 100506127 | Soft | ZNF485 | 220992 | Soft |
| DNM3OS | 100628315 | Soft | RAB33B | 83452 | Soft | LOC100506258 | 100506258 | Soft | ZNF490 | 57474 | Soft |
| DOCK2 | 1794 | Soft | RAB3A | 5864 | Soft | LOC100506271 | 100506271 | Soft | ZNF493 | 284443 | Soft |
| DOCK3 | 1795 | Soft | RAB3D | 9545 | Soft | LOC100506444 | 100506444 | Soft | ZNF501 | 115560 | Soft |
| DOCK6 | 57572 | Soft | RAB40A | 142684 | Soft | LOC100506472 | 100506472 | Soft | ZNF516 | 9658 | Soft |
| DOK4 | 55715 | Soft | RAB40C | 57799 | Soft | LOC100506476 | 100506476 | Soft | ZNF517 | 340385 | Soft |
| DPP4 | 1803 | Soft | RAB6B | 51560 | Soft | LOC100506548 | 100506548 | Soft | ZNF529 | 57711 | Soft |
| DPY19L2P2 | 349152 | Soft | RAB7B | 338382 | Soft | LOC100506679 | 100506679 | Soft | ZNF529-AS1 | 101927599 | Soft |
| DPYD | 1806 | Soft | RAB8B | 51762 | Soft | LOC100506688 | 100506688 | Soft | ZNF546 | 339327 | Soft |
| DPYSL4 | 10570 | Soft | RABGAP1L | 9910 | Soft | LOC100506746 | 100506746 | Soft | ZNF548 | 147694 | Soft |
| DRC3 | 83450 | Soft | RABL2A | 11159 | Soft | LOC100506990 | 100506990 | Soft | ZNF550 | 162972 | Soft |
| DRD4 | 1815 | Soft | RAD51-AS1 | 100505648 | Soft | LOC100507002 | 100507002 | Soft | ZNF554 | 115196 | Soft |
| DTNA | 1837 | Soft | RAET1G | 353091 | Soft | LOC100507053 | 100507053 | Soft | ZNF559 | 84527 | Soft |
| DTX3 | 196403 | Soft | RAG1 | 5896 | Soft | LOC100507158 | 100507156 | Soft | ZNF559-ZNF177 | 100529215 | Soft |

-continued

| GeneSymbol | gene_id | Status | GeneSymbol | gene_id | Status | GeneSymbol | gene_id | Status |
|---|---|---|---|---|---|---|---|---|
| DTX4 | 23220 | Soft | RALGDS | 5900 | Soft | LOC100507283 | 100507283 | Soft | ZNF572 | 137209 | Soft |
| DUOX1 | 905 | Soft | RAPZC-AS1 | 101928578 | Soft | LOC100507291 | 100507291 | Soft | ZNF575 | 284346 | Soft |
| DUSP10 | 11221 | Soft | RAPGEF3 | 10411 | Soft | LOC100507346 | 100507346 | Soft | ZNF577 | 84765 | Soft |
| DUSP19 | 142679 | Soft | RAPGEF4 | 11069 | Soft | LOC100507373 | 100507373 | Soft | ZNF581 | 51545 | Soft |
| DUSPSP1 | 574029 | Soft | RARA-AS1 | 101929 | Soft | LOC100507477 | 100507477 | Soft | ZNF585A | 199704 | Soft |
| DYRK1B | 9149 | Soft | RARRESZ | 5919 | Soft | LOC100507487 | 100507487 | Soft | ZNF596 | 169270 | Soft |
| EBF1 | 1879 | Soft | RARRES3 | 5920 | Soft | LOC100507547 | 100507547 | Soft | ZNF599 | 148103 | Soft |
| EBF4 | 57593 | Soft | RASA4 | 10156 | Soft | LOC100507642 | 100507642 | Soft | ZNF605 | 100289635 | Soft |
| EBI3 | 10148 | Soft | RASA4B | 100271927 | Soft | LOC100652768 | 100652768 | Soft | ZNF608 | 57507 | Soft |
| EDN1 | 1906 | Soft | RASA4CP | 401331 | Soft | LOC100652999 | 100652999 | Soft | ZNF615 | 284370 | Soft |
| EDN2 | 1907 | Soft | RASD2 | 23551 | Soft | LOC100996634 | 100996634 | Soft | ZNF630 | 57232 | Soft |
| EDNRA | 1909 | Soft | RASSF2 | 9770 | Soft | LOC100996693 | 100996693 | Soft | ZNF648 | 127665 | Soft |
| EFCAB12 | 90288 | Soft | RASSF4 | 83937 | Soft | LOC101060389 | 101060389 | Soft | ZNF654 | 55279 | Soft |
| EFCAB13 | 124989 | Soft | RASSF5 | 83593 | Soft | LOC101448202 | 101448202 | Soft | ZNF662 | 389114 | Soft |
| EFCAB6 | 64800 | Soft | RASSF9 | 9182 | Soft | LOC101926935 | 101926935 | Soft | ZNF699 | 374879 | Soft |
| EFEMP2 | 30008 | Soft | RBM43 | 375287 | Soft | LOC101927045 | 101927045 | Soft | ZNF713 | 349075 | Soft |
| EFHB | 151651 | Soft | RBM5-AS1 | 100775107 | Soft | LOC101927056 | 101927056 | Soft | ZNF747 | 65988 | Soft |
| EFHC1 | 114327 | Soft | RBMS3 | 27303 | Soft | LOC101927204 | 101927204 | Soft | ZNF775 | 285971 | Soft |
| EFHD1 | 80303 | Soft | RBP5 | 83758 | Soft | LOC101927229 | 101927229 | Soft | ZNF789 | 285989 | Soft |
| EFNA3 | 1944 | Soft | RCOR2 | 283248 | Soft | LOC101927282 | 101927282 | Soft | ZNF790 | 388536 | Soft |
| EFNA4 | 1945 | Soft | RDM1 | 201299 | Soft | LOC101927356 | 101927356 | Soft | ZNF808 | 38838558 | Soft |
| EFNB3 | 1949 | Soft | RECK | 8434 | Soft | LOG101927365 | 101927365 | Soft | ZNF815P | 401303 | Soft |
| EGF | 1950 | Soft | REEP2 | 51308 | Soft | LOC101927391 | 101927391 | Soft | ZNF821 | 55565 | Soft |
| EGFL8 | 80864 | Soft | REEP6 | 92840 | Soft | LOC101927415 | 101927415 | Soft | ZNF83 | 55769 | Soft |
| EGLN3 | 12399 | Soft | REM2 | 161253 | Soft | LOC101927482 | 101927482 | Soft | ZNF836 | 162962 | Soft |
| EIF3J-AS1 | 645212 | Soft | REPS2 | 9185 | Soft | LOC101927501 | 101927501 | Soft | ZNF837 | 116412 | Soft |
| EIF4E3 | 317649 | Soft | RERG | 85004 | Soft | LOC101927740 | 101927740 | Soft | ZNF84 | 7637 | Soft |
| ELN | 2006 | Soft | RFTN2 | 130132 | Soft | LOC101927759 | 101927759 | Soft | ZNF846 | 162993 | Soft |
| EMILIN3 | 90187 | Soft | RFX2 | 5990 | Soft | LOC101927770- | 101927770 | Soft | ZNF862 | 643641 | Soft |
| EMX2 | 2018 | Soft | RGAG4 | 340526 | Soft | LOC101927780 | 101927780 | Soft | ZP1 | 22917 | Soft |
| ENDOV | 284131 | Soft | RGS11 | 8786 | Soft | LOC101927843 | 101927843 | Soft | ZP3 | 7784 | Soft |
| ENKUR | 219670 | Soft | RGS14 | 10636 | Soft | LOC101927865 | 101927865 | Soft | ZSCAN16-AS1 | 100129195 | Soft |
| ENO2 | 2026 | Soft | RGS3 | 5998 | Soft | LOC101927934 | 101927934 | Soft | ZSCAN2 | 54993 | Soft |
| ENO3 | 2027 | Soft | RHBDL1 | 9028 | Soft | LOC101928034 | 101928034 | Soft | ZSCAN23 | 222696 | Soft |
| ENPP3 | 5169 | Soft | RHBDL2 | 54933 | Soft | LOC101928063 | 101928063 | Soft | ZSCAN30 | 100101467 | Soft |
| EPB41L4A-AS1 | 114915 | Soft | RHOU | 58480 | Soft | LOC101928068 | 101928068 | Soft | ZSCAN31 | 64288 | Soft |
| LOC101928222 | 101928222 | Soft | ZXDA | 7789 | Soft | LOC101928100 | 101928100 | Soft | ZSWIM4 | 65249 | Soft |
| | | | | | | LOC101928103 | 101928103 | Soft | ZSWIM5 | 57643 | Soft |

\* \* \* \* \*

SEQUENCE LISTING

```
<160> NUMBER OF SEQ ID NOS: 29

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
tctggaagga gaccggtct                                              19

<210> SEQ ID NO 2
<211> LENGTH: 19
<212> TYPE: DNA
```

```
<213> ORGANISM: Artificial sequence
<220> FEATURE:
<223> OTHER INFORMATION: Synthetic

<400> SEQUENCE: 2
tacaaataaa tggacagtg                                              19

<210> SEQ ID NO 3
<211> LENGTH: 22
<212> TYPE: DNA
<213> ORGANISM: Artificial sequence
<220> FEATURE:
<223> OTHER INFORMATION: Synthetic

<400> SEQUENCE: 3
gtcaggagat cgagaccatc ct                                          22

<210> SEQ ID NO 4
<211> LENGTH: 17
<212> TYPE: DNA
<213> ORGANISM: Artificial sequence
<220> FEATURE:
<223> OTHER INFORMATION: Synthetic

<400> SEQUENCE: 4
agtggcgcaa tctcggc                                                17

<210> SEQ ID NO 5
<211> LENGTH: 25
<212> TYPE: DNA
<213> ORGANISM: Artificial sequence
<220> FEATURE:
<223> OTHER INFORMATION: Synthetic

<400> SEQUENCE: 5
agctactcgg gaggctgagg cagga                                       25

<210> SEQ ID NO 6
<211> LENGTH: 19
<212> TYPE: DNA
<213> ORGANISM: Artificial sequence
<220> FEATURE:
<223> OTHER INFORMATION: Synthetic

<400> SEQUENCE: 6
actggcgctg caacaagac                                              19

<210> SEQ ID NO 7
<211> LENGTH: 23
<212> TYPE: DNA
<213> ORGANISM: Artificial sequence
<220> FEATURE:
<223> OTHER INFORMATION: Synthetic

<400> SEQUENCE: 7
cactgctgct gagatcaatg aaa                                         23

<210> SEQ ID NO 8
<211> LENGTH: 18
<212> TYPE: DNA
<213> ORGANISM: Artificial sequence
<220> FEATURE:
<223> OTHER INFORMATION: Synthetic

<400> SEQUENCE: 8
ttgcagcctt ctcagcca                                               18
```

<210> SEQ ID NO 9
<211> LENGTH: 25
<212> TYPE: DNA
<213> ORGANISM: Artificial sequence
<220> FEATURE:
<223> OTHER INFORMATION: Synthetic

<400> SEQUENCE: 9
aattcagatg aagtggact tgtgt                                           25

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
acactgcgcc aacacagaaa                                                20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
ttcccagtgg tggtgatgaa                                                20

<210> SEQ ID NO 12
<211> LENGTH: 19
<212> TYPE: DNA
<213> ORGANISM: Artificial sequence
<220> FEATURE:
<223> OTHER INFORMATION: Synthetic

<400> SEQUENCE: 12
gcgaggagtg ggtgtgtga                                                 19

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
ctatgagaag ggcgtgcaga g                                              21

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
tcgggcaagt ccaccactac                                                20

<210> SEQ ID NO 15
<211> LENGTH: 20
<212> TYPE: DNA
<213> ORGANISM: Artificial sequence
<220> FEATURE:

-continued

<223> OTHER INFORMATION: Synthetic

<400> SEQUENCE: 15
aaggggctgg aatgcaactt                                                20

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
cggtgagact gaaccgctat                                                20

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
gactgcctgt ccctacaact acc                                            23

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
caccaatgac agtaccgccc                                                20

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
ctcggctgga cggatgtctg                                                20

<210> SEQ ID NO 20
<211> LENGTH: 23
<212> TYPE: DNA
<213> ORGANISM: Artificial sequence
<220> FEATURE:
<223> OTHER INFORMATION: Synthetic

<400> SEQUENCE: 20
tcttaacgtc actaaacgaa aac                                            23

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
cgatgacgtt ccgaccaagc                                                20

<210> SEQ ID NO 22
<211> LENGTH: 20
<212> TYPE: DNA
<213> ORGANISM: Artificial sequence
<220> FEATURE:
<223> OTHER INFORMATION: Synthetic

<400> SEQUENCE: 22
agacagacct ggggttcctt					20

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
tggatgttta gagcgccctt					20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
tgtctcacct cgcggacaag					20

<210> SEQ ID NO 25
<211> LENGTH: 22
<212> TYPE: DNA
<213> ORGANISM: Artificial sequence
<220> FEATURE:
<223> OTHER INFORMATION: Synthetic

<400> SEQUENCE: 25
ctggtggacc tcctttcta gg					22

<210> SEQ ID NO 26
<211> LENGTH: 21
<212> TYPE: DNA
<213> ORGANISM: Artificial sequence
<220> FEATURE:
<223> OTHER INFORMATION: Synthetic

<400> SEQUENCE: 26
agttcatacg gacccagaac c					21

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
gtcagtctcc cgtctgggac					20

<210> SEQ ID NO 28
<211> LENGTH: 20
<212> TYPE: DNA
<213> ORGANISM: Artificial sequence
<220> FEATURE:
<223> OTHER INFORMATION: Synthetic

```
<400> SEQUENCE: 28
gctacctaga ccacgatgtg                                           20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
gctcacacga taccagaccc                                           20
```